United States Patent
Brook et al.

(10) Patent No.: US 11,407,767 B2
(45) Date of Patent: Aug. 9, 2022

(54) HETEROCYCLYL SUBSTITUTED PYRROLOPYRIDINES THAT ARE INHIBITORS OF THE CDK12 KINASE

(71) Applicant: The University of Nottingham, Nottingham (GB)

(72) Inventors: David Brook, Nottingham (GB); Chris Hayes, Nottingham (GB); Nicholas Bennett, Nottingham (GB); Matthew Palframan, Nottingham (GB); Sue Cramp, Essex (GB); Richard Bull, Essex (GB); Michael Bodnarchuk, Essex (GB)

(*) Notice: Subject to any disclaimer, the term of this patent is extended or adjusted under 35 U.S.C. 154(b) by 36 days.

(21) Appl. No.: 16/649,512

(22) PCT Filed: Sep. 21, 2018

(86) PCT No.: PCT/GB2018/052697
§ 371 (c)(1),
(2) Date: Mar. 20, 2020

(87) PCT Pub. No.: WO2019/058132
PCT Pub. Date: Mar. 28, 2019

(65) Prior Publication Data
US 2020/0247824 A1  Aug. 6, 2020

(30) Foreign Application Priority Data
Sep. 22, 2017  (GB) ..................................... 1715342

(51) Int. Cl.
| C07D 401/14 | (2006.01) |
| C07D 471/04 | (2006.01) |
| C07D 519/00 | (2006.01) |
| A61K 31/437 | (2006.01) |
| A61P 33/02  | (2006.01) |
| A61P 35/04  | (2006.01) |

(52) U.S. Cl.
CPC ............ *C07D 519/00* (2013.01); *A61P 33/02* (2018.01); *A61P 35/04* (2018.01); *C07D 471/04* (2013.01)

(58) Field of Classification Search
CPC .. C07D 401/14; C07D 471/04; C07D 519/00; A61K 31/437
USPC .............................. 514/303, 210.21; 546/119
See application file for complete search history.

(56) References Cited

FOREIGN PATENT DOCUMENTS

| WO | WO 03/051886   | 6/2003  |
| WO | WO 2010/003133 | 1/2010  |
| WO | WO 2013/173506 | 11/2013 |
| WO | WO 2017/023996 | 2/2017  |
| WO | WO 2017/163076 | 9/2017  |

OTHER PUBLICATIONS

Kettle et al., Journal of Medicinal Chemistry (2015), 58(6), 2834-2844.*
International Search Report and Written Opinion issued for International Application No. PCT/GB2018/052697 dated Oct. 19, 2018.
Kettle et al., "Discovery and Optimization of a Novel Series of Dyrk1B Kinase Inhibitors to Explore a MEK Resistance Hypothesis," *Journal of Medicinal Chemistry*, 58(6): 2834-2844, Mar. 26, 2015.
Montgomery et al., "Discovery and characterization of a novel class of pyrazolopyrimidinedione, tRNA synthesis inhibitors," *The Journal of Antibiotics*, 68(6): 361-367, Dec. 3, 2014.

* cited by examiner

*Primary Examiner* — Niloofar Rahmani
(74) *Attorney, Agent, or Firm* — Klarquist Sparkman, LLP

(57) ABSTRACT

This invention related to compounds that are inhibitors of the CDK12 kinase. The compounds are useful in the treatment of disorders mediated by the CDK12 kinase including myotonic dystrophy type 1 (DM1) and other disorders caused by the generation of RNA repeat expansion transcripts. In particular, the invention relates to compounds of the formula (I), or a pharmaceutically acceptable salts or N-oxides thereof, wherein $R^{1a}$, $R^2$, $R^3$, $R^{4a}$, $R^{4b}$ and $R^{4c}$ are as defined herein.

14 Claims, No Drawings

HETEROCYCLYL SUBSTITUTED PYRROLOPYRIDINES THAT ARE INHIBITORS OF THE CDK12 KINASE

CROSS REFERENCE TO RELATED APPLICATIONS

This is the U.S. National Stage of International Application No. PCT/GB2018/052697, filed Sep. 21, 2018, which was published in English under PCT Article 21(2), which in turn claims the benefit of GB Application No. 1715342.0, filed Sep. 22, 2017, which is incorporated herein by reference in its entirety.

This invention relates to compounds that are inhibitors of the CDK12 kinase. Such compounds are useful in the treatment of myotonic dystrophy type 1 (DM1) and other disorders caused by the generation of RNA repeat expansion transcripts.

This invention also relates to pharmaceutical formulations comprising said compounds and methods of treating diseases (e.g. DM1) using said compounds.

BACKGROUND OF THE INVENTION

Myotonic dystrophy type 1 (DM1) is the most common adult muscular dystrophy. It is a highly debilitating condition, which affects 1 in 8000. There are more than 100,000 patients in developed countries, with no treatment and an average life expectancy of 58 years. In addition to the health-related issues there is a very high social cost to DM1, 50-70% of DM1 patients of working age are likely to be unemployed. Figures produced by the Muscular Dystrophy Association USA indicate that the cost of DM to the US economy in terms of medical and non-medical expenses and lost income is roughly $450 million dollars per annum. DM1 is primarily a neuromuscular disorder, which also affects a range of other systems. Skeletal muscle features include weakness, wasting, myotonia, and pain. Patients often have facial and neck muscle weakness and mild ptosis (heavy eye-lids), which produce a characteristic facial appearance. Limb weakness is initially distal, affecting the finger flexors, causing substantial disability, and ankle dorsiflexion resulting in foot drop.

As the disease progresses proximal weakness becomes more apparent. Myotonia is a characteristic feature, obvious in most symptomatic adults; the commonest manifestation of which is difficulty in relaxing the grip but it can also affect the facial muscles, tongue, and other bulbar muscles causing problems when talking, chewing, and swallowing. Difficulty swallowing and sucking food into the lungs in the later stages of the disease contribute towards chest infections and represent a major cause of morbidity and mortality. Irritable bowel-like symptoms are extremely common with constipation, diarrhoea and abdominal pain. Cardiac conduction abnormalities are frequent and the incidence of cardiac symptoms and ECG changes increases with time. In the eyes, iridescent multi-coloured capsular cataracts are observed, often very early in the disease process. Endocrine abnormalities include testicular atrophy with associated reduced fertility and insulin resistance is often present. Premature male-pattern frontal balding is very often evident in men. CNS involvement includes specific patterns of psychological dysfunction and personality traits, cognitive impairment/mental retardation, neuropathological abnormalities and excessive daytime sleepiness. Respiratory insufficiency due to respiratory muscle weakness and reduced central drive, and sleep apnea (pauses in breathing) are observed. These features show an obvious deterioration with time that is also evident for skeletal muscle involvement and other physical aspects of the disease.

At present, no effective disease modifying treatment is available for DM1 and the active management of patients involves symptomatic treatment of the various systems affected and anticipatory surveillance of cardiorespiratory complications. Symptomatic treatments of DM1 include sodium channel blockers (e.g. mexiletine, phenytoin and procainamide) to treat myotonia; CNS stimulant drugs (e.g. modafinil) to address daytime sleepiness; and dehydroepiandrosterone (DHEA), creatine supplementation and mecasermin rinfabate to improve muscle weakness.

Myotonic Dystrophy type 1 is caused by a repeat expansion mutation in the 3'-untranslated region of the DMPK (dystrophia myotonica protein kinase) gene. When expressed the DMPK expansion transcripts remain in the nucleus where they form foci (Ranum et al. Myotonic Dystrophy: RNA Pathogenesis Comes into Focus. American Journal of Human Genetics. 2004; 74(5):793-804).

Directly targeting the repeat expansion transcript to neutralize the harmful repeats or promote transcript degradation and subsequent clearance from the cell has been attempted using either ribozymes or antisense oligonucleotides (Langlois, M. A. et al. (2003). Molecular therapy: the journal of the American Society of Gene Therapy, 7: 670-680; Wheeler, T. M. et al. Nature, 488: 111-115; and Mulders, S. A. et al. (2009). Proc Natl Acad Sci USA, 106: 13915-13920). Other methods to target the repeat sequence directly have involved the introduction of a blocking molecule, such as morpholino oligonucleotides or small molecules that physically prevent binding of MBNL (muscleblind-like splicing regulator 1) protein by sitting in the groove of the RNA and preventing protein association and binding (Wheeler, T. M. et al. (2009). Science, 325: 336-339).

Cyclin-dependent kinases (CDKs) are a large family of kinases associated with regulating cellular processes. CDK 1, 2, 4 and 6 are associated with regulation of cell cycle phases. CDK 7, 8, 9, 11, 12 and 13 regulate gene transcription.

CDK12 phosphorylates the C-terminal domain (CTD) of the large subunit of RNA polymerase II (POLR2A), thereby acting as a key regulator of transcription elongation. CDK12 regulates the expression of genes involved in DNA repair and is required for the maintenance of genomic stability.

A significant role for CDK12 in foci formation has been identified and it has been found that treatment with a CDK12 inhibitor leads to the dissolution of foci and degradation of the mutant transcripts. Inhibition of CDK12 is therefore expected to be useful in the treatment of conditions such as Myotonic Dystrophy type 1.

CDK12 is also implicated in cancer. CDK12 is a transcription-associated CDK that phosphorylates the CTD of RNA pol II and it is essential for DNA damage response (DDR), splicing, and differentiation. CDK12 mutations as well as overexpression have been reported in various malignancies, including breast cancer and ovarian cancer, (Paculová and Kohoutek Cell Div (2017) 12:7).

Johannes et al (ChemMedChem 10.1002/cmdc.201700695) disclose certain small molecule selective CDK 12 inhibitors which are stated to be useful in the treatment of cancers and that combination of a CDK12 inhibitor and a PARP inhibitor may provide a synergistic therapeutic effect.

Johnson et al. (2016, Cell Reports 17, 2367-2381 Nov. 22, 2016) discloses that CDK12 inhibition is effective in reversing PARP inhibitor resistance in BRCA wild-type and mutated triple negative breast cancer and suggests that the combined use of a CDK12 inhibitor and a PARP inhibitor would be useful in the treatment of cancers resistant to a PARP inhibitor, such as PARP resistant triple negative breast cancer.

Gao et al. (2018, Cell Chemical Biology 25, 1-8) disclose certain compounds that covalently bind to CDK12 showed growth inhibitory effects in lung cancer and neuroblastoma cells.

CDK12 inhibition may also be useful in the treatment of visceral leishmaniasis, a devastating parasitic disease caused by infection with *Leishmania donovani* and *L. infantum* (Wyllie et. al. (Nature, volume 560, pages 192-197 (2018)).

WO2010/0003133 discloses certain compounds which are started to be CDK inhibitors.

WO2017/163076 (published after the priority date of this patent application) discloses the use of certain CDK12 inhibitors for the treatment or prevention of conditions caused by the generation of repeat expansion transcripts including Myotonic Dystrophy type 1, Myotonic Dystrophy type 2, Fragile X associated tremor/ataxia syndrome, amyotrophic lateral sclerosis (ALS) and frontotemporal dementia (C9ORF72), Huntington's Disease like 2, Huntington's Disease, Spinocerebellar Ataxia Types 1, 2, 3, 6, 7, 8, 10, 31, 17, Dentatorubral-pallidoluysian atrophy and Spinal and Bulbar Muscular Atrophy.

There remains a need for novel CDK12 inhibitors for the treatment and/or prevention of CDK12 mediated diseases, for example Myotonic Dystrophy type 1, cancer and other diseases disclosed herein.

BRIEF SUMMARY OF THE DISCLOSURE

In accordance with the present inventions, there is provided a compound of formula (I), or a pharmaceutically acceptable salt or N-oxide thereof:

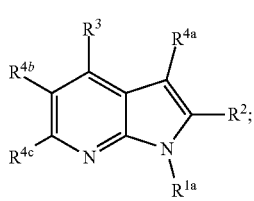

(I)

wherein
$R^{1a}$ is independently selected from: H and $C_1$-$C_6$-alkyl;
$R^2$ is independently selected from H, $C_1$-$C_6$-alkyl, $C_1$-$C_6$-haloalkyl, $C_2$-$C_6$-alkenyl, $C_2$-$C_6$-alkynyl, halo, nitro, cyano, $OR^{5a}$, $SR^{6a}$, $NR^{6a}R^{7a}$, $C(O)R^{6a}$, $C(O)OR^{6a}$, $C(O)NR^{6a}R^{6a}$, $S(O)_2R^{6a}$, $S(O)_2NR^{6a}R^{6a}$, $-L^1-L^2-R^8$;
$R^3$ is a 9- or 10-membered bicyclic heteroaryl group; said heteroaryl group comprising at least one nitrogen in the bicyclic ring system; wherein $R^3$ is optionally substituted with a single $R^{4d}$ group and from 0 to 6 $R^{4e}$ groups;
$R^{4a}$ and $R^{4c}$ are each independently selected from H, fluoro, chloro and $C_1$-$C_6$-alkyl;
$R^{4b}$ and $R^{4e}$ are each independently at each occurrence selected from H, fluoro, chloro, $C_1$-$C_6$-alkyl, $C_1$-$C_6$-haloalkyl, $C_2$-$C_6$-alkenyl, $C_2$-$C_6$-alkynyl, $OR^{5b}$, $SR^{6b}$ and $NR^{6b}R^{7b}$;
$R^{4d}$ is independently selected from $C_1$-$C_3$-alkylene-$R^9$ or $O$—$C_1$-$C_3$-alkylene-$R^9$;

-$L^1$- is independently absent or is selected from —$(CR^{10a}R^{10a})_{n1}NR^{11a}$—, —$(CR^{10c}R^{10c})_{n2}O$—, —$C_0$-$C_3$-alkylene-$NR^{11b}(CR^{10b}R^{10b})_{m1}NR^{11c}$—, —$C_0$-$C_3$-alkylene-$L^{3a}$-$C_0$-$C_3$-alkylene-$NR^{11d}$— and $C_2$-$C_6$-alkenyl;
wherein where $L^1$ is —$(CR^{10a}R^{10a})_{n1}NR^{11a}$— it is optionally the case that: A) a single $R^{10a}$ group and $R^{11a}$ together form a $C_1$-$C_4$-alkylene, said alkylene optionally being interrupted by an oxygen, nitrogen or sulphur atom; or B) two $R^{10a}$ groups together form a $C_1$-$C_4$-alkylene, said alkylene optionally being interrupted by an oxygen, nitrogen or sulphur atom;
wherein where $L^1$ is —$C_0$-$C_3$-alkylene-$NR^{11b}$ $(CR^{10b}R^{10b})_{m1}NR^{11c}$— it is optionally the case that A) $R^{11b}$ and $R^{11c}$ together form a $C_2$-$C_4$-alkylene; B) a single $R^{10b}$ group and either $R^{11b}$ or $R^{11c}$ together form a $C_1$-$C_4$-alkylene, said alkylene optionally being interrupted by an oxygen, nitrogen or sulphur atom; C) two $R^{10b}$ groups together form a $C_1$-$C_4$-alkylene, said alkylene optionally being interrupted by an oxygen, nitrogen or sulphur atom; or D) a single $R^{10b}$ group and $R^{11b}$ together form a $C_1$-$C_4$-alkylene and a single $R^{10b}$ group and $R^{11c}$ together form a $C_1$-$C_4$-alkylene;
wherein where -$L^1$- includes an alkylene group, that alkylene group is optionally substituted with from 1 to 4 $R^{12a}$ groups; and where -$L^1$- includes a phenyl, naphthyl, or heteroaryl group, that phenyl, naphthyl or heteroaryl is optionally substituted with from 1 to 4 $R^{13a}$ groups;
-$L^2$- is independently absent or is selected from $C(O)$-$L^4$- and $SO_2$-$L^4$-
-$L^{3a}$- and -$L^{3b}$- are each independently selected from phenyl, naphthyl, 5-, 6-, 9- or 10-membered heteroaryl;
-$L^4$- is selected from —$(CR^{10c}R^{10c})_{n3}NR^{11e}$, —$(CR^{10c}R^{10c})_{n4}O$—, —$C_0$-$C_3$-alkylene-$NR^{11f}(CR^{10d}R^{10d})_{m2}NR^{11g}$— and —$C_0$-$C_3$-alkylene-$L^{3b}$-$C_0$-$C_3$-alkylene-$NR^{11h}$—;
wherein where $L^4$ is —$(CR^{10c}R^{10c})_{n3}NR^{11e}$— it is optionally the case that: A) a single $R^{10c}$ group and $R^{11e}$ together form a $C_1$-$C_4$-alkylene, said alkylene optionally being interrupted by an oxygen, nitrogen or sulphur atom; or B) two $R^{10c}$ groups together form a $C_1$-$C_4$-alkylene, said alkylene optionally being interrupted by an oxygen, nitrogen or sulphur atom;
wherein where $L^4$ is —$C_0$-$C_3$-alkylene-$NR^{11f}$ $(CR^{10d}R^{10d})_{m2}NR^{11g}$— it is optionally the case that A) $R^{11}$ and $R^{11g}$ together form a $C_2$-$C_4$-alkylene; B) a single $R^{10d}$ group and either $R^{11f}$ or $R^{11g}$ together form a $C_1$-$C_4$-alkylene, said alkylene optionally being interrupted by an oxygen, nitrogen or sulphur atom; C) two $R^{10d}$ groups together form a $C_1$-$C_5$-alkylene, said alkylene optionally being interrupted by an oxygen, nitrogen or sulphur atom; or D) a single $R^{10d}$ group and $R^{11f}$ together form a $C_1$-$C_4$-alkylene and a single $R^{10d}$ group and $R^{11g}$ together form a $C_1$-$C_4$-alkylene;
wherein where -$L^4$- includes an alkylene group, that alkylene group is optionally substituted with from 1 to 4 $R^{12b}$ groups; and where -$L^4$- includes a phenyl, naphthyl, or heteroaryl group, that phenyl, naphthyl or heteroaryl is optionally substituted with from 1 to 4 $R^{13b}$ groups;
$R^{5a}$, $R^{5b}$, $R^{5d}$ and $R^{5e}$ are each independently at each occurrence selected from H, $C_1$-$C_6$-alkyl (wherein said $C_1$-$C_6$-alkyl group may be optionally substituted with from 1 to 3 $OR^{5c}$ or $NR^{6c}R^{7c}$ groups) and $C_1$-$C_6$-haloalkyl;
$R^{5c}$ and $R^{5d}$ are independently at each occurrence selected from H, $C_1$-$C_6$-alkyl and $C_1$-$C_6$-haloalkyl;
$R^{6a}$, $R^{6b}$, $R^{6d}$ and $R^{6e}$ are each independently at each occurrence selected from H and $C_1$-$C_6$-alkyl (wherein said $C_1$-$C_6$-alkyl group may be optionally substituted with from 1 to 3 $OR^{5c}$ or $NR^{6c}R^{7c}$ groups);

$R^{6c}$ is independently at each occurrence selected from H and $C_1$-$C_6$-alkyl;

$R^{7a}$, $R^{7b}$, $R^{7d}$ and $R^{7e}$ are each independently at each occurrence selected from H, $C_1$-$C_6$-alkyl (wherein said $C_1$-$C_6$-alkyl group may be optionally substituted with a 5-membered heterocycloalkyl group or from 1 to 3 $OR^{5c}$ or $NR^{6c}R^{7c}$ groups), $C(O)R^{14a}$, $C(O)OR^{14a}$ $C(O)NHR^{14a}$, $S(O)_2R^{14a}$ and $S(O)_2NHR^{14a}$;

$R^{7c}$ is independently at each occurrence selected from H, $C_1$-$C_6$-alkyl, $C(O)R^{14b}$, $C(O)OR^{14b}$, $C(O)NHR^{14b}$, $S(O)_2R^{14b}$ and $S(O)_2NHR^{14b}$;

$R^8$ is independently selected from H, $S(O)_2R^{15}$, $C(O)R^{15}$, $C(O)OR^{15}$, $S(O)_2$—$C_0$-$C_3$-alkylene-$R^{15}$, $C(O)$—$C_0$-$C_3$-alkylene-$R^{15}$ and $C_0$-$C_3$-alkylene-$R^{15}$; wherein $R^{15}$ is independently selected from phenyl, $C_3$-$C_7$-cycloalkyl, $C_1$-$C_6$-alkyl, 5- to 7-membered heterocycloalkyl, 5-, 6-, 9- and 10-membered heteroaryl; wherein where any $R^8$ group includes heterocycloalkyl, alkylene, cycloalkyl or alkyl, that heterocycloalkyl, cycloalkyl or alkyl group is optionally substituted with from 1 to 4 $R^{12c}$ groups; and where any $R^8$ group includes phenyl or heteroaryl, that phenyl or heteroaryl is optionally substituted with from 1 to 4 $R^{13c}$ groups;

or $R^8$ is a group that can react with the SH of a cysteine to form a covalent bond between a carbon atom of $R^8$ and the sulphur atom of the cysteine;

$R^9$ is independently selected from H, phenyl, 5- to 7-membered heterocycloalkyl, 5-, 6-, 9- and 10-membered heteroaryl; wherein where any $R^9$ group is heterocycloalkyl, that is optionally substituted with from 1 to 4 $R^{12d}$ groups; and where any $R^9$ group is phenyl or heteroaryl, that phenyl or heteroaryl is optionally substituted with from 1 to 4 $R^{13d}$ groups;

$R^{10a}$, $R^{10b}$, $R^{10c}$ and $R^{10d}$ are each independently at each occurrence selected from H, $C_1$-$C_6$-alkyl, $CH_2OR^{5f}$ and benzyl;

$R^{11a}$, $R^{11b}$, $R^{11c}$, $R^{11d}$, $R^{11e}$, $R^{11f}$, $R^{11g}$, $R^{11h}$ are each independently selected from: H and $C_1$-$C_6$-alkyl;

$R^{12a}$, $R^{12c}$ and $R^{12d}$ are each independently at each occurrence selected from oxo, $C_1$-$C_6$-alkyl, $C_1$-$C_6$-haloalkyl, $C_2$-$C_6$-alkenyl, $C_2$-$C_6$-alkynyl, halo, nitro, cyano, $OR^{5d}$, $SR^{6d}$, $NR^{6d}R^{7d}$, $C(O)R^{6d}$, $C(O)OR^{6d}$, $C(O)NR^{6d}R^{6d}$, $S(O)_2R^{6d}$, $S(O)_2NR^{6d}R^{6d}$;

$R^{12b}$ is independently at each occurrence selected from oxo, $C_1$-$C_6$-alkyl, $C_1$-$C_6$-haloalkyl, $C_2$-$C_6$-alkenyl, $C_2$-$C_6$-alkynyl, halo, nitro, cyano, $OR^{5d}$, $SR^{6d}$, $NR^{6d}R^{7d}$, $C(O)R^{6d}$, $C(O)OR^{6d}$, $C(O)NR^{6d}R^{6d}$, $S(O)_2R^{6d}$, $S(O)_2NR^{6d}R^{6d}$ or wherein two $R^{12b}$ groups together with the carbon atom to which they are attached form a $C_3$-$C_6$-cycloalkyl;

$R^{13a}$, $R^{13b}$, $R^{13c}$ and $R^{13d}$ are each independently at each occurrence selected from $C_1$-$C_6$-alkyl, $C_1$-$C_6$-haloalkyl, $C_2$-$C_6$-alkenyl, $C_2$-$C_6$-alkynyl, halo, nitro, cyano, $OR^{5e}$, $SR^{6e}$, $NR^{6e}R^{7e}$, $C(O)R^{6e}$, $C(O)OR^{6e}$, $C(O)NR^{6e}R^{6e}$, $S(O)_2R^{6e}$, $S(O)_2NR^{6e}R^{6e}$;

$R^{14a}$ is independently selected from $C_1$-$C_6$-alkyl and $C_3$-$C_5$-cycloalkyl; wherein said $C_1$-$C_6$-alkyl or $C_3$-$C_5$-cycloalkyl group may be optionally substituted with from 1 to 3 $OR^{5c}$ or $NR^{6c}R^{7c}$ groups;

$R^{14b}$ is independently selected from $C_1$-$C_6$-alkyl and $C_3$-$C_5$-cycloalkyl;

n1, n2, n3 and n4 are each independently an integer selected from 1, 2, 3 and 4; and m1 and m2 are each independently an integer selected from 2, 3 and 4.

In accordance with the present inventions, there is provided a compound of formula (Ia), or a pharmaceutically acceptable salt or N-oxide thereof:

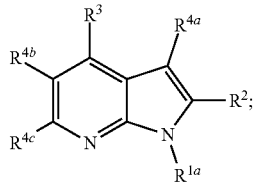

(Ia)

wherein $R^{1a}$ is independently selected from: H and $C_1$-$C_6$-alkyl;

$R^2$ is independently selected from H, $C_1$-$C_6$-alkyl, $C_1$-$C_6$-haloalkyl, $C_2$-$C_6$-alkenyl, $C_2$-$C_6$-alkynyl, halo, nitro, cyano, $OR^{5a}$, $SR^{6a}$, $NR^{6a}R^{7a}$, $C(O)R^{6a}$, $C(O)OR^{6a}$, $C(O)NR^{6a}R^{6a}$, $S(O)_2R^{6a}$, $S(O)_2NR^{6a}R^{6a}$, -$L^1$-$L^2$-$R^8$;

$R^3$ is independently selected from a 5- or 6-membered monocyclic heteroaryl group and a 9- or 10-membered bicyclic heteroaryl group; said heteroaryl group comprising at least one nitrogen in the monocyclic ring or bicyclic ring system; wherein $R^3$ is optionally substituted with a single $R^{4d}$ group and from 0 to 6 $R^{4e}$ groups;

$R^{4a}$ and $R^{4c}$ are each independently selected from H, fluoro, chloro and $C_1$-$C_6$-alkyl;

$R^{4b}$ and $R^{4e}$ are each independently at each occurrence selected from H, fluoro, chloro, $C_1$-$C_6$-alkyl, $C_1$-$C_6$-haloalkyl, $C_2$-$C_6$-alkenyl, $C_2$-$C_6$-alkynyl, $OR^{5b}$, $SR^{6b}$ and $NR^{6b}R^{7b}$;

$R^{4d}$ is independently selected from $C_1$-$C_3$-alkylene-$R^9$ or $O$—$C_1$-$C_3$-alkylene-$R^9$;

-$L^1$- is independently absent or is selected from —$(CR^{10a}R^{10a})_{n1}NR^{11a}$—, —$(CR^{10c}R^{10c})_{n2}O$—, —$C_0$-$C_3$-alkylene-$NR^{11b}(CR^{10b}R^{10b})_{m1}NR^{11c}$— and —$C_0$-$C_3$-alkylene-$L^{3a}$-$C_0$-$C_3$-alkylene-$NR^{11d}$;

wherein where $L^1$ is —$(CR^{10a}R^{10a})_{n1}NR^{11a}$— it is optionally the case that: A) a single $R^{10a}$ group and $R^{11a}$ together form a $C_1$-$C_4$-alkylene, said alkylene optionally being interrupted by an oxygen, nitrogen or sulphur atom; or B) two $R^{10a}$ groups together form a $C_1$-$C_4$-alkylene, said alkylene optionally being interrupted by an oxygen, nitrogen or sulphur atom;

wherein where $L^1$ is —$C_0$-$C_3$-alkylene-$NR^{11b}(CR^{10b}R^{10b})_{m1}NR^{11c}$— it is optionally the case that A) $R^{11b}$ and $R^{11c}$ together form a $C_2$-$C_4$-alkylene; B) a single $R^{10b}$ group and either $R^{11b}$ or $R^{11c}$ together form a $C_1$-$C_4$-alkylene, said alkylene optionally being interrupted by an oxygen, nitrogen or sulphur atom; C) two $R^{10b}$ groups together form a $C_1$-$C_4$-alkylene, said alkylene optionally being interrupted by an oxygen, nitrogen or sulphur atom; or D) a single $R^{10b}$ group and $R^{11b}$ together form a $C_1$-$C_4$-alkylene and a single $R^{10b}$ group and $R^{11c}$ together form a $C_1$-$C_4$-alkylene;

wherein where -$L^1$- includes an alkylene group, that alkylene group is optionally substituted with from 1 to 4 $R^{12a}$ groups; and where -$L^1$- includes a phenyl, naphthyl, or heteroaryl group, that phenyl, naphthyl or heteroaryl is optionally substituted with from 1 to 4 $R^{13a}$ groups;

-$L^2$- is independently absent or is selected from $C(O)$-$L^4$- and $SO_2$-$L^4$-

-$L^{3a}$- and -$L^{3b}$- are each independently selected from phenyl, naphthyl, 5-, 6-, 9- or 10-membered heteroaryl;

-$L^4$- is selected from —$(CR^{10c}R^{10c})_{n3}NR^{11e}$—, —$(CR^{10c}R^{10c})_{n4}O$—, —$C_0$-$C_3$-alkylene-$NR^{11f}(CR^{10d}R^{10d})_{m2}NR^{11g}$— and —$C_0$-$C_3$-alkylene-$L^{3b}$-$C_0$-$C_3$-alkylene-$NR^{11h}$—;

wherein where $L^4$ is —$(CR^{10c}R^{10c})_{n3}NR^{11e}$— it is optionally the case that: A) a single $R^{10c}$ group and $R^{11e}$ together form a $C_1$-$C_4$-alkylene, said alkylene optionally being interrupted by an oxygen, nitrogen or sulphur atom; or B) two $R^{10c}$ groups together form a $C_1$-$C_4$-alkylene, said alkylene optionally being interrupted by an oxygen, nitrogen or sulphur atom;

wherein where $L^4$ is —$C_0$-$C_3$-alkylene-$NR^{11f}$ $(CR^{10d}R^{10d})_{m2}NR^{11g}$— it is optionally the case that A) $R^{11f}$ and $R^{11g}$ together form a $C_2$-$C_4$-alkylene; B) a single $R^{10d}$ group and either $R^{11f}$ or $R^{11g}$ together form a $C_1$-$C_4$-alkylene, said alkylene optionally being interrupted by an oxygen, nitrogen or sulphur atom; C) two $R^{10d}$ groups together form a $C_1$-$C_5$-alkylene, said alkylene optionally being interrupted by an oxygen, nitrogen or sulphur atom; or D) a single $R^{10d}$ group and $R^{11f}$ together form a $C_1$-$C_4$-alkylene and a single $R^{10d}$ group and $R^{11g}$ together form a $C_1$-$C_4$-alkylene;

wherein where -$L^4$- includes an alkylene group, that alkylene group is optionally substituted with from 1 to 4 $R^{12b}$ groups; and where -$L^4$- includes a phenyl, naphthyl, or heteroaryl group, that phenyl, naphthyl or heteroaryl is optionally substituted with from 1 to 4 $R^{13b}$ groups;

$R^{5a}$, $R^{5b}$, $R^{5d}$ and $R^{5e}$ are each independently at each occurrence selected from H, $C_1$-$C_6$-alkyl (wherein said $C_1$-$C_6$-alkyl group may be optionally substituted with from 1 to 3 $OR^{5c}$ or $NR^{6c}R^{7c}$ groups) and $C_1$-$C_6$-haloalkyl;

$R^{5c}$ is independently at each occurrence selected from H, $C_1$-$C_6$-alkyl and $C_1$-$C_6$-haloalkyl;

$R^{6a}$, $R^{6b}$, $R^{6d}$ and $R^{6e}$ are each independently at each occurrence selected from H and $C_1$-$C_6$-alkyl (wherein said $C_1$-$C_6$-alkyl group may be optionally substituted with from 1 to 3 $OR^{5c}$ or $NR^{6c}R^{7c}$ groups);

$R^{6c}$ is independently at each occurrence selected from H and $C_1$-$C_6$-alkyl;

$R^{7a}$, $R^{7b}$, $R^{7d}$ and $R^{7e}$ are each independently at each occurrence selected from H, $C_1$-$C_6$-alkyl (wherein said $C_1$-$C_6$-alkyl group may be optionally substituted with a 5-membered heterocycloalkyl group or from 1 to 3 $OR^{5c}$ or $NR^{6c}R^{7c}$ groups), $C(O)R^{14a}$, $C(O)OR^{14a}$, $C(O)NHR^{14a}$, $S(O)_2R^{14a}$ and $S(O)_2NHR^{14a}$;

$R^{7c}$ is independently at each occurrence selected from H, $C_1$-$C_6$-alkyl, $C(O)R^{14b}$, $C(O)OR^{14b}$, $C(O)NHR^{14b}$, $S(O)_2R^{14b}$ and $S(O)_2NHR^{14b}$;

$R^8$ is independently selected from H, $S(O)_2R^{15}$, $C(O)R^{15}$, $S(O)_2$—$C_0$-$C_3$-alkylene-$R^{15}$, $C(O)$—$C_0$-$C_3$-alkylene-$R^{15}$ and $C_0$-$C_3$-alkylene-$R^{15}$; wherein $R^{15}$ is independently selected from phenyl, $C_3$-$C_7$-cycloalkyl, $C_1$-$C_6$-alkyl, 5- to 7-membered heterocycloalkyl, 5-, 6-, 9- and 10-membered heteroaryl; wherein where any $R^8$ group includes heterocycloalkyl, alkylene, cycloalkyl or alkyl, that heterocycloalkyl, cycloalkyl or alkyl group is optionally substituted with from 1 to 4 $R^{12c}$ groups; and where any $R^8$ group includes phenyl or heteroaryl, that phenyl or heteroaryl is optionally substituted with from 1 to 4 $R^{13c}$ groups;

or $R^8$ is a group that can react with the SH of a cysteine to form a covalent bond between a carbon atom of $R^8$ and the sulphur atom of the cysteine;

$R^9$ is independently selected from H, phenyl, 5- to 7-membered heterocycloalkyl, 5-, 6-, 9- and 10-membered heteroaryl; wherein where any $R^9$ group is heterocycloalkyl, that is optionally substituted with from 1 to 4 $R^{12d}$ groups; and where any $R^9$ group is phenyl or heteroaryl, that phenyl or heteroaryl is optionally substituted with from 1 to 4 $R^{13d}$ groups;

$R^{10a}$, $R^{10b}$, $R^{10c}$ and $R^{10d}$ are each independently at each occurrence selected from H and $C_1$-$C_6$-alkyl;

$R^{11a}$, $R^{11b}$, $R^{11c}$, $R^{11d}$, $R^{11e}$, $R^{11f}$, $R^{11g}$, $R^{11h}$ are each independently selected from: H and $C_1$-$C_6$-alkyl;

$R^{12a}$, $R^{12b}$, $R^{12c}$ and $R^{12d}$ are each independently at each occurrence selected from oxo, $C_1$-$C_6$-alkyl, $C_1$-$C_6$-haloalkyl, $C_2$-$C_6$-alkenyl, $C_2$-$C_6$-alkynyl, halo, nitro, cyano, $OR^{5d}$, $SR^{6d}$, $NR^{6d}R^{7d}$, $C(O)R^{6d}$, $C(O)OR^{6d}$, $C(O)NR^{6d}R^{6d}$, $S(O)_2R^{6d}$, $S(O)_2NR^{6d}R^{6d}$;

$R^{13a}$, $R^{13b}$, $R^{13c}$ and $R^{13d}$ are each independently at each occurrence selected from $C_1$-$C_6$-alkyl, $C_1$-$C_6$-haloalkyl, $C_2$-$C_6$-alkenyl, $C_2$-$C_6$-alkynyl, halo, nitro, cyano, $OR^{5e}$, $SR^{6e}$, $NR^{6e}R^{7e}$, $C(O)R^{6e}$, $C(O)OR^{6e}$, $C(O)NR^{6e}R^{6e}$, $S(O)_2R^{6e}$, $S(O)_2NR^{6e}R^{6e}$;

$R^{14a}$ is independently selected from $C_1$-$C_6$-alkyl and $C_3$-$C_5$-cycloalkyl; wherein said $C_1$-$C_6$-alkyl or $C_3$-$C_5$-cycloalkyl group may be optionally substituted with from 1 to 3 $OR^{5c}$ or $NR^{6c}R^{7c}$ groups;

$R^{14b}$ is independently selected from $C_1$-$C_6$-alkyl and $C_3$-$C_5$-cycloalkyl;

n1, n2, n3 and n4 are each independently an integer selected from 1, 2, 3 and 4; and m1 and m2 are each independently an integer selected from 2, 3 and 4.

In an embodiment, the compound of formula (I) is a compound of formula (II):

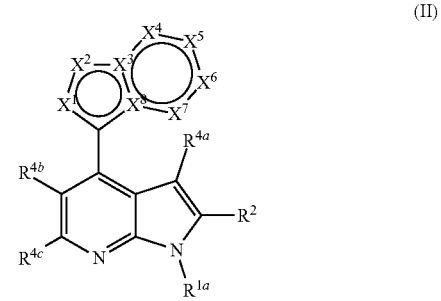

(II)

wherein $R^{1a}$, $R^2$, $R^{4a}$, $R^{4c}$ and $R^{4b}$ are as described above for formula (I); and wherein $X^1$ is independently selected from N and $CR^{4f}$;

$X^2$ is independently selected from N and $CR^{4g}$;

$X^3$ is independently selected from N and C;

$X^4$ is independently selected from N and $CR^{4h}$;

$X^5$ is independently selected from N and $CR^{4i}$;

$X^6$ is independently selected from N and $CR^{4j}$;

$X^7$ is independently selected from N and $CR^{4k}$;

$X^8$ is independently selected from N and C;

wherein at least one of $X^1$, $X^2$, $X^3$, $X^4$, $X^5$, $X^6$, $X^7$ and $X^8$ is N and no more than four of $X^1$, $X^2$, $X^3$, $X^4$, $X^5$, $X^6$, $X^7$ and $X^8$ are N;

$R^{4f}$, $R^{4g}$, $R^{4h}$ and $R^{4k}$ are each independently selected from H, fluoro and chloro and $C_1$-$C_3$ alkyl;

$R^{4i}$ and $R^{4j}$ are each independently selected from H, fluoro, chloro, $C_1$-$C_6$-alkyl, $C_1$-$C_6$-haloalkyl, $C_2$-$C_6$-alkenyl, $C_2$-$C_6$-alkynyl, $OR^{5b}$, $SR^{6b}$ and $NR^{6b}R^{7b}$; and optionally wherein a single one of $R^{4i}$ and $R^{4j}$ is $R^{4d}$.

In an embodiment, the compound of formula (I) is a compound of formula (III):

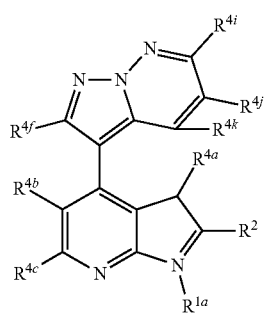

(III)

wherein $R^{1a}$, $R^2$, $R^{4a}$, $R^{4c}$ and $R^{4b}$ are as described above for formula (I); and wherein $R^{4f}$, $R^{4i}$, $R^{4j}$ and $R^{4k}$ are as described above for formula (II).

In an embodiment, the compound of formula (I) is a compound of formula (IV):

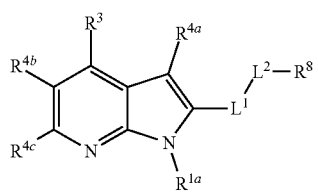

(IV)

wherein $R^{1a}$, $R^3$, $R^{4a}$, $R^{4b}$ and $R^{4c}$ are as described above for formula (I); and wherein $L^1$ and $L^2$ must not be absent. Thus, in this embodiment, -$L^1$- is independently selected from: —$(CR^{10a}R^{10a})_{n1}NR^{11a}$—, —$(CR^{10c}R^{10c})_{n2}O$—, —$C_0$-$C_3$-alkylene-$NR^{11b}(CR^{10b}R^{10b})_{m1}NR^{11c}$— and —$C_0$-$C_3$-alkylene-$L^{3a}$-$C_0$-$C_3$-alkylene-$NR^{11d}$—; and -$L^2$- is independently selected from: $C(O)$-$L^4$- and $SO_2$-$L^4$-.

In an embodiment, the compound of formula (I) is a compound of formula (V):

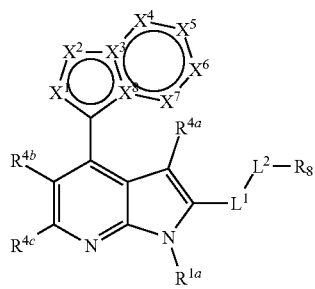

(V)

wherein $R^{1a}$, $R^2$, $R^{4a}$, $R^{4c}$ and $R^{4b}$ are as described above for formula (I); and wherein $R^{4f}$, $R^{4i}$, $R^{4j}$ and $R^{4k}$ are as described above for formula (II).

In an embodiment, the compound of formula (I) is a compound of formula (VI):

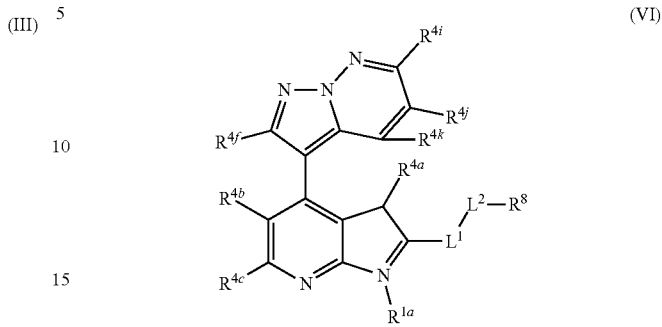

(VI)

wherein $R^{1a}$, $R^{4a}$, $R^{4c}$ and $R^{4b}$ are as described above for formula (I); wherein $R^{4f}$, $R^{4i}$, $R^{4j}$ and $R^{4k}$ are as described above for formula (II); and wherein $L^1$, $L^2$ and $R^8$ are as described above for formula (IV).

In particularly preferred embodiments of formulae (IV), (V) and (VI), $L^1$ and $L^2$ have the following definitions:
-$L^1$- is selected from —$(CR^{10a}R^{10a})_{n1}NR^{11a}$— and -$L^{3a}$-alkylene-$NR^{11d}$;
wherein where $L^1$ is —$(CR^{10a}R^{10a})_{n1}NR^{11a}$— it is optionally the case that: A) a single $R^{10a}$ group and $R^{11a}$ together form a $C_1$-$C_4$-alkylene;
wherein where -$L^1$- includes an alkylene group, that alkylene group is optionally substituted with from 1 to 4 $R^{12a}$ groups; and where -$L^1$- includes a phenyl, naphthyl, or heteroaryl group, that phenyl, naphthyl or heteroaryl is optionally substituted with from 1 to 4 $R^{13a}$ groups;
-$L^2$- is selected from $C(O)$-$L^4$- and $SO_2$-$L^4$-
-$L^{3a}$- and -$L^{3b}$- are each independently selected from phenyl, naphthyl, 5-, 6-, 9- or 10-membered heteroaryl;
-$L^4$- is selected from —$(CR^{10c}R^{10c})_{n3}NR^{11e}$— and -$L^{3b}$-$NR^{11h}$—;
wherein where $L^4$ is —$(CR^{10c}R^{10c})_{n3}NR^{11e}$— it is optionally the case that: A) a single $R^{10c}$ group and $R^{11e}$ together form a $C_1$-$C_4$-alkylene, said alkylene optionally being interrupted by an oxygen, nitrogen or sulphur atom;
wherein where -$L^4$- includes an alkylene group, that alkylene group is optionally substituted with from 1 to 4 $R^{12b}$ groups; and where -$L^4$- includes a phenyl, naphthyl, or heteroaryl group, that phenyl, naphthyl or heteroaryl is optionally substituted with from 1 to 4 $R^{13b}$ groups.

In particularly preferred embodiments of formulae (IV), (V) and (VI), $R^8$ is a group that can react with the SH of a cysteine to form a covalent bond between a carbon atom of $R^8$ and the sulphur atom of the cysteine.

The following statements apply to compounds of any of formulae (I) to (VI). These statements are independent and interchangeable. In other words, any of the features described in any one of the following statements may (where chemically allowable) be combined with the features described in one or more other statements below. In particular, where a compound is exemplified or illustrated in this specification, any two or more of the statements below which describe a feature of that compound, expressed at any level of generality, may be combined so as to represent subject matter which is contemplated as forming part of the disclosure of this invention in this specification.

$R^{1a}$ may be $C_1$-$C_6$-alkyl. Typically, however, $R^{1a}$ is H.
$R^2$ may be independently selected from H, $C_1$-$C_6$-alkyl, $C_1$-$C_6$-haloalkyl, $C_2$-$C_6$-alkenyl, $C_2$-$C_6$-alkynyl, halo, nitro, cyano, $OR^{5a}$, $SR^{6a}$, $NR^{6a}R^{7a}$, $C(O)R^{6a}$, $C(O)OR^{6a}$, $C(O)NR^{6a}R^{6a}$, $S(O)_2R^{6a}$ and $S(O)_2NR^{6a}R^{6a}$. $R^2$ may be selected from H and $C_1$-$C_6$-alkyl. $R^2$ may be $C(O)NR^{6a}R^{6a}$.

$R^2$ may be $-L^1-L^2-R^8$.

It may be that $-L^1-$ is $-(CR^{10a}R^{10a})_{n1}NR^{11a}-$ wherein it is optionally the case that: A) a single $R^{10a}$ group and $R^{11a}$ together form a $C_1$-$C_4$-alkylene, said alkylene optionally being interrupted by an oxygen, nitrogen or sulphur atom; or B) two $R^{10a}$ groups together form a $C_1$-$C_4$-alkylene, said alkylene optionally being interrupted by an oxygen, nitrogen or sulphur atom.

It may be that $L^1$- is $-(CR^{10a}R^{10a})_{n1}NR^{11a}-$ without either of the optional possibilities A) and B) described above for formula (I). Thus, it may be that $-L^1-$ is $-(CR^{10a}R^{10a})_{n1}NR^{11a}-$. n1 may be 1 or n1 may be 2. $R^{10a}$ may independently at each occurrence be H. $-L^1-$ may be $-CH_2-NR^{11a}-$. Alternatively, $-L^1-$ may be $-CH_2CH_2-NR^{11a}-$. In any of these embodiments, $R^{11a}$ may be H. Alternatively, $R^{11a}$ may be $C_1$-$C_6$-alkyl.

It may be that $L^1-$ is $-(CR^{10a}R^{10a})_{n1}NR^{11a}-$, wherein a single $R^{10a}$ group and $R^{11a}$ together form a $C_1$-$C_4$-alkylene, said alkylene optionally being interrupted by an oxygen, nitrogen or sulphur atom. It may be that $L^1-$ is $-(CR^{10a}R^{10a})_{n1}NR^{11a}-$, wherein a single $R^{10a}$ group and $R^{11a}$ together form a $C_1$-$C_4$-alkylene.

It may be that $-L^1-$ has the structure:

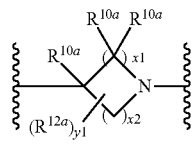

wherein x1 is an integer selected from 0, 1, 2, 3 or 4; x2 is an integer selected from 1, 2, 3 and 4; providing the sum of x1 and x2 is 2, 3, 4 or 5; and y1 is an integer from 0 to 3. y1 may be 0.

It may be that the sum of x1 and x2 is 3. It may be that x1 is 1 and x2 is 2. It may be that $-L^1-$ has the structure:

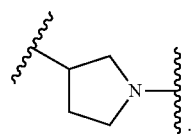

It may be that the sum of x1 and x2 is 4. It may be that x1 is 2 and x2 is 2. It may be that $-L^1-$ has the structure:

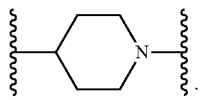

It may be that x1 is 1 and x2 is 3. It may be that $-L^1-$ has the structure:

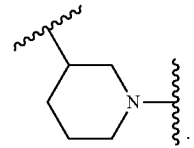 [SMILES: *C1CCCN(*)C1]

It may be that $L^1$ is $-C_0$-$C_3$-alkylene-$NR^{11b}(CR^{10b}R^{10b})_{m1}NR^{11c}-$ and that it is optionally the case that A) $R^{11b}$ and $R^{11c}$ together form a $C_2$-$C_4$-alkylene; B) a single $R^{10b}$ group and either $R^{11b}$ or $R^{11c}$ together form a $C_1$-$C_4$-alkylene, said alkylene optionally being interrupted by an oxygen, nitrogen or sulphur atom; C) two $R^{10b}$ groups together form a $C_1$-$C_4$-alkylene, said alkylene optionally being interrupted by an oxygen, nitrogen or sulphur atom; or D) a single $R^{10b}$ group and $R^{11b}$ together form a $C_1$-$C_4$-alkylene and a single $R^{10b}$ group and $R^{11c}$ together form a $C_1$-$C_4$-alkylene. It may be that $L^1$ is $-C_0$-$C_3$-alkylene-$NR^{11b}(CR^{10b}R^{10b})_{m1}NR^{11c}-$ and $R^{11b}$ and $R^{11c}$ together form a $C_2$-$C_4$-alkylene.

It may be that $-L^1-$ has the structure:

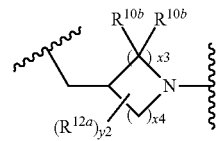

wherein x3 is an integer selected from 2, 3 or 4; x4 is an integer selected from 2, 3 and 4; providing the sum of x3 and x4 is 4 or 5; and y2 is an integer from 0 to 3. y2 may be 0.

It may be that x3 is 2 and x4 is 2. $-L^1-$ may have the structure:

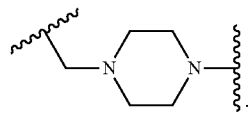 [SMILES: *CN1CCN(*)CC1]

$-L^1-$ may be $-C_0$-$C_3$-alkylene-$L^{3a}$-$C_0$-$C_3$-alkylene-$NR^{11d}$. $-L^1-$ may be $-L^{3a}$-$C_0$-$C_3$-alkylene-$NR^{11d}$. $-L^1-$ may be $-C_0$-$C_3$-alkylene-$L^{3a}$-$NR^{11d}$. $-L^1-$ may be $-L^{3a}$-$NR^{11d}$. $-L^{3a}-$ may be phenyl.

$-L^1-$ may have the structure:

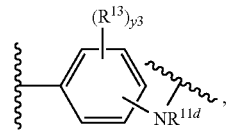

wherein y3 is an integer from 0 to 4. y3 may be 0. $R^{11d}$ may be H. $R^{11d}$ may be $C_1$-$C_6$-alkyl.

The group $NR^{11d}$ may be orientated para to the point of connection of the rest of the molecule to the phenyl ring. $-L^1-$ may have the structure:

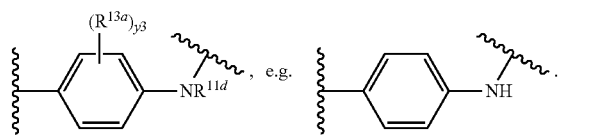

The group $NR^{11d}$ may be orientated meta to the point of connection of the rest of the molecule to the phenyl ring. $-L^1-$ may have the structure:

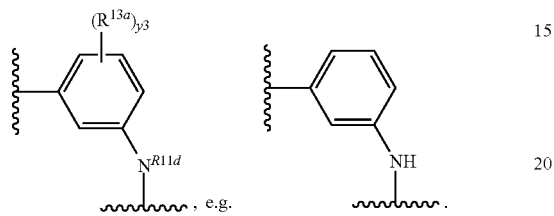

The group $NR^{11d}$ may be orientated ortho to the point of connection of the rest of the molecule to the phenyl ring. $-L^1-$ may have the structure:

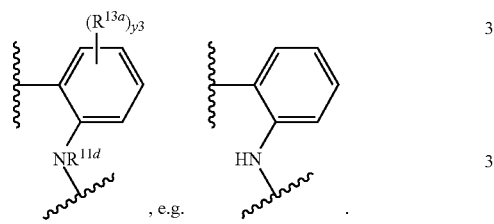

$R^2$ may be $-L^1-L^2-R^8$, wherein $-L^1-L^2-R^8$ may be selected from:

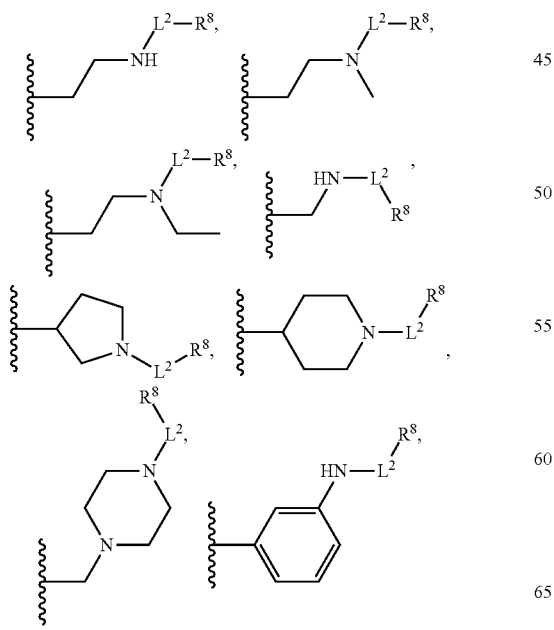

$R^2$ may be $-L^1-L^2-R^8$, wherein $-L^1-L^2-R^8$ may be selected from:

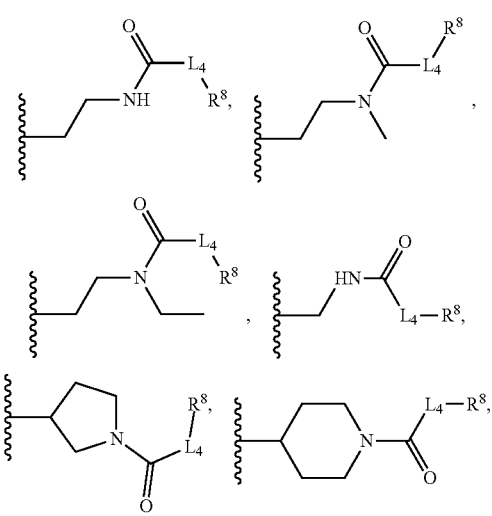

$R^2$ may be $-L^1-L^2-R^8$, wherein $L^2$ is $C(O)-L^4$ and $-L^1-L^2-R^8$ may be selected from:

-continued

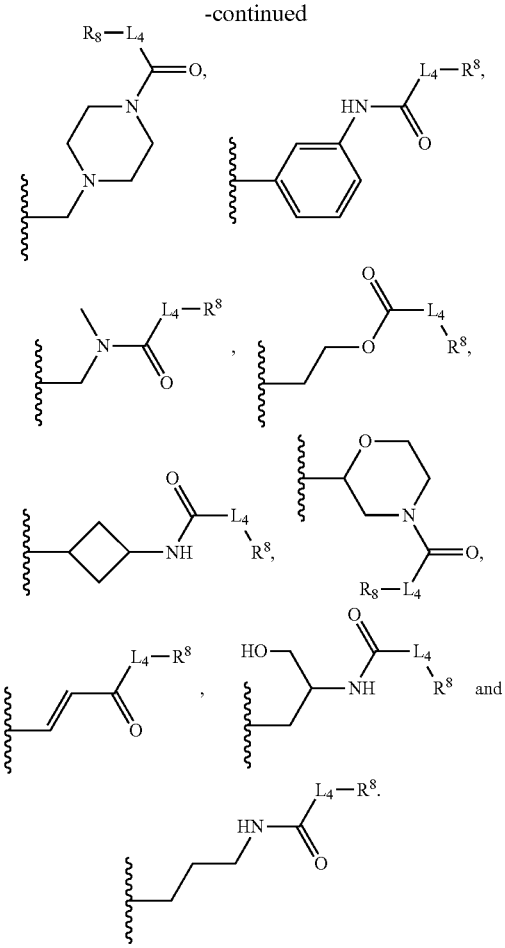

$R^2$ may be $-L^1-L^2-R^8$, wherein $L^2$ is $C(O)-L^4$ and $-L^1-L^2-R^8$ may be selected from:

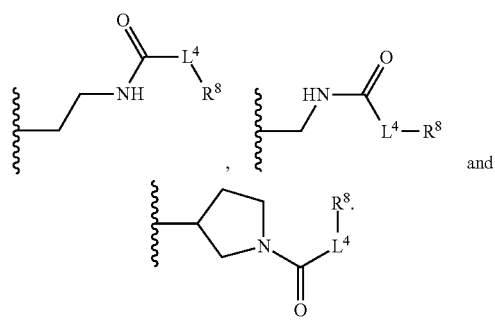

$-L^2-$ may be absent. Preferably, however, $-L^2-$ is selected from $-C(O)-L^4-$ and $-SO_2-L^4-$.

$-L^2-$ may be $-C(O)-L^4-$.

It may be that $-L^4-$ is $-(CR^{10c}R^{10c})_{n3}NR^{11e}-$ wherein it is optionally the case that: A) a single $R^{10c}$ group and $R^{11e}$ together form a $C_1-C_4$-alkylene, said alkylene optionally being interrupted by an oxygen, nitrogen or sulphur atom; or B) two $R^{10c}$ groups together form a $C_1-C_4$-alkylene, said alkylene optionally being interrupted by an oxygen, nitrogen or sulphur atom.

It may be that $L^4-$ is $-(CR^{10c}R^{10c})_{n3}NR^{11e}-$ without either of the optional possibilities A) and B) described above. Thus, it may be that $-L^4-$ is $-(CR^{10c}R^{10c})_{n3}NR^{11e}-$. n3 may be 1 or n1 may be 3. $R^{10c}$ may independently at each occurrence be H. $-L^4-$ may be $-CH_2-NR^{11e}-$. Alternatively, $-L^4-$ may be $-CH_2CH_2-NR^{11e}-$. In any of these embodiments, $R^{11e}$ may be H. Alternatively, $R^{11e}$ may be $C_1-C_6$-alkyl.

It may be that $-L^4-$ is $-(CR^{10c}R^{10c})_{n3}NR^{11e}-$, wherein a single $R^{10c}$ group and $R^{11e}$ together form a $C_1-C_4$-alkylene, said alkylene optionally being interrupted by an oxygen, nitrogen or sulphur atom. It may be that $-L^4-$ is $-(CR^{10c}R^{10c})_{n3}NR^{11e}-$, wherein a single $R^{10c}$ group and $R^{11e}$ together form a $C_1-C_4$-alkylene.

It may be that $-L^4-$ has the structure:

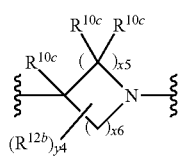

wherein x5 is an integer selected from 0, 1, 2, 3 or 4; x6 is an integer selected from 1, 2, 3 and 4; providing the sum of x5 and x6 is 2, 3, 4 or 5; and y4 is an integer from 0 to 3. y4 may be 0.

It may be that the sum of x5 and x6 is 2. It may be that x5 is 1 and x6 is 2. It may be that $-L^4-$ has the structure:

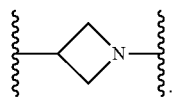

It may be that the sum of x5 and x6 is 3. It may be that x5 is 1 and x6 is 2. It may be that $-L^4-$ has the structure:

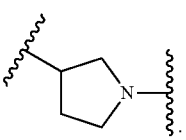 [SMILES: *C1CCN(*)C1]

It may be that x5 is 0 and x6 is 3. It may be that $-L^4-$ has the structure:

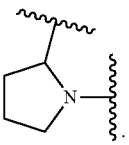 [SMILES: *C1CCCN1*]

It may be that the sum of x5 and x6 is 4. It may be that x5 is 2 and x6 is 2. It may be that $-L^4-$ has the structure:

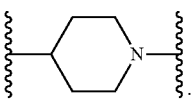

It may be that x5 is 1 and x6 is 3. It may be that -L$^4$- has the structure:

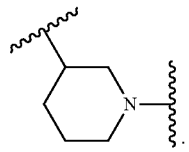 [SMILES: *C1CCCN(*)C1]

It may be that x5 is 0 and x6 is 4. It may be that -L$^4$- has the structure:

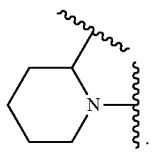 [SMILES: *C1CCCCN1*]

It may be that -L$^4$- is —(CR$^{10c}$R$^{10c}$)$_{n3}$NR$^{11e}$—, wherein a single R$^{10c}$ group and R$^{11e}$ together form a C$_1$-C$_4$-alkylene, said alkylene being interrupted by an oxygen, nitrogen or sulphur atom. It may be that -L$^4$- is —(CR$^{10c}$R$^{10c}$)$_{n3}$NR$^{11e}$—, wherein a single R$^{10c}$ group and R$^{11e}$ together form a C$_1$-C$_4$-alkylene, said alkylene being interrupted by an oxygen atom.

It may be that -L$^4$- has the structure:

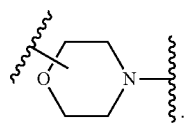

It may be that -L$^4$- has the structure:

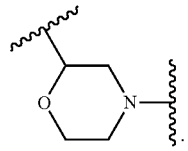

It may be that -L$^4$- has the structure:

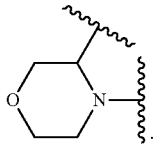 [SMILES: *C1COCCN1*]

-L$^4$- may be —C$_0$-C$_3$-alkylene-L$^{3b}$-C$_0$-C$_3$-alkylene-NR$^{11h}$. -L$^1$- may be -L$^{3b}$-C$_0$-C$_3$-alkylene-NR$^{11h}$. -L$^1$- may be —C$_0$-C$_3$-alkylene-L$^{3b}$-NR$^{11h}$. -L$^1$- may be -L$^{3b}$- NR$^{11h}$. -L$^{3b}$- may be phenyl.

-L$^4$- may have the structure:

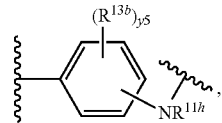

wherein y5 is an integer from 0 to 4. y5 may be 0. R$^{11h}$ may be H. R$^{11h}$ may be C$_1$-C$_6$-alkyl.

The group NR$^{11h}$ may be orientated para to the point of connection of the rest of the molecule to the phenyl ring. -L$^4$- may have the structure:

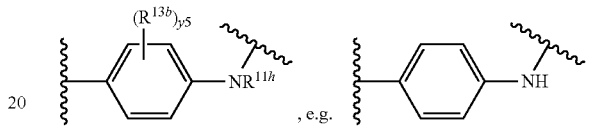

, e.g.

The group NR$^{11h}$ may be orientated meta to the point of connection of the rest of the molecule to the phenyl ring. -L$^4$- may have the structure:

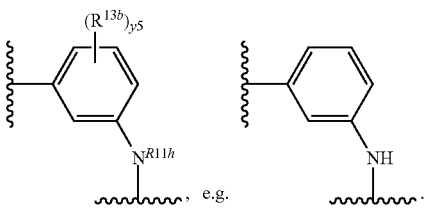

, e.g.

The group NR$^{11h}$ may be orientated ortho to the point of connection of the rest of the molecule to the phenyl ring. -L$^4$- may have the structure:

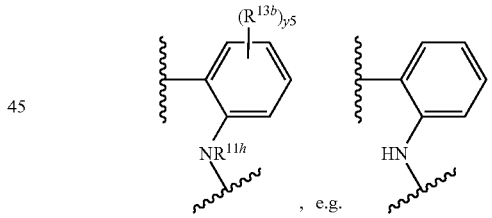

, e.g.

R$^2$ may be -L$^1$-L$^2$-R$^8$, wherein -L$^1$-L$^2$-R$^8$ may be selected from:

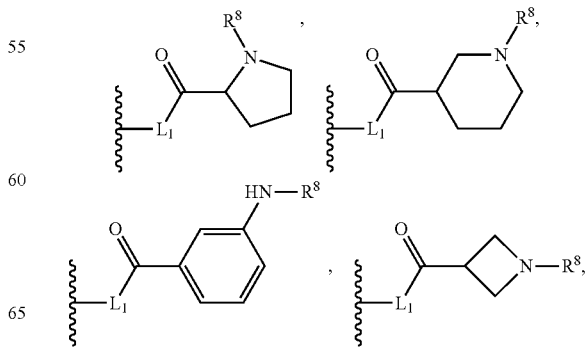

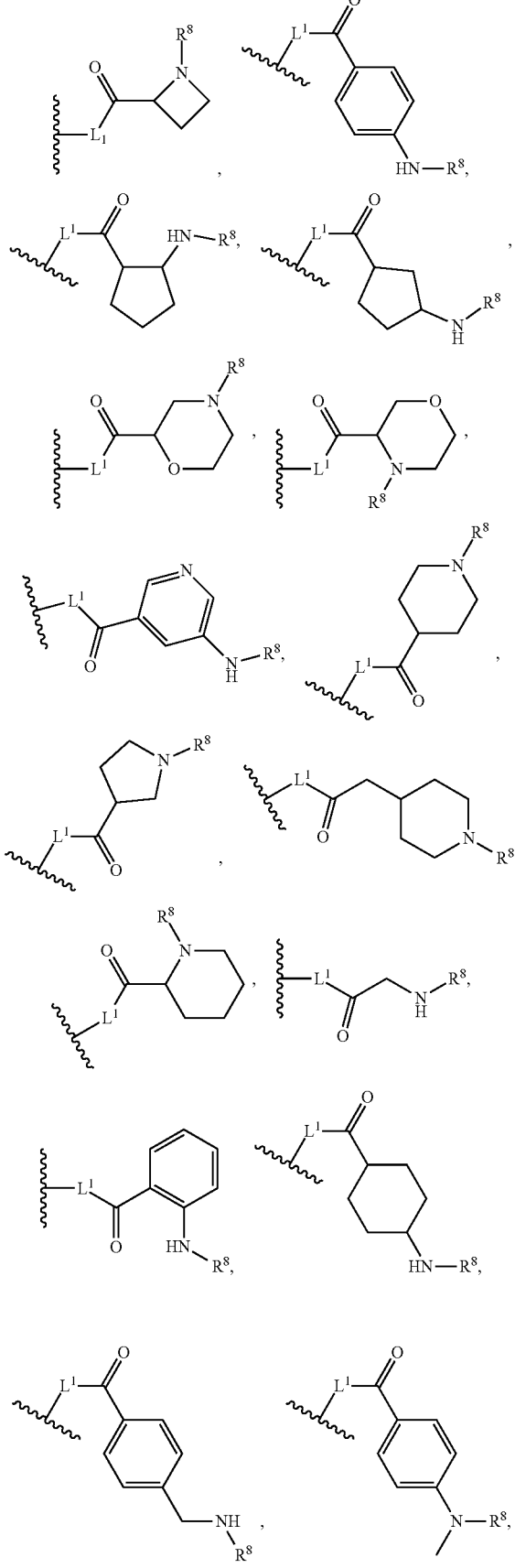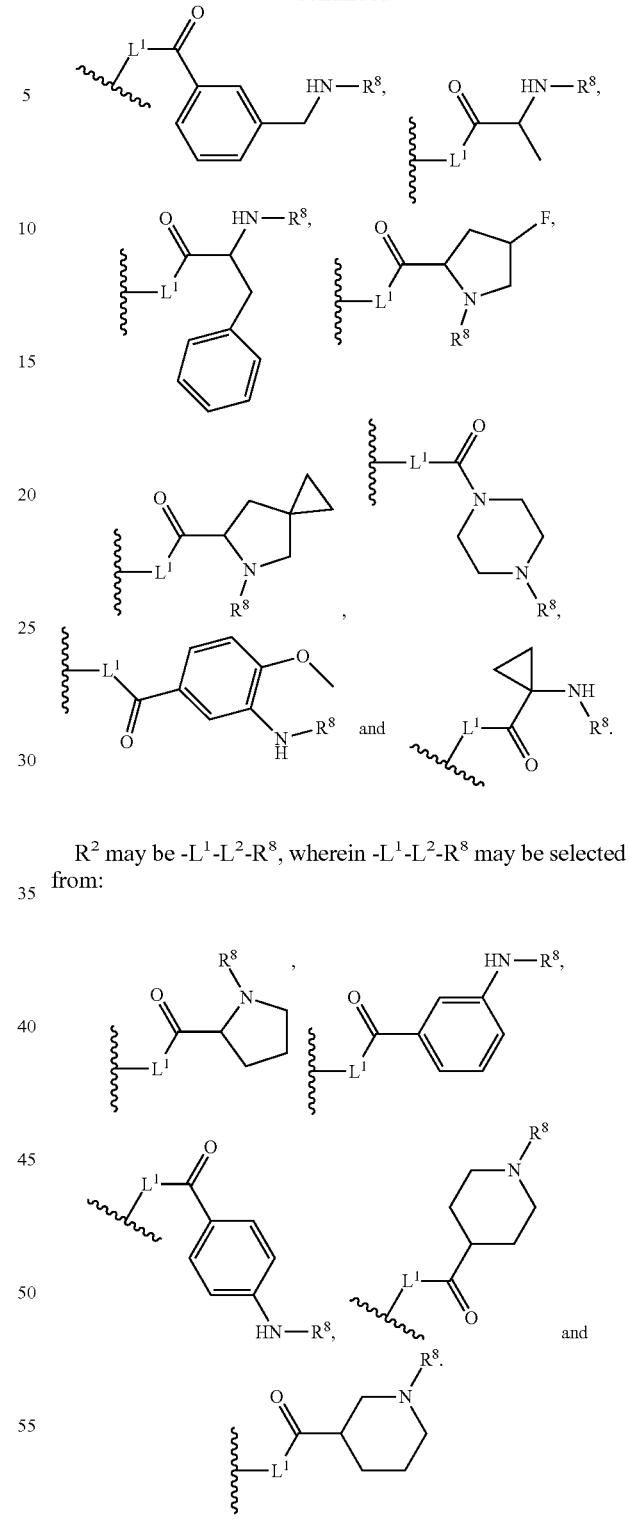

$R^2$ may be $-L^1-L^2-R^8$, wherein $-L^1-L^2-R^8$ may be selected from:

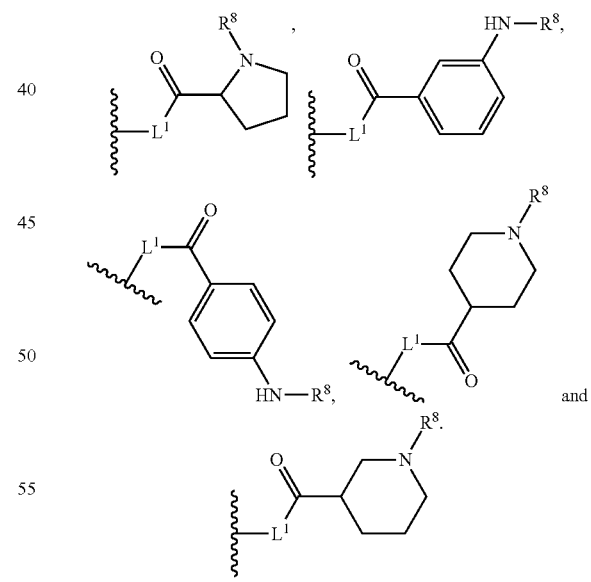

It may be that $-L^1-$ is selected from $-(CR^{10a}R^{10a})_{n1}NR^{11a}-$ and $-L^{3a}$-alkylene-$NR^{11d}-$; wherein where $L^1$ is $-(CR^{10a}R^{10a})_{n1}NR^{11a}-$ it is optionally the case that: A) a single $R^{10a}$ group and $R^{11a}$ together form a $C_1$-$C_4$-alkylene; wherein where $-L^1-$ includes an alkylene group, that alkylene group is optionally substituted with from 1 to 4 $R^{12a}$ groups; and where $-L^1-$ includes a phenyl, naphthyl, or heteroaryl group, that phenyl, naphthyl or heteroaryl is optionally substituted with from 1 to 4 $R^{13a}$ groups;

-$L^2$- is selected from C(O)-$L^4$- and $SO_2$-$L^4$-;

-$L^{3a}$- and -$L^{3b}$- are each independently selected from phenyl, naphthyl, 5-, 6-, 9- or 10-membered heteroaryl;

-$L^4$- is selected from —$(CR^{10c}R^{10c})_{n3}NR^{11e}$— and -$L^{3b}$-$NR^{11h}$—; wherein where $L^4$ is —$(CR^{10c}R^{10c})_{n3}NR^{11e}$— it is optionally the case that: A) a single $R^{10c}$ group and $R^{11e}$ together form a $C_1$-$C_4$-alkylene, said alkylene optionally being interrupted by an oxygen, nitrogen or sulphur atom; wherein where -$L^4$- includes an alkylene group, that alkylene group is optionally substituted with from 1 to 4 $R^{12b}$ groups; and where -$L^4$- includes a phenyl, naphthyl, or heteroaryl group, that phenyl, naphthyl or heteroaryl is optionally substituted with from 1 to 4 $R^{13b}$ groups.

It may be that -$L^1$- is selected —$(CR^{10a}R^{10a})_{n1}NR^{11a}$—,

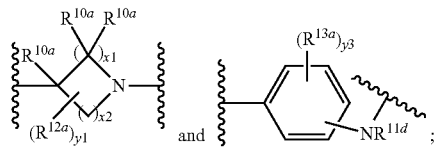

-$L^2$- is —C(O)-$L^4$-; and

-$L^4$- is selected from:

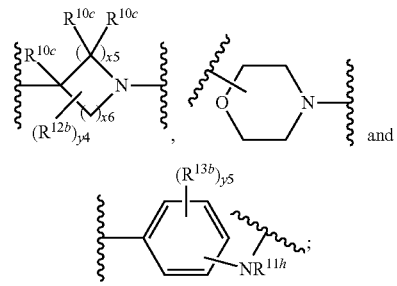

wherein x1 is an integer selected from 0, 1, 2, 3 or 4; x2 is an integer selected from 1, 2, 3 and 4; providing that the sum of x1 and x2 is 2, 3, 4 or 5; x5 is an integer selected from 0, 1, 2, 3 or 4; x6 is an integer selected from 1, 2, 3 and 4; providing that the sum of x5 and x6 is 2, 3, 4 or 5; y1 is an integer from 0 to 3; y3 is an integer from 0 to 4; and y4 is an integer from 0 to 3; and y5 is an integer from 0 to 4.

It may be that $R^2$ is -$L^1$-$L^2$-$R^8$, wherein -$L^1$-$L^2$-$R^8$ may be selected from:

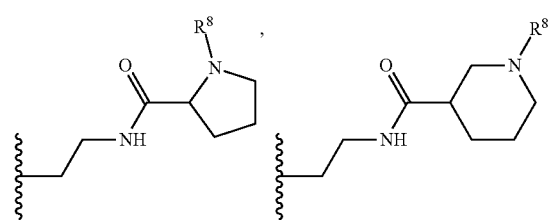

-continued

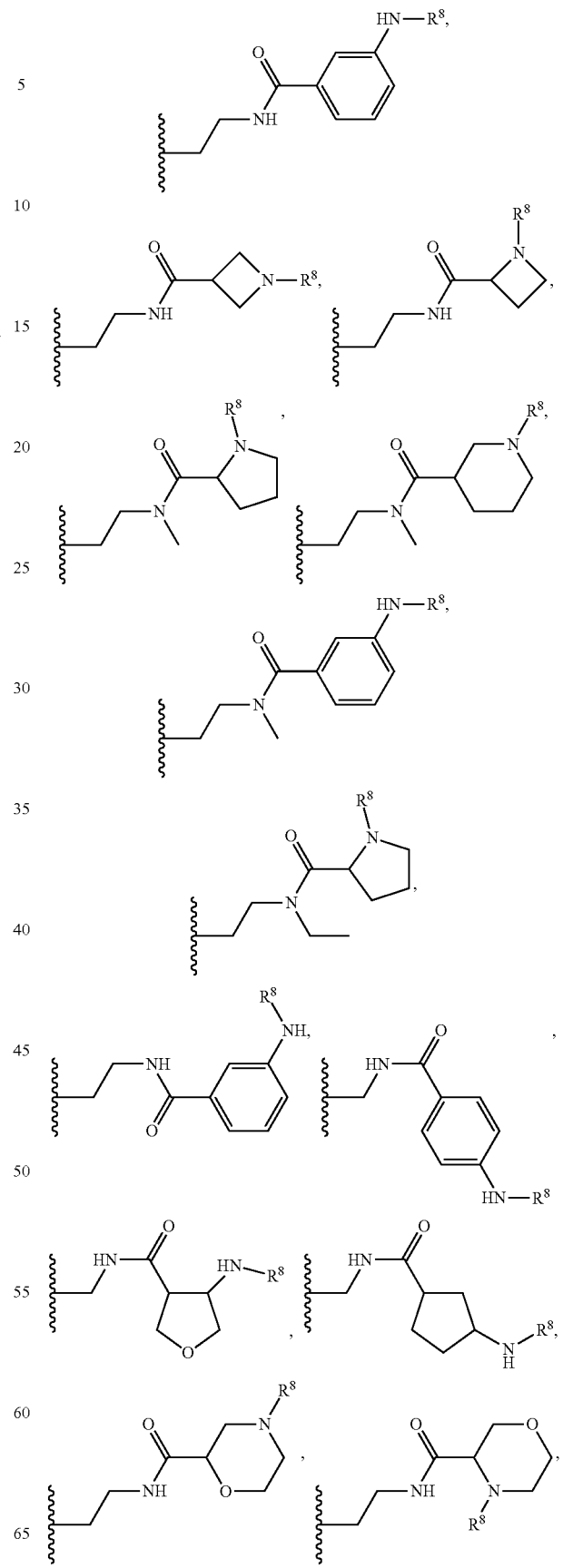

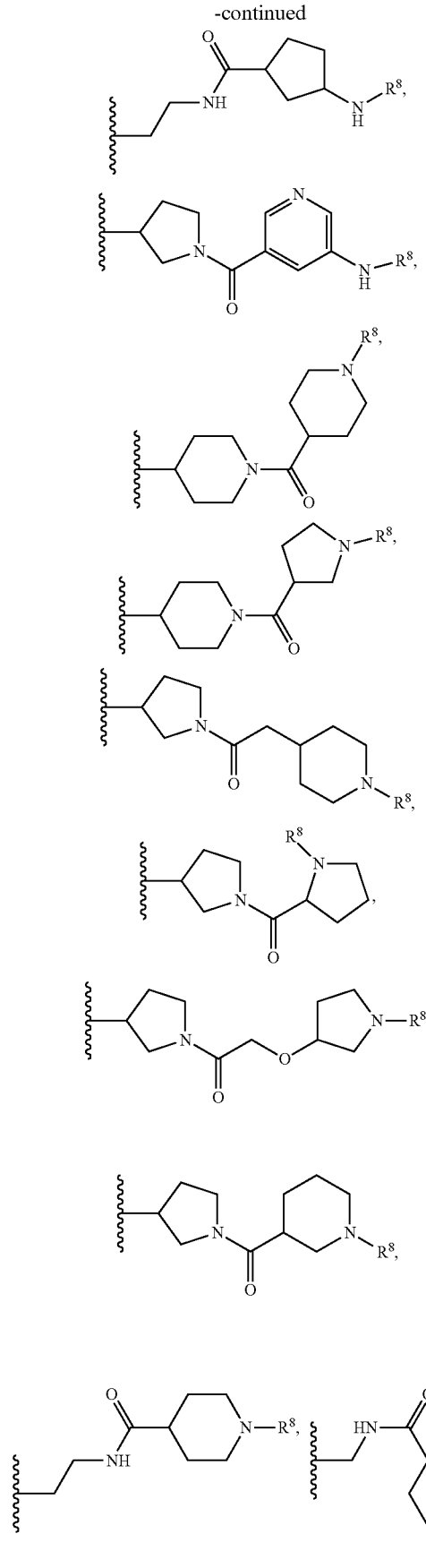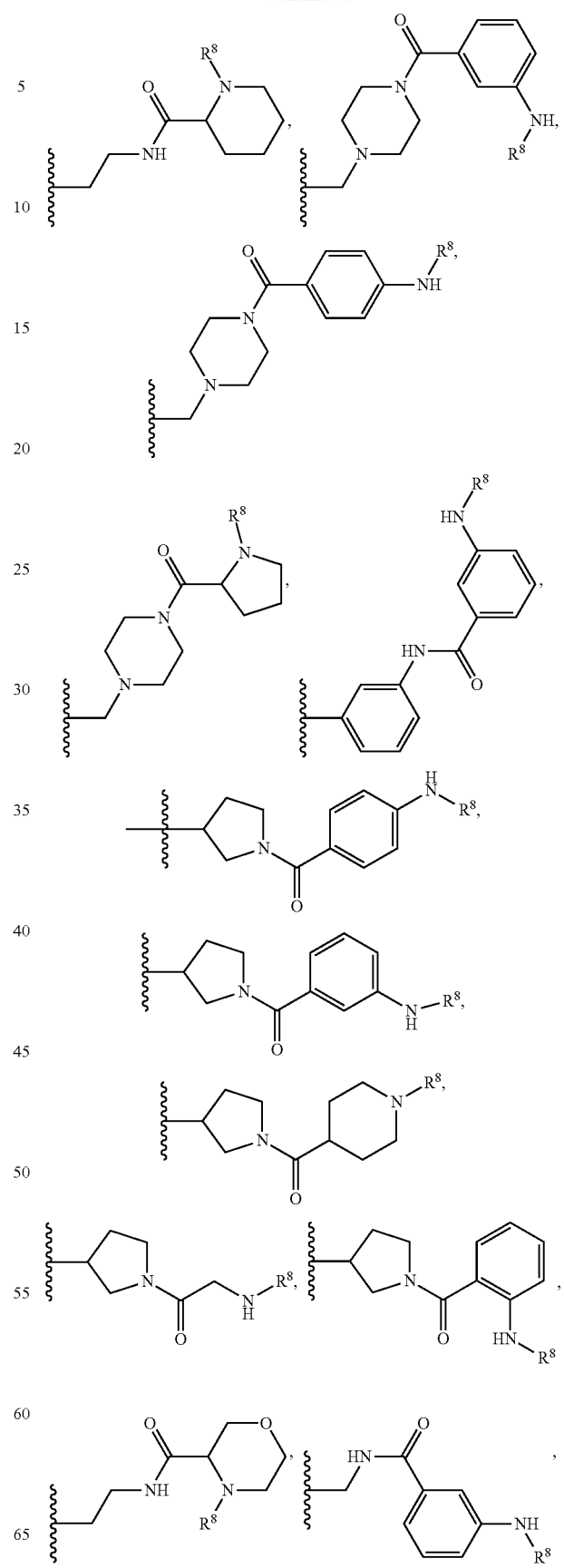

-continued
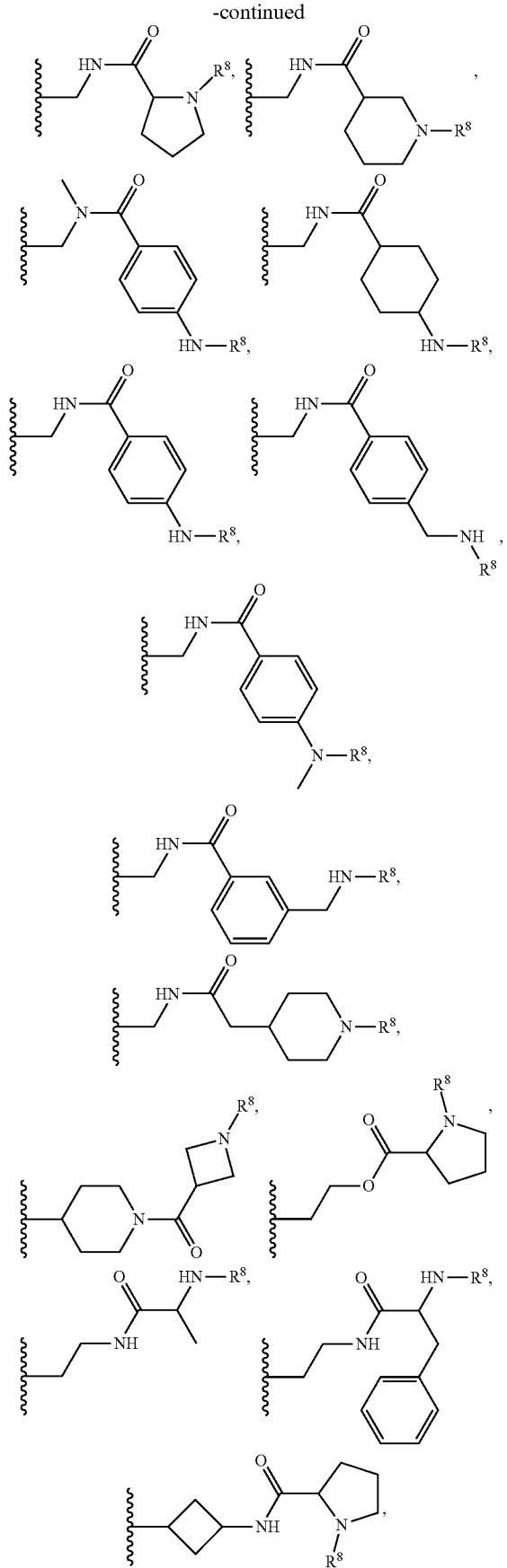
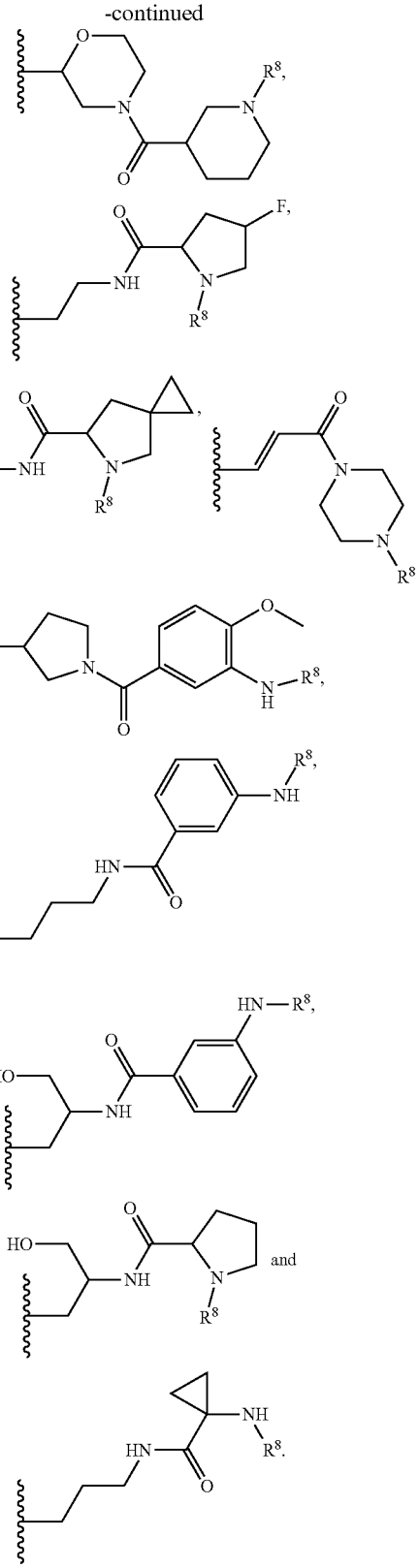
$R^3$ is a 9- or 10-membered bicyclic heteroaryl group; said heteroaryl group comprising at least one nitrogen in the bicyclic ring system; wherein $R^3$ is optionally substituted with a single $R^{4d}$ group and from 0 to 6 $R^{4e}$ groups.

$R^3$ may have the structure:

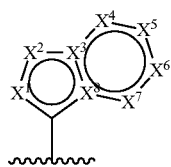

wherein $X^1$ is independently selected from N and $CR^{4f}$;
$X^2$ is independently selected from N and $CR^{4g}$;
$X^3$ is independently selected from N and C;
$X^4$ is independently selected from N and $CR^{4h}$;
$X^5$ is independently selected from N and $CR^{4i}$;
$X^6$ is independently selected from N and $CR^{4j}$;
$X^7$ is independently selected from N and $CR^{4k}$;
$X^8$ is independently selected from N and C;
wherein at least one of $X^1$, $X^2$, $X^3$, $X^4$, $X^5$, $X^6$, $X^7$ and $X^8$ is N and no more than four of $X^1$, $X^2$, $X^3$, $X^4$, $X^5$, $X^6$, $X^7$ and $X^8$ are N;
$R^{4f}$, $R^{4g}$, $R^{4h}$ and $R^{4k}$ are each independently selected from H, fluoro and chloro and $C_1$-$C_3$ alkyl;
$R^{4i}$ and $R^{4j}$ are each independently selected from H, fluoro, chloro, $C_1$-$C_6$-alkyl, $C_1$-$C_6$-haloalkyl, $C_2$-$C_6$-alkenyl, $C_2$-$C_6$-alkynyl, $OR^{5b}$, $SR^{6b}$ and $NR^{6b}R^{7b}$; and optionally wherein a single one of $R^{4i}$ and $R^{4j}$ is $R^{4a}$.

$X^2$ may be N. $X^2$ may be $CR^{4g}$.
$X^3$ may be N. $X^3$ may be C.
$X^4$ may be N. $X^4$ may be $CR^{4h}$.
$X^5$ may be N. $X^5$ may be $CR^{4i}$.
$X^6$ may be N. $X^5$ may be $CR^{4j}$.
$X^7$ may be N. $X^7$ may be $CR^{4k}$.
$X^8$ may be N. $X^8$ may be C.
It may be that at least two of $X^1$, $X^2$, $X^3$, $X^4$, $X^5$, $X^6$, $X^7$ and $X^8$ is N. It may be that three of $X^1$, $X^2$, $X^3$, $X^4$, $X^5$, $X^6$, $X^7$ and $X^8$ are N. It may be that $X^2$, $X^3$ and $X^4$ are each N.

$R^3$ may have the structure:

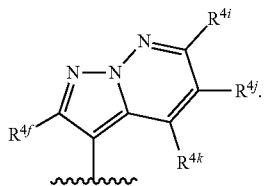

$R^{4f}$ may be H. $R^{4i}$ may be H. $R^{4j}$ may be H. $R^{4k}$ may be H. It may be that each of $R^{4f}$, $R^{4i}$, $R^{4j}$ and $R^{4k}$ are H.

$R^{4a}$ may be H. $R^{4b}$ may be H. $R^{4c}$ may be H. It may be that each of $R^{4a}$, $R^{4b}$ and $R^{4c}$ is H.

$R^{5a}$ may be independently at each occurrence selected from H and $C_1$-$C_6$-alkyl. $R^{5b}$ may be independently at each occurrence selected from H and $C_1$-$C_6$-alkyl. $R^{5c}$ may be independently at each occurrence selected from H and $C_1$-$C_6$-alkyl. $R^{5d}$ may be independently at each occurrence selected from H and $C_1$-$C_6$-alkyl. $R^{5e}$ may be independently at each occurrence selected from H and $C_1$-$C_6$-alkyl. $R^{5a}$ may at each occurrence be H. $R^{5b}$ may at each occurrence be H. $R^{5c}$ may at each occurrence be H. $R^{5d}$ may at each occurrence be H. $R^{5e}$ may at each occurrence be H.

$R^{6a}$ may be independently at each occurrence selected from H and $C_1$-$C_6$-alkyl. $R^{6b}$ may be independently at each occurrence selected from H and $C_1$-$C_6$-alkyl. $R^{6c}$ may be independently at each occurrence selected from H and $C_1$-$C_6$-alkyl. $R^{6d}$ may be independently at each occurrence selected from H and $C_1$-$C_6$-alkyl. $R^{6e}$ may be independently at each occurrence selected from H and $C_1$-$C_6$-alkyl. $R^{6a}$ may at each occurrence be H. $R^{6b}$ may at each occurrence be H. $R^{6c}$ may at each occurrence be H. $R^{6d}$ may at each occurrence be H. $R^{6e}$ may at each occurrence be H.

$R^{7a}$ may be independently at each occurrence selected from H and $C_1$-$C_6$-alkyl. $R^{7b}$ may be independently at each occurrence selected from H and $C_1$-$C_6$-alkyl. $R^{7c}$ may be independently at each occurrence selected from H and $C_1$-$C_6$-alkyl. $R^{7d}$ may be independently at each occurrence selected from H and $C_1$-$C_6$-alkyl. $R^{7e}$ may be independently at each occurrence selected from H and $C_1$-$C_6$-alkyl. $R^{7a}$ may at each occurrence be H. $R^{7b}$ may at each occurrence be H. $R^{7c}$ may at each occurrence be H. $R^{7d}$ may at each occurrence be H. $R^{7e}$ may at each occurrence be H.

$R^8$ may be independently selected from H, $S(O)_2R^{15}$, $C(O)R^{15}$, $C(O)OR^{15}$, $S(O)_2$—$C_0$-$C_3$-alkylene-$R^{15}$, $C(O)$—$C_0$-$C_3$-alkylene-$R^{15}$ and $C_0$-$C_3$-alkylene-$R^{15}$; wherein $R^{15}$ is independently selected from phenyl, $C_3$-$C_7$-cycloalkyl, $C_1$-$C_6$-alkyl, 5- to 7-membered heterocycloalkyl, 5-, 6-, 9- and 10-membered heteroaryl; wherein where any $R^8$ group includes heterocycloalkyl, alkylene, cycloalkyl or alkyl, that heterocycloalkyl, cycloalkyl or alkyl group is optionally substituted with from 1 to 4 $R^{12c}$ groups; and where any $R^8$ group includes phenyl or heteroaryl, that phenyl or heteroaryl is optionally substituted with from 1 to 4 $R^{13c}$ groups. $R^8$ may be H.

Alternatively, $R^8$ may be a group that can react with the SH of a cysteine to form a covalent bond between a carbon atom of $R^8$ and the sulphur atom of the cysteine. Such groups typically include α-, β-unsaturated carbonyl groups, carbonyl groups with a leaving group situated α to the carbonyl carbon and carbonyl groups with a leaving group situated β to the carbonyl carbon.

$R^8$ may be selected from groups having a structure selected from:

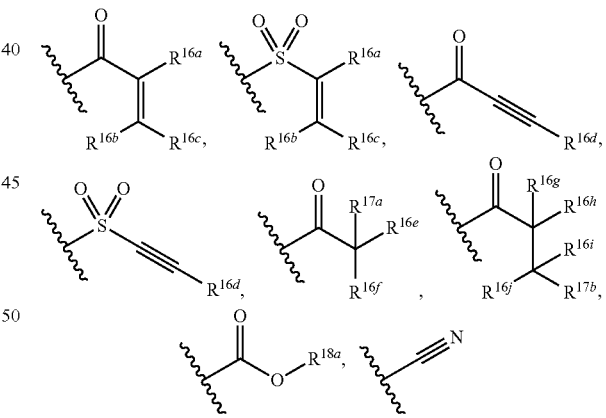

and
wherein $R^{16a}$ is independently selected from H, CN, $C_1$-$C_6$-alkyl and $C_1$-$C_6$-haloalkyl (which may be optionally substituted with a O—$R^{18a}$ group or a $NR^{18b}R^{18b}$ group);
$R^{16b}$, $R^{16c}$, $R^{16d}$, $R^{16e}$, $R^{16f}$, $R^{16g}$, $R^{16h}$, $R^{16i}$ and $R^{16j}$ are each independently selected from H, $C_1$-$C_6$-alkyl and $C_1$-$C_6$-haloalkyl (which may be optionally substituted with a O—$R^{18b}$ group or a $NR^{18c}R^{18c}$ group); or
$R^{16a}$ and $R^{16c}$ together with the carbon atoms to which they are attached form a $C_3$-$C_6$-cycloalkenyl;
$R^{17a}$ and $R^{17b}$ are each independently selected from CN, halo and $OS(O)_2R^{19}$;

$R^{18a}$, $R^{18b}$ and $R^{18c}$ are independently selected from H and $C_1$-$C_6$-alkyl; and $R^{19}$ is independently selected from $C_1$-$C_6$-alkyl and phenyl (which may be optionally substituted with from 1 to 3 groups selected from $C_1$-$C_6$-alkyl, $C_1$-$C_6$-haloalkyl, halo, O—$C_1$-$C_6$-alkyl, O—$C_1$-$C_6$-haloalkyl and nitro).

$R^8$ may be selected from groups having a structure selected from:

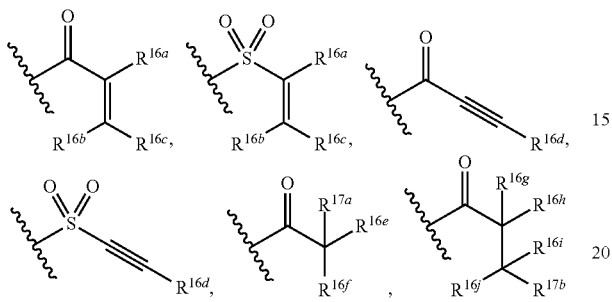

and
wherein $R^{16a}$ is independently selected from H, CN and $C_1$-$C_6$-alkyl (which may be optionally substituted with a O—$R^{18a}$ group or a $NR^{18b}R^{18b}$ group);

$R^{16b}$, $R^{16c}$, $R^{16d}$, $R^{16e}$, $R^{16f}$, $R^{16g}$, $R^{16h}$, $R^{16i}$ and $R^{16j}$ are each independently selected from H and $C_1$-$C_6$-alkyl (which may be optionally substituted with a O—$R^{18a}$ group or a $NR^{18b}R^{18b}$ group);

$R^{17a}$ and $R^{17b}$ are each independently selected from CN, halo and $OS(O)_2R^{19}$;

$R^{18a}$, $R^{18b}$ and $R^{18c}$ are independently selected from H and $C_1$-$C_6$-alkyl; and $R^{19}$ is independently selected from $C_1$-$C_6$-alkyl and phenyl (which may be optionally substituted with from 1 to 3 groups selected from $C_1$-$C_6$-alkyl, $C_1$-$C_6$-haloalkyl, halo, O—$C_1$-$C_6$-alkyl, O—$C_1$-$C_6$-haloalkyl and nitro).

$R^8$ may be selected from groups having a structure selected from:

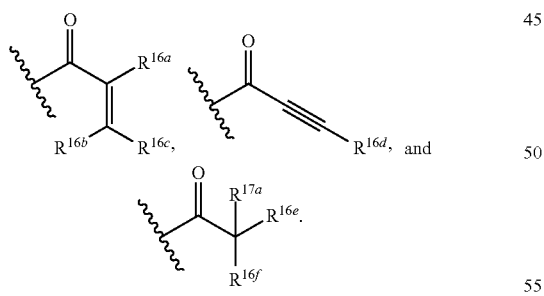

Exemplary $R^8$ groups that can react with the SH of a cysteine to form a covalent bond between a carbon atom of $R^8$ and the sulphur atom of the cysteine include:

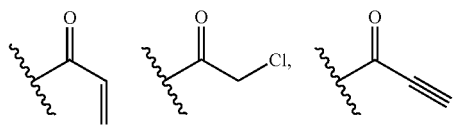

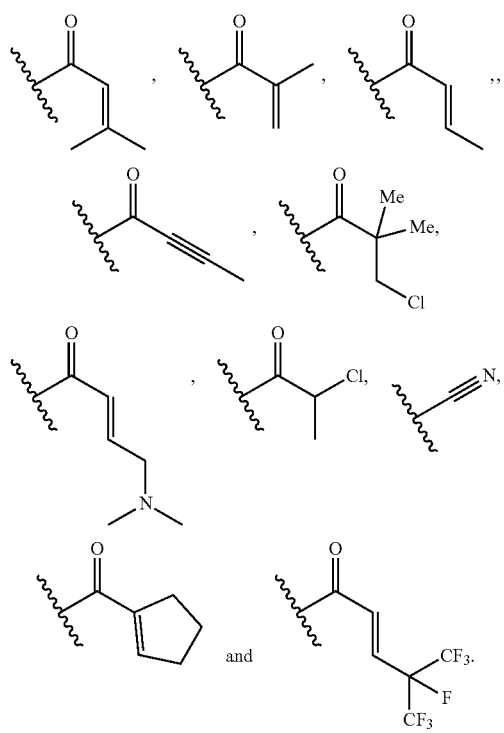

Exemplary $R^8$ groups that can react with the SH of a cysteine to form a covalent bond between a carbon atom of $R^8$ and the sulphur atom of the cysteine include:

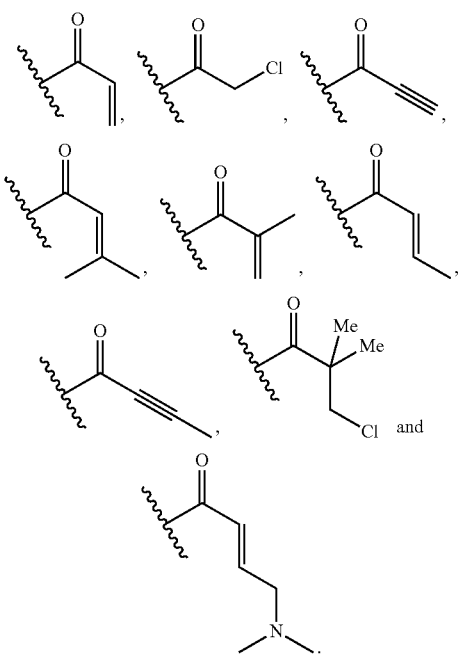

Exemplary $R^8$ groups that can react with the SH of a cysteine to form a covalent bond between a carbon atom of $R^8$ and the sulphur atom of the cysteine include:

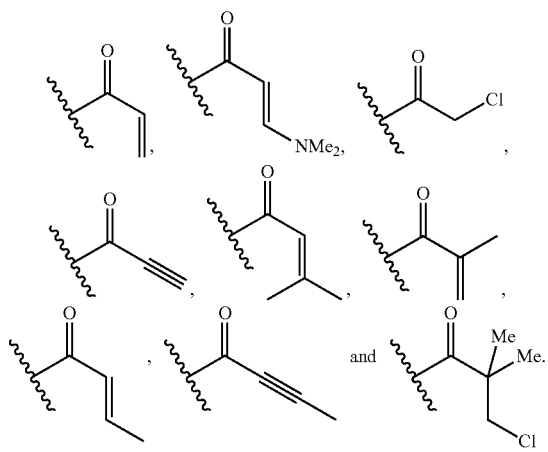

$R^{10a}$ may be at each occurrence be H. $R^{10b}$ may be at each occurrence be H. $R^{10c}$ may be at each occurrence be H. $R^{10d}$ may be at each occurrence be H. $R^{10a}$, $R^{10b}$, $R^{10c}$ and $R^{10d}$ are each at each occurrence H.

$R^{11a}$ may be H. $R^{11b}$ may be H. $R^{11c}$ may be H. $R^{11d}$ may be H. $R^{11e}$ may be H. $R^{11f}$ may be H. $R^{11g}$ may be H. $R^{11h}$ may be H.

$R^{12a}$, $R^{12b}$, $R^{12c}$ and $R^{12d}$ may independently at each occurrence be selected from oxo, $C_1$-$C_6$-alkyl, $OR^{5d}$ and $NR^{6d}R^{7d}$. $R^{12a}$, $R^{12b}$, $R^{12c}$ and $R^{12d}$ may independently at each occurrence be $C_1$-$C_6$-alkyl.

$R^{13a}$, $R^{13b}$, $R^{13c}$ and $R^{13d}$ may independently at each occurrence be selected from $C_1$-$C_6$-alkyl, $C_1$-$C_6$-haloalkyl, halo, O—$C_1$-$C_6$-alkyl and O—$C_1$-$C_6$-haloalkyl.

$R^{14a}$ may be independently at each occurrence selected from $C_1$-$C_6$-alkyl and $C_3$-$C_5$-cycloalkyl.

Particular compounds of the present invention include any one of the compounds in Example 1 to 216, or a pharmaceutically acceptable salt or N-oxide thereof.

Particular compounds of the present invention include any one of the compounds in Example 1 to 203, or a pharmaceutically acceptable salt or N-oxide thereof.

Still further particular compounds are any of the compound numbers 1 to 203 disclosed herein having $IC_{50}$ of less than 1 µM, preferably less than 100 nM, against CDK12 in Table 1 of Example 217.

Still further particular compounds are any one of compound numbers 204 to 216 disclosed herein having an $IC_{50}$ of less than 1 µM, preferably less than 100 nM, against CDK12 in Table 1 of Example 217.

Still further particular compounds are any of the compounds disclosed herein having an $IC_{50}$ of less than 10 µM, preferably less than 1 µM in the nuclear foci assay in Example 218. For example, any one of compound numbers 6, 7, 10, 11, 20, 21, 22, 27, 28, 32, 33, 34, 35, 36 ad 39 in Table 2 of Example 218.

Also provided is a pharmaceutical formulation comprising a compound of the formula (I), or a pharmaceutically acceptable salt or N-oxide thereof, and a pharmaceutically acceptable excipient.

A further aspect provides a compound of the formula (I), or a pharmaceutically acceptable salt or N-oxide thereof, for use as a medicament.

Further provided is a compound of the formula (I), or a pharmaceutically acceptable salt or N-oxide thereof, for use in the treatment of a condition which is modulated by CDK12. Conditions modulated by CDK12 include, but are not limited to, those conditions disclosed in in the Background to the invention herein.

Also provided is a compound of formula (I), or a pharmaceutically acceptable salt or N-oxide thereof, for use in the treatment of a disease selected from myotonic dystrophy (e.g. myotonic dystrophy type 1 and myotonic dystrophy type 2), Fragile X associated tremor/ataxia syndrome, amyotrophic lateral sclerosis (ALS) and frontotemporal dementia (C9ORF72), Huntington's Disease like 2, Huntington's Disease, Spinocerebellar Ataxia Types 1, 2, 3, 6, 7, 8, 10, 31, 17, Dentatorubral-pallidoluysian atrophy and Spinal and Bulbar Muscular Atrophy and Cancer.

Also provided is a method of treating a disease selected from myotonic dystrophy (e.g. myotonic dystrophy type 1 and myotonic dystrophy type 2), Fragile X associated tremor/ataxia syndrome, amyotrophic lateral sclerosis (ALS) and frontotemporal dementia (C9ORF72), Huntington's Disease like 2, Huntington's Disease, Spinocerebellar Ataxia Types 1, 2, 3, 6, 7, 8, 10, 31, 17, Dentatorubral-pallidoluysian atrophy and Spinal and Bulbar Muscular Atrophy and Cancer, the method comprising administering to said subject an effective amount of a compound of the formula (I), or a pharmaceutically acceptable salt or N-oxide thereof.

Also provided is the use of a compound of formula (I), or a pharmaceutically acceptable salt or N-oxide thereof, for use in the manufacture of a medicament for treatment of a disease selected from myotonic dystrophy (e.g. myotonic dystrophy type 1 and myotonic dystrophy type 2), Fragile X associated tremor/ataxia syndrome, amyotrophic lateral sclerosis (ALS) and frontotemporal dementia (C9ORF72), Huntington's Disease like 2, Huntington's Disease, Spinocerebellar Ataxia Types 1, 2, 3, 6, 7, 8, 10, 31, 17, Dentatorubral-pallidoluysian atrophy and Spinal and Bulbar Muscular Atrophy and Cancer.

The disease may be myotonic dystrophy. The disease may be myotonic dystrophy type 1.

The disease may be a cancer. For example, a cancer in which CDK12 is over expressed. It may be that the cancer is selected from breast cancer (including triple negative breast cancer, ER positive breast cancer, HER-2 positive breast cancer), lung cancer, ovarian cancer (including BRCA-mutated ovarian cancer) and neuroblastoma. For example, breast cancer (including triple negative breast cancer), ER positive breast cancer, HER-2 positive breast cancer) and ovarian cancer (including triple negative breast cancer).

The compound of formula (I), or a pharmaceutically acceptable salt or N-oxide thereof, may be used alone or in combination with another anti-cancer agent in the treatment of a cancer. CDK12 inhibition may be useful in the sensitisation of a tumour to PARP inhibitors or other DNA damaging agents or to overcome tumour resistance to a PARP inhibitor or DNA damaging agent (Paculová et al *Cell Division* 12 (2017): 7).

Accordingly it may be that the compound of formula (i), or a pharmaceutically acceptable salt or N-oxide thereof, is for use together with a PARP inhibitor in the treatment of a cancer. For example, a PARP inhibitor selected from olaparib, rucaparib, niraparib and veliparib.

It may be that the compound of formula (I), or a pharmaceutically acceptable salt or N-oxide thereof, is for use together with a DNA damaging agent inhibitor in the treatment of a cancer. For example the compound may be used together with a platinum anticancer agent (e.g. Cisplatin, carboplatin or oxaliplatin) or an alkylating agent (e.g. a nitrogen mustard, nitrosourea or alkyl sulfonate).

When the compound of formula (I), or a pharmaceutically acceptable salt or N-oxide thereof, is for use together with another anti-cancer agent the compounds may be administered separately, sequentially or simultaneously to the subject being treated.

Also provided is a compound of formula (I), or a pharmaceutically acceptable salt or N-oxide thereof, for use in the treatment of an infection caused by or associated with *Leishmania* parasites, for example in the treatment of visceral leishmaniasis.

Also provided is a method of treating an infection caused by or associated with *Leishmania* parasites, for example the treatment of visceral leishmaniasis, the method comprising administering to said subject an effective amount of a compound of the formula (I), or a pharmaceutically acceptable salt or N-oxide thereof.

Also provided is the use of a compound of formula (I), or a pharmaceutically acceptable salt or N-oxide thereof, for use in the manufacture of a medicament for treatment of an infection caused by or associated with *Leishmania* parasites, for example in the treatment of visceral leishmaniasis. Also provided is a method of inhibiting CDK12 activity in a human or animal subject in need of such inhibition, the method comprising administering to said subject an effective amount of a compound of the formula (I), or a pharmaceutically acceptable salt or N-oxide thereof.

Preferred, suitable, and optional features of any one particular aspect of the present invention are also preferred, suitable, and optional features of any other aspect.

The present invention is also described in the following clauses:

1. A compound of formula (I), or a pharmaceutically acceptable salt or N-oxide thereof:

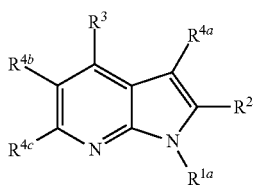

(I)

wherein
$R^{1a}$ is independently selected from: H and $C_1$-$C_6$-alkyl;
$R^2$ is independently selected from H, $C_1$-$C_6$-alkyl, $C_1$-$C_6$-haloalkyl, $C_2$-$C_6$-alkenyl, $C_2$-$C_6$-alkynyl, halo, nitro, cyano, $OR^{5a}$, $SR^{6a}$, $NR^{6a}R^{7a}$, $C(O)R^{6a}$, $C(O)OR^{6a}$, $C(O)NR^{6a}R^{6a}$, $S(O)_2R^{6a}$, $S(O)_2NR^{6a}R^{6a}$, -$L^1$-$L^2$-$R^8$;
$R^3$ is independently selected from a 5- or 6-membered monocyclic heteroaryl group and a 9- or 10-membered bicyclic heteroaryl group; said heteroaryl group comprising at least one nitrogen in the monocyclic ring or bicyclic ring system; wherein $R^3$ is optionally substituted with a single $R^{4d}$ group and from 0 to 6 $R^{4e}$ groups;
$R^{4a}$ and $R^{4c}$ are each independently selected from H, fluoro, chloro and $C_1$-$C_6$-alkyl;
$R^{4b}$ and $R^{4e}$ are each independently at each occurrence selected from H, fluoro, chloro, $C_1$-$C_6$-alkyl, $C_1$-$C_6$-haloalkyl, $C_2$-$C_6$-alkenyl, $C_2$-$C_6$-alkynyl, $OR^{5b}$, $SR^{6b}$ and $NR^{6b}R^{7b}$;
$R^{4d}$ is independently selected from $C_1$-$C_3$-alkylene-$R^9$ or O—$C_1$-$C_3$-alkylene-$R^9$;
-$L^1$- is independently absent or is selected from —$(CR^{10a}R^{10a})_{n1}NR^{11a}$—, —$(CR^{10c}R^{10c})_{n2}O$—, —$C_0$-$C_3$-alkylene-$NR^{11b}(CR^{10b}R^{10b})_{m1}NR^{11c}$— and —$C_0$-$C_3$-alkylene-$L^{3a}$-$C_0$-$C_3$-alkylene-$NR^{11d}$;
wherein where $L^1$ is —$(CR^{10a}R^{10a})_{n1}NR^{11a}$— it is optionally the case that: A) a single $R^{10a}$ group and $R^{11a}$ together form a $C_1$-$C_4$-alkylene, said alkylene optionally being interrupted by an oxygen, nitrogen or sulphur atom; or B) two $R^{10a}$ groups together form a $C_1$-$C_4$-alkylene, said alkylene optionally being interrupted by an oxygen, nitrogen or sulphur atom;
wherein where $L^1$ is —$C_0$-$C_3$-alkylene-$NR^{11b}(CR^{10b}R^{10b})_{m1}NR^{11c}$— it is optionally the case that A) $R^{11b}$ and $R^{11c}$ together form a $C_1$-$C_4$-alkylene; B) a single $R^{10b}$ group and either $R^{11b}$ or $R^{11c}$ together form a $C_1$-$C_4$-alkylene, said alkylene optionally being interrupted by an oxygen, nitrogen or sulphur atom; C) two $R^{10b}$ groups together form a $C_1$-$C_4$-alkylene, said alkylene optionally being interrupted by an oxygen, nitrogen or sulphur atom; or D) a single $R^{10b}$ group and $R^{11b}$ together form a $C_1$-$C_4$-alkylene and a single $R^{10b}$ group and $R^{11c}$ together form a $C_1$-$C_4$-alkylene;
wherein where -$L^1$- includes an alkylene group, that alkylene group is optionally substituted with from 1 to 4 $R^{12a}$ groups; and where -$L^1$- includes a phenyl, naphthyl, or heteroaryl group, that phenyl, naphthyl or heteroaryl is optionally substituted with from 1 to 4 $R^{13a}$ groups;
-$L^2$- is independently absent or is selected from $C(O)$-$L^4$- and $SO_2$-$L^4$-.
-$L^{3a}$- and -$L^{3b}$- are each independently selected from phenyl, naphthyl, 5-, 6-, 9- or 10-membered heteroaryl;
-$L^4$- is selected from —$(CR^{10c}R^{10c})_{n3}NR^{11e}$, —$(CR^{10c}R^{10c})_{n4}O$—, —$C_0$-$C_3$-alkylene-$NR^{11f}(CR^{10d}R^{10d})_{m2}NR^{11g}$— and —$C_0$-$C_3$-alkylene-$L^{3b}$-$C_0$-$C_3$-alkylene-$NR^{11h}$—;
wherein where $L^4$ is —$(CR^{10c}R^{10c})_{n3}NR^{11e}$— it is optionally the case that: A) a single $R^{10c}$ group and $R^{11e}$ together form a $C_1$-$C_4$-alkylene, said alkylene optionally being interrupted by an oxygen, nitrogen or sulphur atom; or B) two $R^{10c}$ groups together form a $C_1$-$C_4$-alkylene, said alkylene optionally being interrupted by an oxygen, nitrogen or sulphur atom;
wherein where $L^4$ is —$C_0$-$C_3$-alkylene-$NR^{11f}(CR^{10d}R^{10d})_{m2}NR^{11g}$— it is optionally the case that A) $R^{11f}$ and $R^{11g}$ together form a $C_1$-$C_4$-alkylene; B) a single $R^{10d}$ group and either $R^{11f}$ or $R^{11g}$ together form a $C_1$-$C_4$-alkylene, said alkylene optionally being interrupted by an oxygen, nitrogen or sulphur atom; C) two $R^{10d}$ groups together form a $C_1$-$C_5$-alkylene, said alkylene optionally being interrupted by an oxygen, nitrogen or sulphur atom; or D) a single $R^{10d}$ group and $R^{11f}$ together form a $C_1$-$C_4$-alkylene and a single $R^{10d}$ group and $R^{11g}$ together form a $C_1$-$C_4$-alkylene;
wherein where -$L^4$- includes an alkylene group, that alkylene group is optionally substituted with from 1 to 4 $R^{12b}$ groups; and where -$L^4$- includes a phenyl, naphthyl, or heteroaryl group, that phenyl, naphthyl or heteroaryl is optionally substituted with from 1 to 4 $R^{13b}$ groups;
$R^{5a}$, $R^{5b}$, $R^{5d}$ and $R^{5e}$ are each independently at each occurrence selected from H, $C_1$-$C_6$-alkyl (wherein said $C_1$-$C_6$-alkyl group may be optionally substituted with from 1 to 3 $OR^{5c}$ or $NR^{6c}R^{7c}$ groups) and $C_1$-$C_6$-haloalkyl;
$R^{5c}$ is independently at each occurrence selected from H, $C_1$-$C_6$-alkyl and $C_1$-$C_6$-haloalkyl;
$R^{6a}$, $R^{6b}$, $R^{6d}$ and $R^{6e}$ are each independently at each occurrence selected from H and $C_1$-$C_6$-alkyl (wherein said $C_1$-$C_6$-alkyl group may be optionally substituted with from 1 to 3 $OR^{5c}$ or $NR^{6c}R^{7c}$ groups);

$R^{6c}$ is independently at each occurrence selected from H and $C_1$-$C_6$-alkyl;

$R^{7a}$, $R^{7b}$, $R^{7d}$ and $R^{7e}$ are each independently at each occurrence selected from H, $C_1$-$C_6$-alkyl (wherein said $C_1$-$C_6$-alkyl group may be optionally substituted with a 5-membered heterocycloalkyl group or from 1 to 3 $OR^{5c}$ or $NR^{6c}R^{7c}$ groups), $C(O)R^{14a}$, $C(O)OR^{14a}$, $C(O)NHR^{14a}$, $S(O)_2R^{14a}$ and $S(O)_2NHR^{14a}$;

$R^{7c}$ is independently at each occurrence selected from H, $C_1$-$C_6$-alkyl, $C(O)R^{14b}$, $C(O)OR^{14b}$, $C(O)NHR^{14b}$, $S(O)_2R^{14b}$ and $S(O)_2NHR^{14b}$;

$R^8$ is independently selected from H, $S(O)_2R^{15}$, $C(O)R^{15}$, $S(O)_2$—$C_0$-$C_3$-alkylene-$R^{15}$, $C(O)$—$C_0$-$C_3$-alkylene-$R^{15}$ and $C_0$-$C_3$-alkylene-$R^{15}$; wherein $R^{15}$ is independently selected from phenyl, $C_3$-$C_7$-cycloalkyl, $C_1$-$C_6$-alkyl, 5- to 7-membered heterocycloalkyl, 5-, 6-, 9- and 10-membered heteroaryl; wherein where any $R^8$ group includes heterocycloalkyl, alkylene, cycloalkyl or alkyl, that heterocycloalkyl, cycloalkyl or alkyl group is optionally substituted with from 1 to 4 $R^{12c}$ groups; and where any $R^8$ group includes phenyl or heteroaryl, that phenyl or heteroaryl is optionally substituted with from 1 to 4 $R^{13}$ groups
or $R^8$ is a group that can react with the SH of a cysteine to form a covalent bond between a carbon atom of $R^8$ and the sulphur atom of the cysteine;

$R^9$ is independently selected from H, phenyl, 5- to 7-membered heterocycloalkyl, 5-, 6-, 9- and 10-membered heteroaryl; wherein where any $R^9$ group is heterocycloalkyl, that is optionally substituted with from 1 to 4 $R^{12d}$ groups; and where any $R^9$ group is phenyl or heteroaryl, that phenyl or heteroaryl is optionally substituted with from 1 to 4 $R^{13d}$ groups;

$R^{10a}$, $R^{10b}$, $R^{10c}$ and $R^{10d}$ are each independently at each occurrence selected from H and $C_1$-$C_6$-alkyl;

$R^{11a}$, $R^{11b}$, $R^{11c}$, $R^{11d}$, $R^{11e}$, $R^{11f}$, $R^{11g}$, $R^{11h}$ are each independently selected from: H and $C_1$-$C_6$-alkyl;

$R^{12a}$, $R^{12b}$, $R^{12c}$ and $R^{12d}$ are each independently at each occurrence selected from oxo, $C_1$-$C_6$-alkyl, $C_1$-$C_6$-haloalkyl, $C_2$-$C_6$-alkenyl, $C_2$-$C_6$-alkynyl, halo, nitro, cyano, $OR^{5d}$, $SR^{6d}$, $NR^{6d}R^{7d}$, $C(O)R^{6d}$, $C(O)OR^{6d}$, $C(O)NR^{6d}R^{6d}$, $S(O)_2R^{6d}$, $S(O)_2NR^{6d}R^{6d}$;

$R^{13a}$, $R^{13b}$, $R^{13c}$ and $R^{13d}$ are each independently at each occurrence selected from $C_1$-$C_6$-alkyl, $C_1$-$C_6$-haloalkyl, $C_2$-$C_6$-alkenyl, $C_2$-$C_6$-alkynyl, halo, nitro, cyano, $OR^{5e}$, $SR^{6e}$, $NR^{6e}R^{7e}$, $C(O)R^{6e}$, $C(O)OR^{6e}$, $C(O)NR^{6e}R^{6e}$, $S(O)_2R^{6e}$, $S(O)_2NR^{6e}R^{6e}$;

$R^{14a}$ is independently selected from $C_1$-$C_6$-alkyl and $C_3$-$C_5$-cycloalkyl; wherein said $C_1$-$C_6$-alkyl or $C_3$-$C_5$-cycloalkyl group may be optionally substituted with from 1 to 3 $OR^{5c}$ or $NR^{6c}R^{7c}$ groups;

$R^{14b}$ is independently selected from $C_1$-$C_6$-alkyl and $C_3$-$C_5$-cycloalkyl;

n1, n2, n3 and n4 are each independently an integer selected from 1, 2, 3 and 4; and m1 and m2 are each independently an integer selected from 2, 3 and 4.

2. A compound of clause 1, wherein $R^2$ is -$L^1$-$L^2$-$R^8$.

3. A compound of clause 2, wherein -$L^1$- is selected from —$(CR^{10a}R^{10a})_{n1}NR^{11a}$— and -$L^{3a}$-alkylene-$NR^{11d}$—;
wherein where $L^1$ is —$(CR^{10a}R^{10a})_{n1}NR^{11a}$— it is optionally the case that: A) a single $R^{10a}$ group and $R^{11a}$ together form a $C_1$-$C_4$-alkylene;
wherein where -$L^1$- includes an alkylene group, that alkylene group is optionally substituted with from 1 to 4 $R^{12a}$ groups; and where -$L^1$- includes a phenyl, naphthyl, or heteroaryl group, that phenyl, naphthyl or heteroaryl is optionally substituted with from 1 to 4 $R^{13a}$ groups;

-$L^2$- is selected from $C(O)$-$L^4$- and $SO_2$-$L^4$-
-$L^{3a}$- and -$L^{3b}$- are each independently selected from phenyl, naphthyl, 5-, 6-, 9- or 10-membered heteroaryl;
-$L^4$- is selected from —$(CR^{10c}R^{10c})_{n3}NR^{11e}$— and -$L^{3b}$-$NR^{11h}$—
wherein where $L^4$ is —$(CR^{10c}R^{10c})_{n3}NR^{11e}$— it is optionally the case that: A) a single $R^{10c}$ group and $R^{11e}$ together form a $C_1$-$C_4$-alkylene, said alkylene optionally being interrupted by an oxygen, nitrogen or sulphur atom;
wherein where -$L^4$- includes an alkylene group, that alkylene group is optionally substituted with from 1 to 4 $R^{12b}$ groups; and where -$L^4$- includes a phenyl, naphthyl, or heteroaryl group, that phenyl, naphthyl or heteroaryl is optionally substituted with from 1 to 4 $R^{13b}$ groups.

4. A compound of clause 3, wherein -$L^1$- is selected —$(CR^{10a}R^{10a})_{n1}NR^{11a}$—,

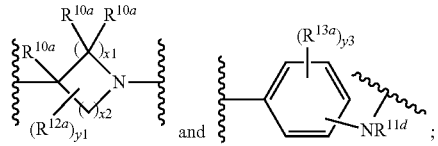

-$L^2$- is —$C(O)$-$L^4$-; and
-$L^4$- is selected from:

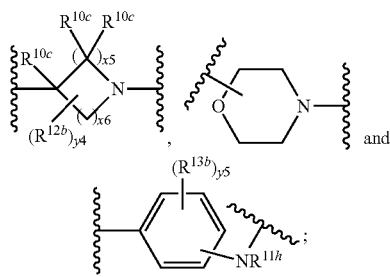

wherein x1 is an integer selected from 0, 1, 2, 3 or 4; x2 is an integer selected from 1, 2, 3 and 4; providing that the sum of x1 and x2 is 2, 3, 4 or 5; x5 is an integer selected from 0, 1, 2, 3 or 4; x6 is an integer selected from 1, 2, 3 and 4; providing that the sum of x5 and x6 is 2, 3, 4 or 5; y1 is an integer from 0 to 3; y3 is an integer from 0 to 4; and y4 an integer from 0 to 3; and y5 is an integer from 0 to 4.

5. A compound of any one of clauses 2 to 4, wherein $R^8$ is a group that can react with the SH of a cysteine to form a covalent bond between a carbon atom of $R^8$ and the sulphur atom of the cysteine.

6. A compound of clause 5, wherein $R^8$ has a structure selected from:

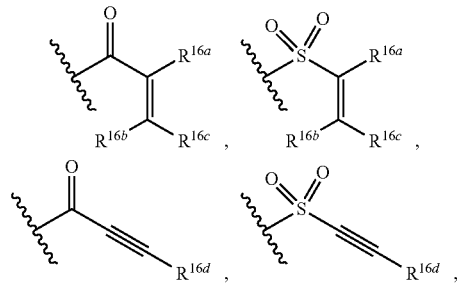

-continued

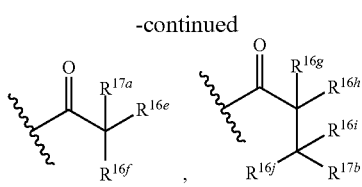

and
wherein $R^{16a}$ is independently selected from H, CN and $C_1$-$C_6$-alkyl (which may be optionally substituted with a O—$R^{18a}$ group or a $NR^{18b}R^{18b}$ group);
$R^{16b}$, $R^{16c}$, $R^{16d}$, $R^{16e}$, $R^{16f}$, $R^{16g}$, $R^{16h}$, $R^{16i}$ and $R^{16j}$ are each independently selected from H and $C_1$-$C_6$-alkyl (which may be optionally substituted with a O—$R^{18a}$ group or a $NR^{18b}R^{18b}$ group);
$R^{17a}$ and $R^{17b}$ are each independently selected from CN, halo and $OS(O)_2R^{19}$;
$R^{18a}$, $R^{18b}$ and $R^{18c}$ are independently selected from H and $C_1$-$C_6$-alkyl; and
$R^{19}$ is independently selected from $C_1$-$C_6$-alkyl and phenyl (which may be optionally substituted with from 1 to 3 groups selected from $C_1$-$C_6$-alkyl, $C_1$-$C_6$-haloalkyl, halo, O—$C_1$-$C_6$-alkyl, O—$C_1$-$C_6$-haloalkyl and nitro).

7. A compound of any one of clauses 2 to 4, wherein $R^8$ is independently selected from H, $S(O)_2R^{15}$, $C(O)R^{15}$, $S(O)_2$—$C_0$-$C_3$-alkylene-$R^{15}$, $C(O)$—$C_0$-$C_3$-alkylene-$R^{15}$ and $C_0$-$C_3$-alkylene-$R^{15}$; wherein $R^{15}$ is independently selected from phenyl, $C_3$-$C_7$-cycloalkyl, $C_1$-$C_6$-alkyl, 5- to 7-membered heterocycloalkyl, 5-, 6-, 9- and 10-membered heteroaryl; wherein where any $R^8$ group includes heterocycloalkyl, alkylene, cycloalkyl or alkyl, that heterocycloalkyl, cycloalkyl or alkyl group is optionally substituted with from 1 to 4 $R^{12c}$ groups; and where any $R^8$ group includes phenyl or heteroaryl, that phenyl or heteroaryl is optionally substituted with from 1 to 4 $R^{13c}$ groups.

8. A compound of clause 1, wherein $R^2$ is independently selected from H, $C_1$-$C_6$-alkyl, $C_1$-$C_6$-haloalkyl, $C_2$-$C_6$-alkenyl, $C_2$-$C_6$-alkynyl, halo, nitro, cyano, $OR^{5a}$, $SR^{6a}$, $NR^{6a}R^{7a}$, $C(O)R^{6a}$, $C(O)OR^{6a}$, $C(O)NR^{6a}R^{6a}$, $S(O)_2R^{6a}$ and $S(O)_2NR^{6a}R^{6a}$.

9. A compound of any one of clauses 1 to 8, wherein $R^{1a}$ is H.

10. A compound of any preceding clauses, wherein $R^3$ has the structure:

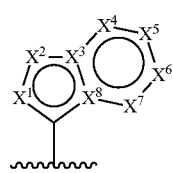

wherein $X^1$ is independently selected from N and $CR^{4f}$;
$X^2$ is independently selected from N and $CR^{4g}$;
$X^3$ is independently selected from N and C;
$X^4$ is independently selected from N and $CR^{4h}$;
$X^5$ is independently selected from N and $CR^{4i}$;
$X^6$ is independently selected from N and $CR^{4j}$;
$X^7$ is independently selected from N and $CR^{4k}$;
$X^8$ is independently selected from N and C;
wherein at least one of $X^1$, $X^2$, $X^3$, $X^4$, $X^5$, $X^6$, $X^7$ and $X^8$ is N and no more than four of $X^1$, $X^2$, $X^3$, $X^4$, $X^5$, $X^6$, $X^7$ and $X^8$ are N;

$R^{4f}$, $R^{4g}$, $R^{4h}$ and $R^{4k}$ are each independently selected from H, fluoro and chloro and $C_1$-$C_3$ alkyl;
$R^{4i}$ and $R^{4j}$ are each independently selected from H, fluoro, chloro, $C_1$-$C_6$-alkyl, $C_1$-$C_6$-haloalkyl, $C_2$-$C_6$-alkenyl, $C_2$-$C_6$-alkynyl, $OR^{5b}$, $SR^{6b}$ and $NR^{6b}R^{7b}$; and optionally wherein a single one of $R^{4i}$ and $R^{4j}$ is $R^{4d}$.

11. A compound of clause 10, wherein $R^3$ has the structure:

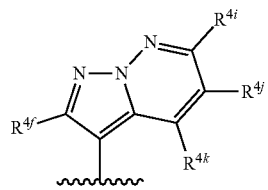

12. A compound of clause 11, wherein each of $R^{4f}$, $R^{4i}$, $R^{4j}$ and $R^{4k}$ are H.

13. A compound of any one of clauses 1 to 12, wherein each of $R^{4a}$, $R^{4b}$ and $R^{4c}$ is H.

14. A pharmaceutical formulation comprising a compound of any one of clauses 1 to 13, or a pharmaceutically acceptable salt or N-oxide thereof, and a pharmaceutically acceptable excipient.

15. A compound of any one of clauses 1 to 13, or a pharmaceutically acceptable salt or N-oxide thereof, for use as a medicament.

16. A compound of any one of clauses 1 to 13, or a pharmaceutically acceptable salt or N-oxide thereof, for use in the treatment of a condition which is mediated by CDK12.

17. A compound of any one of clauses 1 to 13, or a pharmaceutically acceptable salt or N-oxide thereof, for use in the treatment of a disease selected from myotonic dystrophy (e.g. myotonic dystrophy type 1 and myotonic dystrophy type 2), Fragile X associated tremor/ataxia syndrome, amyotrophic lateral sclerosis (ALS) and frontotemporal dementia (C9ORF72), Huntington's Disease like 2, Huntington's Disease, Spinocerebellar Ataxia Types 1, 2, 3, 6, 7, 8, 10, 31, 17, Dentatorubral-pallidoluysian atrophy and Spinal and Bulbar Muscular Atrophy and Cancer.

18. A compound for use of clause 17, wherein the disease is myotonic dystrophy type 1.

DETAILED DESCRIPTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "halo" or "halogen" refers to one of the halogens, group 17 of the periodic table. In particular the term refers to fluorine, chlorine, bromine and iodine. Preferably, the term refers to fluorine or chlorine.

The term $C_m$-$C_n$ refers to a group with m to n carbon atoms.

The term "$C_1$-$C_6$-alkyl" refers to a linear or branched hydrocarbon chain containing 1, 2, 3, 4, 5 or 6 carbon atoms, for example methyl, ethyl, n-propyl, iso-propyl, n-butyl, sec-butyl, tert-butyl, n-pentyl and n-hexyl. "$C_1$-$C_4$-alkyl" similarly refers to such groups containing up to 4 carbon atoms. Alkylene groups are divalent alkyl groups and may likewise be linear or branched and have two points of attachment to the remainder of the molecule. Furthermore, an alkylene group may, for example, correspond to one of those alkyl groups listed in this paragraph. The alkyl and alkylene groups may be unsubstituted or substituted by one or more substituents. Possible substituents are described below. Substituents for the alkyl group may be halogen, e.g. fluorine, chlorine, bromine and iodine, OH, $C_1$-$C_4$-alkoxy.

The term "$C_1$-$C_6$-alkoxy" refers to an alkyl group which is attached to a molecule via oxygen. This includes moieties where the alkyl part may be linear or branched and may contain 1, 2, 3, 4, 5 or 6 carbon atoms, for example methyl, ethyl, n-propyl, iso-propyl, n-butyl, sec-butyl, tert-butyl, n-pentyl and n-hexyl. Therefore, the alkoxy group may be methoxy, ethoxy, n-propoxy, iso-propoxy, n-butoxy, sec-butoxy, tert-butoxy, n-pentoxy and n-hexoxy. The alkyl part of the alkoxy group may be unsubstituted or substituted by one or more substituents. Possible substituents are described below. Substituents for the alkyl group may be halogen, e.g. fluorine, chlorine, bromine and iodine, OH, $C_1$-$C_6$ alkoxy.

The term "$C_1$-$C_6$-haloalkyl" refers to a hydrocarbon chain substituted with at least one halogen atom independently chosen at each occurrence, for example fluorine, chlorine, bromine and iodine. The halogen atom may be present at any position on the hydrocarbon chain. For example, $C_{1-6}$-haloalkyl may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl.

The term "$C_2$-$C_6$-alkenyl" refers to a branched or linear hydrocarbon chain containing at least one double bond and having 2, 3, 4, 5 or 6 carbon atoms. The double bond(s) may be present as the E or Z isomer. The double bond may be at any possible position of the hydrocarbon chain. For example, the "$C_{2-6}$ alkenyl" may be ethenyl, propenyl, butenyl, butadienyl, pentenyl, pentadienyl, hexenyl and hexadienyl.

The term "$C_2$-$C_6$ alkynyl" refers to a branched or linear hydrocarbon chain containing at least one triple bond and having 2, 3, 4, 5 or 6 carbon atoms. The triple bond may be at any possible position of the hydrocarbon chain. For example, the "$C_{2-6}$ alkynyl" may be ethynyl, propynyl, butynyl, pentynyl and hexynyl.

The term "$C_3$-$C_8$-cycloalkyl" refers to a saturated hydrocarbon ring system containing 3, 4, 5, 6, 7 or 8 carbon atoms. For example, the "$C_3$-$C_6$-cycloalkyl" may be cyclopropyl, cyclobutyl, cyclopentyl, cyclohexyl, bicycle[2.1.1]hexane or bicycle[1.1.1]pentane.

The term "$C_{3-6}$ cycloalkenyl" includes a hydrocarbon ring system containing 3 to 6 carbon atoms and at least one double bond (e.g. 1 or 2 double bonds). For example, $C_{3-6}$ cycloalkenyl may be cyclobutenyl, cyclopentenyl or cyclohexenyl.

The term "heterocyclyl", "heterocyclic" or "heterocycle" means a non-aromatic saturated or partially saturated monocyclic or fused, bridged, or spiro bicyclic heterocyclic ring system(s). Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles comprising at least one nitrogen in a ring position include, for example, azetidinyl, pyrrolidinyl, piperidinyl, piperazinyl, morpholinyl, thiomorpholinyl, tetrahydrotriazinyl, tetrahydropyrazolyl, tetrahydropyridinyl, homopiperidinyl, homopiperazinyl, 3,8-diaza-bicyclo[3.2.1]octanyl, 8-aza-bicyclo[3.2.1]octanyl, 2,5-Diaza-bicyclo[2.2.1]heptanyl and the like. Typical sulfur containing heterocycles include tetrahydrothienyl, dihydro-1,3-dithiol, tetrahydro-2H-thiopyran, and hexahydrothiepine. Other heterocycles include dihydro oxathiolyl, tetrahydro oxazolyl, tetrahydro-oxadiazolyl, tetrahydrodioxazolyl, tetrahydrooxathiazolyl, hexahydrotriazinyl, tetrahydro oxazinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O), for example, 2 oxopyrrolidinyl, 2-oxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example Advanced Organic Chemistry, by Jerry March, 4th Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane, and quinuclidine.

By "spiro bi-cyclic ring systems" is meant that the two ring systems share one common spiro carbon atom, i.e. the heterocyclic ring is linked to a further carbocyclic or heterocyclic ring through a single common spiro carbon atom. Examples of spiro ring systems include 3,8-diaza-bicyclo[3.2.1]octane, 2,5-Diaza-bicyclo[2.2.1]heptane, 6-azaspiro[3.4]octane, 2-oxa-6-azaspiro[3.4]octane, 2-azaspiro[3.3]heptane, 2-oxa-6-azaspiro[3.3]heptane, 6-oxa-2-azaspiro[3.4]octane, 2,7-diaza-spiro[4.4]nonane, 2-azaspiro[3.5]nonane, 2-oxa-7-azaspiro[3.5]nonane and 2-oxa-6-azaspiro[3.5]nonane.

The term "aromatic" when applied to a substituent as a whole means a single ring or polycyclic ring system with 4n+2 electrons in a conjugated π system within the ring or ring system where all atoms contributing to the conjugated π system are in the same plane.

The term "aryl" refers to an aromatic hydrocarbon ring system. The ring system has 4n+2 electrons in a conjugated π system within a ring where all atoms contributing to the conjugated π system are in the same plane. For example, the "aryl" may be phenyl and naphthyl. The aryl system itself may be substituted with other groups.

The term "heteroaryl" refers to an aromatic mono- or bicyclic ring incorporating one or more (for example 1-4, particularly 1, 2 or 3) heteroatoms selected from nitrogen, oxygen or sulfur. The ring or ring system has 4n+2 electrons in a conjugated π system where all atoms contributing to the conjugated π system are in the same plane.

Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl and imidazo[1,2-b][1,2,4]triazinyl. Examples of heteroaryl groups comprising at least one nitrogen in a ring position include pyrrolyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, indolyl, isoindolyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl and pteridinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

Particular examples of bicyclic heteroaryl groups containing a six membered ring fused to a five membered ring include but are not limited to benzofuranyl, benzothiophenyl, benzimidazolyl, benzoxazolyl, benzisoxazolyl, benzothiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl, pyrrolopyridine, and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

The term "optionally substituted" refers to either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically, including the compounds of the formulae (I) to (IV) and the compounds in the Examples.

A bond terminating in a "⌇" represents that the bond is connected to another atom that is not shown in the structure. A bond terminating inside a cyclic structure and not terminating at an atom of the ring structure represents that the bond may be connected to any of the atoms in the ring structure where allowed by valency.

A "-" in a substituent group denotes the point of attachment of that substituent to the rest of the molecule. Where a group is a linker group having two "-"s indicated, the "-" on the left indicates the attachment of the linker group to the bicyclic core of the molecule depicted in formula (I), either directly or via other linker groups. Likewise, the "-" on the right indicates the attachment of the linker group to groups that are further away from the bicyclic core of the molecule depicted in formula (I) than the linker group. Thus, in the group -$L^1$- the "-" on the left denotes the point of attachment to the 5 membered ring in the bicyclic core (at the position neighbouring $NR^{1a}$) and the "-" on the right denotes the point of attachment to -$L^2$-$R^8$ in formula (I). Likewise, in the group -L$^2$- the "-" on the left denotes the point of attachment to -L$^1$- and the "-" on the right denotes the point of attachment to —R$^8$ in formula (I).

Where a moiety is substituted, it may be substituted at any point on the moiety where chemically possible and consistent with atomic valency requirements. The moiety may be substituted by one or more substituents, e.g. 1, 2, 3 or 4 substituents; optionally there are 1 or 2 substituents on a group. Where there are two or more substituents, the substituents may be the same or different.

Substituents are only present at positions where they are chemically possible, the person skilled in the art being able to decide (either experimentally or theoretically) without undue effort which substitutions are chemically possible and which are not.

Ortho, meta and para substitution are well understood terms in the art. For the absence of doubt, "ortho" substitution is a substitution pattern where adjacent carbons possess a substituent, whether a simple group, for example the fluoro group in the example below, or other portions of the molecule, as indicated by the bond ending in "⌇".

"Meta" substitution is a substitution pattern where two substituents are on carbons one carbon removed from each other, i.e. with a single carbon atom between the substituted carbons. In other words, there is a substituent on the second atom away from the atom with another substituent. For example, the groups below are meta substituted.

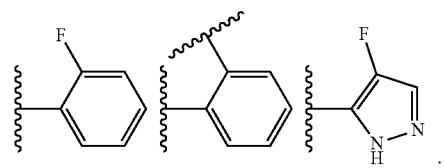

"Para" substitution is a substitution pattern where two substituents are on carbons two carbons removed from each other, i.e. with two carbon atoms between the substituted carbons. In other words, there is a substituent on the third atom away from the atom with another substituent. For example, the groups below are para substituted.

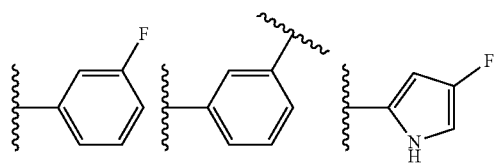

By "acyl" is meant an organic radical derived from, for example, an organic acid by the removal of the hydroxyl group, e.g. a radical having the formula R—C(O)—, where R may be selected from H, C$_{1-6}$-alkyl, C$_{3-8}$-cycloalkyl, phenyl, benzyl or phenethyl group, e.g. R is H or C$_{1-3}$-alkyl. In one embodiment acyl is alkyl-carbonyl. Examples of acyl groups include, but are not limited to, formyl, acetyl, propionyl and butyryl. A particular acyl group is acetyl (also represented as Ac).

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The various functional groups and substituents making up the compounds of the present invention are typically chosen such that the molecular weight of the compound does not exceed 1000. More usually, the molecular weight of the compound will be less than 750, for example less than 700, or less than 650, or less than 600, or less than 550. More preferably, the molecular weight is less than 525 and, for example, is 500 or less.

Suitable or preferred features of any compounds of the present invention may also be suitable features of any other aspect.

The invention contemplates pharmaceutically acceptable salts of the compounds of the invention. These may include the acid addition and base salts of the compounds. These may be acid addition and base salts of the compounds.

Suitable acid addition salts are formed from acids which form non-toxic salts. Examples include the acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts. For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by for example, one or more of the following methods:
(i) by reacting the compound of the invention with the desired acid or base;
(ii) by removing an acid- or base-labile protecting group from a suitable precursor of the compound of the invention or by ring-opening a suitable cyclic precursor, for example, a lactone or lactam, using the desired acid or base; or
(iii) by converting one salt of the compound of the invention to another by reaction with an appropriate acid or base or by means of a suitable ion exchange column.

These methods are typically carried out in solution. The resulting salt may precipitate out and be collected by filtration or may be recovered by evaporation of the solvent. The degree of ionisation in the resulting salt may vary from completely ionised to almost non-ionised.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Where a compound of the invention has two or more stereocentres any combination of (R) and (S) stereoisomers is contemplated. The combination of (R) and (S) stereoisomers may result in a diastereomeric mixture or a single diastereoisomer. The compounds of the invention may be present as a single stereoisomer or may be mixtures of stereoisomers, for example racemic mixtures and other enantiomeric mixtures, and diasteroemeric mixtures. Where the mixture is a mixture of enantiomers the enantiomeric excess may be any of those disclosed above. Where the compound is a single stereoisomer the compounds may still contain other diastereoisomers or enantiomers as impurities. Hence a single stereoisomer does not necessarily have an enantiomeric excess (e.e.) or diastereomeric excess (d.e.) of 100% but could have an e.e. or d.e. of about at least 85%

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess Mps1 kinase inhibitory activity.

Compounds and salts described in this specification may be isotopically-labelled (or "radio-labelled"). Accordingly, one or more atoms are replaced by an atom having an atomic mass or mass number different from the atomic mass or mass number typically found in nature. Examples of radionuclides that may be incorporated include $^2$H (also written as "D" for deuterium), $^3$H (also written as "T" for tritium), $^{11}$C, $^{13}$C, $^{14}$C, $^{15}$O, $^{17}$O, $^{18}$O, $^{18}$F and the like. The radionuclide that is used will depend on the specific application of that radio-labeled derivative. For example, for in vitro competition assays, $^3$H or $^{14}$C are often useful. For radio-imaging applications, $^{11}$C or $^{18}$F are often useful. In some embodiments, the radionuclide is $^3$H. In some embodiments, the radionuclide is $^{14}$C. In some embodiments, the radionuclide is $^{11}$C. And in some embodiments, the radionuclide is $^{18}$F.

It is also to be understood that certain compounds of the invention may exist in solvated as well as unsolvated forms such as, for example, hydrated forms. It is to be understood that the invention encompasses all such solvated forms that possess CDK12 inhibitory activity.

It is also to be understood that certain compounds of the invention may exhibit polymorphism, and that the invention encompasses all such forms that possess CDK12 inhibitory activity.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

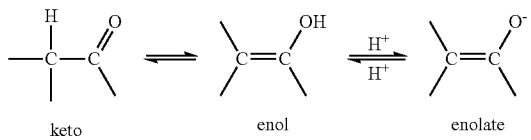

keto      enol      enolate

Compounds of the invention containing an amine function may also form N-oxides. A reference herein to a compound of the formula (I) that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle or heteroaryl group. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn.*

*Comm.* 1977, 7, 509-514) in which the amine compound is reacted with m-chloroperoxybenzoic acid (MCPBA), for example, in an inert solvent such as dichloromethane.

In one embodiment the compound of formula (I) is not in the form of an N-oxide.

In another embodiment the compound of formula (I) is not in the form of a salt. Alternatively, the compound of formula (I) may be in the form of a pharmaceutically acceptable salt.

The in vivo effects of a compound of the formula (I) may be exerted in part by one or more metabolites that are formed within the human or animal body after administration of a compound of the formula (I).

Synthesis

In the description of the synthetic methods described below and in the referenced synthetic methods that are used to prepare the staring materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively, necessary starting materials are obtainable by analogous procedures to those illustrated which are within the ordinary skill of an organic chemist.

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example $BF_3.OEt_2$. A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

Further information on the preparation of the compounds of the invention is provided in the Examples section. The general reaction schemes and specific methods described in the Examples form a further aspect of the invention. The compounds of the invention can be made according to or analogously to the methods described in the Examples.

The resultant compound of formula (I) from the processes defined above can be isolated and purified using techniques well known in the art.

Compounds of the invention may exist in a single crystal form or in a mixture of crystal forms or they may be amorphous. Thus, compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

The processes defined herein may further comprise the step of subjecting the compound of formula (I) to a salt exchange, particularly in situations where the compound of formula (I) is formed as a mixture of different salt forms. The salt exchange suitably comprises immobilising the compound of formula II on a suitable solid support or resin, and eluting the compounds with an appropriate acid to yield a single salt of the compound of formula (I).

In a further aspect of the invention, there is provided a compound of formula (I) obtainable by any one of the processes defined herein.

In a further aspect of the invention, there is provided a compound of formula (I) obtained by any one of the processes defined herein.

In a further aspect of the invention, there is provided a compound of formula (I) directly obtained by any one of the processes defined herein.

Certain of the intermediates described in the reaction schemes above and in the Examples herein are novel. Such novel intermediated, or a salt thereof, particularly a pharmaceutically acceptable salt thereof form a further aspect of the invention.

Pharmaceutical Compositions

In accordance with another aspect, the present invention provides a pharmaceutical formulation comprising a compound of formula (I), or a pharmaceutically acceptable salt or N-oxide thereof, and a pharmaceutically acceptable excipient.

Conventional procedures for the selection and preparation of suitable pharmaceutical formulations are described in, for example, "Pharmaceuticals—The Science of Dosage Form Designs", M. E. Aulton, Churchill Livingstone, 1988.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy of a condition is an amount sufficient to symptomatically relieve in a warm-blooded animal, particularly a human the symptoms of the condition or to slow the progression of the condition.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the invention will naturally vary according to the nature and severity of the conditions, the age and sex of the animal or patient and the route of administration, according to well-known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

In the following sections discussing uses and applications a reference to "compound of the formula (I)" is intended to encompass all of the compounds of the invention disclosed herein, for example any of the compounds of formulae (I) to (VI).

In accordance with another aspect, the present invention provides a compound of formula (I), or a pharmaceutically acceptable salt or N-oxide thereof, for use as a medicament.

In accordance with another aspect, there is provided a compound of formula (I), or a pharmaceutically acceptable salt or N-oxide thereof, for use in the treatment of a condition which is modulated by CDK12. Generally conditions that are modulated by CDK12 are conditions that would be treated by the inhibition of CDK12 using a compound of formula (I), or a pharmaceutically acceptable salt or N-oxide thereof. A compound of formula (I), or a pharmaceutically acceptable salt or N-oxide thereof, may be for use in the treatment of a condition treatable by the inhibition of CDK12.

In a further aspect, the present invention provides a method of inhibiting CDK12 in vitro or in vivo, said method comprising treating a population of cells with an effective amount of a compound of formula (I), or a pharmaceutically acceptable salt or N-oxide thereof, as defined herein.

In another aspect, the present invention provides a method of inhibiting CDK12 action in a human or animal subject in need of such inhibition, the method comprising administering to the subject an effective amount of a compound of formula (I), or a pharmaceutically acceptable salt or N-oxide thereof.

In another aspect is provided a compound of the formula (I), or a pharmaceutically acceptable salt or N-oxide thereof, for use as a medicament.

In another aspect is provided a compound of the formula (I), or a pharmaceutically acceptable salt or N-oxide thereof, for use in the treatment of a condition which is modulated by CDK12.

In another aspect is provided a compound of formula (I), or a pharmaceutically acceptable salt or N-oxide thereof, for use in the treatment of a disease selected from myotonic dystrophy (e.g. myotonic dystrophy type 1 or myotonic dystrophy type 2), Fragile X associated tremor/ataxia syndrome, amyotrophic lateral sclerosis (ALS) and frontotemporal dementia (C9ORF72), Huntington's Disease like 2, Huntington's Disease, Spinocerebellar Ataxia Types 1, 2, 3, 6, 7, 8, 10, 31, 17, Dentatorubral-pallidoluysian atrophy and Spinal and Bulbar Muscular Atrophy and Cancer.

In another aspect is provided a method of treating a disease selected from myotonic dystrophy (e.g. myotonic dystrophy type 1 and myotonic dystrophy type 2), Fragile X associated tremor/ataxia syndrome, amyotrophic lateral sclerosis (ALS) and frontotemporal dementia (C9ORF72), Huntington's Disease like 2, Huntington's Disease, Spinocerebellar Ataxia Types 1, 2, 3, 6, 7, 8, 10, 31, 17, Dentatorubral-pallidoluysian atrophy and Spinal and Bulbar Muscular Atrophy and Cancer, the method comprising administering to said subject an effective amount of a compound of the formula (I), or a pharmaceutically acceptable salt or N-oxide thereof.

In another aspect is provided the use of a compound of formula (I), or a pharmaceutically acceptable salt or N-oxide thereof, for use in the manufacture of a medicament for treatment of a disease selected from myotonic dystrophy (e.g. myotonic dystrophy type 1 and myotonic dystrophy type 2), Fragile X associated tremor/ataxia syndrome, amyotrophic lateral sclerosis (ALS) and frontotemporal dementia (C9ORF72), Huntington's Disease like 2, Huntington's Disease, Spinocerebellar Ataxia Types 1, 2, 3, 6, 7, 8, 10, 31, 17, Dentatorubral-pallidoluysian atrophy and Spinal and Bulbar Muscular Atrophy and Cancer.

The disease may be myotonic dystrophy. The disease may be myotonic dystrophy type 1.

Routes of Administration

The compounds of the invention or pharmaceutical composition comprising the active compound may be administered to a subject by any convenient route of administration, whether systemically/peripherally or topically (i.e. at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; or by implant.

General Synthetic Schemes

Compounds of the invention may be prepared using the general methods described below. It will be evident to those skilled in the art that the use of protecting groups may be necessary at any stage of the syntheses in order to enable the transformation to take place selectively at the desired position. The introduction and removal of protecting groups may be undertaken by standard procedures known to those skilled in the art.

reagent W—B—Z-A-Q wherein B and A are each independently either —C(O)— or —S(O)$_2$— and Q is a leaving group such as a halogen, preferably Cl, or OH (only when B is —C(O)—). In the case that Q is a halogen the reaction is performed in the presence of a base such as Et$_3$N or DIPEA in a solvent such as DCM or DMF at 0° C. to r.t.; in the case that X is OH the reaction is performed using a coupling agent such as T3P, HATU or EDCI in the presence of a base such as Et$_3$N or DIPEA in a solvent such as DCM, DMF or THF at 0° C. to r.t. Compounds W—B—Z-A-Q are either commercially available or can be made by standard methods.

Alternatively a subset of compounds of the invention in which R$^2$ is X—NR$^x$—B—Z-A-W may be prepared from compounds 5 by reaction with a reagent W-AQ wherein A is either —C(O)— or —S(O)$_2$— and Q is a leaving group such as a halogen, preferably Cl, or OH (only when A is —C(O)—) using similar conditions as for the conversion of compounds 3 to compounds I. Compounds W-AQ are either commercially available or can be made by standard methods. Compounds 5 are compounds of the invention I wherein R$^2$ is —XNR$^x$BZ.

Compounds 5 can be prepared from compounds 3 by reaction with a reagent Z-BQ wherein B is either —C(O)— or —S(O)$_2$— and Q is a leaving group such as a halogen, preferably Cl, or OH (only when A is —C(O)—) using similar conditions as for the conversion of 3 to I. Compounds 3 are compounds of the invention I wherein R$^2$ is —XNR$^x$R$^y$.

Compounds 3 can be prepared from compounds 2 wherein Y is a leaving group such as Br or Cl by reaction with R$^3$-D wherein D is a group such as SnBu$_3$, B(OH)$_2$ or preferably BPin in the presence of a catalyst such as XPhos-Pd-G3 and a base such as K$_3$PO$_4$ (not required when M is SnBu$_3$) in a suitable solvent such as a mixture of THF, EtOH, H$_2$O at a temperature between room temperature and the boiling point of the solvent. Alternatively compounds 3

Scheme 1

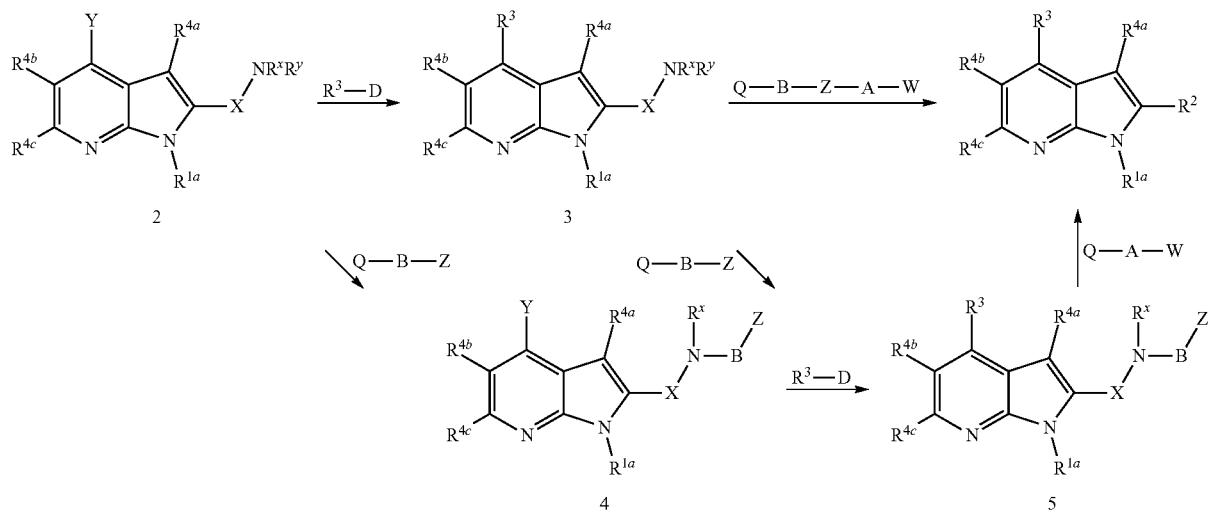

A subset of compounds of the invention in which R$^2$ is X—NR$^x$—B—Z-A-W (wherein B and A are each independently either —C(O)— or —S(O)$_2$—) may be prepared as shown in Scheme 1. Where R$^2$ is X—NR$^x$—B—Z-A-W, they may be prepared by reaction of compounds 3 with a can be prepared from compounds 2 wherein Y is a group such as SnBu$_3$, B(OH)$_2$ or BPin by reaction with R$^3$-D wherein D is a leaving group such as Br or Cl under similar conditions. Compounds R$^3$-D are commercially available or can be prepared using the routes shown in Scheme 7.

Compounds 2 can be prepared using the methods shown in the schemes below.

Alternatively compounds 5 can be prepared from compounds 4 wherein Y is leaving group such as Br or Cl by reaction with $R^3$-D wherein D is a group such as $SnBu_3$, $B(OH)_2$ or preferably BPin using procedures similar to those for the conversion of compounds 2 to compounds 3. Alternatively compounds 5 can be prepared from compounds 4 wherein Y is a group such as $SnBu_3$, $B(OH)_2$ or BPin by reaction with $R^3$-D wherein D is a leaving group such as Br or Cl by similar procedures. Compounds $R^3$-D are commercially available or can be prepared using the routes shown in Scheme 7.

Compounds 4 can be prepared from compounds 2 by reaction with a reagent Z-BQ wherein B is either —C(O)— or —S(O)$_2$— and Q is a leaving group such as a halogen, preferably Cl, or OH (only when B is —C(O)—) using similar conditions as for the conversion of 3 to I.

It will be clear to those skilled in the art that the use of protecting groups may be needed to enable the transformations to take place selectively.

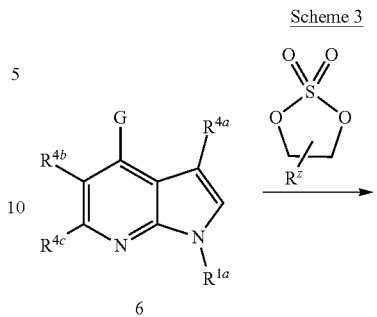

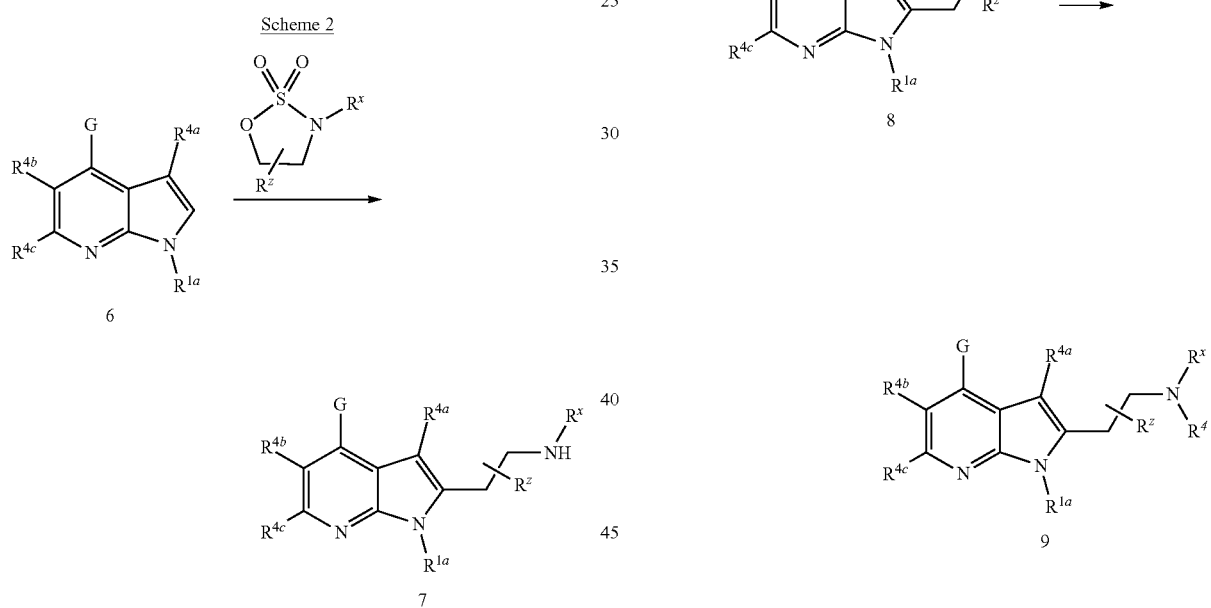

Compounds 2 or 3 wherein X is optionally substituted —CH$_2$CH$_2$— may be prepared as shown in Scheme 2. Compounds 7 wherein G is either Y or $R^3$ may be prepared from compounds 6 by deprotonation with a strong base such as LDA at a temperature between 0° C. and −78° C. followed by alkylation with an electrophile such as tert-butyl 1,2,3-oxathiazolidine-3-carboxylate 2,2-dioxide at a temperature between −78° C. and room temperature.

Compounds 6 or 7 wherein G is $R^3$ can be prepared from compounds 6 or 7 respectively wherein G is Y using the methods shown for the preparation of compounds 3 from compounds 2 in Scheme 1.

Compounds 6 are commercially available or can be prepared by methods known to those skilled in the art or by methods described herein.

Alternatively compounds 2 or 3 wherein X is optionally substituted —CH$_2$CH$_2$— may be prepared as shown in Scheme 3. Compounds 9 wherein G is either Y or $R^3$ may be prepared from compounds 8 by conversion of the alcohol to a leaving group such as Cl or mesylate by standard methods known to those skilled in the art followed by displacement of the leaving group with an amine $R^xR^y$NH in a suitable solvent such as EtOH at elevated temperature such as the boiling point of the solvent. Compounds 8 can be prepared from compounds 6 by deprotonation with a strong base such as LDA at a temperature between 0° C. and −78° C. followed by alkylation with an electrophile such as 1,3,2-dioxathiolane 2,2-dioxide at a temperature between −78° C. and room temperature.

Compounds 6, 8 or 9 wherein G is $R^3$ can be prepared from compounds 6, 8 or 9 respectively wherein G is Y using the methods shown for the preparation of compounds 3 from compounds 2 in Scheme 1.

Scheme 4

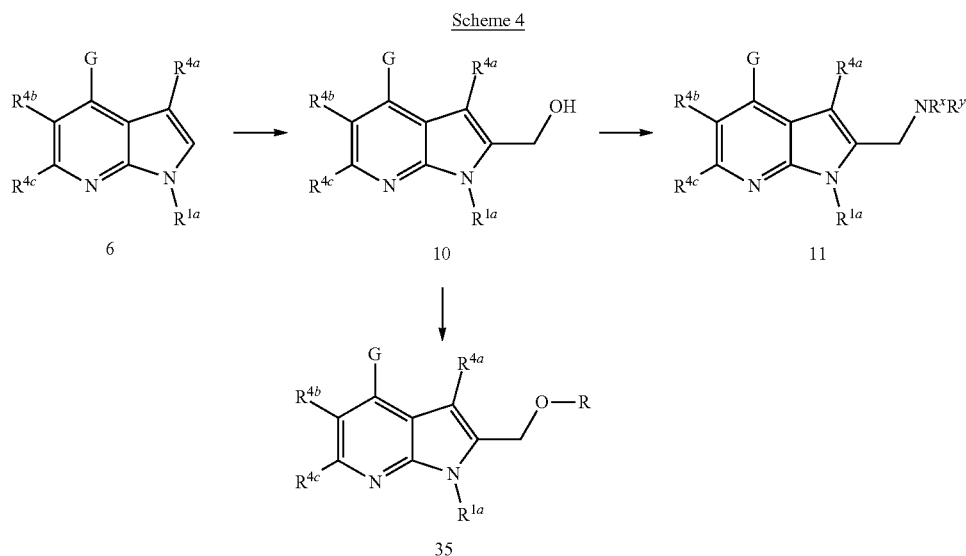

Compounds 2 or 3 wherein X is —CH$_2$— may be prepared as shown in Scheme 4. Compounds 11 wherein G is either Y or R$^3$ may be prepared from compounds 10 by conversion of the alcohol to a leaving group such as Cl or mesylate by standard methods known to those skilled in the art followed by displacement of the leaving group with an amine R$^x$R$^y$NH in a suitable solvent such as EtOH at elevated temperature such as the boiling point of the solvent. In the case that R$^x$ and R$^y$ are both hydrogen the leaving group can be displaced with a suitable nucleophile such as sodium azide in a suitable solvent such as DMF at a suitable temperature such as room temperature and the resulting azide intermediate is then converted to the amine by standard methods of reduction known to those skilled in the art such as using triphenylphosphine in water at a suitable temperature such as 50° C.

Compounds 35 wherein G is either Y or R$^3$ can be prepared from compounds 10 by conversion of the alcohol to a leaving group as described above followed by displacement of the leaving group with an alkoxide RO-M wherein M is a metal such as sodium, in a suitable solvent such as DMF at a suitable temperature such as room temperature. RO-M can be formed in situ by reaction of an alcohol ROH with a suitable base such as NaH by standard methods known to those skilled in the art. Compounds 35 wherein G is R$^3$ are compounds of the invention I wherein R$^2$ is —CH$_2$—OR. In the case that R contains a primary or secondary amine, R can be further elaborated using the methods shown in Scheme 1.

Compounds 10 can be prepared from compounds 6 by deprotonation with a strong base such as LDA in a suitable solvent such as THF at a temperature between 0° C. and −78° C. followed by reaction with an acylating agent such as ethyl formate at a temperature between −78° C. and room temperature. The resulting aldehyde intermediate can be reduced to the alcohol using standard conditions such as sodium borohydride in a suitable solvent such as MeOH at a suitable temperature such as 0° C. to room temperature.

Compounds 6, 10, 11 or 35 wherein G is R$^3$ can be prepared from compounds 6, 10, 11 or 35 respectively wherein G is Y using the methods shown for the preparation of compounds 3 from compounds 2 in Scheme 1.

Compounds 2 or 3 wherein XNR$^x$R$^y$ is

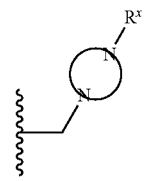

may be prepared using the route shown in Scheme 4 for the preparation of compounds 11 from compounds 10. The alcohol in compounds 10 is converted to a leaving group such as Cl or mesylate by standard methods known to those skilled in the art followed by displacement of the leaving group with an amine

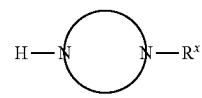

in the presence of a suitable base such as K$_2$CO$_3$ in a suitable solvent such as DMF. In the case that R$^x$ is H or R$^x$ contains a primary or secondary amine, NR$^x$ can be further elaborated using the methods shown in Scheme 1.

Scheme 5

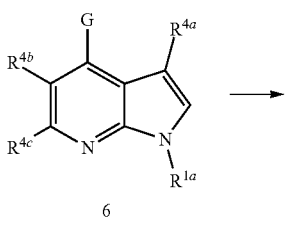

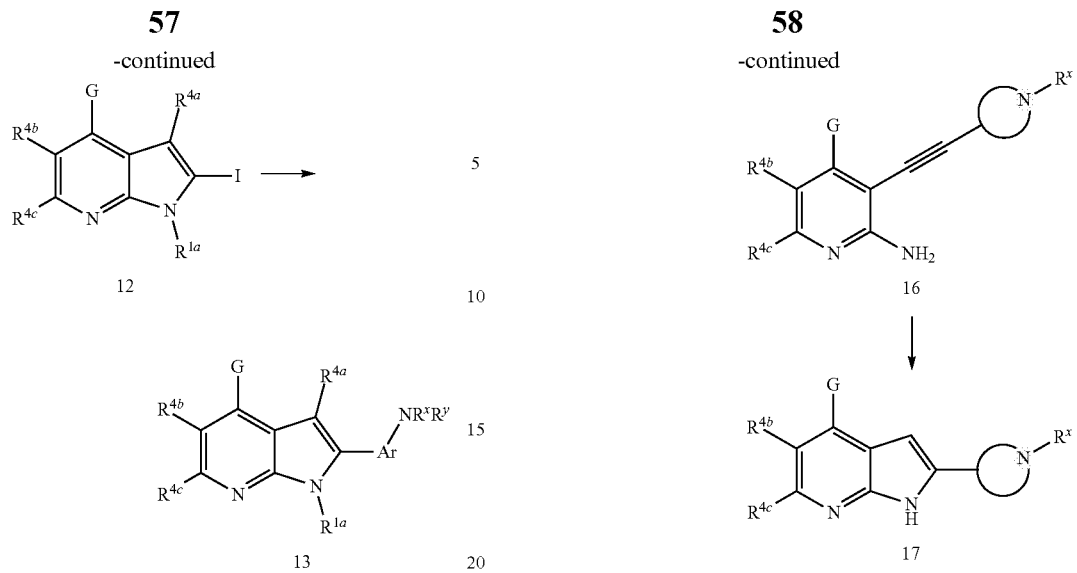

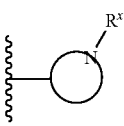

Compounds 2 or 3 wherein X is an aryl group (shown above as —Ar—) may be prepared as shown in Scheme 5. Compounds 13 wherein G is either Y or R³ may be prepared from compounds 12 by reaction with a nucleophile R-M wherein M is a metal such as SnBu₃, BPin or preferably B(OH)₂ in the presence of a catalyst such as PdCl₂(dppf). DCM in the presence of a base such as K₂CO₃ (not required when M is SnBu₃) in a suitable solvent such as DMF at a temperature between room temperature and the boiling point of the solvent.

Compounds 12 may be made from compounds 6 by deprotonation with a strong base such as LDA in a suitable solvent such as THF at a temperature between 0° C. and −78° C. followed by quenching with iodine at a temperature between −78° C. and room temperature.

Compounds 6, 12 or 13 wherein G is R³ can be prepared from compounds 6, 12 or 13 respectively wherein G is Y using the methods shown for the preparation of compounds 3 from compounds 2 in Scheme 1.

Compounds 2 or 3 wherein X is may be prepared as shown in Scheme 6. Compounds 17 wherein G is either Y or R³ may be prepared from compounds 16 by reaction with a base such as potassium tert-butoxide in the presence of a suitable solvent such as NMP at a suitable temperature such as room temperature.

Compounds 16 can be prepared by reaction of compounds 15 with compounds 18 in the presence of a suitable catalyst such as Pd(PPh₃)₂Cl₂ and CuI and a suitable base such as Et₃N in a suitable solvent such as MeCN at a temperature between room temperature and the boiling point of the solvent.

Compounds 18 are commercially available or can be prepared by methods known in the literature e.g. WO2016007722 or WO2016007736.

Compounds 15 can be prepared from compounds 14 by reaction with aqueous ammonia in a suitable solvent such as dioxane at a suitable temperature such as 120° C. under microwave heating.

Compounds 16 or 17 wherein G is R³ can be prepared from compounds 16 or 17 receptively wherein G is Y using the methods shown for the preparation of compounds 3 from compounds 2 in Scheme 1.

Scheme 6

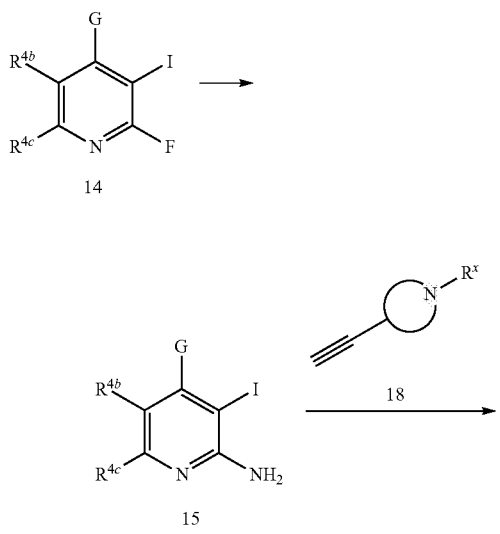

Scheme 7

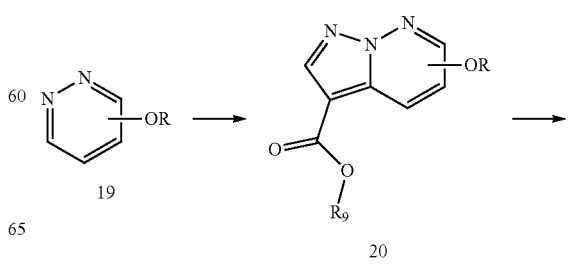

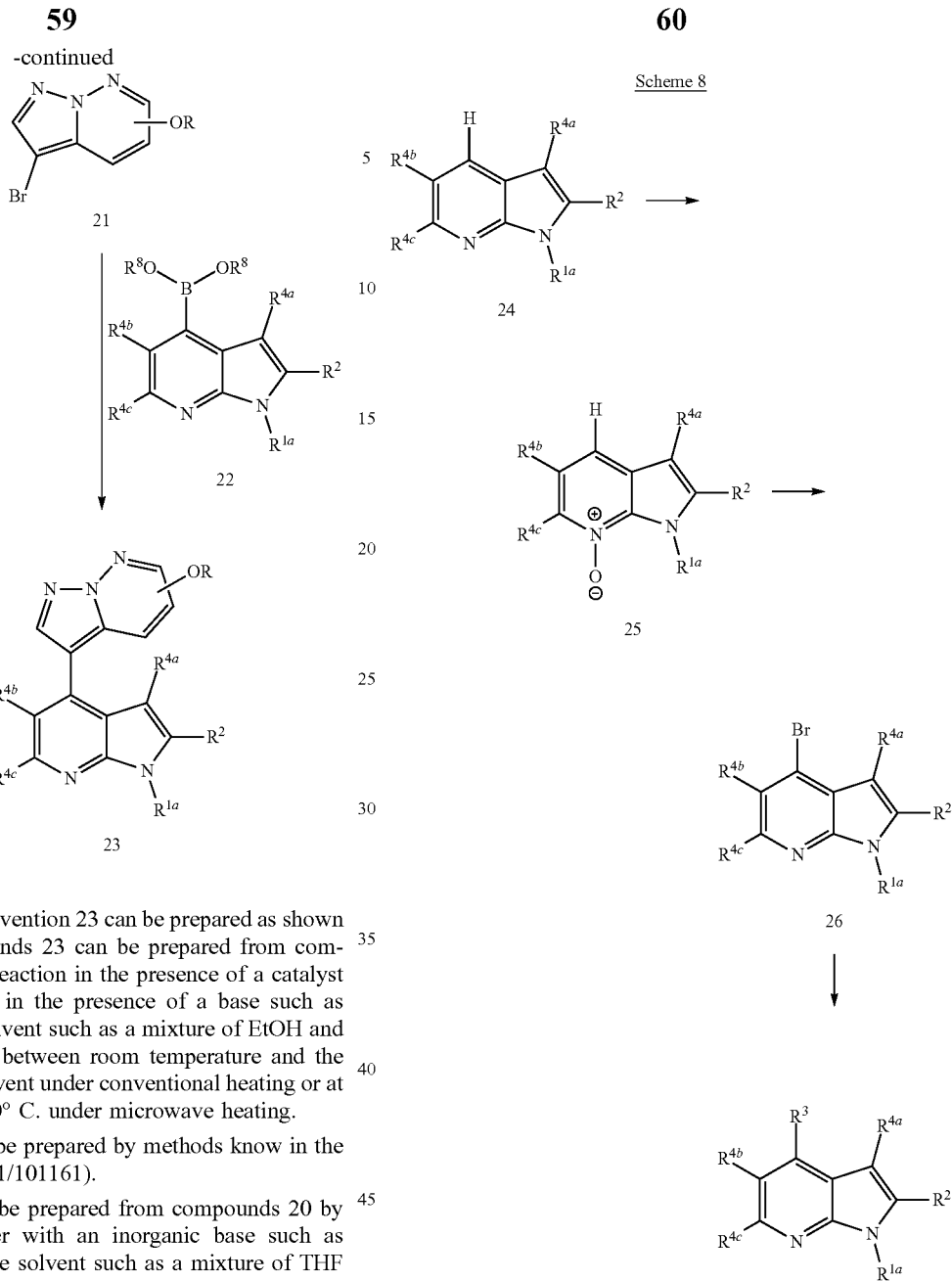

Scheme 8

Compounds of the invention 23 can be prepared as shown in Scheme 7. Compounds 23 can be prepared from compounds 21 and 22 by reaction in the presence of a catalyst such as Xphos-Pd-G3 in the presence of a base such as $K_3PO_4$ in a suitable solvent such as a mixture of EtOH and $H_2O$ at a temperature between room temperature and the boiling point of the solvent under conventional heating or at temperatures up to 140° C. under microwave heating.

Compounds 22 can be prepared by methods know in the literature (e.g. WO2011/101161).

Compounds 21 can be prepared from compounds 20 by hydrolysis of the ester with an inorganic base such as $LiOH.H_2O$ in a suitable solvent such as a mixture of THF and $H_2O$ at a suitable temperature such as room temperature followed by decarboxylative-bromination using a suitable source of bromide such as N-bromosuccinimide in the presence of a base such as sodium hydrogen carbonate in a suitable solvent such as DMF at a suitable temperature such as room temperature.

Compounds 20 can be prepared by reaction of hydroxylamine-O-sulfonic acid in water buffered with potassium bicarbonate to pH 5-6 with compounds 19 at a suitable temperature such as room temperature to the boiling point of the solvent, preferably around 70° C. The resulting aminopyridazinium salt is then reacted with an alkyl propiolate such as methyl propiolate in the presence of a suitable base such as potassium carbonate in a suitable solvent such as DMF at a suitable temperature such as room temperature.

Compounds 19 are known in the literature or can be prepared by standard methods known to those skilled in the art.

A subset of compounds of the invention may also be prepared from compounds 26 as shown in Scheme 8 using methods described for the conversion of compounds 2 to compounds 3 in Scheme 1. Compounds 26 may be prepared from compounds 25 by reaction with a suitable source of bromide such as tetramethylammonium bromide in the presence of methanesulfonic anhydride in a suitable solvent such as DMF at a suitable temperature such as from 0° C. to room temperature.

Compounds 25 can be prepared from compounds 24 by reaction with an oxidising agent such as mCPBA in a suitable solvent such as EtOAc at a suitable temperature such as from 0° C. to room temperature.

Compounds 24 are known in the literature or may be prepared by standard methods known to those skilled in the art or may be prepared using the methods described herein.

Scheme 9

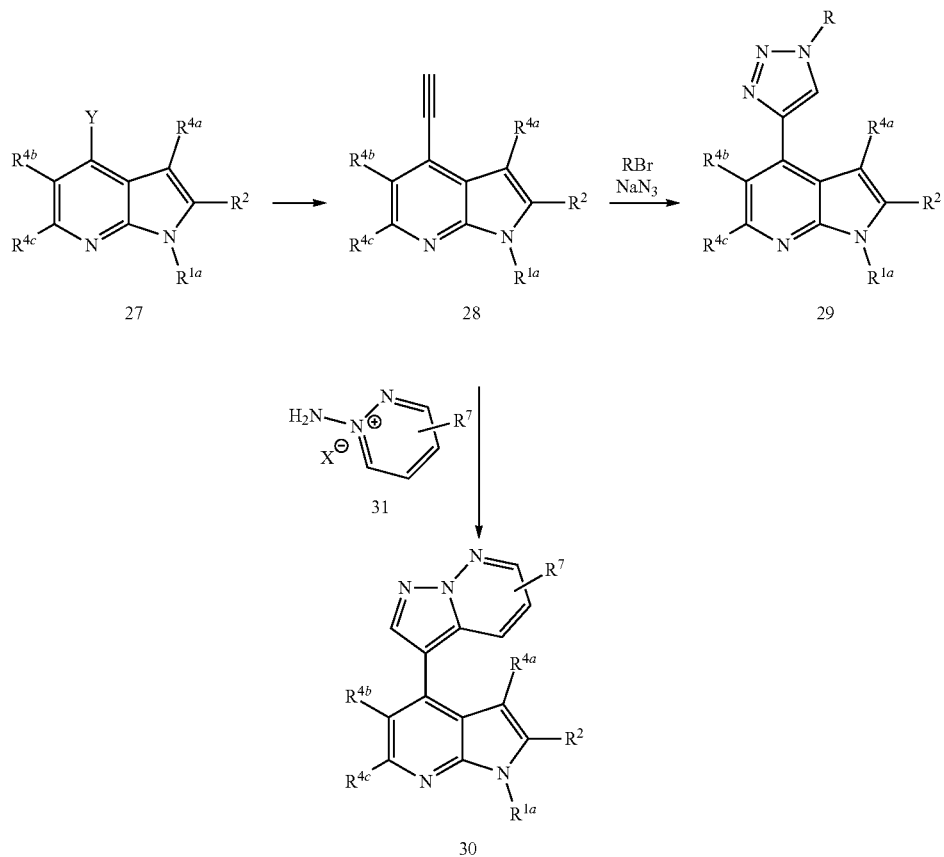

A subset of compounds of the invention in which $R^3$ is a 1H-1,2,3-triazol-4-yl substituted at the 1-position or an optionally substituted pyrazolo[1,5-b]pyridazin3-yl substituent can be prepared as shown in Scheme 9. Compounds 29 can be prepared from compounds 28 by reaction with an alkyl halide R—Br and sodium azide in the presence of copper sulfate and sodium ascorbate in the presence of a suitable solvent such as a mixture of tert-butanol and water at a suitable temperature such as room temperature.

Compounds 30 can be prepared from compounds 28 by reaction with an optionally substituted 1-aminopyridazinium salt 31 in the presence of a base such as potassium hydroxide or DBU in a suitable solvent such as a mixture of DCM and water if the base is potassium hydroxide or MeCN if the base is DBU, at a suitable temperature such as from 0° C. to room temperature according to methods known in the literature (e.g. WO2003051886).

Compounds 31 are known in the literature or can be prepared by methods known to those skilled in the art or by methods described herein in Scheme 7 (in the first part of the preparation of compounds 20 from compounds 19).

Compounds 28 can be prepared from compounds 27 wherein Y is a leaving group such as bromide by reaction with ethynyltrimethylsilane followed by removal of the trimethylsilyl group as described in ACS Combinatorial Science, 2015, 17, 1, 5-10.

Scheme 10

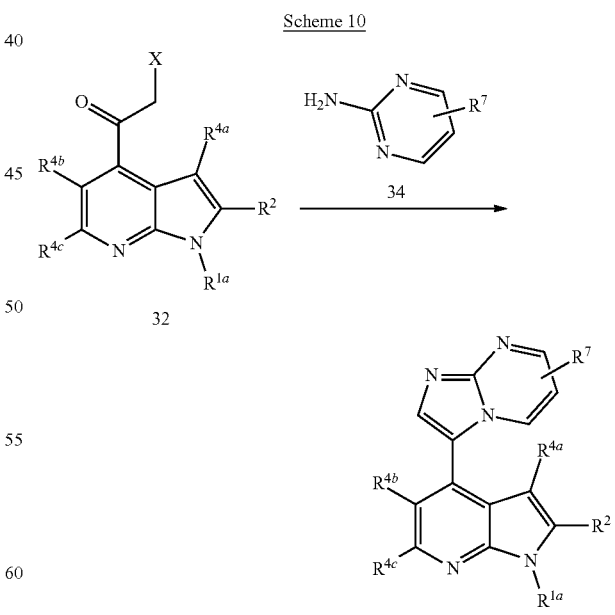

A subset of compounds of the invention in which $R^3$ is an optionally substituted imidazo[1,2-a]pyrimidin-3-yl substituent can be prepared as shown in Scheme 10. Compounds 33 can be prepared by reaction of a halo-ketone 32 wherein X is a halogen, preferably Br, with an optionally substituted 2-amino-pyrimidine 34 in the presence of a base such as sodium hydrogen carbonate in a suitable solvent such as iso-propanol as a suitable temperature such as from room temperature to the boiling point of the solvent.

Compounds 32 can be prepared according to standard methods in the literature such as reported in J. Med. Chem. (2008), 51(3), 487.

Compounds 34 are commercially available or can be prepared by standard methods known to those skilled in the art.

Scheme 11

36

37

A subset of compounds of the invention I in which $R^2$ is —CONR$^x$R$^y$ can be prepared as shown in Scheme 11. Compounds 37 wherein G is $R^3$ or a leaving group such as bromide or chloride can be prepared from compounds 36 by reaction with an amine R$^x$R$^y$NH in a suitable solvent such as methanol at elevated temperature such as in a sealed tube at around 100° C.

Compounds 36 or 37 wherein G is $R^3$ can be prepared from compounds 36 or 37 respectively wherein G is Y using the methods shown for the preparation of compounds 3 from compounds 2 in Scheme 1.

Compounds 36 wherein G is Y are commercially available or known in the literature.

Examples

Abbreviations Used in the Experimental Section

Brett Phos Pd G3 [(2-Di-cyclohexylphosphino-3,6-dimethoxy-2',4',6'-triisopropyl-1,1'-biphenyl)-2-(2'-amino-1,1'-biphenyl)]palladium(II) methanesulfonate methanesulfonate
DAD Diode array
DCC N,N'-Dicyclohexylcarbodiimide
DCM Dichloromethane
DIPEA Di-isopropylethylamine
DMAP 4-(Dimethylamino)pyridine
DMC Dimethylcarbonate
DMF N,N-dimethylformamide
DMSO Dimethylsulphoxide
EDC.HCl (3-Dimethylaminopropyl)-N'-ethylcarbodiimide hydrochloride
FCC Flash column chromatography
h Hour(s)
HATU (1-[Bis(dimethylamino)methylene]-1H-1,2,3-triazolo[4,5-b]pyridinium 3-oxid hexafluorophosphate)
HMN Diatomaceous earth
HOBt Hydroxybenzotriazole
HPLC High performance liquid chromatography
IMS Industrial methylated spirits
IPA Isopropanol
LCMS Liquid chromatography-mass spectrometry
LDA Lithium diisopropylamide
mCPBA 3-Chloroperbenzoic acid
MDAP Mass-directed autopurification
MeCN Acetonitrile
MsCl Methanesulfonyl chloride
NMP 1-Methyl-2-pyrrolidinone
Pd(dppf)Cl$_2$. DCM [1,1'-Bis(diphenylphosphino)ferrocene]dichloropalladium(II), complex with DCM (1:1)
Petrol Petroleum ether bp 40-60° C.
Rt Retention time
r.t. Room temperature
SFC Supercritical Fluid Chromatography
T3P Propylphosphonic anhydride solution
TEA Triethylamine
TFA Trifluoroacetic acid
THF Tetrahydrofuran
TLC Thin layer chromatography
X-Phos-Pd-G3 (2-Dicyclohexylphosphino-2',4',6'-triisopropyl-1,1'-biphenyl)[2-(2'-amino-1,1'-biphenyl)]palladium(II) methanesulfonate In the procedures that follow, after each starting material, reference to an Intermediate/Example number is usually provided. This is provided merely for assistance to the skilled chemist. The starting material may not necessarily have been prepared from the batch referred to.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

The nomenclature of the unknown structures was assigned using ChemDraw Professional version 16.0.

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane (b=0 ppm). J values are given in Hz through-out. NMR spectra were assigned using CMC-Assist Version 2.3 or SpinWorks version 3.

Alternatively, NMR spectra were obtained on a Bruker DPX-400 spectrometer with a BBFO probe operating at 400 MHz, or on a Bruker AV-400 spectrometer with a BBFO probe operating at 400 MHz, or on a Bruker AV3-400 spectrometer with a BBFO probe operating at 400 MHz, or on a Bruker AV3-400HD spectrometer with a Prodigy Cryoprobe operating at 400 MHz or on a Bruker DRX 500 spectrometer with a Cryoprobe probe operating at 500 MHz. The chemical shifts are quoted in parts per million (ppm) relative to residual solvent peaks. All coupling constants are quoted in Hertz. Assignments were made on the basis of chemical shift using standard Bruker software with no modifications.

The Liquid Chromatography Mass Spectroscopy (LCMS) systems used are:

Method 1

Acquity UPLC (binary pump/PDA detector)+ZQ Mass Spectrometer with an ACQUITY UPLC BEH $C_{18}$ 1.7 μm, 100×2.1 mm, maintained at 40° C. Elution with A: water+0.1% formic acid; B: acetonitrile+0.1% formic acid. Gradient:

| Gradient - Time | flow mL/min | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA. MS ionization method—Electrospray (positive and negative ion).

Method 2

Acquity i-Class (quaternary pump/PDA detector)+Quattro Micro Mass Spectrometer with an ACQUITY UPLC BEH $C_{18}$ 1.7 μm, 100×2.1 mm, maintained at 40° C. Elution with A: water+0.1% formic acid; B: acetonitrile+0.1% formic acid. Gradient:

| Gradient - Time | flow mL/min | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA. MS ionization method—Electrospray (positive and negative ion).

Method 3

Acquity H-Class (quaternary pump/PDA detector)+QDa Mass Spectrometer, Acquity UPLC CSH C18 1.7 μm, 50×2.1 mm at 40° C. Elution with A: water+0.1% formic acid; B: acetonitrile+0.1% formic acid. Gradient:

| Gradient - Time | flow mL/min | % A | % B |
|---|---|---|---|
| 0.00 | 1.0 | 97 | 3 |
| 1.50 | 1.0 | 1 | 99 |
| 1.90 | 1.0 | 1 | 99 |
| 2.00 | 1.0 | 97 | 3 |
| 2.50 | 1.0 | 97 | 3 |

Detection—MS, UV diode array 190-400 nm. MS ionization method—Electrospray (positive and negative ion).

Method 4

Agilent 1260 HPLC (binary pump detector)+Agilent 6120 Mass Spectrometer, Waters XBridge C18 3.5 μm, 30×2.1 mm at 40° C. Elution with A: 0.1% aqueous ammonia; B: acetonitrile. Gradient:

| Gradient - Time | flow mL/min | % A | % B |
|---|---|---|---|
| 0.00 | 0.8 | 95 | 5 |
| 3.00 | 0.8 | 5 | 95 |
| 3.10 | 0.8 | 0 | 100 |
| 3.50 | 0.8 | 0 | 100 |
| 3.51 | 0.8 | 95 | 5 |
| 4.50 | 0.8 | 95 | 5 |

Detection—MS, UV 254 nm. MS ionization method—Electrospray (positive and negative ion).

The MDAP purification systems used are:

MDAP Method (Acidic)

Agilent Technologies 1260 Infinity purification system with an XSELECT CSH Prep C18 column (19×250 mm, 5 μm OBD) maintained at RT Mobile Phase A: 0.1% aqueous formic acid Mobile Phase B: 0.1% formic acid in acetonitrile Flow Rate: 20 ml/min Gradient Program: 10%-95%, 22 min, centered around a specific focused gradient Sample: Injection of a 20-60 mg/ml solution in DMSO (+optional formic acid and water)

MDAP Method (Basic)

Agilent Technologies 1260 Infinity purification system with an XBridge Prep C18 OBD column (19×250 mm, 5 μm OBD) maintained at RT Mobile Phase A: 0.1% aqueous ammonia Mobile Phase B: 0.1% ammonia in acetonitrile Flow Rate: 20 ml/min Gradient Program: 10%-95%, 22 min, centered around a specific focused gradient Sample: Injection of a 20-60 mg/ml solution in DMSO+ optional formic acid and water)

Purification by Supercritical Fluid Chromatography (SFC) was performed using either Waters Thar Prep100 preparative SFC system (P200 CO2 pump, 2545 modifier pump, 2998 UV/VIS detector, 2767 liquid handler with Stacked Injection Module) or Waters Thar Investigator semi preparative system (Waters Fluid Delivery Module, 2998 UV/VIS detector, Waters Fraction Collection Module). Where the Waters 2767 liquid handler was used it acted as both auto-sampler and fraction collector.

Appropriate isocratic methods were selected based on methanol, ethanol or isopropanol solvent systems under un-modified or basic conditions. The modifier used under basic conditions was diethyl amine (0.1% V/V). Alternate modifiers such as formic acid (0.1% V/V), acetic acid (0.1% V/V), etc may be used as an acidic modifier.

The purification was controlled either by Waters Fractionlynx or Waters Chromscope software through monitoring at 210-400 nm and triggered a threshold collection value at an appropriate wavelength. Collected fractions were analysed by SFC (Waters/Thar SFC systems with Waters SQD or Waters UPCC with Waters QDa). The fractions that contained the desired product were concentrated by vacuum centrifugation.

Where products were purified by flash column chromatography (FCC), 'flash silica' refers to silica gel for chromatography, 0.035 to 0.070 mm (220 to 440 mesh) (e.g. Fluka silica gel 60) or pre-packed columns supplied by Interchim or Isolute or use of the CombiFlash® Companion purification system or use of the Biotage SP1 purification system. All of the solvents used were of analytical grade and were used as received. Petroleum ether refers to light petroleum, bp 40-60° C.

Intermediate 1: 4-Chloro-6-methyl-1H-pyrrolo[2,3-b]pyridine a. 6-Methyl-1H-pyrrolo[2,3-b]pyridine 7-oxide

A solution of 6-methyl-1H-pyrrolo[2,3-b]pyridine (1.07 g, 8.1 mmol) in ethyl acetate (37 mL) at 0° C. was treated with mCPBA (2.1 g, 12.2 mmol) then stirred at 0° C. for 40 mins. mCPBA (0.21 g, 1.2 mmol) was added at 0° C. then left to warm to r.t and stirred overnight. Saturated aqueous sodium bicarbonate was added and the organic layer was separated. The aqueous was extracted with ethyl acetate, the combined organic phase was washed with saturated sodium bicarbonate, brine then dried ($Na_2SO_4$) and concentrated in vacuo. The aqueous layers were combined and extracted with 2-methyltetrahydrofuran and the combined extracts were dried ($Na_2SO_4$) and concentrated in vacuo. The two crude products were dissolved in hot methanol, combined, preadsorbed onto diatomaceous earth and purified by FCC eluting with 0-10% MeOH/DCM to afford the title compound as a pale orange solid (0.57 g, 48%)
LCMS (Method 3): Rt 0.74 min, m/z 149.1[MH$^+$].

b. 4-Chloro-6-methyl-1H-pyrrolo[2,3-b]pyridine

A suspension of 6-methyl-1H-pyrrolo[2,3-b]pyridine 7-oxide (100 mg, 0.68 mmol) in anhydrous DMF (3 ml) was treated with methanesulfonyl chloride (0.13 ml, 1.7 mmol) and heated at 75° C. overnight. After cooling to room temperature it was neutralised with 6N NaOH, resulting suspension filtered, and washed with water. The aqueous was extracted with ethyl acetate and the organic extracts were combined, washed with saturated sodium bicarbonate, brine, dried ($Na_2SO_4$) and concentrated in vacuo. The crude product was dissolved in DCM/MeOH, preadsorbed onto HMN and purified by FCC eluting with a gradient from 0-30% EtOAc/DCM to afford the title compound as a white solid (50 mg, 42%)
LCMS (Method 3): Rt 1.14 min, m/z 167.1[MH$^+$].

Intermediate 2: 4-Chloro-N,N-dimethyl-1H-pyrrolo[2,3-b]pyridine-2-carboxylic acid A mixture of methyl 4-chloro-1H-pyrrolo[2,3-b]pyridine-2-carboxylate (278 mg, 1.32 mmol) and potassium carbonate (456 mg, 3.30 mmol) in methanol (15 mL) and water (5 mL) was heated at 65° C. overnight. After cooling to room temperature, it was concentrated in vacuo. The aqueous solution was acidified with conc. hydrochloric acid to pH=2, and the mixture was extracted with ethyl acetate (×3). The organic extracts were combined, dried ($Na_2SO_4$) and concentrated in vacuo to afford the title compound as a white solid (250 mg, 96%)
LCMS (Method 3): Rt 1.16 min, m/z 196.9 [MH$^+$].

Intermediate 3: 4-Chloro-N,N-dimethyl-1H-pyrrolo[2,3-b]pyridine-2-carboxamide To a mixture of a 4-chloro-1H-pyrrolo[2,3-b]pyridine-2-carboxylic acid (Intermediate 2, 120 mg, 0.61 mmol), HOBt (103 mg, 0.76 mmol), and EDC.HCl (146 mg, 0.76 mmol) in DMF (10 mL) was added dimethylamine.HCl (62 mg, 0.76 mmol) in dioxane (2 mL) and the mixture was stirred at r.t. overnight. The solvent was concentrated in vacuo, and the residue was partitioned between ethyl acetate and saturated aqueous sodium bicarbonate solution. The organic layer was washed with brine, dried ($Na_2SO_4$) and concentrated in vacuo. The crude product was purified by FCC eluting with a gradient from 0-5% Methanol/DCM to afford the title compound as an off-white solid (110 mg, 81%)
LCMS (Method 3): Rt 1.49 min, m/z 223.9[MH$^+$].

Intermediate 4: 4-Chloro-N-(2-methoxyethyl)-1H-pyrrolo[2,3-b]pyridine-2-carboxamide A mixture of methyl 4-chloro-1H-pyrrolo[2,3-b]pyridine-2-carboxylate (Intermediate 2, 223 mg, 1.06 mmol) and 2-methoxyethan-1-amine (0.79 mL, 10.59 mmol) in MeOH (3 mL) was sealed in a vial and stirred and heated at 100° C. for 12 h. After cooling, the mixture was diluted with EtOAc and washed with an aqueous saturated solution of sodium bicarbonate. The aqueous was extracted with EtOAc and the combined organic phases were washed with brine, dried ($Na_2SO_4$) and concentrated in vacuo to give the title compound as a yellow solid (250 mg, 93%).
LCMS (Method 3): Rt 1.40 min, m/z 254/256 [MH$^+$].

By proceeding in a similar manner to Intermediate 4, the following compounds were prepared:

Intermediate 5: 4-Chloro-N-isobutyl-1H-pyrrolo[2,3-b]pyridine-2-carboxamide

Starting from 2-methylpropan-1-amine and methyl 4-chloro-1H-pyrrolo[2,3-b]pyridine-2-carboxylate (Intermediate 2).
LCMS (Method 3): Rt 1.68 min, m/z 252/254 [MH$^+$].

Intermediate 6: 4-chloro-N-isobutyl-1H-pyrrolo[2,3-b]pyridine-2-carboxamide

Starting from $N^1,N^1$-dimethylethane-1,2-diamine and methyl 4-chloro-1H-pyrrolo[2,3-b]pyridine-2-carboxylate (Intermediate 2).
LCMS (Method 3): Rt 1.42 min, m/z 267/269 [MH$^+$].

Intermediate 7: 4-Chloro-N-methyl-1H-pyrrolo[2,3-b]pyridine-2-carboxamide

Starting from methyl amine and methyl 4-chloro-1H-pyrrolo[2,3-b]pyridine-2-carboxylate (Intermediate 2).
LCMS (Method 3): Rt 0.99 min, m/z 210/212 [MH$^+$].

Intermediate 8: 4-Chloro-1H-pyrrolo[2,3-b]pyridine-2-carboxamide

A vial was charged with methyl 4-chloro-1H-pyrrolo[2,3-b]pyridine-2-carboxylate (Intermediate 2, 0.81 g, 3.80 mmol) and 7N methanolic ammonia (22 mL, 151.93 mmol). The sealed vessel was irradiated in the microwave (100° C., 10 h). After cooling, the reaction mixture was concentrated in vacuo and the residue was dissolved in EtOAc and washed with a saturated aqueous solution of $NaHCO_3$, brine, dried ($Na_2SO_4$) and concentrated in vacuo to give the title compound.
LCMS (Method 3): Rt 1.23 min, m/z 196/168 [MH$^+$].

Intermediate 9: 4-((4-Bromo-1H-pyrrolo[2,3-b]pyridin-2-yl)methyl)morpholine

A mixture of (4-bromo-1-(phenylsulfonyl)-1H-pyrrolo[2,3-b]pyridin-2-yl)methyl methanesulfonate (which can be prepared as described in WO2009112475 or WO2008034860) (0.12 g, 0.28 mmol) and morpholine (0.060 g, 0.68 mmol) in THF (2.5 mL) was heated at 100°

C. for 1 h. Potassium hydroxide solution (5% in MeOH, 2 mL) was added and the mixture was heated at 120° C. for 10 mins in the microwave. The reaction mixture was concentrated in vacuo and the residue was purified by FCC eluting with 0-40% EtOAc in cyclohexane to afford the title compound.

LCMS (Method 3): Rt 0.95 min, m/z 296, 298 [MH$^+$].

By proceeding in a similar manner to Intermediate 9, the following compounds were prepared:

Intermediate 10: N1-((4-Bromo-1H-pyrrolo[2,3-b]pyridin-2-yl)methyl)-N2,N2-dimethylethane-1,2-diamine Starting from (4-bromo-1-(phenylsulfonyl)-1H-pyrrolo[2,3-b]pyridin-2-yl)methyl methanesulfonate (which can be prepared as described in WO2009112475 or WO2008034860) and N,N-dimethylethylenediamine.

LCMS (Method 3): Rt 0.94 min, m/z 297, 299 [MH$^+$].

Intermediate 11: (4-Bromo-1-(phenylsulfonyl)-1H-pyrrolo[2,3-b]pyridin-2-yl)methanamine A mixture of (4-bromo-1-(phenylsulfonyl)-1H-pyrrolo[2,3-b]pyridin-2-yl)methyl methanesulfonate (which can be prepared as described in WO2009112475 or WO2008034860) (0.50 g, 1.1 mmol) and 7N ammonia solution in methanol (8.5 mL) in THF (3 mL) was heated at 120° C. in a microwave for 1 h. The reaction mixture was concentrated in vacuo and the residue was taken up in ethyl acetate, washed with a saturated aqueous sodium bicarbonate solution and brine, dried (Na$_2$SO$_4$) and concentrated in vacuo to afford the title compound.

LCMS (Method 3): Rt 0.85 min, m/z 366, 368 [MH$^+$].

Intermediate 12: N-((4-Bromo-1-(phenylsulfonyl)-1H-pyrrolo[2,3-b]pyridin-2-yl)methyl)-2-morpholinoacetamide A solution of (4-bromo-1-(phenylsulfonyl)-1H-pyrrolo[2,3-b]pyridin-2-yl)methanamine (Intermediate 11, 96 mg, 0.26 mmol), TBTU (84 mg, 0.26 mmol) and 4-morpholine acetic acid (34 mg, 0.24 mmol) was treated with DIPEA (0.2 mL, 1.2 mmol). The reaction mixture was stirred at room temperature overnight then concentrated in vacuo. The residue was taken up in ethyl acetate, washed with a saturated aqueous sodium bicarbonate solution and brine, dried (Na$_2$SO$_4$) and concentrated in vacuo to afford the title compound which was used in the next step without purification.

LCMS (Method 3): Rt 0.98 min, m/z 493, 495 [MH$^+$].

By proceeding in a similar manner to Intermediate 12, the following compounds were prepared:

Intermediate 13: N-((4-bromo-1-(phenylsulfonyl)-1H-pyrrolo[2,3-b]pyridin-2-yl)methyl)-2-(4-methylpiperazin-1-yl)acetamide Starting from (4-bromo-1-(phenylsulfonyl)-1H-pyrrolo[2,3-b]pyridin-2-yl)methanamine (Intermediate 11) and N-methyl piperidine acetic acid.

LCMS (Method 3): Rt 0.91 min, m/z 506, 508 [MH$^+$].

Intermediate 14: 4-Bromo-2-(chloromethyl)-1-(phenylsulfonyl)-1H-pyrrolo[2,3-b]pyridine A solution of 4-bromo-1-(phenylsulfonyl)-1H-pyrrolo[2,3-b]pyridine-2-methanol (1.1 g, 3.0 mmol) in DCM (25 mL) at 0° C. was treated with methanesulfonyl chloride (0.52 g, 4.5 mmol) and triethylamine (0.76 g, 7.5 mmol). The reaction mixture was stirred at room temperature for 6 h then diluted with DCM and washed with a 0.1M aqueous HCl solution, a saturated aqueous sodium bicarbonate solution and brine and concentrated in vacuo. The residue was purified by FCC eluting with 0-30% ethyl acetate in cyclohexane to afford the title compound.

LCMS (Method 3) Rt. 1.63 min, m/z 385, 387, 389 [MH$^+$].

Intermediate 15: tert-Butyl 4-((4-bromo-1-(phenylsulfonyl)-1H-pyrrolo[2,3-b]pyridin-2-yl)methyl)piperazine-1-carboxylate A mixture of 4-bromo-2-(chloromethyl)-1-(phenylsulfonyl)-1H-pyrrolo[2,3-b]pyridine (Intermediate 14, 0.20 g, 0.52 mmol) and tert-butyl piperazine carboxylate (0.97 g, 0.52 mmol) in THF (2 mL) was heated at 110° C. for 1 h in the microwave then at 120° C. for 1 h. A further portion of tert-butyl piperazine carboxylate (1.9 g, 1.0 mmol) was added and the reaction mixture was heated at 120° C. for another 1 h. The reaction mixture was concentrated in vacuo and the residue was taken up in ethyl acetate, washed with a saturated aqueous sodium bicarbonate solution and brine, dried (Na$_2$SO$_4$) and concentrated in vacuo. The crude product was purified by FCC eluting with 0-10% of a 2M ammonia solution in MeOH in DCM to afford the title compound.

LCMS (Method 3): Rt 1.47 min, m/z 535, 537 [MH$^+$].

Intermediate 16: 4-Bromo-2-((4-methylpiperazin-1-yl_methyl)-1-phenylsulfonyl)-1H-pyrrolo[2,3-b]pyridine A mixture of (4-bromo-1-(phenylsulfonyl)-1H-pyrrolo[2,3-b]pyridin-2-yl)methyl methanesulfonate (which can be prepared as described in WO2009112475 or WO2008034860) (0.248 g, 0.56 mmol) and N-methylpiperazine (0.14 g, 1.4 mmol) in THF (2.5 mL) was heated at 100° C. in the microwave for 30 mins. After cooling, the mixture was concentrated in vacuo and the residue was dissolved in ethyl acetate and washed with saturated aqueous sodium bicarbonate and brine, dried (Na$_2$SO$_4$) and concentrated in vacuo to give the title compound (0.136 g) as a yellow solid.

LCMS (Method 3) Rt 0.95 min, m/z 449, 451 [MH$^+$].

Intermediate 17: tert-Butyl 4-(imidazo[1,2-a]pyrimidin-3-yl)-1H-pyrrolo[2,3-b]pyridine-1-carboxylate A solution of tert-butyl 4-(2-bromoacetyl)-1H-pyrrolo[2,3-b]pyridine-1-carboxylate (which can be prepared according to J. Med. Chem., 2008, 51(3), 487) (0.051 g, 0.15 mmol), 2-aminopyrimidine (0.018 g, 0.188 mmol) and sodium bicarbonate (0.025 g, 0.03 mmol) in isopropanol (1 mL) was stirred and heated at 80° C. for 2 h. After cooling, the mixture was concentrated in vacuo and the residue was suspended in water and extracted with DCM. The organic phase was filtered through a phase separator and the filtrate was concentrated in vacuo. The residue was purified by FCC eluting with 0-4% methanol in DCM to give the title compound (0.017 g) as a yellow gum.

LCMS (Method 3) Rt 1.14 min m/z 280 (MH$^+$-t-Bu]

Intermediate 18: 1-Acryloylazetidine-2-carboxylic Acid

A solution of azetidine-2-carboxylic acid (505 mg, 5.00 mmol) in 2M KOH (7.50 mL, 15.0 mmol) at 0° C. was treated dropwise with acryloyl chloride (0.60 mL, 7.50 mmol), and then stirred at 0° C. for 1 h. The aqueous phase was washed with Et$_2$O (2×10 mL), and then the pH was adjusted to pH 2 with 6M HCl (aq), and extracted with CHCl$_3$ (5×50 mL). The combined organic phases were washed with brine (10 mL) dried (Na$_2$SO$_4$), filtered, and concentrated in vacuo. The resulting gum was triturated with Et$_2$O (3×10 mL) to give the title compound (201 mg, 26%) as a white solid.

$^1$H NMR (400 MHz, d$_6$-DMSO) Mixture of rotamers 12.92 (1H, s), 6.31 (0.5H, dd, J=17.0, 10.3 Hz), 6.24-6.00 (1.5H, m), 5.71 (0.5H, dd, J=10.3, 2.1 Hz), 5.61 (0.5H, dd, J=10.0, 2.5 Hz), 5.00 (0.5H, dd, J=9.8, 5.1 Hz), 4.59 (0.5H, dd, J=9.5, 5.5 Hz), 4.24-4.09 (1H, m), 3.92-3.74 (1H, m), 2.71-2.51 (1H, m), 2.22-2.05 (1H, m).

By proceeding in a similar manner to Intermediate 18, the following compounds were prepared:

Intermediate 19: 1-Acryloylazetidine-3-carboxylic Acid

Starting from azetidine-3-carboxylic acid and acryloyl chloride.

$^1$H NMR (400 MHz, d$_6$-DMSO) 12.72 (1H, s), 6.30 (1H, dd, J=17.0, 10.3 Hz), 6.09 (1H, dd, J=17.0, 2.2 Hz), 5.67 (1H, dd, J=10.3, 2.2 Hz), 4.37 (1H, t, J=8.8 Hz), 4.24 (1H, dd, J=8.5, 5.9 Hz), 4.08 (1H, t, J=9.6 Hz), 3.93 (1H, dd, J=9.9, 6.0 Hz), 3.42 (1H, tt, J=9.1, 5.9 Hz).

Intermediate 20: (S)-1-Acryloylpiperidine-3-carboxylic Acid

Starting from (S)-piperidine-3-carboxylic acid and acryloyl chloride.

$^1$H NMR (400 MHz, DMSO) Mixture of rotamers 12.41 (1H, s), 6.79 (1H, app. dt, J=16.6, 10.9), 6.06 (1H, app. t, J=15.0), 5.65 (1H, d, J=10.4), 4.40 (0.5H, d, J=12.2 Hz), 3.95-3.73 (1.5H, m), 3.44 (0.5H, dd, J=13.5, 8.6 Hz), 3.20-2.97 (1H, m), 2.82 (0.5H, t, J=11.7 Hz), 2.48-2.38 (0.5H, m), 2.30 (0.5H, m), 2.01-1.84 (1H, m), 1.76-1.51 (2H, m), 1.46-1.30 (1H, m).

Intermediate 21: (R)-1-Acryloylpiperidine-3-carboxylic Acid

Starting from (R)-piperidine-3-carboxylic acid and acryloyl chloride.

$^1$H NMR (400 MHz, d$_6$-DMSO) Mixture of rotamers 12.41 (1H, s), 6.79 (1H, app. dt, J=16.6, 10.9), 6.06 (1H, app. t, J=15.0), 5.65 (1H, d, J=10.4), 4.40 (0.5H, d, J=12.2 Hz), 3.95-3.73 (1.5H, m), 3.44 (0.5H, dd, J=13.5, 8.6 Hz), 3.20-2.97 (1H, m), 2.82 (0.5H, t, J=11.7 Hz), 2.48-2.38 (0.5H, m), 2.30 (0.5H, m), 2.01-1.84 (1H, m), 1.76-1.51 (2H, m), 1.46-1.30 (1H, m).

Intermediate 22: 1-Acryloylpiperidine-4-carboxylic Acid

Starting from piperidine-4-carboxylic acid and acryloyl chloride.

$^1$H NMR (400 MHz, CDCl$_3$) 9.22 (1H, s), 6.56 (1H, dd, J=16.9, 10.6 Hz), 6.27 (1H, dd, J=16.9, 1.8 Hz), 5.70 (1H, dd, J=10.6, 1.8 Hz), 4.43 (1H, d, J=12.9 Hz), 3.94 (1H, d, J=13.2 Hz), 3.20 (1H, t, J=11.6 Hz), 2.96 (1H, t, J=11.3 Hz), 2.61 (1H, tt, J=10.5, 4.1 Hz), 1.99 (2H, d, J=12.7 Hz), 1.83-1.61 (2H, m).

Intermediate 23: tert-Butyl (2-(4-chloro-1-(phenylsulfonyl)-1H-pyrrolo[2,3-b]pyridin-2-yl)ethyl) carbamate A stirred solution of 1-(benzenesulfonyl)-4-chloro-pyrrolo[2,3-b]pyridine (5.86 g, 20.0 mmol) (which can be prepared as described in US2014/200227) in dry THF (80 mL) at −78° C. was treated dropwise with a freshly prepared solution of LDA (25.0 mL, 1.0M in THF/hexane, 25.0 mmol) over 10 min. The resulting solution was stirred at −78° C. for 1 h. tert-Butyl 1,2,3-oxathiazolidine-3-carboxylate 2,2-dioxide (6.69 g, 30.0 mmol) (which can be prepared as described in *Tetrahedron Letters* 2007, 48, 7460-7463) was added in one portion at −78° C. The resulting solution was stirred at −78° C. for 2 h, then warmed to room temperature over 30 min and stirred for an additional 6 h. The mixture was quenched by the addition of water (1.0 mL) the concentrated under reduced pressure to approx. 40 mL. 6M HCl was added until the pH reached 2 and the resulting solution was stirred for 1 h. The solution was concentrated in vacuo, then slowly diluted with a saturated aqueous solution of NaHCO$_3$ until pH=9. The aqueous phase was extracted with EtOAc and the combined organic layers were washed with brine, dried (MgSO$_4$), filtered, and concentrated in vacuo. The residue was purified by FCC eluting with 20-50% EtOAc in petrol to give the title compound (6.55 g, 75%) as a yellow gum.

LCMS (Method 4): Rt 3.23 min, m/z 436, 438 [MH$^+$].

By proceeding in a similar manner to Intermediate 22, the following compounds were prepared:

Intermediate 24: tert-Butyl (2-(5-chloro-1-(phenylsulfonyl)-1H-pyrrolo[2,3-b]pyridin-2-yl)ethyl) carbamate Starting from 5-chloro-1-(phenylsulfonyl)-1H-pyrrolo[2,3-b]pyridine (Intermediate 90) and tert-butyl 1,2,3-oxathiazolidine-3-carboxylate 2,2-dioxide (which can be prepared as described in *Tetrahedron Letters* 2007, 48, 7460-7463).

LCMS (Method 4): Rt 3.21 min, m/z 436, 438 [MH$^+$].

Intermediate 25: 2-(1-(Phenylsulfonyl)-4-(pyrazolo[1,5-b]pyridazin-3-yl)-1H-pyrrolo[2,3-b]pyridin-2-yl)ethan-1-amine tert-Butyl (2-(4-chloro-1-(phenylsulfonyl)-1H-pyrrolo[2,3-b]pyridin-2-yl)ethyl) carbamate (Intermediate 23, 3.26 g, 7.50 mmol), 3-(4,4,5,5-tetramethyl-1,3,2-dioxaborolan-2-yl)pyrazolo[1,5-b]pyridazine (2.29 g, 9.37 mmol), potassium phosphate (4.77 g, 22.5 mmol) and X-Phos-Pd-G3 (253 mg, 0.30 mmol) were added to a flame dried flask under argon and purged with argon three times. Degassed THF/ethanol/water (4:1:1, 45 mL) was added, and the reaction mixture was heated at 50° C. for 6 h, The reaction mixture was diluted with water and extracted with ethyl acetate. The combined organic layers were washed with brine, and concentrated in vacuo. The residue was suspended in DCM and TFA (25 mL) was added. The reaction mixture was stirred at r.t. for 1 h then concentrated in vacuo. The residue was dissolved in DCM and a saturated aqueous solution of NaHCO$_3$ was added until the pH=9. The layers were separated and the aqueous layer was extracted with DCM. The combined organic layers were washed with brine, dried (MgSO$_4$) and concentrated in vacuo. The residue was purified by FCC eluting with 7.5-12.5% methanol in DCM to give the title compound (6.55 g) as a yellow solid.

LCMS (Method 4): Rt 2.42 min, m/z 419 [MH$^+$].

By proceeding in a similar manner to Intermediate 25, the following compounds were prepared:

Intermediate 26: tert-Butyl 3-(4-(1-(phenylsulfonyl)-1H-indol-3-yl)-1H-pyrrolo[2,3-b]pyridin-2-yl)pyrrolidine-1-carboxylate Starting from tert-butyl 3-(4-bromo-1H-pyrrolo[2,3-b]pyridin-2-yl)pyrrolidine-1-carboxylate (Intermediate 74) and 1-(phenylsulfonyl)-3-indolylboronic acid to give a ca. 2:1 mixture of the title compound and the des-phenylsulfonyl analogue.

LCMS (Method 3): Rt 1.53 min, m/z 543.4 [MH$^+$].

Intermediate 27: tert-Butyl (2-(5-chloro-4-(pyrazolo[1,5-b]pyridazin-3-yl)-1H-pyrrolo[2,3-b]pyridin-2-yl)ethyl)carbamate Starting from tert-butyl (2-(4-bromo-5-chloro-1H-pyrrolo[2,3-b]pyridin-2-yl)ethyl)carbamate (Intermediate 91) and 3-(4,4,5,5-tetramethyl-1,3,2-dioxaborolan-2-yl)pyrazolo[1,5-b]pyridazine $^1$H NMR (400 MHz, CDCl$_3$) 11.09 (1H, s), 8.41 (1H, dd, J=4.4, 1.9 Hz), 8.38 (2H, s), 7.96 (1H, dd, J=9.0, 1.9 Hz), 7.10 (1H, dd, J=9.0, 4.4 Hz), 6.10 (1H, d, J=2.1 Hz), 4.91 (1H, s), 3.64-3.45 (2H, m), 3.05 (2H, t, J=6.9 Hz) 1.42 (9H, s).

Intermediate 28: Acryloyl-D-proline

To a solution of D-proline (1.00 g, 8.69 mmol) in 1M NaOH (26.1 mL, 26.06 mmol) was added a solution of acryloyl chloride (1.18 g, 13.03 mmol) in DCM (10 mL) dropwise. The mixture was stirred at r.t. for 30 min before the phases were separated. The aqueous layer was washed with DCM then acidified with concentrated hydrochloric acid. The aqueous layer was saturated with NaCl then extracted with EtOAc. The combined organic layers were dried (Na$_2$SO$_4$) and concentrated in vacuo and azeotroped with xylenes. This gave the title compound as a white solid (860 mg, 59%).

LCMS (Method 3): Rt 0.76 min, m/z 170 [MH$^+$].

By proceeding in a similar manner to Intermediate 28, the following compounds were prepared:

Intermediate 29: (S)-1-Acryloylpyrrolidine-3-carboxylic Acid

Starting from (S)-pyrrolidine-3-carboxylic acid and acryloyl chloride.

LCMS (Method 3): Rt 0.73 min, m/z 170 [MH$^+$].

Intermediate 30: (R)-1-Acryloylpyrrolidine-3-carboxylic Acid

Starting from (R)-pyrrolidine-3-carboxylic acid and acryloyl chloride.

$^1$H NMR (400 MHz, d$_6$-DMSO): 2.22-1.89 (2H, m), 3.21-2.98 (1H, m), 3.79-3.36 (4H, m), 5.66 (1H, dd, J=2.3, 10.5 Hz), 6.17-6.08 (1H, m), 6.63-6.51 (1H, m), 12.55 (1H, br s).

Intermediate 31: 4-(N-methylacrylamido)benzoic Acid

Starting from 4-(methylamino)benzoic acid and acryloyl chloride

LCMS (Method 3): Rt 1.08 min, m/z 206 [MH$^+$].

Intermediate 32: 3-(Acrylamidomethyl)benzoic Acid

Starting from 3-(aminomethyl)benzoic acid and acryloyl chloride

LCMS (Method 3): Rt 0.87 min, m/z 206 [MH$^+$].

Intermediate 33: 2-(1-Acryloylpiperidin-4-yl)acetic Acid

Starting from 2-(piperidin-4-yl)acetic acid and acryloyl chloride.

LCMS (Method 3): Rt 0.80 min, m/z 198 [MH$^+$].

Intermediate 34: (1R,3R)-3-acrylamidocyclopentane-1-carboxylic Acid

Starting from (1R,3R)-3-aminocyclopentane-1-carboxylic acid (which can be prepared as described in WO2011008247 or J. Med. Chem. 2005, 48(24), 7675) and acryloyl chloride.

LCMS (Method 3): Rt 0.76 min, m/z 184.0 [MH$^+$].

Intermediate 35: 4-Acryloylmorpholine-2-carboxylic Acid

Starting from 2-morpholinecarboxylic acid and acryloyl chloride.

LCMS (Method 3): Rt 1.06 min, m/z 186 [MH$^+$].

Intermediate 36: (R)-4-Acryloylmorpholine-3-carboxylic Acid

Starting from (R)-morpholine-3-carboxylic acid and acryloyl chloride.

LCMS (Method 3): Rt 0.84 min, m/z 186 [MH$^+$].

Intermediate 37: (S)-4-Acryloylmorpholine-3-carboxylic Acid

Starting from (S)-morpholine-3-carboxylic acid and acryloyl chloride.

LCMS (Method 3): Rt 0.72 min, m/z 186 [MH$^+$].

Intermediate 38: 5-Acrylamidonicotinic Acid

Starting from 5-aminopyridine-3-carboxylic acid and acryloyl chloride.

LCMS (Method 3): Rt 0.79 min, m/z 193 [MH$^+$].

Intermediate 39: (3R,4R)-4-Acryloylamidotetrahydrofuran-3-carboxylic Acid

Starting from (3R,4R)-4-aminotetrahydrofuran-3-carboxylic acid (which can be prepared as described in Organic & Biomolecular Chemistry 2004, 2(19), 2763-2776) and acryloyl chloride and used directly in the next step.

Intermediate 40: 4-Acrylamido-N-(2-(1-(phenylsulfonyl)-4-(pyrazolo[1,5-b]pyridazin-3-yl)-1H-pyrrolo[2,3-b]yridine-2-yl)ethyl)benzamide EDC.HCl (143 mg, 0.75 mmol) was added to a solution of 2-(1-(phenylsulfonyl)-4-(pyrazolo[1,5-b]pyridazin-3-yl)-1H-pyrrolo[2,3-b]pyridin-2-yl)ethan-1-amine (Intermediate 25, 209 mg, 0.50 mmol), 4-acrylamidobenzoic acid (143 mg, 0.75 mmol), TEA (0.216 mL, 1.50 mmol) and HOBt (3.5 mg, 0.0259 mmol) in DMF (2.0 mL) and the mixture was stirred at r.t. for 48 h. The mixture was diluted with water (25 mL) and extracted with CHCl$_3$ and the combined organic layers were washed with a saturated aqueous solution of Na$_2$CO$_3$ (25 mL), brine (25 mL), dried (MgSO$_4$) and concentrated in vacuo. The residue was purified by FCC eluting with 4-10% MeOH in DCM to give the title compound (196 mg, 66%) as a yellow solid.

LCMS (Method 4s)—Rt 2.58 min, m/z 592 [MH$^+$].

Intermediate 41: 2-(4-Chloro-1-(phenylsulfonyl)-1H-pyrrolo[2,3-b]pyridin-2-yl)ethan-1-amine A solution of tert-butyl (2-(4-chloro-1-(phenylsulfonyl)-1H-pyrrolo[2,3-b]pyridin-2-yl)ethyl)carbamate (Intermediate 23, 1.30 g, 3.00 mmol) in DCM (20 mL) was treated with TFA (10 mL). The reaction mixture was stirred at r.t. for 4 h then concentrated in vacuo. The residue was slowly diluted with a saturated aqueous solution of NaHCO$_3$ until pH=9 and then extracted with DCM. The combined organic layers were washed with brine, dried (MgSO$_4$), filtered, and concentrated in vacuo, to give the title compound (989 mg, 98%) as a pale yellow solid $^1$H (400 MHz, CDCl$_3$): 1.66 (2H, s), 3.21 (2H, t, J=6.7 Hz), 3.32 (2H, t, J=6.7 Hz), 6.49 (1H, s), 7.14 (1H, d, J=5.3 Hz), 7.52-7.42 (2H, m), 7.61-7.52 (1H, m), 8.17-8.08 (2H, m), 8.24 (1H, d, J=5.3 Hz)

Intermediate 42: tert-Butyl (S)-2-((2-(4-chloro-1-(phenylsulfonyl)-1H-pyrrolo[2,3-b]pyridin-2-yl)ethyl)carbamoyl)pyrrolidine-1-carboxylate HATU (1.33 g, 3.50 mmol) was added to a solution of (S)-1-(tert-butoxycarbonyl)piperidine-2-carboxylic acid (which can be prepared as described in *Organic Letters*, 2011, 13(2), 216-219) (753 mg, 3.5 mmol) and TEA (1.56 mL, 11.25 mmol) in DCM (5 mL) and the resultant mixture was stirred for 5 min. The solution was then added to a solution of 2-(4-chloro-1-(phenylsulfonyl)-1H-pyrrolo[2,3-b]pyridin-2-yl)ethan-1-amine (Intermediate 41, 989 mg, 2.95 mmol) in DCM (25.0 mL) and the mixture was then stirred overnight. The reaction was quenched with a saturated aqueous solution of Na$_2$CO$_3$ (25 mL) and extracted with DCM and the combined organic layers were washed with a saturated aqueous solution of Na$_2$CO$_3$, brine, dried (MgSO$_4$) and concentrated in vacuo. The residue was purified by FCC eluting with 33-100% EtOAc in petrol to give the title compound (871 mg, 66%) as a yellow solid.

$^1$H (400 MHz, CDCl$_3$): 1.38 (9H, s), 1.86 (2H, s), 2.48-2.01 (2H, m), 3.54-3.20 (4H, m), 3.84-3.64 (2H, m), 4.27 (1H, s), 6.50 (1H, s), 7.15 (1, d, J=5.3 Hz), 7.18 (1, s), 7.52-7.43 (2H, m), 7.61-7.53 (1H, m), 8.15-8.07 (2H, m), 8.24 (1H, d, J=5.3 Hz)

Intermediate 43: tert-butyl (S)-2-((2-(1-(phenylsulfonyl)-4-(pyrazolo[1,5-b]pyridazin-3-yl)-1H-pyrrolo[2,3-b]pyridin-2-yl)ethyl)carbamoyl)pyrrolidine-1-carboxylate (S)-2-((2-(4-chloro-1-(phenylsulfonyl)-1H-pyrrolo[2,3-b]pyridin-2-yl)ethyl)carbamoyl)pyrrolidine-1-carboxylate (Intermediate 42, 871 mg, 1.99 mmol), 3-(4,4,5,5-tetramethyl-1,3,2-dioxaborolan-2-yl)pyrazolo[1,5-b]pyridazine (609 mg, 2.48 mmol), potassium phosphate (1.26 g, 5.97 mmol) and X-Phos-Pd-G3 (67 mg, 0.08 mmol) were added to a flame dried flask under argon and purged with argon three times. A mixture of THF/ethanol/water (4:1:1, 12 mL) was degassed then added to the solids, and the reaction mixture was heated at 50° C. for 6 h, After cooling, the reaction mixture was diluted with water (50 mL) and extracted with ethyl acetate. The combined organic layers were washed with brine, dried (MgSO$_4$) and concentrated in vacuo. The residue was purified by FCC eluting with petrol: EtOAc:MeOH with a gradient from 5:5:1 to 0:10:1) to give the title compound (361 mg, 30%) as a yellow solid.

LCMS (Method 4): Rt 3.00 min, m/z 616, [MH$^+$].

By proceeding in a similar manner to Intermediate 43, the following compounds were prepared:

Intermediate 44: tert-Butyl (S)-2-((2-(4-(1-methyl-1H-pyrazol-4-yl)-1-(phenylsulfonyl)-1H-pyrrolo[2,3-b]pyridin-2-yl)ethyl)carbamoyl)pyrrolidine-1-carboxylate Starting from tert-butyl (S)-2-((2-(4-chloro-1-(phenylsulfonyl)-1H-pyrrolo[2,3-b]pyridin-2-yl)ethyl)carbamoyl) pyrrolidine-1-carboxylate (Intermediate 42), and 1-methylpyrazole-4-boronic acid pinacol ester.

LCMS (Method 4): Rt 2.76, m/z 579 [MH$^+$].

Intermediate 45: tert-Butyl (S)-2-((2-(1-(phenylsulfonyl)-4-(pyridine-4-yl)-1H-pyrrolo[2,3-b]pyridine-2-yl)ethyl)carbamoyl)pyrrolidine-1-carboxylate Starting from tert-butyl (S)-2-((2-(4-chloro-1-(phenylsulfonyl)-1H-pyrrolo[2,3-b]pyridine-2-yl)ethyl)carbamoyl) pyrrolidine-1-carboxylate (Intermediate 42), and 4-pyridineboronic acid pinacol ester.

LCMS (Method 4): Rt 2.78, m/z 576 [MH$^+$].

Intermediate 46: (S)—N-(2-(1-(phenylsulfonyl)-4-(pyrazolo[1,5-b]pyridazin-3-yl)-1H-pyrrolo[2,3-b]pyridin-2-yl)ethyl)pyrrolidine-2-carboxamide A solution tert-butyl (S)-2-((2-(1-(phenylsulfonyl)-4-(pyrazolo[1,5-b]pyridazin-3-yl)-1H-pyrrolo[2,3-b]pyridin-2-yl)ethyl)carbamoyl)pyrrolidine-1-carboxylate (Intermediate 43, 307 mg, 0.50 mmol) in DCM (8 mL) was treated with TFA (2 mL). The reaction mixture was stirred at r.t. for 3 h then concentrated in vacuo. The residue was slowly diluted with a saturated aqueous solution of NaHCO$_3$ until pH=9 and with DCM. The combined organic layers were washed with brine, dried (MgSO$_4$), filtered, and concentrated in vacuo. The residue was purified by FCC eluting with 5-12.5% MeOH in DCM to give the title compound (203 mg, 79%) as a pale yellow solid LCMS (Method 4): Rt 2.58 min, m/z 516, [MH$^+$].

Intermediate 47: tert-Butyl (S)-2-((2-(1-(phenylsulfonyl)-4-(pyrazolo[1,5-b]pyridazin-3-yl)-1H-pyrrolo[2,3-b]pyridin-2-yl)ethyl)carbamoyl)piperidine-1-carboxylate HATU (380 mg, 1.00 mmol) was added to a solution of (S)-1-(tert-butoxycarbonyl)piperidine-2-carboxylic acid (which can be prepared as described in US2015/126500) (229 mg, 1.00 mmol) and TEA (0.55 mL, 4.00 mmol) in DMC (2 mL) and the mixture was stirred for 5 min. The solution was then added to a solution of 2-(1-(phenylsulfonyl)-4-(pyrazolo[1,5-b]pyridazin-3-yl)-1H-pyrrolo[2,3-b]pyridin-2-yl)ethan-1-amine (Intermediate 25, 313 mg, 0.75 mmol) in DMC (5.0 mL) and the mixture was stirred for 30 min. The reaction was quenched with a saturated aqueous solution of $Na_2CO_3$ (20 mL) and extracted with $CHCl_3$. The combined organic layers were washed with a saturated aqueous solution of $Na_2CO_3$, brine, dried ($Na_2SO_4$) and concentrated in vacuo. The residue was purified by FCC eluting with 50-100% EtOAc in petrol to give the title compound (471 mg, 99%) as a yellow solid.

LCMS (Method 4): Rt 2.97 min, m/z 630 [MH$^+$].

By proceeding in a similar manner to Intermediate 47, the following compounds were prepared:

Intermediate 48: tert-Butyl (R)-2-((2-(1-(phenylsulfonyl)-4-(pyrazolo[1,5-b]pyridazin-3-yl)-1H-pyrrolo[2,3-b]pyridin-2-yl)ethyl)carbamoyl)piperidine-1-carboxylate Starting from 2-(1-(phenylsulfonyl)-4-(pyrazolo[1,5-b]pyridazin-3-yl)-1H-pyrrolo[2,3-b]pyridin-2-yl)ethan-1-amine (Intermediate 25) and (R)-1-(tert-butoxycarbonyl)piperidine-2-carboxylic acid (which can be prepared as described in US2015/126500).

LCMS (Method 4): Rt 2.97 min, m/z 630 [MH$^+$].

Intermediate 49: (S)—N-(2-(1-(Phenylsulfonyl)-4-(pyrazolo[1,5-b]pyridazin-3-yl)-1H-pyrrolo[2,3-b]pyridin-2-yl)ethyl)piperidine-2-carboxamide A solution of tert-butyl (S)-2-((2-(1-(phenylsulfonyl)-4-(pyrazolo[1,5-b]pyridazin-3-yl)-1H-pyrrolo[2,3-b]pyridin-2-yl)ethyl)carbamoyl)piperidine-1-carboxylate (Intermediate 47, 471 mg, 0.75 mmol) in DCM (5 mL) was treated with TFA (2.5 mL). The reaction mixture was stirred at r.t. for 3 h then concentrated in vacuo. The residue was dissolved in DCM and saturated aqueous $NaHCO_3$ was added until the pH=9. The layers were separated and the aqueous layer was extracted with DCM. The combined organic layers were washed with brine, dried ($Na_2SO_4$) and concentrated in vacuo to give the title compound (371 mg, 94%) as a yellow solid.

LCMS (Method 4): Rt 2.59 min, m/z 530, [MH$^+$].

By proceeding in a similar manner to Intermediate 49, the following compounds were prepared:

Intermediate 50: (R)—N-(2-(1-(phenylsulfonyl)-4-(pyrazolo[1,5-b]pyridazin-3-yl)-1H-pyrrolo[2,3-b]pyridin-2-yl)ethyl)piperidine-2-carboxamide Starting from tert-butyl (R)-2-((2-(1-(phenylsulfonyl)-4-(pyrazolo[1,5-b]pyridazin-3-yl)-1H-pyrrolo[2,3-b]pyridin-2-yl)ethyl)carbamoyl)piperidine-1-carboxylate (Intermediate 48).

LCMS (Method 4): Rt 2.59 min, m/z 530 [MH$^+$].

Intermediate 51: 2-(4-chloro-1-(phenylsulfonyl)-1H-pyrrolo[2,3-b]pyridin-2-yl)ethan-1-ol A stirred solution of 1-(benzenesulfonyl)-4-chloro-pyrrolo[2,3-b]pyridine (4.39 g, 15.0 mmol) (which can be prepared as described in US2014/200227) in dry THF (42 mL) at −78° C. was treated dropwise with a freshly prepared solution of LDA (18.0 mL, 1.0M in THF/hexane, 18.0 mmol) over 10 min. The resulting orange solution was stirred at −78° C. for 1 h. Then 1,3,2-dioxathiolane 2,2-dioxide (2.79 g, 22.5 mmol) was added in one portion at −78° C. The resulting solution was stirred at −78° C. for 2 h, then warmed to room temperature over 30 min and stirred for an additional 1 h. The reaction was quenched by the addition of water, then 12M HCl was added and the resulting solution stirred at 30° C. overnight. The solution was concentrated under reduced pressure, then slowly diluted with a saturated aqueous solution of $NaHCO_3$ until pH=9. The aqueous phase was extracted with EtOAc and. the combined organic layers were washed with brine, dried ($MgSO_4$), and concentrated in vacuo. The residue was purified by FCC eluting with 30-50% EtOAc in petrol to give the title compound (3.22 g, 64%) as a pale yellow solid.

LCMS (Method 4): Rt 2.63 min, m/z 337/339 [MH$^+$].

Intermediate 52: 2-(4-chloro-1-(phenylsulfonyl)-1H-pyrrolo[2,3-b]pyridin-2-yl)ethyl methanesulfonate A stirred solution of 2-(4-chloro-1-(phenylsulfonyl)-1H-pyrrolo[2,3-b]pyridin-2-yl)ethan-1-ol (Intermediate 51, 3.19 g, 9.50 mmol) and TEA (2.64 mL, 19.0 mmol) in dry DCM (30 mL) at 0° C. was treated dropwise with MsCl (0.81 mL, 10.45 mmol). The resulting solution was stirred at 0° C. for 1 h. The reaction was quenched by the addition of water and the layers were separated. The aqueous phase was extracted with DCM and the combined organic layers were washed with brine, dried ($MgSO_4$), and concentrated in vacuo to give the title compound (3.77 g, 96%) as a pale yellow oil which was used without further purification.

LCMS (Method 4): Rt 2.87 min, m/z 415, 417 [MH$^+$].

Intermediate 53: tert-Butyl (2-(4-chloro-1-(phenylsulfonyl)-1H-pyrrolo[2,3-b]pyridin-2-yl)ethyl)(methyl)carbamate A solution of 2-(4-chloro-1-(phenylsulfonyl)-1H-pyrrolo[2,3-b]pyridin-2-yl)ethyl methanesulfonate (Intermediate 52, 3.10 g, 7.50 mmol) in 8M methylamine in ethanol (37.5 mL) was sealed in a pressure reactor and heated at 80° C. for 1 h. The reaction was cooled to r.t. and concentrated in vacuo. The residue was diluted with dioxane, cooled to 5° C. then treated with solid $NaHCO_3$ (2.52 g, 30 mmol) and $Boc_2O$ (4.90 g, 22.5 mmol). The resulting solution was stirred at r.t. overnight. The reaction was quenched by the addition of water and the aqueous phase was extracted with DCM. The combined organic layers were washed with brine, dried ($MgSO_4$), and concentrated in vacuo. The residue was purified by FCC eluting with 20-50% EtOAc in petrol to give the title compound (2.20 g, 65%) as a pale yellow oil.

LCMS (Method 4): Rt 3.30 min, m/z 450, 452 [MH$^+$].

Intermediate 54: tert-Butyl methyl(2-(1-(phenylsulfonyl)-4-(pyrazolo[1,5-b]pyridazin-3-yl)-1H-pyrrolo[2,3-b]pyridin-2-yl)ethyl)carbamate tert-Butyl (2-(4-chloro-1-(phenylsulfonyl)-1H-pyrrolo[2,3-b]pyridin-2-yl)ethyl) (methyl)carbamate (Intermediate 53, 2.24 g, 5.00 mmol), 3-(4,4,5,5-tetramethyl-1,3,2-dioxaborolan-2-yl)pyrazolo[1,5-b]pyridazine (1.47 g, 6.00 mmol), potassium phosphate (3.18 g, 15.0 mmol) and X-Phos-Pd-G3 (169 mg, 0.20 mmol) were added to a flame dried flask under argon and purged with argon three times. Degassed THF/ethanol/water (4:1:1, 25 mL) was added, and the reaction mixture was heated at 50° C. for 6 h. After cooling, the reaction mixture was diluted with water and extracted with ethyl acetate. The combined organic layers were washed with brine, and concentrated in vacuo. The residue was purified by FCC eluting with 50-100% EtOAc in petrol to give the title compound (2.68 g, 100%) as a yellow solid.
LCMS (Method 4): Rt 3.00 min, m/z 533 [MH$^+$].

Intermediate 55: tert-Butyl (2-(4-chloro-1H-pyrrolo [2,3-b]pyridin-2-yl)ethyl)carbamate 3M aqueous NaOH (5.0 mL) was added to a solution of tert-butyl (2-(4-chloro-1-(phenylsulfonyl)-1H-pyrrolo[2,3-b]pyridin-2-yl)ethyl)carbamate (Intermediate 23, 1.30 g, 3.00 mmol) in dioxane (10 mL). The reaction mixture was heated at 60° C. for 5 h then cooled to r.t. and treated with 1M HCl until the pH=7. The mixture was extracted with ethyl acetate and the combined organic layers were washed with brine, and concentrated in vacuo. The residue was purified by FCC eluting with 0-8% MeOH in a 1:1 mixture of petrol and EtOAc to give the title compound (658 mg, 73%) as a yellow solid.
LCMS (Method 4): Rt 2.80 min, m/z 296, 298 [MH$^+$].
By proceeding in a similar manner to Intermediate 55, the following compounds were prepared:

Intermediate 56: tert-Butyl (2-(5-chloro-1H-pyrrolo [2,3-b]pyridin-2-yl)ethyl)carbamate Starting from tert-butyl (2-(5-chloro-1-(phenylsulfonyl)-1H-pyrrolo[2,3-b]pyridin-2-yl)ethyl)carbamate (Intermediate 24)

LCMS (Method 4): Rt 2.81 min, m/z 296, 298 [MH$^+$].

Intermediate 57: (4-chloro-1-(phenylsulfonyl)-1H-pyrrolo[2,3-b]pyridin-2-yl)methanol To a stirred solution of 1-(benzenesulfonyl)-4-chloropyrrolo[2,3-b]pyridine (2.92 g, 10.0 mmol) (which can be prepared as described in US2014/200227) in dry THF (39 mL) at −78° C. was added freshly prepared LDA (11.0 mL, 1.0M in THF/hexane, 11.0 mmol) over 10 min. The resulting orange solution was stirred at −78° C. for 1 hour. Distilled ethyl formate (1.20 mL, 15.0 mmol) was added rapidly at −78° C. and the resulting solution was stirred at −78° C. for 1 h. The mixture was allowed to warm to room temperature over 30 min and was quenched by the addition of acetic acid (0.69 mL, 12.0 mmol). The solution was concentrated in vacuo to ca. 10 mL, then diluted with MeOH. It was cooled to 0° C. and sodium borohydride (380 mg, 10.0 mmol) was added in 4 portions over 10 min. The resulting solution was stirred for 1 h at 0° C. before a further amount of sodium borohydride (380 mg, 10.0 mmol) was added in 2 portions over 10 min. The resulting solution was stirred for 1 hour at 0° C., then warmed to room temperature and stirred for 3 hours. The reaction was diluted with saturated aqueous NaHCO$_3$ and extracted with EtOAc. The combined organic layers were washed with brine, dried (MgSO4), and concentrated in vacuo. The residue was purified by FCC eluting with 20-50% EtOAc in hexane to give the title compound (2.34 g, 73%) as a yellow gum.
LCMS (Method 4): Rt 2.61 min, m/z 323, 325 [MH$^+$].

Intermediate 58: (1-(Phenylsulfonyl)-4-(pyrazolo[1, 5-b]pyrrolo[2,3-b]pyridin-2-yl) methanamine A mixture of 3-(2-(chloromethyl)-1-(phenylsulfonyl)-1H-pyrrolo[2,3-b]pyridin-4-yl)pyrazolo[1,5-b]pyridazine (Intermediate 98, 600 mg, 1.42 mmol) and sodium azide (184 mg, 2.83 mmol) in DMF was stirred at room temperature for 20 min. Triphenylphosphine (743 mg, 2.83 mmol) and water (2 mL) were added and the mixture was heated at 40° C. for 5.5 h. After cooling, the mixture was filtered and the solid was washed with a little methanol. The combined filtrates were concentrated in vacuo and DCM was added. The resultant solid was removed by filtration and the filtrate was purified by FCC eluting with 0-5% 2 M NH$_3$/MeOH in DCM to give the title compound as a pale yellow solid (403 mg, 70%).
LCMS (Method 3): Rt 0.94 min, m/z 427.1 [M+Na]$^+$.

Intermediate 59: (1-(phenylsulfonyl)-4-(pyrazolo[1, 5-b]pyridazin-3-yl)-1H-pyrrolo[2,3-b]pyridin-2-yl) methanol (4-Chloro-1-(phenylsulfonyl)-1H-pyrrolo[2,3-b]pyridin-2-yl)methanol (Intermediate 57, 1.932 g, 6.0 mmol), 3-(4,4,5,5-tetramethyl-1,3,2-dioxaborolan-2-yl)pyrazolo[1,5-b] pyridazine (1.62 g, 6.60 mmol), potassium phosphate (4.19 g, 19.80 mmol) and X-Phos-Pd-G3 (380 mg, 0.45 mmol) were added to a flame dried flask under argon and purged with argon three times. Degassed THF/ethanol/water (2:1:1, 60 mL) was added, and the reaction mixture was heated at 60° C. for 20 h. After cooling, the mixture was diluted with water and extracted with ethyl acetate. The combined organic layers were washed with brine, and concentrated in vacuo. The residue was purified by FCC eluting with 1-8% MeOH in EtOAc to give the title compound (1.58 g, 65%) as a yellow solid.
LCMS (Method 4): Rt 2.44 min, m/z 406.0 [MH$^+$].

Intermediate 60: tert-Butyl 4-((1-(phenylsulfonyl)-4-(pyrazolo[1,5-b]pyridazin-3-yl)-1H-pyrrolo[2,3-b] pyridin-2-yl)methyl)piperazine-1-carboxylate A stirred solution of (1-(phenylsulfonyl)-4-(pyrazolo[1,5-b]pyridazin-3-yl)-1H-pyrrolo[2,3-b]pyridin-2-yl)methanol (Intermediate 59, 405 mg, 1.00 mmol) in DCM (10 mL) at 0° C. was treated with thionyl chloride (86 □L, 1.20 mmol). The resulting solution was stirred at r.t. for 1 h, then concentrated in vacuo. The residue was dissolved in DMF (4 mL) and treated with K$_2$CO$_3$ (345 mg, 2.50 mmol) and tert-butyl piperazine-1-carboxylate (233 mg, 1.25 mmol) (prepared as described in *Bioorganic and Medicinal Chemistry Letters*, 2015, 25(4), 881-886). The reaction was diluted with water and extracted with EtOAc. The combined organic layers were washed with brine, dried (MgSO$_4$) and concentrated in vacuo. The residue was purified by FCC eluting with 30-100% EtOAc in petrol to give the title compound (495 mg, 86%) as a yellow gum.
LCMS (Method 4): Rt 3.21 min, m/z 574.0 [MH$^+$].
By proceeding in a similar manner to Intermediate 60, the following compounds were prepared:

Intermediate 61: tert-Butyl 7-((1-(phenylsulfonyl)-4-(pyrazolo[1,5-b]pyridazin-3-yl)-1H-pyrrolo[2,3-b] pyridin-2-yl)methyl)-2,7-diazaspiro[4.5]decane-2-carboxylate Starting from (1-(phenylsulfonyl)-4-(pyrazolo[1,5-b] pyridazin-3-yl)-1H-pyrrolo[2,3-b]pyridin-2-yl)methanol (Intermediate 59) and tert-butyl 2,7-diazaspiro[4.5]decane-2-carboxylate but using DIPEA in THF for the second step.
LCMS (Method 3): Rt 1.16 min, m/z 628 [MH$^+$].

Intermediate 62: tert-Butyl ((1-(phenylsulfonyl)-4-(pyrazolo[1,5-b]pyridazin-3-yl)-1H-pyrrolo[2,3-b]pyridine-2-yl)methyl)pyrrolidin-3-yl)methyl)carbamate Starting from 3-(2-(chloromethyl)-1-(phenylsulfonyl)-1H-pyrrolo[2,3-b]pyridin-4-yl)pyrazolo[1,5-b]pyridazine (Intermediate 98) and tert-butyl (pyrrolidin-3-ylmethyl)carbamate.
LCMS (Method 3) Rt 0.99 min, m/z 588 [MH$^+$]

Intermediate 63: 3-(1-(Phenylsulfonyl)-2-(piperazin-1-ylmethyl)-1H-pyrrolo[2,3-b]pyridin-4-yl)pyrazolo[1,5-b]pyridazine A solution of tert-butyl 4-((1-(phenylsulfonyl)-4-(pyrazolo[1,5-b]pyridazin-3-yl)-1H-pyrrolo[2,3-b]pyridin-2-yl)methyl)piperazine-1-carboxylate (Intermediate 60, 745 mg, 1.30 mmol) in DCM (6 mL) was treated with TFA (2 mL). The reaction mixture was stirred at r.t. for 2 h then concentrated in vacuo. The residue was dissolved in DCM and saturated aqueous NaHCO$_3$ was added until the pH=9. The layers were separated and the aqueous layer was extracted with DCM. The combined organic layers were washed with brine, dried (MgSO$_4$) and concentrated in vacuo to give the title compound (603 mg, 98%) as a yellow solid.
LCMS (Method 4): Rt 2.580 min, m/z 474 [MH$^+$].
By proceeding in a similar manner to Intermediate 63, the following compounds were prepared:

Intermediate 64: 7-((1-(Phenylsulfonyl)-4-(pyrazolo[1,5-b]pyridazin-3-yl)-1H-pyrrolo[2,3-b]pyridin-2-yl)methyl)-2,7-diazaspiro[4.5]decane Starting from tert-Butyl 7-((1-(phenylsulfonyl)-4-(pyrazolo[1,5-b]pyridazin-3-yl)-1H-pyrrolo[2,3-b]pyridin-2-yl)methyl)-2,7-diazaspiro[4.5]decane-2-carboxylate (Intermediate 61). The product was used directly in the next step.

Intermediate 65: (1-((1-(Phenylsulfonyl)-4-(pyrazolo[1.5-b]]pyridazin-3-yl)-1H-pyrrolo[2,3-b]pyridine-2-yl)methyl)pyrrolidin-3-yl-methanamine Starting from tert-butyl ((1-(phenylsulfonyl)-4-(pyrazolo[1,5-b]pyridazin-3-yl)-1H-pyrrolo[2,3-b]pyridine-2-yl)methyl)pyrrolidin-3-yl)methyl)carbamate (Intermediate 62)
LCMS (Method 3); Rt 0.75 min, m/z 488 [MH$^+$].

Intermediate 66: 4-Chloro-2-iodo-1-(phenylsulfonyl)-1H-pyrrolo[2,3-b]pyridine A stirred solution of 1-(benzenesulfonyl)-4-chloro-pyrrolo[2,3-b]pyridine (1.17 g, 4.0 mmol) (which can be prepared as described in US2014/200227) in dry THF (80 mL) at −78° C. was treated dropwise with a freshly prepared solution of LDA (4.0 mL, 1.0M in THF/hexane, 4.0 mmol) over 10 min. The resulting orange solution was stirred at −78° C. for 1 h. Iodine (1.06 g, 4.2 mmol) was added in one portion at −78° C. and the resulting solution was stirred at −78° C. for 30 min. The reaction was quenched by the addition of water and the solution was warmed to r.t. and extracted with EtOAc. The combined organic layers were washed with brine, dried (MgSO$_4$), and concentrated in vacuo to give the title compound (1.67 g, quant.) as a yellow solid.

LCMS (Method 4): Rt 3.19 min, m/z 419, 421 [MH$^+$].

Intermediate 67: 3-(4-Chloro-1-(phenylsulfonyl)-1H-pyrrolo[2,3-b]pyridin-2-yl)aniline 4-Chloro-2-iodo-1-(phenylsulfonyl)-1H-pyrrolo[2,3-b]pyridine (Intermediate 66, 1.67 g, 4.0 mmol), 3-aminophenylboronic acid monohydrate (696 mg, 4.50 mmol), potassium carbonate (1.57 g, 11.4 mmol) and Pd(dppf)Cl$_2$. DCM (342 mg, 0.42 mmol) were added to a flame dried flask under argon and purged with argon three times. Degassed dioxane/water (3:1, 40 mL) was added, and the reaction mixture was heated at 90° C. for 6 h. After cooling, the mixture was diluted with water and extracted with ethyl acetate. The combined organic layers were washed with brine, dried (MgSO$_4$) and concentrated in vacuo. The residue was purified by FCC eluting with 10-90% EtOAc in Petrol to give the title compound (1.02 g, 66%) as a yellow solid.
LCMS (Method 4): Rt 2.97 min, m/z 384, 386 [MH$^+$].

Intermediate 68: 3-(1-(Phenylsulfonyl)-4-(pyrazolo[1,5-b]pyridazin-3-yl)-1H-pyrrolo[2,3-b]pyridin-2-yl)aniline 3-(4-Chloro-1-(phenylsulfonyl)-1H-pyrrolo[2,3-b]pyridin-2-yl)aniline (Intermediate 67, 1.02 g, 2.65 mmol), 3-(4,4,5,5-tetramethyl-1,3,2-dioxaborolan-2-yl)pyrazolo[1,5-b]pyridazine (735 mg, 3.00 mmol), potassium phosphate (1.27 g, 6.00 mmol) and X-Phos-Pd-G3 (126 mg, 0.15 mmol) were added to a flame dried flask under argon and purged with argon three times. Degassed THF/ethanol/water (4:1:2, 21 mL) was added, and the reaction mixture was heated at 60° C. for 6 h. After cooling, the mixture was diluted with water and extracted with ethyl acetate. The combined organic layers were washed with brine, and concentrated in vacuo. The residue was purified by FCC eluting with 50-100% EtOAc in petrol to give the title compound (1.08 g, 88%) as a yellow solid.
LCMS (Method 4): Rt 2.68 min, m/z 467 [MH$^+$].

Intermediate 69: N-((4-Bromo-1-(phenylsulfonyl)-1H-pyrrolo[2,3-b]pyridin-2-yl)methyl)cyclopropanecarboxamide A solution of (4-bromo-1-(phenylsulfonyl)-1H-pyrrolo[2,3-b]pyridin-2-yl)methanamine (Intermediate 11, 218 mg, 0.596 mmol) in DCM (3 mL) was treated with triethylamine (0.250 mL, 1.8 mmol), followed by addition of a solution of cyclopropanecarbonyl chloride (75 mg, 0.715 mmol) in DCM (2 mL). The mixture was stirred at room temperature overnight then partitioned between saturated aqueous NaHCO$_3$ and DCM. The aqueous layer was extracted further with DCM, filtered through a phase separator, and concentrated in vacuo. The residue was purified by FCC eluting with 0-40% EtOAc in cyclohexane to give the title compound (180 mg, 70%) as a white solid.
LCMS (Method 3): Rt 1.40 min, m/z 434.1/436.1 [MH$^+$].
By proceeding in a similar manner to Intermediate 69, the following compounds were prepared:

Intermediate 70: N-((4-Bromo-1-(phenylsulfonyl)-1H-pyrrolo[2,3-b]pyridin-2-yl)methyl)cyclopropanesulfonamide Starting from (4-bromo-1-(phenylsulfonyl)-1H-pyrrolo[2,3-b]pyridin-2-yl)methanamine (Intermediate 11) and cyclopropanesulfonyl chloride.
LCMS (Method 3): Rt 1.45 min, m/z 470.0/472.0 [MH$^+$].

Intermediate 71: N-((4-Bromo-1-(phenylsulfonyl)-1H-pyrrolo[2,3-b]pyridin-2-yl)methyl)-2-(dimethylamino)acetamide To a solution of (4-bromo-1-(phenylsulfonyl)-1H-pyrrolo[2,3-b]pyridin-2-yl)methanamine (Intermediate 11,228 mg, 623 mmol) in DMF (3 mL) was added DIPEA (0.323 mL, 1.87 mmol), followed by N,N-dimethylglycine (71 mg, 0.685 mmol) and HATU (261 mg, 0.685 mmol). The resulting mixture was stirred at room temperature for 22 h. The mixture was purified on an SCX-2 cartridge, eluting with 2 M ammonia in MeOH. The residue was purified further by FCC eluting with 0-5% MeOH in DCM to give the title compound as a yellow solid (120 mg, 43%).
LCMS (Method 3): Rt 0.94 min, m/z 451.1/453.1 [MH$^+$].

Intermediate 72: 4-Bromo-3-iodopyridin-2-amine

A mixture of 4-bromo-2-fluoro-3-iodopyridine (11.1 g, 36.8 mmol) in conc. aqueous ammonia solution (36.8 mL) and dioxane (23 mL) was split between 3 microwave vials. Each vial was heated in the microwave at 120° C. for 1 h then cooled to r.t. The reaction mixtures were combined, diluted with ethyl acetate and the phases separated. The aqueous layer was extracted with ethyl acetate and the combined organic layer was washed with brine, dried (Na$_2$SO$_4$) and concentrated in vacuo to give the title compound as a white solid (9.39 g).
LCMS (Method 3): Rt 0.92 min, m/z 299, 301 [MH$^+$].

Intermediate 73: tert-Butyl 3-((2-amino-4-bromopyridin-3-yl)ethynyl)pyrrolidine-1-carboxylate A mixture of 4-bromo-3-iodopyridin-2-amine (Intermediate 72, 5.93 g, 19.8 mmol), and tert-butyl 3-ethynylpyrrolidine-1-carboxylate (3.48 g, 17.8 mmol) in acetonitrile (60 mL) and trimethylamine (12 mL) was degassed with argon. Copper (I) iodide (370 mg, 1.9 mmol) and bis(triphenylphosphine)palladium (II) chloride (695 mg, 1.0 mmol) were added and the reaction mixture was heated at 55° C. for 2 h. After cooling, the mixture was diluted with ethyl acetate and isohexane and then washed with water and brine, dried (Na$_2$SO$_4$) and concentrated in vacuo. The crude product was purified by FCC, eluting with 0-100% EtOAc in isohexane to give the title compound as a brown solid (3.9 g, 60%).
LCMS (Method 3): Rt 1.24 min, m/z 366, 368 [MH$^+$].

Intermediate 74: tert-Butyl 3-(4-bromo-1H-pyrrolo[2,3-b]pyridin-2-yl)pyrrolidine-1-carboxylate A mixture of tert-butyl 3-((2-amino-4-bromopyridin-3-yl)ethynyl)pyrrolidine-1-carboxylate (Intermediate 73, 3.88 g, 10.6 mmol) in NMP (50 mL) under argon was treated with potassium tert-butoxide (2.67 g, 23.8 mmol) and the reaction mixture was stirred at r.t. for 2 h. A saturated ammonium chloride solution was added resulting in precipitation of a gummy solid. The solvent was decanted off and the solid was dissolved in ethyl acetate and washed with water. The organic phase was concentrated in vacuo to afford the title compound as a brown foam (3.13 g, 81%). The combined aqueous solutions were extracted with ethyl acetate and the organic phase was concentrated in vacuo. The residue was treated with water to precipitate a gum which was extracted into ethyl acetate. The ethyl acetate was washed with water and concentrated in vacuo to afford a second batch of the title compound (0.71 g, 18%).
LCMS (Method 3): Rt 1.46 min, m/z 366, 368 [MH$^+$].

Intermediate 75: Methyl 6-methoxypyrazolo[1,5-b]pyridazine-3-carboxylate

To a stirred solution of hydroxylamine-O-sulfonic acid (4.06 g, 36.0 mmol) in water (12.5 mL) was added potassium bicarbonate until the pH=5-6. 3-Methoxypyridazine (prepared as described in *J. Med. Chem,* 2004, 47(19), 4716-4730) (2.42 g, 22.0 mmol) was added and the resulting solution was placed in a preheated aluminium heating block at 70° C. for 2 h, After cooling, the pH was adjusted to 7-8 using potassium bicarbonate and the solution was concentrated in vacuo. The residue was suspended in DMF (18 mL) and methyl propiolate (1.60 mL, 18 mmol) was added followed by the portion wise addition of potassium carbonate (6.07 g, 44.0 mmol), the mixture was stirred at r.t. for 36 h. The reaction mixture was diluted with water and extracted with EtOAc. The combined organic layers were washed with brine, dried (MgSO$_4$) and concentrated. The residue was purified by FCC eluting with 10-50% ethyl acetate in petrol to give the title compound (346 mg, 13%).
LCMS (Method 4): Rt 2.22 min, m/z 208, 209 [MH$^+$].

By proceeding in a similar manner to Intermediate 75, the following compounds were prepared:

Intermediate 76: Methyl 5-methoxypyrazolo[1,5-b]pyridazine-3-carboxylate

Starting from 4-methoxypyridazine (which was prepared as described in *J. Med. Chem.,* 2004, 47(19), 4716-4730), hydroxylamine-O-sulfonic acid and methyl propiolate.
LCMS (Method 4): Rt 2.08 min, m/z 208 [MH$^+$].

Intermediate 77: Methyl 5-(2-methoxyethoxy)pyrazolo[1,5-b]pyridazine-3-carboxylate Starting from 4-(2-methoxyethoxy)pyridazine (Intermediate 87), hydroxylamine-O-sulfonic acid and methyl propiolate
LCMS (Method 4): Rt 2.10 min, m/z 252, 253 [MH$^+$].

Intermediate 78: Methyl 5-((2,2-dimethyl-1,3-dioxolan-4-yl)methoxy)pyrazolo[1,5-b]pyridazine-3-carboxylate Starting from 4-((2,2-dimethyl-1,3-dioxolan-4-yl)methoxy)pyridazine (Intermediate 88), hydroxylamine-O-sulfonic acid and methyl propiolate
LCMS (Method 4): Rt 2.38 min, m/z 308, 309 [MH$^+$].

Intermediate 79: Methyl 6-methylpyrazolo[1,5-b]pyridazine-3-carboxylate

Starting from 2-methylpyridazine, hydroxylamine-O-sulfonic acid and methyl propiolate.
LCMS (Method 4): Rt 1.97 min, m/z 192, 193 [MH$^+$].

Intermediate 80: 3-Bromo-6-methoxypyrazolo[1,5-b]pyridazine

Methyl 6-methoxypyrazolo[1,5-b]pyridazine-3-carboxylate (Intermediate 75, 623 mg, 3.17 mmol) in THF (8 mL) was treated with a solution of LiOH.H$_2$O (342 mg, 8.40 mmol) in water (4 mL). The resulting solution was stirred at r.t. for 14 hours. The solvent was removed in vacuo and the residue was dissolved in water and the pH was adjusted to pH 3 using 6M HCl. The resulting precipitate was collected by filtration and washed with water and Et$_2$O and air dried. The solid was dissolved in DMF (6 mL) and was treated with N-bromosuccinimide (587 mg, 3.30 mmol) and sodium hydrogen carbonate (756 mg, 9.00 mmol) and the resulting mixture was stirred at r.t. for 4 h. The reaction mixture was diluted with water and extracted with EtOAc and the combined organic layers were washed with brine, dried (MgSO$_4$) and concentrated in vacuo. The residue was purified by FCC eluting with 2-20% EtOAc in petrol to afford the title compound as a white solid (484 mg, 71%).

LCMS (Method 4): Rt 2.46 min, m/z 228, 230 [MH$^+$].

By proceeding in a similar manner to Intermediate 80, the following compounds were prepared:

Intermediate 81: 3-Bromo-5-methoxypyrazolo[1,5-b]pyridazine

Starting from methyl 5-methoxypyrazolo[1,5-b]pyridazine-3-carboxylate (Intermediate 76).

LCMS (Method 4): Rt 2.21 min, m/z 228, 230 [MH$^+$].

Intermediate 82: 3-Bromo-5-(2-methoxyethoxy)pyrazolo[1,5-b]pyridazine

Starting from methyl 5-(2-methoxyethoxy)pyrazolo[1,5-b]pyridazine-3-carboxylate (Intermediate 77).

LCMS (Method 4): Rt 2.29 min, m/z 272, 274 [MH$^+$].

Intermediate 83: 3-Bromo-5-((2,2-dimethyl-1,3-dioxolan-4-yl)methoxy)pyrazolo[1,5-b]pyridazine Starting from methyl 5-((2,2-dimethyl-1,3-dioxolan-4-yl)methoxy)pyrazolo[1,5-b]pyridazine-3-carboxylate (Intermediate 78).

LCMS (Method 4): Rt 2.57 min, m/z 328, 330 [MH$^+$].

Intermediate 84: 3-Bromo-6-methylpyrazolo[1,5-b]pyridazine

Starting from methyl 6-methylpyrazolo[1,5-b]pyridazine-3-carboxylate (Intermediate 79)

LCMS (Method 4): Rt 2.19 min, m/z 211, 213 [MH$^+$].

Intermediate 85: 3,6-Dichloro-4-(2-methoxyethoxy)pyridazine

2-Methoxyethan-1-ol (1.03 mL, 13.2 mmol) was added drop wise to a stirred suspension of sodium hydride in THF (26 mL) at 0° C. and the mixture was stirred at 0° C. for 30 min. A solution of 3,4,6-trichloropyridazine (1.99 11.0 mmol) in THF (5 mL) was added and the resulting solution was stirred at r.t. overnight, and concentrated in vacuo. The residue was diluted with water and extracted with EtOAc. The combined organic layers were washed with brine, dried (MgSO$_4$) and concentrated in vacuo. The residue was purified by FCC eluting with 5-50% EtOAc in petrol to afford the title compound as a pale yellow oil (1.13 g, 45%).

$^1$H NMR (400 MHz, CDCl$_3$) 7.04 (1H, s), 4.35-4.28 (2H, m), 3.89-3.82 (2H, m), 3.46 (3H, s).

By proceeding in a similar manner to Intermediate 85, the following compounds were prepared:

Intermediate 86: 3,6-Dichloro-4-((2,2-dimethyl-1,3-dioxolan-4-yl)methoxy)pyridazine Starting from (2,2-dimethyl-1,3-dioxolan-4-yl)methanol and 3,4,6-trichloropyridazine.

LCMS (Method 4): Rt 2.34 min, m/z 279, 281 [MH$^+$].

Intermediate 87: 4-(2-Methoxyethoxy)pyridazine 3,6-Dichloro-4-(2-methoxyethoxy)pyridazine (Intermediate 85, 1.12 g, 5.06 mmol), ammonium formate (945 mg, 15.0 mmol) and 10% palladium on carbon (126 mg) were added to a flame dried flask under argon. The flask was purged with argon (×3), then H$_2$O (5 mL) and MeOH (50 mL) were added. The flask again purged with argon (×3), then with hydrogen (×2). The mixture was stirred under a balloon of hydrogen at r.t. overnight. The flask was then purged with argon (×3), and the catalyst was removed by filtration through a pad of Celite™, and the filtrate was concentrated in vacuo. The residue was purified by FCC eluting with 5-50% EtOAc in petrol to afford the title compound as a pale yellow oil (775 mg, 100%).

LCMS (Method 4): Rt 0.27 min, m/z 155 [MH$^+$].

By proceeding in a similar manner to Intermediate 87, the following compounds were prepared:

Intermediate 88: 4-((2,2-Dimethyl-1,3-dioxolan-4-yl)methoxy)pyridazine

Starting from 3,6-dichloro-4-((2,2-dimethyl-1,3-dioxolan-4-yl)methoxy)pyridazine (Intermediate 88)

LCMS (Method 4): Rt 0.75 min, m/z 211 [MH$^+$].

Intermediate 89: 3-(5-Chloro-1-(phenylsulfonyl)-1H-pyrrolo[2,3-b]pyridin-4-yl)pyrazolo[1,5-b]pyridazine 4-Bromo-5-chloro-1-(phenylsulfonyl)-1H-pyrrolo[2,3-b]pyridine (which can be prepared as described in WO2006/127587 A1) (243 mg, 0.65 mmol), 3-(4,4,5,5-tetramethyl-1,3,2-dioxaborolan-2-yl)pyrazolo[1,5-b]pyridazine (159 g, 0.65 mmol), potassium phosphate (413 g, 1.95 mmol) and X-Phos-Pd-G3 (21 mg, 0.026 mmol) were added to a flame dried flask under argon and purged with argon three times. Degassed THF/ethanol/water (4:1:1, 3 mL) was added, and the reaction mixture was heated at 50° C. for 6 h. After cooling, the mixture was diluted with water and extracted with ethyl acetate. The combined organic layers were washed with brine, dried (MgSO$_4$) and concentrated in vacuo. The residue was purified by FCC eluting with 25-100% EtOAc in petrol to give the title compound (159 g, 60%) as a yellow solid.

LCMS (Method 4): Rt 2.98 min, m/z 410, 412 [MH$^+$].

Intermediate 90: 5-Chloro-1-(phenylsulfonyl)-1H-pyrrolo[2,3-b]pyridine

A stirred solution of 5-chloro-1H-pyrrolo[2,3-b]pyridine (3.80 g, 25.0 mmol), TEA (6.99 mL, 50 mmol) and DMAP (244 mg, 2.00 mmol) in dry DCM (25 mL) at 0° C. was treated dropwise with benzenesulfonyl chloride (4.00 mL, 31.25 mmol) over 5 min. The resulting solution was stirred at 0° C. for 1 h, then allowed to warm to r.t. overnight. The reaction was quenched by the addition of saturated aqueous solution of NaHCO$_3$. The aqueous phase was extracted with DCM and the combined organic layers were washed with brine, dried (MgSO$_4$), filtered, and concentrated in vacuo. The residue was purified by FCC eluting with Petrol:DCM:MeOH (gradient elution from 100:50:0 to 50:50:3) to give the title compound (5.32 g, 73%) as a yellow solid.

LCMS (Method 4): Rt 2.99 min, m/z 293, 295 [MH$^+$].

Intermediate 91: tert-Butyl (2-(4-bromo-5-chloro-1H-pyrrolo [2,3-b]pyridin-2-yl)ethyl)carbamate To a solution of tert-butyl (2-(5-chloro-1H-pyrrolo[2,3-b]pyridin-2-yl)ethyl)carbamate (Intermediate 56, 2.80 g, 9.46) in ethyl acetate (30 mL) at 0° C., was added mCPBA (2.33 g, 10.4 mmol), and the solution was stirred at 0° C. for 1 hour, then warmed to r.t, and stirred overnight. The solvent was removed in vacuo and the residue was diluted with an aqueous 30% solution of potassium carbonate, and extracted with 10% MeOH/DCM. The combined organic layers were washed with brine, dried (Na$_2$SO$_4$) and filtered. The filtrate was concentrated in vacuo to give the crude 2-(2-((tert-butoxycarbonyl)amino)ethyl)-5-chloro-1H-pyrrolo[2,3-b]pyridine 7-oxide (2.23 g, 7.15 mmol, 75%) which was used directly in the next step.

To the crude 2-(2-((tert-butoxycarbonyl)amino)ethyl)-5-chloro-1H-pyrrolo[2,3-b]pyridine 7-oxide (2.23 g, 7.15 mmol) in DMF at 0° C. (7.0 mL) was added tetramethyl ammonium bromide (1.32 g, 8.58 mmol) followed by portion wise addition of methylsulfonyl anhydride (1.74 g, 10.01 mmol). The reaction mixture was stirred at 0° C. for 30 minutes and at r.t. for 2 hours. The reaction was diluted with water and extracted with EtOAc. The combined organic layers were washed with brine, dried (MgSO$_4$), filtered, and the filtrate was concentrated in vacuo. The residue was purified by FCC eluting with 25-50% EtOAc in petrol to give the title compound (854 mg, 32%) as a yellow solid.

LCMS (Method 4): Rt 3.04 min, m/z 374, 376 [MH$^+$].

Intermediate 92: (4-Bromo-1-((2-(trimethylsilyl)ethoxy)methyl)-1H-pyrrolo[2,3-b]pyridin-2-yl)methanol To a solution of 4-bromo-1-((2-(trimethylsilyl)ethoxy)methyl)-1H-pyrrolo[2,3-b]pyridine (3.185 g, 9.7 mmol) in THF (70 mL) at −78° C. under argon was added dropwise LDA (1 M in THF, 12.6 mL, 12.6 mmol). The resulting green solution was allowed to warm to −20° C., then paraformaldehyde (1.74 g, 57.9 mmol) was added. The mixture was allowed to warm slowly to room temperature then quenched with water and extracted with EtOAc/cyclohexane. The organic layer was dried and concentrated in vacuo. The residue was purified by FCC eluting with 0-20% EtOAc in cyclohexane to give the title compound as an orange oil (0.79 g, 23%).

LCMS (Method 3): Rt 1.66 min, m/z 357, 359 [MH$^+$].

Intermediate 93: 4-Bromo-2-(((1-methylpiperidin-4-yl)oxy)methyl)-1-((2-(trimethylsilyl)ethoxy)methyl)-1H-pyrrolo[2,3-b]pyridine To a solution of (4-bromo-1-((2-(trimethylsilyl)ethoxy)methyl)-1H-pyrrolo[2,3-b]pyridin-2-yl)methanol (Intermediate 92, 570 mg, 1.60 mmol) in DCM (12 mL) was added triethylamine (404 mg, 3.99 mmol), then methanesulfonyl chloride (274 mg, 2.39 mmol). The resulting mixture was stirred at room temperature for 80 min. Further triethylamine (152 mg, 1.50 mmol) and methanesulfonyl chloride (57 mg, 0.50 mmol) were added and the mixture was stirred for a further 1 h. The mixture was washed with saturated aqueous NaHCO$_3$ solution, dried and concentrated in vacuo to give crude 4-bromo-2-(chloromethyl)-1-((2-(trimethylsilyl)ethoxy)methyl)-1H-pyrrolo[2,3-b] (0.85 g) which was used directly in the next step.

To N-methyl-4-piperidinol (257 mg, 2.24 mmol) in DMF (2 mL) under argon was added sodium hydride (60% dispersion in oil, 90 mg, 2.25 mmol) and the mixture was stirred at room temperature until gas evolution ceased. The slurry was then added to the crude 4-bromo-2-(chloromethyl)-1-((2-(trimethylsilyl)ethoxy)methyl)-1H-pyrrolo[2,3-b]pyridine (0.30 g) under argon and the resulting green mixture was stirred at room temperature for 1 h. The mixture was quenched with water and extracted with 50% EtOAc/cyclohexane and EtOAc. The combined organic extracts were dried (Na$_2$SO$_4$), filtered, and concentrated in vacuo. The residue was purified by FCC eluting with 0-10% 2 M NH$_3$/MeOH in DCM to give the title compound as a yellow oil (66 mg, 26%).

LCMS (Method 3): Rt 1.24 min, m/z 454, 456 [MH$^+$].

By proceeding in a similar manner to Intermediate 93, the following compounds were prepared:

Intermediate 94: 2-((4-Bromo-1-((2-(trimethylsilyl)ethoxy)methyl)-1H-pyrrolo[2,3-b]pyridin-2-yl)methoxy)-N,N-dimethylethan-1-amine Starting from (4-bromo-1-((2-(trimethylsilyl)ethoxy)methyl)-1H-pyrrolo[2,3-b]pyridin-2-yl)methanol (Intermediate 92) and 2-dimethylaminoethanol.

LCMS (Method 3): Rt 1.20 min, m/z 428, 430 [MH$^+$].

Intermediate 95: 3-(2-(((1-Methylpiperidin-4-yl)oxy)methyl)-1-((2-(trimethylsilyl)ethoxy)methyl)-1H-pyrrolo[2,3-b]pyridin-4-yl)pyrazolo[1,5-b]pyridazine A solution of 4-bromo-2-(((1-methylpiperidin-4-yl)oxy)methyl)-1-((2-(trimethylsilyl)ethoxy)methyl)-1H-pyrrolo[2,3-b]pyridine (Intermediate 93, 66 mg, 0.145 mmol), 3-(4,4,5,5-tetramethyl-1,3,2-dioxaborolan-2-yl)pyrazolo[1,5-b]pyridazine (53 mg, 0.216 mmol), and potassium phosphate (90 mg, 0.425 mmol) in ethanol-water (2:1, 1.66 mL) was degassed with argon. XPhos Pd G3 (8 mg, 0.0095 mmol) was added and degassing was continued before the mixture was heated at 120° C. in a microwave for 1 h. The mixture was diluted with EtOAc and washed with brine, dried (Na$_2$SO$_4$), filtered, and concentrated in vacuo. The residue was purified by FCC eluting with 0-10% 2 M NH$_3$/MeOH in DCM to give the title compound as a yellow gum (75 mg, quant.).

LCMS (Method 3): Rt 1.13 min, m/z 493 [MH$^+$].

By proceeding in a similar manner to Intermediate 95, the following compounds were prepared:

Intermediate 96: N,N-Dimethyl-2-((4-(pyrazolo[1,5-b]pyridazin-3-yl)-1-((2-(trimethylsilyl)ethoxy)methyl)-1H-pyrrolo[2,3-b]pyridin-2-yl)methoxy)ethan-1-amine Starting from 2-((4-bromo-1-((2-(trimethylsilyl)ethoxy)methyl)-1H-pyrrolo[2,3-b]pyridin-2-yl)methoxy)-N,N-dimethylethan-1-amine (Intermediate 94) and 3-(4,4,5,5-tetramethyl-1,3,2-dioxaborolan-2-yl)pyrazolo[1,5-b]pyridazine.

LCMS (Method 3): Rt 1.11 min, m/z 467 [MH$^+$].

Intermediate 97: 1-propioloylpiperidine-4-carboxylic Acid

To a solution of propiolic acid (1.63 g, 23.23 mmol) in DCM (20 mL) was added DCC (2.40 g, 11.61 mmol) portionwise. The mixture was stirred at r.t. for 10 min before the solid was removed by filtration. The filtrate was added dropwise to a suspension of piperidine-4-carboxylic acid (1.00 g, 7.74 mmol) in an saturated aqueous solution of $Na_2CO_3$ (20 mL). The resultant mixture was stirred for 50 min before the phases were separated. The organic layer was extracted with an saturated aqueous solution of $Na_2CO_3$ and the combined aqueous layers were was washed with DCM. The aqueous layer was acidified with concentrated hydrochloric acid then extracted with EtOAc. The combined organic layers were dried ($Na_2SO_4$) and concentrated in vacuo before being azeotroped with xylenes. This gave the title compound as a pale yellow solid (647 mg, 46%).

LCMS (Method 3): Rt 0.65 min, m/z 182 [MH+].

Intermediate 98: 3-(2-(Chloromethyl)-1-(phenylsulfonyl)-1H-pyrrolo[2,3-b]pyridin-4-yl)pyrazolo[1,5-b]pyridazine To a solution of (1-(phenylsulfonyl)-4-(pyrazolo[1,5-b]pyridazin-3-yl)-1H-pyrrolo[2,3-b]pyridin-2-yl)methanol (Intermediate 59, 200 mg, 0.493 mmol) in DCM (5 mL) at 0° C. under argon was added DIPEA (0.34 mL, 1.97 mmol), followed by methanesulfonyl chloride (0.11 mL, 1.48 mmol). The resulting mixture was stirred at 0° C. for 15 min, then allowed to warm to room temperature and stirred for 45 min. The mixture was re-cooled to 0° C. and further DIPEA (0.34 mL, 1.97 mmol) and methanesulfonyl chloride (0.11 mL, 1.48 mmol) was added and the mixture was stirred for 45 min. The ice bath was removed and stirring was continued for a further 2 h. Methanol (10 mL) resulting in the formation of a solid. The DCM was removed by evaporation and the solid was collected by filtration, washed with methanol and dried under vacuum to give the title compound (190 mg, 91%).

LCMS (Method 3): Rt 1.36 min, m/z 424.2, 426.1 [MH+].

Intermediate 99: tert-Butyl 4-((2-amino-4-bromopyridin-3-yl)ethynyl)piperidine-1-carboxylate A mixture of 4-bromo-3-iodopyridin-2-amine (790 mg, 2.64 mmol), tert-butyl 4-ethynylpiperidine-1-carboxylate (664 mg, 3.17 mmol), $Pd(PPh_3)_2Cl_2$ (93 mg, 0.13 mmol), Cu(I)I (50 mg, 0.26 mmol), $Et_3N$ (1.5 mL, 10.75 mmol) and MeCN (5 mL) was degassed with argon The mixture was then stirred and heated at 45° C. for 1.75 h. After cooling, the mixture was diluted with water and extracted with a mixture of EtOAc/isohexane. The organic layer was dried ($Na_2SO_4$) and concentrated in vacuo. The residue was purified by FCC, eluting with 10-70% EtOAc in isohexane to give the title compound as a solid (761 mg, 75%).

LCMS (Method 3): Rt 1.32 min, m/z 380, 382 [MH+].

Intermediate 100: tert-Butyl 4-(4-bromo-1H-pyrrolo[2,3-b]pyridin-2-yl)piperidine-1-carboxylate To a solution of tert-butyl 4-((2-amino-4-bromopyridin-3-yl)ethynyl)piperidine-1-carboxylate (Intermediate 99, 761 mg, 1.99 mmol) in NMP (10 mL) under an atmosphere of argon was added potassium tert-butoxide (557 mg, 4.96 mmol). The resultant mixture was stirred at r.t. for 2.5 h then diluted with water. The mixture was filtered and the filtrate was extracted with EtOAc, dried ($Na_2SO_4$) and concentrated in vacuo. The resultant solid was washed with water and dried under reduced pressure to give the title compound as a brown solid (570 mg, 76%).

LCMS (Method 3): Rt 1.52 min, m/z 380, 382 [MH+].

Intermediate 101: Methyl (R,E)-1-(4-(dimethylamino)but-2-enoyl)pyrrolidine-3-carboxylate A solution of (R)-methyl pyrrolidine-3-carboxylate hydrochloride (224 mg, 1.4 mmol), 4-dimethylaminobut-2-enoic acid (262 mg, 2.0 mmol), EDC. HCl (311 mg, 1.6 mmol), DIPEA (0.47 mL, 2.7 mmol) and HOBT.$xH_2O$ (274 mg, 2.0 mmol) in DMF (2.0 mL) was stirred at room temperature for 30 mins then concentrated in vacuo. The residue was purified by FCC eluting with 0-10% [2M $NH_3$/MeOH] in DCM to afford the title compound as a yellow oil (380 mg, quant.)

LCMS (Method 3): Rt 0.44 min, m/z 241 [MH+].

By proceeding in a similar manner to Intermediate 101, the following compounds were prepared:

Intermediate 102: Ethyl (E)-1-(4-(dimethylamino)but-2-enoyl)piperidine-4-carboxylate Starting from piperidine-4-carboxylic acid ethyl ester and 4-dimethylaminobut-2-enoic acid.

LCMS (Method 3): Rt 0.72 min, m/z 269 [MH+].

Intermediate 103: Ethyl (E)-2-(1-(4-(dimethylamino)but-2-enoyl)piperidin-4-yl)acetate Starting from ethyl piperidine-4-acetate hydrochloride and 4-dimethylaminobut-2-enoic acid.

LCMS (Method 3): Rt 0.69 min, m/z 283 [MH+].

Intermediate 104: Ethyl (R,E)-2-((1-(4-(dimethylamino)but-2-enoyl)pyrrolidin-3-yl)oxy)acetate Starting from ethyl 2-((3R)-3-pyrrolidinyloxy)acetate and 4-dimethylaminobut-2-enoic acid.

LCMS (Method 3): Rt 0.65 min, m/z 285 [MH+].

Intermediate 105: Ethyl (R,E)-1-(4-(dimethylamino)but-2-enoyl)piperidine-3-carboxylate Starting from ethyl (R)-nipecotate and 4-dimethylaminobut-2-enoic acid.

LCMS (Method 3): Rt 0.70 min, m/z 269 [MH+].

Intermediate 106: Methyl (E)-5-(4-(dimethylamino)but-2-enamido)nicotinate

T3P (461 mg, 1.45 mmol) was added to a mixture of methyl 5-aminopyridine-3-carboxylate (110 mg, 0.724 mmol), 4-dimethylaminobut-2-enoic acid (140 mg, 1.09 mmol) and TEA (513 mg, 5.07 mmol) in DMF (1 mL). After 45 mins, water was added and the mixture was extracted with DCM, washed with water, dried and concentrated in vacuo. The residue was purified by FCC, eluting with 1-10% 2M ammonia/MeOH in DCM to give the title compound (37 mg) as a pale brown solid.

LCMS (Method 3): Rt 0.61 min, m/z 264 [MH+].

Intermediate 107: Lithium (E)-5-(4-(dimethylamino)but-2-enamido)nicotinate

A mixture of methyl (E)-5-(4-(dimethylamino)but-2-enamido)nicotinate (Intermediate 106, 40 mg, 0.15 mmol) and 2M LiOH (0.091 mL, 0.18 mmol) in MeOH (0.5 mL) and water (0.5 mL) was stirred at room temperature for 2 h. Solid $CO_2$ was added and the mixture was concentrated in vacuo. The residue was treated with 1 mL IMS, filtered to remove insoluble $Li_2CO_3$ then the filtrate was concentrated in vacuo to give the title compound (40 mg, quant.) as a yellow solid.

$^1$H NMR (400 MHz, d6-DMSO): 2.32 (6H, s), 3.22 (2H, dd, J=6.6, 1.5 Hz), 6.30 (1H, dt, J=15.3, 1.6 Hz), 6.95 (1H, dt, J=15.4, 6.5 Hz), 8.40 (1H, dd, J=2.4, 1.8 Hz), 8.78 (1H, d, J=1.8 Hz), 9.03 (1H, d, J=2.4 Hz).

By proceeding in a similar manner to Intermediate 107, the following compounds were prepared:

Intermediate 108: Lithium (E)-1-(4-(dimethyl-amino)but-2-enoyl)piperidine-4-carboxylate Starting from ethyl (E)-1-(4-(dimethylamino)but-2-enoyl)piperidine-4-carboxylate (Intermediate 102).
LCMS (Method 3): Rt 0.26 min, m/z 240 [MH$^+$].

Intermediate 109: (R,E)-1-(4-(Dimethylamino)but-2-enoyl)pyrrolidine-3-carboxylate Starting from methyl (R,E)-1-(4-(dimethylamino)but-2-enoyl)pyrrolidine-3-carboxylate (Intermediate 101).
LCMS (Method 3): Rt 0.19 min, m/z 227 [MH$^+$].

Intermediate 110: Lithium (E)-2-(1-(4-(dimethyl-amino)but-2-enoyl)piperidin-4-yl)acetate Starting from ethyl (E)-2-(1-(4-(dimethylamino)but-2-enoyl)piperidin-4-yl)acetate (Intermediate 103).
LCMS (Method 3): Rt 0.22 min, m/z 255 [MH$^+$].

Intermediate 111: Lithium (R,E)-2-((1-(4-(dimethyl-amino)but-2-enoyl)pyrrolidin-3-yl)oxy)acetate Starting from ethyl (R,E)-2-((1-(4-(dimethylamino)but-2-enoyl)pyrrolidin-3-yl)oxy)acetate (Intermediate 104)
LCMS (Method 3): Rt 0.18 min, m/z 257 [MH$^+$].

Intermediate 112: Lithium (R,E)-1-(4-(dimethyl-amino)but-2-enoyl)piperidine-3-carboxylate Starting from ethyl (R,E)-1-(4-(dimethylamino)but-2-enoyl)piperidine-3-carboxylate. (Intermediate 105)
LCMS (Method 3): Rt 0.28 min, m/z 241 [MH$^+$].

Intermediate 113: ((R)-2-chloropropanoyl)-D-proline

A mixture of (R)-2-Chloropropanoic acid (377 mg, 3.5 mmol) in DCM (3.0 mL) was treated with DCC (376 mg, 1.8 mmol) and the mixture was stirred at room temperature for 30 mins. The mixture was filtered and the filtrate was added to a mixture of D-proline (100 mg, 0.87 mmol) in 1M aqueous NaOH (3.0 mL, 3.0 mmol) and the resultant mixture was stirred at room temperature for 1 h. The phases were separated and the aqueous layer was washed with DCM then acidified with 1N aqueous HCl and extracted with EtOAc. The aqueous layer was saturated with sodium chloride then extracted again with EtOAc. The combined organic layers were dried and concentrated in vacuo. The residue was treated with xylenes and concentrated in vacuo. The solid was slurried in isohexane, collected by filtration and dried to afford the title compound (133 mg, 74%).

$^1$H NMR (400 MHz, CDCl$_3$ 241721): 1.69 (3H, d, J=6.7 Hz), 2.00-2.22 (3H, m), 2.25-2.35 (1H, m), 3.60-3.67 (1H, m), 3.77-3.85 (1H, m), 4.52 (1H, q, J=6.6 Hz), 4.57-4.62 (1H, m).

Intermediate 114: N-Methyl-1-(1-(phenylsulfonyl)-4-(pyrazolo[1,5-b]pyridazin-3-yl)-1H-pyrrolo[2,3-b]pyridin-2-yl)methanamine A solution of 3-(2-(chloromethyl)-1-(phenylsulfonyl)-1H-pyrrolo[2,3-b]pyridin-4-yl)pyrazolo[1,5-b]pyridazine (prepared as in step 1 of Intermediate 60, 43 mg, 0.101 mmol) in methylamine solution (2 M in THF, 5.1 mL, 10.1 mmol) was stirred at room temperature for 4.5 h. The mixture was filtered and the filtrates were evaporated. The residue was purified by column chromatography (4 g silica, 0-10% 2 M NH$_3$ in MeOH/DCM) to give the title compound (36 mg, 86%).
LCMS (Method 3): Rt 0.98 min, m/z 419.1 [MH$^+$].

Intermediate 114A: 3-Acrylamido-4-methoxybenzoic Acid

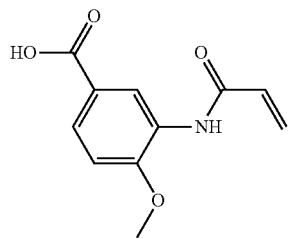 [SMILES: C=CC(=O)Nc1cc(C(=O)O)ccc1OC]

Starting from 3-amino-4-methoxybenzoic acid and acryloyl chloride.
LCMS (Method 3): Rt 1.10 min, m/z 222 [MH$^+$].

Intermediate 115: (1s,3s)-3-(4-(Pyrazolo[1,5-b]pyridazin-3-yl)-1H-pyrrolo[2,3-b]pyridin-2-yl)cyclobutan-1-amine

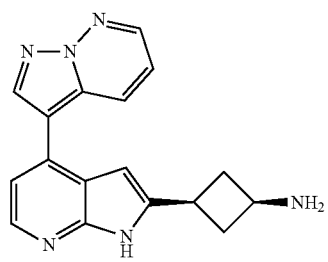 [SMILES: N[C@H]1C[C@@H](c2cc3c(-c4cnn5ncccc45)ccnc3[nH]2)C1]

c. tert-butyl ((1s,3s)-3-ethynylcyclobutyl)carbamate

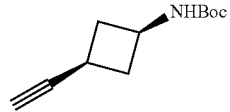

A solution of dimethyl (1-diazo-2-oxopropyl)phosphonate (0.66 mL, 2.76 mmol) in methanol (6 mL) was treated with cis-Boc-3-formyl-cyclobutylamine (0.5 g, 2.51 mmol) and then potassium carbonate (0.52 g, 3.76 mmol). The mixture was stirred at room temperature overnight. The reaction mixture was filtered and the filtrate was evaporated to dryness, The residue was partitioned between ethyl acetate/iso-hexane (1:1) and water. The aqueous phase was further extracted with ethyl acetate/iso-hexane (1:1). The combined organic layers were washed with brine, dried over MgSO$_4$, filtered and the filtrate was evaporated to dryness to give the title compound (0.57 g) as a cream solid. The same procedure was repeated with the same method and same amounts to yield a cream solid (0.56 g). The combined solids were purified by FCC (ethyl acetate/iso-hexane) to yield the title compound as a white crystalline solid (0.68 g, 69% yield).

LCMS (Method 3): Rt 1.23 min, m/z 140 [M-t-Bu+H$^+$].

d. tert-Butyl ((1s,3s)-3-((2-amino-4-bromopyridin-3-yl)ethynyl)cyclobutyl)carbamate

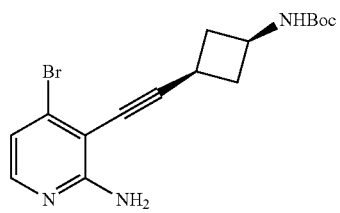 [SMILES: CC(C)(C)OC(=O)N[C@H]1C[C@@H](C#Cc2c(Br)ccnc2N)C1]

Prepared by proceeding in a similar manner to Intermediate 73, starting from 4-bromo-3-iodopyridin-2-amine (Intermediate 72) and tert-butyl ((1s,3s)-3-ethynylcyclobutyl)carbamate (Intermediate 115a).

LCMS (Method 3): Rt 1.16 min, m/z 366 [MH$^+$].

e. (1s,3s)-3-(4-Bromo-1H-pyrrolo[2,3-b]pyridin-2-yl)cyclobutan-1-amine

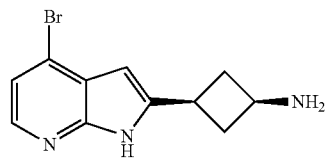 [SMILES: N[C@H]1C[C@@H](c2cc3c(Br)ccnc3[nH]2)C1]

Prepared by proceeding in a similar manner to Intermediate 74, starting from tert-butyl ((1s,3s)-3-((2-amino-4-bromopyridin-3-yl)ethynyl)cyclobutyl)carbamate (Intermediate 115b).

LCMS (Method 3): Rt 0.69 min, m/z 266 [MH$^+$].

f. (1s,3s)-3-(4-(Pyrazolo[1,5-b]pyridazin-3-yl)-1H-pyrrolo[2,3-b]pyridin-2-yl)cyclobutan-1-amine

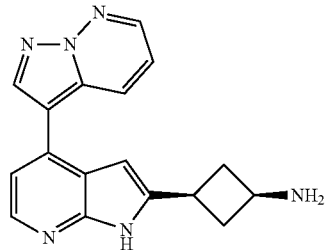 [SMILES: N[C@H]1C[C@@H](c2cc3c(-c4cnn5ncccc45)ccnc3[nH]2)C1]

Prepared by proceeding in a similar manner to Example 119, starting from (1s,3s)-3-(4-bromo-1H-pyrrolo[2,3-b]pyridin-2-yl)cyclobutan-1-amine (Intermediate 115c) and 3-(4,4,5,5-tetramethyl-1,3,2-dioxaborolan-2-yl)pyrazolo[1,5-b]pyridazine.

LCMS (Method 3): Rt 0.61 min, m/z 305 [MH$^+$].

Intermediate 116: Acryloyl-L-proline

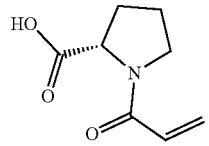

Starting from L-proline.
LCMS (Method 3): Rt 0.76 min, m/z 170 [MH$^+$].

Intermediate 117: tert-Butyl (3S)-3-(3-(4-(pyrazolo[1,5-b]pyridazin-3-yl)-1H-pyrrolo[2,3-b]pyridin-2-yl)pyrrolidine-1-carbonyl)piperidine-1-carboxylate

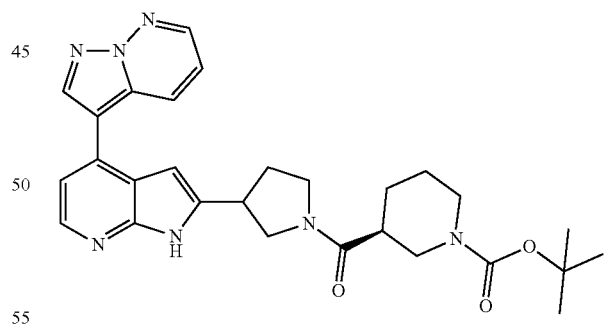

To a solution of S-Boc-piperidine-3-carboxylic acid (121 mg, 0.526 mmol) in DMF (1 mL) and DIPEA (0.27 mL, 1.58 mmol) was added T3P (251 mg, 0.789 mmol). After 15 minutes 3-[2-(pyrrolidin-3-yl)-1H-pyrrolo[2,3-b]pyridine-4-yl)pyrazolo[1,5-b]pyridazine (Example 122, 80 mg, 0.263 mmol) was added. The reaction mixture was stirred for 30 minutes, then water (10 mL) was added. The target material was extracted with DCM. The DCM phase was dried, filtered and the filtrate was evaporated to dryness. The residue was purified by FCC (MeOH/DCM) to yield the title compound (89 mg).

LCMS (Method 3): Rt 1.06 min, m/z 516 [MH+].

Intermediate 118: ((S)-Piperidin-3-yl)(3-(4-(pyrazolo[1,5-b]pyridazin-3-yl)-1H-pyrrolo[2,3-b]pyridin-2-yl)pyrrolidin-1-yl)methanone

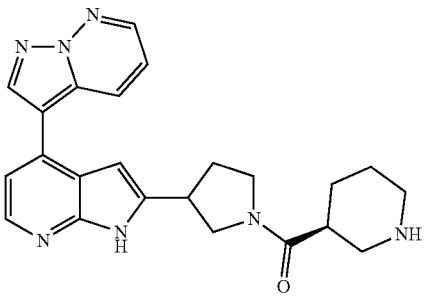 [SMILES: O=C([C@H]1CCCNC1)N1CCC(c2cc3c(-c4cnn5ncccc45)ccnc3[nH]2)C1]

Prepared by proceeding in a similar manner to Example 139, starting from tert-butyl (3S)-3-(3-(4-(pyrazolo[1,5-b]pyridazin-3-yl)-1H-pyrrolo[2,3-b]pyridin-2-yl)pyrrolidine-1-carbonyl)piperidine-1-carboxylate (Intermediate 117).

LCMS (Method 3): Rt 0.63 min, m/z 416 [MH+].

Intermediate 119: (2S,4R)-1-acryloyl-4-fluoropyrrolidine-2-carboxylic Acid

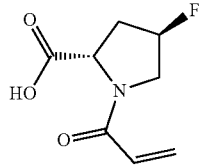

a. (2S,4R)-4-Fluoropyrrolidine-2-carboxylic Acid

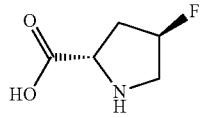

(2S,4R)-4-Fluoropyrrolidine-1,2-dicarboxylic acid 1-tert-butyl ester (400 mg, 1.71 mmol) was dissolved in DCM (2 mL). TFA (1 mL, 13 mmol) was added and the mixture was stirred at room temperature for 3 hours. The solvents were removed under reduced pressure to give a white solid which was used for the next step without further purification.

$^1$H NMR (400 MHz, DMSO) 9.81 (2H, bs), 5.53-5.40 (1H, m), 4.52 (1H, dd, J=7.6, 11.0 Hz), 3.64-3.46 (1H, m), 3.49 (1H, s), 2.62-2.54 (1H, m), 2.39-2.20 (1H, m).

b. (2S,4R)-1-Acryloyl-4-fluoropyrrolidine-2-carboxylic Acid

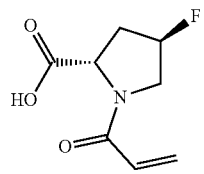

Prepared by proceeding in a similar manner to Intermediate 28 starting from (2S,4R)-4-fluoropyrrolidine-2-carboxylic acid and acryloyl chloride (Intermediate 119a).

$^1$H NMR (400 MHz, DMSO) 12.67-12.67 (1H, bs), 6.66-6.59 (0.7H, m), 6.42-6.35 (0.3H, m), 6.20-6.12 (1H, m), 5.76-5.66 (1H, m), 5.47-5.25 (1H, m), 4.80 (0.3H, t, J=8.2 Hz), 4.35 (0.7H, t, J=8.7 Hz), 4.09-3.93 (1H, m), 3.84-3.69 (1H, m), 3.52-3.36 (0.3H, m), 2.73-2.52 (0.7H, m), 2.42-2.24 (0.3H, m), 2.18-1.98 (0.7H, m).

Intermediate 120: (S)-5-Acryloyl-5-azaspiro[2.4]heptane-6-carboxylic Acid

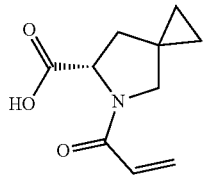

a. (S)-5-azaspiro[2.4]heptane-6-carboxylic Acid

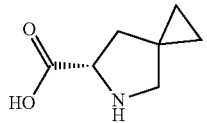

(S)-5-Boc-5-azaspiro[2,4]heptane-6-carboxylic acid (583 mg, 2.42 mmol) was dissolved in DCM (2 mL). TFA (1 mL, 13 mmol) was added and the mixture was stirred at room temperature for 3 hours. The solvents were removed under reduced pressure to give a white solid which was used for the next step without further purification.

$^1$H NMR (400 MHz, DMSO) 9.74-9.74 (1H, m), 8.91-8.91 (1H, m), 4.49 (1H, s), 3.16 (2H, s), 2.25-2.19 (1H, m), 2.05-1.99 (1H, m), 0.86-0.61 (4H, m).

b. (S)-5-Acryloyl-5-azaspiro[2.4]heptane-6-carboxylic Acid

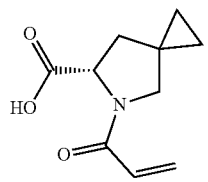

Prepared by proceeding in a similar manner to Intermediate 28 starting from (S)-5-azaspiro[2.4]heptane-6-carboxylic acid (2.42 mmol) and acryloyl chloride (Intermediate 120a).

$^1$H NMR (400 MHz, DMSO) 12.59-12.59 (1H, bs), 6.52 (0.7H, dd, J=10.5, 16.8 Hz), 6.41 (0.3H, dd, J=10.5, 17.1 Hz), 6.17-6.09 (1H, m), 5.72-5.61 (1H, m), 4.78 (0.3H, dd, J=2.2, 8.7 Hz), 4.46-4.41 (0.7H, m), 3.61 (0.7H, d, J=9.8 Hz), 3.52-3.46 (1H, m), 3.20 (0.3H, d, J=11.9 Hz), 2.49-2.42 (0.3H, m), 2.25 (0.7H, dd, J=8.7, 12.7 Hz), 1.85-1.72 (1H, m), 0.62-0.53 (4H, m).

Intermediate 121: 1-(Piperazin-1-yl)prop-2-en-1-one

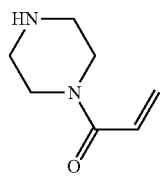

a. tert-Butyl 4-acryloylpiperazine-1-carboxylate

1-Boc-piperazine (1 g, 5.37 mmol) was dissolved in THF (20 mL). DIPEA (2.3 mL, 13.42 mmol) was added, followed by dropwise addition of acryloyl chloride (0.52 mL, 6.44 mmol). The mixture was stirred for one hour at room temperature, then diluted with ethyl acetate/i-hexane, washed with water and brine, dried over MgSO$_4$, filtered and the filtrate was evaporated to dryness. The residue was purified by FCC (ethyl acetate/i-hexane) to yield the title compound (1.12 g).
LCMS (Method 3): Rt 1.11 min, m/z 141 [M-Boc+H$^+$].

b. 1-(Piperazin-1-yl)prop-2-en-1-one

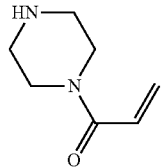

tert-Butyl 4-acryloylpiperazine-1-carboxylate (155 mg, 0.645 mmol) was dissolved in DCM (6 mL) and TFA (3 mL) was added. The mixture was stirred at room temperature for 20 minutes, then diluted with toluene and evaporated to dryness. The residue was dissolved in DCM, and washed with NaOH (1M, 2 mL) and with brine. The solvent was removed under reduced pressure and the residue was used for the next step without further purification.
LCMS (Method 3): Rt 0.13 min, m/z 141 [MH$^+$].

Intermediate 122: (E)-3-(4-(Pyrazolo[1,5-b]pyridazin-3-yl)-1H-pyrrolo[2,3-b]pyridin-2-yl)acrylic Acid

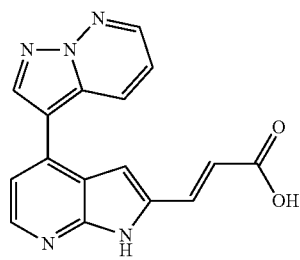 [SMILES: O=C(O)/C=C/c1cc2c(-c3cnn4ncccc34)ccnc2[nH]1]

a. 4-Bromo-1-(phenylsulfonyl)-1H-pyrrolo[2,3-b]pyridine

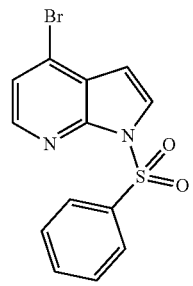 [SMILES: O=S(=O)(c1ccccc1)n1ccc2c(Br)ccnc21]

4-Bromo-1H-pyrrolo[2,3-b]pyridine (10.5 g, 53.3 mmol) was dissolved in THF (200 mL) under argon and cooled to 0° C. Sodium hydride (1.41 g, 58.65 mmol) was added portionwise and after 30 minutes benzenesulfonyl chloride (7.5 mL, 58.65 mmol) was added. The reaction mixture was allowed to warm up to room temperature and stirred at room temperature overnight. The mixture was poured into water (1.8 L) and stirred one hour at room temperature. The solid formed was collected by filtration and dried in a vacuum oven at 45° C. (18.1 g)

$^1$H NMR (400 MHz, DMSO) 8.25 (1H, d, J=5.2 Hz), 8.14-8.11 (2H, m), 8.07 (1H, d, J=4.1 Hz), 7.77-7.73 (1H, m), 7.66-7.61 (3H, m), 6.81 (1H, d, J=4.0 Hz).

b. 4-Bromo-1-(phenylsulfonyl)-1H-pyrrolo[2,3-b]pyridine-2-carbaldehyde

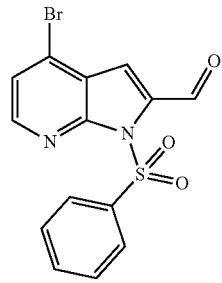 [SMILES: O=Cc1cc2c(Br)ccnc2n1S(=O)(=O)c1ccccc1]

A solution of diisopropylamine (1.6 mL, 11.57 mmol) was dissolved in THF (15 mL and cooled to −78° C. under argon. n-Butyllihium (0.88 mL, 10.68 mmol) was added dropwise and after stirring 5 minutes at −78° C., the mixture was allowed to warm up to 0° C. stirred at 0° C. for 5 minutes and then cooled again to −78° C. A solution of 4-bromo-1-(phenylsulfonyl)-1H-pyrrolo[2,3-b]pyridine (Intermediate 122a, 3 g, 8.90 mmol) in THF (15 mL) added dropwise with stirring. The mixture was stirred at −78° C. for 30 minutes then ethyl formate (1.4 mL, 17.79 mmol) was added and the mixture was stirred at −78° C. for 15 minutes and subsequently quenched with saturated ammonium chloride solution. The reaction mixture was diluted with ethyl acetate/i-hexane and the organic phase was dried over MgSO$_4$ and filtered. The filtrate was evaporated to dryness to yield the title compound as a yellow solid (3.05 g).

$^1$H NMR (400 MHz, CDCl$_3$) 10.64 (1H, s), 8.40 (1H, d, J=5.2 Hz), 8.19-8.16 (2H, m), 7.65-7.60 (1H, m), 7.54-7.50 (2H, m), 7.47-7.43 (2H, m).

c. tert-Butyl (E)-3-(4-bromo-1-(phenylsulfonyl)-1H-pyrrolo[2,3-b]pyridin-2-yl)acrylate

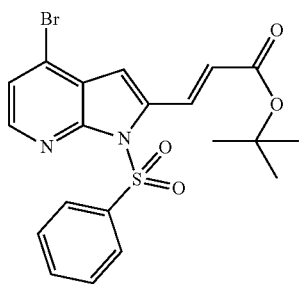 [SMILES: CC(C)(C)OC(=O)/C=C/c1cc2c(Br)ccnc2n1S(=O)(=O)c1ccccc1]

4-Bromo-1-(phenylsulfonyl)-1H-pyrrolo[2,3-b]pyridine-2-carbaldehyde (Intermediate 122b, 1 g, 2.74 mmol) and (tert-butoxycarbonylmethylene)triphenylphosphorane (1.13 g, 3.01 mmol) were combined in DCM (20 mL) and stirred at room temperature under argon overnight. Then the solvent was removed under reduced pressure and the residue was purified by FCC (ethyl acetate/i-hexane) to yield the title compound as a white gum (1.2 g, mixture of two isomers).

LCMS (Method 3): Rt 1.64, 1.71 min, m/z 462, 464 [MH$^+$].

d. tert-Butyl (E)-3-(1-(phenylsulfonyl)-4-(pyrazolo[1,5-b]pyridazin-3-yl)-1H-pyrrolo[2,3-b]pyridin-2-yl)acrylate

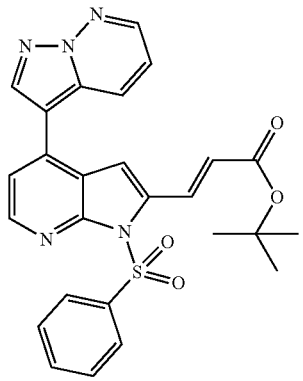 [SMILES: CC(C)(C)OC(=O)/C=C/c1cc2c(-c3cnn4ncccc34)ccnc2n1S(=O)(=O)c1ccccc1]

Prepared by proceeding in a similar manner to Example 119 starting from tert-butyl (E)-3-(4-bromo-1-(phenylsulfonyl)-1H-pyrrolo[2,3-b]pyridin-2-yl)acrylate (Intermediate 122c) and 3-(4,4,5,5-tetramethyl-1,3,2-dioxaborolan-2-yl)pyrazolo[1,5-b]pyridazine as a mixture of two isomers.

LCMS (Method 3): Rt 1.47, 1.54 min, m/z 502 [MH$^+$].

e. tert-Butyl (E)-3-(4-(pyrazolo[1,5-b]pyridazin-3-yl)-1H-pyrrolo[2,3-b]pyridin-2-yl)acrylate

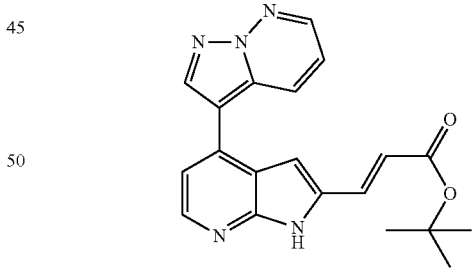

tert-Butyl (E)-3-(1-(phenylsulfonyl)-4-(pyrazolo[1,5-b]pyridazin-3-yl)-1H-pyrrolo[2,3-b]pyridin-2-yl)acrylate (Intermediate 122d, 135 mg, 0.269 mmol) was dissolved in a mixture of dioxane (2 mL) and isopropanol (0.4 mL). NaOH (3M, 0.83 mL) was added and the mixture was heated at 65° C. for one hour. The reaction mixture was cooled to room temperature and water (20 Ml) was added. The yellow solid formed was collected by filtration (65 mg).

LCMS (Method 3): Rt 1.26 min, m/z 362 [MH$^+$].

f. (E)-3-(4-(Pyrazolo[1,5-b]pyridazin-3-yl)-1H-pyrrolo[2,3-b]pyridin-2-yl)acrylic Acid

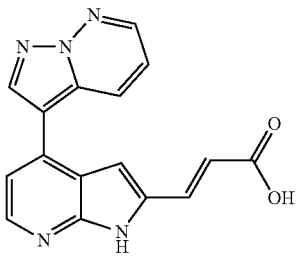 [SMILES: O=C(O)/C=C/c1cc2c(-c3cnn4ncccc34)ccnc2[nH]1]

tert-Butyl (E)-3-(4-(pyrazolo[1,5-b]pyridazin-3-yl)-1H-pyrrolo[2,3-b]pyridin-2-yl)acrylate (Intermediate 122e, 65 mg, 0.180 mmol) was dissolved in DCM (4 mL). TFA (2 mL) was added and the mixture was stirred at room temperature for 50 minutes. The solvents were removed under reduced pressure to give the title compound as a yellow solid (62 mg) which was used for the next step without further purification as a TFA salt.

LCMS (Method 3): Rt 0.90 min, m/z 306 [MH$^+$].

Intermediate 123: (S)—N-(2-(4-(+yrazolo[1,5-b]pyridazin-3-yl)-1H-pyrrolo[2,3-b]pyridin-2-yl)ethyl)piperidine-3-carboxamide

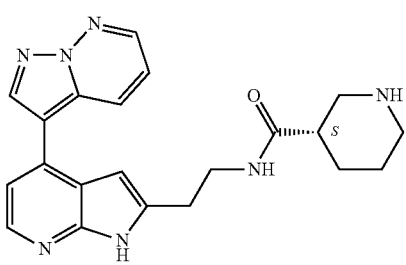

a. tert-Butyl (S)-3-((2-(1-(phenylsulfonyl)-4-(pyrazolo[1,5-b]pyridazin-3-yl)-1H-pyrrolo[2,3-b]pyridin-2-yl)ethyl)carbamoyl)piperidine-1-carboxylate

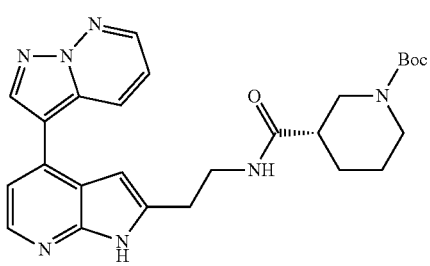

Prepared by proceeding in a similar manner to Intermediate 47, starting from 2-(1-(phenylsulfonyl)-4-(pyrazolo[1,5-b]pyridazin-3-yl)-1H-pyrrolo[2,3-b]pyridin-2-yl)ethan-1-amine (Intermediate 25) and (S)-1-(tert-butoxycarbonyl)piperidine-3-carboxylic acid (which can be prepared as described in *Tetrahedron*, 2016, 72(25), 3567-3578).

LCMS (Method 4): Rt 2.901 min, m/z 630.2 [MH$^+$]

b. (S)—N-(2-(4-(Pyrazolo[1,5-b]pyridazin-3-yl)-1H-pyrrolo[2,3-b]pyridin-2-yl)ethyl)piperidine-3-carboxamide

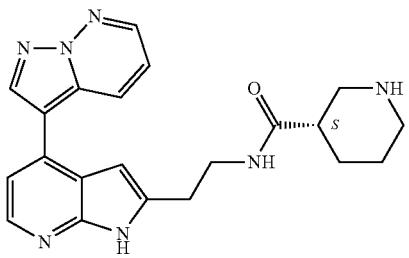

A solution of tert-butyl (S)-3-((2-(1-(phenylsulfonyl)-4-(pyrazolo[1,5-b]pyridazin-3-yl)-1H-pyrrolo[2,3-b]pyridin-2-yl)ethyl)carbamoyl)piperidine-1-carboxylate (Intermediate 123a, 1.61 g, 2.56 mmol) in DCM (24 mL) was treated with TFA (8 mL). The reaction mixture was stirred at r.t. for 3 h then concentrated in vacuo, and then azetroped with toluene. The residue was dissolved in dioxane (20 mL) and IPA (5 mL) and then treated with 3M aqueous NaOH (5 mL). The reaction mixture was stirred and heated at 50° C. for 24 hour. After cooling, the mixture was treated with 6N HCl until the pH=7, then concentrated in vacuo. The residue was purified by FCC eluting with 7.5-15% 2M ammonia in MeOH in DCM to give the title compound (876 mg, 87%) as a yellow solid.

LCMS (Method 4): Rt 2.126 min, m/z 390.2 [MH$^+$].

By proceeding in a similar manner to Intermediate 18, the following compounds were prepared:

Intermediate 124: Acryloylphenylalanine

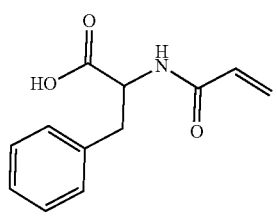 [SMILES: C=CC(=O)NC(Cc1ccccc1)C(=O)O]

Starting from phenylalanine and acryloyl chloride.
$^1$H NMR (400 MHz, DMSO) 2.90 (1H, dd, J=13.8, 9.6) 3.10 (1H, dd, J=13.8, 4.9), 4.52 (1H, ddd, J=9.6, 8.1, 4.9), 5.58 (1H, dd, J=10.2, 2.2), 6.05 (1H, dd, J=17.1, 2.2), 6.28 (1H, dd, J=17.1, 10.2), 7.37-7.13 (5H, m), 8.44 (1H, d, J=8.1), 12.73 (1H, s).

Intermediate 125: Acryloylalanine

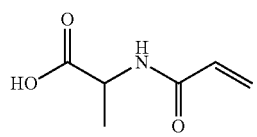

Starting from alanine and acryloyl chloride.

¹H NMR (400 MHz, DMSO) 1.30 (3H, d, J=7.3). 4.28 (1H, app p, J=7.3), 5.62 (1H, dd, J=10.2, 2.2), 6.10 (2H, dd, J=17.1), 6.29 (1H, dd, J=17.1, 10.2), 8.40 (1H, s), 12.52 (1H, s).

Intermediate 126: 1-Acrylamidocyclopropane-1-carboxylic Acid

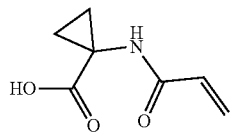

Starting from 1-aminocyclopropane-1-carboxylic acid and acryloyl chloride.

¹H NMR δ$_H$ (400 MHz, DMSO-d$_6$) 1.08-0.86 (2H, m), 1.52-1.26 (2H, m), 5.60 (1H, dd, J=9.8, 2.5), 6.09 (1H, dd, J=17.1, 2.5), 6.18 (1H, dd, J=17.1, 9.8), 8.61 (1H, s), 12.37 (1H, s).

Intermediate 127: 2-(4-(Pyrazolo[1,5-b]pyridazin-3-yl)-1H-pyrrolo[2,3-b]pyridin-2-yl)ethyl L-prolinate

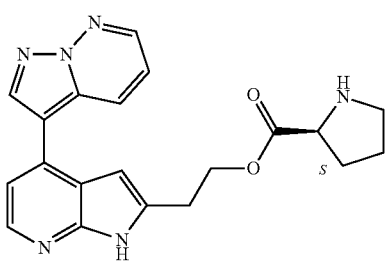

a. 2-(1-(Phenylsulfonyl)-4-(pyrazolo[1,5-b]pyridazin-3-yl)-1H-pyrrolo[2,3-b]pyridin-2-yl)ethan-1-ol

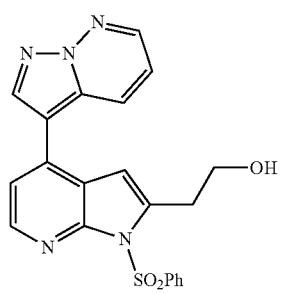

Prepared by proceeding in a similar manner to Intermediate 54, starting from 2-(4-chloro-1-(phenylsulfonyl)-1H-pyrrolo[2,3-b]pyridin-2-yl)ethan-1-ol (Intermediate 51) and 3-(4,4,5,5-tetramethyl-1,3,2-dioxaborolan-2-yl)pyrazolo[1,5-b]pyridazine.

LCMS (Method 4): Rt 2.459 min, m/z 420.0 [MH⁺].

b. 1-(tert-Butyl) 2-(2-(1-(phenylsulfonyl)-4-(pyrazolo[1,5-b]pyridazin-3-yl)-1H-pyrrolo[2,3-b]pyridin-2-yl)ethyl) (S)-pyrrolidine-1,2-dicarboxylate

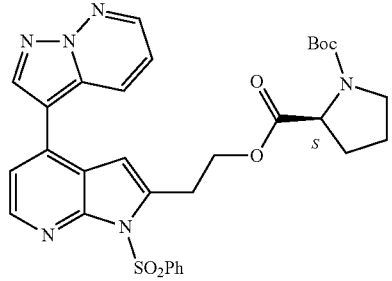

HATU (942 mg, 2.48 mmol) was added to a solution of (S)-1-(tert-butoxycarbonyl)piperidine-2-carboxylic acid (which can be prepared as described in *Organic Letters*, 2011, 13(2), 216-219) (533 mg, 2.48 mmol) and TEA (1.03 mL, 7.44 mmol) in DCM (2.5 mL) and the resultant mixture was stirred for 15 min. The solution was then added to a solution of 2-(1-(phenylsulfonyl)-4-(pyrazolo[1,5-b]pyridazin-3-yl)-1H-pyrrolo[2,3-b]pyridin-2-yl)ethan-1-ol (Intermediate 127a, 523 mg, 1.24 mmol) in DCM (2.5 mL) and the mixture was stirred for 24 h. The reaction was quenched by addition of saturated aqueous solution of Na$_2$CO$_3$ and extracted with CHCl$_3$. The combined organic layers were washed with a saturated aqueous solution of Na$_2$CO$_3$, brine, dried (Na$_2$SO$_4$) and filtered. The filtrate was concentrated in vacuo and the residue was purified by FCC eluting with Petrol:EtOAc:MeOH (50:50:1 to 0:100:1) to give the title compound (739 mg, 97%) as a yellow oil.

LCMS (Method 4): Rt 3.077 min, m/z 617.2 [MH⁺].

c. 2-(1-(Phenylsulfonyl)-4-(pyrazolo[1,5-b]pyridazin-3-yl)-1H-pyrrolo[2,3-b]pyridin-2-yl)ethyl L-prolinate

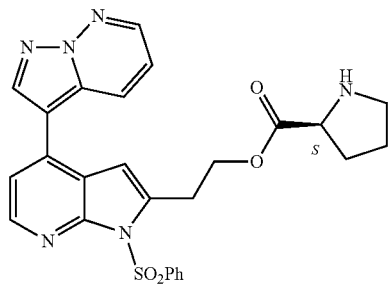

A solution 1-(tert-butyl) 2-(2-(1-(phenylsulfonyl)-4-(pyrazolo[1,5-b]pyridazin-3-yl)-1H-pyrrolo[2,3-b]pyridin-2-yl)ethyl) (S)-pyrrolidine-1,2-dicarboxylate (Intermediate 127b, 739 mg, 1.20 mmol) in DCM (20 mL) was treated with TFA (4 mL). The reaction mixture was stirred at r.t. for 2 h then concentrated in vacuo. The residue was diluted with DCM and slowly quenched with a saturated aqueous solution of NaHCO$_3$ until pH=9. The layers were separated. The combined organic layers were washed with brine, dried (MgSO$_4$), filtered, and the filtrate was concentrated in vacuo. The residue was purified by FCC eluting with 4-8% MeOH in DCM to give the title compound (488 mg, 76%) as a pale yellow solid LCMS (Method 4): Rt 2.664 min, m/z 517.1 [MH⁺].

d. 2-(4-(Pyrazolo[1,5-b]pyridazin-3-yl)-1H-pyrrolo[2,3-b]pyridin-2-yl)ethyl L-prolinate

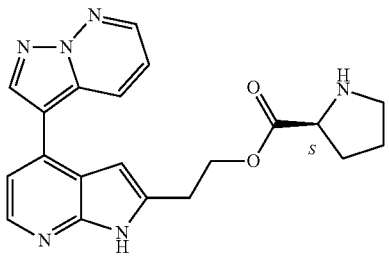

A solution of 2-(1-(phenylsulfonyl)-4-(pyrazolo[1,5-b]pyridazin-3-yl)-1H-pyrrolo[2,3-b]pyridin-2-yl)ethyl L-prolinate (Intermediate 127c, 232 mg, 0.45 mmol) in THF (2.25 mL) was treated with TBAF.3H$_2$O (283 mg, 0.90 mmol). The reaction mixture was stirred at r.t. for 6 h, then at 80° C. for 50 min, and then concentrated in vacuo. The residue was purified by FCC eluting with 10-15% 2N ammonia in MeOH in DCM to give the title compound (34 mg, 20%) as a pale yellow solid
LCMS (Method 4): Rt 2.226 min, m/z 377.2 [MH$^+$].

Intermediate 128: 3-(4-(Pyrazolo[1,5-b]pyridazin-3-yl)-1H-pyrrolo[2,3-b]pyridin-2-yl)propan-1-amine

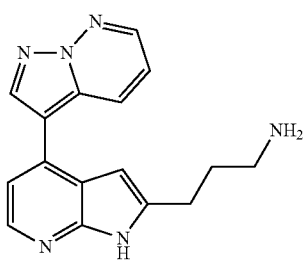 [SMILES: NCCCc1cc2c(-c3cnn4ncccc34)ccnc2[nH]1]

a. tert-Butyl (3-(4-chloro-1-(phenylsulfonyl)-1H-pyrrolo[2,3-b]pyridin-2-yl)propyl)carbamate

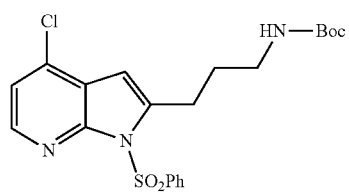

A stirred solution of 1-(benzenesulfonyl)-4-chloro-pyrrolo[2,3-b]pyridine (5.86 g, 20.0 mmol) and tert-butyl 1,2,3-oxathiazinane-3-carboxylate 2,2-dioxide (which can be prepared as described in *Organic Letters*, 2013, 15(23), 6094-60975, 93 g, 25.0 mmol) in dry THF (25 mL) at −78° C. was treated dropwise with a freshly prepared solution of LDA (25.0 mL, 1.0M in THF/hexane, 25.0 mmol) over 10 min. The resulting solution was stirred at −78° C. for 12 h, then allowed to warm to room temperature over 1 hour 30 min and stirred for an additional 24 h at room temperature.

The mixture was quenched by the addition of water (1.0 mL) followed by the addition of 3M HCl until the pH reached 2 and the resulting solution was stirred for 2 h. The solution was concentrated in vacuo, then slowly diluted with a saturated aqueous solution of NaHCO$_3$ until pH=9. The aqueous phase was extracted with ethyl acetate and the combined organic layers were washed with brine, dried (MgSO$_4$), filtered, and the filtrate was concentrated in vacuo. The residue was purified by FCC eluting with 20-50% ethyl acetate in petrol to give the title compound (4.57 g, 51%) as a yellow gum.
LCMS (Method 4): Rt 3.272 min, m/z 450.1 [MH$^+$].

b. tert-Butyl (3-(4-chloro-1H-pyrrolo[2,3-b]pyridin-2-yl)propyl)carbamate

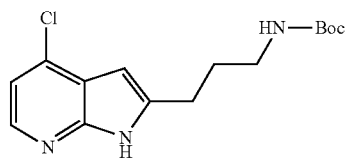 [SMILES: CC(C)(C)OC(=O)NCCCc1cc2c(Cl)ccnc2[nH]1]

Prepared by proceeding in a similar manner to Intermediate 55 starting from tert-butyl (3-(4-chloro-1-(phenylsulfonyl)-1H-pyrrolo[2,3-b]pyridin-2-yl)propyl)carbamate (Intermediate 128a)
LCMS (Method 4): Rt 2.917 min, m/z 310.1 [MH$^+$].

c. tert-Butyl (3-(4-(pyrazolo[1,5-b]pyridazin-3-yl)-1H-pyrrolo[2,3-b]pyridin-2-yl)propyl)carbamate

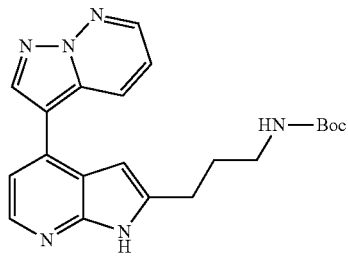 [SMILES: CC(C)(C)OC(=O)NCCCc1cc2c(-c3cnn4ncccc34)ccnc2[nH]1]

Prepared by proceeding in a similar manner to Intermediate 54, starting from tert-butyl (3-(4-chloro-1H-pyrrolo[2,3-b]pyridin-2-yl)propyl)carbamate (Intermediate 128b) and 3-(4,4,5,5-tetramethyl-1,3,2-dioxaborolan-2-yl)pyrazolo[1,5-b]pyridazine.
LCMS (Method 4): Rt 2.566 min, m/z 393.2[MH$^+$].

d. 3-(4-(Pyrazolo[1,5-b]pyridazin-3-yl)-1H-pyrrolo[2,3-b]pyridin-2-yl)propan-1-amine

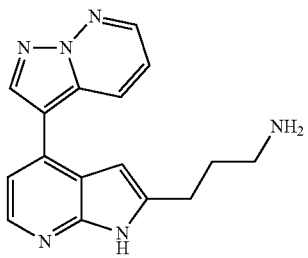 [SMILES: NCCCc1cc2c(-c3cnn4ncccc34)ccnc2[nH]1]

A suspension of tert-butyl (3-(4-(pyrazolo[1,5-b]pyridazin-3-yl)-1H-pyrrolo[2,3-b]pyridin-2-yl)propyl)carbamate (Intermediate 128c, 1.36 g, 3.50 mmol) in DCM (24 mL) was treated with 4N HCl in dioxane (12 mL). The reaction mixture was stirred at r.t. for 12 h then concentrated in vacuo. The residue was slowly diluted with a saturated aqueous solution of $NaHCO_3$ until pH=9 and extracted with $CHCl_3$:IPA (3:1) 3×100 mL. The combined organic layers were washed with brine, dried ($Na_2SO_4$), filtered, and the filtrate was concentrated in vacuo. The residue was purified by FCC eluting with 7.5-15% 2M ammonia in MeOH in DCM to give the title compound (972 mg, 95%) as a yellow solid.

LCMS (Method 4): Rt 2.131 min, m/z 293.2 [MH$^+$].

Example 1: 3-(6-Methyl-1H-pyrrolo[2,3-b]pyridin-4-yl)pyrazolo[1,5-b]pyridazine

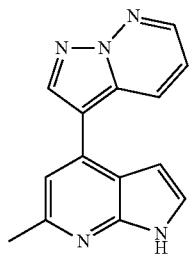 [SMILES: Cc1cc(-c2cnn3ncccc23)c2cc[nH]c2n1]

A mixture of 4-chloro-6-methyl-1H-pyrrolo[2,3-b]pyridine (47 mg, 0.291 mmol), 3-(4,4,5,5-tetramethyl-1,3,2-dioxaborolan-2-yl)pyrazolo[1,5-b]pyridazine (107 mg, 0.436 mmol), X Phos Pd G3 (19.6 mg, 0.023 mmol) and potassium phosphate (124 mg, 0.582 mmol) in degassed ethanol (3.0 mL) and water (1.5 mL) was heated at 140° C. for 30 mins in the microwave. After cooling it was partitioned between ethyl acetate and water and the organic layer was separated, washed with brine, dried ($Na_2SO_4$) and concentrated in vacuo. The crude product was purified by MDAP (Basic) to afford the title compound as a glass (27 mg, 37%)

LCMS (Method 1): Rt 2.12 min, m/z 249.8 [MH$^+$].

$^1$H NMR (400 MHz, d$_6$-DMSO): 2.59 (3H, s), 6.56 (1H, d, J=3.5 Hz), 7.19 (1H, s), 7.34 (1H, dd, J=4.4, 9.1 Hz), 7.43 (1H, d, J=3.5 Hz), 8.48 (1H, dd, J=1.8, 9.2 Hz), 8.56-8.58 (2H, m), 11.59 (1H, s)

By proceeding in a similar manner to Example 1, the following compounds were prepared:

Example 2: N,N-Dimethyl-4-(pyrazolo[1,5-b]pyridazin-3-yl)-1H-pyrrolo[2,3-b]pyridine-2-carboxamide

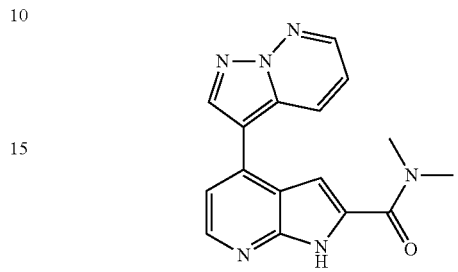

Starting from 4-chloro-N,N-dimethyl-1H-pyrrolo[2,3-b]pyridine-2-carboxamide (Intermediate 2) and 3-(4,4,5,5-tetramethyl-1,3,2-dioxaborolan-2-yl)pyrazolo[1,5-b]pyridazine LCMS (Method 1): Rt 2.43 min, m/z 306.9 [MH$^+$].

$^1$H NMR (400 MHz, d$_6$-DMSO): 3.06 (3H, s), 3.26 (3H, s), 6.96 (1H, s), 7.34-7.39 (2H, m), 8.39 (1H, d, J=4.9 Hz), 8.50 (1H, dd, J=1.8, 9.1 Hz), 8.57-8.60 (1H, m), 8.68 (1H, s), 12.22 (1H, s).

Example 3: N-(2-Methoxyethyl)-4-(pyrazolo[1,5-b]pyridazin-3-yl)-1H-pyrrolo[2,3-b]pyridine-2-carboxamide

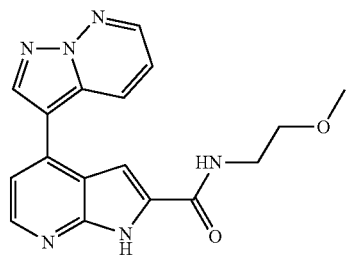 [SMILES: COCCNC(=O)c1cc2c(-c3cnn4ncccc34)ccnc2[nH]1]

Starting from 4-chloro-N-(2-methoxyethyl)-1H-pyrrolo[2,3-b]pyridine-2-carboxamide (Intermediate 4) and 3-(4,4,5,5-tetramethyl-1,3,2-dioxaborolan-2-yl)pyrazolo[1,5-b]pyridazine LCMS (Method 1): Rt 2.63 min, m/z 337.0 [MH$^+$].

$^1$H NMR (400 MHz, d$_6$-DMSO): 3.29 (3H, s), 3.52-3.44 (4H, m), 7.42-7.36 (2H, m), 7.48 (1H, s), 8.40 (1H, d, J=4.9 Hz), 8.54 (1H, dd, J=1.8, 9.2 Hz), 8.64-8.58 (2H, m), 8.66 (1H, s), 12.26 (1H, s).

Example 4: N-Isobutyl-4-(pyrazolo[1,5-b]pyridazin-3-yl)-1H-pyrrolo[2,3-b]pyridine-2-carboxamide

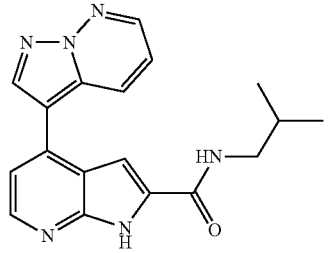 [SMILES: CC(C)CNC(=O)c1cc2c(-c3cnn4ncccc34)ccnc2[nH]1]

Starting from 4-chloro-N-isobutyl-1H-pyrrolo[2,3-b]pyridine-2-carboxamide (Intermediate 5) and 3-(4,4,5,5-tetramethyl-1,3,2-dioxaborolan-2-yl)pyrazolo[1,5-b]pyridazine.

LCMS (Method 1): Rt 3.31 min, m/z 335.0 [MH$^+$].

$^1$H NMR (400 MHz, d$_6$-DMSO): 0.92 (6H, d, J=6.7 Hz), 1.91-1.80 (1H, m), 3.18-3.11 (2H, m), 7.43-7.36 (2H, m), 7.47 (1H, d, J=2.0 Hz), 8.39 (1H, d, J=4.9 Hz), 8.52-8.47 (1H, m), 8.54 (1H, dd, J=1.9, 9.1 Hz), 8.60 (1H, dd, J=1.8, 4.4 Hz), 8.66 (1H, s), 12.24 (1H, s).

Example 5: N-(2-(Dimethylamino)ethyl)-4-(pyrazolo[1,5-b]pyridazin-3-yl)-1H-pyrrolo[2,3-b]pyridine-2-carboxamide

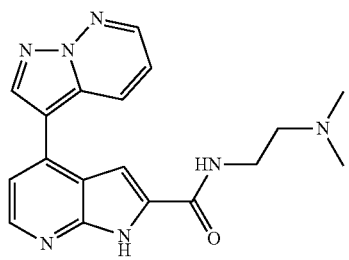 [SMILES: CN(C)CCNC(=O)c1cc2c(-c3cnn4ncccc34)ccnc2[nH]1]

Starting from 4-chloro-N-isobutyl-1H-pyrrolo[2,3-b]pyridine-2-carboxamide (Intermediate 6) and 3-(4,4,5,5-tetramethyl-1,3,2-dioxaborolan-2-yl)pyrazolo[1,5-b]pyridazine.

LCMS (Method 1): Rt 1.99 min, m/z 349.9 [MH$^+$].

$^1$H NMR (400 MHz, d$_6$-DMSO): 2.19 (6H, s), 2.42 (2H, dd, J=6.8, 6.8 Hz), 3.40 (2H, q, J=6.4 Hz), 7.43-7.35 (3H, m), 8.39 (1H, d, J=4.9 Hz), 8.47 (1H, t, J=5.6 Hz), 8.53 (1H, dd, J=1.8, 9.1 Hz), 8.61 (1H, dd, J=1.8, 4.4 Hz), 8.65 (1H, s), 11.92 (1H, br s).

Example 6: 4-(Pyrazolo[1,5-b]pyridazin-3-yl)-1H-pyrrolo[2,3-b]pyridine-2-carboxamide

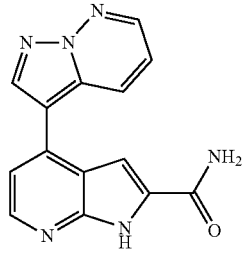 [SMILES: NC(=O)c1cc2c(-c3cnn4ncccc34)ccnc2[nH]1]

Starting from 4-chloro-1H-pyrrolo[2,3-b]pyridine-2-carboxamide (Intermediate 8) and 3-(4,4,5,5-tetramethyl-1,3,2-dioxaborolan-2-yl)pyrazolo[1,5-b]pyridazine.

LCMS (Method 1): Rt 2.27 min, m/z 278.9 [MH$^+$].

$^1$H NMR (400 MHz, d$_6$-DMSO): 7.51-7.35 (4H, m), 8.00 (1H, br s), 8.40 (1H, d, J=5.0 Hz), 8.53 (1H, dd, J=1.9, 9.1 Hz), 8.61 (1H, dd, J=1.8, 4.4 Hz), 8.64 (1H, s), 12.22 (1H, br s).

Example 7: N-Methyl-4-(pyrazolo[1,5-b]pyridazin-3-yl)-1H-pyrrolo[2,3-b]pyridine-2-carboxamide

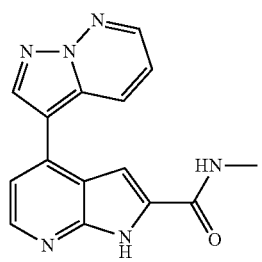 [SMILES: CNC(=O)c1cc2c(-c3cnn4ncccc34)ccnc2[nH]1]

Starting from 4-chloro-N-methyl-1H-pyrrolo[2,3-b]pyridine-2-carboxamide (Intermediate 7) and 3-(4,4,5,5-tetramethyl-1,3,2-dioxaborolan-2-yl)pyrazolo[1,5-b]pyridazine.

LCMS (Method 1): Rt 2.42 min, m/z 292.9 [MH$^+$].

$^1$H NMR (400 MHz, d$_6$-DMSO): 2.82 (3H, d, J=4.1 Hz), 7.41-7.33 (3H, m), 8.39-8.37 (1H, m), 8.55-8.47 (2H, m), 8.62-8.58 (1H, m), 8.62 (1H, s), 11.70 (1H, br s).

Example 8: 3-(3-Methyl-1H-pyrrolo[2,3-b]pyridin-4-yl)pyrazolo[1,5-b]pyridazine

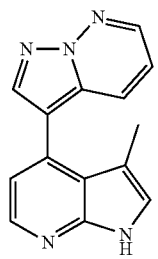 [SMILES: Cc1c[nH]c2nccc(-c3cnn4ncccc34)c12]

Starting from 4-chloro-3-methyl-1H-pyrrolo[2,3-b]pyridine and 3-(4,4,5,5-tetramethyl-1,3,2-dioxaborolan-2-yl)pyrazolo[1,5-b]pyridazine.

Example 9: 3-(5-Methyl-1H-pyrrolo[2,3-b]pyridin-4-yl)pyrazolo[1,5-b]pyridazine

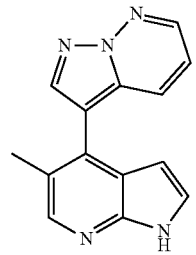 [SMILES: Cc1cnc2[nH]ccc2c1-c1cnn2ncccc12]

Starting from 4-chloro-5-methyl-1H-pyrrolo[2,3-b]pyridine and 3-(4,4,5,5-tetramethyl-1,3,2-dioxaborolan-2-yl)pyrazolo[1,5-b]pyridazine.

LCMS (Method 1): Rt 2.29 min, m/z 249.9 [MH$^+$].

$^1$H NMR (400 MHz, d$_6$-DMSO): 2.32 (3H, s), 6.10-6.05 (1H, m), 7.25 (1H, dd, J=4.4, 9.0 Hz), 7.45-7.40 (1H, m), 7.96 (1H, dd, J=1.9, 9.1 Hz), 8.21 (1H, s), 8.37 (1H, s), 8.55 (1H, dd, J=1.8, 4.4 Hz), 11.64 (1H, s).

Example 10: 3-(2-Benzyl-1H-pyrrolo[2,3-b]pyridin-4-yl)pyrazolo[1,5-b]pyridazine

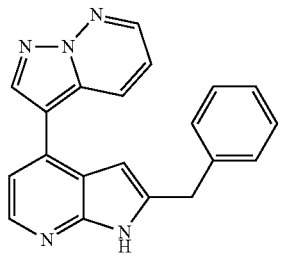 [SMILES: c1ccc(Cc2cc3c(-c4cnn5ncccc45)ccnc3[nH]2)cc1]

Starting from 4-bromo-2-(phenylmethyl)-1-(phenylsulfonyl)-1H-pyrrolo[2,3-b]pyridine (which can be prepared as described in WO2015148597 or WO2014052699) and 3-(4,4,5,5-tetramethyl-1,3,2-dioxaborolan-2-yl)pyrazolo[1,5-b]pyridazine LCMS (Method 1): Rt 3.37 min, m/z 326.0 [MH$^+$].

$^1$H NMR (400 MHz, d$_6$-DMSO): 4.10 (2H, s), 6.39 (1H, d, J=1.9 Hz), 7.36-7.20 (7H, m), 8.19 (1H, d, J=4.9 Hz), 8.43 (1H, dd, J=1.9, 9.1 Hz), 8.57-8.53 (2H, m), 11.78 (1H, s).

Example 11: (4-(Pyrazolo[1,5-b]pyridazin-3-yl)-1H-pyrrolo[2,3-b]pyridin-2-yl)methanol

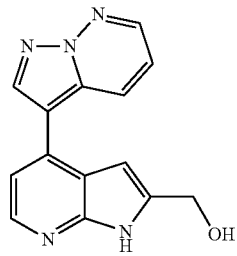 [SMILES: OCc1cc2c(-c3cnn4ncccc34)ccnc2[nH]1]

Starting from 4-bromo-1-(phenylsulfonyl)-1H-pyrrolo[2,3-b]pyridine-2-methanol (which can be prepared as described in WO2009112475 or WO2008034860) and 3-(4,4,5,5-tetramethyl-1,3,2-dioxaborolan-2-yl)pyrazolo[1,5-b]pyridazine.

LCMS (Method 1): Rt 1.97 min, m/z 265.9 [MH$^+$].

$^1$H NMR (400 MHz, d$_6$-DMSO): 4.64 (2H, s), 5.32 (1H, s), 6.50-6.48 (1H, m), 7.26 (1H, d, J=5.0 Hz), 7.35 (1H, dd, J=4.4, 9.1 Hz), 8.23 (1H, d, J=5.0 Hz), 8.45 (1H, dd, J=1.9, 9.1 Hz), 8.58-8.55 (2H, m), 11.74 (1H, s).

Example 12: 4-((4-(Pyrazolo[1,5-b]pyridazin-3-yl)-1H-pyrrolo[2,3-b]pyridin-2-yl)methyl)morpholine

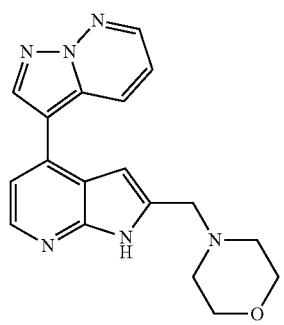 [SMILES: c1cnn2ncc(-c3ccnc4[nH]c(CN5CCOCC5)cc34)c2c1]

Starting from 4-((4-bromo-1H-pyrrolo[2,3-b]pyridin-2-yl)methyl)morpholine (Intermediate 9) and 3-(4,4,5,5-tetramethyl-1,3,2-dioxaborolan-2-yl)pyrazolo[1,5-b]pyridazine.

LCMS (Method 1): Rt 1.96 min, m/z 335.0 [MH$^+$].

$^1$H NMR (400 MHz, d$_6$-DMSO): 2.43 (4H, t, J=4.4 Hz), 3.58 (4H, t, J=4.6 Hz), 3.66 (2H, s), 6.50 (1H, d, J=1.8 Hz), 7.27 (1H, d, J=5.0 Hz), 7.35 (1H, dd, J=4.4, 9.1 Hz), 8.23 (1H, d, J=5.0 Hz), 8.45 (1H, dd, J=1.9, 9.1 Hz), 8.59-8.56 (2H, m), 11.75 (1H, s).

Example 13: 2-Morpholino-N-((4-(pyrazolo[1,5-b]pyridazin-3-yl)-1H-pyrrolo[2,3-b]pyridin-2-yl)methyl)acetamide

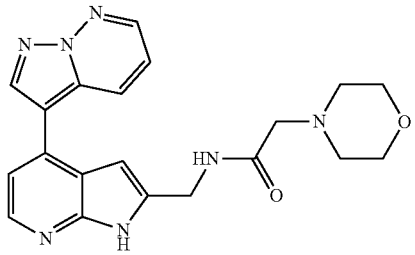 [SMILES: O=C(CN1CCOCC1)NCc1cc2c(-c3cnn4ncccc34)ccnc2[nH]1]

Starting from N-((4-bromo-1-(phenylsulfonyl)-1H-pyrrolo[2,3-b]pyridin-2-yl)methyl)-2-morpholinoacetamide (Intermediate 12) and 3-(4,4,5,5-tetramethyl-1,3,2-dioxaborolan-2-yl)pyrazolo[1,5-b]pyridazine.

LCMS (Method 1): Rt 2.75 min, m/z 392.0 [MH$^+$].

$^1$H NMR (400 MHz, d$_6$-DMSO): 2.44 (4H, t, J=4.5 Hz), 2.99 (2H, s), 3.59 (4H, t, J=4.6 Hz), 4.50 (2H, d, J=6.0 Hz), 6.42-6.41 (1H, m), 7.27 (1H, d, J=4.9 Hz), 7.34 (1H, dd, J=4.4, 9.0 Hz), 8.23 (1H, d, J=4.9 Hz), 8.27 (1H, t, J=5.9 Hz), 8.43 (1H, dd, J=1.8, 9.1 Hz), 8.52 (1H, s), 8.57 (1H, dd, J=1.8, 4.3 Hz), 11.68 (1H, s).

Example 14: 2-(4-Methylpiperazin-1-yl)-N-((4-(pyrazolo[1,5-b]pyridazin-3-yl)-1H-pyrrolo[2,3-b]pyridin-2-yl)methyl)acetamide

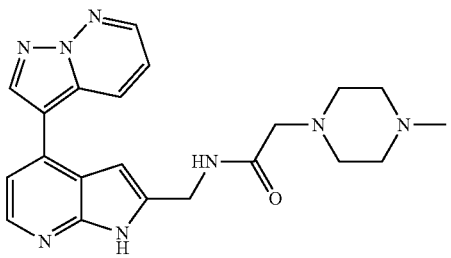 [SMILES: CN1CCN(CC(=O)NCc2cc3c(-c4cnn5ncccc45)ccnc3[nH]2)CC1]

Starting from N-((4-bromo-1-(phenylsulfonyl)-1H-pyrrolo[2,3-b]pyridin-2-yl)methyl)-2-(4-methylpiperazin-1-yl)acetamide (Intermediate 13) and 3-(4,4,5,5-tetramethyl-1,3,2-dioxaborolan-2-yl)pyrazolo[1,5-b]pyridazine.

LCMS (Method 1): Rt 2.72 min, m/z 405.0 [MH$^+$].

$^1$H NMR (400 MHz, d$_6$-DMSO): 2.20 (3H, s), 2.53-2.31 (8H, m), 2.99 (2H, s), 4.50 (2H, d, J=5.8 Hz), 6.41 (1H, s), 7.28 (1H, d, J=5.0 Hz), 7.35 (1H, dd, J=4.3, 9.0 Hz), 8.25-8.17 (2H, m), 8.43 (1H, dd, J=1.6, 9.1 Hz), 8.53 (1H, s), 8.58 (1H, dd, J=1.5, 4.2 Hz), 11.69 (1H, s).

Example 15: tert-Butyl 4-((4-(pyrazolo[1,5-b]pyridazin-3-yl)-1H-pyrrolo[2,3-b]pyridin-2-yl)methyl)piperazine-1-carboxylate

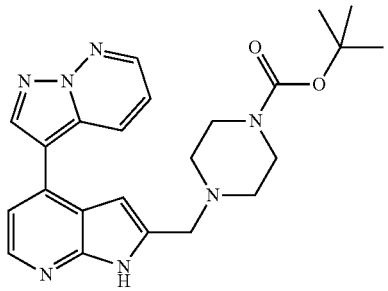 [SMILES: CC(C)(C)OC(=O)N1CCN(Cc2cc3c(-c4cnn5ncccc45)ccnc3[nH]2)CC1]

Starting from tert-butyl 4-((4-bromo-1-(phenylsulfonyl)-1H-pyrrolo[2,3-b]pyridin-2-yl)methyl)piperazine-1-carboxylate (Intermediate 15) and 3-(4,4,5,5-tetramethyl-1,3,2-dioxaborolan-2-yl)pyrazolo[1,5-b]pyridazine. After the initial 1 h heating a 2M solution of potassium hydroxide in methanol (9 eq.) was added and the reaction mixture was heated at 120° C. in the microwave for a further 10 mins.

LCMS (Method 1): Rt 2.73 min, m/z 434.3 [MH$^+$].

$^1$H NMR (400 MHz, d$_6$-DMSO): 1.37 (9H, s), 2.39 (4H, t, J=4.9 Hz), 3.35-3.27 (4H, m), 3.68 (2H, s), 6.49 (1H, d, J=1.8 Hz), 7.27 (1H, d, J=5.0 Hz), 7.35 (1H, dd, J=4.4, 9.1 Hz), 8.23 (1H, d, J=4.9 Hz), 8.45 (1H, dd, J=1.9, 9.1 Hz), 8.57 (1H, dd, J=1.8, 4.4 Hz), 8.58 (1H, s), 11.75 (1H, s).

Example 16: 3-(2-((4-Methylpiperazin-1-yl)methyl)-1H-pyrrolo[2,3-b]pyridin-4-yl)pyrazolo[1,5-b]pyridazine

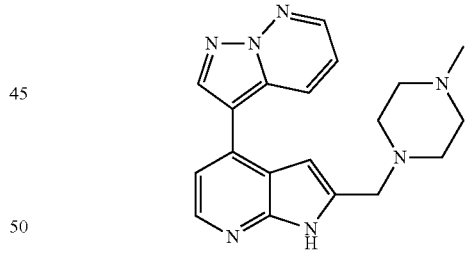

Starting from 4-bromo-2-((4-methylpiperazin-1-yl)methyl)-1-(phenylsulfonyl)-1H-pyrrolo[2,3-b]pyridine (Intermediate 16) and 3-(4,4,5,5-tetramethyl-1,3,2-dioxaborolan-2-yl)pyrazolo[1,5-b]pyridazine. After the initial 1 h heating a 2M solution of potassium hydroxide in methanol (9 eq.) was added and the reaction mixture was heated at 120° C. in the microwave for a further 10 mins.

LCMS (Method 1): Rt 1.78 min, m/z 348.0 [MH$^+$].

$^1$H NMR (400 MHz, d$_6$-DMSO): 2.13 (3H, s), 2.50-2.20 (8H, m), 3.64 (2H, s), 6.47 (1H, d, J=1.8 Hz), 7.26 (1H, d, J=5.0 Hz), 7.34 (1H, dd, J=4.4, 9.1 Hz), 8.23 (1H, d, J=5.0 Hz), 8.44 (1H, dd, J=1.9, 9.1 Hz), 8.60-8.54 (2H, m), 11.72 (1H, s).

Example 17: N1,N1-Dimethyl-N2-((4-(pyrazolo[1,5-b]pyridazin-3-yl)-1H-pyrrolo[2,3-b]pyridin-2-yl)methyl)ethane-1,2-diamine

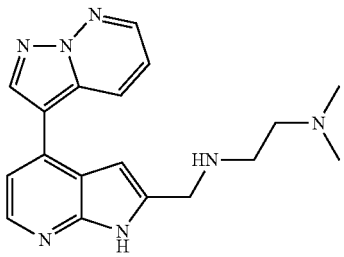 [SMILES: CN(C)CCNCc1cc2c(-c3cnn4ncccc34)ccnc2[nH]1]

Starting from N1-((4-bromo-1H-pyrrolo[2,3-b]pyridin-2-yl)methyl)-N2,N2-dimethylethane-1,2-diamine (Intermediate 10) and 3-(4,4,5,5-tetramethyl-1,3,2-dioxaborolan-2-yl)pyrazolo[1,5-b]pyridazine.

LCMS (Method 1): Rt 2.81 min, m/z 336.0 [MH$^+$]

$^1$H NMR (400 MHz, d$_6$-DMSO): 2.18 (6H, s), 2.42 (2H, t, J=6.1 Hz), 2.63 (2H, t, J=6.3 Hz), 3.89 (2H, s), 6.50 (1H, s), 7.26 (1H, d, J=5.0 Hz), 7.34 (1H, dd, J=4.4, 9.1 Hz), 8.21 (1H, d, J=5.0 Hz), 8.45 (1H, dd, J=1.8, 9.1 Hz), 8.59-8.54 (2H, m), 11.70-11.67 (1H, m). alkyl NH not observed.

Example 18: 4-(Pyrazolo[1,5-a]pyridin-3-yl)-1H-pyrrolo[2,3-b]pyridine

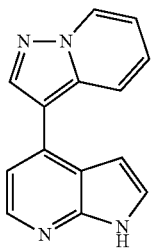 [SMILES: c1ccn2ncc(-c3ccnc4[nH]ccc34)c2c1]

Starting from 4-bromo-1H-pyrrolo[2,3-b]pyridine (99 mg, 0.5 mmol) and 3-(4,4,5,5-tetramethyl-1,3,2-dioxaborolan-2-yl)pyrazolo[1,5-a]pyridine (which was prepared as described in WO2011/101161 A1).

LCMS (Method 1): Rt 2.35 min, m/z 234.9 [MH$^+$].

$^1$H NMR (400 MHz, d$_6$-DMSO): 6.63 (1H, dd, J=1.9, 3.5 Hz), 7.04 (1H, dt, J=1.2, 6.8 Hz), 7.29 (1H, d, J=4.9 Hz), 7.40 (1H, ddd, J=1.1, 6.7, 9.0 Hz), 7.52 (1H, dd, J=2.6, 3.3 Hz), 7.95 (1H, td, J=1.1, 9.0 Hz), 8.27 (1H, d, J=4.9 Hz), 8.52 (1H, s), 8.82 (1H, td, J=1.0, 7.0 Hz), 11.75 (1H, s).

Example 19: 4-(1-Ethyl-1H-pyrazol-5-yl)-1H-pyrrolo[2,3-b]pyridine

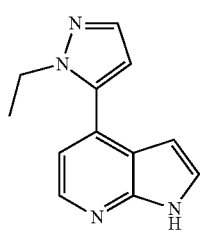 [SMILES: CCn1nccc1-c1ccnc2[nH]ccc12]

Starting from 4-bromo-1H-pyrrolo[2,3-b]pyridine and 1-ethyl-5-(4,4,5,5-tetramethyl-1,3,2-dioxaborolan-2-yl)-1H-pyrazole.

LCMS (Method 1): Rt 2.76 min, m/z 212.6 [MH$^+$].

$^1$H NMR (400 MHz, d$_6$-DMSO): 1.27 (3H, t, J=7.2 Hz), 4.15 (2H, q, J=7.2 Hz), 6.37 (1H, dd, J=1.9, 3.5 Hz), 6.52 (1H, d, J=1.8 Hz), 7.11 (1H, d, J=4.9 Hz), 7.57 (1H, dd, J=2.7, 3.3 Hz), 7.62 (1H, d, J=1.8 Hz), 8.32 (1H, d, J=4.9 Hz), 11.91 (1H, s).

Example 20: 6-(1H-Pyrrolo[2,3-b]pyridin-4-yl)-1H-indazole

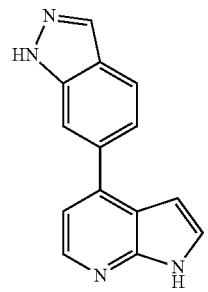

Starting from 4-bromo-1H-pyrrolo[2,3-b]pyridine and 6-(4,4,5,5-tetramethyl-1,3,2-dioxaborolan-2-yl)-1H-indazole.

LCMS (Method 1): Rt 2.55 min, m/z 235.1 [MH$^+$].

$^1$H NMR (400 MHz, d$_6$-DMSO): 6.65 (1H, dd, J=1.9, 3.5 Hz), 7.26 (1H, d, J=4.9 Hz), 7.52 (1H, dd, J=1.4, 8.4 Hz), 7.57 (1H, dd, J=2.7, 3.5 Hz), 7.88-7.88 (1H, m), 7.93 (1H, d, J=8.4 Hz), 8.16 (1H, t, J=1.2 Hz), 8.31 (1H, d, J=5.0 Hz), 11.80 (1H, s), 13.19 (1H, s).

Example 21: 5-(1H-Pyrrolo[2,3-b]pyridin-4-yl)-1H-benzo[d][1,2,3]triazole

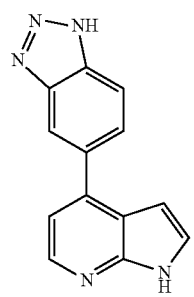 [SMILES: c1cc(-c2ccc3[nH]nnc3c2)c2cc[nH]c2n1]

Starting from 4-bromo-1H-pyrrolo[2,3-b]pyridine and 5-(4,4,5,5-tetramethyl-[1,3,2]dioxaborolan-2-yl)-1H-benzotriazole LCMS (Method 1): Rt 2.14 min, m/z 235.9 [MH$^+$].

$^1$H NMR (400 MHz, d$_6$-DMSO): 6.65 (1H, dd, J=1.9, 3.5 Hz), 7.30 (1H, d, J=5.0 Hz), 7.59 (1H, dd, J=2.6, 3.3 Hz), 7.84 (1H, dd, J=1.2, 8.6 Hz), 8.09 (1H, d, J=8.6 Hz), 8.23 (1H, s), 8.33 (1H, d, J=4.9 Hz), 11.85 (1H, s).

Example 22: 6-Methoxy-3-(1H-pyrrolo[2,3-b]pyridin-4-yl)pyrazolo[1,5-b]pyridazine

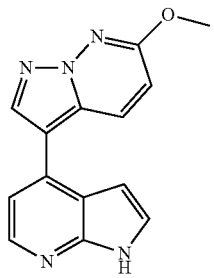 [SMILES: COc1ccc2c(-c3ccnc4[nH]ccc34)cnn2n1]

Starting from 3-bromo-6-methoxypyrazolo[1,5-b]pyridazine (Intermediate 80) and 4-(4,4,5,5-tetramethyl-1,3,2-dioxaborolan-2-yl)-1H-pyrrolo[2,3-b]pyridine (which was prepared as described in WO2009/93981).

LCMS (Method 2): Rt 2.66 min, m/z 266.2 [MH⁺].

$^1$H NMR (400 MHz, d$_6$-DMSO): 4.02 (3H, s), 6.62 (1H, dd, J=1.7, 3.4 Hz), 7.04 (1H, d, J=9.6 Hz), 7.26 (1H, d, J=4.9 Hz), 7.56-7.52 (1H, m), 8.27 (1H, d, J=4.9 Hz), 8.33 (1H, d, J=9.7 Hz), 8.40 (1H, s), 11.79 (1H, s).

Example 23: 5-Methoxy-3-(1H-pyrrolo[2,3-b]pyridin-4-yl)pyrazolo[1,5-b]pyridazine

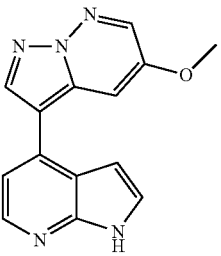 [SMILES: COc1cnn2ncc(-c3ccnc4[nH]ccc34)c2c1]

Starting from 3-bromo-5-methoxypyrazolo[1,5-b]pyridazine (Intermediate 81) and 4-(4,4,5,5-tetramethyl-1,3,2-dioxaborolan-2-yl)-1H-pyrrolo[2,3-b]pyridine (which was prepared as described in WO2009/93981).

LCMS (Method 1): Rt 2.43 min, m/z 266.1 [MH⁺].

$^1$H NMR (400 MHz, d$_6$-DMSO): 3.95 (3H, s), 6.65 (1H, d, J=3.4 Hz), 7.33 (1H, d, J=5.0 Hz), 7.55-7.51 (1H, m), 7.60 (1H, d, J=3.1 Hz), 8.28 (1H, d, J=4.9 Hz), 8.39 (1H, d, J=3.0 Hz), 8.48 (1H, s), 11.77 (1H, s).

Example 24: 5-(2-Methoxyethoxy)-3-(1H-pyrrolo[2,3-b]pyridin-4-yl)pyrazolo[1,5-b]pyridazine

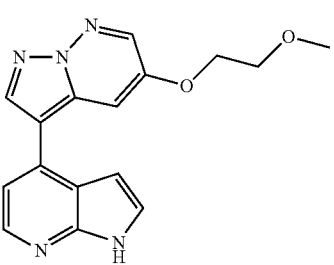 [SMILES: COCCOc1cnn2ncc(-c3ccnc4[nH]ccc34)c2c1]

Starting from 3-bromo-5-(2-methoxyethoxy) pyrazolo[1,5-b]pyridazine (Intermediate 82) and 4-(4,4,5,5-tetramethyl-1,3,2-dioxaborolan-2-yl)-1H-pyrrolo[2,3-b]pyridine (which was prepared as described in WO2009/93981).

LCMS (Method 1): Rt 3.14 min, m/z 309.9 [MH⁺].

$^1$H NMR (400 MHz, d$_6$-DMSO): 3.76-3.68 (2H, m), 4.34-4.27 (2H, m), 6.65 (1H, dd, J=1.8, 3.5 Hz), 7.32 (1H, d, J=5.0 Hz), 7.55-7.49 (1H, m), 7.64 (1H, d, J=3.1 Hz), 8.27 (1H, d, J=5.0 Hz), 8.40 (1H, d, J=3.1 Hz), 8.48 (1H, s), 11.75 (1H, s). 3H are obscured by water.

Example 25: 5-((2,2-Dimethyl-1,3-dioxolan-4-yl)methoxy)-3-(1H-pyrrolo[2,3-b]pyridin-4-yl)pyrazolo[1,5-b]pyridazine

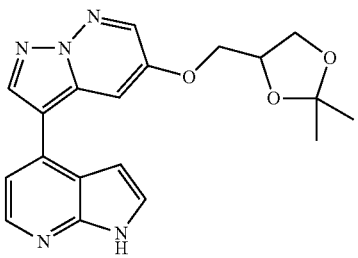 [SMILES: CC1(C)OCC(COc2cnn3ncc(-c4ccnc5[nH]ccc45)c3c2)O1]

Starting from 3-bromo-5-((2,2-dimethyl-1,3-dioxolan-4-yl)methoxy)pyrazolo[1,5-b]pyridazine (Intermediate 83) and 4-(4,4,5,5-tetramethyl-1,3,2-dioxaborolan-2-yl)-1H-pyrrolo[2,3-b]pyridine (which was prepared as described in WO2009/93981).

LCMS (Method 1): Rt 3.54 min, m/z 366.3 [MH⁺].

$^1$H NMR (400 MHz, d$_6$-DMSO): 1.32 (3H, s), 1.37 (3H, s), 3.79 (1H, dd, J=6.4, 8.4 Hz), 4.12 (1H, dd, J=6.7, 8.4 Hz), 4.20 (1H, dd, J=6.5, 10.6 Hz), 4.27 (1H, dd, J=3.9, 10.6 Hz), 4.52-4.43 (1H, m), 6.66 (1H, dd, J=1.8, 3.5 Hz), 7.32 (1H, d, J=5.0 Hz), 7.55-7.50 (1H, m), 7.68 (1H, d, J=3.1 Hz), 8.28 (1H, d, J=4.9 Hz), 8.40 (1H, d, J=2.9 Hz), 8.49 (1H, s), 11.75 (1H, s).

Example 26: 6-Methyl-3-(1H-pyrrolo[2,3-b]pyridin-4-yl)pyrazolo[1,5-b]pyridazine

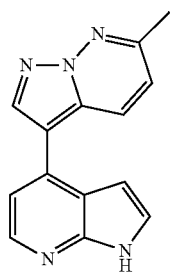 [SMILES: Cc1ccc2c(-c3ccnc4[nH]ccc34)cnn2n1]

Starting from 3-bromo-6-methylpyrazolo[1,5-b]pyridazine (Intermediate 84) and 4-(4,4,5,5-tetramethyl-1,3,2-dioxaborolan-2-yl)-1H-pyrrolo[2,3-b]pyridine (which was prepared as described in WO2009/93981).

LCMS (Method 1): Rt 3.06 min, m/z 250.1 [MH⁺].

$^1$H NMR (400 MHz, d$_6$-DMSO): 2.59 (3H, s), 6.64 (1H, dd, J=1.9, 3.5 Hz), 7.31-7.25 (2H, m), 7.59-7.50 (1H, m), 8.28 (1H, d, J=4.9 Hz), 8.37 (1H, d, J=9.2 Hz), 8.51 (1H, s), 11.81-11.79 (1H, m).

Example 27: 3-(2-Methyl-1H-pyrrolo[2,3-b]pyridin-4-yl)pyrazolo[1,5-b]pyridazine

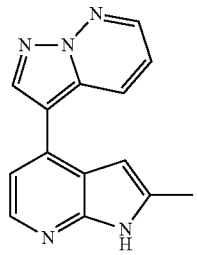 [SMILES: Cc1cc2c(-c3cnn4ncccc34)ccnc2[nH]1]

A mixture of 4-bromo-2-methyl-1H-pyrrolo[2,3-b]pyridine (121 mg, 0.57 mmol), 3-(4,4,5,5-tetramethyl-1,3,2-dioxaborolan-2-yl)pyrazolo[1,5-b]pyridazine (155 mg, 0.63 mmol), Brett Phos Pd G3 (23 mg, 0.023 mmol) and potassium phosphate (243 mg, 1.15 mmol) in degassed ethanol (3 mL) and water (1.5 mL) was heated at 140° C. for 30 mins in the microwave. After cooling, the mixture was partitioned between ethyl acetate and water and the organic layer was separated, washed with brine, dried ($Na_2SO_4$) and concentrated in vacuo. The crude product was purified by MDAP (Basic) to afford the title compound as a solid (30 mg, 21%).

LCMS (Method 1): Rt 2.24 min, m/z 249.9 [MH$^+$].

$^1$H NMR (400 MHz, $d_6$-DMSO): 2.43 (3H, s), 6.32-6.34 (1H, m), 7.23 (1H, d, J=5.0 Hz), 7.34 (1H, dd, J=4.4, 9.1 Hz), 8.17 (1H, d, J=5.0 Hz), 8.44 (1H, dd, J=1.8, 9.1 Hz), 8.55-8.57 (2H, m), 11.62 (1H, s).

Example 28: 3-(1H-Pyrrolo[2,3-b]pyridin-4-yl)pyrazolo[1,5-b]pyridazine

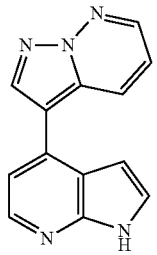 [SMILES: c1cnn2ncc(-c3ccnc4[nH]ccc34)c2c1]

A mixture of 1H-pyrrolo[2,3-b]pyridine-4-boronic acid pinacol ester (92 mg, 0.38 mmol), 3-bromopyrazolo[1,5-b]pyridazine (50 mg, 0.25 mmol), Pd(PPh$_3$)$_4$ (15 mg, 0.013 mmol) and cesium carbonate (165 mg, 0.51 mmol) in DMF (2.4 mL) and water (0.8 mL) in a microwave tube was degassed then heated to 150° C. for 30 mins. The reaction mixture was diluted with ethyl acetate and water and the phases were separated. The aqueous phase was extracted with ethyl acetate and the combined organic phase was washed with brine, dried ($Na_2SO_4$) and concentrated in vacuo to a brown semi-solid. The crude product was purified by MDAP (acidic) to afford the title compound (30 mg, 51%) as an off-white solid.

LCMS (Method 1): Rt 2.13 min, m/z 235.9 [MH$^+$].

$^1$H NMR (400 MHz, $d_6$-DMSO): 6.64 (1H, dd, J=1.9, 3.5 Hz), 7.31 (1H, d, J=4.9 Hz), 7.35 (1H, dd, J=4.4, 9.1 Hz), 7.59-7.53 (1H, m), 8.29 (1H, d, J=4.9 Hz), 8.47 (1H, dd, J=1.9, 9.1 Hz), 8.58 (1H, dd, J=1.8, 4.4 Hz), 8.61 (1H, s), 11.81 (1H, s).

Example 29: 3-(1H-Pyrrolo[2,3-b]pyridin-4-yl)imidazo[1,2-a]pyrimidine

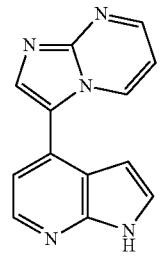 [SMILES: c1cnc2ncc(-c3ccnc4[nH]ccc34)n2c1]

A solution of tert-butyl 4-(imidazo[1,2-a]pyrimidin-3-yl)-1H-pyrrolo[2,3-b]pyridine-1-carboxylate (Intermediate 17, 0.017 g, 0.051 mmol) and TFA (0.5 mL) in DCM (2 ML) was stirred at room temperature for 4 h. The solution was concentrated in vacuo and the residue was purified by FCC eluting with 0-10% methanol in DCM to give the title compound (0.011 g) as an off-white solid.

LCMS (Method 1): Rt 1.78 min, m/z 235.9 [MH$^+$]

$^1$H NMR (400 MHz, $d_6$-DMSO) 11.78 (1H, s), 8.99 (1H, dd, J=2.0, 6.8 Hz), 8.70 (1H, s), 8.60 (1H, dd, J=2.0, 4.1 Hz), 8.32-8.30 (1H, m), 7.74 (1H, d, J=4.9 Hz), 7.61 (1H, t, J=3.0 Hz), 7.13-7.07 (2H, m);

Example 30: 2-(4-(Pyrazolo[1,5-b]pyridazin-3-yl)-1H-pyrrolo[2,3-b]pyridin-2-yl)ethan-1-amine

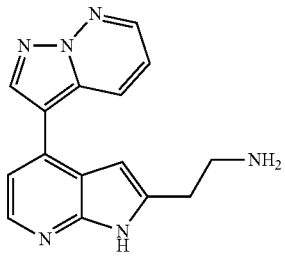 [SMILES: NCCc1cc2c(-c3cnn4ncccc34)ccnc2[nH]1]

3M aqueous NaOH (10 mL) was added to a solution of 2-(1-(phenylsulfonyl)-4-(pyrazolo[1,5-b]pyridazin-3-yl)-1H-pyrrolo[2,3-b]pyridin-2-yl)ethan-1-amine (Intermediate 25, 2.23 g, 5.32 mmol) in dioxane (30 mL) and IPA (5 mL). The reaction mixture was heated at 70° C. for 6 h then cooled to r.t. and treated with 6M HCl until the pH=7. The mixture was concentrated in vacuo and the residue was dissolved in DCM:MeOH (10:1) filtered, and dry loaded onto celite and purified by FCC eluting with 10-15% 2M ammonia in methanol in DCM to give the title compound (1.413 g, 95%) as a yellow solid.

LCMS (Method 1): Rt 1.59 min, m/z 279.3 [MH$^+$].

$^1$H NMR (400 MHz, $d_6$-DMSO): 2.86-2.78 (2H, m), 2.95-2.87 (2H, m), 6.36 (1H, s), 7.24 (1H, d, J=5.0 Hz), 7.33 (1H, dd, J=4.4, 9.1 Hz), 8.18 (1H, d, J=5.0 Hz), 8.45 (1H, dd, J=1.8, 9.1 Hz), 8.60-8.53 (2H, m). NH protons not observed.

By proceeding in a similar manner to Example 30, the following compounds were prepared:

Example 31: N-ethyl-2-(4-(pyrazolo[1,5-b]pyridazin-3-yl)-1H-pyrrolo[2,3-b]pyridin-2-yl)ethan-1-amine

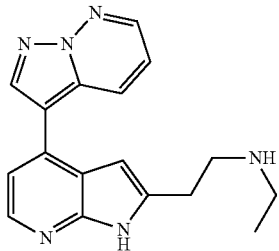 [SMILES: CCNCCc1cc2c(-c3cnn4ncccc34)ccnc2[nH]1]

Starting from 2-(1-(Phenylsulfonyl)-4-(pyrazolo[1,5-b]pyridazin-3-yl)-1H-pyrrolo[2,3-b]pyridin-2-yl)ethan-1-amine (Intermediate 33, 780 mg, 1.86 mmol) using EtOH in place of IPA to give the title compound as the minor component (14%) as a yellow solid alongside the previously reported 2-(4-(pyrazolo[1,5-b]pyridazin-3-yl)-1H-pyrrolo[2,3-b]pyridin-2-yl)ethan-1-amine (Example 30, 62%)

LCMS (Method 1): Rt 2.90 min, m/z 307.4 [MH$^+$].

$^1$H NMR (400 MHz, d$_6$-DMSO): 1.01 (3H, t, J=7.1 Hz), 2.58 (2H, q, J=7.1 Hz), 2.88 (4H, s), 6.37 (1H, s), 7.24 (1H, d, J=5.0 Hz), 7.33 (1H, dd, J=4.4, 9.1 Hz), 8.18 (1H, d, J=5.0 Hz), 8.45 (1H, dd, J=1.9, 9.1 Hz), 8.59-8.54 (2H, m), 11.63 (1H, br s). Alkyl NH not observed.

Example 32: (S)-1-Acryloyl-N-(2-(4-(pyrazolo[1,5-b]pyridazin-3-yl)-1H-pyrrolo[2,3-b]pyridin-2-yl)ethyl)pyrrolidine-2-carboxamide

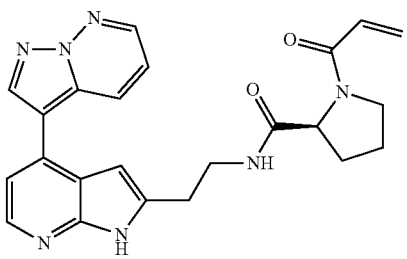 [SMILES: C=CC(=O)N1CCC[C@H]1C(=O)NCCc1cc2c(-c3cnn4ncccc34)ccnc2[nH]1]

T3P (50% solution in EtOAc, 1.59 mL, 2.25 mmol) was added to a solution of acryloyl-L-proline (190 mg, 1.125 mmol) (which can be prepared as described in *Journal of Organic Chemistry*, 1991, 56(23), 6551) and TEA (0.84 mL, 6.00 mmol) in DCM (2.0 mL) and the mixture was stirred for 5 min. The solution was then added to a solution of 2-(4-(pyrazolo[1,5-b]pyridazin-3-yl)-1H-pyrrolo[2,3-b]pyridin-2-yl)ethan-1-amine (Example 30, 208 mg, 0.075 mmol) in DCM (5.0 mL) and the resultant mixture was stirred for 45 min. The reaction was quenched by addition of a saturated aqueous solution of Na$_2$CO$_3$ and extracted with CHCl$_3$. The organic layers were washed with brine, dried (MgSO$_4$) and concentrated in vacuo. The residue was purified by FCC eluting with 4-10% methanol in DCM to give the title compound (101 mg, 31%) as a yellow solid.

LCMS (Method 1): Rt 2.20 min, m/z 430.3 [MH$^+$].

$^1$H NMR (400 MHz, d$_6$-DMSO): 1.65-1.86 (3H, m), 1.91-2.01 (0.6H, m), 2.06-2.16 (0.4H, m), 2.89-2.96 (2H, m), 3.35-3.56 (3.4H, m), 3.60-3.66 (0.6H, m), 4.29 (0.6H, dd, J=3.5, 8.5 Hz), 4.36 (0.4H, dd, J=2.8, 8.5 Hz), 5.27 (0.4H, dd, J=2.6, 10.1 Hz), 5.64 (0.6H, dd, J=2.4, 10.3 Hz), 5.95 (0.4H, dd, J=2.6, 16.7 Hz), 6.05-6.14 (1H, m), 6.41 (1H, dd, J=1.8, 13.2 Hz), 6.57 (0.6H, dd, J=10.3, 16.8 Hz), 7.25 (1H, d, J=5.0 Hz), 7.34 (1H, dd, J=4.4, 9.2 Hz), 8.02 (0.6H, t, J=5.6 Hz), 8.17-8.21 (1.4H, m), 8.46 (1H, ddd, J=1.7, 7.0, 8.4 Hz), 8.56-8.62 (2H, m), 11.61 (0.6H, s), 11.66 (0.4H, s).

By proceeding in a similar manner to Example 32, the following compounds were prepared:

Example 33: (R)-1-Acryloyl-N-(2-(4-(pyrazolo[1,5-b]pyridazin-3-yl)-1H-pyrrolo[2,3-b]pyridin-2-yl)ethyl)pyrrolidine-2-carboxamide

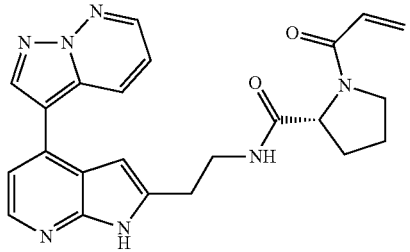 [SMILES: C=CC(=O)N1CCC[C@@H]1C(=O)NCCc1cc2c(-c3cnn4ncccc34)ccnc2[nH]1]

Starting from 2-(4-(pyrazolo[1,5-b]pyridazin-3-yl)-1H-pyrrolo[2,3-b]pyridin-2-yl)ethan-1-amine (Example 30) and acryloyl-D-proline (Intermediate 28)

LCMS (Method 1): Rt 2.21 min, m/z 430.3 [MH$^+$].

$^1$H NMR (400 MHz, d$_6$-DMSO): 1.65-1.86 (3H, m), 1.91-2.01 (0.6H, m), 2.06-2.16 (0.4H, m), 2.87-2.96 (2H, m), 3.38-3.55 (3.4H, m), 3.60-3.66 (0.6H, m), 4.29 (0.6H, dd, J=3.4, 8.4 Hz), 4.36 (0.4H, dd, J=2.8, 8.5 Hz), 5.27 (0.4H, dd, J=2.5, 10.1 Hz), 5.64 (0.6H, dd, J=2.4, 10.3 Hz), 5.95 (0.4H, dd, J=2.6, 16.6 Hz), 6.05-6.14 (1H, m), 6.41 (1H, dd, J=1.7, 13.2 Hz), 6.57 (0.6H, dd, J=10.3, 16.7 Hz), 7.25 (1H, d, J=5.1 Hz), 7.34 (1H, dd, J=4.4, 9.1 Hz), 8.03 (0.6H, t, J=5.7 Hz), 8.17-8.21 (1.4H, m), 8.46 (1H, ddd, J=1.9, 6.3, 9.1 Hz), 8.54-8.62 (2H, m), 11.62 (0.6H, s), 11.66 (0.4H, s).

Example 34: (R)-1-Acryloyl-N-(2-(4-(pyrazolo[1,5-b]pyridazin-3-yl)-1H-pyrrolo[2,3-b]pyridin-2-yl)ethyl)piperidine-3-carboxamide

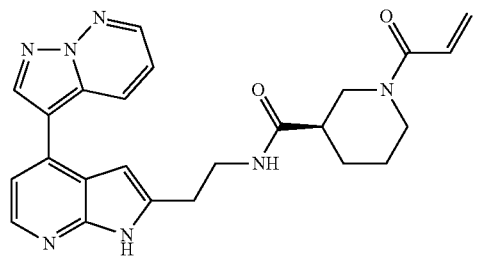 [SMILES: C=CC(=O)N1CCC[C@@H](C(=O)NCCc2cc3c(-c4cnn5ncccc45)ccnc3[nH]2)C1]

Starting from 2-(4-(pyrazolo[1,5-b]pyridazin-3-yl)-1H-pyrrolo[2,3-b]pyridin-2-yl)ethan-1-amine (Example 30) and (R)-1-acryloylpiperidine-3-carboxylic acid (Intermediate 21).

LCMS (Method 1): Rt 2.29 min, m/z 444.5 [MH+].

¹H NMR (400 MHz, d₆-DMSO): 1.36-1.17 (1H, m), 1.83-1.48 (3H, m), 2.28-2.14 (1H, m), 2.72-2.59 (1H, m), 3.15-2.85 (3H, m), 3.50-3.40 (2H, m), 4.03-3.81 (1H, m), 4.43-4.14 (1H, m), 5.68-5.47 (1H, m), 6.10-5.95 (1H, m), 6.40 (1H, s), 6.83-6.63 (1H, m), 7.26 (1H, d, J=4.9 Hz), 7.33 (1H, dd, J=4.4, 9.2 Hz), 8.10-8.00 (1H, m), 8.20 (1H, d, J=4.9 Hz), 8.49-8.43 (1H, m), 8.60-8.54 (2H, m), 11.68 (1H, s).

Example 35: (S)-1-acryloyl-N-(2-(4-(pyrazolo[1,5-b]pyridazin-3-yl)-1H-pyrrolo[2,3-b]pyridin-2-yl)ethyl)piperidine-3-carboxamide

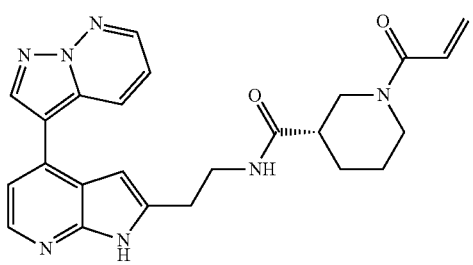 [SMILES: C=CC(=O)N1CCC[C@H](C(=O)NCCc2cc3c(-c4cnn5ncccc45)ccnc3[nH]2)C1]

Starting from 2-(4-(pyrazolo[1,5-b]pyridazin-3-yl)-1H-pyrrolo[2,3-b]pyridin-2-yl)ethan-1-amine (Example 30) and (S)-1-acryloylpiperidine-3-carboxylic acid (Intermediate 19).

LCMS (Method 1): Rt 2.29 min, m/z 444.3 [MH+].

¹H NMR (400 MHz, d₆-DMSO): 1.37-1.15 (1H, m), 1.70-1.49 (2H, m), 1.83-1.72 (1H, m), 2.28-2.13 (1H, m), 2.73-2.59 (1H, m), 3.16-2.85 (3H, m), 3.52-3.39 (2H, m), 4.02-3.80 (1H, m), 4.43-4.15 (1H, m), 5.69-5.48 (1H, m), 6.11-5.96 (1H, m), 6.41 (1H, s), 6.83-6.64 (1H, m), 7.27-7.23 (1H, m), 7.33 (1H, dd, J=4.4, 9.1 Hz), 8.10-7.99 (1H, m), 8.20 (1H, d, J=5.0 Hz), 8.49-8.43 (1H, m), 8.60-8.54 (2H, m), 11.68 (1H, s).

Example 36: 3-Acrylamido-N-(2-(4-(pyrazolo[1,5-b]pyridazin-3-yl)-1H-pyrrolo[2,3-b]pyridin-2-yl)ethyl)benzamide

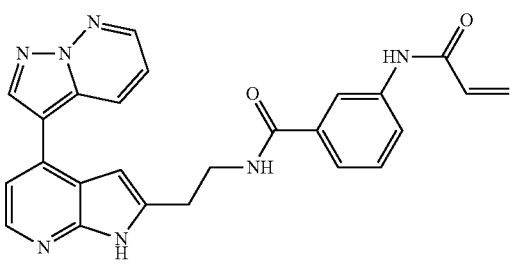 [SMILES: C=CC(=O)Nc1cccc(C(=O)NCCc2cc3c(-c4cnn5ncccc45)ccnc3[nH]2)c1]

Starting from 2-(4-(pyrazolo[1,5-b]pyridazin-3-yl)-1H-pyrrolo[2,3-b]pyridin-2-yl)ethan-1-amine (Example 30) and 3-acrylamidobenzoic acid.

LCMS (Method 1): Rt 2.47 min, m/z 452.3 [MH+].

¹H NMR (400 MHz, d₆-DMSO): 3.05 (2H, t, J=7.0 Hz), 3.67 (2H, q, J=6.6 Hz), 5.77 (1H, dd, J=2.0, 10.0 Hz), 6.27 (1H, dd, J=2.0, 17.0 Hz), 6.39-6.47 (2H, m), 7.24 (2H, q, J=4.5 Hz), 7.39 (1H, t, J=7.9 Hz), 7.51 (1H, td, J=1.3, 7.7 Hz), 7.84 (1H, dd, J=1.3, 8.0 Hz), 8.09 (1H, t, J=1.6 Hz), 8.20 (1H, d, J=5.0 Hz), 8.41 (1H, dd, J=1.8, 9.1 Hz), 8.54 (1H, dd, J=1.9, 4.4 Hz), 8.56 (1H, s), 8.62 (1H, t, J=5.6 Hz), 10.27 (1H, s), 11.72 (1H, s).

Example 37: 1-Acryloyl-N-(2-(4-(pyrazolo[1,5-b]pyridazin-3-yl)-1H-pyrrolo[2,3-b]pyridin-2-yl)ethyl)azetidine-3-carboxamide

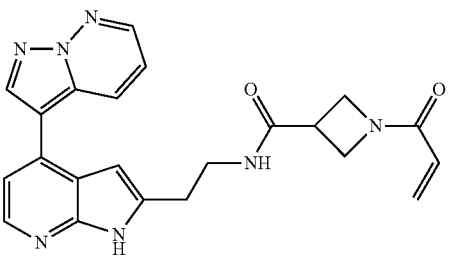 [SMILES: C=CC(=O)N1CC(C(=O)NCCc2cc3c(-c4cnn5ncccc45)ccnc3[nH]2)C1]

Starting from 2-(4-(pyrazolo[1,5-b]pyridazin-3-yl)-1H-pyrrolo[2,3-b]pyridin-2-yl)ethan-1-amine (Example 30) and 1-acryloylazetidine-3-carboxylic acid (Intermediate 17).

LCMS (Method 1): Rt 2.08 min, m/z 416.4 [MH+].

¹H NMR (400 MHz, d₆-DMSO): 2.92 (2H, t, J=7.0 Hz), 3.54-3.44 (2H, m), 3.89-3.82 (1H, m), 3.97 (1H, t, J=9.3 Hz), 4.16-4.09 (1H, m), 4.25 (1H, t, J=8.7 Hz), 5.63 (1H, dd, J=2.2, 10.3 Hz), 6.06 (1H, dd, J=2.3, 17.1 Hz), 6.22 (1H, dd, J=10.3, 17.0 Hz), 6.41 (1H, d, J=1.7 Hz), 7.25 (1H, d, J=5.0 Hz), 7.35 (1H, dd, J=4.5, 9.2 Hz), 8.16 (1H, t, J=5.7 Hz), 8.20 (1H, d, J=5.0 Hz), 8.46 (1H, dd, J=1.8, 9.2 Hz), 8.57 (1H, d, J=1.8 Hz), 8.58 (1H, s), 11.69 (1H, s). 1H obscured by water.

Example 38: 1-Acryloyl-N-(2-(4-(pyrazolo[1,5-b]pyridazin-3-yl)-1H-pyrrolo[2,3-b]pyridin-2-yl)ethyl)azetidine-3-carboxamide

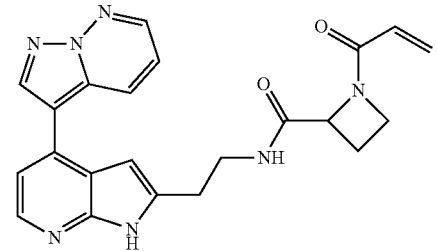 [SMILES: C=CC(=O)N1CCC1C(=O)NCCc1cc2c(-c3cnn4ncccc34)ccnc2[nH]1]

Starting from 2-(4-(pyrazolo[1,5-b]pyridazin-3-yl)-1H-pyrrolo[2,3-b]pyridin-2-yl)ethan-1-amine (Example 30) and 1-acryloylazetidine-2-carboxylic acid (Intermediate 18).

LCMS (Method 1): Rt 2.25 min, m/z 416.4 [MH+].

¹H NMR (400 MHz, d₆-DMSO): 2.15-1.91 (1H, m), 2.48-2.30 (1H, m), 3.00-2.86 (2H, m), 3.61-3.44 (2H, m), 3.80 (1H, t, J=7.6 Hz), 4.10 (1H, t, J=7.6 Hz), 4.63 (0.6H, dd, J=5.7, 9.2 Hz), 4.79 (0.4H, dd, J=5.1, 9.2 Hz), 5.25 (0.4H, dd, J=2.9, 9.7 Hz), 5.65 (0.6H, dd, J=2.2, 10.2 Hz), 5.96-5.79 (1H, m), 6.08 (0.5H, dd, J=2.1, 17.0 Hz), 6.26 (0.5H, dd, J=10.3, 17.0 Hz), 6.46-6.38 (1H, m), 7.25 (1H, d, J=5.0 Hz), 7.34 (1H, dd, J=4.4, 9.0 Hz), 8.23-8.16 (1.6H, m), 8.36-8.29 (0.4H, m), 8.50-8.43 (1H, m), 8.59-8.54 (1.5H, m), 8.63 (0.5H, s), 11.74-11.56 (1H, m).

Resolution of Example 38 by Chiral SFC

Example 31 was resolved by chiral SFC using a YMC Cellulose-SC column (10×250 mm, 5 micron) eluting with 55% EtOH:45% CO₂, 70 mL/min, 120 bar, 40° C., DAD 225 nm.

Example 39: Faster Running Component—(Unknown Absolute Configuration)

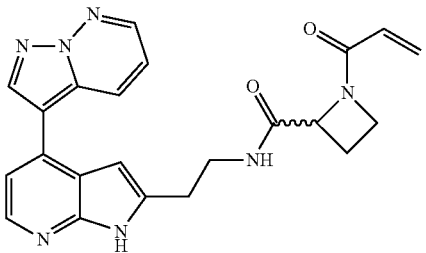 [SMILES: C=CC(=O)N1CCC1C(=O)NCCc1cc2c(-c3cnn4ncccc34)ccnc2[nH]1]

The title compound was isolated as a yellow solid.
Analytical SFC using YMC Cellulose-SC (4.6×250 mm, 5 micron) eluting with 55% EtOH:45% CO₂, 5.0 mL/min, 120 bar, 40° C., DAD 225 nm retention time 7.0 min.

Example 40: Slower Running Component—(Unknown Absolute Configuration)

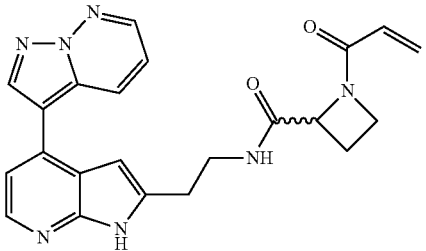 [SMILES: C=CC(=O)N1CCC1C(=O)NCCc1cc2c(-c3cnn4ncccc34)ccnc2[nH]1]

The title compound was isolated as a yellow solid.
Analytical SFC using YMC Cellulose-SC (4.6×250 mm, 5 micron) eluting with 55% EtOH:45% CO₂, 5.0 mL/min, 120 bar, 40° C., DAD 225 nm retention time 9.0 min.

Example 41: (S)-1-(2-Chloroacetyl)-N-(2-(4-(pyrazolo[1,5-b]pyridazin-3-yl)-1H-pyrrolo[2,3-b]pyridin-2-yl)ethyl)pyrrolidine-2-carboxamide

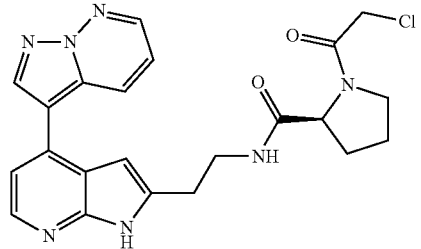 [SMILES: O=C(NCCc1cc2c(-c3cnn4ncccc34)ccnc2[nH]1)[C@@H]1CCCN1C(=O)CCl]

Starting from 2-(4-(pyrazolo[1,5-b]pyridazin-3-yl)-1H-pyrrolo[2,3-b]pyridin-2-yl)ethan-1-amine (Example 30) and (2-chloroacetyl)-L-proline.
LCMS (Method 1): Rt 2.29 min, m/z 452.3 [MH⁺].

¹H NMR (400 MHz, d₆-DMSO): 2.02-1.58 (4H, m), 2.98-2.83 (2H, m), 3.58-3.35 (4H, m), 3.71 (0.3H, d, J=13.7 Hz), 4.09 (0.2H, d, J=13.7 Hz), 4.40-4.19 (2.5H, m), 6.54-6.34 (1H, m), 7.29-7.20 (1H, m), 7.37-7.31 (1H, m), 8.03-7.97 (0.7H, m), 8.27-8.16 (1.3H, m), 8.50-8.43 (1H, m), 8.61-8.50 (2H, m), 11.74-11.56 (1H, m).

Example 42: (S)-1-(3-Methylbut-2-enoyl)-N-(2-(4-(pyrazolo[1,5-b]pyridazin-3-yl)-1H-pyrrolo[2,3-b]pyridin-2-yl)ethyl)pyrrolidine-2-carboxamide

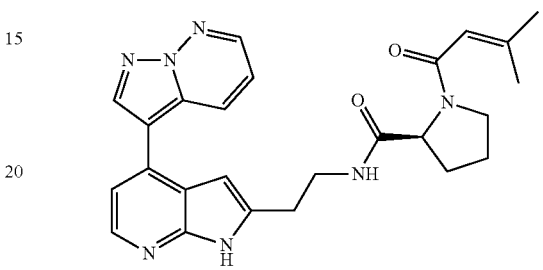

Starting from 2-(4-(pyrazolo[1,5-b]pyridazin-3-yl)-1H-pyrrolo[2,3-b]pyridin-2-yl)ethan-1-amine (Example 30) and (3-methylbut-2-enoyl)-L-proline (which can be prepared as described in *Journal of the Chemical Society—Perkin Transactions* 1, 1998, 5, 969-976).

LCMS (Method 1): Rt 2.54 min, m/z 458.5 [MH⁺].

¹H NMR (400 MHz, d₆-DMSO): 1.50 (1H, s), 2.16-1.61 (9H, m), 2.97-2.85 (2H, m), 3.56-3.35 (4H, m), 4.28-4.17 (1H, m), 5.50-5.46 (0.3H, m), 5.90-5.86 (0.7H, m), 6.44-6.39 (1H, m), 7.26-7.22 (1H, m), 7.33 (1H, dd, J=4.4, 9.2 Hz), 8.00-7.91 (0.7H, m), 8.17-8.11 (0.3H, m), 8.19 (1H, d, J=5.1 Hz), 8.50-8.43 (1H, m), 8.60-8.53 (2H, m), 11.71-11.57 (1H, m).

Example 43: (S)-1-Methacryloyl-N-(2-(4-(pyrazolo[1,5-b]pyridazin-3-yl)-1H-pyrrolo[2,3-b]pyridin-2-yl)ethyl)pyrrolidine-2-carboxamide

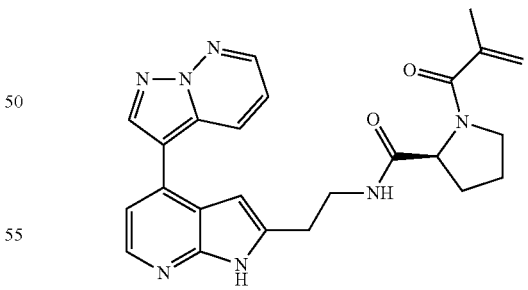

Starting from (S)—N-(2-(4-(pyrazolo[1,5-b]pyridazin-3-yl)-1H-pyrrolo[2,3-b]pyridin-2-yl)ethyl)pyrrolidine-2-carboxamide (Example 82) and methylacrylic acid.

LCMS (Method 2): Rt 2.36 min, m/z 444.1 [MH⁺].

¹H NMR (400 MHz, d₆-DMSO): 2.13-1.62 (7H, m), 2.90 (2H, t, J=6.8 Hz), 3.55-3.35 (4H, m), 4.32-4.19 (1H, m), 4.88 (1H, d, J=7.9 Hz), 5.16 (0.5H, s), 5.22 (0.5H, s), 6.45-6.36 (1H, m), 7.25 (1H, d, J=5.0 Hz), 7.38-7.30 (1H, m), 7.97-7.89 (0.6H, m), 8.13-8.05 (0.4H, m), 8.19 (1H, d, J=5.0 Hz), 8.50-8.43 (1H, m), 8.61-8.54 (2H, m), 11.70-11.57 (1H, m).

Example 44: (S,E)-1-(But-2-enoyl)-N-(2-(4-(pyrazolo[1,5-b]pyridazin-3-yl)-1H-pyrrolo[2,3-b]pyridin-2-yl)ethyl)pyrrolidine-2-carboxamide

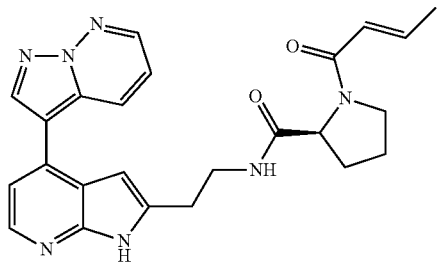 [SMILES: C/C=C/C(=O)N1CCC[C@H]1C(=O)NCCc1cc2c(-c3cnn4ncccc34)ccnc2[nH]1]

Starting from (S)—N-(2-(4-(pyrazolo[1,5-b]pyridazin-3-yl)-1H-pyrrolo[2,3-b]pyridin-2-yl)ethyl)pyrrolidine-2-carboxamide (Example 82) and crotonic acid.

LCMS (Method 2): Rt 2.37 min, m/z 444.1 [MH$^+$].

$^1$H NMR (400 MHz, d$_6$-DMSO): 1.53 (1H, dd, J=1.6, 6.9 Hz), 2.16-1.61 (6H, m), 2.98-2.83 (2H, m), 3.65-3.34 (4H, m), 4.36-4.22 (1H, m), 5.87-5.77 (0.3H, dd, J=1.7, 14.9 Hz), 6.30-6.19 (0.7H, dd, J=1.7, 15.0 Hz), 6.46-6.38 (1H, m), 6.73-6.50 (1H, m), 7.27-7.22 (1H, m), 7.37-7.31 (1H, m), 8.01-7.95 (0.6H, m), 8.21-8.15 (1.4H, m), 8.50-8.43 (1H, m), 8.59-8.54 (1.4H, m), 8.61 (0.6H, s), 11.69-11.56 (1H, m).

Example 45: (S)-1-(3-Chloro-2,2-dimethylpropanoyl)-N-(2-(4-(pyrazolo[1,5-b]pyridazin-3-yl)-1H-pyrrolo[2,3-b]pyridin-2-yl)ethyl)pyrrolidine-2-carboxamide

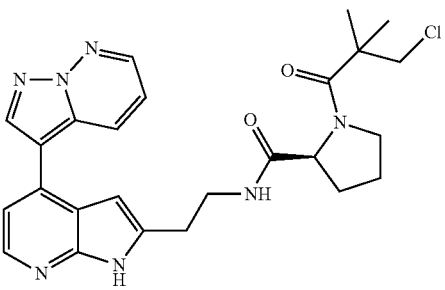 [SMILES: CC(C)(CCl)C(=O)N1CCC[C@H]1C(=O)NCCc1cc2c(-c3cnn4ncccc34)ccnc2[nH]1]

Starting from (S)—N-(2-(4-(pyrazolo[1,5-b]pyridazin-3-yl)-1H-pyrrolo[2,3-b]pyridin-2-yl)ethyl)pyrrolidine-2-carboxamide (Example 82) and 3-chloro-2,2-dimethylpropanoic acid.

LCMS (Method 2): Rt 2.73 min, m/z 494.1 [MH$^+$].

$^1$H NMR (400 MHz, d$_6$-DMSO): 1.29-1.11 (6H, m), 1.98-1.52 (4H, m), 2.90 (2H, t, J=6.8 Hz), 3.50-3.37 (2H, m), 3.76-3.53 (4H, m), 4.29 (1H, br s), 6.45-6.39 (1H, m), 7.25 (1H, d, J=5.0 Hz), 7.33 (1H, dd, J=4.4, 9.1 Hz), 7.79 (1H, br s), 8.19 (1H, d, J=5.0 Hz), 8.47 (1H, dd, J=1.9, 9.1 Hz), 8.56 (1H, dd, J=1.9, 4.5 Hz), 8.59 (1H, s), 11.61 (1H, s).

Example 46: (S)-1-Acryloyl-N-methyl-N-(2-(4-(pyrazolo[1,5-b]pyridazin-3-yl)-1H-pyrrolo[2,3-b]pyridin-2-yl)ethyl)pyrrolidine-2-carboxamide

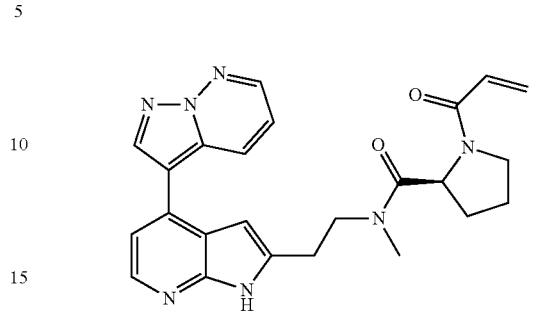

Starting from N-methyl-2-(4-(pyrazolo[1,5-b]pyridazin-3-yl)-1H-pyrrolo[2,3-b]pyridin-2-yl)ethan-1-amine (Example 96) and acryloyl-L-proline.

LCMS (Method 1): Rt 2.35 min, m/z 444.4 [MH$^+$].

$^1$H NMR (400 MHz, d$_6$-DMSO): 1.52-1.44 (0.3H, m), 1.65-1.54 (0.7H, m), 1.80-1.71 (1H, m), 1.88-1.83 (0.3H, m), 2.09-1.95 (0.7H, m), 2.21-2.11 (0.3H, m), 2.38-2.30 (0.7H, m), 2.80 (0.7H, s), 2.88 (0.3H, s), 3.02-2.91 (3H, m), 3.20-3.12 (1H, m), 3.83-3.61 (2H, m), 4.77-4.66 (0.5H, m), 4.96-4.85 (0.5H, m), 5.30-5.20 (0.3H, m), 5.78-5.64 (0.7H, m), 6.04-5.90 (0.3H, m), 6.12 (0.7H, dd, J=2.4, 16.7 Hz), 6.42 (1H, d, J=17.9 Hz), 6.67-6.52 (1H, m), 7.30-7.24 (1H, m), 7.37-7.31 (1H, m), 8.21 (1H, dd, J=5.0, 9.0 Hz), 8.49-8.40 (1H, m), 8.61-8.55 (2H, m), 11.86-11.65 (1H, m) some protons obscured by solvent.

Example 47: (R)-1-Acryloyl-N-methyl-N-(2-(4-(pyrazolo[1,5-b]pyridazin-3-yl)-1H-pyrrolo[2,3-b]pyridin-2-yl)ethyl)pyrrolidine-2-carboxamide

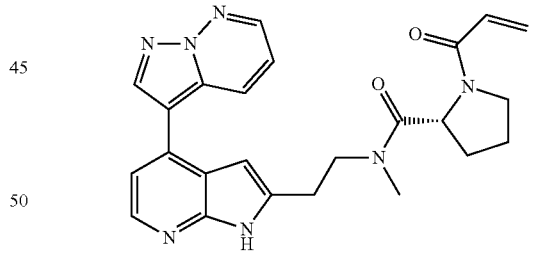

Starting from N-methyl-2-(4-(pyrazolo[1,5-b]pyridazin-3-yl)-1H-pyrrolo[2,3-b]pyridin-2-yl)ethan-1-amine (Example 96) and acryloyl-D-proline (Intermediate 28).

LCMS (Method 2): Rt 2.34 min, m/z 444.2 [MH$^+$].

$^1$H NMR (400 MHz, d$_6$-DMSO): 2.23-1.42 (4H, m), 3.29-2.73 (5H, m), 3.87-3.39 (3.8H, m), 4.07-3.92 (0.2H, m), 4.96-4.61 (1.2H, m), 5.31-5.19 (0.3H, m), 5.78-5.64 (0.8H, m), 6.05-5.89 (0.4H, m), 6.16-6.08 (0.6H, m), 6.47-6.38 (0.5H, m), 6.67-6.51 (1.2H, m), 7.37-7.23 (2H, m), 8.24-8.18 (1H, m), 8.49-8.40 (1H, m), 8.61-8.54 (2H, m), 11.89-11.61 (1H, m).

Example 48: (S)-1-Acryloyl-N-methyl-N-(2-(4-(pyrazolo[1,5-b]pyridazin-3-yl)-1H-pyrrolo[2,3-b]pyridin-2-yl)ethyl)piperidine-3-carboxamide

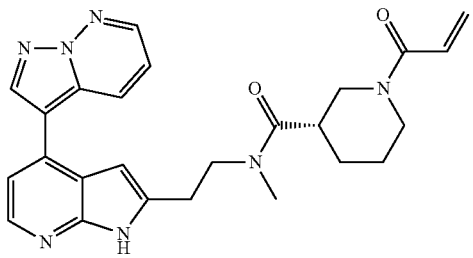 [SMILES: C=CC(=O)N1CCC[C@H](C(=O)N(C)CCc2cc3c(-c4cnn5ncccc45)ccnc3[nH]2)C1]

Starting from N-methyl-2-(4-(pyrazolo[1,5-b]pyridazin-3-yl)-1H-pyrrolo[2,3-b]pyridin-2-yl)ethan-1-amine (Example 96) and (S)-1-acryloylpiperidine-3-carboxylic acid (Intermediate 20).

LCMS (Method 1): Rt 2.44 min, m/z 458.4 [MH$^+$].

$^1$H NMR (400 MHz, de-DMSO): 1.83-1.01 (4H, m), 2.70-2.40 (2H, m), 3.12-2.79 (6H, m), 4.06-3.56 (3H, m), 4.44-4.21 (1H, m), 5.70-5.46 (1H, m), 6.14-5.92 (1H, m), 6.47-6.37 (1H, m), 6.59-6.48 (0.2H, m), 6.84-6.62 (0.8H, m), 7.29-7.22 (1H, m), 7.37-7.30 (1H, m), 8.24-8.16 (1H, m), 8.49-8.39 (1H, m), 8.60-8.52 (2H, m), 11.88-11.64 (1H, m).

Example 49: 3-Acrylamido-N-methyl-N-(2-(4-(pyrazolo[1,5-b]pyridazin-3-yl)-1H-pyrrolo[2,3-b]pyridin-2-yl)ethyl)benzamide

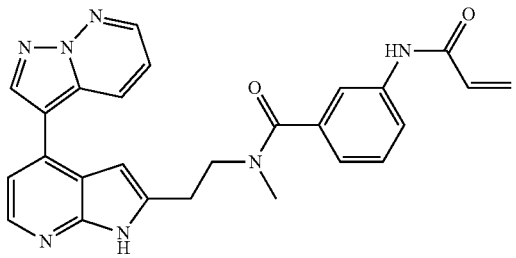 [SMILES: C=CC(=O)Nc1cccc(C(=O)N(C)CCc2cc3c(-c4cnn5ncccc45)ccnc3[nH]2)c1]

Starting from N-methyl-2-(4-(pyrazolo[1,5-b]pyridazin-3-yl)-1H-pyrrolo[2,3-b]pyridin-2-yl)ethan-1-amine (Example 96) and 3-acrylamidobenzoic acid.

LCMS (Method 1): Rt 2.45 min, m/z 466.4 [MH$^+$].

$^1$H NMR (400 MHz, d$_6$-DMSO, 80° C.): 3.16-2.83 (5H, m), 3.72-3.57 (1H, m), 3.92-3.79 (1H, m), 5.76 (1H, d, J=10.3 Hz), 6.57-6.18 (3H, m), 6.76-6.64 (0.5H, m), 7.07-6.95 (0.5H, m), 7.39-7.11 (3H, m), 7.83-7.49 (2H, m), 8.31-8.12 (1H, m), 8.67-8.34 (3H, m), 10.34-10.09 (1H, m), 11.58 (0.5H, s), 11.82 (0.5H, s).

Example 50: (S)-1-Acryloyl-N-ethyl-N-(2-(4-(pyrazolo[1,5-b]pyridazin-3-yl)-1H-pyrrolo[2,3-b]pyridin-2-yl)ethyl)pyrrolidine-2-carboxamide

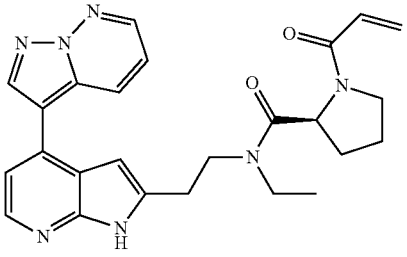 [SMILES: C=CC(=O)N1CCC[C@H]1C(=O)N(CC)CCc1cc2c(-c3cnn4ncccc34)ccnc2[nH]1]

Starting from N-ethyl-2-(4-(pyrazolo[1,5-b]pyridazin-3-yl)-1H-pyrrolo[2,3-b]pyridin-2-yl)ethan-1-amine (Example 31) and acryloyl-L-proline.

LCMS (Method 1): Rt 2.71 min, m/z 458.4 [MH$^+$].

$^1$H NMR (400 MHz, d$_6$-DMSO): 1.08 (3H, m), 2.41-1.53 (4H, m), 3.96-2.86 (8H, s), 4.71 (0.3H, dd, J=3.9, 8.5 Hz), 4.94-4.81 (0.7H, m), 5.52-5.38 (0.3H, m), 5.72-5.64 (0.7H, m), 5.85-5.78 (0.1H, m), 6.07-5.94 (0.2H, m), 6.17-6.09 (0.7H, m), 6.44-6.37 (0.5H, m), 6.69-6.49 (1.5H, m), 7.30-7.23 (1H, m), 7.37-7.30 (1H, m), 8.23-8.17 (1H, m), 8.49-8.40 (1H, m), 8.62-8.54 (2H, m), 11.89-11.60 (1H, m).

Example 51: (S)-1-Acryloyl-N-(2-(4-(1-methyl-1H-pyrazol-5-yl)-1H-pyrrolo[2,3-b]pyridin-2-yl)ethyl)pyrrolidine-2-carboxamide

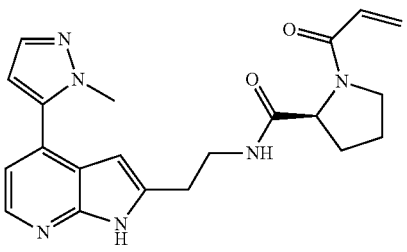 [SMILES: C=CC(=O)N1CCC[C@H]1C(=O)NCCc1cc2c(-c3ccnn3C)ccnc2[nH]1]

Starting from 2-(4-(1-methyl-1H-pyrazol-5-yl)-1H-pyrrolo[2,3-b]pyridin-2-yl)ethan-1-amine (Example 100) and acryloyl-L-proline.

LCMS (Method 1): Rt 2.53 min, m/z 393.4 [MH$^+$].

$^1$H NMR (400 MHz, d$_6$-DMSO): 2.20-1.59 (4H, m), 2.95-2.82 (2H, m), 3.68-3.35 (4H, m), 3.88-3.82 (3H, m), 4.28 (0.6H, dd, J=3.5, 8.4 Hz), 4.35 (0.4H, dd, J=2.9, 8.6 Hz), 5.28 (0.4H, dd, J=2.7, 10.0 Hz), 5.66 (0.6H, dd, J=2.4, 10.3 Hz), 6.24-5.94 (2.4H, m), 6.62-6.52 (1.6H, m), 7.13-7.08 (1H, m), 7.60-7.55 (1H, m), 8.03-7.97 (0.6H, m), 8.18-8.13 (0.4H, m), 8.24-8.19 (1H, m), 11.80-11.64 (1H, m).

Example 52: (R)-1-Acryloyl-N-(2-(4-(1-methyl-1H-pyrazol-5-yl)-1H-pyrrolo[2,3-b]pyridin-2-yl)ethyl)pyrrolidine-2-carboxamide

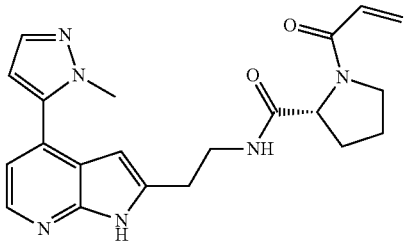 [SMILES: C=CC(=O)N1CCC[C@@H]1C(=O)NCCc1cc2c(-c3ccnn3C)ccnc2[nH]1]

Starting from 2-(4-(1-methyl-1H-pyrazol-5-yl)-1H-pyrrolo[2,3-b]pyridin-2-yl)ethan-1-amine (Example 100) and acryloyl-D-proline (Intermediate 28).

LCMS (Method 1): Rt 2.52 min, m/z 393.4 [MH$^+$].

$^1$H NMR (400 MHz, d$_6$-DMSO): 2.17-1.61 (4H, m), 2.95-2.84 (2H, m), 3.68-3.35 (4H, m), 3.87-3.82 (3H, m), 4.27 (0.6H, dd, J=3.5, 8.5 Hz), 4.35 (0.4H, dd, J=2.9, 8.6 Hz), 5.28 (0.4H, dd, J=2.7, 10.0 Hz), 5.66 (0.6H, dd, J=2.4, 10.3 Hz), 6.02-5.94 (0.4H, m), 6.23-6.04 (2H, m), 6.62-6.52 (1.6H, m), 7.14-7.09 (1H, m), 7.60-7.56 (1H, m), 8.04-7.96 (0.6H, m), 8.18-8.13 (0.4H, m), 8.24-8.19 (1H, m), 11.80-11.66 (1H, m).

Example 53: (S)-1-Acryloyl-N-(2-(5-chloro-4-(pyrazolo[1,5-b]pyridazin-3-yl)-1H-pyrrolo[2,3-b]pyridin-2-yl)ethyl)pyrrolidine-2-carboxamide

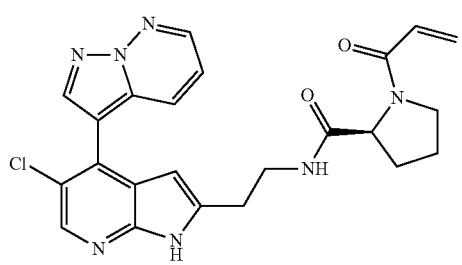 [SMILES: C=CC(=O)N1CCC[C@H]1C(=O)NCCc1cc2c(-c3cnn4ncccc34)c(Cl)cnc2[nH]1]

Starting from 2-(5-chloro-4-(pyrazolo[1,5-b]pyridazin-3-yl)-1H-pyrrolo[2,3-b]pyridin-2-yl)ethan-1-amine (Example 101) and acryloyl-L-proline.

LCMS (Method 1): Rt 3.28 min, m/z 464.3 [MH$^+$].

$^1$H NMR (400 MHz, d$_6$-DMSO: 2.14-1.55 (4H, m), 2.92-2.81 (2H, m), 3.63-3.36 (4H, m), 4.24 (0.6H, dd, J=3.6, 8.5 Hz), 4.32 (0.4H, dd, J=2.9, 8.6 Hz), 5.25 (0.4H, dd, J=2.6, 10.0 Hz), 5.63 (0.6H, dd, J=2.4, 10.3 Hz), 5.97-5.90 (0.4H, m), 6.11-6.00 (2H, m), 6.60-6.49 (0.6H, m), 7.36-7.27 (1H, m), 7.97 (0.6H, t, J=5.7 Hz), 8.10-8.03 (1H, m), 8.13 (0.4H, t, J=5.7 Hz), 8.30-8.25 (1H, m), 8.40 (0.4H, s), 8.43 (0.6H, s), 8.61-8.56 (1H, m), 11.95-11.79 (1H, m).

Example 54 (R)-1-Acryloyl-N-(2-(5-chloro-4-(pyrazolo[1,5-b]pyridazin-3-yl)-1H-pyrrolo[2,3-b]pyridin-2-yl)ethyl)pyrrolidine-2-carboxamide

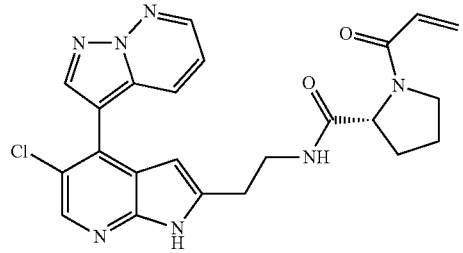 [SMILES: C=CC(=O)N1CCC[C@@H]1C(=O)NCCc1cc2c(-c3cnn4ncccc34)c(Cl)cnc2[nH]1]

Starting from 2-(5-chloro-4-(pyrazolo[1,5-b]pyridazin-3-yl)-1H-pyrrolo[2,3-b]pyridin-2-yl)ethan-1-amine (Example 101) and acryloyl-D-proline (Intermediate 28).

LCMS (Method 1): Rt 3.28 min, m/z 464.3 [MH$^+$].

$^1$H NMR (400 MHz, d$_6$-DMSO: 2.15-1.54 (4H, m), 2.95-2.81 (2H, m), 3.63-3.32 (4H, m), 4.24 (0.6H, dd, J=3.5, 8.5 Hz), 4.32 (0.4H, dd, J=2.8, 8.5 Hz), 5.24 (0.4H, dd, J=2.6, 10.1 Hz), 5.63 (0.6H, dd, J=2.4, 10.3 Hz), 5.98-5.90 (0.4H, m), 6.12-6.00 (2H, m), 6.59-6.49 (0.6H, m), 7.35-7.28 (1H, m), 7.96 (0.6H, t, J=5.8 Hz), 8.10-8.03 (1H, m), 8.13 (0.4H, t, J=6.0 Hz), 8.29-8.25 (1H, m), 8.44-8.39 (1H, m), 8.62-8.56 (1H, m), 11.95-11.79 (1H, m).

Example 55: (S)-1-Acryloyl-N-(2-(5-chloro-4-(pyrazolo[1,5-b]pyridazin-3-yl)-1H-pyrrolo[2,3-b]pyridin-2-yl)ethyl)piperidine-3-carboxamide

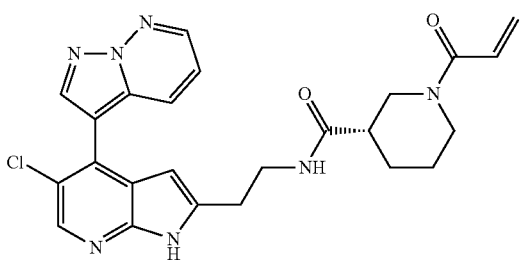 [SMILES: C=CC(=O)N1CCC[C@H](C(=O)NCCc2cc3c(-c4cnn5ncccc45)c(Cl)cnc3[nH]2)C1]

Starting from 2-(5-chloro-4-(pyrazolo[1,5-b]pyridazin-3-yl)-1H-pyrrolo[2,3-b]pyridin-2-yl)ethan-1-amine (Example 101) and (S)-1-acryloylpiperidine-3-carboxylic acid (Intermediate 20).

LCMS (Method 1): Rt 3.33 min, m/z 478.3 [MH$^+$].

$^1$H NMR (400 MHz, d$_6$-DMSO: 1.34-1.15 (1H, m), 1.79-1.44 (3H, m), 2.25-2.10 (1H, m), 2.73-2.57 (1H, m), 2.87 (2H, t, J=6.8 Hz), 3.14-2.90 (1H, m), 4.43-3.77 (2H, m), 5.70-5.51 (1H, m), 6.12-5.95 (2H, m), 6.84-6.60 (1H, m), 7.31 (1H, dd, J=4.4, 9.1 Hz), 8.04-7.96 (1H, m), 8.06 (1H, dd, J=1.9, 9.1 Hz), 8.28 (1H, s), 8.41 (1H, s), 8.61-8.55 (1H, m), 11.92 (1H, s). 2H obscured by water.

Example 56: 3-Acrylamido-N-(2-(5-chloro-4-(pyrazolo[1,5-b]pyridazin-3-yl)-1H-pyrrolo[2,3-b]pyridin-2-yl)ethyl)benzamide

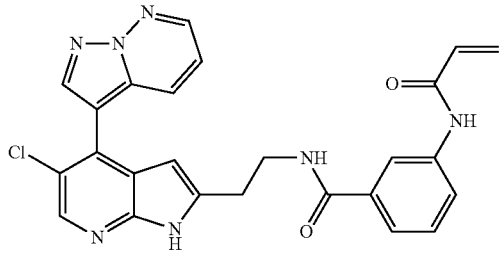 [SMILES: C=CC(=O)Nc1cccc(C(=O)NCCc2cc3c(-c4cnn5ncccc45)c(Cl)cnc3[nH]2)c1]

Starting from 2-(5-chloro-4-(pyrazolo[1,5-b]pyridazin-3-yl)-1H-pyrrolo[2,3-b]pyridin-2-yl)ethan-1-amine (Example 101 and 3-acrylamidobenzoic acid.

LCMS (Method 1: Rt 3.56 min, m/z 486.3 [MH$^+$].

$^1$H NMR (400 MHz, d$_6$-DMSO: 3.02 (2H, t, J=6.8 Hz), 3.62 (2H, q, J=6.5 Hz), 5.80-5.74 (1H, m), 6.10-6.04 (1H, m), 6.27 (1H, dd, J=1.9, 17.1 Hz), 6.44 (1H, dd, J=10.1, 17.1 Hz), 7.17 (1H, dd, J=4.4, 9.3 Hz), 7.38 (1H, t, J=8.0 Hz), 7.50-7.44 (1H, m), 7.87-7.81 (1H, m), 8.01 (1H, dd, J=1.8, 9.1 Hz), 8.09-8.04 (1H, m), 8.28 (1H, s), 8.40 (1H, s), 8.61-8.52 (2H, m), 10.29 (1H, s), 12.01-11.92 (1H, m).

Example 57: 4-Acrylamido-N-((4-(pyrazolo[1,5-b]pyridazin-3-yl)-1H-pyrrolo[2,3-b]pyridin-2-yl)methyl)benzamide

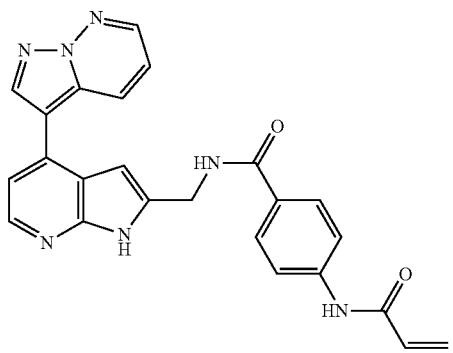 [SMILES: C=CC(=O)Nc1ccc(C(=O)NCc2cc3c(-c4cnn5ncccc45)ccnc3[nH]2)cc1]

Starting from (4-(pyrazolo[1,5-b]pyridazin-3-yl)-1H-pyrrolo[2,3-b]pyridin-2-yl)methanamine (Example 196) and 4-acrylamidobenzoic acid LCMS (Method 1): Rt 2.53 min, m/z 438.3 [MH$^+$].

$^1$H NMR (400 MHz, d$_6$-DMSO): 4.67 (2H, d, J=5.5 Hz), 5.79 (1H, dd, J=2.0, 10.1 Hz), 6.29 (1H, dd, J=2.0, 17.0 Hz), 6.46 (1H, dd, J=10.1, 17.2 Hz), 6.51 (1H, d, J=1.8 Hz), 7.27 (1H, d, J=5.0 Hz), 7.33 (1H, dd, J=4.4, 9.1 Hz), 7.75 (2H, d, J=8.8 Hz), 7.89 (2H, d, J=8.9 Hz), 8.24 (1H, d, J=5.0 Hz), 8.44 (1H, dd, J=1.9, 9.1 Hz), 8.54 (1H, s), 8.56 (1H, dd, J=1.8, 4.4 Hz), 8.87 (1H, t, J=5.6 Hz), 10.37 (1H, s), 11.75 (1H, s).

Example 58: (3R,4R)-4-Acrylamido-N-((4-(pyrazolo[1,5-b]pyridazin-3-yl)-1H-pyrrolo[2,3-b]pyridin-2-yl)methyl)tetrahydrofuran-3-carboxamide

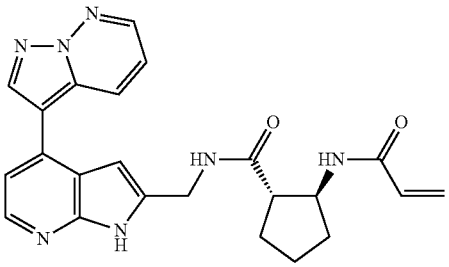 [SMILES: C=CC(=O)N[C@H]1CCC[C@@H]1C(=O)NCc1cc2c(-c3cnn4ncccc34)ccnc2[nH]1]

Starting from (4-(pyrazolo[1,5-b]pyridazin-3-yl)-1H-pyrrolo[2,3-b]pyridin-2-yl)methanamine (Example 196) and (3R,4R)-4-acryloylamidotetrahydrofuran-3-carboxylic acid (Intermediate 39).

LCMS (Method 2): Rt 2.07 min, m/z 432.1 [MH$^+$].

$^1$H NMR (400 MHz, d$_6$-DMSO): 3.31-3.22 (1H, m), 3.60 (1H, dd, J=5.4, 8.6 Hz), 4.07-3.83 (3H, m), 4.40-4.30 (1H, m), 4.56-4.47 (1H, m), 4.78-4.68 (1H, m), 5.30 (1H, dd, J=2.3, 10.2 Hz), 5.94 (1H, dd, J=2.2, 17.0 Hz), 6.17 (1H, dd, J=10.1, 17.2 Hz), 6.51-6.45 (1H, m), 7.27 (1H, d, J=5.0 Hz), 7.35 (1H, dd, J=4.4, 9.1 Hz), 8.25-8.18 (2H, m), 8.50-8.43 (2H, m), 8.62-8.55 (2H, m), 11.53 (1H, s).

Example 59: (1R,3R)-3-Acrylamido-N-((4-(pyrazolo[1,5-b]pyridazin-3-yl)-1H-pyrrolo[2,3-b]pyridin-2-yl)methyl)cyclopentane-1-carboxamide

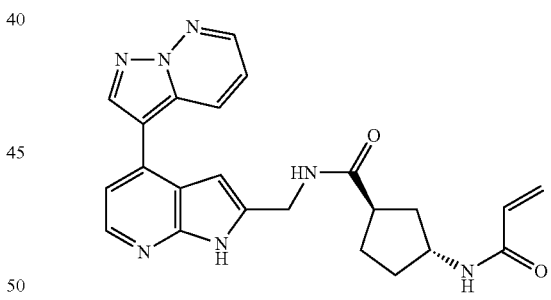

Starting from (4-(pyrazolo[1,5-b]pyridazin-3-yl)-1H-pyrrolo[2,3-b]pyridin-2-yl)methanamine (Example 196) and (1R,3R)-3-acrylamidocyclopentane-1-carboxylic acid (Intermediate 34).

LCMS (Method 2): Rt 2.22 min, m/z 430.2 [MH$^+$].

$^1$H NMR (400 MHz, d$_6$-DMSO): 1.51-1.38 (1H, m), 1.78-1.62 (2H, m), 2.05-1.86 (3H, m), 2.90-2.79 (1H, m), 4.23-4.12 (1H, m), 4.46 (2H, d, J=5.5 Hz), 5.55 (1H, dd, J=2.4, 10.0 Hz), 6.06 (1H, dd, J=2.5, 17.0 Hz), 6.20 (1H, dd, J=10.1, 17.1 Hz), 6.45-6.41 (1H, m), 7.27 (1H, d, J=5.0 Hz), 7.34 (1H, dd, J=4.4, 9.1 Hz), 8.08-8.03 (1H, m), 8.23 (1H, d, J=5.0 Hz), 8.30 (1H, t, J=5.5 Hz), 8.42 (1H, dd, J=1.8, 9.2 Hz), 8.53 (1H, s), 8.57 (1H, dd, J=1.8, 4.3 Hz), 11.69 (1H, s).

Example 60: 4-Acryloyl-N-(2-(4-(pyrazolo[1,5-b]pyridazin-3-yl)-1H-pyrrolo[2,3-b]pyridin-2-yl)ethyl)morpholine-2-carboxamide

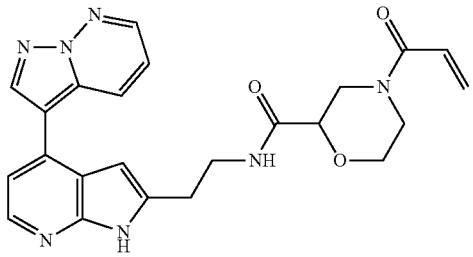 [SMILES: C=CC(=O)N1CCOC(C(=O)NCCc2cc3c(-c4cnn5ncccc45)ccnc3[nH]2)C1]

Starting from (4-(pyrazolo[1,5-b]pyridazin-3-yl)-1H-pyrrolo[2,3-b]pyridin-2-yl)methanamine (Example 196) and 4-acryloylmorpholine-2-carboxylic acid (Intermediate 35) using DIPEA instead of Et$_3$N.

LCMS (Method 1): Rt 2.21 min, m/z 446.4 [MH$^+$].

$^1$H NMR (400 MHz, d$_6$-DMSO): 2.67-2.54 (0.4H, m), 3.02-2.83 (2.6H, m), 3.25-3.08 (1H, m), 3.58-3.42 (3H, m), 4.10-3.78 (3.5H, m), 4.53-4.41 (0.5H, m), 5.75-5.63 (1H, m), 6.19-6.02 (1H, m), 6.45-6.40 (1H, m), 6.82-6.64 (1H, m), 7.25 (1H, d, J=5.0 Hz), 7.33 (1H, dd, J=4.4, 9.1 Hz), 8.13-7.98 (1H, m), 8.19 (1H, d, J=5.0 Hz), 8.45 (1H, dd, J=1.7, 9.2 Hz), 8.56 (1H, dd, J=1.7, 4.4 Hz), 8.58 (1H, s), 11.68 (1H, s).

Resolution of Example 60 by Chiral SFC

Example 60 was resolved by chiral SFC using a YMC Amylose-C column eluting with 55% EtOH (+0.1% diethylamine): 45% CO$_2$, 15 mL/min, 120 bar, 40° C., DAD 230 nm.

Example 61 Faster Running—(Unknown Absolute Configuration)

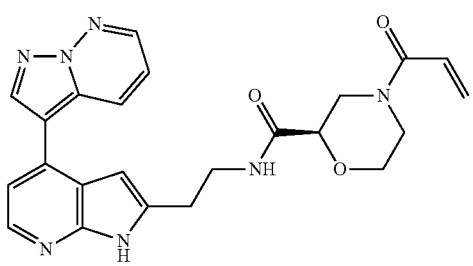 [SMILES: C=CC(=O)N1CCO[C@@H](C(=O)NCCc2cc3c(-c4cnn5ncccc45)ccnc3[nH]2)C1]

Analytical SFC using YMC Amylose-C (2×150 3 micron) eluting with 55% EtOH (+0.1% diethylamine): 45% CO$_2$, 0.95 mL/min, 120 bar, 40° C., DAD 230 nm retention time 5.3 min.

Example 62 Slower Running—(Unknown Absolute Configuration)

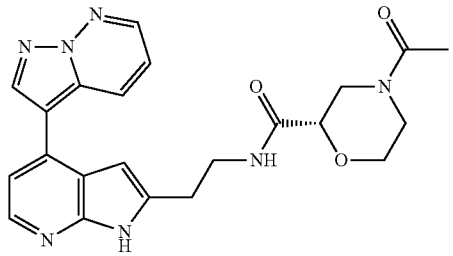 [SMILES: CC(=O)N1CCO[C@H](C(=O)NCCc2cc3c(-c4cnn5ncccc45)ccnc3[nH]2)C1]

Analytical SFC using YMC Amylose-C (2×150 3 micron) eluting with 55% EtOH (+0.1% diethylamine): 45% CO$_2$, 0.95 mL/min, 120 bar, 40° C., DAD 230 nm retention time 6.2 min.

Example 63: (R)-4-Acryloyl-N-(2-(4-(pyrazolo[1,5-b]pyridazin-3-yl)-1H-pyrrolo[2,3-b]pyridin-2-yl)ethyl)morpholine-3-carboxamide

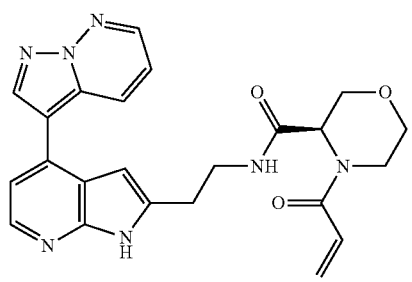 [SMILES: C=CC(=O)N1CCOC[C@@H]1C(=O)NCCc1cc2c(-c3cnn4ncccc34)ccnc2[nH]1]

Starting from (4-(pyrazolo[1,5-b]pyridazin-3-yl)-1H-pyrrolo[2,3-b]pyridin-2-yl)methanamine (Example 196) and (R)-4-acryloylmorpholine-3-carboxylic acid (Intermediate 36) using DIPEA instead of Et$_3$N.

LCMS (Method 1): Rt 2.17 min, m/z 446.4 [MH$^+$].

$^1$H NMR (400 MHz, d$_6$-DMSO): 3.02-2.86 (2.5H, m), 3.58-3.41 (3.5H, m), 3.85-3.66 (1.5H, m), 4.13-3.99 (0.5H, m), 4.32-4.17 (1H, m), 4.49-4.42 (0.4H, m), 4.79-4.69 (0.6H, m), 5.48-5.39 (0.4H, m), 5.74-5.65 (0.6H, m), 6.04-5.94 (0.4H, m), 6.18-6.08 (0.6H, m), 6.51-6.34 (1.4H, m), 6.80 (0.6H, dd, J=10.5, 16.4 Hz), 7.25 (1H, d, J=5.0 Hz), 7.34 (1H, dd, J=4.5, 9.1 Hz), 8.16-8.04 (1H, m), 8.19 (1H, d, J=5.0 Hz), 8.50-8.42 (1H, m), 8.63-8.53 (2H, m), 11.67 (1H, s). 1H obscured by water.

Example 64: (1R,3R)-3-Acrylamido-N-(2-(4-(pyrazolo[1,5-b]pyridazin-3-yl)-1H-pyrrolo[2,3-b]pyridin-2-yl)ethyl)cyclopentane-1-carboxamide

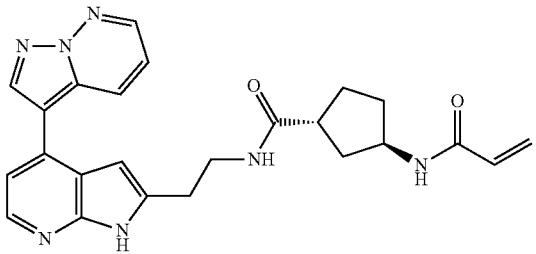 [SMILES: C=CC(=O)N[C@@H]1CC[C@@H](C(=O)NCCc2cc3c(-c4cnn5ncccc45)ccnc3[nH]2)C1]

Starting from (4-(pyrazolo[1,5-b]pyridazin-3-yl)-1H-pyrrolo[2,3-b]pyridin-2-yl)methanamine (Example 196) and (1R,3R)-3-acrylamidocyclopentane-1-carboxylic acid (Intermediate 34) using DIPEA instead of Et$_3$N.

LCMS (Method 1): Rt 2.34 min, m/z 444.4 [MH$^+$].

$^1$H NMR (400 MHz, d$_6$-DMSO): 1.46-1.33 (1H, m), 1.67-1.54 (2H, m), 1.96-1.77 (3H, m), 2.76-2.65 (1H, m), 2.91 (2H, t, J=6.9 Hz), 3.52-3.39 (2H, m), 4.19-4.08 (1H, m), 5.54 (1H, dd, J=2.4, 10.0 Hz), 6.05 (1H, dd, J=2.3, 17.1 Hz), 6.18 (1H, dd, J=10.0, 17.1 Hz), 6.42-6.36 (1H, m), 7.25 (1H, d, J=4.9 Hz), 7.34 (1H, dd, J=4.5, 9.1 Hz), 7.93 (1H, t, J=5.7 Hz), 8.05-7.98 (1H, m), 8.19 (1H, d, J=5.0 Hz), 8.46 (1H, dd, J=1.9, 9.1 Hz), 8.60-8.53 (2H, m), 11.67 (1H, s).

Example 65: N-(5-(3-(4-(Pyrazolo[1,5-b]pyridazin-3-yl)-1H-pyrrolo[2,3-b]pyridin-2-yl)pyrrolidine-1-carbonyl)pyridin-3-yl)acrylamide

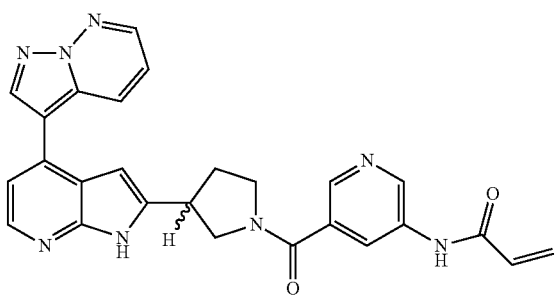 [SMILES: C=CC(=O)Nc1cncc(C(=O)N2CCC(c3cc4c(-c5cnn6ncccc56)ccnc4[nH]3)C2)c1]

Starting from 3-(2-(pyrrolidin-3-yl)-1H-pyrrolo[2,3-b]pyridin-4-yl)pyrazolo[1,5-b]pyridazine (Example 125) and 5-acrylamidonicotinic acid (Intermediate 38) using DIPEA instead of Et$_3$N.

LCMS (Method 1): Rt 2.54 min, m/z 479.4 [MH$^+$].

$^1$H NMR (400 MHz, d$_6$-DMSO): 2.48-2.12 (2H, m), 3.80-3.58 (4H, m), 4.13-3.88 (1H, m), 5.87-5.80 (1H, m), 6.36-6.26 (1H, m), 6.50-6.39 (1.6H, m), 6.57-6.53 (0.4H, m), 7.37-7.24 (2H, m), 8.26-8.19 (1H, m), 8.36-8.31 (1H, m), 8.51-8.41 (2H, m), 8.58-8.54 (1H, m), 8.59 (0.6H, s), 8.64 (0.4H, s), 8.85-8.80 (1H, m), 10.53 (1H, s), 11.76 (0.5H, s), 11.86 (0.5H, s).

Example 66: (E)-4-(Dimethylamino)-1-(4-(4-(4-(pyrazolo[1,5-b]pyridazin-3-yl)-1H-pyrrolo[2,3-b]pyridin-2-yl)piperidine-1-carbonyl)piperidin-1-yl)but-2-en-1-one

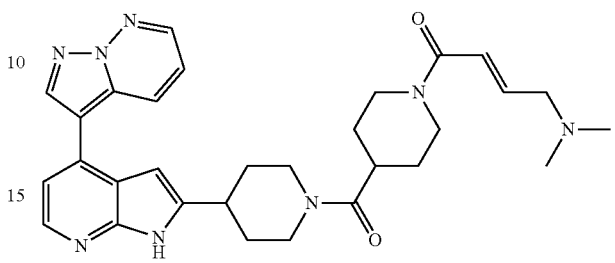

Starting from 3-(2-(piperidin-4-yl)-1H-pyrrolo[2,3-b]pyridine-4-yl)pyrazolo[1,5-b]pyridazine (Example 102) and lithium (E)-1-(4-(dimethylamino)but-2-enoyl)piperidine-4-carboxylate (Intermediate 108) using DIPEA instead of Et$_3$N.

LCMS (Method 1): Rt 2.17 min, m/z 541.4 [MH$^+$].

$^1$H NMR (400 MHz, d$_6$-DMSO): 1.78-1.27 (6H, m), 2.13-1.95 (2H, m), 2.15 (6H, s), 2.82-2.61 (2H, m), 3.26-2.92 (6H, m), 4.19-3.98 (2H, m), 4.56-4.33 (2H, m), 6.41-6.37 (1H, m), 6.63-6.52 (2H, m), 7.26 (1H, d, J=5.1 Hz), 7.34 (1H, dd, J=4.4, 9.1 Hz), 8.21 (1H, d, J=5.1 Hz), 8.45 (1H, dd, J=1.9, 9.1 Hz), 8.57 (1H, dd, J=1.8, 4.5 Hz), 8.59 (1H, s), 11.76-11.68 (1H, m).

Example 67: (R,E)-4-(Dimethylamino)-1-(3-(4-(4-(pyrazolo[1,5-b]pyridazin-3-yl)-1H-pyrrolo[2,3-b]pyridin-2-yl)piperidine-1-carbonyl)pyrrolidin-1-yl)but-2-en-1-one

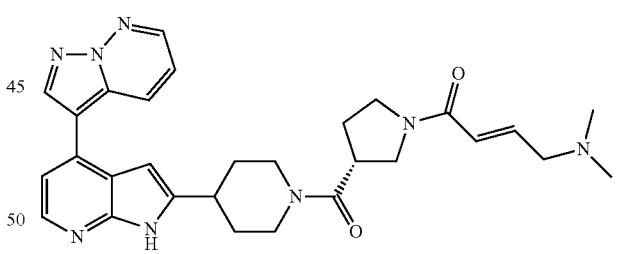

Starting from 3-(2-(piperidin-4-yl)-1H-pyrrolo[2,3-b]pyridine-4-yl)pyrazolo[1,5-b]pyridazine (Example 102) and lithium (R,E)-1-(4-(dimethylamino)but-2-enoyl)pyrrolidine-3-carboxylate (Intermediate 109) using DIPEA instead of Et$_3$N.

LCMS (Method 1): Rt 2.13 min, m/z 527.4 [MH$^+$].

$^1$H NMR (400 MHz, d$_6$-DMSO): 2.23-1.50 (12H, m), 2.82-2.64 (1H, m), 3.80-2.96 (9H, m), 4.17-4.06 (1H, m), 4.56-4.45 (1H, m), 6.43-6.31 (2H, m), 6.66-6.54 (1H, m), 7.26 (1H, d, J=5.0 Hz), 7.34 (1H, dd, J=4.4, 9.0 Hz), 8.21 (1H, d, J=5.0 Hz), 8.48-8.42 (1H, m), 8.58-8.54 (1H, m), 8.59 (1H, s), 11.72 (1H, s).

Example 68: (S,E)-4-(Dimethylamino)-N-(5-(3-(4-(pyrazolo[1,5-b]pyridazin-3-yl)-1H-pyrrolo[2,3-b]pyridin-2-yl)pyrrolidine-1-carbonyl)pyridin-3-yl)but-2-enamide

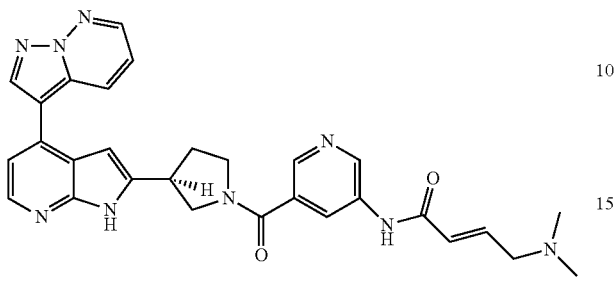

Starting from 3-(2-(pyrrolidin-3-yl)-1H-pyrrolo[2,3-b]pyridin-4-yl)pyrazolo[1,5-b]pyridazine (Example 125) and lithium (E)-5-(4-(dimethylamino)but-2-enamido)nicotinate (Intermediate 107) using DIPEA instead of Et$_3$N.

LCMS (Method 1): Rt 2.09 min, m/z 536.4.

$^1$H NMR (400 MHz, d$_6$-DMSO): 2.20-2.15 (6H, m), 2.47-2.20 (2H, m), 3.11-3.01 (2H, m), 3.79-3.56 (4H, m), 4.10-3.87 (1H, m), 6.32-6.23 (1H, m), 6.56-6.45 (1H, m), 6.83-6.73 (1H, m), 7.37-7.24 (2H, m), 8.26-8.19 (1H, m), 8.34-8.30 (1H, m), 8.51-8.41 (2H, m), 8.58-8.54 (1H, m), 8.59 (0.5H, s), 8.64 (0.5H, s), 8.84-8.79 (1H, m), 10.48-10.39 (1H, m), 11.91-11.70 (1H, m).

Example 69: (E)-4-(Dimethylamino)-1-(4-(2-oxo-2-(3-(4-(pyrazolo[1,5-b]pyridazin-3-yl)-1H-pyrrolo[2,3-b]pyridin-2-yl)pyrrolidin-1-yl)ethyl)piperidin-1-yl)but-2-en-1-one

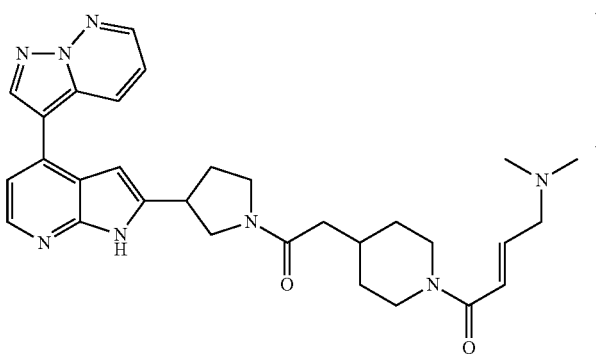

Starting from 3-(2-(pyrrolidin-3-yl)-1H-pyrrolo[2,3-b]pyridin-4-yl)pyrazolo[1,5-b]pyridazine (Example 125) lithium (E)-2-(1-(4-(dimethylamino)but-2-enoyl)piperidin-4-yl)acetate (Intermediate 110) using DIPEA instead of Et$_3$N.

LCMS (Method 2): Rt 2.01 min, m/z 541.3 [MH$^+$].

$^1$H NMR (400 MHz, d$_6$-DMSO): 1.17-0.94 (2H, m), 1.80-1.63 (2H, m), 2.04-1.91 (1H, m), 2.16-2.07 (6H, m), 2.44-2.16 (4H, m), 2.65-2.54 (1H, m), 3.10-2.91 (3H, m), 3.70-3.42 (4H, m), 4.08-3.80 (2H, m), 4.43-4.28 (1H, m), 6.60-6.42 (3H, m), 7.30-7.25 (1H, m), 7.34 (1H, dd, J=4.4, 9.1 Hz), 8.25-8.20 (1H, m), 8.49-8.43 (1H, m), 8.58-8.55 (1H, m), 8.60 (1H, s), 11.81 (1H, s).

Example 70: (2R)-2-Chloro-1-((2R)-2-(3-(4-(pyrazolo[1,5-b]pyridazin-3-yl)-1H-pyrrolo[2,3-b]pyridin-2-yl)pyrrolidine-1-carbonyl)pyrrolidin-1-yl)propan-1-one

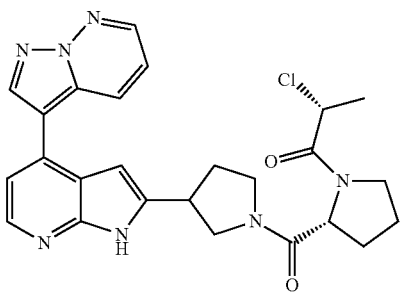 [SMILES: C[C@@H](Cl)C(=O)N1CCC[C@@H]1C(=O)N1CCC(c2cc3c(-c4cnn5ncccc45)ccnc3[nH]2)C1]

Starting from 3-(2-(pyrrolidin-3-yl)-1H-pyrrolo[2,3-b]pyridin-4-yl)pyrazolo[1,5-b]pyridazine (Example 125) and lithium ((R)-2-chloropropanoyl)-D-prolinate (Intermediate 113) using DIPEA instead of Et$_3$N.

LCMS (Method 1): Rt 2.89 min, m/z 492.1 [MH$^+$].

$^1$H NMR (400 MHz, d$_6$-DMSO): 1.55-1.38 (3H, m), 2.49-1.67 (6H, m), 3.78-3.36 (5.5H, m), 4.00-3.81 (1.5H, m), 4.68-4.49 (1H, m), 4.98-4.84 (1H, m), 6.64-6.42 (1H, m), 7.31-7.25 (1H, m), 7.34 (1H, dd, J=4.4, 9.1 Hz), 8.26-8.20 (1H, m), 8.51-8.43 (1H, m), 8.62-8.54 (1.6H, m), 8.67 (0.4H, s), 11.89-11.75 (1H, m).

Example 71: (E)-4-(Dimethylamino)-1-((3R)-3-(2-oxo-2-(3-(4-(pyrazolo[1,5-b]pyridazin-3-yl)-1H-pyrrolo[2,3-b]pyridin-2-yl)pyrrolidin-1-yl)ethoxy)pyrrolidin-1-yl)but-2-en-1-one

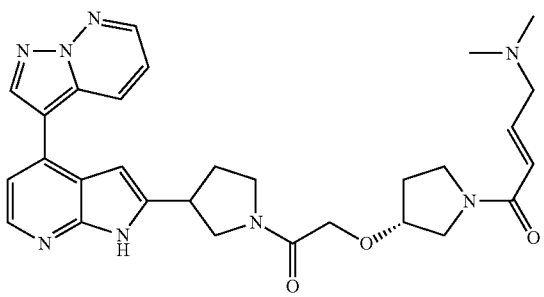 [SMILES: CN(C)C/C=C/C(=O)N1CC[C@@H](OCC(=O)N2CCC(c3cc4c(-c5cnn6ncccc56)ccnc4[nH]3)C2)C1]

Starting from 3-(2-(pyrrolidin-3-yl)-1H-pyrrolo[2,3-b]pyridin-4-yl)pyrazolo[1,5-b]pyridazine (Example 125) and lithium (R,E)-2-((1-(4-(dimethylamino)but-2-enoyl)pyrrolidin-3-yl)oxy)acetate (Intermediate 111) using DIPEA instead of Et$_3$N.

LCMS (Method 1): Rt 2.06 min, m/z 543.3 [MH$^+$].

$^1$H NMR (400 MHz, d$_6$-DMSO): 2.45-1.77 (10H, m), 3.05-2.92 (2.5H, m), 3.69-3.42 (7H, m), 3.94-3.83 (1H, m), 4.18-4.09 (2.5H, m), 4.26-4.19 (0.5H, m), 6.39-6.26 (1H, m), 6.51-6.44 (1H, m), 6.66-6.53 (1H, m), 7.30-7.25 (1H, m), 7.37-7.31 (1H, m), 8.25-8.21 (1H, m), 8.48-8.43 (1H, m), 8.59-8.55 (1H, m), 8.62-8.59 (1H, m), 11.82 (1H, s). 0.5H obscured by water.

Example 72: (E)-4-(Dimethylamino)-1-((3R)-3-(3-(4-(pyrazolo[1,5-b]pyridazin-3-yl)-1H-pyrrolo[2,3-b]pyridin-2-yl)pyrrolidine-1-carbonyl)piperidin-1-yl)but-2-en-1-one

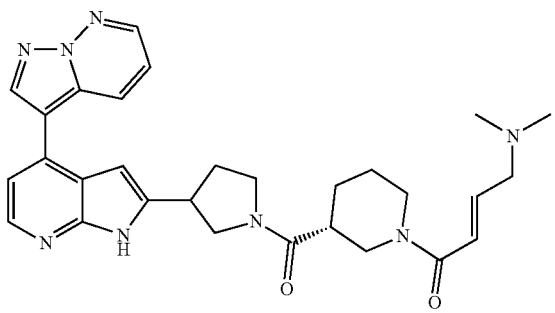 [SMILES: CN(C)C/C=C/C(=O)N1CCC[C@@H](C(=O)N2CCC(c3cc4c(-c5cnn6ncccc56)ccnc4[nH]3)C2)C1]

Starting from 3-(2-(pyrrolidin-3-yl)-1H-pyrrolo[2,3-b]pyridin-4-yl)pyrazolo[1,5-b]pyridazine (Example 125) and lithium (R,E)-1-(4-(dimethylamino)but-2-enoyl)piperidine-3-carboxylate (Intermediate 112) using DIPEA instead of Et$_3$N.

LCMS (Method 1): Rt 2.17 min, m/z 527.3.

$^1$H NMR (400 MHz, d6-DMSO): 4.64-1.07 (24H, m), 6.69-6.44 (3H, m), 7.30-7.25 (1H, m), 7.38-7.31 (1H, m), 8.23 (1H, d, J=5.0 Hz), 8.50-8.42 (1H, m), 8.64-8.54 (2H, m), 11.82 (1H, s).

Example 73: (S)-1-Propionyl-N-(2-(4-(pyrazolo[1,5-b]pyridazin-3-yl)-1H-pyrrolo[2,3-b]pyridin-2-yl)ethyl)pyrrolidine-2-carboxamide

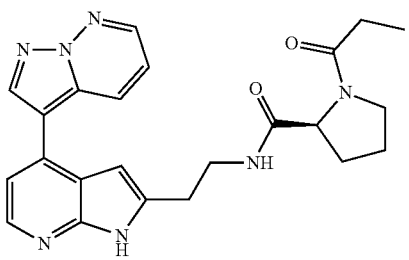 [SMILES: CCC(=O)N1CCC[C@H]1C(=O)NCCc1cc2c(-c3cnn4ncccc34)ccnc2[nH]1]

EDC.HCl (107 mg, 0.269 mmol) was added to a solution of 2-(4-(pyrazolo[1,5-b]pyridazin-3-yl)-1H-pyrrolo[2,3-b]pyridin-2-yl)ethan-1-amine (Example 30, 208 mg, 0.0.75 mmol), propionyl-L-proline (46 mg, 0.269 mmol) TEA (0.113 mL, 0.81 mmol) and HOBt (3.5 mg, 0.0259 mmol) in DMF (2.0 mL) and stirred at r.t. for 12 h. The mixture was diluted with water and extracted with CHCl$_3$. The combined organic layers were washed with a saturated aqueous solution of Na$_2$CO$_3$ (25 mL), and brine (25 mL), dried (MgSO$_4$) and concentrated in vacuo. The residue was purified by FCC eluting with 4-10% methanol in DCM to give the title compound (77 mg, 83%) as a yellow solid.

LCMS (Method 1): Rt 2.27 min, m/z 432.4 [MH$^+$].

$^1$H NMR (400 MHz, d$_6$-DMSO): 0.65 (1H, t, J=7.4 Hz), 0.91 (2H, t, J=7.4 Hz), 2.13-1.58 (5H, m), 2.27-2.18 (1H, m), 3.00-2.84 (2H, m), 3.57-3.19 (4H, m), 4.23-4.17 (1H, m), 6.44-6.37 (1H, m), 7.27-7.22 (1H, m), 7.37-7.31 (1H, m), 7.90 (0.6H, t, J=5.7 Hz), 8.14 (0.4H, t, J=5.6 Hz), 8.19 (1H, d, J=5.0 Hz), 8.50-8.43 (1H, m), 8.59-8.54 (1.4H, m), 8.61 (0.6H, s), 11.69-11.57 (1H, m).

By proceeding in a similar manner to Example 73, the following compounds were prepared:

Example 75: 1-Acryloyl-N-(2-(4-(pyrazolo[1,5-b]pyridazin-3-yl)-1H-pyrrolo[2,3-b]pyridin-2-yl)ethyl)piperidine-3-carboxamide

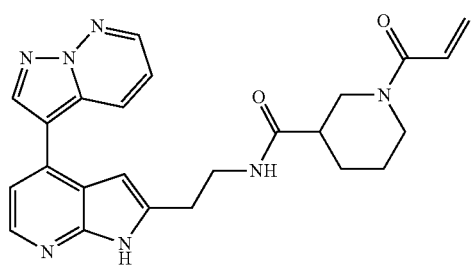 [SMILES: C=CC(=O)N1CCCC(C(=O)NCCc2cc3c(-c4cnn5ncccc45)ccnc3[nH]2)C1]

Starting from 2-(4-(pyrazolo[1,5-b]pyridazin-3-yl)-1H-pyrrolo[2,3-b]pyridin-2-yl)ethan-1-amine (Example 30) and 1-acryloylpiperidine-3-carboxylic acid.

LCMS (Method 1): Rt 2.29 min, m/z 444.4 [MH$^+$].

$^1$H NMR (400 MHz, d$_6$-DMSO): 1.21-1.28 (1H, m), 1.55-1.67 (2H, m), 1.73-1.81 (1H, m), 2.16-2.25 (1H, m), 2.62-2.71 (1H, m), 2.91 (2H, t, J=6.9 Hz), 2.97 (0.5H, t, J=12.3 Hz), 3.10 (0.5H, t, J=12.1 Hz), 3.41-3.49 (2H, m), 3.87 (0.5H, d, J=13.1 Hz), 3.96 (0.5H, d, J=13.1 Hz), 4.20 (0.5H, d, J=11.7 Hz), 4.37 (0.5H, d, J=12.2 Hz), 5.52 (0.5H, d, J=10.7 Hz), 5.63 (0.5H, d, J=10.8 Hz), 5.98-6.08 (1H, m), 6.40 (1H, s), 6.64-6.82 (1H, m), 7.25 (1H, d, J=4.8 Hz), 7.33 (1H, dd, J=4.4, 9.0 Hz), 8.01-8.08 (1H, m), 8.20 (1H, d, J=4.9 Hz), 8.43-8.48 (1H, m), 8.55-8.58 (2H, m), 11.67 (1H, s).

Example 76: 4-Acrylamido-N-(2-(4-(pyrazolo[1,5-b]pyridazin-3-yl)-1H-pyrrolo[2,3-b]pyridin-2-yl)ethyl)benzamide

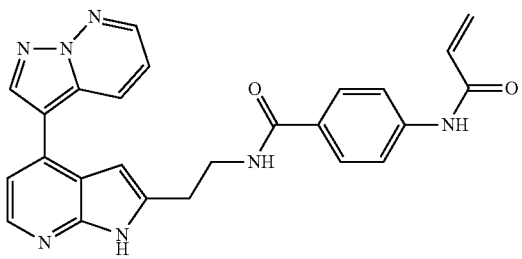 [SMILES: C=CC(=O)Nc1ccc(C(=O)NCCc2cc3c(-c4cnn5ncccc45)ccnc3[nH]2)cc1]

Starting from 2-(4-(pyrazolo[1,5-b]pyridazin-3-yl)-1H-pyrrolo[2,3-b]pyridin-2-yl)ethan-1-amine (Example 30) and 4-acrylamidobenzoic acid.

LCMS (Method 1): Rt 2.46 min, m/z 452.3 [MH$^+$].

$^1$H NMR (400 MHz, d$_6$-DMSO): 3.05 (2H, t, J=7.0 Hz), 3.67 (2H, q, J=6.5 Hz), 5.79 (1H, dd, J=2.0, 10.1 Hz), 6.28 (1H, dd, J=2.0, 17.0 Hz), 6.41-6.49 (2H, m), 7.24-7.28 (2H, m), 7.72 (2H, d, J=8.8 Hz), 7.81 (2H, d, J=8.8 Hz), 8.20 (1H, d, J=5.0 Hz), 8.42 (1H, dd, J=1.8, 9.1 Hz), 8.53-8.56 (3H, m), 10.34 (1H, s), 11.73 (1H, s).

Example 77: 1-Acryloyl-N-(2-(4-(pyrazolo[1,5-b]pyridazin-3-yl)-1H-pyrrolo[2,3-b]pyridin-2-yl)ethyl)piperidine-4-carboxamide

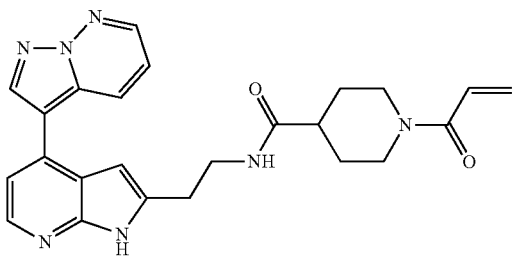 [SMILES: C=CC(=O)N1CCC(C(=O)NCCc2cc3c(-c4cnn5ncccc45)ccnc3[nH]2)CC1]

Starting from 2-(4-(pyrazolo[1,5-b]pyridazin-3-yl)-1H-pyrrolo[2,3-b]pyridin-2-yl)ethan-1-amine (Example 30) and 1-acryloylpiperidine-4-carboxylic acid (Intermediate 22).

LCMS (Method 1): Rt 2.20 min, m/z 444.4 [MH$^+$].

$^1$H NMR (400 MHz, d$_6$-DMSO): 1.35-1.45 (2H, m), 1.65 (2H, dd, J=2.8, 13.1 Hz), 2.35 (1H, tdd, J=3.8, 11.4, 11.4 Hz), 2.63 (1H, t, J=12.1 Hz), 2.90 (2H, t, J=6.9 Hz), 3.01 (1H, t, J=12.5 Hz), 3.44 (2H, q, J=6.5 Hz), 3.97 (1H, d, J=13.3 Hz), 4.32 (1H, d, J=12.3 Hz), 5.64 (1H, dd, J=2.4, 10.5 Hz), 6.06 (1H, dd, J=2.4, 16.7 Hz), 6.39 (1H, d, J=1.8 Hz), 6.75 (1H, dd, J=10.5, 16.7 Hz), 7.24-7.26 (1H, m), 7.34 (1H, dd, J=4.5, 9.1 Hz), 7.95 (1H, t, J=5.6 Hz), 8.19 (1H, d, J=5.0 Hz), 8.46 (1H, dd, J=1.9, 9.1 Hz), 8.56-8.58 (2H, m), 11.65 (1H, s).

Example 78: (S)-1-(2-Hydroxyacetyl)-N-(2-(4-(pyrazolo[1,5-b]pyridazin-3-yl)-1H-pyrrolo[2,3-b]pyridin-2-yl)ethyl)pyrrolidine-2-carboxamide

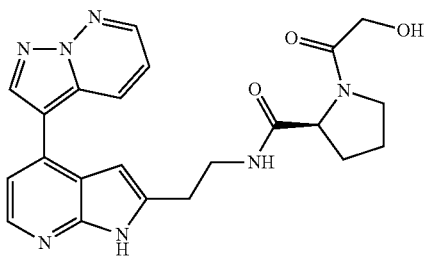 [SMILES: O=C(NCCc1cc2c(-c3cnn4ncccc34)ccnc2[nH]1)[C@@H]1CCCN1C(=O)CO]

Starting from 2-(4-(pyrazolo[1,5-b]pyridazin-3-yl)-1H-pyrrolo[2,3-b]pyridin-2-yl)ethan-1-amine (Example 30) and (2-chloroacetyl)-L-proline hydrolysis of the chloroacetyl group occurring during the reaction.

LCMS (Method 1): Rt 2.03 min, m/z 434.3 [MH$^+$].

$^1$H NMR (400 MHz, d$_6$-DMSO): 1.86-1.57 (3H, m), 2.13-1.89 (1H, m), 2.98-2.86 (2H, m), 3.55-3.26 (4H, m), 3.65-3.58 (1H, m), 3.95-3.89 (1H, m), 4.04 (1H, s), 4.28-4.21 (1H, m), 6.51-6.45 (1H, m), 7.34-7.29 (1H, m), 7.40-7.34 (1H, m), 8.06-8.00 (0.7H, m), 8.25-8.17 (1.3H, m), 8.52-8.45 (1H, m), 8.58 (1H, dd, J=1.8, 4.4 Hz), 8.61 (0.3H, s), 8.63 (0.7H, s), 11.71 (0.7H, s), 11.84 (0.3H, s).

Example 79: (R)-1-(2-Hydroxyacetyl)-N-(2-(4-(pyrazolo[1,5-b]pyridazin-3-yl)-1H-pyrrolo[2,3-b]pyridin-2-yl)ethyl)pyrrolidine-2-carboxamide

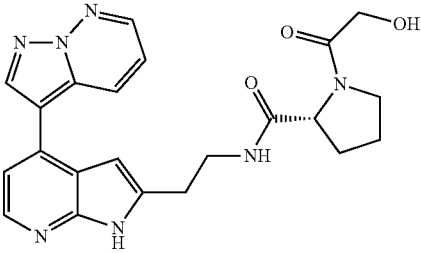 [SMILES: O=C(NCCc1cc2c(-c3cnn4ncccc34)ccnc2[nH]1)[C@H]1CCCN1C(=O)CO]

Starting from 2-(4-(pyrazolo[1,5-b]pyridazin-3-yl)-1H-pyrrolo[2,3-b]pyridin-2-yl)ethan-1-amine (Example 30) and (2-chloroacetyl)-D-proline (which can be prepared as described in GB1150851), hydrolysis of the chloroacetyl group occurring during the reaction.

LCMS (Method 1): Rt 2.03 min, m/z 434.3 [MH$^+$].

$^1$H NMR (400 MHz, d$_6$-DMSO): 2.13-1.56 (4H, m), 2.98-2.87 (2H, m), 3.55-3.28 (4H, m), 3.66-3.58 (1H, m), 3.96-3.89 (1H, m), 4.04 (1H, s), 4.28-4.20 (1H, m), 6.49-6.43 (1H, m), 7.33-7.29 (1H, m), 7.39-7.33 (1H, m), 8.06-8.00 (0.7H, m), 8.24-8.17 (1.3H, m), 8.51-8.45 (1H, m), 8.64-8.56 (2H, m), 11.67 (0.7H, s), 11.81 (0.3H, s).

Example 80: 1-Acryloyl-N-((4-(pyrazolo[1,5-b]pyridazin-3-yl)-1H-pyrrolo[2,3-b]pyridin-2-yl)methyl)piperidine-4-carboxamide

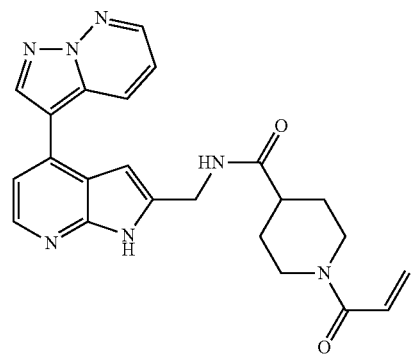 [SMILES: C=CC(=O)N1CCC(C(=O)NCc2cc3c(-c4cnn5ncccc45)ccnc3[nH]2)CC1]

Starting from (4-(pyrazolo[1,5-b]pyridazin-3-yl)-1H-pyrrolo[2,3-b]pyridin-2-yl)methanamine (Example 196) and 1-acryloylpiperidine-4-carboxylic acid.

LCMS (Method 1): Rt 2.23 min, m/z 430.4 [MH$^+$].

$^1$H NMR (400 MHz, d$_6$-DMSO): 1.40-1.53 (2H, m), 1.78 (2H, dd, J=2.3, 12.9 Hz), 2.69 (1H, t, J=12.3 Hz), 3.06 (1H, t, J=12.4 Hz), 4.06 (1H, d, J=13.0 Hz), 4.40 (1H, d, J=12.9 Hz), 4.46 (2H, d, J=5.4 Hz), 5.66 (1H, dd, J=2.4, 10.5 Hz), 6.08 (1H, dd, J=2.4, 16.7 Hz), 6.44 (1H, d, J=1.8 Hz), 6.80 (1H, dd, J=10.5, 16.7 Hz), 7.27 (1H, d, J=4.9 Hz), 7.34 (1H, dd, J=4.5, 9.0 Hz), 8.23 (1H, d, J=5.0 Hz), 8.34 (1H, t, J=5.5 Hz), 8.43 (1H, dd, J=1.8, 9.1 Hz), 8.53 (1H, s), 8.58 (1H, dd, J=1.8, 4.4 Hz), 11.69 (1H, s) plus one proton obscured by solvent.

Example 81: 4-(3-Ethoxypropanamido)-N-(2-(4-(pyrazolo[1,5-b]pyridazin-3-yl)-1H-pyrrolo[2,3-b]pyridin-2-yl)ethyl)benzamide

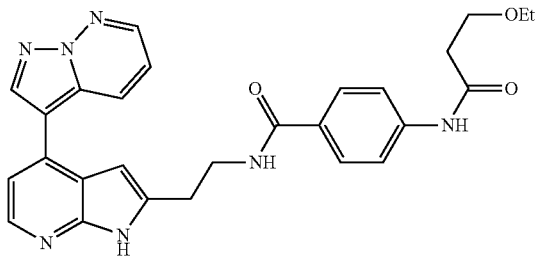 [SMILES: CCOCCC(=O)Nc1ccc(C(=O)NCCc2cc3c(-c4cnn5ncccc45)ccnc3[nH]2)cc1]

3M aqueous NaOH (6 mL) was added to a solution of 4-acrylamido-N-(2-(1-(phenylsulfonyl)-4-(pyrazolo[1,5-b]pyridazin-3-yl)-1H-pyrrolo[2,3-b]pyridin-2-yl)ethyl)benzamide (Intermediate 40, 187 mg, 0.316 mmol) in dioxane (6 mL) and EtOH (6 mL) The reaction mixture was heated at 30° C. for 12 h then cooled to r.t. and treated with 6M HCl until the pH=7. The mixture was concentrated in vacuo and the residue was purified by FCC eluting with 2-10% MeOH in DCM to give the title compound (99 mg, 63%) as a yellow solid.

LCMS (Method 1): Rt 2.60 min, m/z 498.3 [MH+].

$^1$H NMR (400 MHz, d$_6$-DMSO): 1.08 (3H, t, J=7.1 Hz), 2.56 (2H, t, J=6.2 Hz), 3.04 (2H, t, J=7.0 Hz), 3.43 (2H, q, J=6.9 Hz), 3.66 (4H, t, J=6.3 Hz), 6.42 (1H, d, J=1.7 Hz), 7.25 (2H, dd, J=4.7, 8.8 Hz), 7.65 (2H, d, J=8.9 Hz), 7.79 (2H, d, J=8.5 Hz), 8.19 (1H, d, J=5.0 Hz), 8.41 (1H, dd, J=1.8, 9.1 Hz), 8.50 (1H, t, J=5.6 Hz), 8.53-8.57 (2H, m), 10.14 (1H, s), 11.73 (1H, s).

Example 82: (S)—N-(2-(4-(Pyrazolo[1,5-b]pyridazin-3-yl)-1H-pyrrolo[2,3-b]pyridin-2-yl)ethyl)pyrrolidine-2-carboxamide

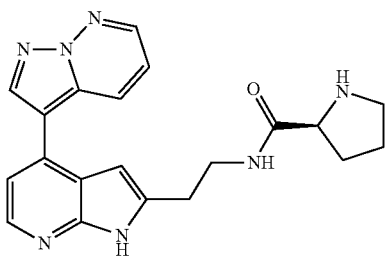 [SMILES: O=C(NCCc1cc2c(-c3cnn4ncccc34)ccnc2[nH]1)[C@@H]1CCCN1]

A solution of (S)—N-(2-(1-(phenylsulfonyl)-4-(pyrazolo[1,5-b]pyridazin-3-yl)-1H-pyrrolo[2,3-b]pyridin-2-yl)ethyl)pyrrolidine-2-carboxamide (Intermediate 46, 190 mg, 0.368 mmol) in dioxane (4 mL) and EtOH (2 mL) was treated with 3M aqueous NaOH (2 mL) and the resultant mixture was stirred at 50° C. for 6 hour. After cooling, the mixture was treated with 6M HCl until the pH=7, then concentrated in vacuo. The residue was purified by FCC eluting with 7.5-15% 2M ammonia in methanol in DCM to give the title compound (96 mg, 70%) as a yellow solid.

LCMS (Method 1): Rt 1.74 min, m/z 376.3 [MH+].

$^1$H NMR (400 MHz, d$_6$-DMSO): 1.63-1.37 (3H, m), 1.91-1.80 (1H, m), 2.80-2.59 (2H, m), 2.97-2.88 (2H, m), 3.56-3.39 (3H, m), 6.42-6.37 (1H, m), 7.25 (1H, d, J=5.0 Hz), 7.34 (1H, dd, J=4.4, 9.1 Hz), 8.05-7.98 (1H, m), 8.19 (1H, d, J=5.0 Hz), 8.45 (1H, dd, J=1.8, 9.1 Hz), 8.59-8.54 (2H, m), 11.66 (1H, s). Pyrrolidine NH not observed.

Example 83: (S)-1-(But-2-ynoyl)-N-(2-(4-(pyrazolo[1,5-b]pyridazin-3-yl)-1H-pyrrolo[2,3-b]pyridin-2-yl)ethyl)pyrrolidine-2-carboxamide

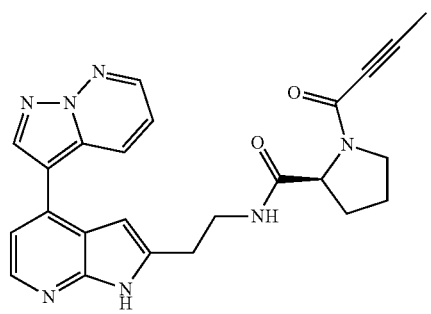 [SMILES: CC#CC(=O)N1CCC[C@H]1C(=O)NCCc1cc2c(-c3cnn4ncccc34)ccnc2[nH]1]

DCC (31 mg, 0.15 mmol) was added to a solution of but-2-ynoic acid (25 mg, 0.30 mmol) in MeCN (1 mL) and the mixture was stirred for 30 min. The precipitate was removed by filtration and the filtrate was added to a solution of (S)—N-(2-(4-(pyrazolo[1,5-b]pyridazin-3-yl)-1H-pyrrolo[2,3-b]pyridin-2-yl)ethyl)pyrrolidine-2-carboxamide (Example 82, 37 mg, 0.10 mmol) and TEA (0.060 mL, 0.40 mmol) in DMC (2.0 mL) and the resultant mixture was stirred at r.t. for 4 h. The reaction was diluted with a saturated aqueous solution of Na$_2$CO$_3$ and extracted with CHCl$_3$. The combined organic layers were washed with brine (20 mL), dried (MgSO$_4$) and concentrated in vacuo. The residue was purified by FCC eluting with 4-10% MeOH in DCM to give the title compound (22 mg, 50%) as a yellow solid.

LCMS (Method 2): Rt 2.32 min, m/z 442.1 [MH+].

$^1$H NMR (400 MHz, d$_6$-DMSO): 1.83-1.65 (4H, m), 2.20-1.96 (3H, m), 2.98-2.85 (2H, m), 3.64-3.35 (4H, m), 4.19 (0.6H, dd, J=3.6, 8.6 Hz), 4.41-4.36 (0.4H, m), 6.44-6.39 (1H, m), 7.27-7.22 (1H, m), 7.37-7.31 (1H, m), 8.10-8.01 (0.6H, m), 8.23-8.16 (1.4H, m), 8.50-8.44 (1H, m), 8.61-8.53 (2H, m), 11.71-11.56 (1H, m).

Example 84: (S,E)-1-(4-(Dimethylamino)but-2-enoyl)-N-(2-(4-(pyrazolo[1,5-b]pyridazin-3-yl)-1H-pyrrolo[2,3-b]pyridin-2-yl)ethyl)pyrrolidine-2-carboxamide

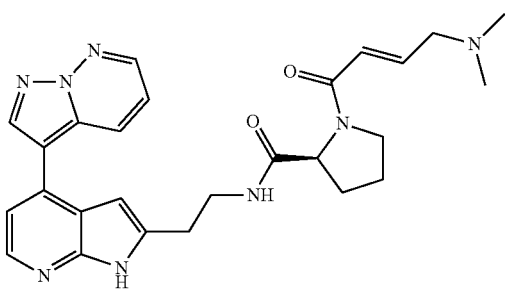 [SMILES: CN(C)C/C=C/C(=O)N1CCC[C@H]1C(=O)NCCc1cc2c(-c3cnn4ncccc34)ccnc2[nH]1]

HATU (125 mg, 0.33 mmol) was added to a solution of (2E)-4-(Dimethylamino)but-2-enoic acid hydrochloride (55 mg, 0.33 mmol) and TEA (0.092 mL, 0.66 mmol) in DCM (1.0 mL) and the mixture was stirred for 5 min The solution was then added to a solution of (S)—N-(2-(4-(pyrazolo[1,5-b]pyridazin-3-yl)-1H-pyrrolo[2,3-b]pyridin-2-yl)ethyl)pyrrolidine-2-carboxamide (Example 82, 82 mg, 0.22 mmol) in DCM (2.0 mL) and the mixture was stirred for 30 min. The reaction was quenched with a saturated aqueous solution of Na$_2$CO$_3$ and extracted with CHCl$_3$. The combined organic layers were washed with a saturated aqueous solution of Na$_2$CO$_3$ (20 mL), brine (20 mL), dried (Na$_2$SO$_4$) and concentrated in vacuo. The residue was purified by FCC on Biotage® SNAP KP-NH eluting with 0-4% MeOH in DCM to give the title compound (87 mg, 82%) as a yellow solid.

LCMS (Method 1): Rt 1.82 min, m/z 487.4 [MH$^+$].

$^1$H NMR (400 MHz, d$_6$-DMSO): 2.02-1.61 (6H, m), 2.13 (4H, s), 2.75-2.70 (0.6H, m), 2.95-2.87 (2H, m), 3.03-2.98 (1.4H, m), 3.66-3.34 (4H, m), 4.28 (0.6H, dd, J=3.3, 8.3 Hz), 4.36 (0.4H, dd, J=3.0, 8.6 Hz), 6.00-5.93 (0.4H, m), 6.39-6.32 (0.6H, m), 6.44-6.40 (1H, m), 6.55-6.46 (0.4H, m), 6.67-6.57 (0.6H, m), 7.27-7.23 (1H, m), 7.33 (1H, dd, J=4.4, 9.1 Hz), 8.04-7.96 (0.6H, m), 8.26-8.16 (1.4H, m), 8.50-8.43 (1H, m), 8.58-8.54 (1.4H, m), 8.61 (0.6H, s), 11.70-11.55 (1H, m).

By proceeding in a similar manner to Example 84, the following compounds were prepared:

Example 85: (S,E)-N-(2-(4-(pyrazolo[1,5-b]pyridazin-3-yl)-1H-pyrrolo[2,3-b]pyridin-2-yl)ethyl)-1-(4-(pyrrolidin-1-yl)but-2-enoyl)pyrrolidine-2-carboxamide

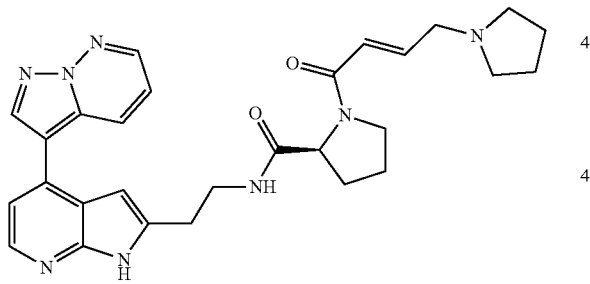

Starting from (S)—N-(2-(4-(pyrazolo[1,5-b]pyridazin-3-yl)-1H-pyrrolo[2,3-b]pyridin-2-yl)ethyl)pyrrolidine-2-carboxamide (Example 82) and (E)-4-(pyrrolidin-1-yl)but-2-enoic acid hydrochloride.

LCMS (Method 1): Rt 1.99 min, m/z 513.4 [MH$^+$].

$^1$H NMR (400 MHz, d$_6$-DMSO): 2.30-1.52 (10H, m), 2.46-2.38 (2H, m), 2.98-2.83 (2.8H, m), 3.20-3.14 (1.2H, m), 3.66-3.35 (4H, m), 4.38-4.24 (1H, m), 6.01-5.94 (0.4H, m), 6.39-6.32 (0.6H, m), 6.45-6.40 (1H, m), 6.71-6.50 (1H, m), 7.27-7.23 (1H, m), 7.34 (1H, dd, J=4.4, 9.1 Hz), 8.03-7.98 (0.6H, m), 8.21-8.17 (1H, m), 8.27-8.21 (0.4H, m), 8.51-8.43 (1H, m), 8.59-8.54 (1.4H, m), 8.62 (0.6H, s), 11.73-11.52 (1H, m).

Example 86: (S,E)-1-(4-Morpholinobut-2-enoyl)-N-(2-(4-(pyrazolo[1,5-b]pyridazin-3-yl)-1H-pyrrolo[2,3-b]pyridin-2-yl)ethyl)pyrrolidine-2-carboxamide

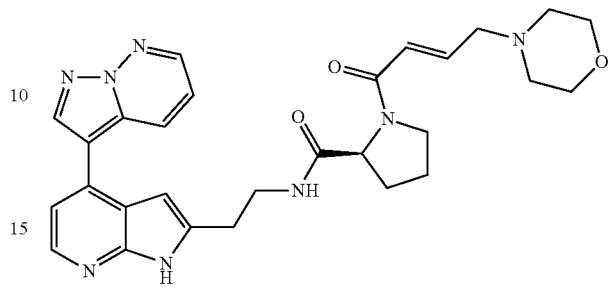

Starting from (S)—N-(2-(4-(pyrazolo[1,5-b]pyridazin-3-yl)-1H-pyrrolo[2,3-b]pyridin-2-yl)ethyl)pyrrolidine-2-carboxamide (Example 82) and (E)-4-morpholinobut-2-enoic acid hydrochloride.

LCMS (Method 1): Rt 1.96 min, m/z 529.5 [MH$^+$].

$^1$H NMR (400 MHz, d$_6$-DMSO): 2.43-1.60 (8H, m), 2.97-2.73 (3H, m), 3.07 (1H, dd, J=1.1, 6.2 Hz), 3.67-3.35 (8H, m), 4.28 (0.6H, dd, J=3.4, 8.4 Hz), 4.35 (0.4H, dd, J=2.9, 8.6 Hz), 6.03-5.94 (0.4H, m), 6.53-6.34 (2H, m), 6.66-6.57 (0.6H, m), 7.28-7.23 (1H, m), 7.34 (1H, dd, J=4.5, 9.1 Hz), 8.04-7.98 (0.6H, m), 8.25-8.16 (1.4H, m), 8.50-8.44 (1H, m), 8.59-8.54 (1.4H, m), 8.62 (0.6H, s), 11.72-11.54 (1H, m).

Example 87: (S,E)-1-(4-(Dimethylamino)but-2-enoyl)-N-(2-(4-(pyrazolo[1,5-b]pyridazin-3-yl)-1H-pyrrolo[2,3-b]pyridin-2-yl)ethyl)piperidine-2-carboxamide

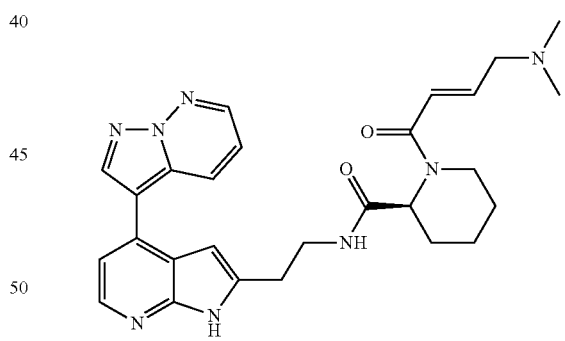

Starting from (S)—N-(2-(4-(pyrazolo[1,5-b]pyridazin-3-yl)-1H-pyrrolo[2,3-b]pyridin-2-yl)ethyl)piperidine-2-carboxamide (Example 90) and (2E)-4-(dimethylamino)but-2-enoic acid hydrochloride.

LCMS (Method 1): Rt 1.96 min, m/z 501.4 [MH$^+$].

$^1$H NMR (400 MHz, d$_6$-DMSO): 1.30-1.11 (3H, m), 1.45-1.37 (2H, m), 2.05-2.01 (0.7H, m), 2.19-2.16 (0.3H, m), 2.78 (4H, d, J=2.7 Hz), 3.00-2.95 (2H, m), 3.24-3.17 (1H, m), 3.55-3.48 (2H, m), 3.89-3.75 (3H, m), 4.56 (1H, s), 4.99 (1H, d, J=4.2 Hz), 6.59-6.43 (2H, m), 6.70 (0.3H, d, J=15.1 Hz), 6.90 (0.7H, d, J=15.0 Hz), 7.41-7.34 (2H, m), 8.01 (0.7H, t, J=5.4 Hz), 8.10 (0.3H, t, J=5.4 Hz), 8.25 (1H, d, J=5.2 Hz), 8.52-8.48 (1H, m), 8.65-8.58 (2H, m), 9.79-9.63 (1H, m), 11.95-11.90 (1H, m).

Example 88: (R,E)-1-(4-(Dimethylamino)but-2-enoyl)-N-(2-(4-(pyrazolo[1,5-b]pyridazin-3-yl)-1H-pyrrolo[2,3-b]pyridin-2-yl)ethyl)piperidine-2-carboxamide Formate Salt

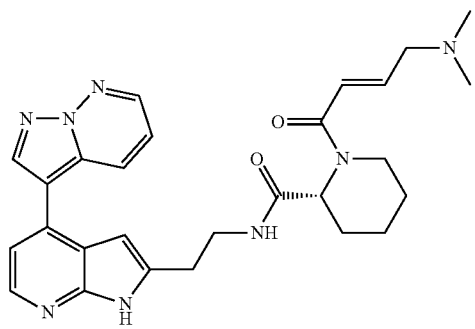 [SMILES: CN(C)C/C=C/C(=O)N1CCCC[C@@H]1C(=O)NCCc1cc2c(-c3cnn4ncccc34)ccnc2[nH]1]

Starting from (R)—N-(2-(4-(pyrazolo[1,5-b]pyridazin-3-yl)-1H-pyrrolo[2,3-b]pyridin-2-yl)ethyl)piperidine-2-carboxamide (Example 91) and (2E)-4-(Dimethylamino)but-2-enoic acid hydrochloride.

LCMS (Method 2): Rt 1.95 min, m/z 501.3 [MH$^+$].

$^1$H NMR (400 MHz, d$_6$-DMSO, 80° C.): 1.31-1.24 (2H, m), 1.46-1.40 (3H, m), 2.09-2.06 (1H, m), 2.14 (5H, s), 3.00-2.94 (4H, m), 3.53 (2H, q, J=6.5 Hz), 3.89 (1H, s), 4.85 (1H, s), 6.38 (2H, s), 6.55-6.50 (1H, m), 7.22 (1H, d, J=5.0 Hz), 7.31 (1H, dd, J=4.4, 9.1 Hz), 7.65 (1H, s), 8.16 (1H, s), 8.20 (1H, d, J=5.0 Hz), 8.41 (1H, dd, J=1.6, 9.1 Hz), 8.53-8.50 (2H, m), 11.40 (1H, s) some protons obscured by solvent.

Example 89: (S)-1-(phenylsulfonyl)-N-(2-(4-(pyrazolo[1,5-b]pyridazin-3-yl)-1H-pyrrolo[2,3-b]pyridin-2-yl)ethyl)pyrrolidine-2-carboxamide

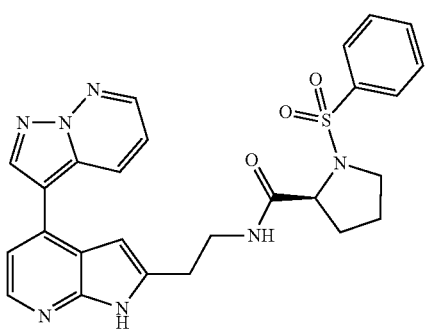 [SMILES: O=C(NCCc1cc2c(-c3cnn4ncccc34)ccnc2[nH]1)[C@@H]1CCCN1S(=O)(=O)c1ccccc1]

EDC.HCl (143 mg, 0.75 mmol) was added to a solution of 2-(1-(phenylsulfonyl)-4-(pyrazolo[1,5-b]pyridazin-3-yl)-1H-pyrrolo[2,3-b]pyridin-2-yl)ethan-1-amine (Intermediate 46, 209 mg, 0.75 mmol), (phenylsulfonyl)-L-proline (191 mg, 0.75 mmol) (which can be prepared as described in WO2012/168226) TEA (0.313 mL, 2.25 mmol) and HOBt (15 mg, 0.01 mmol) in DMF (2.5 mL) and the resultant mixture was stirred at r.t. for 12 h. The reaction was diluted with water and extracted with CHCl$_3$. The combined organic layers were washed with a saturated aqueous solution of Na$_2$CO$_3$ and brine, dried (MgSO$_4$) and concentrated in vacuo. The residue was dissolved in dioxane (4 mL) and EtOH (2 mL) and treated with 3M aqueous NaOH (2 mL).

The reaction mixture was stirred at 50° C. for 6 hour then cooled to r.t. and treated with 6M HCl until the pH=7. The mixture was concentrated in vacuo and the residue was purified by FCC eluting with 1-5% MeOH in DCM to give the title compound (136 mg, 52%) as a yellow solid.

LCMS (Method 1): Rt 2.82 min, m/z 516.4 [MH$^+$].

$^1$H NMR (400 MHz, d$_6$-DMSO): 1.43-1.31 (1H, m), 1.73-1.48 (3H, m), 2.94 (2H, t, J=6.9 Hz), 3.17-3.07 (1H, m), 3.42-3.34 (1H, m), 3.54-3.46 (2H, m), 3.98 (1H, dd, J=3.5, 8.3 Hz), 6.46-6.42 (1H, m), 7.25 (1H, d, J=5.0 Hz), 7.32 (1H, dd, J=4.4, 9.1 Hz), 7.64-7.56 (2H, m), 7.72-7.66 (1H, m), 7.84-7.78 (2H, m), 8.14-8.08 (1H, m), 8.20 (1H, d, J=5.0 Hz), 8.46 (1H, dd, J=1.9, 9.1 Hz), 8.55 (1H, dd, J=1.8, 4.4 Hz), 8.58 (1H, s), 11.70-11.61 (1H, m).

Example 90: (S)—N-(2-(4-(Pyrazolo[1,5-b]pyridazin-3-yl)-1H-pyrrolo[2,3-b]pyridin-2-yl)ethyl)piperidine-2-carboxamide

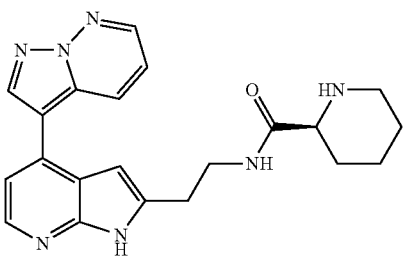 [SMILES: O=C(NCCc1cc2c(-c3cnn4ncccc34)ccnc2[nH]1)[C@@H]1CCCCN1]

A solution of (S)—N-(2-(1-(phenylsulfonyl)-4-(pyrazolo[1,5-b]pyridazin-3-yl)-1H-pyrrolo[2,3-b]pyridin-2-yl)ethyl)piperidine-2-carboxamide (Intermediate 49, 371 mg, 0.70 mmol) in dioxane (6 mL) and EtOH (4 mL) was treated with 3M aqueous NaOH (2 mL) and the mixture was stirred and heated at 50° C. for 2 hour. After cooling, the mixture was treated with 6M HCl until the pH=7 and concentrated in vacuo. The residue was purified by FCC eluting with 7.5-12.5% 2M ammonia in MeOH in DCM to give the title compound (146 mg, 54%) as a yellow solid.

LCMS (Method 4): Rt 2.21 min, m/z 390 [MH$^+$].

$^1$H NMR (400 MHz, CDCl$_3$) 1.39-1.27 (3H, m), 1.56-1.46 (1H, m), 1.78-1.67 (1H, m), 1.96-1.87 (1H, m), 1.99 (1H, s), 2.61-2.50 (1H, m), 2.95-2.86 (1H, m), 3.11 (2H, t, J=6.7 Hz), 3.21-3.14 (1H, m), 3.75-3.66 (2H, m), 6.36 (1H, s), 7.09 (1H, dd, J=9.1, 4.4 Hz), 7.16 (1H, d, J=5.0 Hz), 7.29 (1H, s), 8.20 (1H, dd, J 9.1, 1.9 Hz), 8.32 (1H, d, J=5.0 Hz), 8.40-8.35 (1H, m), 8.42 (1H, s), 11.78 (1H, s), By proceeding in a similar manner to Example 90, the following compounds were prepared:

Example 91: (R)—N-(2-(4-(Pyrazolo[1,5-b]pyridazin-3-yl)-1H-pyrrolo[2,3-b]pyridin-2-yl)ethyl)piperidine-2-carboxamide

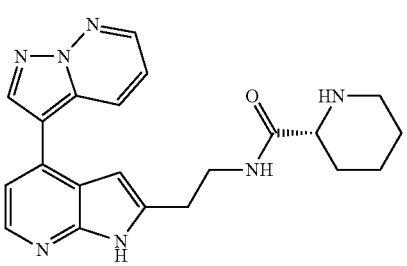 [SMILES: O=C(NCCc1cc2c(-c3cnn4ncccc34)ccnc2[nH]1)[C@H]1CCCCN1]

Starting from (R)—N-(2-(1-(phenylsulfonyl)-4-(pyrazolo[1,5-b]pyridazin-3-yl)-1H-pyrrolo[2,3-b]pyridin-2-yl)ethyl)piperidine-2-carboxamide (Intermediate 50).

LCMS (Method 4): Rt 2.21 min, m/z 390 [MH+].

1H NMR (400 MHz, CDCl3) 1.39-1.27 (3H, m), 1.78-1.67 (1H, m), 1.96-1.87 (1H, m), 1.99 (1H, s), 2.61-2.50 (1H, m), 2.95-2.86 (1H, m), 3.11 (2H, t, J=6.7 Hz), 3.21-3.14 (1H, m), 3.75-3.66 (2H, m), 6.36 (1H, s), 7.09 (1H, dd, J=9.1, 4.4 Hz), 7.16 (1H, d, J=5.0 Hz), 7.29 (1H, s), 8.20 (1H, dd, J=9.1, 1.9 Hz), 8.32 (1H, d, J=5.0 Hz), 8.40-8.35 (1H, m), 8.42 (1H, s), 11.78 (1H, s),

Example 92: (S)-1-Acryloyl-N-(2-(4-(pyrazolo[1,5-b]pyridazin-3-yl)-1H-pyrrolo[2,3-b]pyridin-2-yl)ethyl)piperidine-2-carboxamide

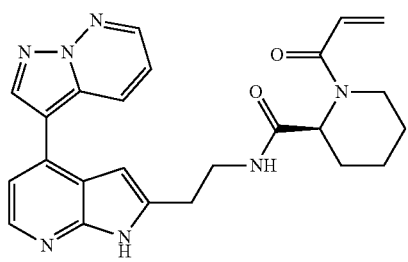 [SMILES: C=CC(=O)N1CCCC[C@H]1C(=O)NCCc1cc2c(-c3cnn4ncccc34)ccnc2[nH]1]

A solution of (S)—N-(2-(4-(pyrazolo[1,5-b]pyridazin-3-yl)-1H-pyrrolo[2,3-b]pyridin-2-yl)ethyl)piperidine-2-carboxamide (Example 92, 70 mg, 0.18 mmol) and TEA (0.100 mL, 0.72 mmol) in DCM (2.0 mL) at r.t. was treated with acryloyl chloride (0.023 mL, 0.27 mmol) and the mixture was stirred for 30 min. The reaction was quenched with a saturated aqueous solution of Na2CO3 and extracted with CHCl3. The combined organic layers were washed with a saturated aqueous solution of Na2CO3, brine, dried (Na2SO4) and concentrated in vacuo. The residue was purified by FCC eluting with 4-8% MeOH in DCM to give the title compound (15 mg, 19%) as a yellow solid.

LCMS (Method 1): Rt 2.46 min, m/z 444.4 [MH+].

1H NMR (400 MHz, d6-DMSO): 1.27-1.17 (2H, m), 1.39-1.33 (3H, m), 2.11-2.01 (1H, m), 3.00-2.90 (2H, m), 3.12 (1H, t, J=12.7 Hz), 3.53-3.47 (2H, m), 4.56 (0.3H, s), 5.01-4.96 (0.7H, m), 5.42 (0.3H, d, J=10.5 Hz), 5.62 (0.7H, dd, J=2.1, 10.6 Hz), 5.93 (0.3H, d, J=17.1 Hz), 6.04 (0.7H, dd, J=1.9, 16.7 Hz), 6.50-6.47 (1.3H, m), 6.75 (0.7H, dd, J=10.6, 16.6 Hz), 7.40-7.33 (2H, m), 7.92 (0.7H, t, J=5.1 Hz), 8.03-8.03 (0.3H, m), 8.24 (1H, d, J=5.0 Hz), 8.49 (1H, dd, J=1.8, 9.1 Hz), 8.65-8.58 (2H, m), 11.92 (1H, s) some protons obscured by solvent.

By proceeding in a similar manner to Example 92 the following compounds were prepared:

Example 93: (R)-1-Acryloyl-N-(2-(4-(pyrazolo[1,5-b]pyridazin-3-yl)-1H-pyrrolo[2,3-b]pyridin-2-yl)ethyl)piperidine-2-carboxamide

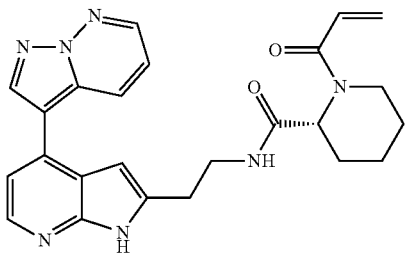 [SMILES: C=CC(=O)N1CCCC[C@@H]1C(=O)NCCc1cc2c(-c3cnn4ncccc34)ccnc2[nH]1]

Starting from (R)—N-(2-(4-(pyrazolo[1,5-b]pyridazin-3-yl)-1H-pyrrolo[2,3-b]pyridin-2-yl)ethyl)piperidine-2-carboxamide (Example 91) and acryloyl chloride.

LCMS (Method 1): Rt 2.45 min, m/z 444.4 [MH+].

1H NMR (400 MHz, d6-DMSO): 1.49-1.05 (5H, m), 2.15-1.96 (1H, m), 2.65-2.55 (0.3H, m), 3.00-2.88 (2H, m), 3.19-3.06 (0.7H, m), 3.56-3.42 (2H, m), 3.85-3.74 (0.7H, m), 4.27-4.16 (0.3H, m), 4.61-4.51 (0.3H, m), 5.03-4.94 (0.7H, m), 5.47-5.37 (0.3H, m), 5.61 (0.7H, dd, J=2.0, 10.5 Hz), 5.98-5.88 (0.3H, m), 6.04 (0.7H, dd, J=2.0, 16.6 Hz), 6.40-6.36 (1H, m), 6.56-6.44 (0.3H, m), 6.75 (0.7H, dd, J=10.5, 16.7 Hz), 7.24 (1H, d, J=5.0 Hz), 7.34 (1H, dd, J=4.4, 9.1 Hz), 7.95-7.86 (0.7H, m), 8.06-7.98 (0.3H, m), 8.19 (1H, d, J=5.0 Hz), 8.46 (1H, dd, J=1.8, 9.1 Hz), 8.60-8.54 (2H, m), 11.65 (1H, s).

Example 94: (S)-1-Acryloyl-N-(2-(4-(1-methyl-1H-pyrazol-4-yl)-1H-pyrrolo[2,3-b]pyridin-2-yl)ethyl)pyrrolidine-2-carboxamide

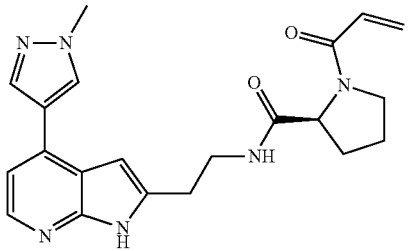 [SMILES: C=CC(=O)N1CCC[C@H]1C(=O)NCCc1cc2c(-c3cnn(C)c3)ccnc2[nH]1]

Starting from (S)—N-(2-(4-(1-methyl-1H-pyrazol-4-yl)-1H-pyrrolo[2,3-b]pyridin-2-yl)ethyl)pyrrolidine-2-carboxamide (Example 106) and acryloyl chloride.

LCMS (Method 1): Rt 2.03 min, m/z 393.4 [MH+].

1H NMR (400 MHz, d6-DMSO): 2.20-1.66 (4H, m), 2.97-2.82 (2H, m), 3.71-3.37 (4H, m), 3.95-3.89 (3H, m), 4.42-4.27 (1H, m), 5.42-5.36 (0.4H, m), 5.71-5.64 (0.6H, m), 6.05-5.98 (0.4H, m), 6.20-6.09 (1H, m), 6.65-6.51 (1.6H, m), 7.18 (1H, d, J=5.1 Hz), 8.11-8.00 (2.6H, m), 8.23-8.17 (0.4H, m), 8.44-8.36 (1H, m), 11.54-11.40 (1H, m).

Example 95: (S)-1-Acryloyl-N-(2-(4-(pyridin-4-yl)-1H-pyrrolo[2,3-b]pyridin-2-yl)ethyl)pyrrolidine-2-carboxamide

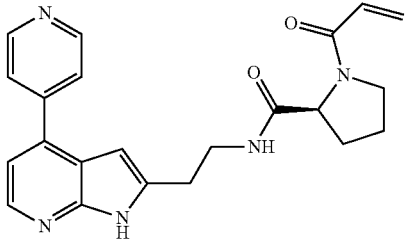 [SMILES: C=CC(=O)N1CCC[C@H]1C(=O)NCCc1cc2c(-c3ccncc3)ccnc2[nH]1]

Starting from (S)—N-(2-(4-(pyridin-4-yl)-1H-pyrrolo[2,3-b]pyridin-2-yl)ethyl) pyrrolidine-2-carboxamide (Example 107) and acryloyl chloride.

LCMS (Method 1): Rt 2.01 min, m/z 390.4 [MH$^+$].

$^1$H NMR (400 MHz, d$_6$-DMSO): 2.17-1.63 (4H, m), 2.98-2.86 (2H, m), 3.67-3.26 (4H, m), 4.38-4.25 (1H, m), 5.32-5.25 (0.4H, m), 5.69-5.62 (0.6H, m), 6.00-5.93 (0.4H, m), 6.16-6.04 (1H, m), 6.50-6.43 (1H, m), 6.63-6.53 (0.6H, m), 7.25 (1H, d, J=5.0 Hz), 7.81-7.73 (2H, m), 8.05-7.97 (0.6H, m), 8.20-8.14 (0.4H, m), 8.28-8.21 (1H, m), 8.78-8.68 (2H, m), 11.83-11.70 (1H, m).

Example 96: N-Methyl-2-(4-(pyrazolo[1,5-b]pyridazin-3-yl)-1H-pyrrolo[2,3-b]pyridin-2-yl)ethan-1-amine

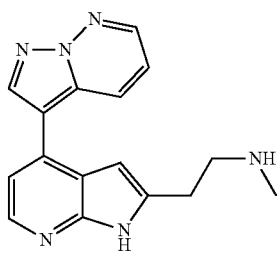 [SMILES: CNCCc1cc2c(-c3cnn4ncccc34)ccnc2[nH]1]

A solution tert-butyl methyl(2-(1-(phenylsulfonyl)-4-(pyrazolo[1,5-b]pyridazin-3-yl)-1H-pyrrolo[2,3-b]pyridin-2-yl)ethyl)carbamate (Intermediate 54, 2.68 g, 5.00 mmol) in DCM (25 mL) was treated with TFA (5 mL). The reaction mixture was stirred at r.t. for 3 h then concentrated in vacuo, and then azetroped with toluene. The residue was dissolved in dioxane (20 mL) and EtOH (10 mL) and then treated with 3M aqueous NaOH (10 mL). The reaction mixture was stirred and heated at 50° C. for 4 hour. After cooling, the mixture was treated with 6N HCl until the pH=7, then concentrated in vacuo. The residue was purified by FCC eluting with 7.5-15% 2M ammonia in MeOH in DCM to give the title compound (597 mg, 41%) as a yellow solid.

LCMS (Method 4): Rt 2.07 min, m/z 293 [MH$^+$].

$^1$H NMR (400 MHz, CDCl$_3$) 1.78 (1H, s), 2.52 (3H, s), 3.02 (4H, s), 6.31 (1H, s), 7.09 (1H, dd, J=9.0, 4.4 Hz), 7.13 (1H, d, J=5.0 Hz), 8.21 (1H, dd, J=9.0, 1.5 Hz), 8.28 (1H, d, J=5.0 Hz), 8.37 (1H, dd, J=4.1, 1.5 Hz), 10.91 (1H, s), 8.42 (1H, s)

Example 97: tert-Butyl (2-(4-(1-methyl-1H-pyrazol-5-yl)-1H-pyrrolo[2,3-b]pyridin-2-yl)ethyl)carbamate tert-Butyl (2-(4-chloro-1H-pyrrolo[2,3-b]pyridin-2-yl)ethyl)carbamate (Intermediate 55, 295 mg, 1.00 mmol), 1-methyl-1H-pyrazole-5-boronic acid pinacol ester (312 mg, 1.50 mmol), potassium phosphate (630 mg, 3.00 mmol) and X-Phos-Pd-G3 (34 mg, 0.04 mmol) were added to a flame dried flask under argon and purged with argon three times. Degassed THF/ethanol/water (3:1:1, 5 mL) was added, and the reaction mixture was heated at 50° C. for 12 h. After cooling, the mixture was diluted with water and extracted with ethyl acetate. The combined organic layers were washed with brine, and concentrated in vacuo. The residue was purified by FCC eluting with Petrol:EtOAc:MeOH (gradient elution, 10:10:1, to 0:10:1) to give the title compound (340 mg, 99%) as a white solid.

LCMS (Method 4): Rt 2.46 min, m/z 342, [MH$^+$].

$^1$H NMR (400 MHz, CDCl$_3$) 1.40 (9H, s), 3.10 (2H, t, J=6.5 Hz), 3.59 (2H, q, J=6.5 Hz), 3.92 (3H, s), 4.81 (1H, s), 6.26 (1H, s), 6.51 (1H, d, J=1.8 Hz), 7.06 (1H, d, J=5.0 Hz), 7.62 (1H, d, J=1.9 Hz), 8.36 (1H, d, J=4.9 Hz), 11.92 (1H, s).

By proceeding in a similar manner to Example 97, the following compounds were prepared:

Example 98: tert-Butyl (2-(4-(1H-pyrazol-4-yl)-1H-pyrrolo[2,3-b]pyridin-2-yl)ethyl)carbamate Starting from tert-butyl (2-(4-chloro-1H-pyrrolo[2,3-b]pyridin-2-yl)ethyl)carbamate (Intermediate 55), and 4-pyrazoleboronic acid pinacol ester.

LCMS (Method 4): Rt 2.21 min, m/z 328 [MH$^+$].

$^1$H NMR (400 MHz, d$_6$-DMSO) 1.36 (9H, s), 2.88 (2H, t, J=7.1 Hz), 3.36-3.32 (2H, m), 6.55 (1H, s), 6.99 (1H, t, J=5.5 Hz), 7.22 (1H, d, J=5.0 Hz), 8.05 (1H, d, J=5.0 Hz), 8.26 (2H, s), 11.46 (1H, s), 13.14 (1H, s).

Example 99: tert-Butyl (2-(4-(pyridin-3-yl)-1H-pyrrolo[2,3-b]pyridin-2-yl)ethyl)carbamate

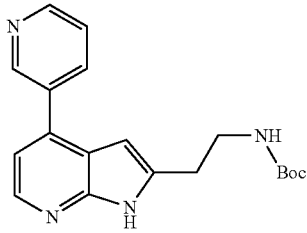 [SMILES: CC(C)(C)OC(=O)NCCc1cc2c(-c3cccnc3)ccnc2[nH]1]

Starting from (2-(4-chloro-1H-pyrrolo[2,3-b]pyridin-2-yl)ethyl)carbamate (Intermediate 55), and 3-pyridinylboronic acid.

LCMS (Method 4): Rt 2.50 min, m/z 339 [MH+].

$^1$H NMR (400 MHz, $d_6$-DMSO): 1.33 (9H, s), 2.89 (2H, t, J=7.0 Hz), 3.37-3.27 (2H, m), 6.41 (1H, s), 6.96 (1H, t, J=5.4), 7.20 (1H, d, J=5.0 Hz), 7.57 (1H, dd, J=7.9, 4.8 Hz), 8.19-8.12 (1H, m), 8.22 (1H, d, J=5.0 Hz), 8.66 (1H, dd, J=4.8, 1.6 Hz), 8.96 (1H, d, J=1.8 Hz), 11.72 (1H, s),

Example 100: 2-(4-(1-Methyl-1H-pyrazol-5-yl)-1H-pyrrolo[2,3-b]pyridin-2-yl)ethan-1-amine

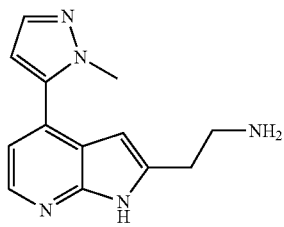 [SMILES: Cn1nccc1-c1ccnc2[nH]c(CCN)cc12]

A solution of tert-butyl (2-(4-(1-methyl-1H-pyrazol-5-yl)-1H-pyrrolo[2,3-b]pyridin-2-yl)ethyl)carbamate (Example 97, 341 mg, 1.00 mmol) in DCM (6 mL) was treated with TFA (3 mL). The reaction mixture was stirred at r.t. for 3 h then concentrated in vacuo, The residue was dissolved in DCM and saturated aqueous NaHCO$_3$ was added until the pH=9. The layers were separated and the aqueous layer was extracted with CHCl$_3$. The combined organic layers were washed with brine, dried (MgSO$_4$) and concentrated in vacuo to give the title compound (240 mg, 99%) as a pale yellow solid.

LCMS (Method 4): Rt 1.91 min, m/z 242 [MH+].

$^1$H NMR (400 MHz, CDCl$_3$) 1.68 (2H, s), 2.98 (2H, t, J=6.1 Hz), 3.17 (2H, t, J=6.1 Hz), 3.91 (3H, s), 6.22 (1H, s), 6.50 (1H, d, J=1.9 Hz), 7.04 (1H, d, J=5.0 Hz), 7.61 (1H, d, J=1.9 Hz), 8.31 (1H, d, J=5.0 Hz), 11.55 (1H, s).

By proceeding in a similar manner to Example 100, the following compounds were prepared:

Example 101: 2-(5-Chloro-4-(pyrazolo[1,5-b]pyridazin-3-yl)-1H-pyrrolo[2,3-b]pyridin-2-yl)ethan-1-amine

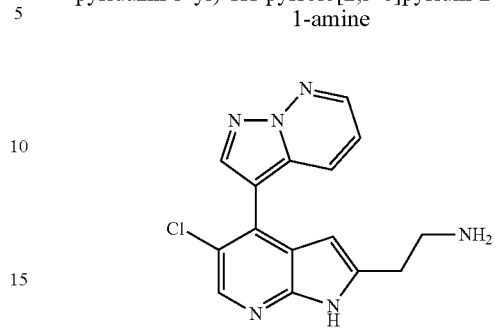

Starting from tert-butyl (2-(5-chloro-4-(pyrazolo[1,5-b]pyridazin-3-yl)-1H-pyrrolo[2,3-b]pyridin-2-yl)ethyl)carbamate (Intermediate 27).

LCMS (Method 1): Rt 2.50 min, m/z 313.3 [MH+].

$^1$H NMR (400 MHz, $d_6$-DMSO): 3.02-2.92 (2H, m), 3.14-3.02 (2H, m), 6.10 (1H, s), 7.32 (1H, dd, J=4.4, 9.1 Hz), 8.08 (1H, dd, J=1.8, 9.1 Hz), 8.29 (1H, s), 8.47-8.33 (2H, m), 8.59 (1H, dd, J=1.8, 4.4 Hz). NH$_2$ obscured by H$_2$O/not observed.

Example 102: 3-(2-(Piperidin-4-yl)-1H-pyrrolo[2,3-b]pyridin-4-yl)pyrazolo[1,5-b]pyridazine

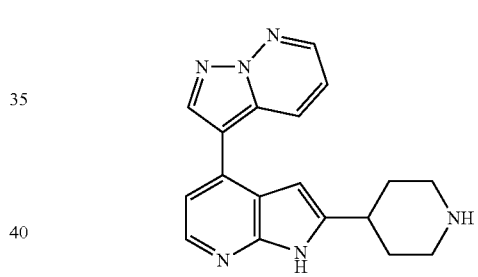

Starting from tert-butyl 4-(4-(pyrazolo[1,5-b]pyridazin-3-yl)-1H-pyrrolo[2,3-b]pyridin-2-yl)piperidine-1-carboxylate (Example 196).

LCMS (Method 3): Rt 0.78 min, m/z 319 [MH+].

$^1$H NMR (400 MHz, CDCl$_3$), 1.79-1.92 (2H, m), 2.10-2.15 (2H, m), 2.81-2.90 (2H, m), 2.98-3.06 (1H, m), 3.24-3.30 (2H, m), 6.35 (1H, s), 7.11 (1H, dd, J=4.4, 9.1 Hz), 7.22 (1H, d, J=5.0 Hz), 8.24 (1H, dd, J=1.9, 9.1 Hz), 8.38-8.41 (2H, m), 8.47 (1H, s), 11.63 (1H, s).

Example 103: 2-(4-(1H-Pyrazol-4-yl)-1H-pyrrolo[2,3-b]pyridin-2-yl)ethan-1-amine

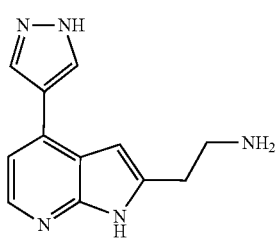 [SMILES: NCCc1cc2c(-c3cn[nH]c3)ccnc2[nH]1]

A solution tert-butyl (2-(4-(1H-pyrazol-4-yl)-1H-pyrrolo[2,3-b]pyridin-2-yl)ethyl)carbamate (Example 98, 163 mg, 0.50 mmol) in DCM (6 mL) was treated with TFA (3 mL). The reaction mixture was stirred at r.t. for 1 h then concentrated in vacuo, The residue was dissolved in DCM and saturated aqueous NaHCO₃ was added until the pH=9. The resulting precipitate was collected by filtration, washed with water and Et₂O, then air dried to give the title compound (90 mg, 79%) as a white solid.

LCMS (Method 4): Rt 2.68 min, m/z 228 [MH⁺].

¹H NMR (400 MHz, d₆-DMSO) 3.01-2.84 (2H, m), 3.76-3.26 (5H, m), 6.63-6.47 (1H, m), 7.22 (1H, d, J=5.0 Hz), 8.05 (1H, d, J=5.0 Hz), 8.27 (2H, s), 11.57 (1H, s).

By proceeding in a similar manner to Example 103, the following compounds were prepared:

Example 104: 2-(4-(Pyridin-3-yl)-1H-pyrrolo[2,3-b]pyridin-2-yl)ethan-1-amine

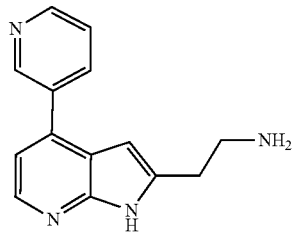 [SMILES: NCCc1cc2c(-c3cccnc3)ccnc2[nH]1]

Starting from tert-butyl (2-(4-(pyridin-3-yl)-1H-pyrrolo[2,3-b]pyridin-2-yl)ethyl)carbamate (Example 99).

LCMS (Method 1): Rt 2.55 min, m/z 239.2 [MH⁺].

¹H NMR (400 MHz, d₆-DMSO: 2.87-2.79 (2H, m), 2.96-2.89 (2H, m), 6.38 (1H, s), 7.20 (1H, d, J=5.0 Hz), 7.57 (1H, ddd, J=0.8, 4.8, 7.9 Hz), 8.17 (1H, ddd, J=1.7, 2.4, 7.9 Hz), 8.22 (1H, d, J=5.0 Hz), 8.66 (1H, dd, J=1.6, 4.8 Hz), 8.96 (1H, dd, J=0.8, 2.3 Hz). NH₂ not observed.

Example 105: (S)-1-Acryloyl-N-(2-(4-(pyridin-3-yl)-1H-pyrrolo[2,3-b]pyridin-2-yl)ethyl)pyrrolidine-2-carboxamide

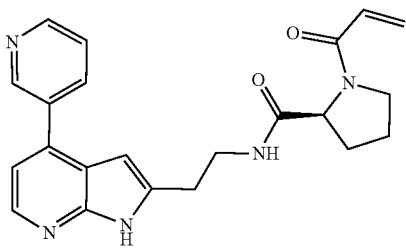 [SMILES: C=CC(=O)N1CCC[C@H]1C(=O)NCCc1cc2c(-c3cccnc3)ccnc2[nH]1]

HATU (380 mg, 1.00 mmol) was added to a solution of acryloyl-L-proline (42 mg, 0.25 mmol) and TEA (0.11 mL, 0.80 mmol) in DCM (1 mL) and the resultant mixture was stirred for 5 min. The solution was then added to a solution of 2-(4-(pyridin-3-yl)-1H-pyrrolo[2,3-b]pyridin-2-yl)ethan-1-amine (Example 104, 47 mg, 0.20 mmol) in DCM (2.0 mL) and the mixture was stirred for 1 h. The reaction was quenched with a saturated aqueous solution of Na₂CO₃ and extracted with CHCl₃. The combined organic layers were washed with a saturated aqueous solution of Na₂CO₃, brine, dried (Na₂SO₄) and concentrated in vacuo. The residue was purified by FCC eluting with 4-10% MeOH in DCM to give the title compound (44 mg, 56%) as a yellow solid.

LCMS (Method 1): Rt 2.13 min, m/z 390.4 [MH⁺].

¹H NMR (400 MHz, d₆-DMSO): 2.17-1.62 (4H, m), 2.99-2.86 (2H, m), 3.67-3.35 (4H, m), 4.39-4.23 (1H, m), 5.29 (0.4H, dd, J=2.7, 10.1 Hz), 5.65 (0.6H, dd, J=2.4, 10.3 Hz), 6.20-5.93 (1.4H, m), 6.44-6.37 (1H, m), 6.57 (0.6H, dd, J=10.3, 16.8 Hz), 7.24-7.18 (1H, m), 7.61-7.53 (1H, m), 8.04-7.96 (0.6H, m), 8.26-8.12 (2.4H, m), 8.70-8.63 (1H, m), 8.99-8.93 (1H, m), 11.82-11.61 (1H, m).

Example 106: (S)—N-(2-(4-(1-methyl-1H-pyrazol-4-yl)-1H-pyrrolo[2,3-b]pyridin-2-yl)ethyl)pyrrolidine-2-carboxamide

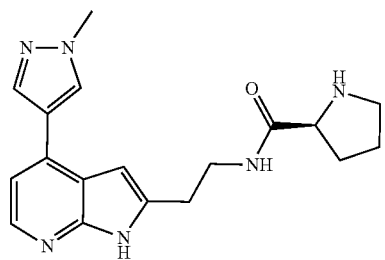 [SMILES: Cn1cc(-c2ccnc3[nH]c(CCNC(=O)[C@@H]4CCCN4)cc23)cn1]

A solution of tert-butyl (S)-2-((2-(4-(1-methyl-1H-pyrazol-4-yl)-1-(phenylsulfonyl)-1H-pyrrolo[2,3-b]pyridin-2-yl)ethyl)carbamoyl)pyrrolidine-1-carboxylate (Intermediate 44, 393 mg, 0.67 mmol) in DCM (4 mL) was treated with TFA (2 mL). The reaction mixture was stirred at r.t. for 3 h then concentrated in vacuo. The residue was azetroped with toluene then diluted in dioxane (6 mL) and treated with 3M aqueous NaOH (3 mL). The reaction mixture was stirred at 50° C. for 6 hour. After cooling, the mixture was treated with 6M HCl until the pH=7, then concentrated in vacuo. The residue was purified by FCC eluting with 7.5-10% 2M ammonia in MeOH in DCM to give the title compound (193 mg, 85%) as a yellow solid.

LCMS (Method 4): Rt 2.03 min, m/z 339 [MH⁺].

¹H NMR (400 MHz, CDCl₃) 1.84-1.71 (2H, m), 2.04-1.91 (1H, m), 2.26-2.13 (1H, m), 3.01-2.88 (1H, m), 3.15-3.03 (3H, m), 3.61-3.47 (1H, m), 3.89-3.79 (2H, m), 4.00 (3H, s), 4.24 (1H, s), 6.39 (1H, s), 6.81 (1H, s), 7.72 (1H, s), 7.92-7.81 (2H, m), 8.16 (1H, s), 11.36 (1H, s).

By proceeding in a similar manner to Example 106, the following compounds were prepared:

Example 107: (S)—N-(2-(4-(Pyridin-4-yl)-1H-pyrrolo[2,3-b]pyridin-2-yl)ethyl)pyrrolidine-2-carboxamide

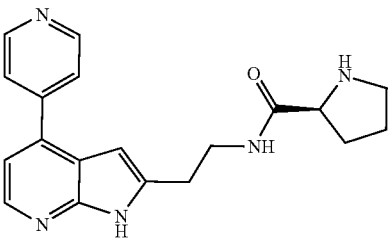 [SMILES: O=C(NCCc1cc2c(-c3ccncc3)ccnc2[nH]1)[C@@H]1CCCN1]

Starting from tert-butyl (S)-2-((2-(1-(phenylsulfonyl)-4-(pyridin-4-yl)-1H-pyrrolo[2,3-b]pyridin-2-yl)ethyl)carbamoyl)pyrrolidine-1-carboxylate (Intermediate 45).

LCMS (Method 1): Rt 2.58 min, m/z 336.4 [MH$^+$].

$^1$H NMR (400 MHz, d$_6$-DMSO): 1.64-1.38 (3H, m), 1.94-1.79 (1H, m), 2.82-2.62 (2H, m), 2.93 (2H, t, J=6.8 Hz), 3.57-3.39 (3H, m), 6.48-6.43 (1H, m), 7.25 (1H, d, J=5.0 Hz), 7.77-7.72 (2H, m), 8.08-8.01 (1H, m), 8.24 (1H, d, J=5.0 Hz), 8.75-8.71 (2H, m), 11.80 (1H, s). Pyrrolidine NH not observed.

Example 108: 3-(2-(Piperazin-1-ylmethyl)-1H-pyrrolo[2,3-b]pyridin-4-yl)pyrazolo[1,5-b]pyridazine

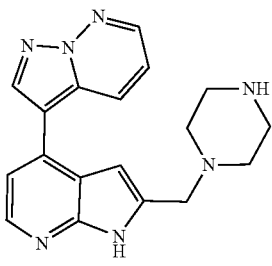 [SMILES: c1cnn2ncc(-c3ccnc4[nH]c(CN5CCNCC5)cc34)c2c1]

A solution of 3-(1-(phenylsulfonyl)-2-(piperazin-1-ylmethyl)-1H-pyrrolo[2,3-b]pyridin-4-yl)pyrazolo[1,5-b]pyridazine (Intermediate 63, 603 mg, 1.27 mmol) in dioxane (9 mL) and EtOH (2 mL) was treated with 2M aqueous NaOH (9 mL). The reaction mixture was stirred and heated at 60° C. for 24 hour. After cooling, the mixture was treated with 6M HCl until the pH=7, then concentrated in vacuo. The residue was loaded onto an SCX-2 cartridge which was eluted with DCM:MeOH (1:1) followed by DCM:2N NH$_3$ in MeOH (1:1). The methanolic ammonia fraction was concentrated in vacuo to afford the title compound (349 mg, 82%) as a yellow solid.

LCMS (Method 1): Rt 2.65 min, m/z 332.3 [MH$^-$].

$^1$H NMR (400 MHz, d$_6$-DMSO): 2.39-2.32 (4H, m), 2.71-2.65 (4H, m), 3.61 (2H, s), 6.47 (1H, s), 7.26 (1H, d, J=5.0 Hz), 7.34 (1H, dd, J=4.5, 9.0 Hz), 8.22 (1H, d, J=4.9 Hz), 8.45 (1H, d, J=8.1 Hz), 8.58-8.56 (2H, m), 11.72 (1H, s) 1H obscured by solvent.

By proceeding in a similar manner to Example 108, the following compounds were prepared:

Example 109: 7-((4-(Pyrazolo[1,5-b]pyridazin-3-yl)-1H-pyrrolo[2,3-b]pyridin-2-yl)methyl)-2,7-diazaspiro[4.5]decane

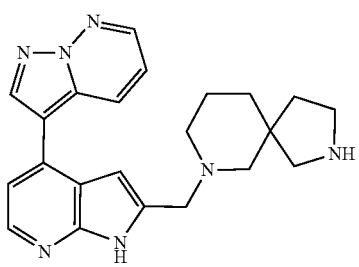 [SMILES: c1cnn2ncc(-c3ccnc4[nH]c(CN5CCCC6(CCNC6)C5)cc34)c2c1]

Starting from 7-((1-(phenylsulfonyl)-4-(pyrazolo[1,5-b]pyridazin-3-yl)-1H-pyrrolo[2,3-b]pyridin-2-yl)methyl)-2,7-diazaspiro[4.5]decane (Intermediate 64).

LCMS (Method 3): Rt 0.60 min, m/z 388 [MH$^+$].

$^1$H NMR (400 MHz, CDCl$_3$): 1.35-1.55 (3H, m), 1.55-1.70 (3H, m), 1.91-2.62 (6H, m), 2.65 (1H, d, J=11.0 Hz), 2.81-2.94 (2H, m), 3.66-3.69 (2H, m), 6.41 (1H, s), 7.11 (1H, dd, J=9.1, 4.4 Hz), 7.18 (1H, d, J=5.0 Hz), 8.22 (1H, dd, J=9.1, 2.0 Hz), 8.32 (1H, d, J=5.0 Hz), 8.38 (1H, dd, J=4.3, 1.9 Hz), 8.44 (1H, s), 9.85 (1H, s).

Example 110: (1-((4-(pyrazolo[1,5-b]]pyridazin-3-yl)-1H-pyrrolo[2,3-b]pyridine-2-yl)methyl)pyrrolidin-3-yl-methanamine

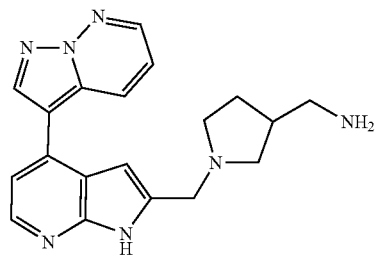 [SMILES: NCC1CCN(Cc2cc3c(-c4cnn5ncccc45)ccnc3[nH]2)C1]

Starting from (1-((1-(Phenylsulfonyl)-4-(pyrazolo[1.5-b]]pyridazin-3-yl)-1H-pyrrolo[2,3-b]pyridine-2-yl)methyl)pyrrolidin-3-yl-methanamine (Intermediate 65).

LCMS (Method 3): Rt 0.66 min, m/z 348 [MH$^+$]

$^1$H NMR (400 MHz, CDCl$_3$) 2.08-1.98 (1H, m), 2.42-2.24 (2H, m), 2.80-2.61 (6H, m), 3.84-3.82 (2H, m), 6.41 (1H, s), 7.18-7.08 (2H, m), 8.22 (1H, dd, J=1.9, 9.1 Hz), 8.44-8.32 (3H, m), 10.16 (1H, s).

Example 111: N-(3-(4-((4-(Pyrazolo[1,5-b]pyridazin-3-yl)-1H-pyrrolo[2,3-b]pyridin-2-yl)methyl)piperazine-1-carbonyl)phenyl)acrylamide

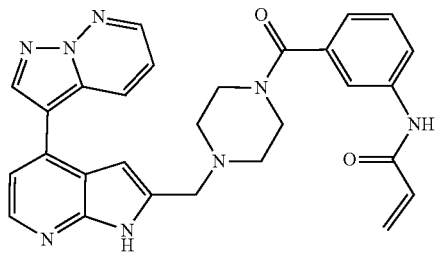 [SMILES: C=CC(=O)Nc1cccc(C(=O)N2CCN(Cc3cc4c(-c5cnn6ncccc56)ccnc4[nH]3)CC2)c1]

A solution of 3-acrylamidobenzoic acid (48 mg, 0.20 mmol), TEA (0.104 mL, 0.75 mmol) and HOBt (3.5 mg) in DMF (1.0 mL) was treated with EDC.HCl (48 mg, 0.20 mmol) and stirred for 5 mins. The solution was added to 3-(2-(piperazin-1-ylmethyl)-1H-pyrrolo[2,3-b]pyridin-4-yl)pyrazolo[1,5-b]pyridazine (Example 108, 66 mg, 0.20 mmol) in DMF (1.0 mL) and the resultant mixture was stirred for 18 hours. The reaction was quenched with water and extracted with CHCl$_3$. The combined organic layers were washed with saturated aqueous Na$_2$CO$_3$, brine, dried (Na$_2$SO$_4$) and concentrated in vacuo. The residue was purified by FCC eluting with 4-10% MeOH in DCM to give the title compound (60 mg, 59%) as a white solid.

LCMS (Method 1): Rt 2.30 min, m/z 507.4 [MH+].

¹H NMR (400 MHz, d₆-DMSO): 3.73 (2H, s), 5.77 (1H, dd, J=2.0, 10.0 Hz), 6.26 (1H, dd, J=2.0, 16.9 Hz), 6.41 (1H, dd, J=10.1, 17.0 Hz), 6.50 (1H, d, J=1.8 Hz), 7.08-7.03 (1H, m), 7.27 (1H, d, J=4.9 Hz), 7.41-7.31 (2H, m), 7.68-7.63 (1H, m), 7.76-7.72 (1H, m), 8.24 (1H, d, J=4.8 Hz), 8.45 (1H, dd, J=1.8, 9.1 Hz), 8.56 (1H, dd, J=1.8, 4.4 Hz), 8.59 (1H, s), 10.26 (1H, s), 11.81-11.73 (1H, m). 8H obscured by DMSO and water.

By proceeding in a similar manner to Example 111, the following compounds were prepared:

Example 112: N-(4-(4-((4-(Pyrazolo[1,5-b]pyridazin-3-yl)-1H-pyrrolo[2,3-b]pyridin-2-yl)methyl)piperazine-1-carbonyl)phenyl)acrylamide

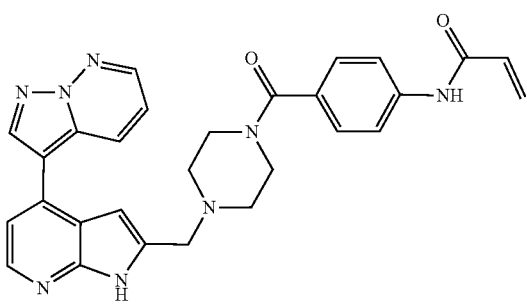 [SMILES: C=CC(=O)Nc1ccc(C(=O)N2CCN(Cc3cc4c(-c5cnn6ncccc56)ccnc4[nH]3)CC2)cc1]

Starting from 3-(2-(piperazin-1-ylmethyl)-1H-pyrrolo[2,3-b]pyridin-4-yl)pyrazolo[1,5-b]pyridazine (Example 108, 66 mg, 0.20 mmol) and 4-acrylamidobenzoic acid.

LCMS (Method 1): Rt 2.27 min, m/z 507.4 [MH+].

¹H NMR (400 MHz, d₆-DMSO): 3.67-3.17 (4H, m), 3.72 (2H, s), 5.78 (1H, dd, J=2.0, 10.1 Hz), 6.27 (1H, dd, J=2.0, 17.0 Hz), 6.44 (1H, dd, J=10.1, 16.9 Hz), 6.50 (1H, d, J=1.8 Hz), 7.27 (1H, d, J=4.9 Hz), 7.39-7.31 (3H, m), 7.73-7.67 (2H, m), 8.23 (1H, d, J=4.9 Hz), 8.45 (1H, dd, J=1.9, 9.1 Hz), 8.57 (1H, dd, J=1.8, 4.5 Hz), 8.58 (1H, s), 10.30 (1H, s), 11.80-11.74 (1H, m). 4H obscured by solvent.

Example 113: (S)-1-(2-(4-((4-(Pyrazolo[1,5-b]pyridazin-3-yl)-1H-pyrrolo[2,3-b]pyridin-2-yl)methyl)piperazine-1-carbonyl)pyrrolidin-1-yl)prop-2-en-1-one

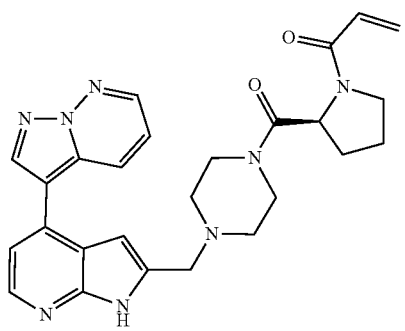 [SMILES: C=CC(=O)N1CCC[C@H]1C(=O)N1CCN(Cc2cc3c(-c4cnn5ncccc45)ccnc3[nH]2)CC1]

A solution of acryloyl-L-proline (43 mg, 0.25 mmol) and TEA (0.22 mL, 1.60 mmol) in DMC (2.0 mL) was treated with T3P (50% solution in EtOAc, 0.36 mL, 0.6 mmol) and the resultant mixture was stirred for 5 mins. The solution was added to 3-(2-(piperazin-1-ylmethyl)-1H-pyrrolo[2,3-b]pyridin-4-yl)pyrazolo[1,5-b]pyridazine (Example 108 66 mg, 0.20 mmol) in DMC (2.0 mL) and the mixture was stirred for 30 min. The reaction was quenched with saturated aqueous Na₂CO₃ and extracted with CHCl₃. The combined organic layers were washed with brine, dried (MgSO₄) and concentrated in vacuo. The residue was purified by FCC eluting with 4-12% MeOH in DCM to give the title compound (59 mg, 61%) as a yellow solid.

LCMS (Method 1): Rt 2.09 min, m/z 485.4 [MH+].

¹H NMR (400 MHz, d₆-DMSO): 2.58-1.63 (8H, m), 3.51-3.39 (2.7H, m), 3.67-3.52 (3.3H, m), 3.77-3.68 (2H, m), 4.83 (0.7H, dd, J=3.7, 8.5 Hz), 5.06 (0.3H, dd, J=2.8, 8.7 Hz), 5.50 (0.3H, dd, J=2.7, 9.9 Hz), 5.66 (0.7H, dd, J=2.3, 10.2 Hz), 6.18-5.99 (1.3H, m), 6.53-6.49 (1H, m), 6.60 (0.7H, dd, J=10.2, 16.7 Hz), 7.30-7.25 (1H, m), 7.38-7.32 (1H, m), 8.26-8.22 (1H, m), 8.46 (1H, dd, J=1.7, 9.1 Hz), 8.61-8.55 (2H, m), 11.82-11.73 (1H, m).

Example 114: 3-(4-(Pyrazolo[1,5-b]pyridazin-3-yl)-1H-pyrrolo[2,3-b]pyridin-2-yl)aniline

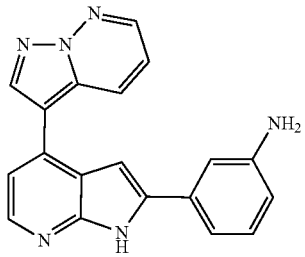 [SMILES: Nc1cccc(-c2cc3c(-c4cnn5ncccc45)ccnc3[nH]2)c1]

A solution of 3-(1-(phenylsulfonyl)-4-(pyrazolo[1,5-b]pyridazin-3-yl)-1H-pyrrolo[2,3-b]pyridin-2-yl)aniline (Intermediate 68, 186 mg, 0.40 mmol) in dioxane (2 mL) was treated with sodium tert-butoxide (57 mg, 0.60 mmol) and the resultant mixture was stirred and heated at 80° C. for 2 hour. After cooling, the mixture was diluted with water and the resulting solid was removed from the liquid by centrifuging to obtain a pellet, which was washed with water and MeCN and dried under vacuum to give the title compound (93 mg, 71%) as a pale yellow solid.

LCMS (Method 1): Rt 2.55 min, m/z 327.2 [MH+].

¹H NMR (400 MHz, d₆-DMSO): 5.16-5.08 (2H, m), 6.61-6.55 (1H, m), 6.92 (1H, d, J=2.0 Hz), 7.18-7.08 (3H, m), 7.30 (1H, d, J=5.0 Hz), 7.36 (1H, dd, J=4.4, 9.1 Hz), 8.27 (1H, d, J=5.0 Hz), 8.50 (1H, dd, J=1.8, 9.1 Hz), 8.58 (1H, dd, J=1.8, 4.4 Hz), 8.68 (1H, s), 12.14 (1H, s).

Example 115: 3-Acrylamido-N-(3-(4-(pyrazolo[1,5-b]pyridazin-3-yl)-1H-pyrrolo[2,3-b]pyridin-2-yl)phenyl)benzamide

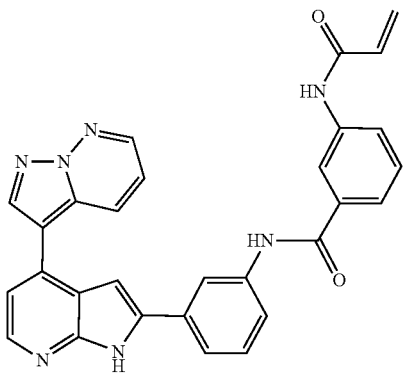 [SMILES: C=CC(=O)Nc1cccc(C(=O)Nc2cccc(-c3cc4c(-c5cnn6ncccc56)ccnc4[nH]3)c2)c1]

EDC.HCl (95 mg, 0.50 mmol) was added to a solution of 3-(4-(pyrazolo[1,5-b]pyridazin-3-yl)-1H-pyrrolo[2,3-b]pyridin-2-yl)aniline (Example 114, 146 mg, 0.40 mmol), 4-acrylamidobenzoic acid (95 mg, 0.50 mmol) TEA (0.113 mL, 0.81 mmol) and DMAP (6.1 mg, 0.05 mmol) in DMF (2.0 mL) and the resultant mixture was stirred at r.t. for 18 h. The mixture was diluted with water and the resulting solid was removed from the liquid by centrifuging to obtain a pellet, which was washed with water and MeCN and dried under vacuum. The residue was purified by FCC eluting with 0-5% MeOH in DCM, then triturated with EtOAc to give the title compound as a yellow solid (26 mg).

LCMS (Method 1): Rt 3.38 min, m/z 500.1 [MH$^+$].

$^1$H NMR (400 MHz, d$_6$-DMSO): 5.82 (1H, dd, J=2.0, 10.1 Hz), 6.32 (1H, dd, J=2.0, 17.0 Hz), 6.48 (1H, dd, J=10.1, 17.0 Hz), 7.04 (1H, d, J=1.8 Hz), 7.34 (1H, d, J=5.0 Hz), 7.38 (1H, dd, J=4.4, 9.1 Hz), 7.47 (1H, t, J=8.0 Hz), 7.72-7.80 (2H, m), 7.83 (2H, d, J=8.9 Hz), 8.00 (2H, d, J=8.7 Hz), 8.29-8.32 (2H, m), 8.52 (1H, dd, J=1.9, 9.2 Hz), 8.59 (1H, dd, J=1.8, 4.4 Hz), 8.72 (1H, s), 10.22 (1H, s), 10.44 (1H, s), 12.35 (1H, s).

Example 116: N-((4-(Pyrazolo[1,5-b]pyridazin-3-yl)-1H-pyrrolo[2,3-b]pyridin-2-yl)methyl)cyclopropanecarboxamide

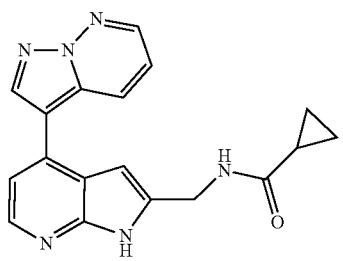 [SMILES: O=C(NCc1cc2c(-c3cnn4ncccc34)ccnc2[nH]1)C1CC1]

A mixture of N-((4-bromo-1-(phenylsulfonyl)-1H-pyrrolo[2,3-b]pyridin-2-yl)methyl)cyclopropanecarboxamide (Intermediate 69, 180 mg, 0.415 mmol), 3-(4,4,5,5-tetramethyl-1,3,2-dioxaborolan-2-yl)pyrazolo[1,5-b]pyridazine (132 mg, 0.539 mmol), XPhos Pd G3 (14 mg, 0.017 mmol) and potassium phosphate (264 mg, 1.24 mmol) in ethanol (7.6 mL) and water (3.8 mL) was degassed with argon for 10 min then heated at 140° C. in a microwave for 1 h. After cooling, the mixture was purified on an SCX-2 cartridge, eluting with 2 M ammonia in MeOH. The residue was purified further by FCC eluting with 0-7.5% MeOH in DCM to give the title compound as a yellow solid.

LCMS (Method 1): Rt 2.85 min, m/z 333.3 [MH$^+$].

$^1$H NMR (400 MHz, d$_6$-DMSO): 0.76-0.62 (4H, m), 1.69-1.60 (1H, m), 4.47 (2H, d, J=5.3 Hz), 6.49 (1H, br s), 7.28 (1H, d, J=5.0 Hz), 7.35 (1H, dd, J=4.5, 9.1 Hz), 8.23 (1H, d, J=5.0 Hz), 8.44 (1H, dd, J=1.9, 9.1 Hz), 8.56-8.51 (2H, m), 8.58 (1H, dd, J=1.9, 4.5 Hz), 11.71 (1H, s).

By proceeding in a similar manner to Example 116, the following compounds were prepared:

Example 117: 2-(Dimethylamino)-N-((4-(pyrazolo[1,5-b]pyridazin-3-yl)-1H-pyrrolo[2,3-b]pyridin-2-yl)methyl)acetamide Formate Salt

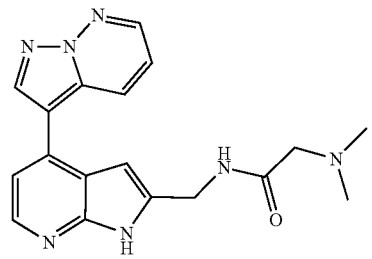 [SMILES: CN(C)CC(=O)NCc1cc2c(-c3cnn4ncccc34)ccnc2[nH]1]

Starting from N-((4-bromo-1-(phenylsulfonyl)-1H-pyrrolo[2,3-b]pyridin-2-yl) methyl)-2-(dimethylamino)acetamide (Intermediate 71) and 3-(4,4,5,5-tetramethyl-1,3,2-dioxaborolan-2-yl)pyrazolo[1,5-b]pyridazine LCMS (Method 1): Rt 2.79 min, m/z 350.2 [MH$^+$].

$^1$H NMR (400 MHz, d$_6$-DMSO): 2.22 (6H, s), 2.94 (2H, s), 4.49 (2H, d, J=6.0 Hz), 6.45-6.40 (1H, m), 7.27 (1H, d, J=4.9 Hz), 7.34 (1H, dd, J=4.4, 9.1 Hz), 8.17 (1H, s), 8.28-8.21 (2H, m), 8.43 (1H, dd, J=1.9, 9.1 Hz), 8.53 (1H, s), 8.57 (1H, dd, J=1.8, 4.4 Hz), 11.67 (1H, s).

Example 118: N-((4-(Pyrazolo[1,5-b]pyridazin-3-yl)-1H-pyrrolo[2,3-b]pyridin-2-yl)methyl)cyclopropanesulfonamide

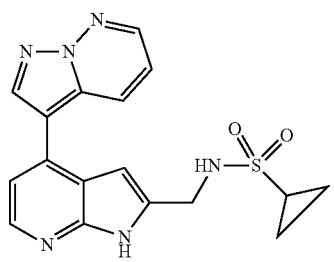 [SMILES: O=S(=O)(NCc1cc2c(-c3cnn4ncccc34)ccnc2[nH]1)C1CC1]

Starting from N-((4-bromo-1-(phenylsulfonyl)-1H-pyrrolo[2,3-b]pyridin-2-yl)methyl)cyclopropanesulfonamide (Intermediate 70).

LCMS (Method 1): Rt 2.44 min, m/z 369.2 [MH$^+$].

$^1$H NMR (400 MHz, d$_6$-DMSO): 0.96-0.82 (4H, m), 2.60-2.51 (1H, m), 4.40 (2H, d, J=5.1 Hz), 6.62 (1H, s), 7.29 (1H, d, J=5.0 Hz), 7.35 (1H, dd, J=4.4, 9.1 Hz), 7.65-7.55

(1H, m), 8.25 (1H, d, J=5.0 Hz), 8.46 (1H, dd, J=1.8, 9.1 Hz), 8.56 (1H, s), 8.58 (1H, dd, J=1.8, 4.5 Hz), 11.70 (1H, s).

Example 119: tert-Butyl 3-(4-(pyrazolo[1,5-b]pyridazin-3-yl)-1H-pyrrolo[2,3-b]pyridin-2-yl)pyrrolidine-1-carboxylate

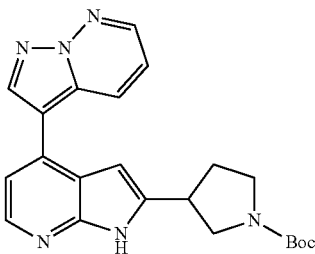 [SMILES: CC(C)(C)OC(=O)N1CCC(c2cc3c(-c4cnn5ncccc45)ccnc3[nH]2)C1]

A mixture of tert-butyl 3-(4-bromo-1H-pyrrolo[2,3-b]pyridin-2-yl)pyrrolidine-1-carboxylate (Intermediate 74, 0.20 g, 0.55 mmol), 3-(4,4,5,5-tetramethyl-1,3,2-dioxaborolan-2-yl)pyrazolo[1,5-b]pyridazine (0.20 g, 0.82 mmol) and potassium phosphate (0.35 g, 1.7 mmol) in ethanol/water (2:1, 5.5 mL) was degassed then treated with X-Phos-Pd-G3 (23 mg, 0.027 mmol). The reaction mixture was heated at 120° C. for 1 h in the microwave. The reaction was then repeated on four times the scale. The reaction mixtures were combined, diluted with ethyl acetate and washed with water and brine, and concentrated in vacuo. The crude product was purified by FCC, eluting with 0-5% 2M ammonia in MeOH in DCM to give the title compound as a yellow solid (1.0 g, 91%).

LCMS (Method 3): Rt 1.09 min, m/z 405 [MH$^+$].

$^1$H NMR (400 MHz, DMSO) 11.76 (1H, s), 8.60-8.55 (2H, m), 8.45 (1H, dd, J=1.6, 9.1 Hz), 8.22 (1H, d, J=5.0 Hz), 7.36-7.26 (2H, m), 6.45 (1H, d, J=3.4 Hz), 3.75 (1H, dd, J=7.4, 10.3 Hz), 3.62-3.51 (1H, m), 3.49-3.38 (2H, m), 2.34-2.27 (1H, m), 2.18-2.07 (1H, m), 1.40 (9H, s) One proton obscured by water Resolution of Example 119 by Chiral SFC Example 119 was resolved by chiral SFC using a YMC Amylose-C column eluting with 55% MeOH (+0.1% diethylamine): 45% CO2, 100 mL/min, 120 bar, 40° C., DAD 225 nm.

Example 120: Faster Running (Unknown Absolute Configuration)

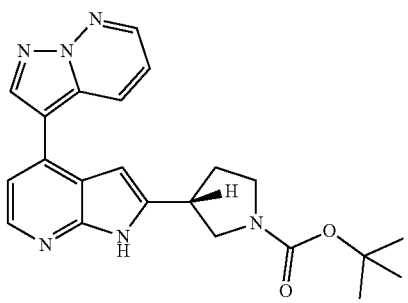

Analytical SFC using YMC Amylose-C (2×150 3 micron) eluting with 55% MeOH (+0.1% diethylamine): 45% CO2, 0.95 mL/min, 120 bar, 40 C, DAD 225 nm retention time 1.3 min.

Example 121: Slower Running (Unknown Absolute Configuration)

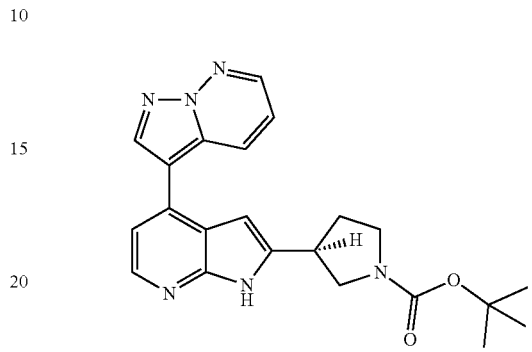

Analytical SFC using YMC Amylose-C (2×150 3 micron) eluting with 55% MeOH (+0.1% diethylamine): 45% CO2, 0.95 mL/min, 120 bar, 40 C, DAD 225 nm retention time 2.7 min.

Example 122: 3-(2-(Pyrrolidin-3-yl)-1H-pyrrolo[2,3-b]pyridin-4-yl)pyrazolo[1,5-b]pyridazine

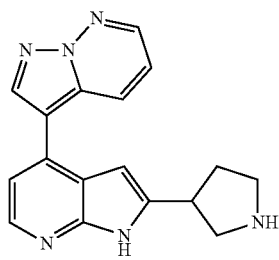 [SMILES: c1cnn2ncc(-c3ccnc4[nH]c(C5CCNC5)cc34)c2c1]

A solution of tert-butyl 3-(4-(pyrazolo[1,5-b]pyridazin-3-yl)-1H-pyrrolo[2,3-b]pyridin-2-yl)pyrrolidine-1-carboxylate (Example 119, 322 mg, 0.80 mmol) in DCM (6 mL) was treated with TFA (3 mL). The reaction mixture was stirred at r.t. for 20 mins then diluted with toluene and concentrated in vacuo. The residue was loaded onto an SCX-2 cartridge and the cartridge was eluted with MeOH followed by 2M ammonia in MeOH. The methanolic ammonia fraction was concentrated in vacuo to afford the title compound as a yellow gum (250 mg)

LCMS (Method 1): Rt 1.74 min, m/z 305.2 [MH$^+$].

$^1$H NMR (400 MHz, CDCl$_3$): 1.98-2.08 (1H, m), 2.29-2.39 (1H, m), 3.05-3.13 (1H, m), 3.16-3.28 (2H, m), 3.34 (1H, dd, J=10.4, 7.1 Hz), 3.49-3.57 (1H, m), 6.34 (1H, s), 7.10 (1H, dd, J=9.1, 4.4 Hz), 7.18 (1H, d, J=5.0 Hz), 8.22 (1H, dd, J=9.1, 1.9 Hz), 8.34 (1H, d, J=5.0 Hz), 8.38 (1H, dd, J=4.4, 1.9 Hz), 8.45 (1H, s).

By proceeding in a similar manner to Example 122, the following compounds were prepared:

Example 123: 4-(1H-Indol-3-yl)-2-(pyrrolidin-3-yl)-1H-pyrrolo[2,3-b]pyridine

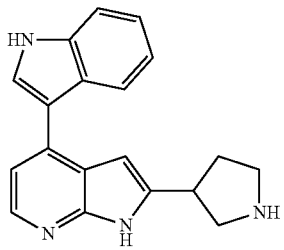 [SMILES: c1ccc2c(-c3ccnc4[nH]c(C5CCNC5)cc34)c[nH]c2c1]

Starting from using tert-butyl 3-(4-(1H-indol-3-yl)-1H-pyrrolo[2,3-b]pyridin-2-yl)pyrrolidine-1-carboxylate (Example 130).

LCMS (Method 3): Rt 0.62 min, m/z 303.2 [MH+].

Example 124: 3-(2-(Pyrrolidin-3-yl)-1H-pyrrolo[2,3-b]pyridin-4-yl)pyrazolo[1,5-b]pyridazine Derived from the Faster Running Boc Derivative (Enantiomer 1)

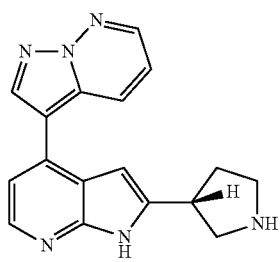

Starting from tert-butyl 3-(4-(pyrazolo[1,5-b]pyridazin-3-yl)-1H-pyrrolo[2,3-b]pyridin-2-yl)pyrrolidine-1-carboxylate, the faster running Boc derivative (Example 120).

LCMS (Method 3): Rt 0.61 min, m/z 305.3 [MH+].

$^1$H NMR (400 MHz, CDCl$_3$ 417069): 2.13-2.04 (1H, m), 2.42-2.29 (1H, m), 3.16-3.06 (1H, m), 3.31-3.17 (2H, m), 3.39 (1H, dd, J=7.4, 10.5 Hz), 3.62-3.51 (1H, m), 6.35 (1H, s), 7.11 (1H, dd, J=4.49.1 Hz), 7.18 (1H, d, J=5.1 Hz), 8.23 (1H, dd, J=1.9, 9.0 Hz), 8.35 (1H, d, J=5.1 Hz), 8.39 (1H, dd, J=1.9, 4.4 Hz), 8.45 (1H, s), 11.25 (1H, s).

Example 125: 3-(2-(Pyrrolidin-3-yl)-1H-pyrrolo[2,3-b]pyridin-4-yl)pyrazolo[1,5-b]pyridazine Derived from the Slower Running Boc Derivative (Enantiomer 2)

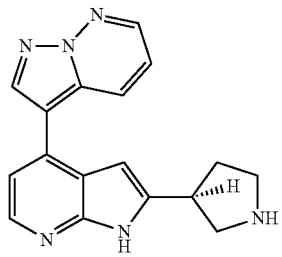

Starting from tert-butyl 3-(4-(pyrazolo[1,5-b]pyridazin-3-yl)-1H-pyrrolo[2,3-b]pyridin-2-yl)pyrrolidine-1-carboxylate, the slower running Boc derivative (Example 121).

LCMS (Method 3): Rt 0.63 min, m/z 305 [MH+].

$^1$H NMR (400 MHz, CDCl$_3$) 2.13-2.04 (1H, m), 2.41-2.30 (1H, m), 3.15-3.07 (1H, m), 3.31-3.19 (2H, m), 3.40 (1H, dd, J=7.4, 10.6 Hz), 3.62-3.54 (1H, m), 6.36 (1H, s), 7.11 (1H, dd, J=4.4, 9.1 Hz), 7.18 (1H, d, J=5.1 Hz), 8.22 (1H, dd, J=1.9, 9.1 Hz), 8.36 (1H, d, J=5.0 Hz), 8.38 (1H, dd, J=1.9, 4.4 Hz), 8.45 (1H, s), 11.44 (1H, s).

Example 126: N-(4-(3-(4-(Pyrazolo[1,5-b]pyridazin-3-yl)-1H-pyrrolo[2,3-b]pyridin-2-yl)pyrrolidine-1-carbonyl)phenyl)acrylamide

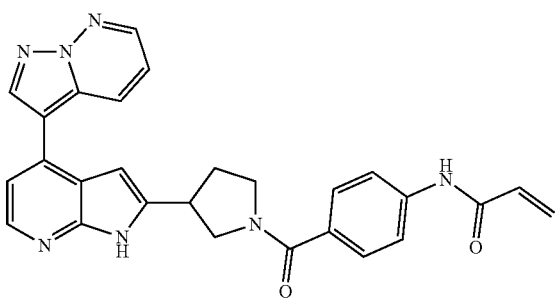 [SMILES: C=CC(=O)Nc1ccc(C(=O)N2CCC(c3cc4c(-c5cnn6ncccc56)ccnc4[nH]3)C2)cc1]

A solution of 4-acrylamidobenzoic acid (35 mg, 0.62 mmol) and DIPEA (32 mg, 0.25 mmol) in DMF (1 mL) was treated with HATU (65 mg, 0.17 mmol) and stirred for 15 mins. The solution was added to 3-(2-(pyrrolidin-3-yl)-1H-pyrrolo[2,3-b]pyridin-4-yl)pyrazolo[1,5-b]pyridazine (Example 122, 50 mg, 0.12 mmol) and stirred for 1 h. Water was added which resulted in the precipitation of a yellow solid. The solid was collected by filtration and washed with water then dissolved up in MeOH/DCM, preadsorbed onto silica and purified by FCC eluting with 0-6% MeOH in DCM. The resulting solid product was sonicated with ethyl acetate and the supernatant was removed by pipette to afford the title compound as a yellow solid (25 mg, 42%) after drying under vacuum.

LCMS (Method 1): Rt 2.68 min, m/z 478.1 [MH+].

$^1$H NMR (400 MHz, d$_6$-DMSO, 80° C.): 2.17-2.29 (1H, m), 2.34-2.44 (1H, m), 3.59-3.74 (4H, m), 3.94-4.02 (1H, m), 5.76 (1H, dd, J=10.0, 1.8 Hz), 6.28 (1H, dd, J=16.9, 1.8 Hz), 6.40-6.49 (2H, m), 7.24 (1H, d, J=5.0 Hz), 7.30 (1H, dd, J=9.0, 4.4 Hz), 7.52 (2H, d, J=8.5 Hz), 7.72 (2H, d, J=8.5

Hz), 8.23 (1H, d, J=5.0 Hz), 8.39 (1H, dd, J=9.1, 1.4 Hz), 8.51-8.55 (2H, m), 10.06 (1H, s), 11.56 (1H, s).

By proceeding in a similar manner as Example 126, the following compounds were prepared:

Example 127: (E)-4-(Dimethylamino)-N-(4-(3-(4-(pyrazolo[1,5-b]pyridazin-3-yl)-1H-pyrrolo[2,3-b]pyridin-2-yl)pyrrolidine-1-carbonyl)phenyl)but-2-enamide Formate Salt

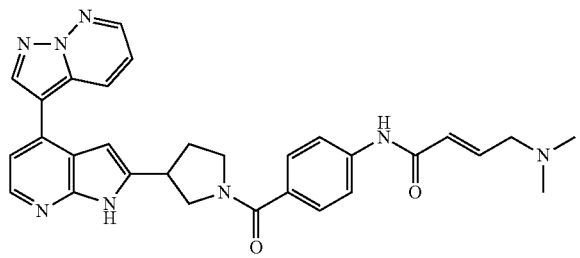 [SMILES: CN(C)C/C=C/C(=O)Nc1ccc(C(=O)N2CCC(c3cc4c(-c5cnn6ncccc56)ccnc4[nH]3)C2)cc1]

Starting from 3-(2-(pyrrolidin-3-yl)-1H-pyrrolo[2,3-b]pyridin-4-yl)pyrazolo[1,5-b]pyridazine (Example 122) and (E)-4-(dimethylamino)but-2-enoic acid (which can be prepared as described in WO2015058163).

LCMS (Method 1): Rt 2.10 min, m/z 535.2 [MH$^+$].

$^1$H NMR (400 MHz, d$_6$-DMSO): 2.11-2.44 (8H, m), 3.07 (2H, d, J=6.0 Hz), 3.54-3.77 (4H, m), 3.89-4.05 (1H, m), 6.28 (1H, d, J=15.3 Hz), 6.48 (1H, d, J=34.3 Hz), 6.76 (1H, dt, J=15.7, 6.2 Hz), 7.27 (1H, dd, J=7.5, 5.3 Hz), 7.33 (1H, dd, J=9.3, 4.4 Hz), 7.50-7.57 (2H, m), 7.72 (2H, d, J=8.4 Hz), 8.17-8.26 (2H, m), 8.46 (1H, dd, J=14.2, 9.1 Hz), 8.54-8.65 (2H, m), 10.24 (1H, s), 11.74 (0.5H, s), 11.86 (0.5H, s).

Example 128: N-(4-(3-(4-(Pyrazolo[1,5-b]pyridazin-3-yl)-1H-pyrrolo[2,3-b]pyridin-2-yl)pyrrolidine-1-carbonyl)phenyl)propiolamide

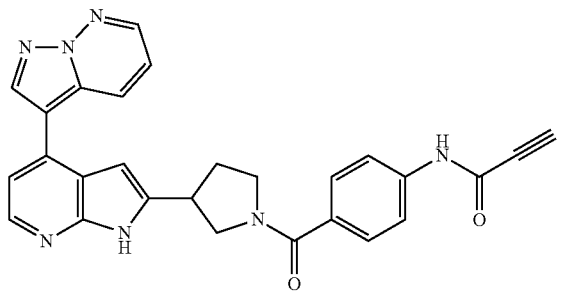 [SMILES: C#CC(=O)Nc1ccc(C(=O)N2CCC(c3cc4c(-c5cnn6ncccc56)ccnc4[nH]3)C2)cc1]

Starting from 3-(2-(pyrrolidin-3-yl)-1H-pyrrolo[2,3-b]pyridin-4-yl)pyrazolo[1,5-b]pyridazine (Example 122) and 4-propiolamidobenzoic acid.

LCMS (Method 1): Rt 2.67 min, m/z 476.2 [MH$^+$].

$^1$H NMR (400 MHz, d$_6$-DMSO): 2.10-2.45 (2H, m), 3.52-3.73 (4H, m), 3.86-4.05 (1H, m), 4.47 (1H, s), 6.45 (0.5H, s), 6.53 (0.5H, s), 7.27 (1H, dd, J=7.6, 5.0 Hz), 7.33 (1H, dd, J=9.2, 4.5 Hz), 7.51-7.58 (2H, m), 7.66 (2H, d, J=8.1 Hz), 8.22 (1H, dd, J=9.8, 4.9 Hz), 8.46 (1H, ddd, J=14.4, 9.2, 1.7 Hz), 8.55-8.65 (2H, m), 11.00 (1H, s), 11.73 (0.5H, s), 11.85 (0.5H, s).

Example 129: N-(4-(3-(4-(1H-Indol-3-yl)-1H-pyrrolo[2,3-b]pyridin-2-yl)pyrrolidine-1-carbonyl)phenyl)acrylamide

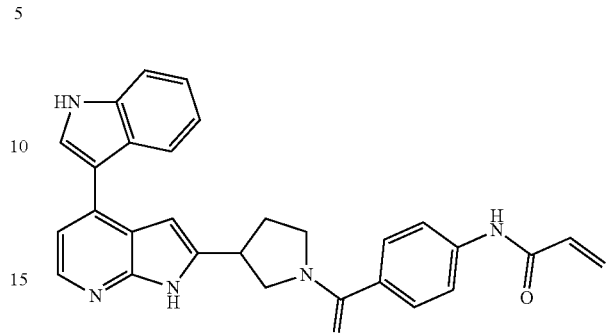

Starting from 4-(1H-Indol-3-yl)-2-(pyrrolidin-3-yl)-1H-pyrrolo[2,3-b]pyridine (Example 123) and 4-acrylamidobenzoic acid.

LCMS (Method 1): Rt 2.96 min, m/z 476.2 [MH$^+$].

$^1$H NMR (400 MHz, d$_6$-DMSO): 2.08-2.44 (2H, m), 3.51-3.75 (4H, m), 3.88-4.07 (1H, m), 5.79 (1H, d, J=10.2 Hz), 6.23-6.34 (1H, m), 6.39-6.55 (2H, m), 7.09-7.16 (1H, m), 7.17-7.23 (1H, m), 7.27-7.34 (1H, m), 7.48-7.60 (3H, m), 7.69-7.77 (2H, m), 7.80-7.96 (2H, m), 8.13-8.22 (1H, m), 10.32 (1H, s), 11.47-11.74 (2H, m).

Example 130: tert-Butyl 3-(4-(1H-indol-3-yl)-1H-pyrrolo[2,3-b]pyridin-2-yl)pyrrolidine-1-carboxylate

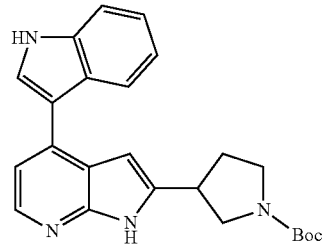 [SMILES: CC(C)(C)OC(=O)N1CCC(c2cc3c(-c4c[nH]c5ccccc45)ccnc3[nH]2)C1]

A solution of tert-butyl 3-(4-(1-(phenylsulfonyl)-1H-indol-3-yl)-1H-pyrrolo[2,3-b]pyridin-2-yl)pyrrolidine-1-carboxylate (Intermediate 26, 180 mg) in 1,4-dioxane (5 mL) was treated with 1 M NaOH solution (5 mL, 5 mmol) and stirred and heated at 70° C. for 1 h. After cooling, the mixture was diluted with water and extracted with 2-methyl-THF. The combined organic extracts were dried (Na$_2$SO$_4$), and concentrated in vacuo to give the title compound (138 mg).

LCMS (Method 3): Rt 1.05 min, m/z 403.3 [MH$^+$].

$^1$H NMR (400 MHz, d$_6$-DMSO), 1.41 (9H, d, J=2.9 Hz), 2.07-2.17 (1H, m), 2.25-2.34 (1H, m), 3.37-3.58 (4H, m), 3.74 (1H, dd, J=7.4, 10.3 Hz), 6.45 (1H, s), 7.10-7.15 (1H, m), 7.17-7.22 (1H, m), 7.30 (1H, d, J=4.9 Hz), 7.49-7.53 (1H, m), 7.84-7.88 (2H, m), 8.17 (1H, d, J=5.0 Hz), 11.57-11.64 (2H, m).

Example 131: 3-((3-(1H-Pyrrolo[2,3-b]pyridin-4-yl)pyrazolo[1,5-b]pyridazin-5-yl)oxy)propane-1,2-diol

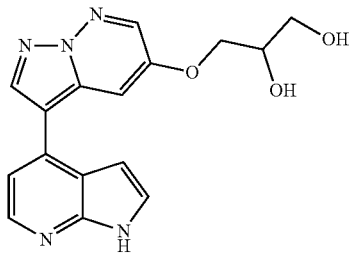 [SMILES: OCC(O)COc1cnn2ncc(-c3ccnc4[nH]ccc34)c2c1]

5-((2,2-Dimethyl-1,3-dioxolan-4-yl)methoxy)-3-(1H-pyrrolo[2,3-b]pyridin-4-yl)pyrazolo[1,5-b]pyridazine (Example 25, 73 mg, 0.20 mmol) in 3M aqueous HCl (2 mL) was heated at 80° C. for 6 h. After cooling, the pH was adjusted to pH 9 with sodium carbonate, and the mixture was extracted with ethyl acetate. The combined organic layers were washed with brine, dried (MgSO$_4$) and concentrated in vacuo, to afford the title compound as a white solid (31 mg, 49%).

LCMS (Method 1): Rt 2.42 min, m/z 326.3 [MH$^+$].

$^1$H NMR (400 MHz, CD$_3$OD): 3.68 (2H, d, J=5.6 Hz), 4.07-3.99 (1H, m), 4.13 (1H, dd, J=6.1, 10.0 Hz), 4.23 (1H, dd, J=3.8, 10.0 Hz), 6.65 (1H, d, J=3.5 Hz), 7.31 (1H, d, J=5.1 Hz), 7.46 (1H, d, J=3.5 Hz), 7.58 (1H, d, J=3.0 Hz), 8.26 (1H, d, J=5.1 Hz), 8.28 (1H, d, J=2.9 Hz), 8.39 (1H, s).

Example 132: 3-(5-Chloro-1H-pyrrolo[2,3-b]pyridin-4-yl)pyrazolo[1,5-b]pyridazine

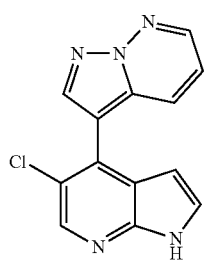 [SMILES: Clc1cnc2[nH]ccc2c1-c1cnn2ncccc12]

3M Aqueous NaOH (3 mL) was added to a solution of 3-(5-chloro-1-(phenylsulfonyl)-1H-pyrrolo[2,3-b]pyridin-4-yl)pyrazolo[1,5-b]pyridazine (Intermediate 89, 150 mg, 0.366 mmol) in dioxane (6 mL) and IPA (1 mL) and the mixture was heated at 70° C. for 6 h. After cooling, the mixture was treated with 6M HCl until the pH=7, then concentrated in vacuo. The residue was purified by FCC eluting with 2-10% MeOH in DCM to give the title compound (42 mg, 42%) as a yellow solid.

LCMS (Method 1): Rt 3.39 min, m/z 270.2, 272.2 [MH$^+$].

$^1$H NMR (400 MHz, d$_6$-DMSO): 6.27 (1H, d, J=3.4 Hz), 7.33 (1H, dd, J=4.4, 9.1 Hz), 7.60 (1H, d, J=3.2 Hz), 8.07 (1H, dd, J=1.9, 9.1 Hz), 8.37 (1H, s), 8.45 (1H, s), 8.60 (1H, dd, J=1.7, 4.4 Hz), 12.04 (1H, s).

Example 133: 4-(1-Ethyl-1H-1,2,3-triazol-4-yl)-1H-pyrrolo[2,3-b]pyridine 4-(1-ethyl-1H-pyrazol-5-yl)-1H-pyrrolo[2,3-b]pyridine

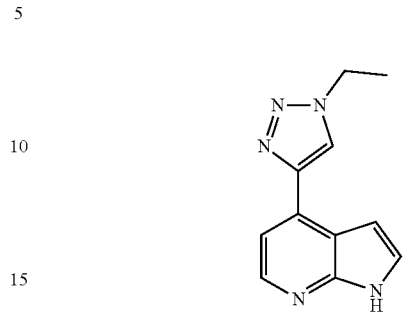

4-Ethynyl-1H-pyrrolo[2,3-b]pyridine (which was prepared as described in *ACS Combinatorial Science*, 2015, 17(1), 5-10) (50 mg, 0.35 mmol), bromoethane (26 □l, 0.35 mmol) and sodium azide (23.8 mg, 0.37 mmol) were suspended in tertBuOH/water (1:1, 1 mL) in a 15 mL centrifuge tube and a solution of copper sulfate (0.5 M, 17.5 µM, 5% mol) and sodium ascorbate (1 M aqueous solution, 35.0 µM, 10% mol) were added. The mixture was stirred at r.t. overnight, then conc. aqueous ammonia (1 ml) and water (3 mL) were added. The resulting precipitate was collected by centrifugation, washed with water, Et$_2$O and dried to give the title compound (37 mg, 50%) as a white solid.

LCMS (Method 1): Rt 2.15 min, m/z 214.0 [MH$^+$].

$^1$H NMR (400 MHz, d$_6$-DMSO): 1.53 (3H, dd, J=7.3, 7.3 Hz), 4.50 (2H, q, J=7.3 Hz), 6.99 (1H, dd, J=2.0, 3.5 Hz), 7.60-7.53 (2H, m), 8.26 (1H, d, J=5.0 Hz), 8.89 (1H, s), 11.77 (1H, br s).

By proceeding in a similar manner to Example 133, the following compounds were prepared:

Example 134: 4-(1-Benzyl-1H-1,2,3-triazol-4-yl)-1H-pyrrolo[2,3-b]pyridine

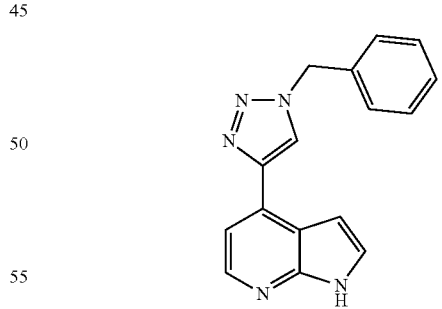

Starting from 4-ethynyl-1H-pyrrolo[2,3-b]pyridine (which was prepared as described in *ACS Combinatorial Science*, 2015, 17(1), 5-10) and benzyl bromide.

LCMS (Method 1): Rt 3.17 min, m/z 275.9 [MH$^+$].

$^1$H NMR (400 MHz, d$_6$-DMSO): 5.71 (2H, s), 6.98 (1H, dd, J=1.9, 3.4 Hz), 7.44-7.31 (5H, m), 7.60-7.53 (2H, m), 8.26 (1H, d, J=4.8 Hz), 9.00 (1H, s), 11.77-11.76 (1H, m).

Example 135: 4-(1-(4-Methoxybenzyl)-1H-1,2,3-triazol-4-yl)-1H-pyrrolo[2,3-b]pyridine

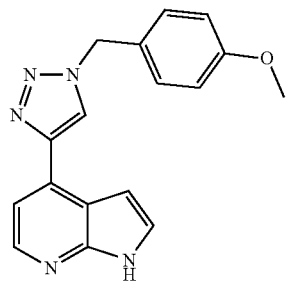 [SMILES: COc1ccc(Cn2cc(-c3ccnc4[nH]ccc34)nn2)cc1]

Starting from 4-ethynyl-1H-pyrrolo[2,3-b]pyridine (which was prepared as described in *ACS Combinatorial Science*, 2015, 17(1), 5-10) and 4-methoxybenzyl bromide.
LCMS (Method 2): Rt 3.17 min, m/z 306.2 [MH$^+$].
$^1$H NMR (400 MHz, d$_6$-DMSO): 3.74 (3H, s), 5.62 (2H, s), 6.99-6.92 (3H, m), 7.41-7.35 (2H, m), 7.58-7.53 (2H, m), 8.25 (1H, d, J=5.0 Hz), 8.94 (1H, s), 11.76 (1H, br s).

Example 136: 4-(1-(Pyridin-3-ylmethyl)-1H-1,2,3-triazol-4-yl)-1H-pyrrolo[2,3-b]pyridine

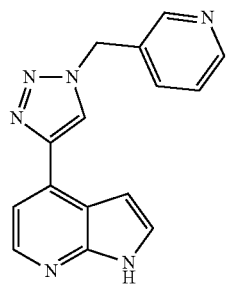 [SMILES: c1cncc(Cn2cc(-c3ccnc4[nH]ccc34)nn2)c1]

Starting from 4-ethynyl-1H-pyrrolo[2,3-b]pyridine (which was prepared as described in *ACS Combinatorial Science*, 2015, 17(1), 5-10) and 3-(bromomethyl)pyridine
LCMS (Method 2): Rt 1.79 min, m/z 277.2 [MH$^+$].
$^1$H NMR (400 MHz, d$_6$-DMSO): 5.78 (2H, s), 6.98 (1H, dd, J=1.9, 3.5 Hz), 7.44 (1H, dd, J=4.7, 7.8 Hz), 7.60-7.54 (2H, m), 7.84-7.79 (1H, m), 8.27 (1H, d, J=4.9 Hz), 8.61-8.54 (1H, m), 8.71 (1H, s), 9.03 (1H, s), 11.78 (1H, s).

Example 137: tert-Butyl (3-(3-(4-(pyrazolo[1,5-b]pyridazin-3-yl)-1H-pyrrolo[2,3-b]pyridin-2-yl)pyrrolidine-1-carbonyl)phenyl)carbamate

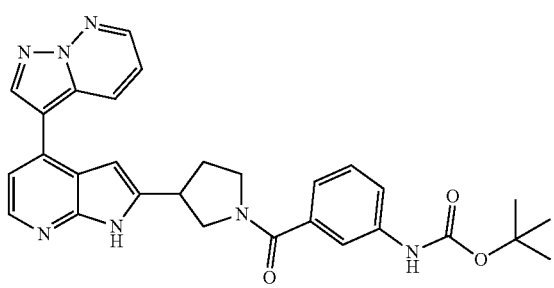 [SMILES: CC(C)(C)OC(=O)Nc1cccc(C(=O)N2CCC(c3cc4c(-c5cnn6ncccc56)ccnc4[nH]3)C2)c1]

A solution of 3-((tert-butoxycarbonyl)amino)benzoic acid (45 mg, 0.19 mmol) and DIPEA (31 mg, 0.24 mmol) in DMF (1.5 mL) was treated with HATU (66 mg, 0.174 mmol) and the mixture was stirred for 15 mins. The solution was added to 3-[2-(pyrrolidin-3-yl)-1H-pyrrolo[2,3-b]pyridine-4-yl)pyrazolo[1,5-b]pyridazine (Example 122, 48 mg, 0.158 mmol) and the resultant mixture was stirred for 1 h Water was added resulting in the precipitation of a yellow solid, which was collected by filtration, washed with water and dried to give the title compound (110 mg) as a yellow solid.
LCMS (Method 3): Rt 1.14 min, m/z 524.3 [MH$^+$].
$^1$H NMR (400 MHz, CDCl$_3$) 1.50-1.44 (9H, m), 2.30-2.21 (0.5H, m), 2.46-2.33 (1H, m), 2.56-2.47 (0.5H, m), 3.73-3.63 (1.5H, m), 3.84-3.74 (1.5H, m), 4.02-3.89 (1.5H, m), 4.26 (0.5H, s), 6.36 (0.5H, s), 6.46 (0.5H, s), 7.26-7.13 (5H, m), 7.48-7.41 (1H, m), 7.65 (0.5H, s), 7.74 (0.5H, s), 8.28-8.16 (2H, m), 8.44-8.36 (2H, m), 12.08 (1H, s).

By proceeding in a similar manner to Example 137, the following compounds were prepared:

Example 138: tert-Butyl 4-(3-(4-(pyrazolo[1,5-b]pyridazin-3-yl)-1H-pyrrolo[2,3-b]pyridin-2-yl)pyrrolidine-1-carbonyl)piperidine-1-carboxylate

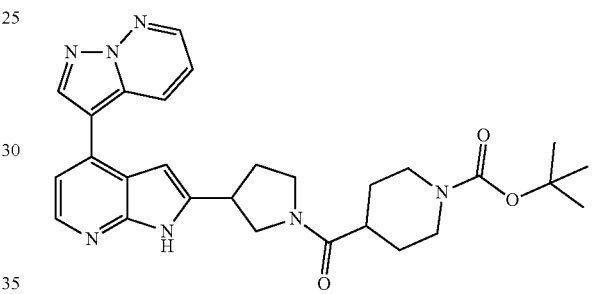

Starting from 1-(tert-butoxycarbonyl)piperidine-4-carboxylic acid (103 mg, 0.45 mmol) and 3-[2-(pyrrolidin-3-yl)-1H-pyrrolo[2,3-b]pyridine-4-yl)pyrazolo[1,5-b]pyridazine (Example 122)
LCMS (Method 3): Rt 1.08 min, m/z 516.3 [MH$^+$].
$^1$H NMR (400 MHz, CDCl$_3$): 1.44 (4.5H, s), 1.46 (4.5H, s), 1.82-1.64 (4H, m), 2.46-2.31 (1H, m), 2.62-2.47 (2H, m), 2.84-2.63 (2H, m), 3.66-3.58 (0.5H, m), 3.88-3.68 (3H, m), 4.00-3.93 (0.5H, m), 4.22-4.07 (3H, m), 6.45 (0.5H, s), 6.49 (0.5H, s), 7.19-7.13 (1H, m), 7.26-7.22 (1H, m), 8.26-8.20 (1H, m), 8.32-8.29 (1H, m), 8.43-8.40 (1H, m), 8.45 (0.5H, s), 8.48 (0.5H, s), 12.17 (0.5H, s), 12.50 (0.5H, s).

Example 139: (3-Aminophenyl)(3-(4-(pyrazolo[1,5-b]pyridazin-3-yl)-1H-pyrrolo[2,3-b]pyridin-2-yl)pyrrolidin-1-yl)methanone

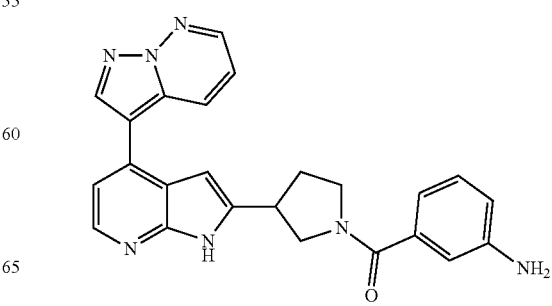

To tert-butyl (3-(3-(4-(pyrazolo[1,5-b]pyridazin-3-yl)-1H-pyrrolo[2,3-b]pyridin-2-yl)pyrrolidine-1-carbonyl)phenyl)carbamate (Example 137, 110 mg, 0.2 mmol) in DCM (4 mL) was added TFA (2 mL). After 20 min at 20° C., toluene was added and the mixture was concentrated in vacuo. The residue was loaded onto an SCX-2 cartridge and the cartridge was eluted with MeOH followed by 2N $NH_3$ in MeOH. The methanolic ammonia fraction was concentrated in vacuo to afford the title compound as a yellow gum (72 mg, quant.)

LCMS (Method 3): Rt 0.84 min, m/z 424.3 [MH$^+$].

$^1$H NMR (400 MHz, MeOD): 2.35-2.17 (1H, m), 2.46-2.38 (0.5H, m), 2.56-2.48 (0.5H, m), 3.80-3.59 (3H, m), 3.90-3.81 (1H, m), 3.95 (0.5H, dd, J=7.0, 10.8 Hz), 4.15 (0.5H, dd, J=7.2, 11.6 Hz), 6.32 (0.5H, s), 6.42 (0.5H, s), 6.86-6.76 (3H, m), 7.24-7.15 (3H, m), 8.28-8.21 (2H, m), 8.45-8.40 (2H, m).

By proceeding in a similar manner to Example 139, the following compounds were prepared:

Example 140: Piperidin-4-yl(3-(4-(pyrazolo[1,5-b]pyridazin-3-yl)-1H-pyrrolo[2,3-b]pyridin-2-yl)pyrrolidin-1-yl)methanone

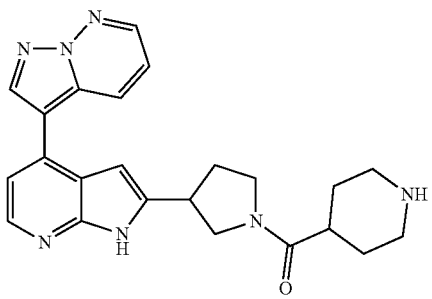 [SMILES: O=C(C1CCNCC1)N1CCC(c2cc3c(-c4cnn5ncccc45)ccnc3[nH]2)C1]

Starting from tert-butyl 4-(3-(4-(pyrazolo[1,5-b]pyridazin-3-yl)-1H-pyrrolo[2,3-b]pyridin-2-yl)pyrrolidine-1-carbonyl)piperidine-1-carboxylate (Example 138).

LCMS (Method 3): Rt 0.64 min, m/z 416.3 [MH$^+$].

$^1$H NMR (400 MHz, CDCl$_3$): 1.80-1.70 (3H, m), 2.42-2.24 (1H, m), 2.73-2.44 (4H, m), 3.15-3.08 (0.5H, m), 3.24-3.15 (1.5H, m), 3.64-3.56 (0.5H, m), 3.85-3.66 (3H, m), 3.92 (0.5H, ddd, J=3.3, 8.5, 12.0 Hz), 4.11-4.05 (0.5H, m), 4.18 (0.5H, dd, J=6.7, 11.2 Hz), 5.53 (1H, s), 5.69 (1H, s), 6.42 (0.5H, s), 6.45 (0.5H, s), 7.17-7.11 (1H, m), 7.23-7.19 (1H, m), 8.24-8.20 (1H, m), 8.31-8.29 (1H, m), 8.42-8.39 (1H, m), 8.44 (0.5H, s), 8.46 (0.5H, s), 11.74 (0.5H, s), 12.07 (0.5H, s).

Example 141: N-(3-(3-(4-(Pyrazolo[1,5-b]pyridazin-3-yl)-1H-pyrrolo[2,3-b]pyridin-2-yl)pyrrolidine-1-carbonyl)phenyl)acrylamide

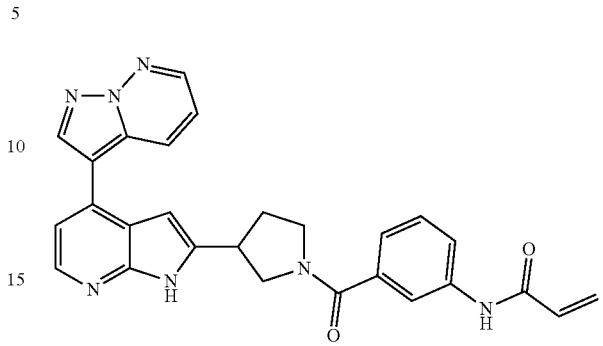

To (3-aminophenyl)(3-(4-(pyrazolo[1,5-b]pyridazin-3-yl)-1H-pyrrolo[2,3-b]pyridin-2-yl)pyrrolidin-1-yl)methanone (Example 139, 32 mg, 0.075 mmol) and DIPEA (20 mg, 0.15 mmol) in THF (2 mL) was added acryloyl chloride (9.1 mg, 0.1 mmol) in THF (0.4 mL). After 15 min the reaction was quenched with water and extracted with ethyl acetate, there was also some insoluble material. The ethyl acetate extracts were dried (Na$_2$SO$_4$) and concentrated in vacuo. The residue was combined with the insoluble material in MeOH/DCM, preadsorbed onto silica and purified by FCC eluting with 0-6% MeOH in DCM. The resulting solid product was sonicated with ethyl acetate and the supernatant was removed by pipette to afford the title compound as a yellow solid (7 mg, 19%) after drying under vacuum.

LCMS (Method 1): Rt 2.72 min, m/z 478.1 [MH$^+$].

$^1$H NMR (400 MHz, d$_6$-DMSO, 80° C.), 2.40-2.18 (2H, m), 3.5-3.7 (4H, m), 3.9-4.0 (1H, m), 5.72 (1H, dd, J=1.9, 10.1 Hz), 6.25 (1H, dd, J=1.9, 17.0 Hz), 6.41 (1H, dd, J=10.1, 17.0 Hz), 6.42 (1H, bs), 7.24-7.19 (2H, m), 7.28 (1H, dd, J=4.3, 9.1 Hz), 7.36 (1H, t, J=7.9 Hz), 7.67 (1H, dd, J=1.1, 8.2 Hz), 7.87 (1H, s), 8.21 (1H, d, J=5.0 Hz), 8.38 (1H, dd, J=1.2, 9.1 Hz), 8.52-8.49 (2H, m), 9.98 (1H, s), 11.55 (1H, s);

Example 142: (E)-4-(Dimethylamino)-N-(3-(3-(4-(pyrazolo[1,5-b]pyridazin-3-yl)-1H-pyrrolo[2,3-b]pyridin-2-yl)pyrrolidine-1-carbonyl)phenyl)but-2-enamide

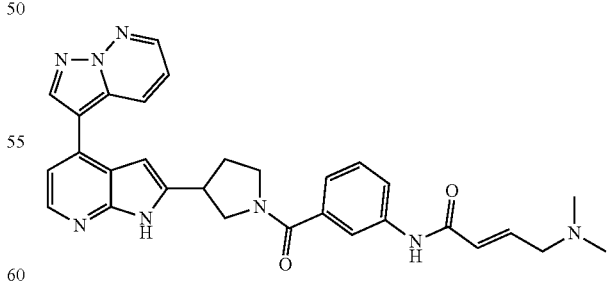

To (3-aminophenyl)(3-(4-(pyrazolo[1,5-b]pyridazin-3-yl)-1H-pyrrolo[2,3-b]pyridin-2-yl)pyrrolidin-1-yl)methanone (Example 139, 36 mg, 0.085 mmol) and DIPEA (44 mg, 0.34 mmol) in THF (2 mL) was added (E)-4-(dimethylamino)but-2-enoyl chloride hydrochloride (16.3 mg, 0.09 mmol) in acetonitrile (0.6 mL). After 15 min the reaction was quenched with water and extracted with ethyl acetate. The aqueous layer was basified with tripotassium phosphate to precipitate a brown solid which was extracted with ethyl acetate. The combined organic layers were dried, evaporated and combined with the brown solid. This material was purified by acidic MDAP followed by FCC eluting with 0-10% 2M ammonia/MeOH in DCM to give the title compound as a yellow gum (2.5 mg, 5.5%).

LCMS (Method 1): Rt 2.18 min, m/z 535.1 [MH$^+$].

$^1$H NMR (400 MHz, d$_6$-DMSO) 2.16 (3H, s), 2.17 (3H, s), 2.44-2.20 (2H, m), 3.07-3.03 (1H, m), 3.17 (1H, d, J=5.3 Hz), 3.72-3.55 (4H, m), 3.85-3.92 (0.5H, m), 3.97-4.06 (0.5H, m), 6.21-6.29 (1H, m), 6.44 (0.5H, bs), 6.53 (0.5H, bs), 6.78-6.69 (1H, m), 7.41-7.19 (4H, m), 7.70-7.64 (1H, m), 7.92-7.90 (1H, m), 8.22 (1H, dd, J=5.0, 12.4 Hz), 8.50-8.41 (1H, m), 8.64-8.55 (2H, m), 10.15-10.19 (1H, m), 11.74 (0.5H, s), 11.85 (0.5H, s);

By proceeding in a similar manner to Example 142, the following compounds were prepared:

Example 143: 1-(4-(3-(4-(Pyrazolo[1,5-b]pyridazin-3-yl)-1H-pyrrolo[2,3-b]pyridin-2-yl)pyrrolidine-1-carbonyl)piperidin-1-yl)prop-2-en-1-one

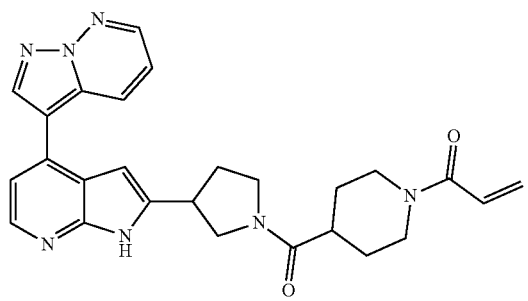 [SMILES: C=CC(=O)N1CCC(C(=O)N2CCC(c3cc4c(-c5cnn6ncccc56)ccnc4[nH]3)C2)CC1]

Starting from piperidin-4-yl(3-(4-(pyrazolo[1,5-b]pyridazin-3-yl)-1H-pyrrolo[2,3-b]pyridin-2-yl)pyrrolidin-1-yl)methanone (Example 140) and acryloyl chloride.

LCMS (Method 1): Rt 2.49 min, m/z 470.2 [MH$^+$].

$^1$H NMR (400 MHz, d$_6$-DMSO), 1.52-1.29 (2H, m), 1.79-1.65 (2H, m), 2.45-2.01 (2H, m), 2.81-2.67 (2H, m), 3.11 (1H, bt, J=12.3 Hz), 3.35-4.09 (5H, m), 4.01-4.12 (1H, m), 4.42 (1H, bs), 5.66 (1H, dd, J=2.3, 10.5 Hz), 6.08 (1H, dd, J=2.3, 16.7 Hz), 6.46 (0.5H, bs), 6.51 (0.5H, bs), 6.80 (1H, dd, J=10.5, 16.7 Hz), 7.29-7.25 (1H, m), 7.32-7.36 (1H, m), 8.21-8.24 (1H, m), 8.48-8.44 (1H, m), 8.59-8.55 (1H, m), 8.59-8.61 (1H, m) and 11.81 (1H, bs).

Example 144: 2-Chloro-N-(4-(3-(4-(pyrazolo[1,5-b]pyridazin-3-yl)-1H-pyrrolo[2,3-b]pyridin-2-yl)pyrrolidine-1-carbonyl)phenyl)acetamide

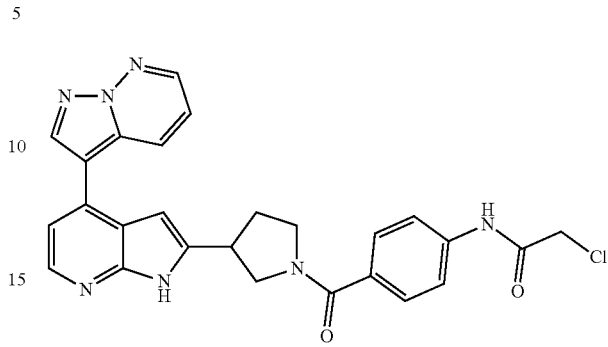

A solution of 4-chloroacetylamidobenzoic acid (31 mg, 0.145 mmol) and DIPEA (24 mg, 0.186 mmol) in DMF (1 mL) was treated with HATU (60 mg, 0.158 mmol) and stirred for 15 mins. The solution was added to 3-[2-(pyrrolidin-3-yl)-1H-pyrrolo[2,3-b]pyridine-4-yl)pyrazolo[1,5-b]pyridazine (Example 122, 37 mg, 0.122 mmol) and the resultant mixture was stirred for 1 h. Water was added resulting in the precipitation of a yellow solid which was collected by filtration, washed with water then dissolved in MeOH/DCM, preadsorbed onto silica and purified by FCC eluting with 0-10% MeOH in DCM. The resulting solid product was sonicated with ethyl acetate and the supernatant was removed by pipette to afford the title compound as a yellow solid (27 mg, 44%) after drying under vacuum.

LCMS (Method 1): Rt 2.77 min, m/z 500.1 [MH$^+$].

$^1$H NMR (400 MHz, d$_6$-DMSO): 2.40-2.15 (2H, m), 3.73-3.59 (4H, m), 3.88-3.96 (1H, m), 4.29-4.27 (2H, bs), 6.44 (0.5H, s), 6.52 (0.5H, bs), 7.36-7.25 (2H, m), 7.52-7.58 (2H, m), 7.68-7.63 (2H, m), 8.22 (1H, dd, J=4.9, 9.9 Hz), 8.41-8.50 (1H, dd, m), 8.64-8.55 (2H, m), 10.49-10.47 (1H, m), 11.73 (0.5H, bs), 11.8 (0.5H, bs);

By proceeding in a similar manner to Example 144, the following compounds were prepared:

Example 145: 2-Chloro-N-(3-(3-(4-(pyrazolo[1,5-b]pyridazin-3-yl)-1H-pyrrolo[2,3-b]pyridin-2-yl)pyrrolidine-1-carbonyl)phenyl)acetamide

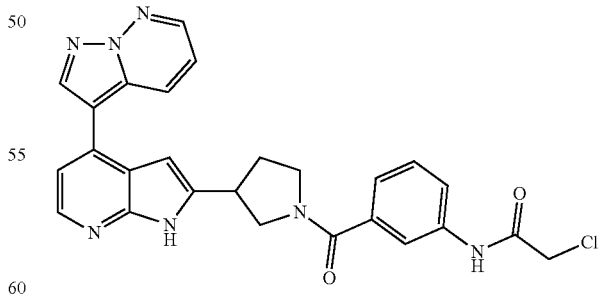

Starting from 3-chloroacetylamidobenzoic acid and 3-[2-(pyrrolidin-3-yl)-1H-pyrrolo[2,3-b]pyridine-4-yl)pyrazolo[1,5-b]pyridazine (Example 122).

LCMS (Method 1): Rt 2.80 min, m/z 500.1 [MH$^+$].

$^1$H NMR (400 MHz, d$_6$-DMSO): 2.15-2.44 (2H, m), 3.54-3.73 (4H, m), 3.84-3.91 (0.5H, m), 3.97-4.04 (0.5H, m), 4.25-4.27 (2H, m), 6.44 (0.5H, bs), 6.53 (0.5H, bs), 7.23-7.29 (2H, m), 7.30-7.36 (1H, m), 7.37-7.44 (1H, m), 7.59-7.65 (1H, m), 7.83 (1H, bs), 8.19-8.25 (1H, m), 8.40-8.50 (1H, m), 8.54-8.64 (2H, m), 10.40-10.45 (1H, m), 11.74 (0.5H, bs) and 11.85 (0.5H, bs).

Example 146: N-(3-(3-(4-(Pyrazolo[1,5-b]pyridazin-3-yl)-1H-pyrrolo[2,3-b]pyridin-2-yl)pyrrolidine-1-carbonyl)phenyl)propiolamide

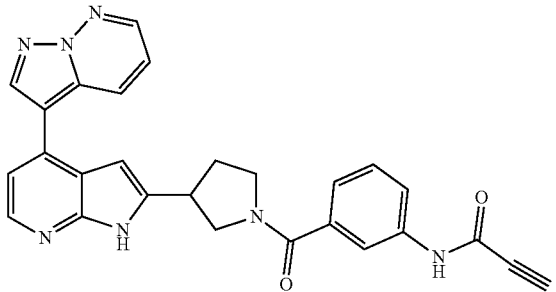 [SMILES: C#CC(=O)Nc1cccc(C(=O)N2CCC(c3cc4c(-c5cnn6ncccc56)ccnc4[nH]3)C2)c1]

Starting from 3-propiolamidobenzoic acid and 3-[2-(pyrrolidin-3-yl)-1H-pyrrolo[2,3-b]pyridine-4-yl)pyrazolo[1,5-b]pyridazine (Example 122).

LCMS (Method 1): Rt 2.72 min, m/z 476.2 [MH⁺].

¹H NMR (400 MHz, d₆-DMSO) 2.41-2.15 (2H, m), 3.74-3.54 (4H, m), 3.82-4.06 (1H, m), 4.45 (1H, m), 6.53 (0.5H, bs), 6.64 (0.5H, bs), 7.43-7.25 (4H, m), 7.68-7.63 (1H, m), 7.83-7.79 (1H, m), 8.22 (1H, dd, J=5.0, 11.0 Hz), 8.50-8.41 (1H, m), 8.64-8.55 (2H, m), 10.94-10.91 (1H, m), 11.73 (0.5H, bs) and 11.85 (0.5H, bs).

Example 147: 1-(4-(3-(4-(Pyrazolo[1,5-b]pyridazin-3-yl)-1H-pyrrolo[2,3-b]pyridin-2-yl)pyrrolidine-1-carbonyl)piperidin-1-yl)prop-2-yn-1-one

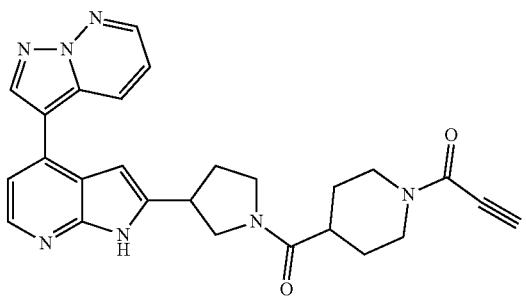 [SMILES: C#CC(=O)N1CCC(C(=O)N2CCC(c3cc4c(-c5cnn6ncccc56)ccnc4[nH]3)C2)CC1]

Propiolic acid (15 mg, 0.214 mmol) in DCM (1.5 ml) was treated with DCCl (25 mg, 0.121 mmol). After 1 h the solid was filtered off and the solution added to piperidin-4-yl-(3-(4-(pyrazolo[1,5-b]pyridazin-3-yl)-1H-pyrrolo[2,3-b]pyridin-2-yl)pyrrolidin-1-yl)methanone (Example 140, 38 mg, 0.092 mmol) and DIPEA (18 mg, 0.139 mmol) in DCM (0.5 mL). After 15 min the reaction was diluted with DCM and washed with water. The organic layer was dried (Na₂SO₄), and concentrated in vacuo. The residue was purified by FCC eluting with 0-20% iPrOH in DCM to afford the title compound as a green solid (8.5 mg, 20%) after drying under vacuum.

LCMS (Method 1): Rt 2.54 min, m/z 468.2 [MH⁺].

¹H NMR (400 MHz, d-DMSO), 1.29-1.56 (2H, m), 1.64-1.85 (2H, m), 2.03-2.45 (2H, m), 2.73-2.84 (2H, m), 3.23 (1H, bt, J=12.3 Hz), 3.35-4.09 (5H, m), 4.18-4.35 (2H, m), 4.52-4.54 (1H, m), 6.46 (0.5H, bs), 6.51 (0.5H, bs), 7.29-7.26 (1H, m), 7.31-7.36 (1H, m), 8.21-8.24 (1H, m), 8.48-8.44 (1H, m), 8.59-8.55 (1H, m), 8.59-8.61 (1H, m) and 11.81 (1H, bs).

Example 148: N-(4-(3-(4-(Pyrazolo[1,5-b]pyridazin-3-yl)-1H-pyrrolo[2,3-b]pyridin-2-yl)pyrrolidine-1-carbonyl)phenyl)acrylamide

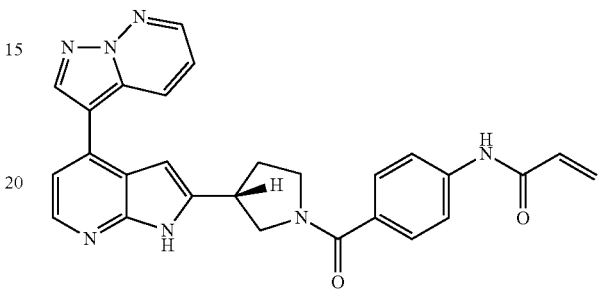

A solution of 4-acrylamidobenzoic acid (40 mg, 0.209 mmol) and DIPEA (36 mg, 0.279 mmol) in DMF (1 mL) was treated with HATU (68 mg, 0.179 mmol) and stirred for 15 mins. The solution was added to 3-(2-(pyrrolidin-3-yl)-1H-pyrrolo[2,3-b]pyridin-4-yl)pyrazolo[1,5-b]pyridazine derived from the faster running Boc derivative (Example 124, 42 mg, 0.138 mmol) and the mixture was stirred for 45 min. Water was added resulting in the precipitation of a yellow solid. The solid was collected by filtration, washed with water then dissolved in MeOH/DCM, preadsorbed onto silica and purified by FCC eluting with 0-10% MeOH in DCM. The resulting solid product was sonicated with ethyl acetate and the supernatant was removed by pipette to afford the title compound as a yellow solid (30 mg, 45%) after drying under vacuum.

LCMS (Method 1): Rt 2.69 min, m/z 478.1 [MH⁺].

¹H NMR (400 MHz, d₆-DMSO): 2.40-2.15 (2H, m), 3.76-3.59 (4H, m), 3.90-4.04 (1H, m) 5.81-5.75 (1H, m), 6.28 (1H, bd, J=16.9 Hz), 6.54-6.40 (2H, m), 7.24-7.30 (1H, m), 7.33 (1H, dd, J=4.3, 9.1 Hz), 7.52-7.58 (2H, m), 7.73 (2H, bd, J=8.2 Hz), 8.2-8.25 (1H, m), 8.41-8.50 (1H, m), 8.64-8.55 (2H, m), 10.32 (1H, bs).

By proceeding in a similar manner to Example 148, the following compounds were prepared:

Example 149: N-(3-(3-(4-(Pyrazolo[1,5-b]pyridazin-3-yl)-1H-pyrrolo[2,3-b]pyridin-2-yl)pyrrolidine-1-carbonyl)phenyl)acrylamide

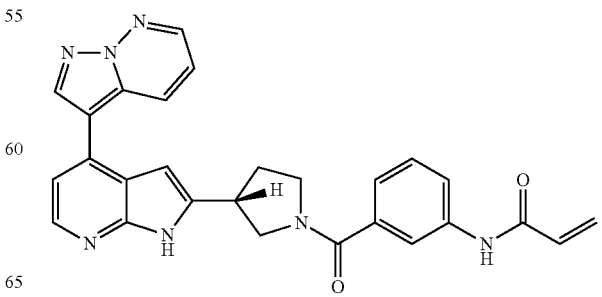

Starting from 3-acrylamidobenzoic acid and 3-(2-(pyrrolidin-3-yl)-1H-pyrrolo[2,3-b]pyridin-4-yl)pyrazolo[1,5-b]pyridazine (Example 124)

LCMS (Method 1): Rt 2.72 min, m/z 478.1 [MH⁺].

¹H NMR (400 MHz, d₆-DMSO) 2.41-2.15 (2H, m), 3.73-3.59 (4H, m), 3.93-3.86 (0.5H, m), 3.98-4.04 (0.5H, m), 5.80-5.74 (1H, m), 6.30-6.23 (1H, m), 6.47-6.37 (1.5H, m), 6.53 (0.5H, bs), 7.21-7.30 (2H, m), 7.30-7.36 (1H, m), 7.36-7.43 (1H, m), 7.71-7.66 (1H, m), 7.93 (1H, bs), 8.25-8.20 (1H, m), 8.49-8.41 (1H, m), 8.60-8.55 (1.5H, m), 8.63 (0.5H, s) and 10.25-10.29 (1H, m).

Example 150: (R)—N-(4-(3-(4-(Pyrazolo[1,5-b]pyridazin-3-yl)-1H-pyrrolo[2,3-b]pyridin-2-yl)pyrrolidine-1-carbonyl)phenyl)propiolamide

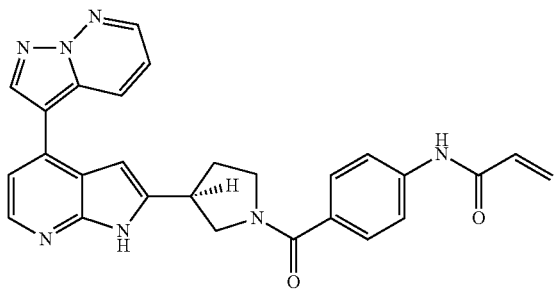

Starting from of 4-acrylamidobenzoic acid and 3-(2-(pyrrolidin-3-yl)-1H-pyrrolo[2,3-b]pyridin-4-yl)pyrazolo[1,5-b]pyridazine (Example 125).

LCMS (Method 1): Rt 2.71 min, m/z 478.1 [MH⁺].

¹H NMR (400 MHz, d₆-DMSO) 2.40-2.15 (2H, m), 3.76-3.59 (4H, m), 3.90-4.04 (1H, m) 5.81-5.75 (1H, m), 6.28 (1H, bd, J=16.9 Hz), 6.54-6.40 (2H, m), 7.24-7.30 (1H, m), 7.33 (1H, dd, J=4.3, 9.1 Hz), 7.52-7.58 (2H, m), 7.73 (2H, bd, J=8.2 Hz), 8.2-8.25 (1H, m), 8.41-8.50 (1H, m), 8.64-8.55 (2H, m), 10.32 (1H, bs);

Example 151: (S)—N-(3-(3-(4-(Pyrazolo[1,5-b]pyridazin-3-yl)-1H-pyrrolo[2,3-b]pyridin-2-yl)pyrrolidine-1-carbonyl)phenyl)acrylamide

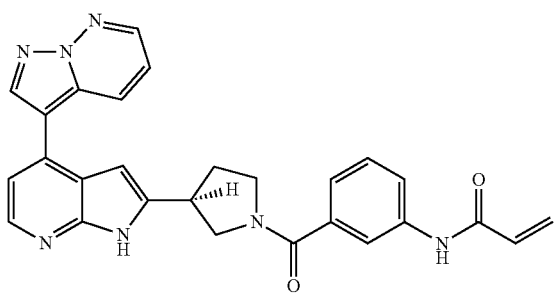

Starting from 3-acrylamidobenzoic acid and 3-(2-(pyrrolidin-3-yl)-1H-pyrrolo[2,3-b]pyridin-4-yl)pyrazolo[1,5-b]pyridazine (Example 125).

LCMS (Method 1): Rt 2.75 min, m/z 478.1 [MH⁺].

¹H NMR (400 MHz, d₆-DMSO): 2.41-2.15 (2H, m), 3.73-3.59 (4H, m), 3.93-3.86 (0.5H, m), 3.98-4.04 (0.5H, m), 5.80-5.74 (1H, m), 6.30-6.23 (1H, m), 6.47-6.37 (1.5H, m), 6.53 (0.5H, bs), 7.21-7.30 (2H, m), 7.30-7.36 (1H, m), 7.36-7.43 (1H, m), 7.71-7.66 (1H, m), 7.93 (1H, bs), 8.25-8.20 (1H, m), 8.49-8.41 (1H, m), 8.60-8.55 (1.5H, m), 8.63 (0.5H, s) and 10.25-10.29 (1H, m)

Example 152: N-(2-Oxo-2-(3-(4-(pyrazolo[1,5-b]pyridazin-3-yl)-1H-pyrrolo[2,3-b]pyridin-2-yl)pyrrolidin-1-yl)ethyl)acrylamide

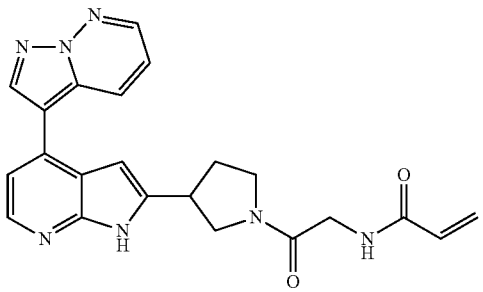 [SMILES: C=CC(=O)NCC(=O)N1CCC(c2cc3c(-c4cnn5ncccc45)ccnc3[nH]2)C1]

Starting from N-acryloylglycine and 3-(2-(pyrrolidin-3-yl)-1H-pyrrolo[2,3-b]pyridin-4-yl)pyrazolo[1,5-b]pyridazine (Example 122).

LCMS (Method 1): Rt 2.24 min, m/z 416.2 [MH⁺].

¹H NMR (400 MHz, d₆-DMSO): 2.04-2.48 (2H, m), 3.33-3.75 (4H, m), 3.86-4.02 (3H, m), 5.60 (1H, dd, J=2.1, 10.2 Hz), 6.11 (1H, dd, J=2.1, 17.1 Hz), 6.38 (1H, dd, J=10.2, 17.1 Hz), 6.48 (0.5H, m), 6.55 (0.5H, m), 7.26-7.30 (1H, m), 7.32-7.37 (1H, m), 8.22-8.30 (2H, m), 8.44-8.49 (1H, m), 8.56-8.58 (1H, m), 8.62 (1H, s) and 11.81 (1H, bs).

Example 153: 1-((2S)-2-(3-(4-(Pyrazolo[1,5-b]pyridazin-3-yl)-1H-pyrrolo[2,3-b]pyridin-2-yl)pyrrolidine-1-carbonyl)pyrrolidin-1-yl)prop-2-en-1-one

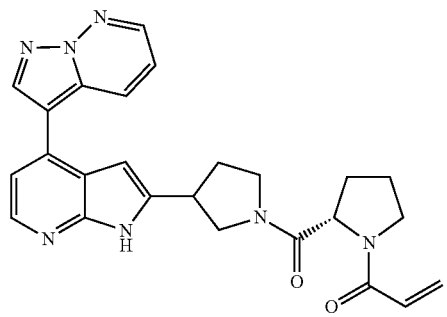 [SMILES: C=CC(=O)N1CCC[C@H]1C(=O)N1CCC(c2cc3c(-c4cnn5ncccc45)ccnc3[nH]2)C1]

Starting from acryloyl-L-proline and 3-(2-(pyrrolidin-3-yl)-1H-pyrrolo[2,3-b]pyridin-4-yl)pyrazolo[1,5-b]pyridazine (Example 122).

LCMS (Method 1): Rt 2.47 min, m/z 456.2 [MH⁺].

¹H NMR (400 MHz, d₆-DMSO): 1.68-2.48 (6H, m), 3.3-3.84 (6H, m), 3.85-3.98 (0.75H, m), 4.16-4.25 (0.25, m), 4.57-4.68 (0.75H, m), 4.81-4.91 (0.25H, m), 5.12-5.72 (1H, m), 5.87-6.30 (1.5H, m), –6.44-6.68 (1.5H, m), 7.26-7.37 (2H, m), 8.21-8.25 (1H, m), 8.44-8.73 (3H, m), 11.77-11.86 (1H, m);

Example 154: 1-((2R)-2-(3-(4-(Pyrazolo[1,5-b]pyridazin-3-yl)-1H-pyrrolo[2,3-b]pyridin-2-yl)pyrrolidine-1-carbonyl)pyrrolidin-1-yl)prop-2-en-1-one

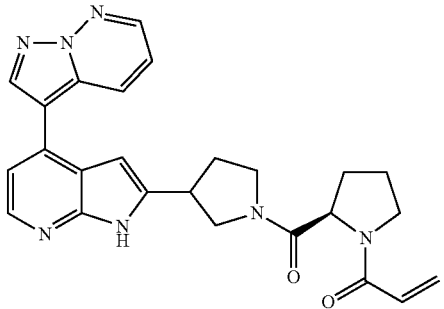 [SMILES: C=CC(=O)N1CCC[C@@H]1C(=O)N1CCC(c2cc3c(-c4cnn5ncccc45)ccnc3[nH]2)C1]

Starting from acryloyl-D-proline (Intermediate 25) and 3-(2-(pyrrolidin-3-yl)-1H-pyrrolo[2,3-b]pyridin-4-yl)pyrazolo[1,5-b]pyridazine (Example 122).

LCMS (Method 1): Rt 2.47 min, m/z 456.2 [MH$^+$].

$^1$H NMR (400 MHz, d$_6$-DMSO): 1.68-2.48 (6H, m), 3.3-3.84 (6H, m), 3.85-3.98 (0.75H, m), 4.16-4.25 (0.25, m), 4.57-4.68 (0.75H, m), 4.81-4.91 (0.25H, m), 5.12-5.72 (1H, m), 5.87-6.30 (1.5H, m), 6.44-6.68 (1.5H, m), 7.26-7.37 (2H, m), 8.21-8.25 (1H, m), 8.44-8.73 (3H, m), 11.77-11.86 (1H, m);

Example 155: 2-Chloro-1-((2S)-2-(3-(4-(pyrazolo[1,5-b]pyridazin-3-yl)-1H-pyrrolo[2,3-b]pyridin-2-yl)pyrrolidine-1-carbonyl)pyrrolidin-1-yl)ethan-1-one

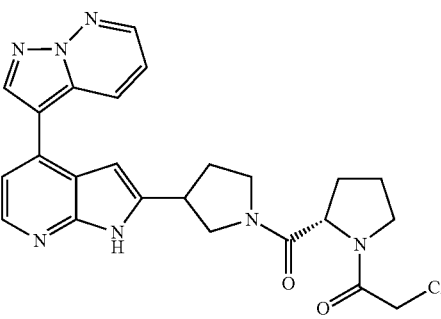

Starting from S—N-chloroacetylproline and 3-(2-(pyrrolidin-3-yl)-1H-pyrrolo[2,3-b]pyridin-4-yl)pyrazolo[1,5-b]pyridazine (Example 122).

LCMS (Method 1): Rt 2.51 min, m/z 478.4 [MH$^+$].

$^1$H NMR (400 MHz, d$_6$-DMSO): 1.67-2.48 (6H, m), 3.3-4.0 (6.75H, m), 4.13-4.24 (0.25, m), 4.27-4.44 (2H, m), 4.51-4.62 (1H, m), 6.44-6.62 (1H, m), 7.26-7.30 (1H, m), 7.31-7.37 (1H, m), 8.21-8.25 (1H, m), 8.43-8.49 (1H, m), 8.54-8.67 (2H, m) 11.78-11.87 (1H, m).

Example 156: 2-Chloro-1-((2R)-2-(3-(4-(pyrazolo[1,5-b]pyridazin-3-yl)-1H-pyrrolo[2,3-b]pyridin-2-yl)pyrrolidine-1-carbonyl)pyrrolidin-1-yl)ethan-1-one

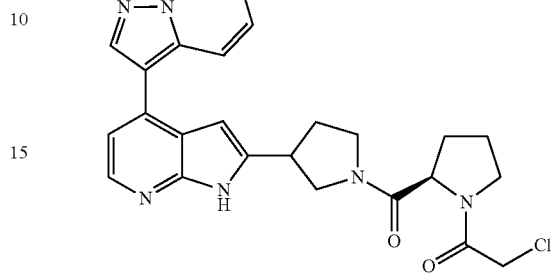

Starting from of R—N-chloroacetylproline and 3-(2-(pyrrolidin-3-yl)-1H-pyrrolo[2,3-b]pyridin-4-yl)pyrazolo[1,5-b]pyridazine (Example 122).

LCMS (Method 1): Rt 2.51 min, m/z 478.4 [MH$^+$].

$^1$H NMR (400 MHz, d$_6$-DMSO): 1.67-2.48 (6H, m), 3.3-4.0 (6.75H, m), 4.13-4.24 (0.25, m), 4.27-4.44 (2H, m), 4.51-4.62 (1H, m), 6.44-6.62 (1H, m), 7.26-7.30 (1H, m), 7.31-7.37 (1H, m), 8.21-8.25 (1H, m), 8.43-8.49 (1H, m), 8.54-8.67 (2H, m) and 11.78-11.87 (1H, m).

Example 157: 2-Chloro-N-(2-oxo-2-(3-(4-(pyrazolo[1,5-b]pyridazin-3-yl)-1H-pyrrolo[2,3-b]pyridin-2-yl)pyrrolidin-1-yl)ethyl)acetamide

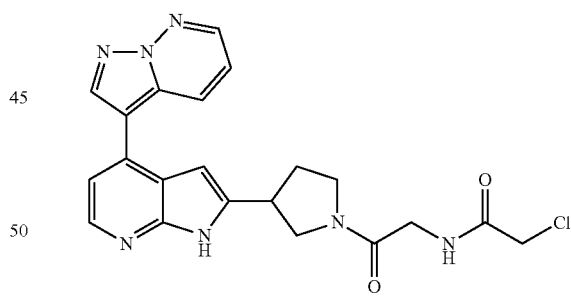

Starting from N-chloroacetylglycine and 3-(2-(pyrrolidin-3-yl)-1H-pyrrolo[2,3-b]pyridin-4-yl)pyrazolo[1,5-b]pyridazine (Example 122).

LCMS (Method 1): Rt 2.31 min, m/z 438.4 [MH$^+$].

$^1$H NMR (400 MHz, d$_6$-DMSO): 2.03-2.48 (2H, m), 3.33-3.73 (4H, m), 3.87-3.99 (3H, m), 4.17 (2H, s), 6.48 (0.5H, bs), 6.54 (0.5H, bs), 7.26-7.29 (1H, m), 7.32-7.37 (1H, m), 8.21-8.24 (1H, m), 8.29-8.35 (1H, m), 8.44-8.48 (1H, m), 8.55-8.58 (1H, m), 8.62 (1H, s) and 11.82 (1H, bs).

Example 158: 2-Chloro-1-(4-(3-(4-(pyrazolo[1,5-b]pyridazin-3-yl)-1H-pyrrolo[2,3-b]pyridin-2-yl)pyrrolidine-1-carbonyl)piperidin-1-yl)ethan-1-one

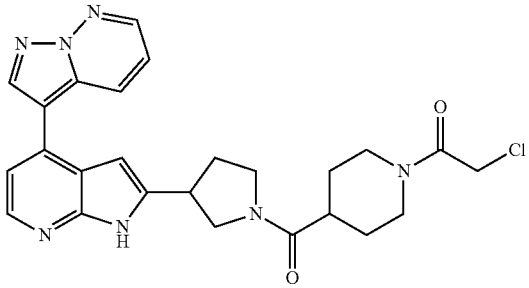 [SMILES: O=C(CCl)N1CCC(C(=O)N2CCC(c3cc4c(-c5cnn6ncccc56)ccnc4[nH]3)C2)CC1]

Starting from 1-(2-chloroacetyl)piperidine-4-carboxylic acid and 3-(2-(pyrrolidin-3-yl)-1H-pyrrolo[2,3-b]pyridin-4-yl)pyrazolo[1,5-b]pyridazine (Example 122).

LCMS (Method 1): Rt 2.57 min, m/z 492.3 [MH$^+$].

$^1$H NMR (400 MHz, d$_6$-DMSO): 1.30-1.64 (2H, m), 1.64-1.78 (2H, m), 2.03-2.45 (2H, m), 2.64-2.80 (2H, m), 3.11 (1H, bt, J=12.3 Hz), 3.35-4.08 (6H, m), 4.27-4.42 (3H, m), 6.46 (0.5H, bs), 6.51 (0.5H, bs), 7.25-7.30 (1H, m), 7.31-7.37 (1H, m), 8.21-8.25 (1H, m), 8.44-8.49 (1H, m), 8.55-8.59 (1H, m), 8.60-8.61 (1H, s) and 11.81 (1H, bs).

Example 159: (R)-2-Chloro-N-(3-(3-(4-(pyrazolo[1,5-b]pyridazin-3-yl)-1H-pyrrolo[2,3-b]pyridin-2-yl)pyrrolidine-1-carbonyl)phenyl)acetamide

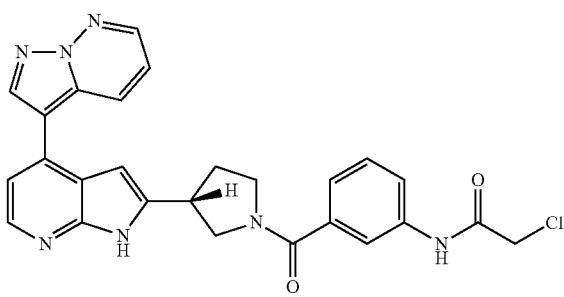

Starting from 3-(2-chloroacetamido)benzoic acid and 3-(2-(pyrrolidin-3-yl)-1H-pyrrolo[2,3-b]pyridin-4-yl)pyrazolo[1,5-b]pyridazine (Example 124).

LCMS (Method 1): Rt 2.77 min, m/z 500.2 [MH$^+$].

$^1$H NMR (400 MHz, d$_6$-DMSO): 2.12-2.44 (2H, m), 3.54-3.73 (4H, m), 3.84-3.91 (0.5H, m), 3.97-4.04 (0.5H, m), 4.25-4.27 (2H, m), 6.44 (0.5H, bs), 6.53 (0.5H, bs), 7.23-7.29 (2H, m), 7.30-7.36 (1H, m), 7.37-7.44 (1H, m), 7.59-7.65 (1H, m), 7.83 (1H, bs), 8.19-8.25 (1H, m), 8.40-8.50 (1H, m), 8.54-8.64 (2H, m), 10.40-10.45 (1H, m), 11.74 (0.5H, bs) and 11.85 (0.5H, bs).

Example 160: (S)-2-Chloro-N-(3-(3-(4-(pyrazolo[1,5-b]pyridazin-3-yl)-1H-pyrrolo[2,3-b]pyridin-2-yl)pyrrolidine-1-carbonyl)phenyl)acetamide

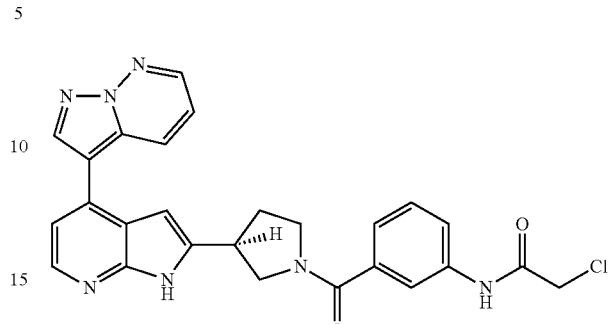

Starting from 3-(2-chloroacetamido)benzoic acid and 3-(2-(pyrrolidin-3-yl)-1H-pyrrolo[2,3-b]pyridin-4-yl)pyrazolo[1,5-b]pyridazine (Example 125).

LCMS (Method 1): Rt 2.78 min, m/z 500.2 [MH$^+$].

$^1$H NMR (400 MHz, d$_6$-DMSO): 2.12-2.44 (2H, m), 3.54-3.73 (4H, m), 3.84-3.91 (0.5H, m), 3.97-4.04 (0.5H, m), 4.25-4.27 (2H, m), 6.44 (0.5H, bs), 6.53 (0.5H, bs), 7.23-7.29 (2H, m), 7.30-7.36 (1H, m), 7.37-7.44 (1H, m), 7.59-7.65 (1H, m), 7.83 (1H, bs), 8.19-8.25 (1H, m), 8.40-8.50 (1H, m), 8.54-8.64 (2H, m), 10.40-10.45 (1H, m), 11.74 (0.5H, bs) and 11.85 (0.5H, bs).

Example 161: 1-((S)-2-((R)-3-(4-(Pyrazolo[1,5-b]pyridazin-3-yl)-1H-pyrrolo[2,3-b]pyridin-2-yl)pyrrolidine-1-carbonyl)pyrrolidin-1-yl)prop-2-en-1-one

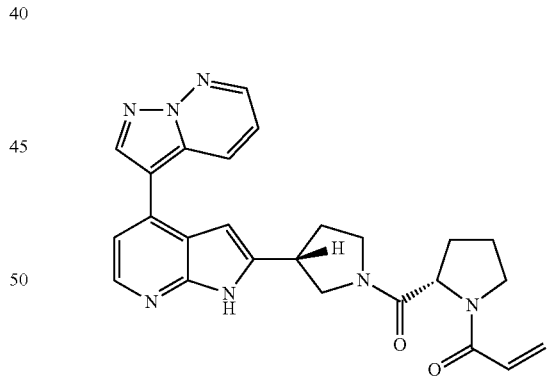

Starting from acryloyl-L-proline and 3-(2-(pyrrolidin-3-yl)-1H-pyrrolo[2,3-b]pyridin-4-yl)pyrazolo[1,5-b]pyridazine (Example 124)

LCMS (Method 1): Rt 2.43 min, m/z 456.3 [MH$^+$].

$^1$H NMR (400 MHz, ds-DMSO): 1.68-2.48 (6H, m), 3.30-3.98 (6H, m), 3.86-3.97 (1H, m), 4.57-4.68 (0.75H, m), 4.81-4.90 (0.25H, m), 5.24-5.72 (1H, m), 5.94-6.29 (1.5H, m), −6.44-6.68 (1.5H, m), 7.26-7.37 (2H, m), 8.21-8.25 (1H, m), 8.44-8.73 (3H, m) 11.79-11.87 (1H, m);

Example 162: 1-((S)-2-((S)-3-(4-(Pyrazolo[1,5-b]pyridazin-3-yl)-1H-pyrrolo[2,3-b]pyridin-2-yl)pyrrolidine-1-carbonyl)pyrrolidin-1-yl)prop-2-en-1-one

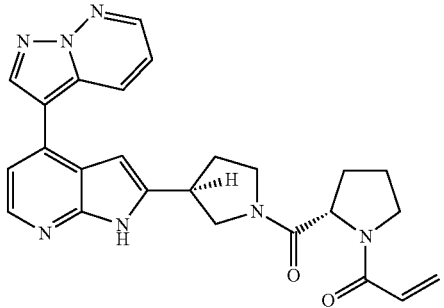

Starting from acryloyl-L-proline and 3-(2-(pyrrolidin-3-yl)-1H-pyrrolo[2,3-b]pyridin-4-yl)pyrazolo[1,5-b]pyridazine (Example 125).

LCMS (Method 1): Rt 2.43 min, m/z 456.3 [MH+].

$^1$H NMR (400 MHz, d$_6$-DMSO): 1.71-2.50 (6H, m), 3.30-3.84 (6H, m), 3.86-3.96 (0.5H, m), 4.16-4.25 (0.5H, m), 4.60-4.66 (0.75H, m), 4.83-4.90 (0.25H, m), 5.21-5.71 (1H, m), 5.94-6.29 (1.5H, m), −6.44-6.67 (1.5H, m), 7.26-7.30 (1H, m), 8.20-8.25 (1H, m), 8.44-8.50 (1H, m), 8.53-8.71 (2H, m) and 11.77-11.86 (1H, m);

Example 163: 3-Methoxy-N-(2-(3-(4-(pyrazolo[1,5-b]pyridazin-3-yl)-1H-pyrrolo[2,3-b]pyridin-2-yl)pyrrolidine-1-carbonyl)phenyl)propanamide Formate Salt

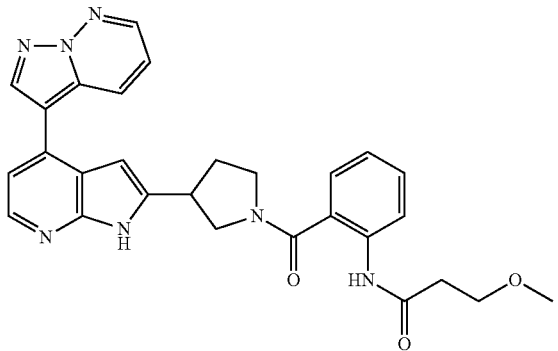 [SMILES: COCCC(=O)Nc1ccccc1C(=O)N1CCC(c2cc3c(-c4cnn5ncccc45)ccnc3[nH]2)C1]

Starting from 2-(3-methoxypropanamido)benzoic acid and 3-(2-(pyrrolidin-3-yl)-1H-pyrrolo[2,3-b]pyridin-4-yl)pyrazolo[1,5-b]pyridazine (Example 122).

LCMS (Method 1): Rt 2.65 min, m/z 510.3 [MH+].

$^1$H NMR (400 MHz, DMSO), 1.96-2.09 (1H, m), 2.23-2.34 (1H, m), 2.58 (2H, t, J=6.7 Hz), 2.65-2.90 (4H, m), 3.11 (1H, t, J=8.3 Hz), 3.50-3.60 (2H, m), 3.79 (3H, s), 6.41 (1H, d, J=1.5 Hz), 7.09-7.15 (1H, m), 7.23 (1H, d, J=5.0 Hz), 7.33 (1H, dd, J=4.4, 9.1 Hz), 7.51-7.57 (1H, m), 7.83 (1H, dd, J=1.5, 7.9 Hz), 8.19 (1H, d, J=5.0 Hz), 8.25 (1H, dd, J=0.9, 8.5 Hz), 8.43 (1H, dd, J=1.8, 9.1 Hz), 8.54-8.57 (2H, m), 10.82 (1H, s), 11.64 (1H, s).

Example 164: 2-Chloro-1-((2R)-2-(3-(4-(pyrazolo[1,5-b]pyridazin-3-yl)-1H-pyrrolo[2,3-b]pyridin-2-yl)pyrrolidine-1-carbonyl)pyrrolidin-1-yl)ethan-1-one

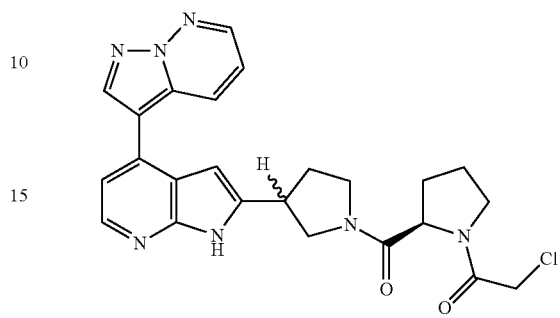

Starting from (2-chloroacetyl)-D-proline and 3-(2-(pyrrolidin-3-yl)-1H-pyrrolo[2,3-b]pyridin-4-yl)pyrazolo[1,5-b]pyridazine (Example 124).

LCMS (Method 1): Rt 2.50 min, m/z 478.3 [MH+].

$^1$H NMR (400 MHz, d$_6$-DMSO): 2.46-1.71 (6H, m), 3.96-3.38 (6.7H, m), 4.24-4.11 (0.6H, m), 4.43-4.29 (1.7H, m), 4.63-4.55 (0.8H, m), 4.84-4.76 (0.2H, m), 6.55-6.46 (1H, m), 7.30-7.25 (1H, m), 7.37-7.32 (1H, m), 8.26-8.20 (1H, m), 8.49-8.43 (1H, m), 8.59-8.54 (1H, m), 8.60 (0.6H, s), 8.66 (0.4H, s), 11.88-11.76 (1H, m).

Example 165: (S)-4-Acryloyl-N-(2-(4-(pyrazolo[1,5-b]pyridazin-3-yl)-1H-pyrrolo[2,3-b]pyridin-2-yl)ethyl)morpholine-3-carboxamide

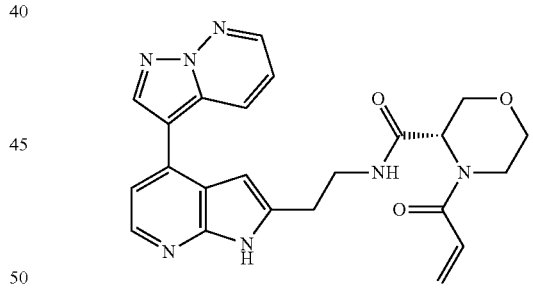

Starting from (4-(pyrazolo[1,5-b]pyridazin-3-yl)-1H-pyrrolo[2,3-b]pyridin-2-yl)methanamine (Example 196) and (S)-4-acryloylmorpholine-3-carboxylic acid (Intermediate 37).

LCMS (Method 1): Rt 2.27 min, m/z 446.4 [MH+].

$^1$H NMR (400 MHz, de-DMSO): 3.05-2.85 (2.5H, m), 3.56-3.42 (3.5H, m), 3.85-3.67 (1.5H, m), 4.12-3.99 (0.5H, m), 4.32-4.17 (1H, m), 4.49-4.43 (0.4H, m), 4.78-4.70 (0.6H, m), 5.48-5.40 (0.4H, m), 5.73-5.66 (0.6H, m), 6.05-5.94 (0.4H, m), 6.17-6.08 (0.6H, m), 6.51-6.33 (1.4H, m), 6.80 (0.6H, dd, J=10.5, 16.7 Hz), 7.25 (1H, d, J=5.0 Hz), 7.34 (1H, dd, J=4.4, 9.1 Hz), 8.15-8.04 (1H, m), 8.20 (1H, d, J=5.0 Hz), 8.46 (1H, dd, J=1.6, 9.2 Hz), 8.64-8.54 (2H, m), 11.67 (1H, s). 1H obscured by water.

189

Example 166: (S)-1-(Cyclopent-1-ene-1-carbonyl)-N-(2-(4-(pyrazolo[1,5-b]pyridazin-3-yl)-1H-pyrrolo[2,3-b]pyridin-2-yl)ethyl)pyrrolidine-2-carboxamide

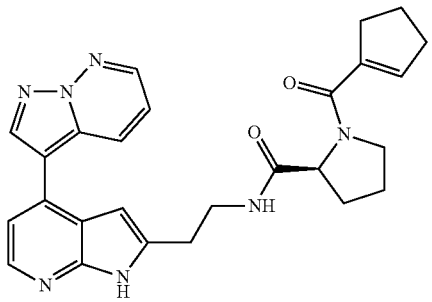 [SMILES: O=C(NCCc1cc2c(-c3cnn4ncccc34)ccnc2[nH]1)[C@@H]1CCCN1C(=O)C1=CCCC1]

Starting from (S)—N-(2-(4-(pyrazolo[1,5-b]pyridazin-3-yl)-1H-pyrrolo[2,3-b]pyridin-2-yl)ethyl)pyrrolidine-2-carboxamide (Example 82), and cyclopent-1-ene-1-carboxylic acid.

LCMS (Method 1): Rt 3.23 min, m/z 470.4 [MH$^+$].

$^1$H NMR (400 MHz, d$_6$-DMSO): 1.88-1.50 (5H, m), 2.21-1.90 (2H, m), 2.48-2.25 (3H, m), 2.96-2.86 (2H, m), 3.61-3.36 (4H, m), 4.34-4.21 (1H, m), 5.75-5.66 (0.4H, m), 6.22-6.14 (0.6H, m), 6.47-6.38 (1H, m), 7.25 (1H, d, J=5.0 Hz), 7.34 (1H, dd, J=4.4, 9.1 Hz), 7.98-7.89 (0.6H, m), 8.12-8.05 (0.4H, m), 8.19 (1H, d, J=5.0 Hz), 8.51-8.42 (1H, m), 8.63-8.53 (2H, m), 11.72-11.56 (1H, m).

Example 167: 3-(2-(((1-Methylpiperidin-4-yl)oxy)methyl)-1H-pyrrolo[2,3-b]pyridin-4-yl)pyrazolo[1,5-b]pyridazine diformate

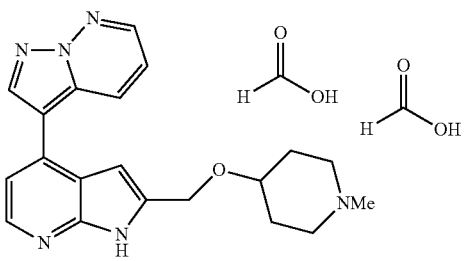

To a solution of 3-(2-(((1-methylpiperidin-4-yl)oxy)methyl)-1-((2-(trimethylsilyl)ethoxy)methyl)-1H-pyrrolo[2,3-b]pyridin-4-yl)pyrazolo[1,5-b]pyridazine (Intermediate 93, 80 mg, 0.163 mmol) in DCM (10 mL) was added TFA (10 mL). After 160 min, the mixture was diluted with toluene and evaporated. The residue was dissolved in water (10 mL) and aqueous ammonium hydroxide solution (33%, 1 mL) was added. After 10 min, the mixture was purified twice on a C-18 cartridge eluting with 0-20% MeOH in H$_2$O containing 0.1% HCO$_2$H to give the title compound (33 mg, 44%).

LCMS (Method 1): Rt 3.07 min, m/z 363.3 [MH$^+$].

$^1$H NMR (400 MHz, d$_6$-DMSO): 1.61-1.44 (2H, m), 1.92-1.79 (2H, m), 2.13-2.01 (2H, m), 2.17 (3H, s), 2.72-2.58 (2H, m), 3.50-3.36 (1H, m), 4.64 (2H, s), 6.58 (1H, s), 7.29 (1H, d, J=5.0 Hz), 7.35 (1H, dd, J=4.4, 9.1 Hz), 8.35-8.12 (2H, m), 8.45 (1H, dd, J=1.8, 9.1 Hz), 8.59-8.56 (2H, m), 11.86 (1H, s).

190

By proceeding in a similar manner to Example 167, the following compounds were prepared:

Example 168: N,N-Dimethyl-2-((4-(pyrazolo[1,5-b]pyridazin-3-yl)-1H-pyrrolo[2,3-b]pyridin-2-yl)methoxy)ethan-1-amine Formate

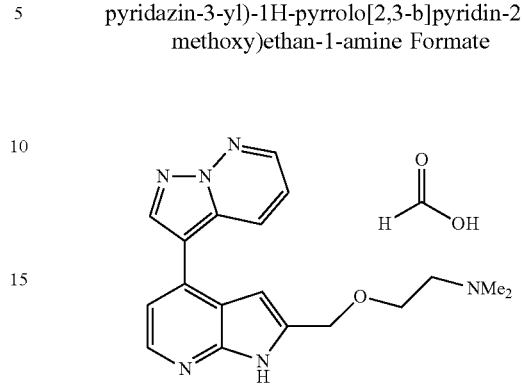

Starting from N,N-Dimethyl-2-((4-(pyrazolo[1,5-b]pyridazin-3-yl)-1-((2-(trimethylsilyl)ethoxy)methyl)-1H-pyrrolo[2,3-b]pyridin-2-yl)methoxy)ethan-1-amine (Intermediate 96)

LCMS (Method 1): Rt 3.07 min, m/z 337.2 [MH$^+$].

$^1$H NMR (400 MHz, d$_6$-DMSO): 2.23 (6H, s), 2.55 (2H, t, J=5.8 Hz), 3.58 (2H, t, J=5.9 Hz), 4.64 (2H, s), 6.60 (1H, s), 7.29 (1H, d, J=5.0 Hz), 7.35 (1H, dd, J=4.5, 9.1 Hz), 8.22 (1H, s), 8.26 (1H, d, J=5.0 Hz), 8.46 (1H, dd, J=1.8, 9.2 Hz), 8.57 (1H, dd, J=1.8, 4.5 Hz), 8.59 (1H, s), 11.96 (1H, s).

Example 169: 2-Chloro-N-(2-(3-(4-(pyrazolo[1,5-b]pyridazin-3-yl)-1H-pyrrolo[2,3-b]pyridin-2-yl)pyrrolidine-1-carbonyl)phenyl)acetamide

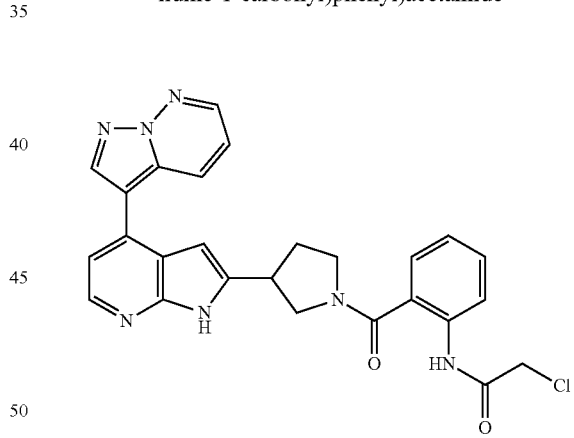

To a solution of 3-(2-(pyrrolidin-3-yl)-1H-pyrrolo[2,3-b]pyridin-4-yl)pyrazolo[1,5-b]pyridazine (Intermediate 91) (30 mg, 0.10 mmol), 2-(2-chloroacetamido)benzoic acid (32 mg, 0.15 mmol) and DIPEA (0.14 mL, 0.79 mmol) in DMF (0.5 mL) was added T3P (110 mg, 0.35 mmol). The mixture was stirred at r.t. for 18 h before the reaction was quenched with water. The resultant brown solid was collected by filtration then purified by FCC, eluting with 0-6% MeOH in DCM. The product was triturated with EtOAc to afford the title compound as a yellow solid.

LCMS (Method 1): Rt 2.83 min, m/z 500.2 [MH$^+$].

$^1$H NMR (400 MHz, d$_6$-DMSO): 2.46-2.07 (2H, m), 3.84-3.41 (4.5H, m), 4.09-3.98 (0.5H, m), 4.25-4.15 (1H, m), 4.27 (1H, s), 6.47-6.43 (0.5H, m), 6.57-6.53 (0.5H, m), 7.30-7.20 (2H, m), 7.37-7.31 (1H, m), 7.49-7.42 (2H, m), 7.82-7.74 (1H, m), 8.26-8.18 (1H, m), 8.51-8.41 (1H, m), 8.60-8.54 (1.5H, m), 8.64 (0.5H, s), 10.28-10.18 (1H, m), 11.73 (0.5H, s), 11.86 (0.5H, s).

By proceeding in a similar manner to Example 169, the following compounds were prepared:

Example 170: 2-Chloro-1-((2R)-2-(3-(4-(pyrazolo[1,5-b]pyridazin-3-yl)-1H-pyrrolo[2,3-b]pyridin-2-yl)pyrrolidine-1-carbonyl)pyrrolidin-1-yl)ethan-1-one

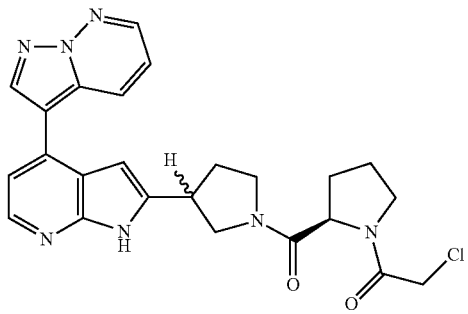 [SMILES: O=C([C@H]1CCCN1C(=O)CCl)N1CCC(c2cc3c(-c4cnn5ncccc45)ccnc3[nH]2)C1]

Starting from (2-chloroacetyl)-D-proline and 3-(2-(pyrrolidin-3-yl)-1H-pyrrolo[2,3-b]pyridin-4-yl)pyrazolo[1,5-b]pyridazine (Example 125).

LCMS (Method 1): Rt 2.50 min, m/z 478.2 [MH$^+$].

$^1$H NMR (400 MHz, d$_6$-DMSO): 1.67-2.47 (6H, m), 3.34-4.01 (7.1H, m), 4.17-4.24 (0.2H, m), 4.27-4.43 (1.7H, m), 4.50-4.63 (0.7H, m), 4.73-4.82 (0.3H, m), 6.44-6.48 (0.5H, m), 6.63-6.50 (0.5H), 7.25-7.30 (1H, m), 7.31-7.37 (1H, m), 8.21-8.25 (1H, m), 8.43-8.50 (1H, m), 8.54-8.58 (1H, m), 8.60 (0.6H, s), 8.66 (0.4H, s), 11.79-11.87 (1H, m);

Example 171: 2-Chloro-1-((2S)-2-(3-(4-(pyrazolo[1,5-b]pyridazin-3-yl)-1H-pyrrolo[2,3-b]pyridin-2-yl)pyrrolidine-1-carbonyl)pyrrolidin-1-yl)ethan-1-one

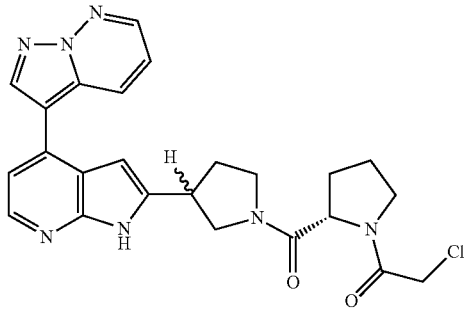 [SMILES: O=C([C@@H]1CCCN1C(=O)CCl)N1CCC(c2cc3c(-c4cnn5ncccc45)ccnc3[nH]2)C1]

Starting from (2-chloroacetyl)-L-proline and 3-(2-(pyrrolidin-3-yl)-1H-pyrrolo[2,3-b]pyridin-4-yl)pyrazolo[1,5-b]pyridazine (Example 124).

LCMS (Method 1): Rt 2.50 min, m/z 478.3 [MH$^+$].

$^1$H NMR (400 MHz, d$_6$-DMSO): 2.50-1.65 (6H, m), 4.01-3.32 (7H, m), 4.43-4.18 (2H, m), 4.62-4.51 (0.8H, m), 4.82-4.73 (0.2H, m), 6.47-6.44 (0.5H, m), 6.61-6.53 (0.5H, m), 7.30-7.25 (1H, m), 7.37-7.31 (1H, m), 8.25-8.21 (1H, m), 8.50-8.43 (1H, m), 8.58-8.54 (1H, m), 8.60 (0.6H, s), 8.66 (0.4H, s), 11.88-11.77 (1H, m).

Example 172: 2-Chloro-1-((2S)-2-(3-(4-(pyrazolo[1,5-b]pyridazin-3-yl)-1H-pyrrolo[2,3-b]pyridin-2-yl)pyrrolidine-1-carbonyl)pyrrolidin-1-yl)ethan-1-one

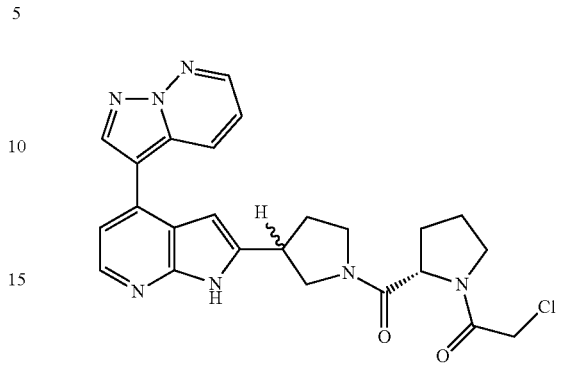

Starting from (2-chloroacetyl)-L-proline and 3-(2-(pyrrolidin-3-yl)-1H-pyrrolo[2,3-b]pyridin-4-yl)pyrazolo[1,5-b]pyridazine (Example 125).

LCMS (Method 1): Rt 2.50 min, m/z 478.4 [MH$^+$].

$^1$H NMR (400 MHz, d$_6$-DMSO): 1.69-2.46 (6H, m), 3.35-3.95 (6.7H, m), 4.10-4.25 (0.6H, m), 4.27-4.44 (1.7H, m), 4.55-4.63 (0.8H, m), 4.76-4.84 (0.2H, m), 6.46-6.55 (1H, m), 7.22-7.30 (1H, m), 7.31-7.38 (1H, m), 8.20-8.26 (1H, m), 8.43-8.50 (1H, m), 8.53-8.59 (1H, m), 8.61 (0.6H, s), 8.66 (0.4H, s), 11.75-11.89 (1H, m).

Example 173: N-(3-(3-(4-(Pyrazolo[1,5-b]pyridazin-3-yl)-1H-pyrrolo[2,3-b]pyridin-2-yl)pyrrolidine-1-carbonyl)phenyl)propionamide

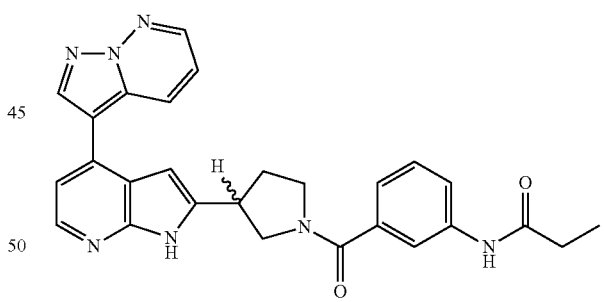

Starting from 3-propionamidobenzoic acid and 3-(2-(pyrrolidin-3-yl)-1H-pyrrolo[2,3-b]pyridin-4-yl)pyrazolo[1,5-b]pyridazine (Example 125).

LCMS (Method 1): Rt 2.72 min, m/z 480.4 [MH$^+$].

$^1$H NMR (400 MHz, d$_6$-DMSO): 1.00-1.13 (3H, m), 2.10-2.45 (4H, m), 3.50-3.76 (4H, m), 3.81-3.92 (0.5H, m), 3.95-4.07 (0.5H, m), 6.42-6.46 (0.5H, m), 6.51-6.55 (0.5H, m), 7.15-7.21 (1H, m), 7.24-7.30 (1H, m), 7.30-7.39 (2H, m), 7.58-7.65 (1H, m), 7.82-7.86 (1H, m), 8.18-8.26 (1H, m), 8.41-8.50 (1H, m), 8.54-8.60 (1.5H, m), 8.63 (0.5H, s), 9.93-10.01 (1H, m), 11.75 (0.5H, s), 11.86 (0.5H, s).

Example 174: 1-(4-(3-(4-(Pyrazolo[1,5-b]pyridazin-3-yl)-1H-pyrrolo[2,3-b]pyridin-2-yl)pyrrolidine-1-carbonyl)piperidin-1-yl)prop-2-yn-1-one

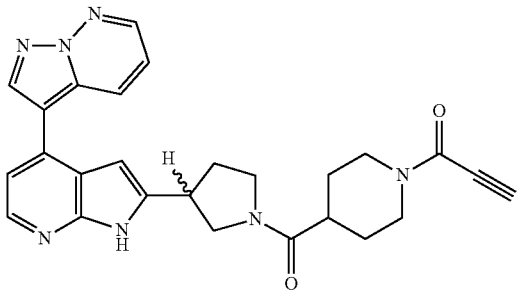 [SMILES: C#CC(=O)N1CCC(C(=O)N2CCC(c3cc4c(-c5cnn6ncccc56)ccnc4[nH]3)C2)CC1]

Starting from 1-propioloylpiperidine-4-carboxylic acid (Intermediate 97) and 3-(2-(pyrrolidin-3-yl)-1H-pyrrolo[2,3-b]pyridin-4-yl)pyrazolo[1,5-b]pyridazine (Example 124)

LCMS (Method 1): Rt 2.50 min, m/z 468.4 [MH$^+$].

$^1$H NMR (400 MHz, d$_6$-DMSO): 1.29-1.58 (2H, m), 1.66-1.87 (2H, m), 2.03-2.46 (2H, m), 2.72-2.86 (2H, m), 3.16-3.49 (2H, m), 3.49-3.82 (3H, m), 3.83-3.92 (0.5H, m), 3.98-4.10 (0.5H, m), 4.18-4.35 (2H, m), 4.51-4.55 (1H, m), 6.44-6.48 (0.5H, m), 6.49-6.53 (0.5H, m), 7.24-7.30 (1H, m), 7.31-7.37 (1H, m), 8.20-8.25 (1H, m), 8.43-8.48 (1H, m), 8.55-8.59 (1H, m), 8.61 (1H, s), 11.75-11.86 (1H, m).

Example 175: 1-(4-(3-(4-(Pyrazolo[1,5-b]pyridazin-3-yl)-1H-pyrrolo[2,3-b]pyridin-2-yl)pyrrolidine-1-carbonyl)piperidin-1-yl)prop-2-yn-1-one

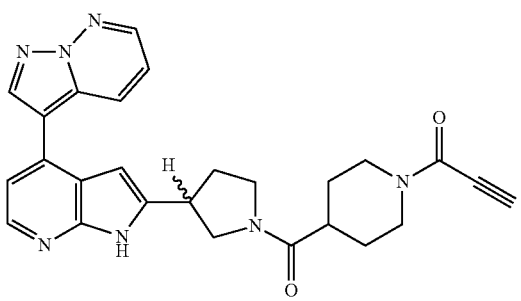 [SMILES: C#CC(=O)N1CCC(C(=O)N2CCC(c3cc4c(-c5cnn6ncccc56)ccnc4[nH]3)C2)CC1]

Starting from 1-propioloylpiperidine-4-carboxylic acid (Intermediate 97) and 3-(2-(pyrrolidin-3-yl)-1H-pyrrolo[2,3-b]pyridin-4-yl)pyrazolo[1,5-b]pyridazine (Example 125).

LCMS (Method 1): Rt 2.51 min, m/z 468.4 [MH$^+$].

$^1$H NMR (400 MHz, d$_6$-DMSO): 1.28-1.57 (2H, m), 1.65-1.87 (2H, m), 2.02-2.46 (2H, m), 2.71-2.86 (2H, m), 3.17-3.92 (5H, m), 3.83-3.92 (0.5H, m), 3.99-4.09 (0.5H, m), 4.18-4.35 (2H, m), 4.52-4.55 (1H, m), 6.44-6.48 (0.5H, m), 6.49-6.53 (0.5H, m), 7.25-7.30 (1H, m), 7.31-7.37 (1H, m), 8.20-8.25 (1H, m), 8.43-8.48 (1H, m), 8.55-8.59 (1H, m), 8.61 (1H, s), 11.76-11.85 (1H, m).

Example 176: 1-((2R)-2-(3-(4-(Pyrazolo[1,5-b]pyridazin-3-yl)-1H-pyrrolo[2,3-b]pyridin-2-yl)pyrrolidine-1-carbonyl)pyrrolidin-1-yl)prop-2-en-1-one

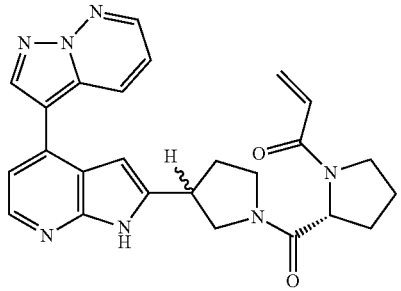 [SMILES: C=CC(=O)N1CCC[C@@H]1C(=O)N1CCC(c2cc3c(-c4cnn5ncccc45)ccnc3[nH]2)C1]

Starting from acryloyl-D-proline (Intermediate 28) and 3-(2-(pyrrolidin-3-yl)-1H-pyrrolo[2,3-b]pyridin-4-yl)pyrazolo[1,5-b]pyridazine (Example 124).

LCMS (Method 1): Rt 2.43 min, m/z 456.4 [MH$^+$].

$^1$H NMR (400 MHz, d$_6$-DMSO): 1.70-2.46 (6H, m), 3.35-3.82 (6H, m), 3.86-3.96 (0.5H, m), 4.15-4.27 (0.5H, m), 4.58-4.67 (0.7H, m), 4.82-4.91 (0.3H, m), 5.11-5.17 (0.2H, m), 5.58-5.63 (0.1H, m), 5.65-5.73 (0.7H, m), 5.86-5.94 (0.2H, m), 6.01-6.31 (1.1H, m), 6.44-6.54 (1H, m), 6.57-6.67 (0.7H, m), 7.26-7.30 (1H, m), 7.31-7.37 (1H, m), 8.20-8.26 (1H, m), 8.43-8.50 (1H, m), 8.53-8.59 (1H, m), 8.59-8.63 (0.6H, m), 8.71 (0.4H, s), 11.75-11.88 (1H, m).

Example 177: 1-((2R)-2-(3-(4-(Pyrazolo[1,5-b]pyridazin-3-yl)-1H-pyrrolo[2,3-b]pyridin-2-yl)pyrrolidine-1-carbonyl)pyrrolidin-1-yl)prop-2-en-1-one

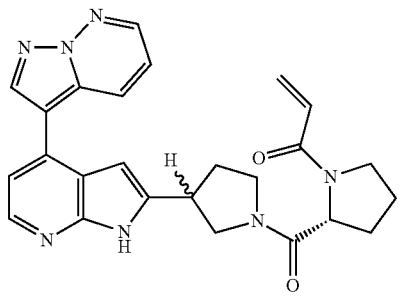 [SMILES: C=CC(=O)N1CCC[C@@H]1C(=O)N1CCC(c2cc3c(-c4cnn5ncccc45)ccnc3[nH]2)C1]

Starting from acryloyl-D-proline (Intermediate 28) and 3-(2-(pyrrolidin-3-yl)-1H-pyrrolo[2,3-b]pyridin-4-yl)pyrazolo[1,5-b]pyridazine (Example 125).

LCMS (Method 1): Rt 2.43 min, m/z 456.4 [MH$^+$].

$^1$H NMR (400 MHz, d$_6$-DMSO): 1.67-2.46 (6H, m), 3.34-3.99 (7H, m), 4.55-4.70 (0.7H, m), 4.79-4.92 (0.3H, m), 5.23-5.29 (0.2H, m), 5.58-5.63 (0.1H, m), 5.66-5.73 (0.7H, m), 5.94-6.29 (1.3H, m), 6.44-6.48 (0.5H, m), 6.53-6.69 (1.2H, m), 7.25-7.37 (2H, m), 8.19-8.26 (1H, m), 8.43-8.52 (1H, m), 8.53-8.63 (1.6H, m), 8.72 (0.4H, s), 11.77-11.88 (1H, m).

Example 178: (S)-1-Acryloyl-N-((4-(pyrazolo[1,5-b]pyridazin-3-yl)-1H-pyrrolo[2,3-b]pyridin-2-yl)methyl)pyrrolidine-3-carboxamide

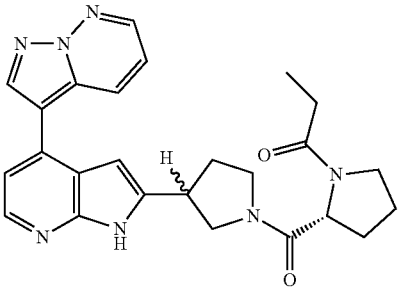 [SMILES: CCC(=O)N1CCC[C@@H]1C(=O)N1CCC(c2cc3c(-c4cnn5ncccc45)ccnc3[nH]2)C1]

Starting from (4-(pyrazolo[1,5-b]pyridazin-3-yl)-1H-pyrrolo[2,3-b]pyridin-2-yl)methanamine (Example 196) and (S)-1-acryloylpyrrolidine-3-carboxylic acid (Intermediate 29).

LCMS (Method 1): Rt 2.17 min, m/z 416.4 [MH$^+$].

$^1$H NMR (400 MHz, d$_6$-DMSO): 1.88-2.19 (2H, m), 2.96-3.18 (1H, m), 3.28-3.82 (4H, m), 4.42-4.55 (2H, m), 5.62-5.68 (1H, m), 6.08-6.16 (1H, m), 6.45-6.49 (1H, m), 6.51-6.61 (1H, m), 7.26-7.30 (1H, m), 7.32-7.39 (1H, m), 8.24 (1H, d, J=5.0 Hz), 8.41-8.47 (1H, m), 8.48-8.55 (1H, m), 8.55 (1H, s), 8.56-8.60 (1H, m), 11.74 (1H, s).

Example 179: (R)-1-Acryloyl-N-((4-(pyrazolo[1,5-b]pyridazin-3-yl)-1H-pyrrolo[2,3-b]pyridin-2-yl)methyl)pyrrolidine-3-carboxamide

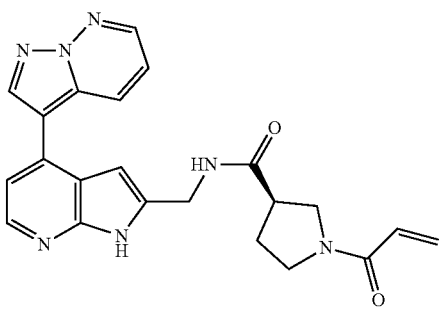 [SMILES: C=CC(=O)N1CC[C@@H](C(=O)NCc2cc3c(-c4cnn5ncccc45)ccnc3[nH]2)C1]

Starting from (4-(pyrazolo[1,5-b]pyridazin-3-yl)-1H-pyrrolo[2,3-b]pyridin-2-yl)methanamine (Example 196) and (R)-1-acryloylpyrrolidine-3-carboxylic acid (Intermediate 30).

LCMS (Method 1): Rt 2.19 min, m/z 416.4 [MH$^+$].

$^1$H NMR (400 MHz, d$_6$-DMSO): 1.89-2.20 (2H, m), 2.95-3.18 (1H, m), 3.29-3.81 (4H, m), 4.43-4.55 (2H, m), 5.62-5.68 (1H, m), 6.08-6.16 (1H, m), 6.45-6.49 (1H, m), 6.51-6.61 (1H, m), 7.26-7.30 (1H, m), 7.32-7.39 (1H, m), 8.24 (1H, d, J=5.0 Hz), 8.41-8.47 (1H, m), 8.48-8.54 (1H, m), 8.55 (1H, s), 8.56-8.60 (1H, m), 11.73 (1H, s).

Example 180: 3-Acrylamido-N-((4-(pyrazolo[1,5-b]pyridazin-3-yl)-1H-pyrrolo[2,3-b]pyridin-2-yl)methyl)benzamide

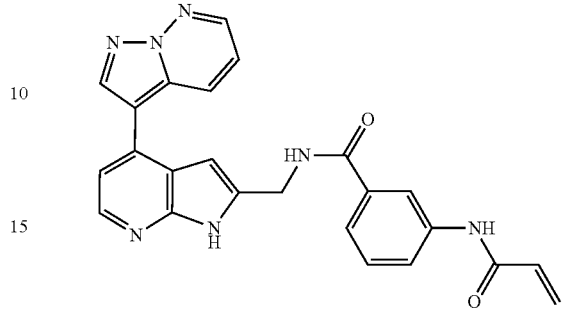

Starting from (4-(pyrazolo[1,5-b]pyridazin-3-yl)-1H-pyrrolo[2,3-b]pyridin-2-yl)methanamine (Example 196) and 3-acrylamidobenzoic acid.

LCMS (Method 1): Rt 2.57 min, m/z 438.3 [MH$^+$].

$^1$H NMR (400 MHz, d$_6$-DMSO): 4.68 (2H, d, J=5.5 Hz), 5.77 (1H, dd, J=2.0, 10.1 Hz), 6.28 (1H, dd, J=2.0, 17.0 Hz), 6.44 (1H, dd, J=10.1, 17.0 Hz), 6.50-6.54 (1H, m), 7.28 (1H, d, J=5.0 Hz), 7.33 (1H, dd, J=4.5, 9.1 Hz), 7.43 (1H, t, J=7.9 Hz), 7.58-7.63 (1H, m), 7.84-7.89 (1H, m), 8.12-8.16 (1H, m), 8.24 (1H, d, J=5.0 Hz), 8.44 (1H, dd, J=1.8, 9.2 Hz), 8.54 (1H, s), 8.56 (1H, dd, J=1.9, 4.4 Hz), 8.94 (1H, t, J=5.6 Hz), 10.29 (1H, s), 11.75 (1H, s).

Example 181: E)-4-(4-(Dimethylamino)but-2-enamido)-N-((4-(pyrazolo[1,5-b]pyridazin-3-yl)-1H-pyrrolo[2,3-b]pyridin-2-yl)methyl)benzamide

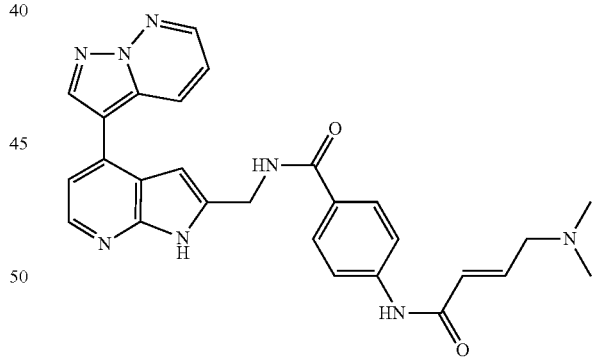

Starting from (4-(pyrazolo[1,5-b]pyridazin-3-yl)-1H-pyrrolo[2,3-b]pyridin-2-yl)methanamine) (Example 196) and (E)-4-(4-(dimethylamino)but-2-enamido)benzoic acid (which was prepared according to WO2015058163).

LCMS (Method 1): Rt 1.97 min, m/z 495.4 [MH$^+$].

$^1$H NMR (400 MHz, d$_6$-DMSO): 2.19 (6H, s), 3.04-3.10 (2H, m), 4.67 (2H, d, J=5.4 Hz), 6.26-6.33 (1H, m), 6.49-6.53 (1H, m), 6.76 (1H, td, J=5.9, 15.4 Hz), 7.27 (1H, d, J=5.0 Hz), 7.33 (1H, dd, J=4.3, 9.0 Hz), 7.70-7.76 (2H, m), 7.84-7.90 (2H, m), 8.24 (1H, d, J=5.0 Hz), 8.44 (1H, dd, J=1.9, 9.1 Hz), 8.54 (1H, s), 8.56 (1H, dd, J=1.8, 4.5 Hz), 8.84 (1H, t, J=5.6 Hz), 10.28 (1H, s), 11.72 (1H, s).

Example 182: (R)-1-Acryloyl-N-((4-(pyrazolo[1,5-b]pyridazin-3-yl)-1H-pyrrolo[2,3-b]pyridin-2-yl)methyl)pyrrolidine-2-carboxamide

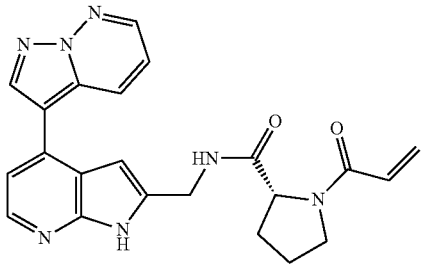 [SMILES: C=CC(=O)N1CCC[C@@H]1C(=O)NCc1cc2c(-c3cnn4ncccc34)ccnc2[nH]1]

Starting from (4-(pyrazolo[1,5-b]pyridazin-3-yl)-1H-pyrrolo[2,3-b]pyridin-2-yl)methanamine (Example 196) and acryloyl-D-proline (Intermediate 28).

LCMS (Method 1): Rt 2.23 min, m/z 416.4 [MH+].

$^1$H NMR (400 MHz, d$_6$-DMSO): 1.72-2.29 (4H, m), 3.39-3.78 (2H, m), 4.36-4.57 (3H, m), 5.45 (0.3H, dd, J=2.4, 10.3 Hz), 5.72 (0.7H, dd, J=2.4, 10.3 Hz), 6.03-6.10 (0.3H, m), 6.23-6.41 (1.2H, m), 6.59-6.69 (1.5H, m), 7.26-7.31 (1H, m), 7.32-7.37 (1H, m), 8.18-8.25 (1H, m), 8.40-8.45 (0.3H, m), 8.48-8.54 (1.7H, m), 8.55-8.64 (1.3H, m), 8.68 (0.7H, s), 11.56 (0.7H, s), 11.71 (0.3H, s).

Example 183: (S)-1-Acryloyl-N-((4-(pyrazolo[1,5-b]pyridazin-3-yl)-1H-pyrrolo[2,3-b]pyridin-2-yl)methyl)pyrrolidine-2-carboxamide

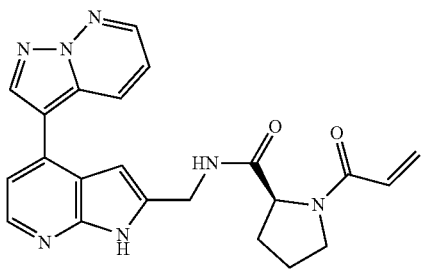 [SMILES: C=CC(=O)N1CCC[C@H]1C(=O)NCc1cc2c(-c3cnn4ncccc34)ccnc2[nH]1]

Starting from (4-(pyrazolo[1,5-b]pyridazin-3-yl)-1H-pyrrolo[2,3-b]pyridin-2-yl)methanamine (Example 196) and acryloyl-L-proline.

LCMS (Method 1): Rt 2.23 min, m/z 416.4 [MH+].

$^1$H NMR (400 MHz, d$_6$-DMSO): 1.75-2.29 (4H, m), 3.40-3.77 (2H, m), 4.37-4.57 (3H, m), 5.42-5.48 (0.3H, m), 5.69-5.76 (0.7H, m), 6.02-6.09 (0.3H, m), 6.23-6.41 (1.2H, m), 6.59-6.69 (1.5H, m), 7.28 (0.3H, d, J=5.0 Hz), 7.30 (0.7H, d, J=5.2 Hz), 7.34 (1H, dd, J=4.4, 9.1 Hz), 8.21 (0.7H, d, J=5.0 Hz), 8.23 (0.3H, d, J=5.0 Hz), 8.40-8.45 (0.3H, m), 8.48-8.54 (1.7H, m), 8.55-8.64 (1.3H, m), 8.68 (0.7H, s), 11.56 (0.7H, s), 11.73 (0.3H, s).

Example 184: (R)-1-Acryloyl-N-((4-(pyrazolo[1,5-b]pyridazin-3-yl)-1H-pyrrolo[2,3-b]pyridin-2-yl)methyl)piperidine-3-carboxamide

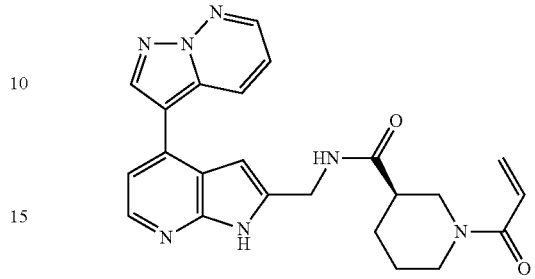

Starting from (4-(pyrazolo[1,5-b]pyridazin-3-yl)-1H-pyrrolo[2,3-b]pyridin-2-yl)methanamine (Example 196) and R-acryloylpiperidine-3-carboxylic acid (Intermediate 21).

LCMS (Method 1): Rt 2.36 min, m/z 430.4 [MH+].

$^1$H NMR (400 MHz, d$_6$-DMSO): 1.24-1.41 (1H, m), 1.57-1.78 (2H, m), 1.84-1.96 (1H, m), 2.27-2.44 (1H, m), 2.64-2.82 (1H, m), 2.97-3.25 (1H, m), 3.93-4.08 (1H, m), 4.19-4.31 (0.5H, m), 4.40-4.54 (2.5H, m), 5.60-5.68 (1H, m), 6.02-6.12 (1H, m), 6.47 (1H, s), 6.74-6.88 (1H, m), 7.28 (1H, d, J=5.0 Hz), 7.35 (1H, dd, J=4.2, 9.0 Hz), 8.24 (1H, d, J=5.0 Hz), 8.39-8.46 (2H, m), 8.55 (1H, s), 8.57 (1H, dd, J=1.8, 4.3 Hz), 11.72 (1H, s).

Example 185: 4-Acrylamido-N-methyl-N-((4-(pyrazolo[1,5-b]pyridazin-3-yl)-1H-pyrrolo[2,3-b]pyridin-2-yl)methyl)benzamide

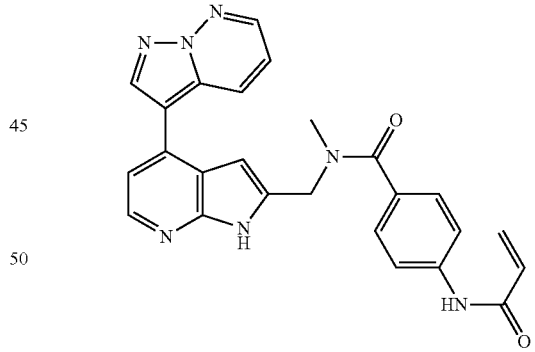

Starting from N-methyl-1-(4-(pyrazolo[1,5-b]pyridazin-3-yl)-1H-pyrrolo[2,3-b]pyridin-2-yl)methanamine (Example 203) and 4-acrylamidobenzoic acid.

LCMS (Method 1): Rt 2.73 min, m/z 452.3 [MH+].

$^1$H NMR (400 MHz, d$_6$-DMSO): 2.99 (3H, s), 4.52-4.95 (2H, m), 5.78 (1H, dd, J=1.9, 10.1 Hz), 6.27 (1H, dd, J=1.9, 17.0 Hz), 6.45 (1H, dd, J=10.2, 16.7 Hz), 6.54 (1H, br s), 7.30 (1H, d, J=5.0 Hz), 7.35 (1H, dd, J=4.4, 9.1 Hz), 7.45-7.52 (2H, m), 7.68-7.76 (2H, m), 8.26 (1H, d, J=5.0 Hz), 8.46 (1H, dd, J=1.9, 9.2 Hz), 8.57 (1H, dd, J=1.8, 4.4 Hz), 8.62 (1H, s), 10.31 (1H, s), 11.85 (1H, s).

Example 186: (S)-1-Acryloyl-N-((4-(pyrazolo[1,5-b]pyridazin-3-yl)-1H-pyrrolo[2,3-b]pyridin-2-yl)methyl)piperidine-3-carboxamide

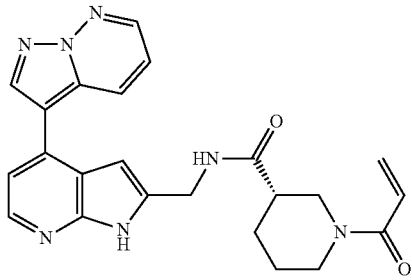 [SMILES: C=CC(=O)N1CCC[C@H](C(=O)NCc2cc3c(-c4cnn5ncccc45)ccnc3[nH]2)C1]

Starting from (4-(pyrazolo[1,5-b]pyridazin-3-yl)-1H-pyrrolo[2,3-b]pyridin-2-yl)methanamine (Example 196) and S-acryloylpiperidine-3-carboxylic acid (Intermediate 20).

LCMS (Method 1): Rt 2.36 min, m/z 430.4 [MH$^+$].

$^1$H NMR (400 MHz, d$_6$-DMSO): 1.41-1.25 (1H, m), 1.78-1.58 (2H, m), 1.95-1.84 (1H, m), 2.45-2.27 (1H, m), 2.82-2.65 (1H, m), 3.09-2.97 (0.5H, m), 3.25-3.15 (0.5H, m), 4.07-3.93 (1H, m), 4.30-4.19 (0.5H, m), 4.53-4.39 (2.5H, m), 5.68-5.60 (1H, m), 6.12-6.03 (1H, m), 6.46 (1H, s), 6.87-6.74 (1H, m), 7.28 (1H, d, J=5.1 Hz), 7.38-7.31 (1H, m), 8.23 (1H, d, J=5.0 Hz), 8.47-8.40 (2H, m), 8.54 (1H, s), 8.57 (1H, dd, J=1.7, 4.4 Hz), 11.72 (1H, s).

Example 187: (1s,4s)-4-Acrylamido-N-((4-(pyrazolo[1,5-b]pyridazin-3-yl)-1H-pyrrolo[2,3-b]pyridin-2-yl)methyl)cyclohexane-1-carboxamide

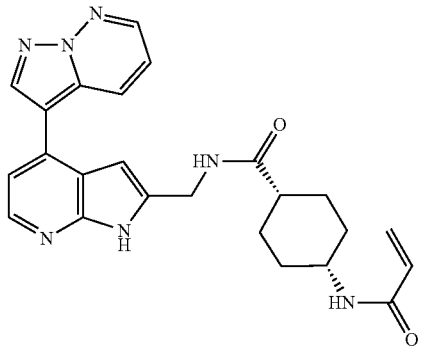 [SMILES: C=CC(=O)N[C@H]1CC[C@@H](C(=O)NCc2cc3c(-c4cnn5ncccc45)ccnc3[nH]2)CC1]

Starting from (4-(pyrazolo[1,5-b]pyridazin-3-yl)-1H-pyrrolo[2,3-b]pyridin-2-yl)methanamine (Example 196) and (1s,4s)-4-acrylamidocyclohexane-1-carboxylic acid (which may be prepared according to WO2016142855).

LCMS (Method 1): Rt 2.33 min, m/z 444.3 [MH$^+$].

$^1$H NMR (400 MHz, d$_6$-DMSO): 1.88-1.43 (8H, m), 2.37-2.26 (1H, m), 3.91-3.81 (1H, m), 4.46 (2H, d, J=5.5 Hz), 5.54 (1H, dd, J=2.3, 10.2 Hz), 6.06 (1H, dd, J=2.4, 17.1 Hz), 6.34 (1H, dd, J=10.3, 17.2 Hz), 6.44-6.41 (1H, m), 7.27 (1H, d, J=5.0 Hz), 7.33 (1H, dd, J=4.4, 9.1 Hz), 7.98 (1H, d, J=7.5 Hz), 8.27-8.20 (2H, m), 8.42 (1H, dd, J=1.8, 9.2 Hz), 8.52 (1H, s), 8.56 (1H, dd, J=1.7, 4.5 Hz), 11.67 (1H, s).

Example 188: 4-Propionamido-N-((4-(pyrazolo[1,5-b]pyridazin-3-yl)-1H-pyrrolo[2,3-b]pyridin-2-yl)methyl)benzamide

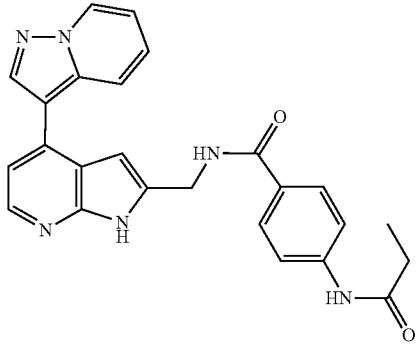 [SMILES: CCC(=O)Nc1ccc(C(=O)NCc2cc3c(-c4cnn5ccccc45)ccnc3[nH]2)cc1]

Starting from (4-(pyrazolo[1,5-b]pyridazin-3-yl)-1H-pyrrolo[2,3-b]pyridin-2-yl)methanamine (Example 196) and 4-propionamidobenzoic acid.

LCMS (Method 1): Rt 2.54 min, m/z 440.3 [MH$^+$].

$^1$H NMR (400 MHz, d$_6$-DMSO): 1.08 (3H, t, J=7.6 Hz), 2.35 (2H, q, J=7.5 Hz), 4.66 (2H, d, J=5.5 Hz), 6.53-6.49 (1H, m), 7.27 (1H, d, J=4.9 Hz), 7.33 (1H, dd, J=4.4, 9.1 Hz), 7.70-7.64 (2H, m), 7.88-7.82 (2H, m), 8.23 (1H, d, J=5.0 Hz), 8.44 (1H, dd, J=1.9, 9.1 Hz), 8.54 (1H, s), 8.56 (1H, dd, J=1.8, 4.4 Hz), 8.82 (1H, t, J=5.7 Hz), 10.08 (1H, s), 11.72 (1H, s).

Example 189: 4-(Acrylamidomethyl)-N-((4-(pyrazolo[1,5-b]pyridazin-3-yl)-1H-pyrrolo[2,3-b]pyridin-2-yl)methyl)benzamide

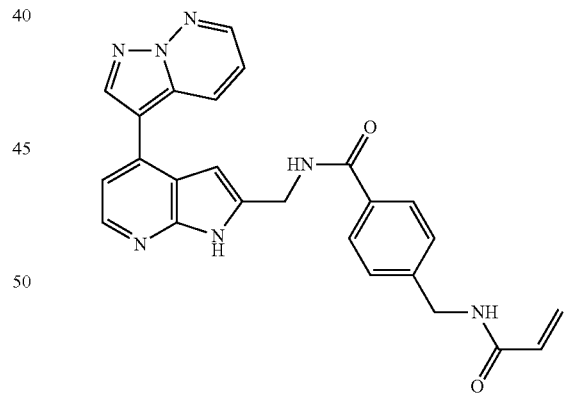

Starting from (4-(pyrazolo[1,5-b]pyridazin-3-yl)-1H-pyrrolo[2,3-b]pyridin-2-yl)methanamine Example 196) and 4-(acrylamidomethyl)benzoic acid.

LCMS (Method 1): Rt 2.41 min, m/z 452.3 [MH$^+$].

$^1$H NMR (400 MHz, d$_6$-DMSO): 4.40 (2H, d, J=6.0 Hz), 4.68 (2H, d, J=5.4 Hz), 5.64 (1H, dd, J=2.2, 10.1 Hz), 6.13 (1H, dd, J=2.2, 17.2 Hz), 6.29 (1H, dd, J=10.1, 17.1 Hz), 6.52-6.48 (1H, m), 7.27 (1H, d, J=5.0 Hz), 7.38-7.29 (3H, m), 7.89-7.84 (2H, m), 8.24 (1H, d, J=4.9 Hz), 8.43 (1H, dd, J=1.8, 9.1 Hz), 8.53 (1H, s), 8.56 (1H, dd, J=1.8, 4.4 Hz), 8.66 (1H, t, J=5.9 Hz), 8.92 (1H, t, J=5.5 Hz), 11.74 (1H, s).

Example 190: 4-(N-Methylacrylamido)-N-((4-(pyrazolo[1,5-b]pyridazin-3-yl)-1H-pyrrolo[2,3-b]pyridin-2-yl)methyl)benzamide

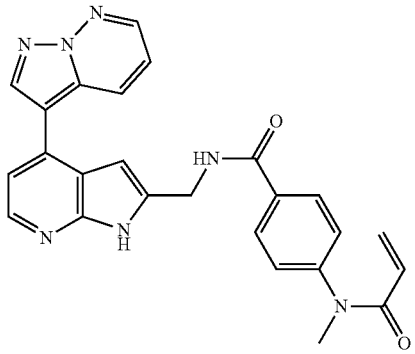 [SMILES: C=CC(=O)N(C)c1ccc(C(=O)NCc2cc3c(-c4cnn5ncccc45)ccnc3[nH]2)cc1]

Starting from (4-(pyrazolo[1,5-b]pyridazin-3-yl)-1H-pyrrolo[2,3-b]pyridin-2-yl)methanamine (Example 196) and 4-(N-methylacrylamido)benzoic acid (Intermediate 31).

LCMS (Method 1): Rt 2.59 min, m/z 452.3 [MH$^+$].

$^1$H NMR (400 MHz, d$_6$-DMSO): 3.28 (3H, s), 4.70 (2H, d, J=5.5 Hz), 5.64-5.56 (1H, m), 6.15-6.03 (1H, m), 6.18 (1H, dd, J=2.7, 16.8 Hz), 6.56-6.52 (1H, m), 7.29 (1H, d, J=4.9 Hz), 7.34 (1H, dd, J=4.4, 9.1 Hz), 7.42-7.37 (2H, m), 8.01-7.94 (2H, m), 8.25 (1H, d, J=5.0 Hz), 8.45 (1H, dd, J=1.8, 9.1 Hz), 8.59-8.54 (2H, m), 9.04 (1H, t, J=5.5 Hz), 11.79 (1H, s).

Example 191: (1r,4r)-4-Acrylamido-N-((4-(pyrazolo[1,5-b]pyridazin-3-yl)-1H-pyrrolo[2,3-b]pyridin-2-yl)methyl)cyclohexane-1-carboxamide

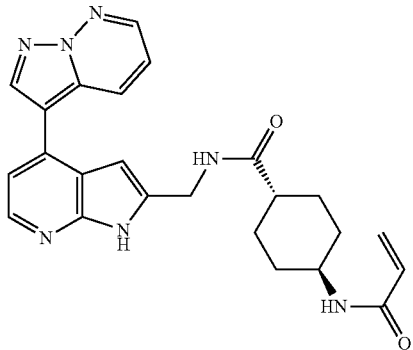 [SMILES: C=CC(=O)N[C@H]1CC[C@H](C(=O)NCc2cc3c(-c4cnn5ncccc45)ccnc3[nH]2)CC1]

Starting from (4-(pyrazolo[1,5-b]pyridazin-3-yl)-1H-pyrrolo[2,3-b]pyridin-2-yl)methanamine (Example 196) and (1r,4r)-4-acrylamidocyclohexane-1-carboxylic acid (which can be prepared according to WO2016142855).

LCMS (Method 1): Rt 2.29 min, m/z 444.3 [MH$^+$].

$^1$H NMR (400 MHz, d$_6$-DMSO): 1.29-1.10 (2H, m), 1.54-1.37 (2H, m), 1.93-1.74 (4H, m), 2.23-2.11 (1H, m), 3.63-3.49 (1H, m), 4.44 (2H, d, J=5.2 Hz), 5.55 (1H, dd, J=2.5, 10.0 Hz), 6.06 (1H, dd, J=2.4, 17.1 Hz), 6.18 (1H, dd, J=10.0, 17.1 Hz), 6.45-6.41 (1H, m), 7.27 (1H, d, J=5.0 Hz), 7.34 (1H, dd, J=4.4, 9.1 Hz), 7.95 (1H, d, J=7.9 Hz), 8.26-8.19 (2H, m), 8.43 (1H, dd, J=1.8, 9.1 Hz), 8.53 (1H, s), 8.58 (1H, dd, J=1.8, 4.4 Hz), 11.67 (1H, s).

Example 192: 3-(Acrylamidomethyl)-N-((4-(pyrazolo[1,5-b]pyridazin-3-yl)-1H-pyrrolo[2,3-b]pyridin-2-yl)methyl)benzamide

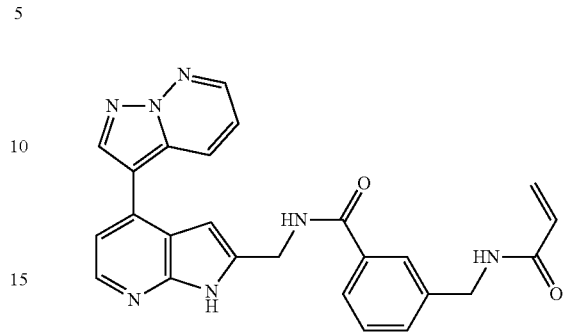

Starting from (4-(pyrazolo[1,5-b]pyridazin-3-yl)-1H-pyrrolo[2,3-b]pyridin-2-yl)methanamine (Example 196) and 3-(acrylamidomethyl)benzoic acid (Intermediate 32).

LCMS (Method 1): Rt 2.49 min, m/z 452.3 [MH$^+$].

$^1$H NMR (400 MHz, de-DMSO): 4.40 (2H, d, J=6.0 Hz), 4.68 (2H, d, J=5.5 Hz), 5.62 (1H, dd, J=2.2, 10.1 Hz), 6.12 (1H, dd, J=2.2, 17.1 Hz), 6.28 (1H, dd, J=10.1, 17.1 Hz), 6.52-6.48 (1H, m), 7.27 (1H, d, J=4.9 Hz), 7.33 (1H, dd, J=4.4, 9.2 Hz), 7.47-7.40 (2H, m), 7.83-7.76 (2H, m), 8.24 (1H, d, J=4.9 Hz), 8.43 (1H, dd, J=1.8, 9.1 Hz), 8.53 (1H, s), 8.56 (1H, dd, J=1.7, 4.4 Hz), 8.64 (1H, t, J=6.1 Hz), 8.96 (1H, t, J=5.6 Hz), 11.75 (1H, s).

Example 193: 2-(1-Acryloylpiperidin-4-yl)-N-((4-(pyrazolo[1,5-b]pyridazin-3-yl)-1H-pyrrolo[2,3-b]pyridin-2-yl)methyl)acetamide

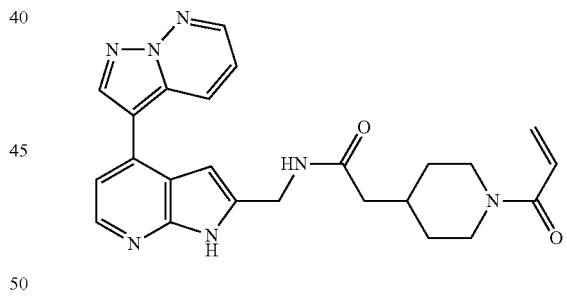

Starting from (4-(pyrazolo[1,5-b]pyridazin-3-yl)-1H-pyrrolo[2,3-b]pyridin-2-yl)methanamine (Example 196) and 2-(1-acryloylpiperidine-4-yl)acetic acid (Intermediate 33).

LCMS (Method 1): Rt 2.32 min, m/z 444.3 [MH$^+$].

$^1$H NMR (400 MHz, d$_6$-DMSO): 1.13-0.94 (2H, m), 1.77-1.60 (2H, m), 2.04-1.91 (1H, m), 2.15-2.08 (2H, m), 2.61 (1H, t, J=12.3 Hz), 3.01 (1H, t, J=12.5 Hz), 4.03-3.93 (1H, m), 4.40-4.31 (1H, m), 4.51-4.42 (2H, m), 5.64 (1H, dd, J=2.5, 10.5 Hz), 6.06 (1H, dd, J=2.5, 16.7 Hz), 6.47-6.43 (1H, m), 6.78 (1H, dd, J=10.5, 16.6 Hz), 7.28 (1H, d, J=5.0 Hz), 7.35 (1H, dd, J=4.4, 9.1 Hz), 8.23 (1H, d, J=4.9 Hz), 8.33 (1H, t, J=5.5 Hz), 8.44 (1H, dd, J=1.8, 9.1 Hz), 8.53 (1H, s), 8.58 (1H, dd, J=1.8, 4.4 Hz), 11.70 (1H, s).

Example 194: (S)-1-(2-(4-(4-(Pyrazolo[1,5-b]pyridazin-3-yl)-1H-pyrrolo[2,3-b]pyridin-2-yl)piperidine-1-carbonyl)pyrrolidin-1-yl)prop-2-en-1-one

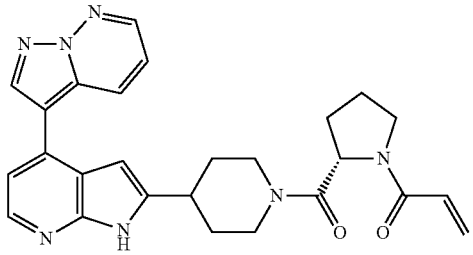 [SMILES: C=CC(=O)N1CCC[C@H]1C(=O)N1CCC(c2cc3c(-c4cnn5ncccc45)ccnc3[nH]2)CC1]

Starting from 3-(2-(piperidin-4-yl)-1H-pyrrolo[2,3-b]pyridine-4-yl)pyrazolo[1,5-b]pyridazine (Example 102) and acryloyl-L-proline.

LCMS (Method 1): Rt 2.51 min, m/z 470.4 [MH$^+$].

$^1$H NMR (400 MHz, d$_6$-DMSO): 2.39-1.45 (8H, m), 2.85-2.64 (1H, m), 3.31-2.98 (2H, m), 3.56-3.41 (0.7H, m), 3.72-3.57 (1.3H, m), 4.19-4.01 (1H, m), 4.50-4.35 (1H, m), 5.00-4.85 (0.7H, m), 5.17-5.07 (0.3H, m), 5.72-5.54 (1H, m), 6.25-6.03 (1.4H, m), 6.44-6.35 (1H, m), 6.68-6.57 (0.6H, m), 7.28-7.23 (1H, m), 7.35 (1H, dd, J=4.4, 9.0 Hz), 8.24-8.19 (1H, m), 8.49-8.42 (1H, m), 8.58-8.54 (1H, m), 8.60 (1H, s), 11.81-11.68 (1H, m)

Example 195: (R)-1-(2-(4-(4-(pPyrazolo[1,5-b]pyridazin-3-yl)-1H-pyrrolo[2,3-b]pyridin-2-yl)piperidine-1-carbonyl)pyrrolidin-1-yl)prop-2-en-1-one

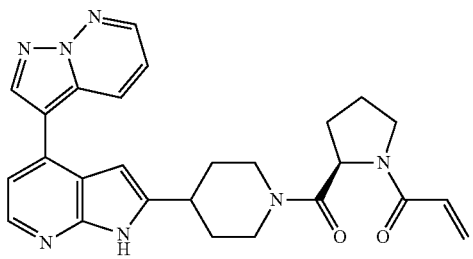 [SMILES: C=CC(=O)N1CCC[C@@H]1C(=O)N1CCC(c2cc3c(-c4cnn5ncccc45)ccnc3[nH]2)CC1]

Starting from 3-(2-(piperidin-4-yl)-1H-pyrrolo[2,3-b]pyridine-4-yl)pyrazolo[1,5-b]pyridazine (Example 102) and acryloyl-D-proline (Intermediate 28)

LCMS (Method 1): Rt 2.51 min, m/z 470.4 [MH$^+$].

$^1$H NMR (400 MHz, d$_6$-DMSO): 2.39-1.49 (8H, m), 2.84-2.64 (1H, m), 3.12-2.98 (1H, m), 3.35-3.13 (1H, m), 3.56-3.41 (0.7H, m), 3.72-3.57 (1.3H, m), 4.19-4.03 (1H, m), 4.50-4.35 (1H, m), 4.99-4.86 (0.7H, m), 5.18-5.07 (0.3H, m), 5.72-5.54 (1H, m), 6.14-6.02 (1H, m), 6.26-6.14 (0.4H, m), 6.45-6.35 (1H, m), 6.69-6.57 (0.6H, m), 7.28-7.23 (1H, m), 7.34 (1H, dd, J=4.4, 9.1 Hz), 8.24-8.19 (1H, m), 8.48-8.42 (1H, m), 8.58-8.54 (1H, m), 8.60 (1H, s), 11.80-11.69 (1H, m).

Example 196: (4-(Pyrazolo[1,5-b]pyridazin-3-yl)-1H-pyrrolo[2,3-b]pyridin-2-yl)methanamine

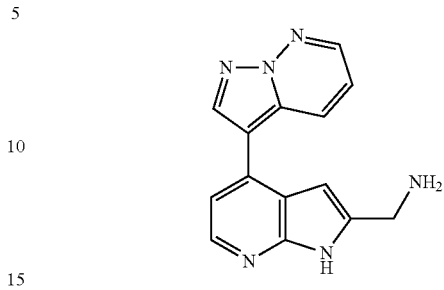

A mixture of (1-(phenylsulfonyl)-4-(pyrazolo[1,5-b]pyridazin-3-yl)-1H-pyrrolo[2,3-b]pyridin-2-yl)methanamine (Intermediate 58, 337 mg, 0.833 mmol) and 2 M NaOH solution (4.2 mL, 8.33 mmol) in 1,4-dioxane (12 mL) and ethanol (3 mL) was heated at 55° C. for 4.5 h. After cooling, the mixture was poured into DCM and the aqueous layer was extracted further with DCM. The combined organic extracts were dried and concentrated in vacuo. The residue was slurried in DCM (10 mL) and the solid was collected by filtration, washed with DCM and dried under vacuum to give the title compound (137 mg, 62%).

LCMS (Method 3): Rt 0.57 min, m/z 265.2 [MH$^+$].

$^1$H NMR (400 MHz, d$_6$-DMSO): 2.00 (2H, s), 3.85 (2H, s), 6.47 (1H, s), 7.25 (1H, d, J=5.0 Hz), 7.34 (1H, dd, J=4.4, 9.1 Hz), 8.20 (1H, d, J=5.0 Hz), 8.46 (1H, dd, J=1.9, 9.1 Hz), 8.56-8.59 (2H, m), 11.61 (1H, s).

Example 197: tert-Butyl 4-(4-(pyrazolo[1,5-b]pyridazin-3-yl)-1H-pyrrolo[2,3-b]pyridin-2-yl)piperidine-1-carboxylate

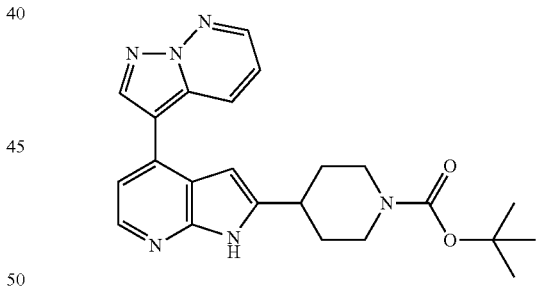

A mixture of tert-butyl 4-(4-bromo-1H-pyrrolo[2,3-b]pyridin-2-yl)piperidine-1-carboxylate (Intermediate 100, 200 mg, 0.53 mmol), 3-(3,3,4,4-tetramethylborolan-1-yl)pyrazolo[1,5-b]pyridazine (193 mg, 0.79 mmol), X-Phos Pd-G3 (22 mg, 0.03 mmol), potassium phosphate (335 mg, 1.58 mmol), IPA (1.2 mL) and water (0.6 mL) was degassed with argon then heated in the microwave at 120° C. for 1 h. The cooled mixture was diluted with EtOAc, washed with water, dried (Na$_2$SO$_4$) then concentrated in vacuo. The residue was purified by FCC, eluting with 0-5% 2M ammonia/MeOH in DCM to give the title compound as a solid (217 mg, 99%).

LCMS (Method 3): Rt 1.07 min, m/z 419 [MH$^+$].

$^1$H NMR (400 MHz, CDCl$_3$), 1.24 (9H, s), 1.77-1.87 (2H, m), 2.11 (2H, d, J=12.0 Hz), 2.91-3.08 (3H, m), 4.27-4.35 (2H, m), 6.36 (1H, d, J=1.6 Hz), 7.12 (1H, dd, J=4.4, 9.1

Hz), 7.20 (1H, d, J=5.0 Hz), 8.22 (1H, dd, J=1.9, 9.1 Hz), 8.30 (1H, d, J=5.1 Hz), 8.40 (1H, dd, J=1.9, 4.3 Hz), 8.45 (1H, s), 11.06 (1H, s).

Example 198: 1-(7-((4-(Pyrazolo[1,5-b]pyridazin-3-yl)-1H-pyrrolo[2,3-b]pyridin-2-yl)methyl)-2,7-diazaspiro[4.5]decan-2-yl)prop-2-en-1-one

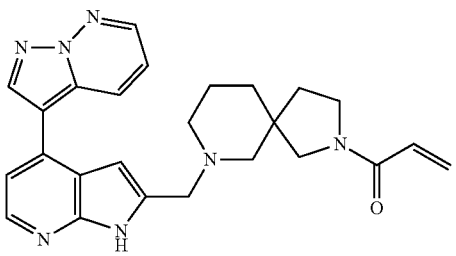 [SMILES: C=CC(=O)N1CCC2(CCCN(Cc3cc4c(-c5cnn6ncccc56)ccnc4[nH]3)C2)C1]

To a solution of 7-((4-(pyrazolo[1,5-b]pyridazin-3-yl)-1H-pyrrolo[2,3-b]pyridin-2-yl)methyl)-2,7-diazaspiro[4.5]decane (Example 109, 32 mg, 0.08 mmol) and DIPEA (43 μL, 0.25 mmol) in DCM (1 mL) cooled in an ice/water bath under argon was added a solution of acryloyl chloride (6.7 μL, 0.08 mmol) in DCM. The reaction was stirred for 2 h then was diluted with DCM and washed with water. The organic layer was dried (Na$_2$SO$_4$) and concentrated in vacuo. The residue was purified by FCC, eluting with 0-10% MeOH in DCM then triturated with EtOAc to give the title compound as a solid (8 mg, 22%).

LCMS (Method 1): Rt 2.14 min, m/z 442.4 [MH$^+$].

$^1$H NMR (400 MHz, d$_6$-DMSO): 2.42-1.73 (10H, m), 3.74-3.11 (6H, m), 5.62-5.55 (1H, m), 6.11-5.99 (1H, m), 6.60-6.42 (2H, m), 7.28-7.23 (1H, m), 7.38-7.31 (1H, m), 8.22 (1H, d, J=5.0 Hz), 8.47-8.40 (1H, m), 8.59-8.53 (2H, m), 11.76-11.64 (1H, m).

Example 199: N-((1-((4-(Pyrazolo[1,5-b]pyridazin-3-yl)-1H-pyrrolo[2,3-b]pyridin-2-yl)methyl)pyrrolidin-3-yl)methyl)acrylamide

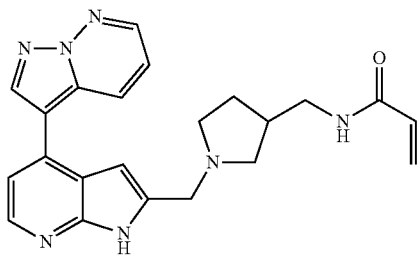 [SMILES: C=CC(=O)NCC1CCN(Cc2cc3c(-c4cnn5ncccc45)ccnc3[nH]2)C1]

To (1-((4-(pyrazolo[1.5-b]]pyridazin-3-yl)-1H-pyrrolo[2,3-b]pyridine-2-yl)methyl)pyrrolidin-3-yl-methanamine (Example 110, 32 mg, 0.092 mmol) in DCM (1 mL) at 00° C. under argon was added DIPEA (48 mg, 0.368 mmol) and acryloyl chloride (13 mg, 0.138 mmol) in DCM (1 mL) was added dropwise with stirring. After 15 min the reaction mixture was diluted with DCM and washed with water. The organic layer was dried (Na$_2$SO$_4$) and concentrated in vacuo. The residue was purified by FCC eluting with 0-20% DCM:MeOH and the product was sonicated with ethyl acetate to give the title compound (6 mg, 16%) as a yellow solid.

LCMS (Method 1): Rt 1.98 min, m/z 402.4 [MH$^+$]

$^1$H NMR (400 MHz, d-DMSO), 1.36-1.45 (1H, m), 1.81-1.91 (1H, m), 2.24-2.32 (2H, m), 2.47-2.68 (3H, m), 3.04-3.18 (2H, m), 3.72-3.75 (2H, m), 5.53 (1H, dd, J=2.4, 10.1 Hz), 6.04 (1H, dd, J=2.4, 17.1 Hz), 6.18 (1H, dd, J=10.1, 17.1 Hz), 6.46 (1H, d, J=1.8 Hz), 7.26 (1H, d, J=5.0 Hz), 7.34 (1H, dd, J=4.4, 9.1 Hz), 8.09 (1H, t, J=5.5 Hz), 8.22 (1H, d, J=5.0 Hz), 8.45 (1H, dd, J=1.8, 9.1 Hz), 8.55-8.59 (2H, m), 11.73 (1H, s).

Example 200: (E)-3-(4-(Dimethylamino)but-2-enamido)-N-(2-(4-(pyrazolo[1,5-b]pyridazin-3-yl)-1H-pyrrolo[2,3-b]pyridin-2-yl)ethyl)benzamide

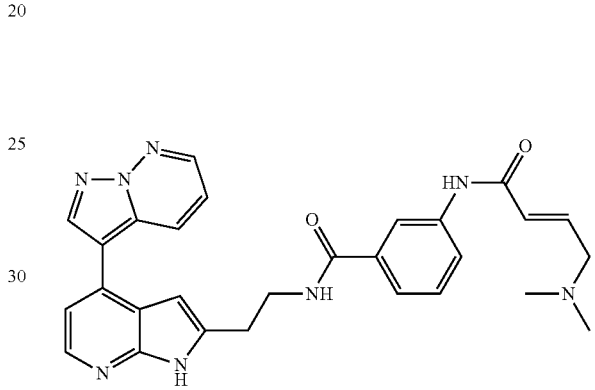

HATU (167 mg, 0.44 mmol) was added to a solution of (2E)-4-(dimethylamino)but-2-enoic acid hydrochloride (66 mg, 0.44 mmol) and TEA (0.270 mL, 1.93 mmol) in DCM (3.0 mL) and the mixture was stirred for 15 mins. 3-Aminobenzoic acid (55 mg, 0.40 mmol) was added and the solution stirred at r.t. over night. A further portion of HATU (167 mg, 0.44 mmol) was added and the solution was stirred for 10 min. The resulting solution was added to a solution of 2-(4-(pyrazolo[1,5-b]pyridazin-3-yl)-1H-pyrrolo[2,3-b]pyridin-2-yl)ethan-1-amine (Example 30, 70 mg, 0.25 mmol) in DCM (1.0 mL) and the mixture was stirred for 60 min. The reaction was quenched by addition of a saturated aqueous solution of Na$_2$CO$_3$ and extracted with CHCl$_3$. The combined organic layers were washed with a saturated aqueous solution of Na$_2$CO$_3$, brine, dried (Na$_2$SO$_4$) and concentrated in vacuo. The residue was purified by FCC using SNAP KP-NH eluting with 0-4% MeOH in DCM. Further purification by MDAP (acidic) gave the title compound (5 mg, 4%).

LCMS (Method 1): Rt 2.09 min, m/z 509.2 [MH$^+$].

$^1$H NMR (400 MHz, d$_6$-DMSO): 2.61 (6H, s), 3.05 (2H, t, J=7.2 Hz), 3.76-3.61 (4H, m), 6.46-6.36 (2H, m), 6.80-6.70 (1H, m), 7.28-7.22 (2H, m), 7.40 (1H, t, J=7.9 Hz), 7.52 (1H, d, J=21.5 Hz), 7.87-7.80 (1H, m), 8.11-8.07 (1H, m), 8.20 (1H, d, J=4.9 Hz), 8.42 (1H, dd, J=1.8, 9.1 Hz), 8.58-8.52 (2H, m), 8.66-8.59 (1H, m), 10.37 (1H, s), 11.77-11.69 (1H, m).

Example 201: (S)-1-(2-Cyanoacetyl)-N-(2-(4-(pyrazolo[1,5-b]pyridazin-3-yl)-1H-pyrrolo[2,3-b]pyridin-2-yl)ethyl)pyrrolidine-2-carboxamide

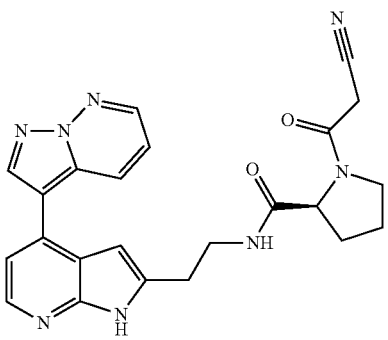 [SMILES: N#CCC(=O)N1CCC[C@H]1C(=O)NCCc1cc2c(-c3cnn4ncccc34)ccnc2[nH]1]

EDC.HCl (114 mg, 0.60 mmol) was added to a stirred solution of (S)—N-(2-(4-(pyrazolo[1,5-b]pyridazin-3-yl)-1H-pyrrolo[2,3-b]pyridin-2-yl)ethyl)pyrrolidine-2-carboxamide (Example 82, 187 mg, 0.50 mmol), cyanoacetic acid (51 mg, 0.60 mmol) TEA (0.140 mL, 2.00 mmol) and HOBt (76 mg, 0.50 mmol) in DCM (5.0 mL) and the mixture was stirred at r.t. for 12 h. The reaction was diluted with DCM and washed with water (25 mL), saturated aqueous solution of. NH₄Cl, a saturated aqueous solution of Na₂CO₃ and brine. The aqueous layers were re-extracted with DCM and the combined organic layers were dried (MgSO₄) and concentrated in vacuo to give the title compound (190 mg, 86%) as a yellow solid.

LCMS (Method 1): Rt 2.23 min, m/z 443.4 [MH⁺].

¹H NMR (400 MHz, d₆-DMSO): 2.16-1.48 (4H, m), 2.99-2.85 (2H, m), 3.55-3.17 (4H, m), 4.03-3.68 (2H, m), 4.31-4.18 (1H, m), 6.43-6.38 (1H, m), 7.25 (1H, d, J=5.0 Hz), 7.36-7032 (1H, m), 8.03 (0.8H, t, J=5.8 Hz), 8.25-8.16 (1.2H, m), 8.49-8.42 (1H, m), 8.61-8.53 (2H, m), 11.72-11.58 (1H, m).

Example 202: (S)-1-(2-Cyano-3-methylbut-2-enoyl)-N-(2-(4-(pyrazolo[1,5-b]pyridazin-3-yl)-1H-pyrrolo[2,3-b]pyridin-2-yl)ethyl)pyrrolidine-2-carboxamide

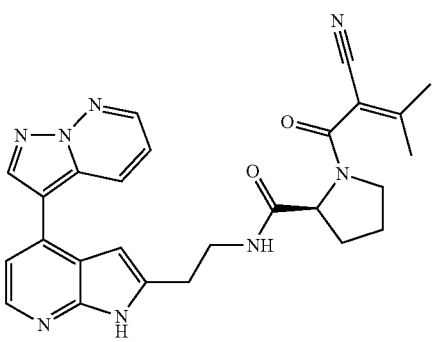 [SMILES: CC(C)=C(C#N)C(=O)N1CCC[C@H]1C(=O)NCCc1cc2c(-c3cnn4ncccc34)ccnc2[nH]1]

To a solution of (S)-1-(2-cyanoacetyl)-N-(2-(4-(pyrazolo[1,5-b]pyridazin-3-yl)-1H-pyrrolo[2,3-b]pyridin-2-yl)ethyl)pyrrolidine-2-carboxamide (Example 201, 88 mg, 0.20 mmol) in methanol (4 mL) was added acetone (29 μL, 0.40 mmol) and piperidine (20 μL, 0.20 mmol). The solution was heated at 45° C. 12 hours. A further portion of acetone (29 μL, 0.40 mmol) was added and the solution was heated at 45° C. 6 hours. Further portions of acetone (290 uL, 4.0 mmol) and piperidine (20 μL, 0.20 mmol) were added and the solution was heated at 45 C° C. 6 hours. After cooling, the mixture was concentrated in vacuo and the residue was purified by FCC eluting with 4-12% MeOH in DCM to give the title compound (34 mg, 35%) as a yellow solid.

LCMS (Method 1): Rt 2.62 min, m/z 483.5 [MH⁺].

¹H NMR (400 MHz, d₆-DMSO): 2.22-1.62 (10H, m), 2.97-2.83 (2H, m), 3.56-3.36 (4H, m), 4.24-4.18 (0.3H, m), 4.34-4.26 (0.7H, m), 6.45-6.39 (1H, m), 7.27-7.22 (1H, m), 7.37-7.30 (1H, m), 8.16 (0.7H, t, J=5.6 Hz), 8.21-8.18 (1H, m), 8.26 (0.3H, t, J=5.6 Hz), 8.50-8.43 (1H, m), 8.60-8.53 (2H, m), 11.73-11.58 (1H, m).

Example 203: N-Methyl-1-(4-(pyrazolo[1,5-b]pyridazin-3-yl)-1H-pyrrolo[2,3-b]pyridin-2-yl)methanamine

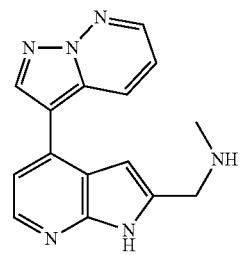 [SMILES: CNCc1cc2c(-c3cnn4ncccc34)ccnc2[nH]1]

A mixture of N-methyl-1-(1-(phenylsulfonyl)-4-(pyrazolo[1,5-b]pyridazin-3-yl)-1H-pyrrolo[2,3-b]pyridin-2-yl)methanamine (Intermediate 114, 36 mg, 0.086 mmol) and 2 M NaOH solution (0.43 mL, 0.86 mmol) in 1,4-dioxane (1 mL) and ethanol (0.5 mL) was degassed with argon then heated at 55° C. for 2.5 h. After cooling, the mixture was extracted with DCM (2×30 mL) and the combined organic extracts were dried and evaporated. The residue was purified by FCC eluting with 0-10% 2 M NH₃/MeOH in DCM to give the title compound (14 mg, 58%).

LCMS (Method 3): Rt 0.65 min, m/z 279.1 [MH⁺].

¹H NMR (400 MHz, CDCl₃), 2.51 (3H, s), 4.01 (2H, s), 6.44 (1H, s), 7.11 (1H, dd, J=4.4, 9.0 Hz), 7.18 (1H, d, J=5.1 Hz), 8.23 (1H, dd, J=1.9, 9.1 Hz), 8.35 (1H, d, J=5.0 Hz), 8.39 (1H, dd, J=1.9, 4.3 Hz), 8.44 (1H, s), 9.98 (1H, s).

By proceeding in a similar manner as Example 126, the following compounds were prepared:

Example 204: N-(2-Methoxy-5-(3-(4-(pyrazolo[1,5-b]pyridazin-3-yl)-1H-pyrrolo[2,3-b]pyridin-2-yl)pyrrolidine-1-carbonyl)phenyl)acrylamide

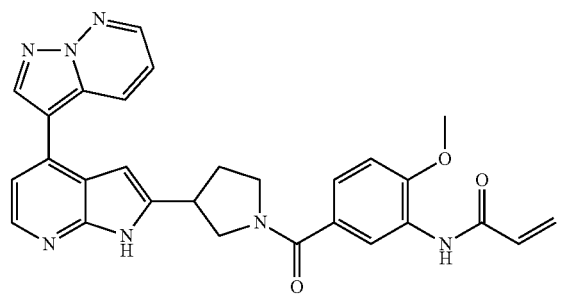 [SMILES: C=CC(=O)Nc1cc(C(=O)N2CCC(c3cc4c(-c5cnn6ncccc56)ccnc4[nH]3)C2)ccc1OC]

Starting from 3-(2-(pyrrolidin-3-yl)-1H-pyrrolo[2,3-b]pyridin-4-yl)pyrazolo[1,5-b]pyridazine (Example 122) and 3-acrylamido-4-methoxybenzoic acid (Intermediate 114A).

LCMS (Method 2): 94.0%, Rt 260 min, m/z 508 [MH⁺].

¹H NMR (400 MHz, d₆-DMSO) 11.85 (0.5H, s), 11.76 (0.5H, s), 9.52-9.48 (1H, m), 8.63 (0.5H, s), 8.60-8.54 (1.5H, m), 8.43 (1H, d, J=9.4 Hz), 8.36-8.31 (1H, m), 8.22 (1H, dd, J=4.9, 10.1 Hz), 7.36-7.31 (2H, m), 7.27 (1H, dd, J=4.9, 7.4 Hz), 7.10 (1H, d, J=8.4 Hz), 6.75-6.66 (1H, m), 6.49 (1H, d, J=33.4 Hz), 6.23 (1H, dd, J=7.6, 17.0 Hz), 5.71 (1H, dd, J=4.4, 9.8 Hz), 4.03-3.94 (1H, m), 3.89 (3H, s), 3.74-3.55 (4H, m), 2.42-2.32 (1H, m), 2.27-2.15 (1H, m).

Example 205: (S)-1-Acryloyl-N-((1S,3R)-3-(4-(pyrazolo[1,5-b]pyridazin-3-yl)-1H-pyrrolo[2,3-b]pyridin-2-yl)cyclobutyl)pyrrolidine-2-carboxamide

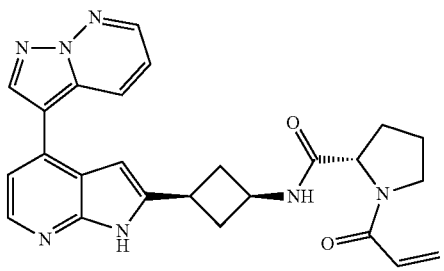 [SMILES: C=CC(=O)N1CCC[C@H]1C(=O)N[C@H]1C[C@@H](c2cc3c(-c4cnn5ncccc45)ccnc3[nH]2)C1]

Starting from (1S,3S)-3-(4-(pyrazolo[1,5-b]pyridazin-3-yl)-1H-pyrrolo[2,3-b]pyridin-2-yl)cyclobutan-1-amine (Intermediate 115) and acryloyl-L-proline (Intermediate 116).

LCMS (Method 2): 99.3%, Rt 2.46 min, m/z 456.4 [MH⁺].

¹H NMR (400 MHz, d₆-DMSO) 8.92 (1H, s), 8.71 (1H, d, J=3.2 Hz), 8.64 (1H, d, J=9.1 Hz), 8.47 (1H, d, J=6.1 Hz), 7.80 (1H, d, J=6.3 Hz), 7.54 (1H, dd, J=4.5, 9.2 Hz), 6.94 (1H, d, J=4.8 Hz), 6.17-6.09 (1H, m), 5.69 (1H, dd, J=2.2, 10.1 Hz), 5.62 (1H, dd, J=2.8, 10.2 Hz), 4.33-4.24 (2H, m), 3.71-3.42 (3H, m), 2.75-2.68 (2H, m), 2.30-2.18 (2H, m), 2.09-1.79 (4H, m), (NH— not observed).

Example 206: 1-((3S)-3-(3-(4-(Pyrazolo[1,5-b]pyridazin-3-yl)-1H-pyrrolo[2,3-b]pyridin-2-yl)pyrrolidine-1-carbonyl)piperidin-1-yl)prop-2-en-1-one

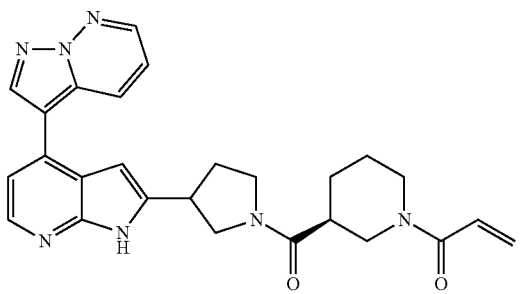 [SMILES: C=CC(=O)N1CCC[C@H](C(=O)N2CCC(c3cc4c(-c5cnn6ncccc56)ccnc4[nH]3)C2)C1]

To a solution of ((S)-piperidin-3-yl)(3-(4-(pyrazolo[1,5-b]pyridazin-3-yl)-1H-pyrrolo[2,3-b]pyridin-2-yl)pyrrolidin-1-yl)methanone (Intermediate 118, 22 mg, 0.0529 mmol) in DCM (1.0 mL) and N,N-diisopropylethylamine (0.028 mL, 0.159 mmol) at −70° C. under argon was added a solution acryloyl chloride (0.0065 mL, 0.0794 mmol) in DCM (0.1 mL) dropwise. The reaction mixture was stirred for 20 minutes. After that time, it was diluted with DCM, washed with water, dried over anhydrous sodium sulfate, filtered and the filtrate was concentrated under reduced pressure. Toluene (10 mL) was added and the mixture was evaporated in vacuo. The resulting residue was triturated with a mixture of ethyl acetate and iso-hexane (1:1) and further purified by FCC eluting with 0-20% iso-propanol in DCM.

LCMS (Method 1): 100%, Rt 2.65 min, m/z 470 [MH⁺].

¹H NMR (400 MHz, DMSO) 11.82-11.78 (1H, m), 8.60 (1H, s), 8.56 (1H, dd, J=1.7, 4.3 Hz), 8.46 (1H, td, J=1.5, 9.1 Hz), 8.24-8.21 (1H, m), 7.34 (1H, dd, J=4.4, 9.1 Hz), 7.28 (1H, t, J=4.8 Hz), 6.90-6.71 (1H, m), 6.52 (0.5H, d, J=4.4 Hz), 6.46 (0.5H, s), 6.14-5.98 (1H, m), 5.68-5.64 (0.8H, m), 5.54-5.50 (0.2H, m), 4.47 (0.5H, d, J=13.1 Hz), 4.34 (0.5H, d, J=4.2 Hz), 4.03-3.98 (1.5H, m), 3.88 (0.5H, dd, J=7.5, 11.3 Hz), 3.74-3.54 (3H, m), 3.48-3.42 (0.5H, m), 3.19-3.11 (0.6H, m), 3.06-3.00 (0.6H, m), 2.70-2.61 (1.1H, m), 2.42-2.39 (0.6H, m), 2.34-2.29 (0.6H, m), 2.26-2.08 (1.3H, m), 1.94-1.58 (3.3H, m), 1.42-1.37 (1.1H, m), 1.24 (0.3H, s).

Example 207: (2S,4R)-1-Acryloyl-4-fluoro-N-(2-(4-(pyrazolo[1,5-b]pyridazin-3-yl)-1H-pyrrolo[2,3-b]pyridin-2-yl)ethyl)pyrrolidine-2-carboxamide

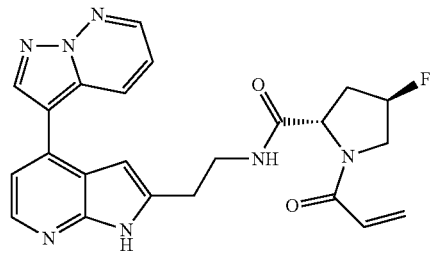 [SMILES: C=CC(=O)N1C[C@H](F)C[C@H]1C(=O)NCCc1cc2c(-c3cnn4ncccc34)ccnc2[nH]1]

(2S,4R)-1-Acryloyl-4-fluoropyrrolidine-2-carboxylic acid (Intermediate 119, 67 mg, 0.359 mmol) and DIPEA (0.19 mL, 1.08 mmol) were dissolved in DMF (1 mL). T3P (0.330 mL, 1.08 mmol) was added and the mixture was stirred at room temperature for 20 minutes. A solution of 2-(4-(pyrazolo[1,5-b]pyridazin-3-yl)-1H-pyrrolo[2,3-b]pyridin-2-yl)ethan-1-amine (Example 30, 50 mg, 0.180 mmol) was added and the mixture was stirred at room temperature for one hour. Water (10 mL) was added to the mixture, which was extracted with DCM (3×40 mL). The DCM phase was passed through a phase separator and evaporated to dryness. The residue was purified by preparative HPLC to yield the title compound (24 mg).

LCMS (Method 2): 94.5% purity, Rt 2.38 min, m/z 448.0 [MH⁺].

¹H NMR (400 MHz, DMSO) 11.69 (0.4H, s), 11.63 (0.6H, s), 8.63 (0.6H, s), 8.58-8.55 (1.3H, m), 8.50-8.44 (1H, m), 8.40-8.35 (0.4H, m), 8.23-8.19 (1.3H, m), 7.36-7.30 (1H, m), 7.27-7.24 (0.9H, m), 6.63-6.55 (0.6H, m), 6.46 (0.5H, d, J=1.6 Hz), 6.41 (0.3H, d, J=1.5 Hz), 6.18-6.09 (0.9H, m), 5.98 (0.3H, dd, J=2.4, 16.6 Hz), 5.69 (0.6H, dd, J=2.2, 10.3 Hz), 5.41-5.18 (1.3H, m), 4.52 (0.3H, t, J=8.0 Hz), 4.40 (0.7H, t, J=8.4 Hz), 4.35-4.23 (0.2H, m), 4.03-3.88 (1.2H, m), 3.84-3.68 (0.9H, m), 3.56-3.40 (2.5H, m), 2.92 (2.4H, q, J=6.9 Hz), 2.39-2.28 (0.7H, m), 2.17-1.87 (1.1H, m).

Example 208: (S)-5-Acryloyl-N-(2-(4-(pyrazolo[1,5-b]pyridazin-3-yl)-1H-pyrrolo[2,3-b]pyridin-2-yl)ethyl)-5-azaspiro[2.4]heptane-6-carboxamide

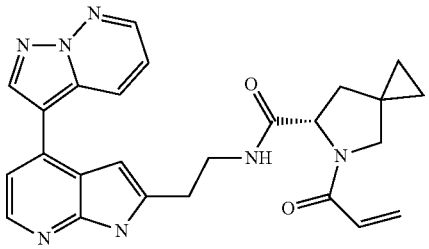 [SMILES: C=CC(=O)N1CC2(CC2)C[C@H]1C(=O)NCCc1cc2c(-c3cnn4ncccc34)ccnc2[nH]1]

Prepared by proceeding in a similar manner as Example 207 starting from 2-(4-(pyrazolo[1,5-b]pyridazin-3-yl)-1H-pyrrolo[2,3-b]pyridin-2-yl)ethan-1-amine (Example 30) and (S)-5-acryloyl-5-azaspiro[2.4]heptane-6-carboxylic acid (Intermediate 120).

LCMS (Method 2): 94.3% purity, Rt 2.59 min, m/z 456.0 [MH$^+$].

$^1$H NMR (400 MHz, DMSO) 11.65 (0.4H, s), 11.62 (0.6H, s), 8.61 (0.6H, s), 8.57-8.56 (1.4H, m), 8.49-8.44 (1H, m), 8.21-8.18 (1H, m), 8.15 (0.4H, t, J=5.7 Hz), 7.99 (0.6H, dd, J=5.7, 5.7 Hz), 7.34 (1H, dd, J=4.4, 9.1 Hz), 7.25 (1H, dd, J=1.4, 5.0 Hz), 6.51-6.40 (1.5H, m), 6.17-6.09 (1H, m), 5.99 (0.4H, dd, J=2.5, 16.7 Hz), 5.64 (0.6H, dd, J=2.4, 10.3 Hz), 5.34 (0.4H, dd, J=2.5, 10.1 Hz), 4.51-4.38 (1H, m), 3.56-3.43 (3.5H, m), 3.24 (0.7H, t, J=12.0 Hz), 2.97-2.88 (2H, m), 2.34-2.24 (0.6H, m), 2.06 (0.7H, dd, J=8.6, 12.4 Hz), 1.67-1.57 (1H, m), 0.53-0.22 (3.6H, m).

Example 209: (E)-1-(4-Acryloylpiperazin-1-yl)-3-(4-(pyrazolo[1,5-b]pyridazin-3-yl)-1H-pyrrolo[2,3-b]pyridin-2-yl)prop-2-en-1-one

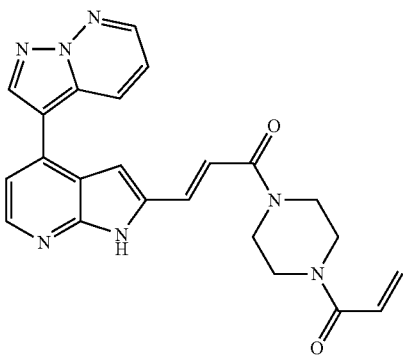 [SMILES: C=CC(=O)N1CCN(C(=O)/C=C/c2cc3c(-c4cnn5ncccc45)ccnc3[nH]2)CC1]

(E)-3-(4-(Pyrazolo[1,5-b]pyridazin-3-yl)-1H-pyrrolo[2,3-b]pyridin-2-yl)acrylic acid (Intermediate 122, 20 mg) was dissolved in DMF (0.5 mL) and DIPEA (0.06 mL, 0.382 mmol) and T3P (61 mg, 0.191 mmol) were added. After stirring for 10 minutes, 1-(piperazin-1-yl)prop-2-en-1-one (Intermediate 121, 20 mg, 0.143 mmol) was added. The reaction mixture was stirred at room temperature for 15 minutes, then diluted with water, basified with NaHCO$_3$ and extracted with DCM. The organic phase was dried, filtered and the filtrate was evaporated to dryness. The residue was purified by FCC (isopropanol/DCM) to yield the title compound as a yellow solid (10 mg).

LCMS (Method 1) 98.2% purity Rt 2.83 min m/z 428 [MH$^+$]

$^1$H NMR (400 MHz, DMSO) 12.19 (1H, s), 8.66 (1H, s), 8.59 (1H, dd, J=1.8, 4.4 Hz), 8.52 (1H, dd, J=1.8, 9.1 Hz), 8.35 (1H, d, J=5.0 Hz), 7.58 (0.4H, s), 7.54 (0.6H, s), 7.44 (0.6H, s), 7.42-7.34 (2.2H, m), 7.13 (1H, d, J=1.6 Hz), 6.86-6.86 (1H, m), 6.20-6.14 (1H, m), 5.76-5.71 (1.2H, m), 3.68-3.55 (8H, m).

Example 210: (S)-1-cyano-N-(2-(4-(pyrazolo[1,5-b]pyridazin-3-yl)-1H-pyrrolo[2,3-b]pyridin-2-yl)ethyl)piperidine-3-carboxamide

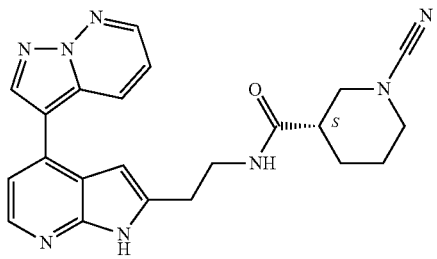

A solution of (S)—N-(2-(4-(pyrazolo[1,5-b]pyridazin-3-yl)-1H-pyrrolo[2,3-b]pyridin-2-yl)ethyl)piperidine-3-carboxamide (Intermediate 123b, 97 mg, 0.25 mmol) and K$_2$CO$_3$ (140 mg, 1.00 mmol) in MeCN (5 mL) was treated with cyanogen bromide (29 mg, 0.275 mmol). The reaction mixture was stirred at r.t. for 12 h then diluted with H$_2$O and extracted with ethyl acetate. The combined organic layers were washed with brine, dried (MgSO$_4$), filtered, and the filtrate was concentrated in vacuo. The residue was purified by FCC eluting with 4-8% MeOH in DCM to give the title compound (13 mg, 13%) as a pale yellow solid.

LCMS (Method 1): 92.4%, Rt 2.40 min, m/z 415 [MH$^+$].

$^1$H NMR (400 MHz, DMSO) 11.67 (1H, s), 8.58-8.55 (2H, m), 8.46 (1H, dd, J=1.8, 9.2 Hz), 8.20 (1H, d, J=5.0 Hz), 8.09 (1H, dd, J=5.6, 5.6 Hz), 7.34 (1H, dd, J=4.5, 9.1 Hz), 7.25 (1H, d, J=5.0 Hz), 6.40 (1H, s), 3.48-3.40 (2H, m), 3.30-3.22 (2H, m), 3.03-2.86 (4H, m), 2.47-2.38 (1H, m), 1.78-1.73 (1H, m), 1.64-1.41 (3H, m).

By proceeding in a similar manner to Example 105, the following compounds were prepared:

Example 211: N-(1-Oxo-3-phenyl-1-((2-(4-(pyrazolo[1,5-b]pyridazin-3-yl)-1H-pyrrolo[2,3-b]pyridin-2-yl)ethyl)amino)propan-2-yl)acrylamide

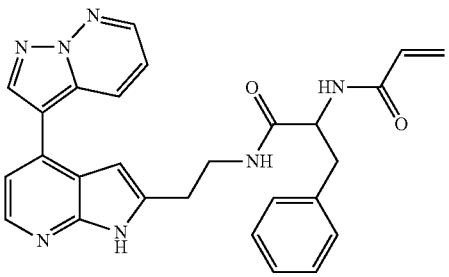 [SMILES: C=CC(=O)NC(Cc1ccccc1)C(=O)NCCc1cc2c(-c3cnn4ncccc34)ccnc2[nH]1]

Starting from 2-(4-(pyrazolo[1,5-b]pyridazin-3-yl)-1H-pyrrolo[2,3-b]pyridin-2-yl)ethan-1-amine (Example 30) and, acryloylphenylalanine (Intermediate 124).

LCMS (Method 4): Rt 2.38 min, m/z 480.2 [MH+].

$^1$H NMR (400 MHz, CDCl$_3$) 2.72 (1H, dd, J=13.7, 9.5) 2.95-2.82 (3H, m), 3.55-3.36 (2H, m), 4.53 (1H, dt, J=9.3, 5.1), 5.49 (1H, dd, J=10.2, 2.2), 5.98 (1H, dd, J=17.1, 2.2), 6.23 (1H, dd, J=17.1, 10.2), 6.40 (1H, d, J=1.9), 7.21-7.07 (5H, m), 7.24 (1H, d, J=5.0), 7.31 (1H, dd, J=9.1, 4.4), 8.19 (1H, d, J=5.0), 8.21 (1H, s), 8.35 (1H, d, J=8.4), 8.44 (1H, dd, J=9.1, 1.8), 8.55 (1H, dd, J=4.4, 1.8), 8.59 (1H, s), 11.65 (1H, s).

Example 212: N-(1-oxo-1-((2-(4-(pyrazolo[1,5-b]pyridazin-3-yl)-1H-pyrrolo[2,3-b]pyridin-2-yl)ethyl)amino)propan-2-yl)acrylamide

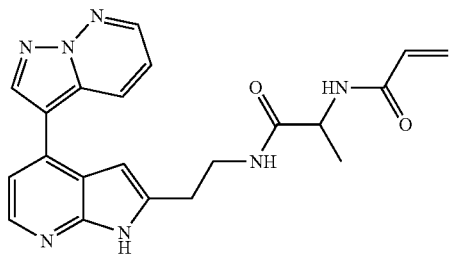 [SMILES: C=CC(=O)NC(C)C(=O)NCCc1cc2c(-c3cnn4ncccc34)ccnc2[nH]1]

Starting from 2-(4-(pyrazolo[1,5-b]pyridazin-3-yl)-1H-pyrrolo[2,3-b]pyridin-2-yl)ethan-1-amine (Example 30) and, acryloylalanine (Intermediate 125).

LCMS (Method 4): Rt 2.094 min, m/z 404.2 [MH+].

$^1$H NMR (400 MHz, CDCl$_3$) 1.40 (3H, d, J=7.0).3.24-3.03 (2H, m), 3.55 (1H, app dt, J=13.0, 7.1), 3.98 (1H, app dt, J=13.0, 6.4), 4.64 (1H, app p, J=7.0), 5.47 (1H, d, J=10.3), 5.97 (1H, ddd, J=17.0, 10.3, 1.0), 6.17 (1H, d, J=17.0), 6.34 (1H, s), 7.15-7.07 (2H, m), 7.51 (1H, bs), 7.64 (1H, bd, J=7.0), 8.21 (1H, dd, J=6.6, 2.5), 8.23 (1H, s), 8.40 (1H, dd, J=4.4, 1.9), 8.43 (1H, s), 11.71 (1H, s).

Example 213: 2-(4-(Pyrazolo[1,5-b]pyridazin-3-yl)-1H-pyrrolo[2,3-b]pyridin-2-yl)ethyl acryloyl-L-prolinate

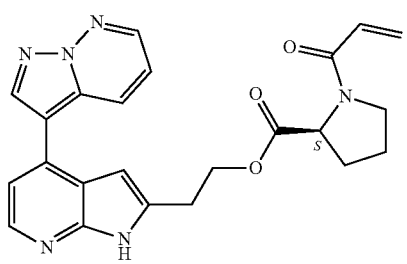

A solution of 2-(4-(pyrazolo[1,5-b]pyridazin-3-yl)-1H-pyrrolo[2,3-b]pyridin-2-yl)ethyl L-prolinate (Intermediate 127d, 34 mg, 0.090 mmol) and TEA (25 µL, 0.180 mmol) in DCM (3.0 mL) at 0° C. was treated with acryloyl chloride (9.8 µL, 0.099 mmol) and the mixture was stirred for 10 min at 0° C. then at r.t for 50 min. The reaction was quenched with a saturated aqueous solution of NaHCO$_3$ and extracted with DCM. The combined organic layers were washed with brine, dried (Na$_2$SO$_4$) and concentrated in vacuo. The residue was purified by FCC eluting with 4-8% MeOH in DCM to give the title compound (17 mg, 44%) as a yellow solid.

LCMS (Method 4): Rt 2.299 min, m/z 431.0[MH+].

$^1$H NMR (400 MHz, CDCl$_3$) 2.12-1.98 (2H, m), 2.34-2.12 (2H, m), 3.09 (1H, dt, J=15.4, 3.5), 3.29 (1H, ddd, J=15.4, 10.2, 4.3), 3.75-3.63 (1H, m), 3.89-3.76 (1H, m), 4.23 (1H, dt, J=10.5, 3.3), 4.61 (1H, dd, J=8.0, 5.1), 4.75 (1H, dt, J=10.5, 4.5), 5.83 (1H, dd, J=10.2, 1.9), 6.37 (1H, s), 6.52 (1H, dd, J=16.8, 10.2), 6.63 (1H, dd, J=16.8, 1.9), 7.11 (1H, dd, J=9.1, 4.4), 7.16 (1H, d, J=5.0), 8.24 (1H, dd, J=9.1, 1.9), 8.34 (1H, d, J=5.0), 8.39 (1H, dd, J=4.4, 1.9), 8.45 (1H, s), 10.71 (1H, s).

By proceeding in a similar manner to Example 105, the following compounds were prepared:

Example 214: 1-Acrylamido-N-(3-(4-(pyrazolo[1,5-b]pyridazin-3-yl)-1H-pyrrolo[2,3-b]pyridin-2-yl)propyl)cyclopropane-1-carboxamide

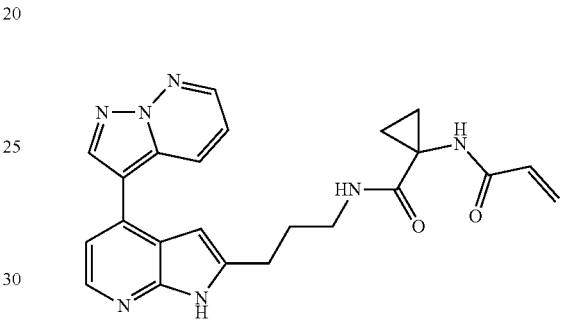

Starting from 3-(4-(pyrazolo[1,5-b]pyridazin-3-yl)-1H-pyrrolo[2,3-b]pyridin-2-yl)propan-1-amine (Example 128d) and 1-acrylamidocyclopropane-1-carboxylic acid (Intermediate 126).

LCMS (Method 4): Rt 2.139 min, m/z 430.2 [MH+].

$^1$H NMR (400 MHz, DMSO-d$_6$) 0.85 (2H, app q, J=4.2), 1.28 (2H, app q, J=4.2), 1.84 (2H, app p, J=7.3), 2.73 (2H, app t, J=7.4), 3.13 (2H, app q, J=6.4), 5.58 (1H, dd, J=10.0, 2.3), 6.08 (1H, dd, J=17.2, 2.3), 6.20 (1H, dd, J=17.2, 10.0), 6.36 (1H, d, J=1.9), 7.24 (1H, d, J=5.0), 7.34 (1H, dd, J=9.1, 4.5), 7.80 (1H, t, J=5.8), 8.19 (1H, d, J=5.0), 8.45 (1H, dd, J=9.1, 1.9), 8.57 (3H, m), 11.65 (1H, s).

Example 215: 3-Acrylamido-N-(3-(4-(pyrazolo[1,5-b]pyridazin-3-yl)-1H-pyrrolo[2,3-b]pyridin-2-yl)propyl)benzamide

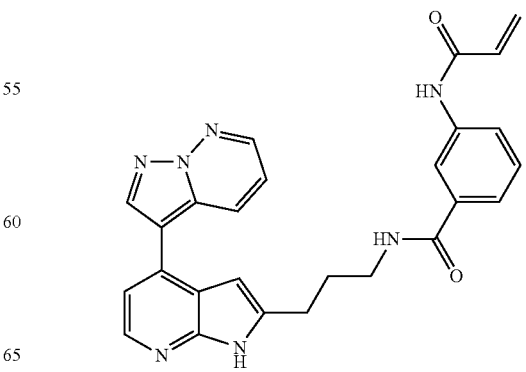

Starting from 3-(4-(pyrazolo[1,5-b]pyridazin-3-yl)-1H-pyrrolo[2,3-b]pyridin-2-yl)propan-1-amine (Intermediate 128d) and 3-acrylamidobenzoic acid LCMS (Method 4): Rt 2.281 min, m/z 466.2 [MH$^+$].

$^1$H NMR (500 MHz, DMSO-d$_6$) 1.98 (2H, app. p, J=7.3), 2.83 (2H, app. t, J=7.5), 3.37-3.29 (2H, m), 5.78 (1H, dd, J=10.1, 2.0), 6.28 (1H, dd, J=17.0, 2.0), 6.51-6.41 (2H, m), 7.25 (1H, d, J=5.0), 7.34 (1H, dd, J=9.1, 4.4), 7.40 (1H, t, J=7.8), 7.52 (1H, dt, J=7.8, 1.4), 7.86 (1H, ddd, J=8.1, 2.2, 1.0), 8.09 (1H, t, J=1.9), 8.19 (1H, d, J=5.0), 8.46 (1H, dd, J=9.1, 1.8), 8.52 (1H, t, J=5.7), 8.56 (1H, dd, J=4.4, 1.8), 8.58 (1H, s), 10.29 (1H, s), 11.69 (1H, s).

Example 216: (S)-1-Acryloyl-N-(3-(4-(pyrazolo[1,5-b]pyridazin-3-yl)-1H-pyrrolo[2,3-b]pyridin-2-yl)propyl)pyrrolidine-2-carboxamide

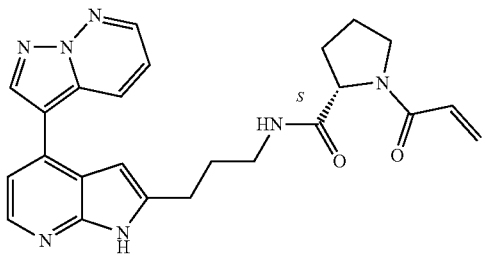

Starting from 3-(4-(pyrazolo[1,5-b]pyridazin-3-yl)-1H-pyrrolo[2,3-b]pyridin-2-yl)propan-1-amine (Example 128d) and acryloyl-L-proline.

LCMS (Method 4): Rt 2.175 min, m/z 444.2 [MH$^+$].

$^1$H NMR (500 MHz, DMSO-d6) (35:65 ration of rotamers) 1.98-1.73 (5H, m), 2.10-1.99 (0.65H, m), 2.24-2.16 (0.35H, m), 2.81-2.72 (2H, m), 3.21-3.06 (2H, m), 3.44 (0.35H, dt, J=11.8, 7.8), 3.60-3.50 (1H, m), 3.68 (0.65H, ddd, J=9.7, 7.6, 4.6), 4.32 (0.65H, dd, J=8.6, 3.6), 4.44 (0.35H, dd, J=8.6, 3.0), 5.61 (0.35H, dd, J=10.2, 2.4), 5.67 (0.65H, dd, J=10.2, 2.4), 6.10 (0.35H, dd, J=16.7, 2.4), 6.14 (0.65H, dd, J=16.7, 2.4), 6.28 (0.35H, dd, J=16.7, 10.2), 6.36 (0.65H, d, J=2.0), 6.37 (0.65H, d, J=1.9), 6.61 (0.35H, dd, J=16.7, 10.2), 7.24 (0.65H, d, J=5.0), 7.25 (0.35H, d, J=5.0), 7.34 (1H, dd, J=9.1, 4.4), 7.94 (0.65H, t, J=5.8), 8.15 (0.35H, t, J=5.8), 8.19 (0.65H, dd, J=5.0), 8.19 (0.35H, dd, J=5.0), 8.46 (1H, m), 8.59-8.53 (2H, m), 11.65 (0.35H, s), 11.67 (0.65H, s).

Example 217: Inhibition of CDK12

Assay buffer comprised 50 mM HEPES pH 7.5, 1 mM DTT, 20 mM MgCl$_2$, 3 mM MnCl$_2$, 3 μM Na$_3$VO$_4$ and 50 μg/ml PEG$_{8000}$. Kinase reactions were carried out in 384-well Optiplates™ (PerkinElmer 6007299). Test compounds were dissolved & diluted in dimethyl sulfoxide (DMSO) and cross diluted into assay buffer with a final DMSO concentration of 1% (v/v) in the assay. Test compounds (or 1% DMSO in control and blank wells) were pre-incubated with 60 nM CDK12/CycK for 30 minutes. After this time 1 μM Adenosine-5'-triphosphate (ATP) and 0.5 μM RBER-IRStide substrate (ProQinase 0863-0000-1) were added to commence the kinase reaction. Incubations were carried out for 1 h at 25° C. with kinase activity determined using the ADP-Glo™ reagent from Promega according to the manufacturer's instructions. Light generated is proportional to kinase activity and measured using a luminometer (EnVision, PerkinElmer). The signal obtained in the blank wells (containing no kinase) was subtracted from all other wells and IC$_{50}$ values were determined by fitting a sigmoidal curve to % inhibition of control versus Log$_{10}$ compound concentration.

Table 1 shows the IC$_{50}$ results for compounds of the invention. "A" represents and IC$_{50}$ value <100 nM, "B" represents and IC50 value in the range 100 nM to 1 μM and "C" represents an IC$_{50}$ value in the range 1 μM to 30 μM.

TABLE 1

| Compound no | CDK12/cyclin K |
| --- | --- |
| 1 | C |
| 2 | C |
| 3 | C |
| 4 | C |
| 5 | C |
| 6 | B |
| 7 | B |
| 8 | C |
| 9 | C |
| 10 | C |
| 11 | B |
| 12 | C |
| 13 | C |
| 14 | C |
| 15 | C |
| 16 | B |
| 17 | C |
| 18 | C |
| 19 | C |
| 20 | B |
| 21 | C |
| 22 | C |
| 23 | C |
| 24 | C |
| 25 | C |
| 26 | C |
| 27 | B |
| 28 | B |
| 29 | C |
| 30 | B |
| 31 | B |
| 32 | A |
| 33 | A |
| 34 | A |
| 35 | A |
| 36 | A |
| 37 | A |
| 38 | A |
| 39 | A |
| 40 | A |
| 41 | B |
| 42 | B |
| 43 | C |
| 44 | C |
| 45 | B |
| 46 | B |
| 47 | C |
| 48 | B |
| 49 | B |
| 50 | C |
| 51 | C |
| 52 | C |
| 53 | A |
| 54 | A |
| 55 | A |
| 56 | A |
| 57 | B |
| 58 | C |
| 59 | C |
| 60 | A |
| 61 | A |
| 62 | A |
| 63 | A |
| 64 | B |
| 65 | A |
| 66 | A |

TABLE 1-continued

| Compound no | CDK12/cyclin K |
| --- | --- |
| 67 | A |
| 68 | A |
| 69 | B |
| 70 | B |
| 71 | B |
| 72 | B |
| 73 | C |
| 75 | A |
| 76 | A |
| 77 | B |
| 78 | B |
| 79 | B |
| 80 | C |
| 81 | A |
| 82 | B |
| 83 | B |
| 84 | C |
| 85 | C |
| 86 | C |
| 87 | C |
| 88 | B |
| 89 | B |
| 92 | A |
| 93 | A |
| 94 | B |
| 95 | C |
| 101 | B |
| 104 | C |
| 105 | C |
| 107 | C |
| 108 | C |
| 111 | B |
| 112 | B |
| 113 | C |
| 114 | A |
| 115 | A |
| 116 | C |
| 117 | C |
| 118 | C |
| 119 | B |
| 122 | A |
| 124 | B |
| 125 | B |
| 126 | A |
| 127 | A |
| 128 | A |
| 129 | A |
| 131 | C |
| 132 | B |
| 133 | C |
| 134 | C |
| 135 | C |
| 136 | C |
| 141 | A |
| 142 | A |
| 143 | A |
| 144 | A |
| 145 | A |
| 146 | A |
| 147 | A |
| 148 | A |
| 149 | A |
| 150 | A |
| 151 | A |
| 152 | A |
| 153 | A |
| 154 | A |
| 155 | A |
| 156 | A |
| 157 | A |
| 158 | A |
| 159 | A |
| 160 | A |
| 161 | B |
| 162 | A |
| 163 | A |
| 164 | A |
| 165 | A |
| 166 | B |
| 167 | C |
| 168 | C |
| 169 | A |
| 170 | A |
| 171 | A |
| 172 | A |
| 173 | A |
| 174 | A |
| 175 | A |
| 176 | A |
| 177 | A |
| 178 | C |
| 179 | C |
| 180 | B |
| 181 | B |
| 182 | C |
| 183 | C |
| 184 | C |
| 185 | A |
| 186 | C |
| 187 | C |
| 188 | C |
| 189 | C |
| 190 | B |
| 191 | C |
| 192 | C |
| 193 | C |
| 194 | A |
| 195 | A |
| 198 | C |
| 199 | C |
| 200 | B |
| 201 | B |
| 202 | C |
| 204 | A |
| 205 | A |
| 206 | A |
| 207 | A |
| 208 | A |
| 209 | A |
| 210 | B |
| 211 | B |
| 212 | B |
| 213 | B |
| 214 | A |
| 215 | A |
| 216 | A |

Example 218: Nuclear Foci Assay

DM1 fibroblasts were treated with compounds in an 11 point dilution series from 20 μM-19 nM for 24 hours. Following treatment, fluorescent in situ hybridisation was performed with a cy3 labelled CAG10 probe, to visualize nuclear foci and cells were analysed on a Molecular Devices plate reader with customised MetaExpress software (Ketley, A. et al. (2014). Hum Mol Genet, 23: 1551-1562). Compounds that reduced nuclear foci in a concentration dependent manner, compared to DMSO treated cells were identified.

Table 2 shows the $IC_{50}$ results for nuclear foci assay for compounds of the invention. "A" represents and $IC_{50}$ value <1 μM, "B" represents and IC50 value in the range 1 μM to 10 μM and "C" represents an $IC_{50}$ value in the range 10 μM to 100 μM.

TABLE 2

| Compound no | Nuclear Foci |
|---|---|
| 6 | B |
| 7 | B |
| 10 | C |
| 11 | B |
| 20 | C |
| 21 | C |
| 22 | C |
| 27 | A |
| 28 | A |
| 32 | A |
| 33 | A |
| 34 | B |
| 35 | A |
| 36 | A |
| 37 | B |
| 39 | A |
| 42 | B |
| 43 | C |
| 44 | B |
| 45 | C |
| 54 | A |
| 55 | B |
| 57 | B |
| 63 | A |
| 69 | C |
| 70 | B |
| 71 | B |
| 72 | B |
| 73 | C |
| 76 | A |
| 83 | B |
| 84 | C |
| 92 | B |
| 94 | C |
| 111 | B |
| 112 | B |
| 113 | C |
| 126 | A |
| 127 | A |
| 129 | B |
| 141 | A |
| 144 | A |
| 145 | A |
| 146 | A |
| 151 | A |
| 156 | A |
| 159 | A |
| 160 | A |
| 161 | A |
| 200 | C |
| 204 | A |
| 207 | A |
| 208 | B |
| 210 | B |
| 211 | B |
| 212 | B |
| 213 | A |

The invention claimed is:

1. A compound of formula (I), or a pharmaceutically acceptable salt or N-oxide thereof:

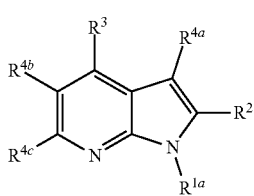

(I)

wherein
$R^{1a}$ is independently selected from: H and $C_1$-$C_6$-alkyl;
$R^2$ is independently selected from H, $C_1$-$C_6$-alkyl, $C_1$-$C_6$-haloalkyl, $C_2$-$C_6$-alkenyl, $C_2$-$C_6$-alkynyl, halo, nitro, cyano, $OR^{5a}$, $SR^{6a}$, $NR^{6a}R^{7a}$, $C(O)R^{6a}$, $C(O)OR^{6a}$, $C(O)NR^{6a}R^{6a}$, $S(O)_2R^{6a}$, $S(O)_2NR^{6a}R^{6a}$, -$L^1$-$L^2$-$R^8$;
wherein $R^3$ has the structure:

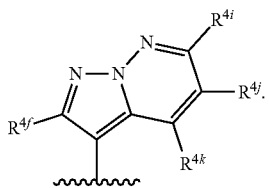

$R^{4a}$ and $R^{4c}$ are each independently selected from H, fluoro, chloro and $C_1$-$C_6$-alkyl;
$R^{4b}$ is selected from H, fluoro, chloro, $C_1$-$C_6$-alkyl, $C_1$-$C_6$-haloalkyl, $C_2$-$C_6$-alkenyl, $C_2$-$C_6$-alkynyl, $OR^{5b}$, $SR^{6b}$ and $NR^{6b}R^{7b}$;
$R^{4d}$ is independently selected from $C_1$-$C_3$-alkylene-$R^9$ or O—$C_1$-$C_3$-alkylene-$R^9$;
$R^{4f}$ and $R^{4k}$ are each independently selected from H, fluoro and chloro and $C_1$-$C_3$ alkyl;
$R^{4i}$ and $R^{4j}$ are each independently selected from H, fluoro, chloro, $C_1$-$C_6$-alkyl, $C_1$-$C_6$-haloalkyl, $C_2$-$C_6$-alkenyl, $C_2$-$C_6$-alkynyl, $OR^{5b}$, $SR^{6b}$ and $NR^{6b}R^{7b}$, or a single one of $R^{4i}$ and $R^{4j}$ is $C_1$-$C_3$-alkylene-$R^9$ or O-$C_1$-$C_3$-alkylene-$R^9$ and the other $R^{4i}$ and $R^{4j}$ is selected from H, fluoro, chloro, $C_1$-$C_6$-alkyl, $C_1$-$C_6$-haloalkyl, $C_2$-$C_6$-alkenyl, $C_2$-$C_6$-alkynyl, $OR^{5b}$, $SR^{6b}$ and $NR^{6b}R^{7b}$;
-$L^1$- is independently absent or is selected from —$(CR^{10a}R^{10a})_{n1}NR^{11a}$—, —$(CR^{10c}R^{10c})_{n2}O$—, —$C_0$-$C_3$-alkylene-$NR^{11b}(CR^{10b}R^{10b})_{m1}NR^{11a}$, —$C_0$-$C_3$-alkylene-$L^{3a}$-$C_0$-$C_3$-alkylene-$NR^{11d}$— and $C_2$-$C_6$-alkenyl;
wherein where $L^1$ is —$(CR^{10a}R^{10a})_{n1}NR^{11a}$— it is optionally the case that: A) a single $R^{10a}$ group and $R^{11a}$ together form a $C_1$-$C_4$-alkylene, said alkylene optionally being interrupted by an oxygen, nitrogen or sulphur atom; or B) two $R^{10a}$ groups together form a $C_1$-$C_4$-alkylene, said alkylene optionally being interrupted by an oxygen, nitrogen or sulphur atom;
wherein where $L^1$ is —$C_0$-$C_3$-alkylene-$NR^{11b}$ $(CR^{10b}R^{10b})_{m1}NR^{11c}$— it is optionally the case that A) $R^{11b}$ and $R^{11c}$ together form a $C_1$-$C_4$-alkylene; B) a single $R^{10b}$ group and either $R^{11b}$ or $R^{11c}$ together form a $C_1$-$C_4$-alkylene, said alkylene optionally being interrupted by an oxygen, nitrogen or sulphur atom; C) two $R^{10b}$ groups together form a $C_1$-$C_4$-alkylene, said alkylene optionally being interrupted by an oxygen, nitrogen or sulphur atom; or D) a single $R^{10b}$ group and $R^{11b}$ together form a $C_1$-$C_4$-alkylene and a single $R^{10b}$ group and $R^{11c}$ together form a $C_1$-$C_4$-alkylene;
wherein where -$L^1$- includes an alkylene group, that alkylene group is optionally substituted with from 1 to 4 $R^{12a}$ groups; and where -$L^1$- includes a phenyl, naphthyl, or heteroaryl group, that phenyl, naphthyl or heteroaryl is optionally substituted with from 1 to 4 $R^{13}a$ groups;
-$L^2$- is independently absent or is selected from $C(O)$-$L^4$- and $SO_2$-$L^4$-$L^{3a}$- and -$L^{3b}$- are each independently selected from phenyl, naphthyl, 5-, 6-, 9- or 10-membered heteroaryl;

-L$^4$- is selected from —(CR$^{10c}$R$^{10c}$)$_{n3}$NR$^{11c}$—, —(CR$^{10c}$R$^{10c}$)$_{n4}$O—, —C$_0$-C$_3$-alkylene-NR$^{11f}$(CR$^{10d}$R$^{10d}$)$_{m2}$NR$^{11g}$— and —C$_0$-C$_3$-alkylene-L$^{3b}$-C$_0$-C$_3$-alkylene-NR$^{11h}$—;

wherein where L$^4$ is —(CR$^{10c}$R$^{10c}$)$_{n3}$NR$^{11e}$— it is optionally the case that: A) a single R$^{10c}$ group and R$^{11e}$ together form a C$_1$-C$_4$-alkylene, said alkylene optionally being interrupted by an oxygen, nitrogen or sulphur atom; or B) two R$^{10c}$ groups together form a C$_1$-C$_4$-alkylene, said alkylene optionally being interrupted by an oxygen, nitrogen or sulphur atom;

wherein where L$^4$ is —C$_0$-C$_3$-alkylene-NR$^{11f}$(CR$^{10d}$R$^{10d}$)$_{m2}$NR$^{11g}$— it is optionally the case that A) R$^{11f}$ and R$^{11g}$ together form a C$_1$-C$_4$-alkylene; B) a single R$^{10d}$ group and either R$^{11f}$ or R$^{11g}$ together form a C$_1$-C$_4$-alkylene, said alkylene optionally being interrupted by an oxygen, nitrogen or sulphur atom; C) two R$^{10d}$ groups together form a C$_1$-C$_5$-alkylene, said alkylene optionally being interrupted by an oxygen, nitrogen or sulphur atom; or D) a single R$^{10d}$ group and R$^{11f}$ together form a C$_1$-C$_4$-alkylene and a single R$^{10d}$ group and R$^{11g}$ together form a C$_1$-C$_4$-alkylene;

wherein where -L$^4$- includes an alkylene group, that alkylene group is optionally substituted with from 1 to 4 R$^{12b}$ groups; and where -L$^4$- includes a phenyl, naphthyl, or heteroaryl group, that phenyl, naphthyl or heteroaryl is optionally substituted with from 1 to 4 R$^{13b}$ groups;

R$^{5a}$, R$^{5b}$, R$^{5d}$ and R$^{5e}$ are each independently at each occurrence selected from H, C$_1$-C$_6$-alkyl (wherein said C$_1$-C$_6$-alkyl group may be optionally substituted with from 1 to 3 OR$^{5c}$ or NR$^{6c}$R$^{7c}$ groups) and C$_1$-C$_6$-haloalkyl;

R$^{5c}$ and R$^{5f}$ are independently at each occurrence selected from H, C$_1$-C$_6$-alkyl and C$_1$-C$_6$-haloalkyl;

R$^{6a}$, R$^{6b}$, R$^{6d}$ and R$^{6e}$ are each independently at each occurrence selected from H and C$_1$-C$_6$-alkyl (wherein said C$_1$-C$_6$-alkyl group may be optionally substituted with from 1 to 3 OR$^{5c}$ or NR$^{6c}$R$^{7c}$ groups);

R$^{6c}$ is independently at each occurrence selected from H and C$_1$-C$_6$-alkyl;

R$^{7a}$, R$^{7b}$, R$^{7d}$ and R$^{7c}$ are each independently at each occurrence selected from H, C$_1$-C$_6$-alkyl (wherein said C$_1$-C$_6$-alkyl group may be optionally substituted with a 5-membered heterocycloalkyl group or from 1 to 3 OR$^5$, or NR$^{6c}$R$^{7c}$ groups), C(O)R$^{14a}$, C(O)OR$^{14a}$, C(O)NHR$^{14a}$, S(O)$_2$R$^{14a}$ and S(O)$_2$NHR$^{14a}$;

R$^{7c}$ is independently at each occurrence selected from H, C$_1$-C$_6$-alkyl, C(O)R$^{14b}$, C(O)OR$^{14b}$, C(O)NHR$^{14b}$, S(O)$_2$R$^{14b}$ and S(O)$_2$NHR$^{14b}$;

R$^8$ is independently selected from H, S(O)$_2$R$^{15}$, C(O)R$^{15}$, C(O)OR$^{15}$, S(O)$_2$—C$_0$-C$_3$-alkylene-R$^{15}$, C(O)—C$_0$-C$_3$-alkylene-R$^{15}$ and C$_0$-C$_3$-alkylene-R$^{15}$; wherein R$^{15}$ is independently selected from phenyl, C$_3$-C$_7$-cycloalkyl, C$_1$-C$_6$-alkyl, 5- to 7-membered heterocycloalkyl, 5-, 6-, 9- and 10-membered heteroaryl; wherein where any R$^8$ group includes heterocycloalkyl, alkylene, cycloalkyl or alkyl, that heterocycloalkyl, cycloalkyl or alkyl group is optionally substituted with from 1 to 4 R$^{12c}$ groups; and where any R$^8$ group includes phenyl or heteroaryl, that phenyl or heteroaryl is optionally substituted with from 1 to 4 R$^{13c}$ groups or R$^8$ is a group that can react with the SH of a cysteine to form a covalent bond between a carbon atom of R$^8$ and the sulphur atom of the cysteine;

R$^9$ is independently selected from H, phenyl, 5- to 7-membered heterocycloalkyl, 5-, 6-, 9- and 10- membered heteroaryl; wherein where any R$^9$ group is heterocycloalkyl, that is optionally substituted with from 1 to 4 R$^{12d}$ groups; and where any R$^9$ group is phenyl or heteroaryl, that phenyl or heteroaryl is optionally substituted with from 1 to 4 R$^{13d}$ groups;

R$^{10a}$, R$^{10b}$, R$^{10c}$ and R$^{10d}$ are each independently at each occurrence selected from H, C$_1$-C$_6$-alkyl, CH$_2$OR$^{5f}$ and benzyl;

R$^{11a}$, R$^{11b}$, R$^{11c}$, R$^{11d}$, R$^{11e}$, R$^{11f}$, R$^{11g}$, R$^{11h}$ are each independently selected from: H and C$_1$-C$_6$-alkyl;

R$^{12a}$, R$^{12c}$ and R$^{12d}$ are each independently at each occurrence selected from oxo, C$_1$-C$_6$-alkyl, C$_1$-C$_6$-haloalkyl, C$_2$-C$_6$-alkenyl, C$_2$-C$_6$-alkynyl, halo, nitro, cyano, OR$^{6d}$, SR$^{6d}$, NR$^{6d}$R$^{7d}$, C(O)R$^{6d}$, C(O)OR$^{6d}$, C(O)NR$^{6d}$R$^{6d}$, S(O)$_2$R$^{6d}$, S(O)$_2$NR$^{6d}$R$^{6d}$;

R$^{12b}$ is independently at each occurrence selected from oxo, C$_1$-C$_6$-alkyl, C$_1$-C$_6$-haloalkyl, C$_2$-C$_6$-alkenyl, C$_2$-C$_6$-alkynyl, halo, nitro, cyano, OR$^{6d}$, SR$^{6d}$, NR$^{6d}$R$^{7d}$, C(O)R$^{6d}$, C(O)OR$^{6d}$, C(O)NR$^{6d}$R$^{6d}$, S(O)$_2$R$^{6d}$, S(O)$_2$NR$^{6d}$R$^{6d}$ or wherein two R$^{12b}$ groups together with the carbon atom to which they are attached form a C$_3$-C$_6$-cycloalkyl;

R$^{13a}$, R$^{13b}$, R$^{13c}$ and R$^{13d}$ are each independently at each occurrence selected from C$_1$-C$_6$-alkyl, C$_1$-C$_6$-haloalkyl, C$_2$-C$_6$-alkenyl, C$_2$-C$_6$-alkynyl, halo, nitro, cyano, OR$^{5e}$, SR$^{6e}$, NR$^{6e}$R$^{7e}$, C(O)R$^{6e}$, C(O)OR$^{6e}$, C(O)NR$^{6e}$R$^{6e}$, S(O)$_2$R$^{6e}$, S(O)$_2$NR$^{6e}$R$^{6e}$;

R$^{14a}$ is independently selected from C$_1$-C$_6$-alkyl and C$_3$-C$_5$-cycloalkyl; wherein said C$_1$-C$_6$-alkyl or C$_3$-C$_5$-cycloalkyl group may be optionally substituted with from 1 to 3 OR$^{5c}$ or NR$^{6c}$R$^{7c}$ groups;

R$^{14b}$ is independently selected from C$_1$-C$_6$-alkyl and C$_3$-C$_5$-cycloalkyl;

n1, n2, n3 and n4 are each independently an integer selected from 1, 2, 3 and 4; and m1 and m2 are each independently an integer selected from 2, 3 and 4.

2. A compound of claim 1, wherein R$^2$ is -L$^1$-L$^2$-R$^8$.

3. A compound of claim 2, wherein -L$^1$- is selected from —(CR$^{10a}$R$^{10a}$)$_{n1}$NR$^{11a}$— and -L$^{3a}$-alkylene-NR$^{11d}$—;

wherein where L$^1$ is —(CR$^{10a}$R$^{10a}$)$_{n1}$NR$^{11a}$— it is optionally the case that: A) a single R$^{10a}$ group and R$^{11a}$ together form a C$_1$-C$_4$-alkylene;

wherein where -L$^1$- includes an alkylene group, that alkylene group is optionally substituted with from 1 to 4 R$^{12a}$ groups; and where -L$^1$- includes a phenyl, naphthyl, or heteroaryl group, that phenyl, naphthyl or heteroaryl is optionally substituted with from 1 to 4 R$^{13a}$ groups;

-L$^2$- is selected from C(O)-L$^4$- and SO$_2$-L$^4$-

L$^{3a}$- and -L$^{3b}$- are each independently selected from phenyl, naphthyl, 5-, 6-, 9- or 10-membered heteroaryl;

-L$^4$- is selected from —(CR$^{10c}$R$^{10c}$)$_{n3}$NR$^{11e}$— and -L$^{3b}$-NR$^{11b}$—;

wherein where L$^4$ is —(CR$^{10c}$R$^{10c}$)$_{n3}$NR$^{11e}$— it is optionally the case that: A) a single R$^{10c}$ group and R$^{11e}$ together form a C$_1$-C$_4$-alkylene, said alkylene optionally being interrupted by an oxygen, nitrogen or sulphur atom;

wherein where -L$^4$- includes an alkylene group, that alkylene group is optionally substituted with from 1 to 4 R$^{12b}$ groups; and where -L$^4$- includes a phenyl, naphthyl, or heteroaryl group, that phenyl, naphthyl or heteroaryl is optionally substituted with from 1 to 4 R$^{13b}$ groups.

4. A compound of claim 3, wherein -L¹- is selected —(CR$^{10a}$R$^{10a}$)$_{n1}$NR$^{11a}$—,

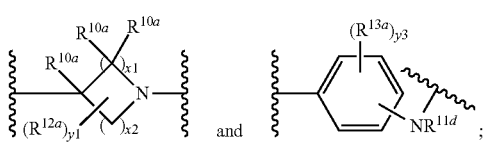

L²- is —C(O)-L⁴-; and
L⁴- is selected from:

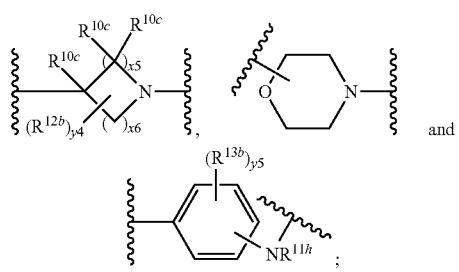

wherein x1 is an integer selected from 0, 1, 2, 3 or 4; x2 is an integer selected from 1, 2, 3 and 4; providing that the sum of x1 and x2 is 2, 3, 4 or 5; x5 is an integer selected from 0, 1, 2, 3 or 4; x6 is an integer selected from 1, 2, 3 and 4; providing that the sum of x5 and x6 is 2, 3, 4 or 5; y1 is an integer from 0 to 3; y3 is an integer from 0 to 4; and y4 is an integer from 0 to 3; and y5 is an integer from 0 to 4.

5. A compound of claim 1, wherein -L¹-L²-R⁸ is selected from:

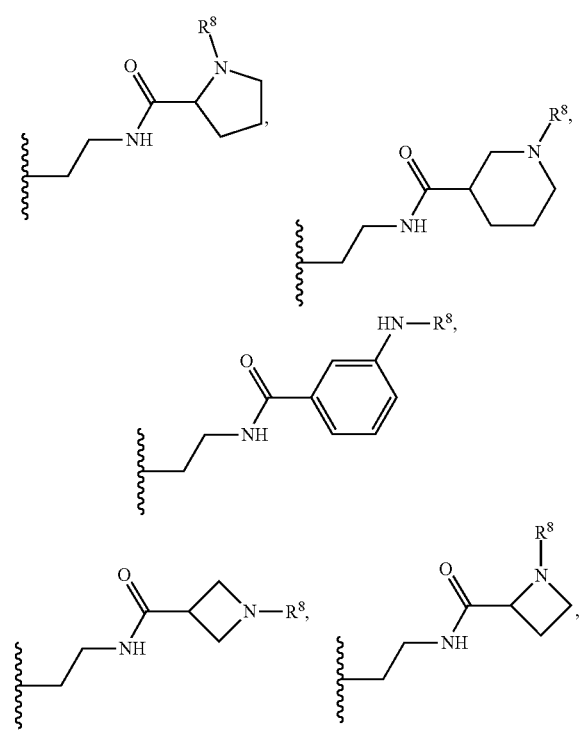

-continued

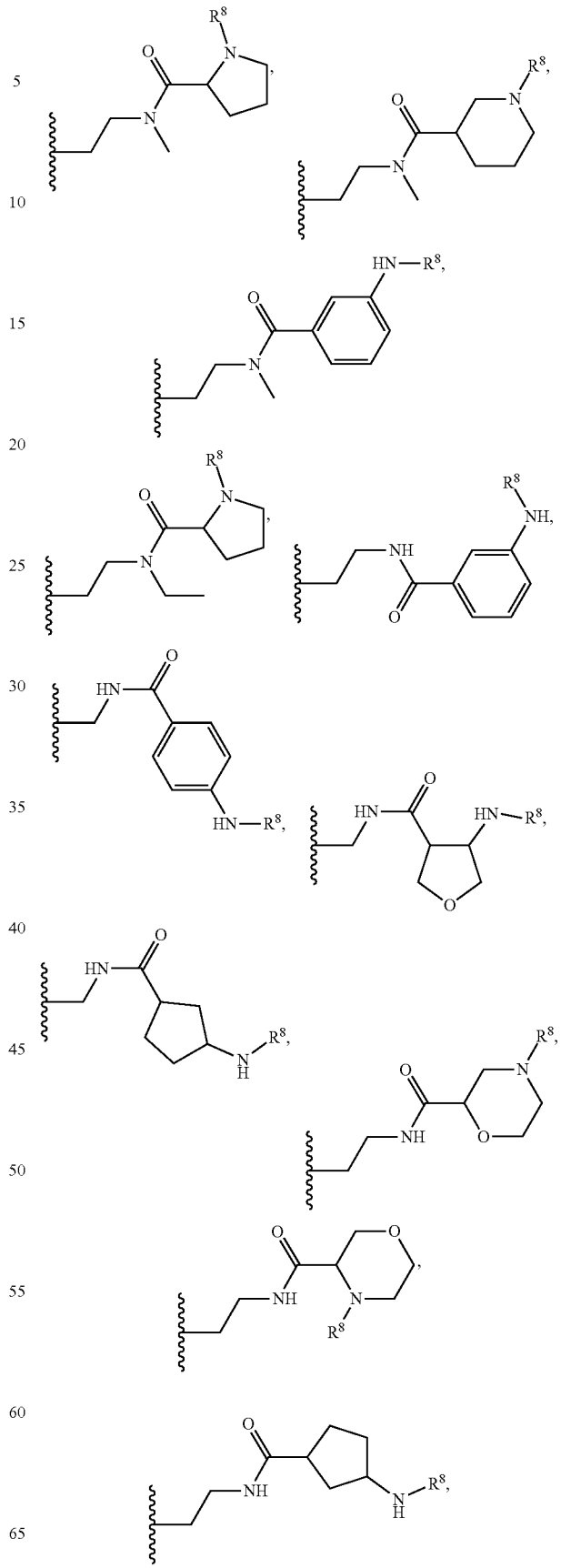

225
-continued
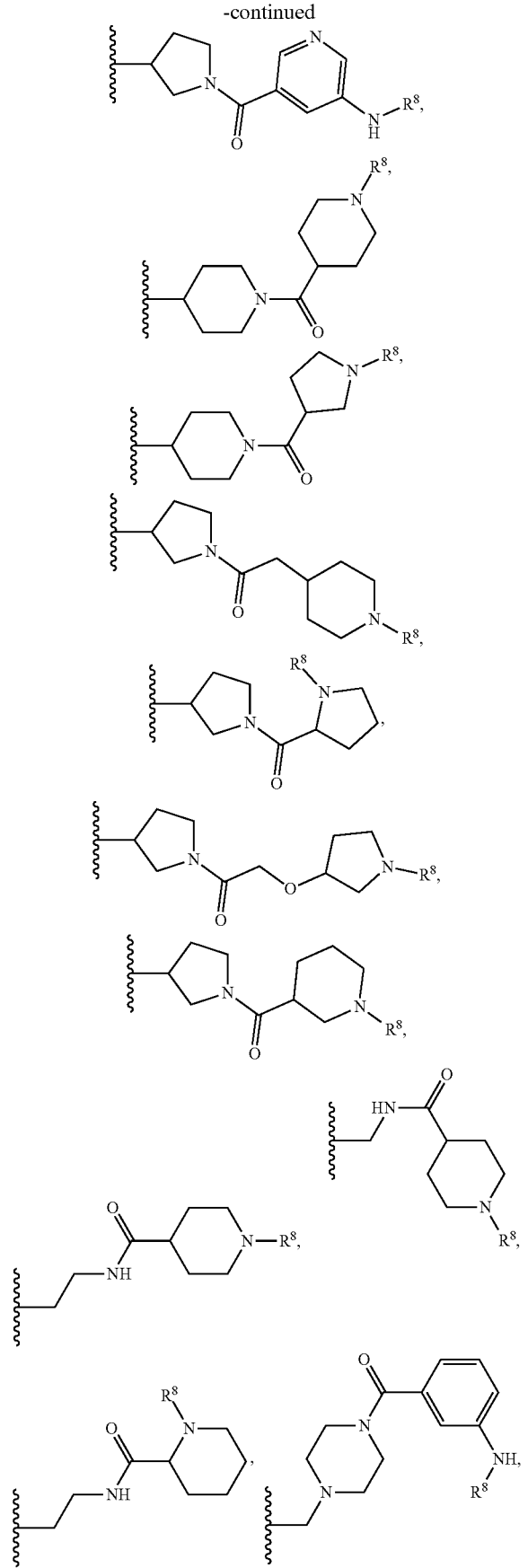
226
-continued
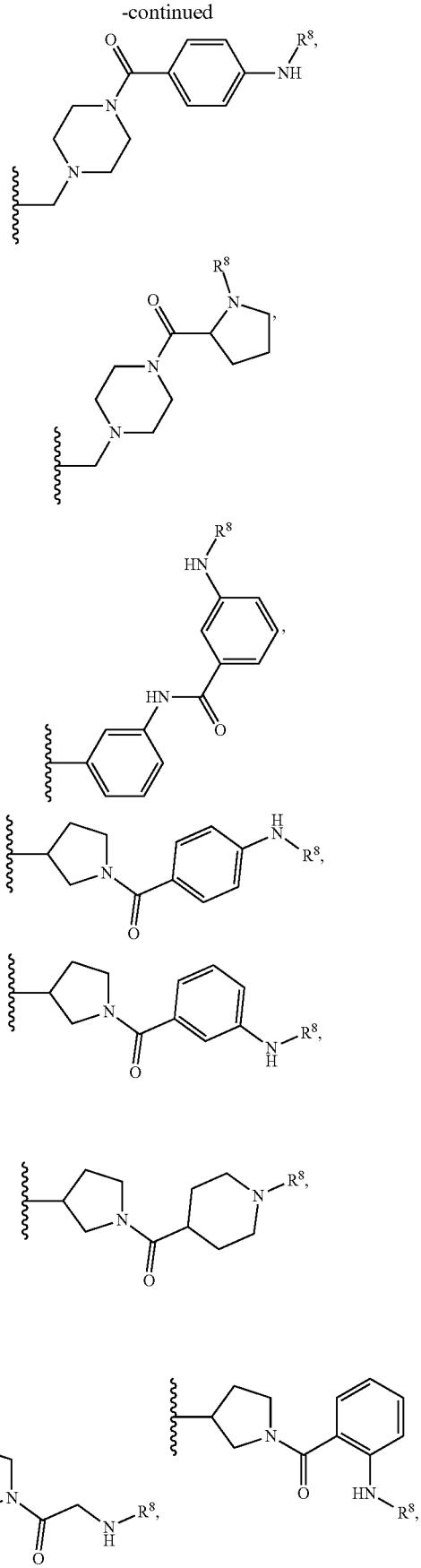

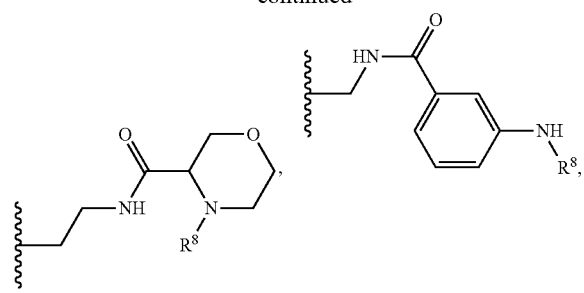
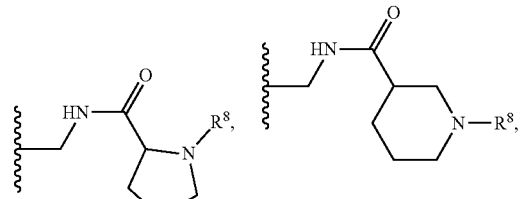
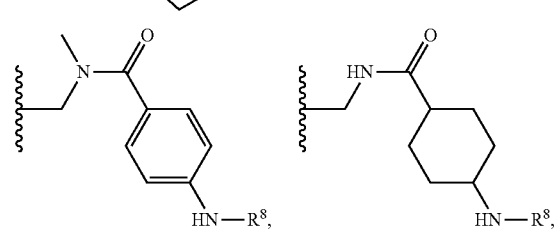
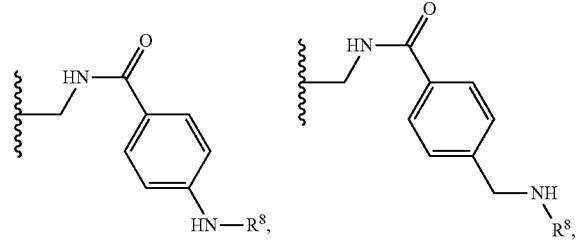
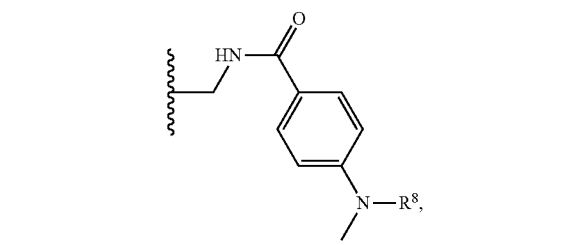
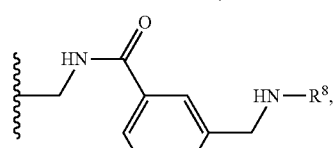
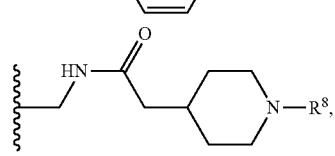
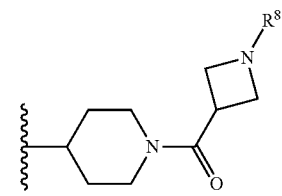
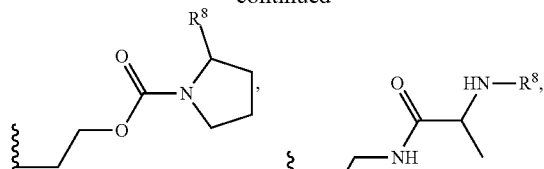
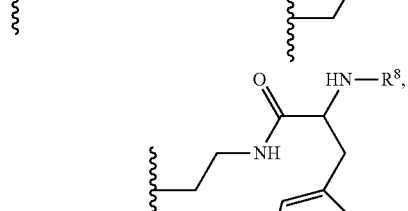
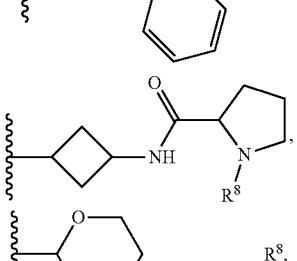
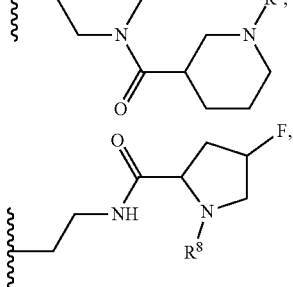
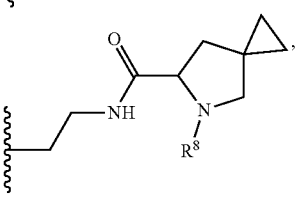
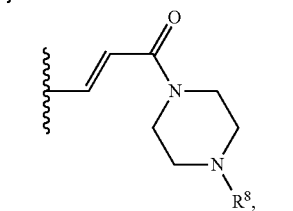
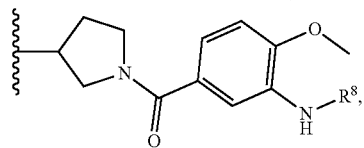
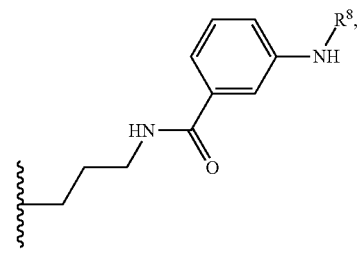

-continued

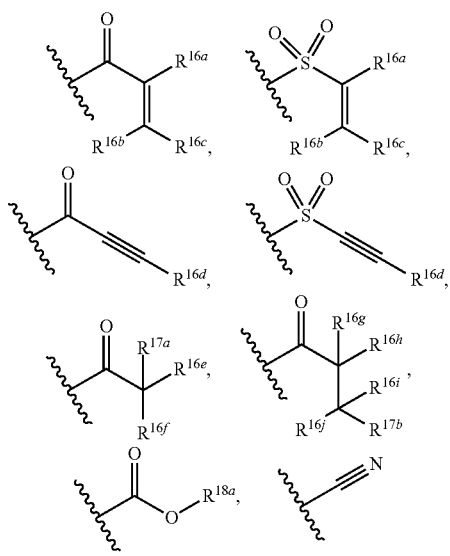

6. A compound of claim 1, wherein $R^8$ is a group that can react with the SH of a cysteine to form a covalent bond between a carbon atom of $R^8$ and the sulphur atom of the cysteine.

7. A compound of claim 6, wherein $R^8$ has a structure selected from:

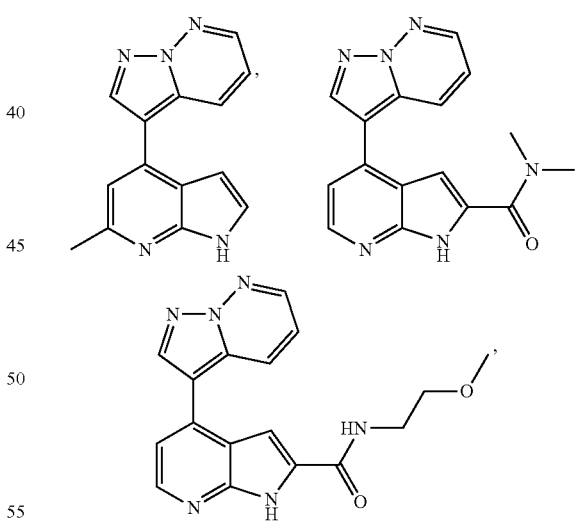

and
wherein $R^{16a}$ is independently selected from H, CN, $C_1$-$C_6$-alkyl and $C_1$-$C_6$-haloalkyl (which may be optionally substituted with a O—$R^{18b}$ group or a $NR^{18c}R^{18c}$ group);

$R^{16b}$, $R^{16c}$, $R^{16d}$, $R^{16e}$, $R^{16f}$, $R^{16g}$, $R^{16h}$, $R^{16i}$ and $R^{16j}$ are each independently selected from H, $C_1$-$C_6$-alkyl and $C_1$-$C_6$-haloalkyl (which may be optionally substituted with a O—$R^{18a}$ group or a $NR^{18b}R^{18b}$ group); or $R^{16a}$ and $R^{16c}$ together with the carbon atoms to which they are attached form a $C_3$-$C_6$-cycloalkenyl;

$R^{17a}$ and $R^{17b}$ are each independently selected from CN, halo and $OS(O)_2R^{19}$;

$R^{18a}$, $R^{18b}$ and $R^{18c}$ are independently selected from H and $C_1$-$C_6$-alkyl; and $R^{19}$ is independently selected from $C_1$-$C_6$-alkyl and phenyl (which may be optionally substituted with from 1 to 3 groups selected from $C_1$-$C_6$-alkyl, $C_1$-$C_6$-haloalkyl, halo, O—$C_1$-$C_6$-alkyl, O—$C_1$-$C_6$-haloalkyl and nitro).

8. A compound of claim 2, wherein $R^8$ is independently selected from H, $S(O)_2R^{15}$, $C(O)R^{15}$, $C(O)OR^{15}$, $S(O)_2$—$C_0$-$C_3$-alkylene-$R^{15}$, $C(O)$—$C_0$-$C_3$-alkylene-$R^{15}$ and $C_0$-$C_3$-alkylene-$R^{15}$; wherein $R^{15}$ is independently selected from phenyl, $C_3$-$C_7$-cycloalkyl, $C_1$-$C_6$-alkyl, 5- to 7-membered heterocycloalkyl, 5-, 6-, 9- and 10- membered heteroaryl; wherein where any $R^8$ group includes heterocycloalkyl, alkylene, cycloalkyl or alkyl, that heterocycloalkyl, cycloalkyl or alkyl group is optionally substituted with from 1 to 4 $R^{12c}$ groups; and where any $R^8$ group includes phenyl or heteroaryl, that phenyl or heteroaryl is optionally substituted with from 1 to 4 $R^{13c}$ groups.

9. A compound of claim 1, wherein $R^2$ is independently selected from H, $C_1$-$C_6$-alkyl, $C_1$-$C_6$-haloalkyl, $C_2$-$C_6$-alkenyl, $C_2$-$C_6$-alkynyl, halo, nitro, cyano, $OR^{5a}$, $SR^{6a}$, $NR^{6a}R^{7a}$, $C(O)R^{6a}$, $C(O)OR^{6a}$, $C(O)NR^{6a}R^{6a}$, $S(O)_2R^{6a}$ and $S(O)_2NR^{6a}R^{6a}$.

10. A compound of claim 1, wherein $R^1a$ is H.

11. A compound of claim 1, wherein each of $R^{4f}$, $R^{4i}$, $R^{4j}$ and $R^{4k}$ are H.

12. A compound of claim 1, wherein each of $R^{4a}$, $R^{4b}$ and $R^{4c}$ is H.

13. A compound of claim 1 wherein the compound of formula (I) is selected from:

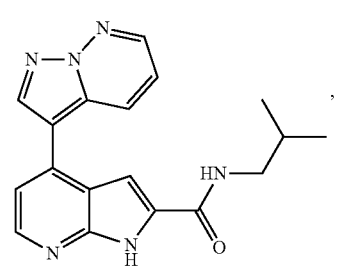

231
-continued
232
-continued
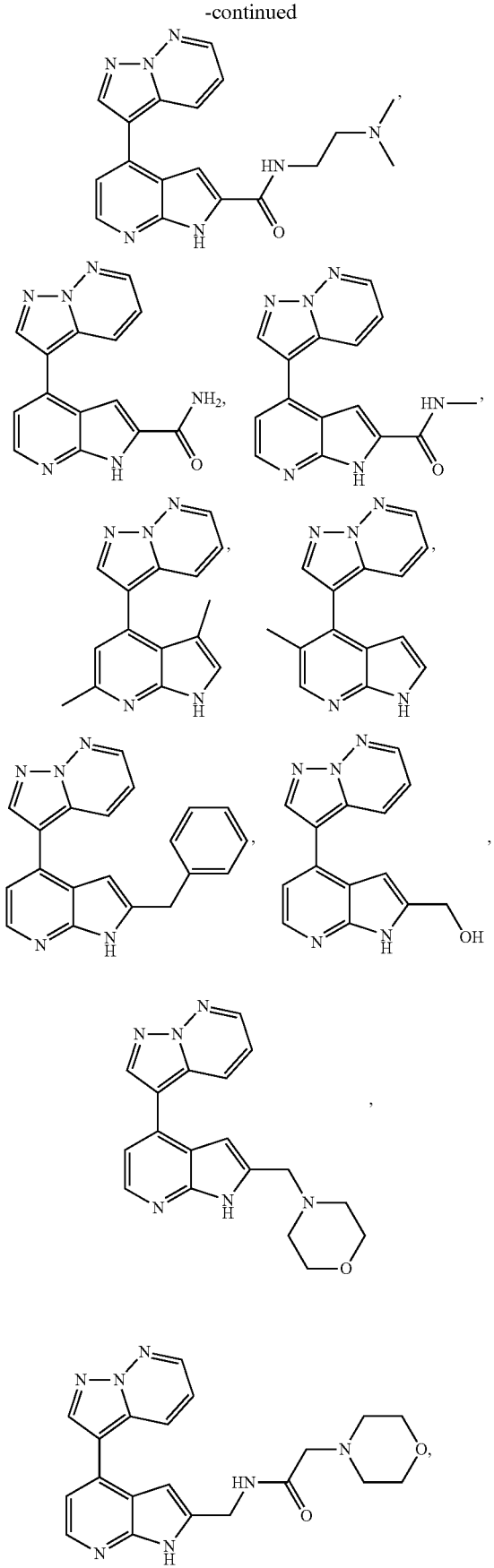
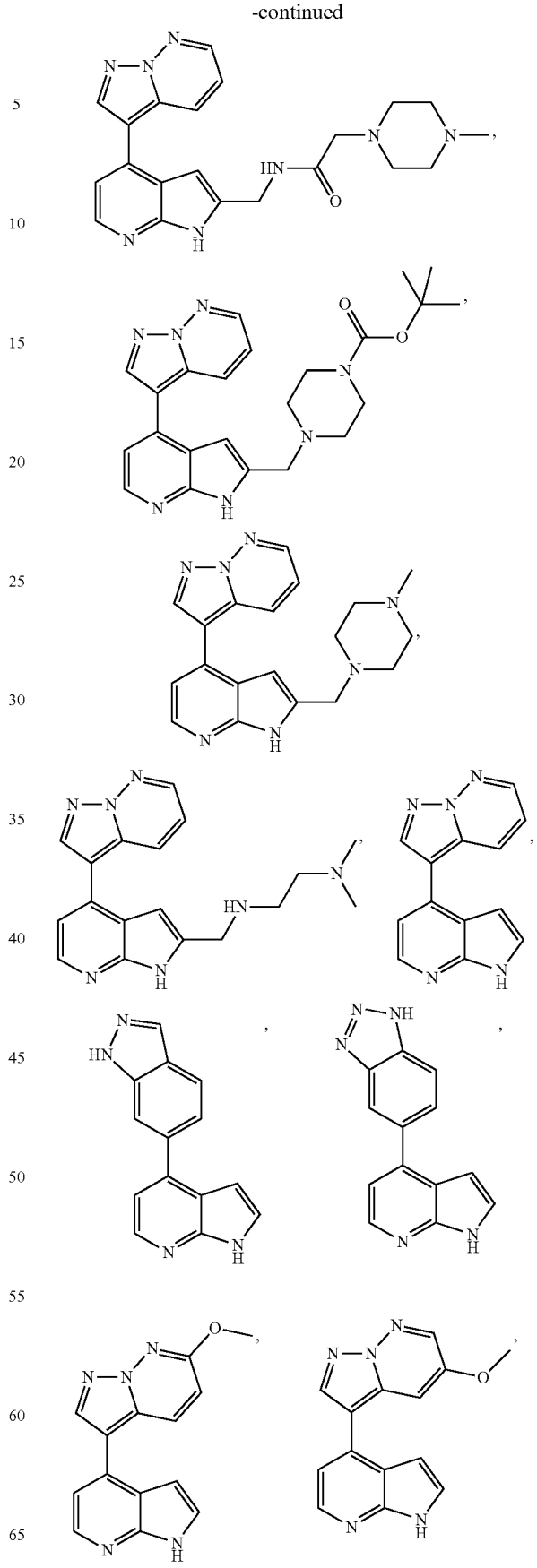

233
-continued
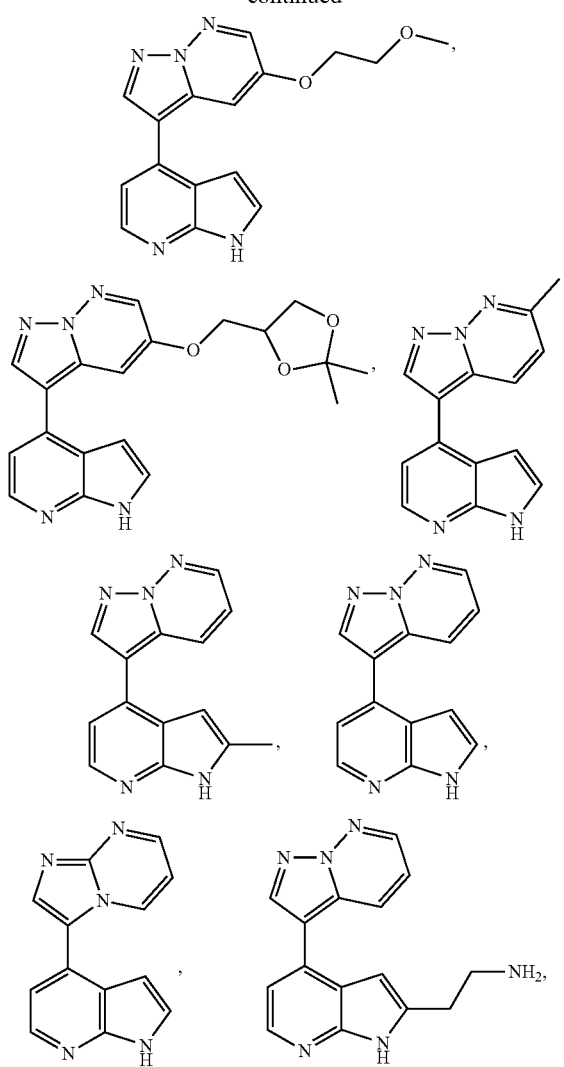
234
-continued
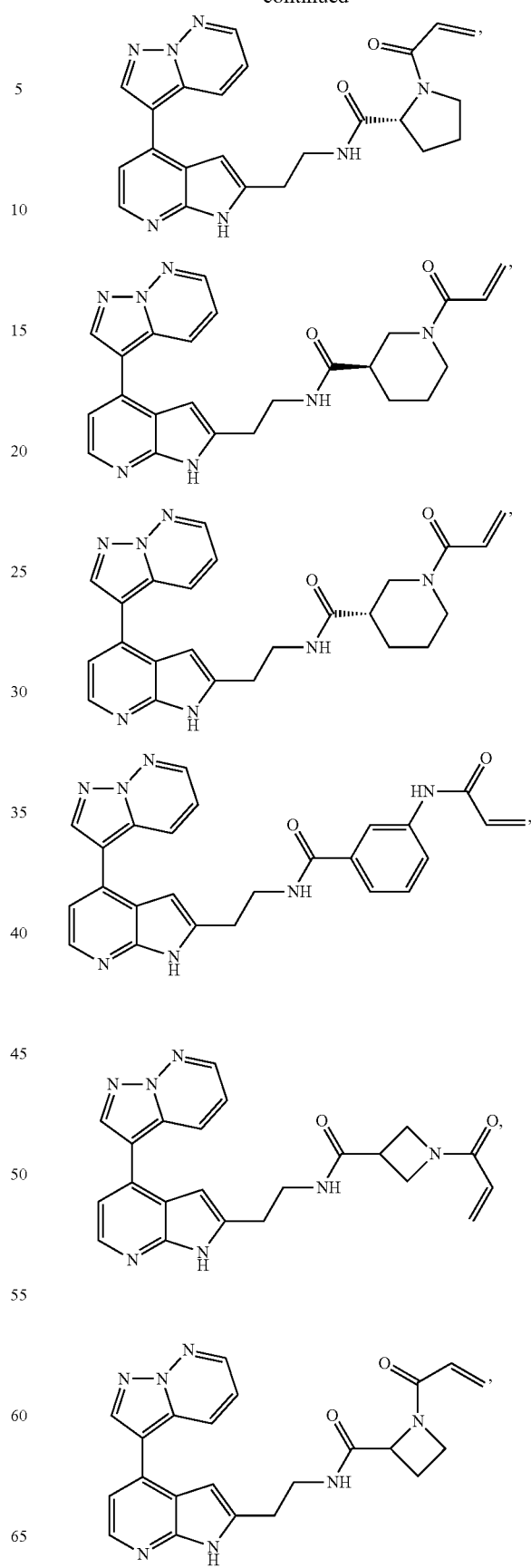

235
-continued
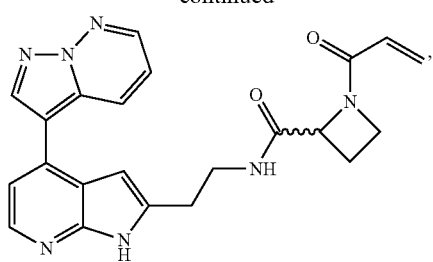
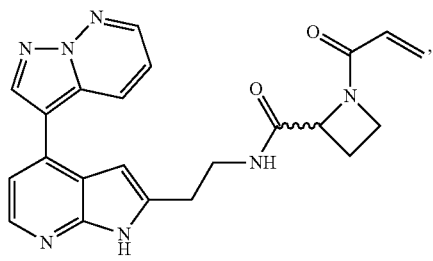
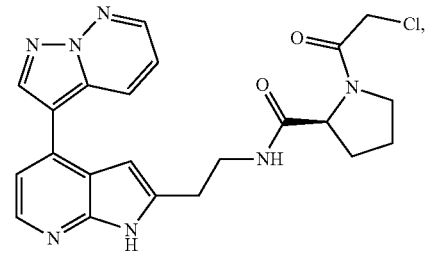
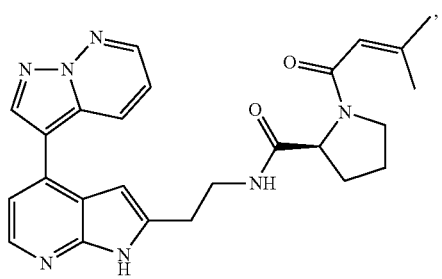
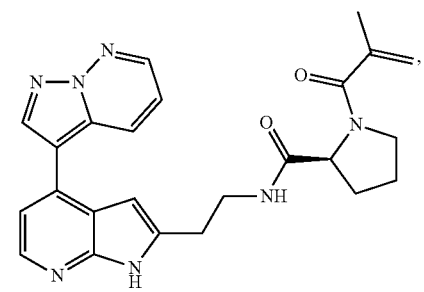
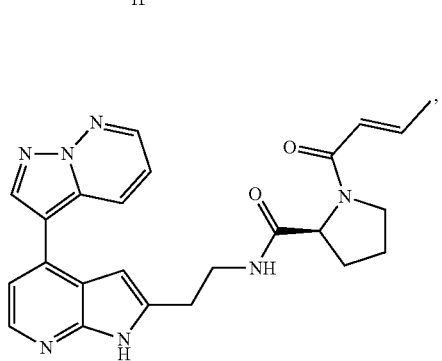
236
-continued
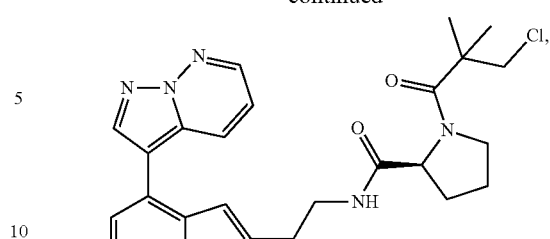
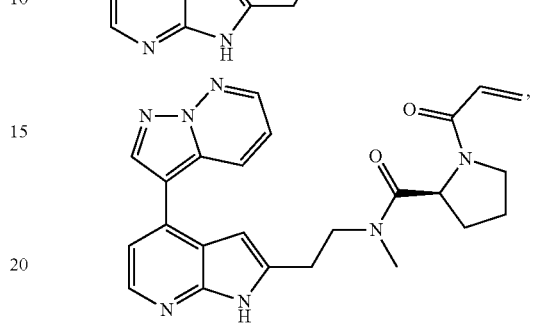
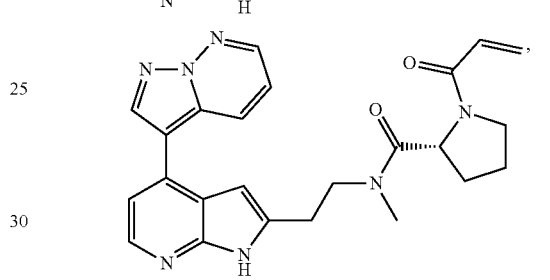
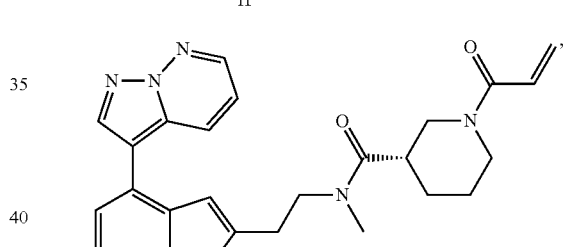
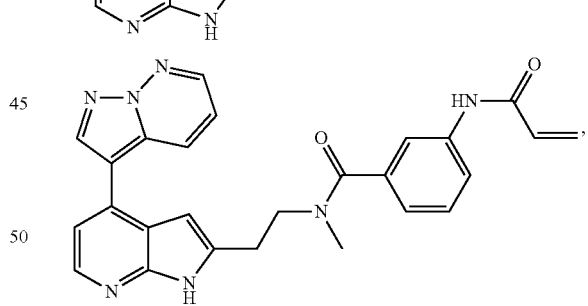
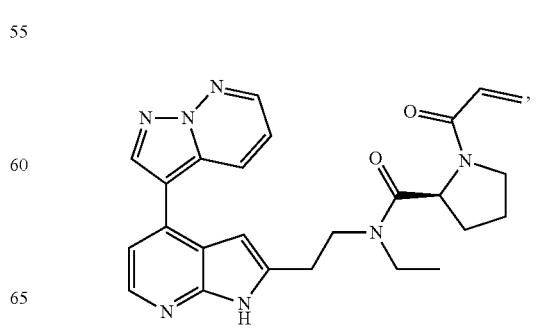

237
-continued
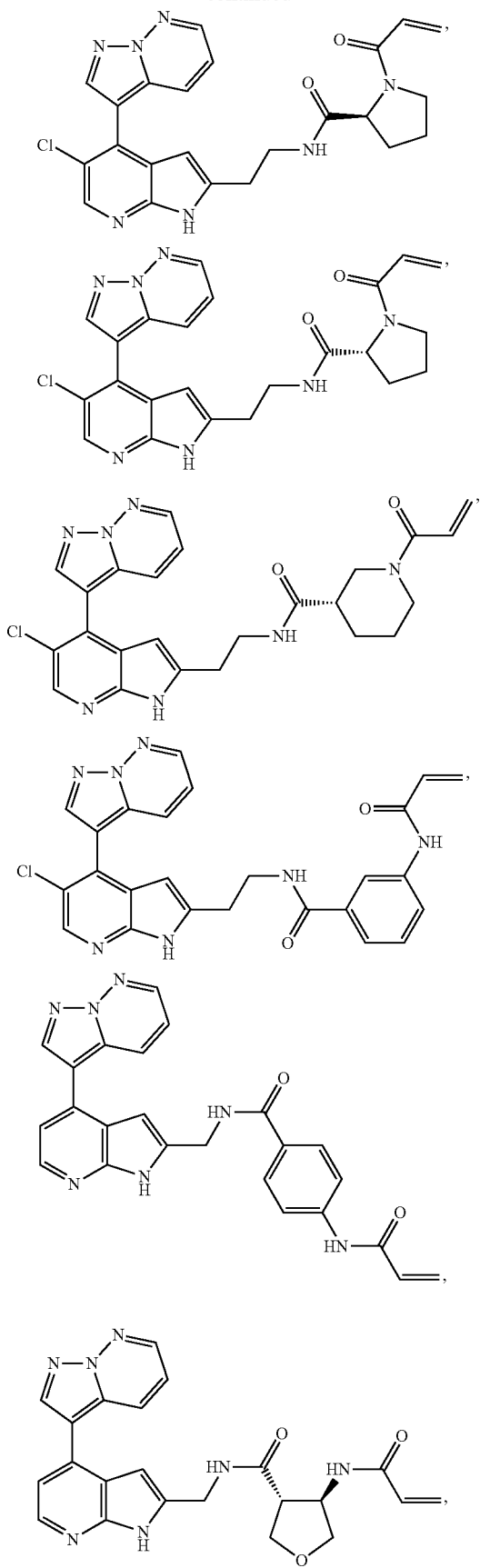
238
-continued
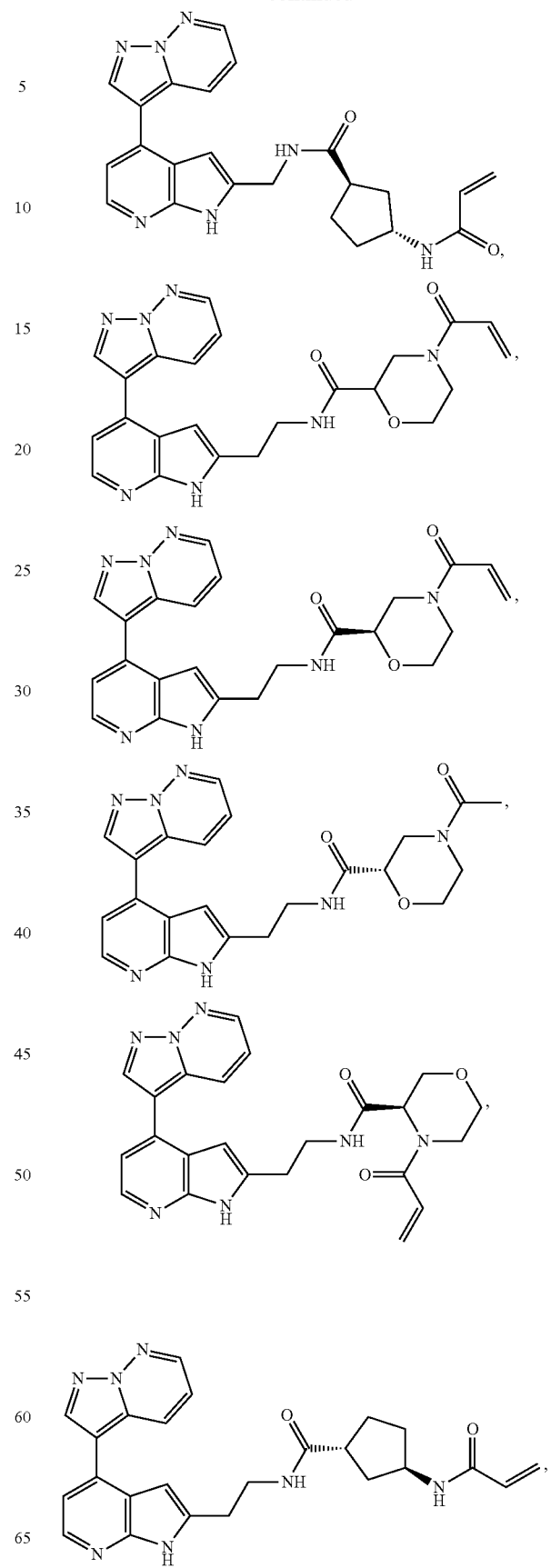

239
-continued
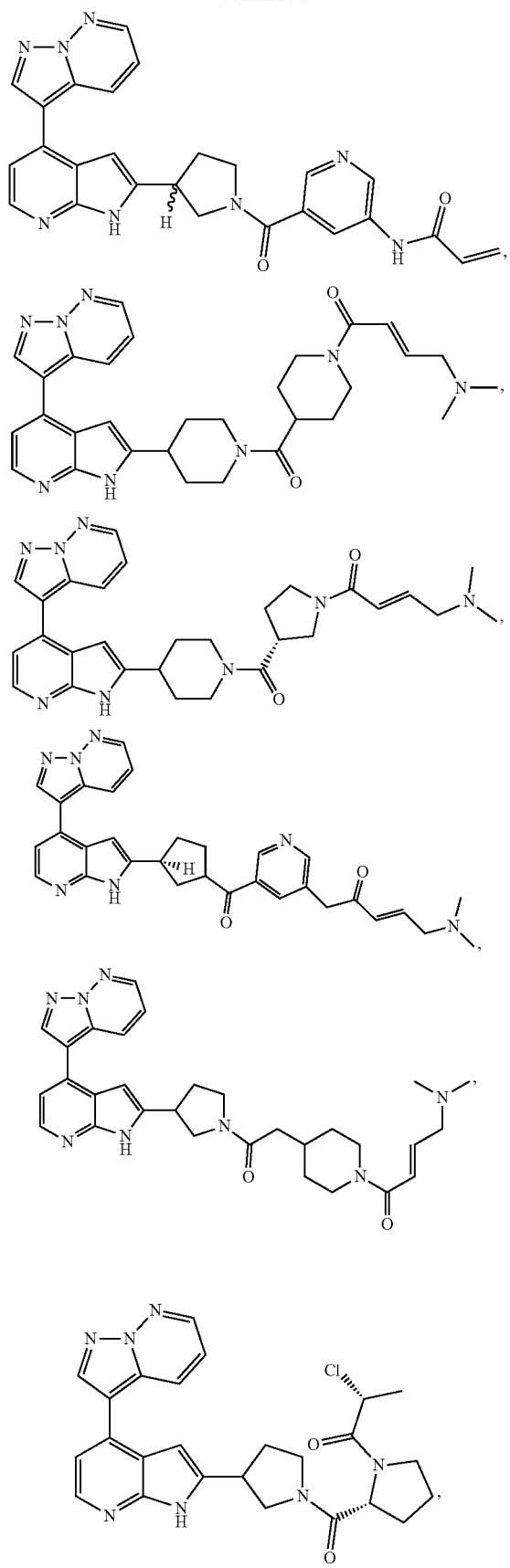
240
-continued
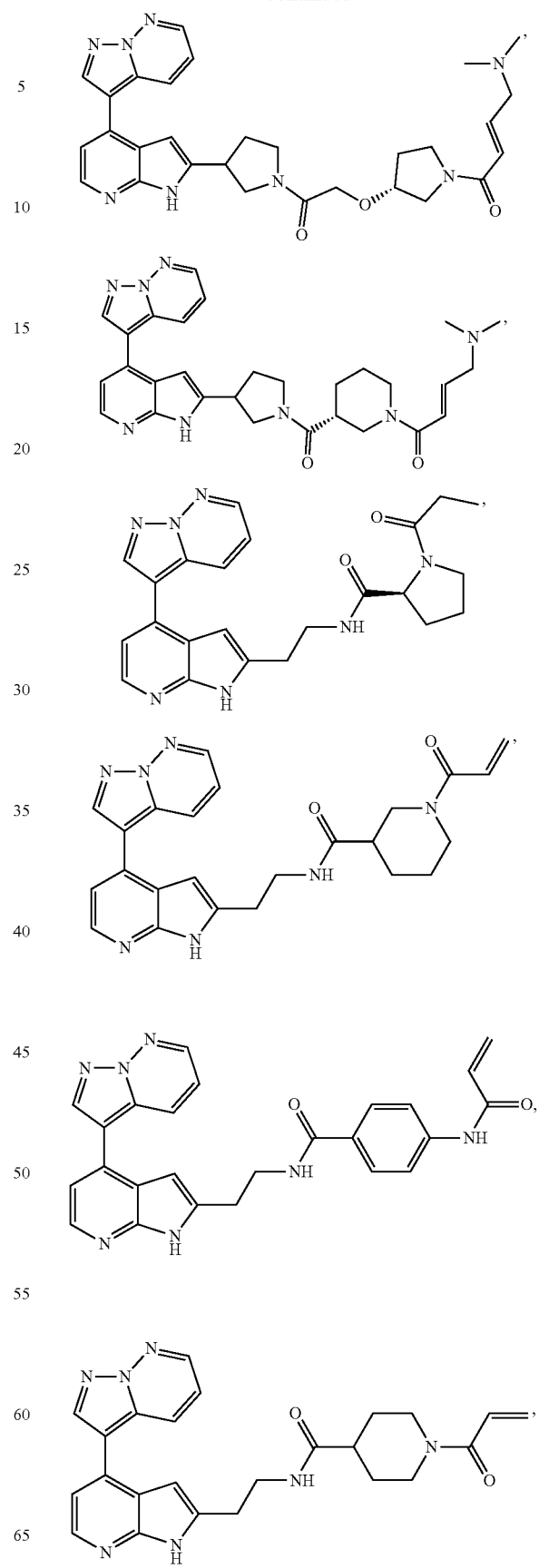

241
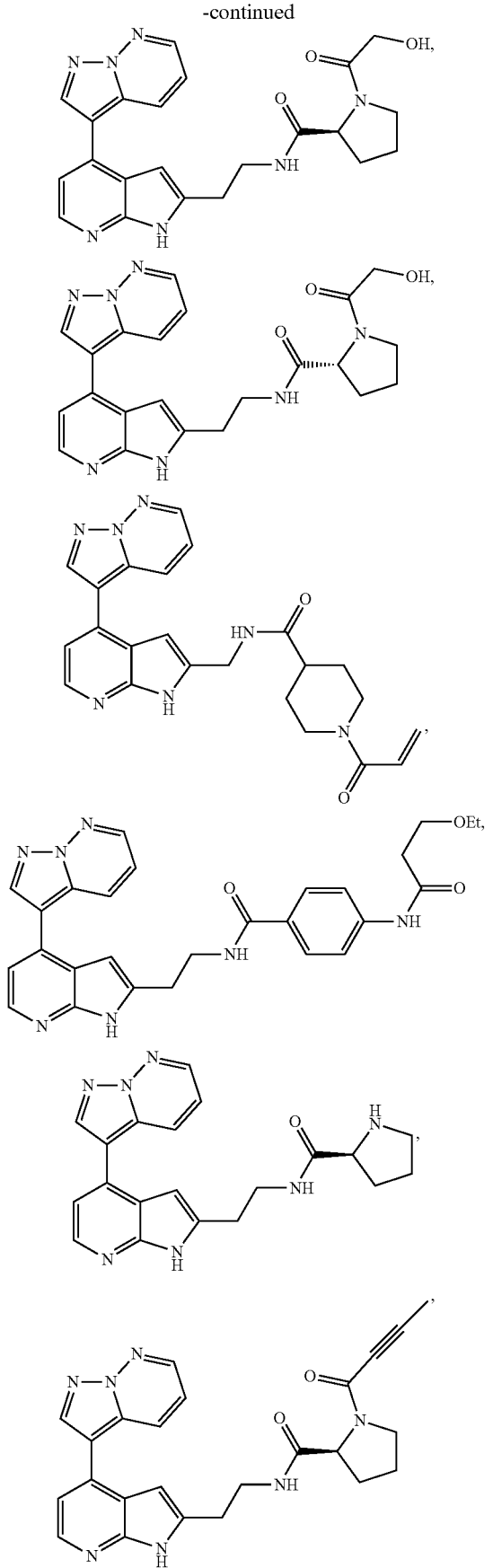
242
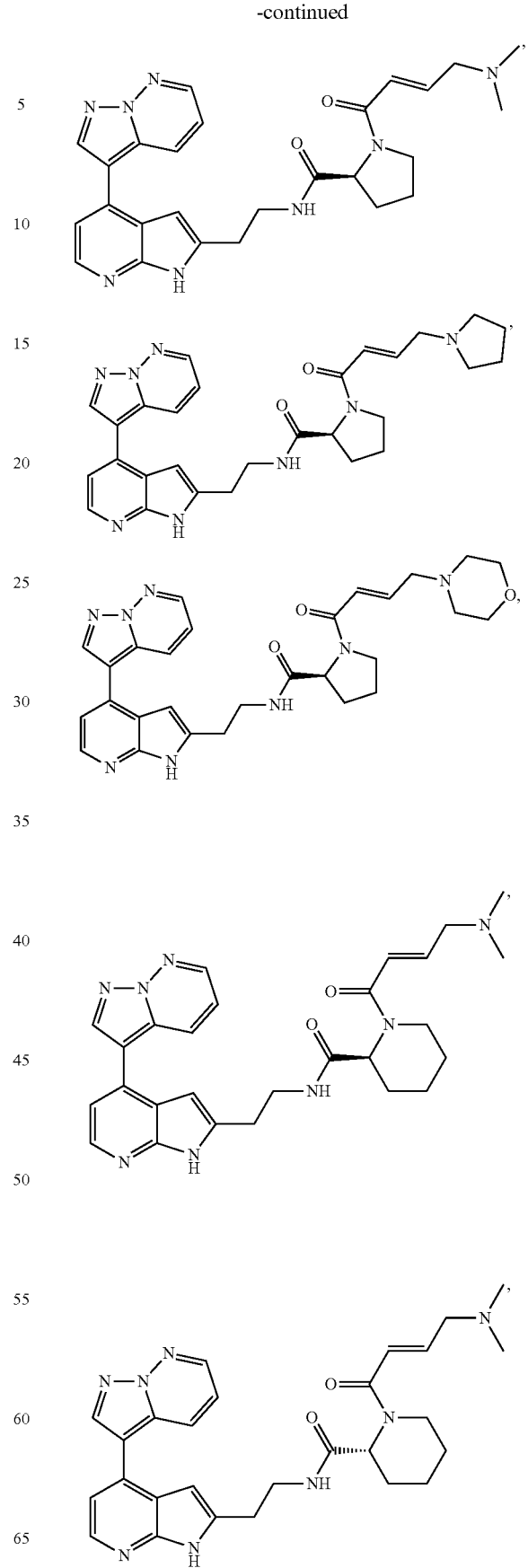

243
-continued
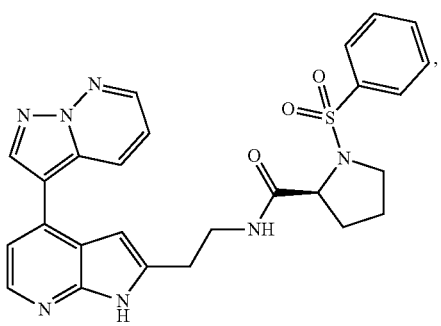
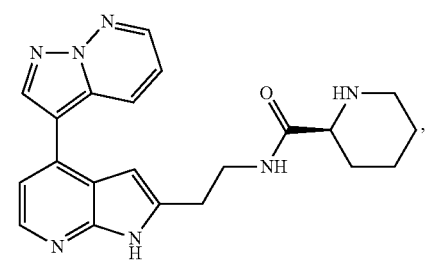
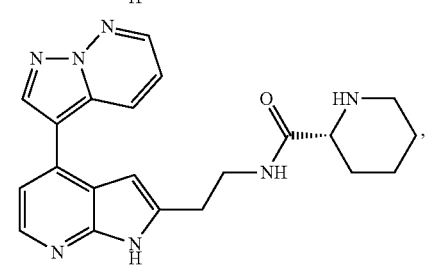
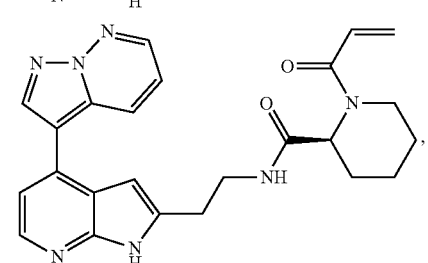
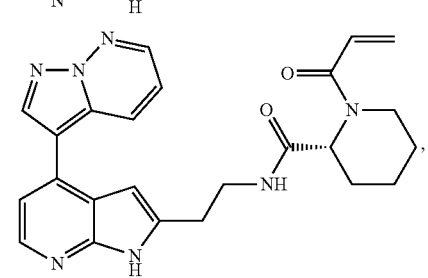
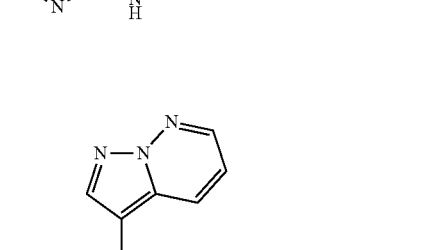
244
-continued
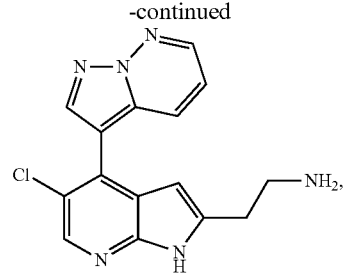
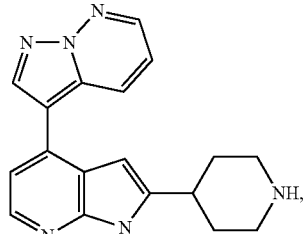
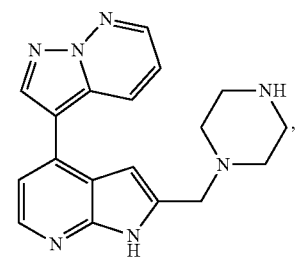
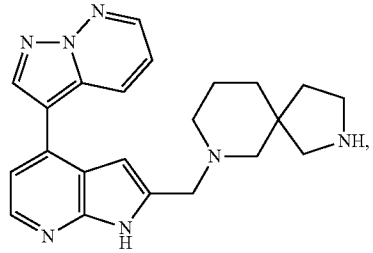
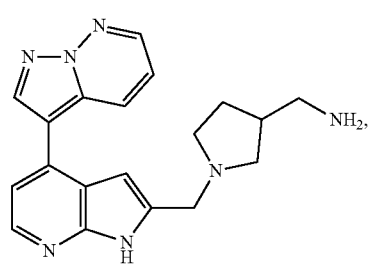
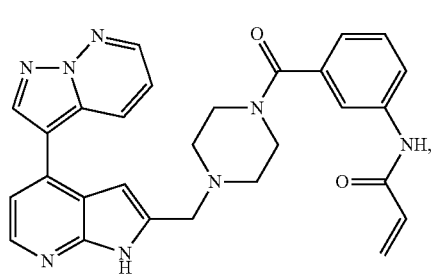

245
-continued
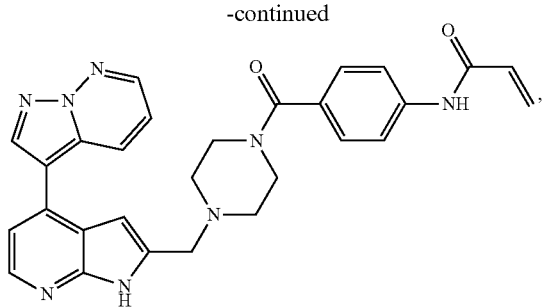
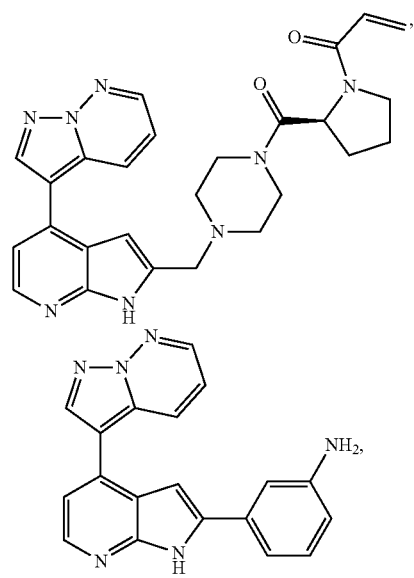
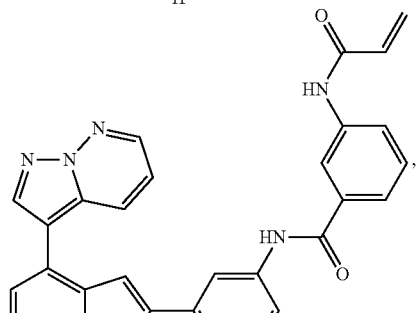
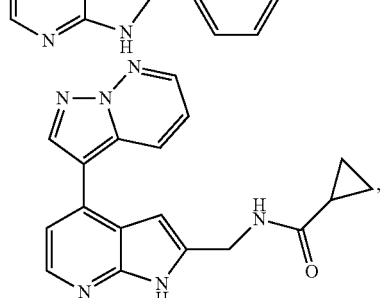
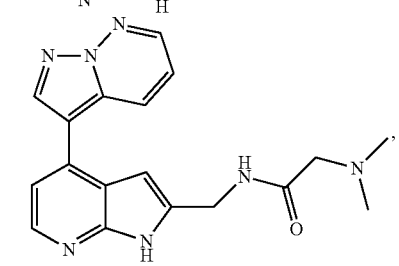
246
-continued
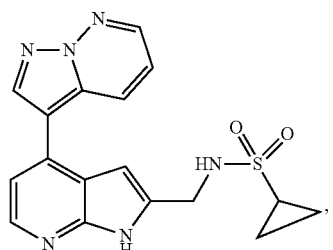
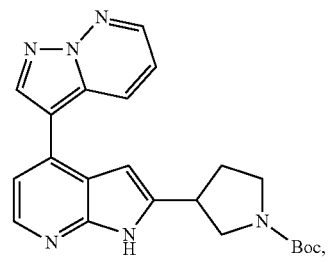
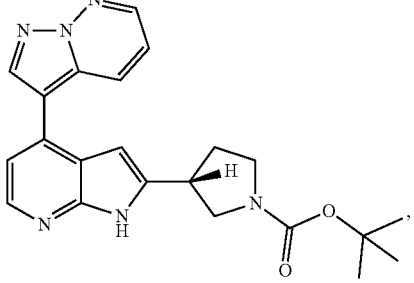
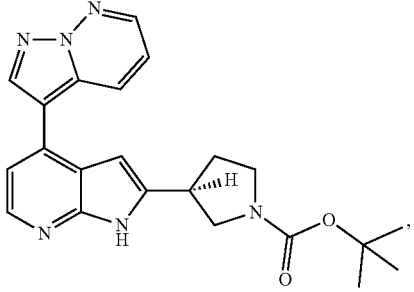
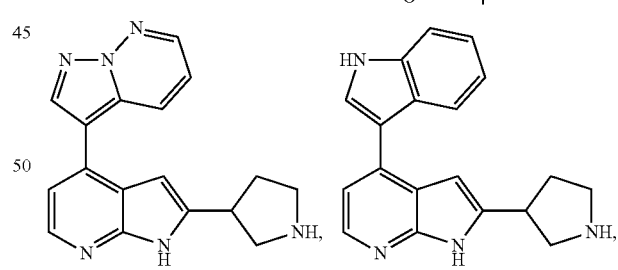
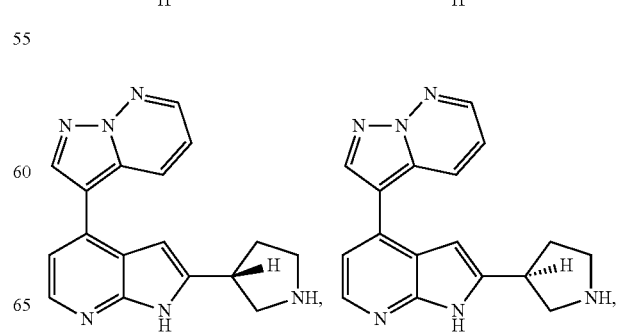

247
-continued
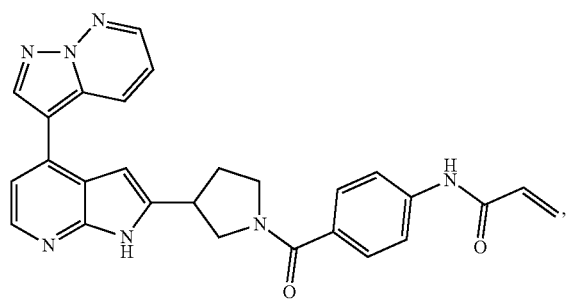
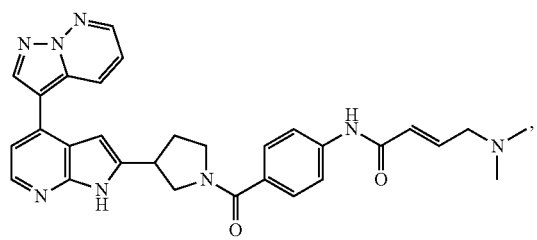
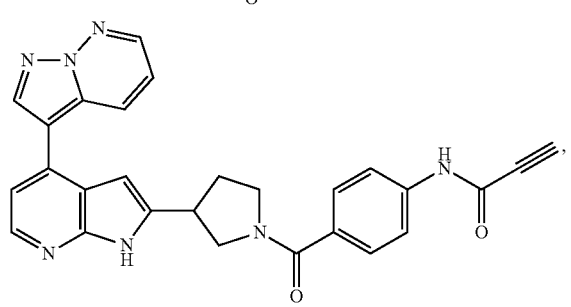
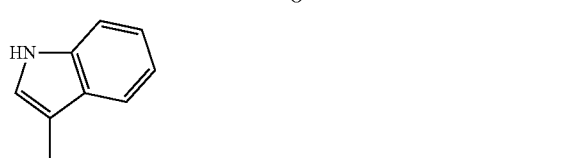
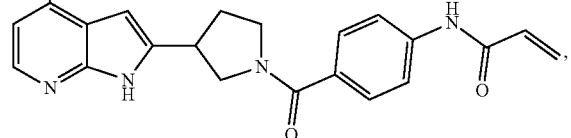
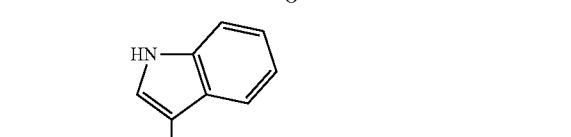
248
-continued
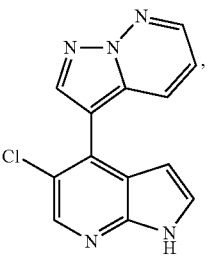
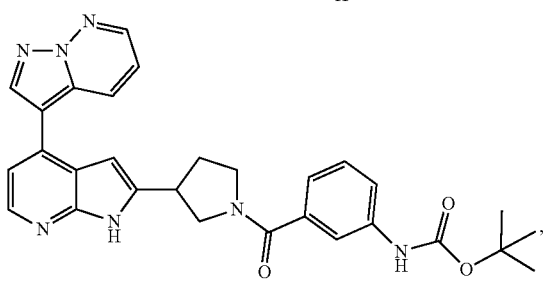
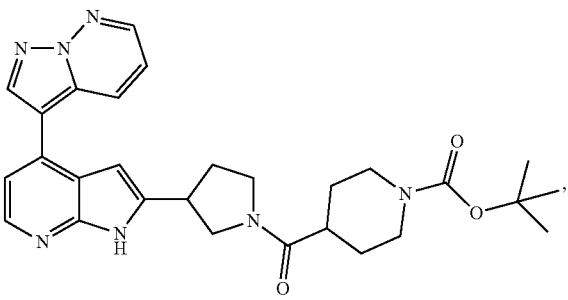
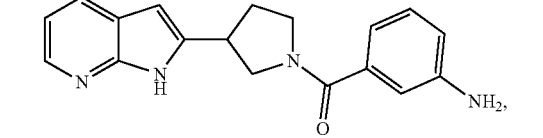
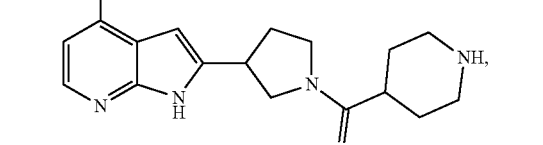

249
-continued
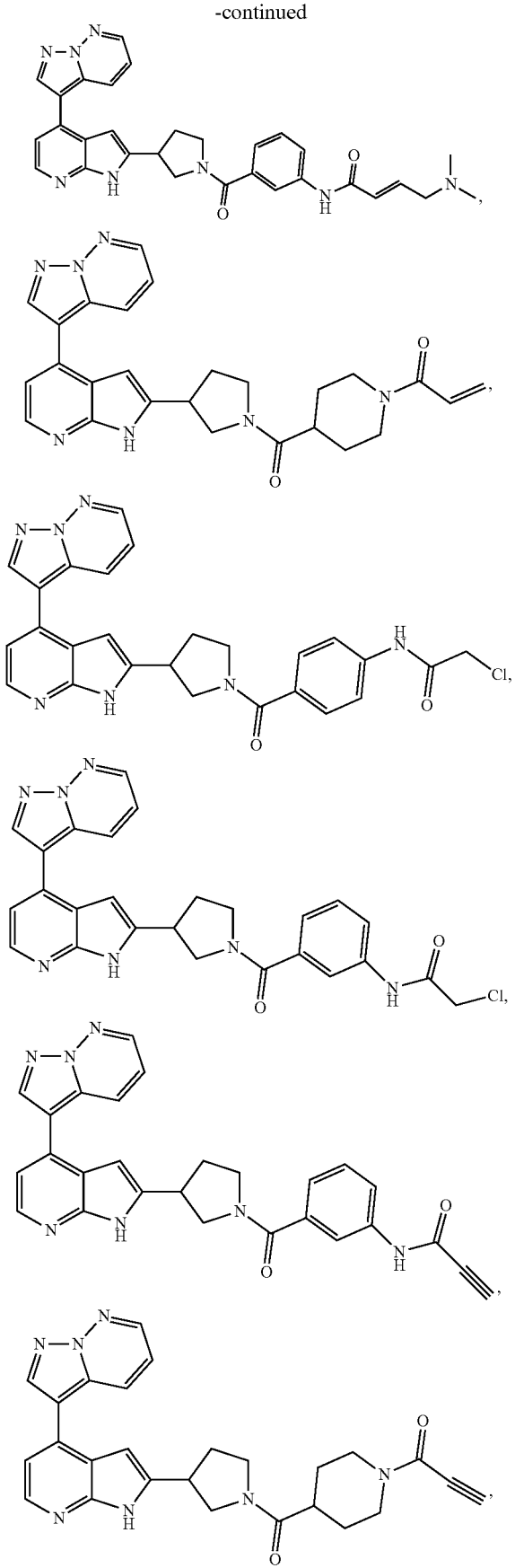
250
-continued
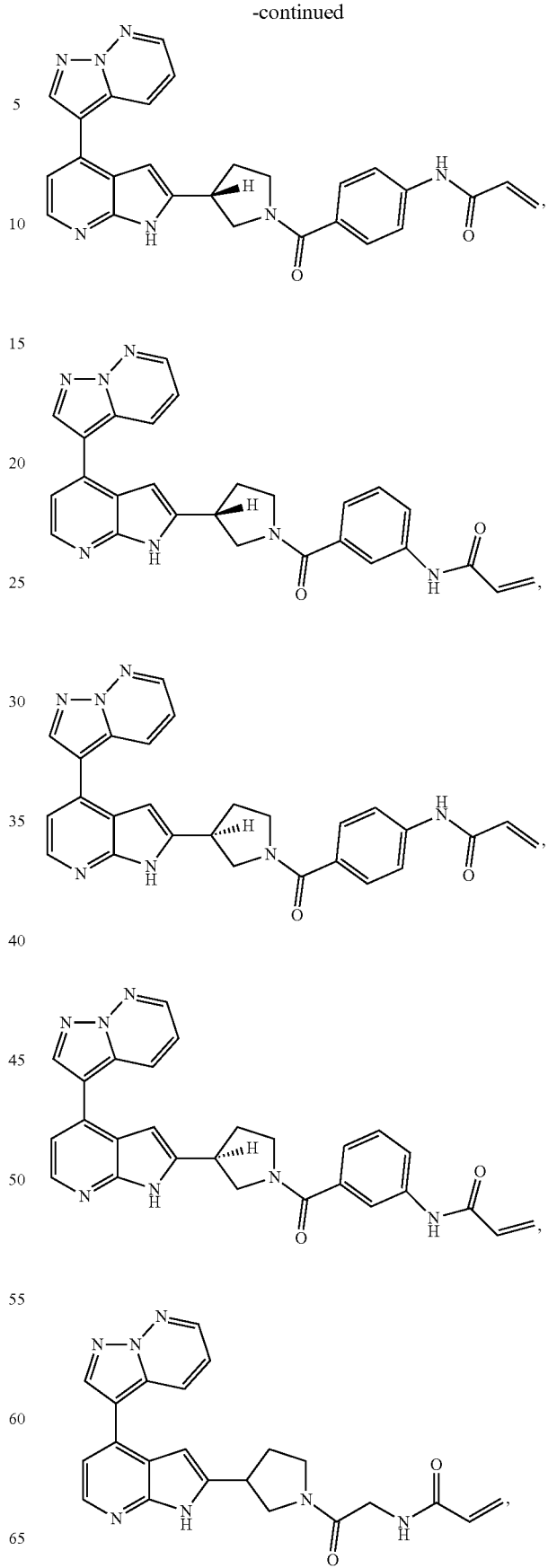

251
-continued
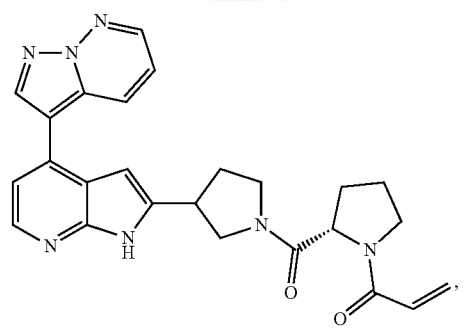
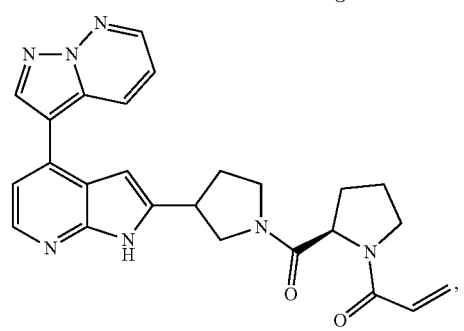
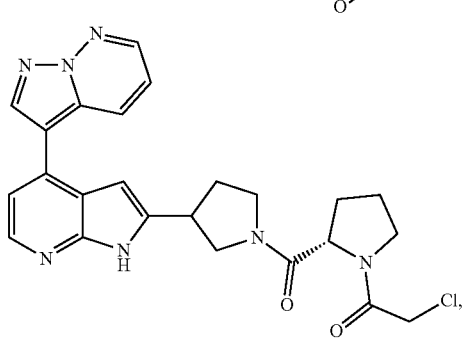
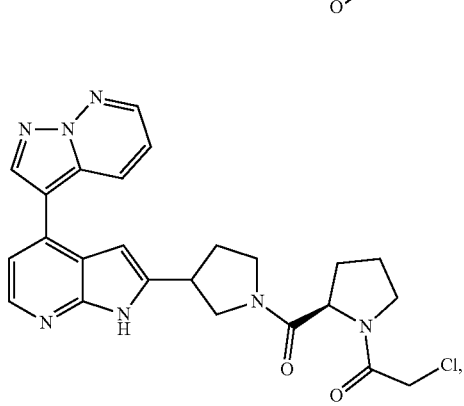
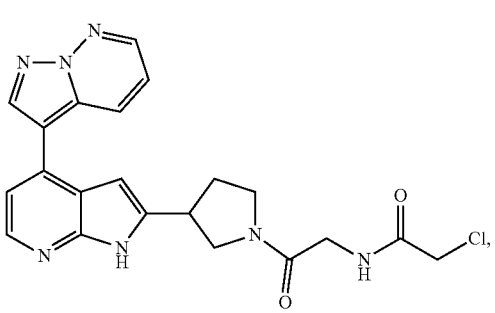
252
-continued
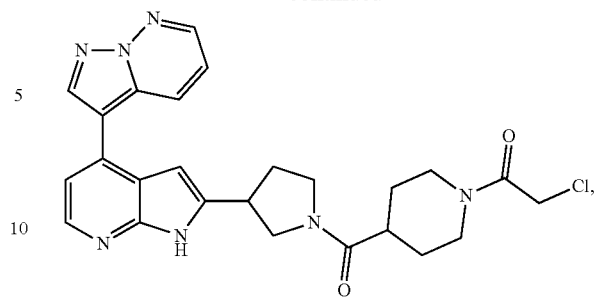
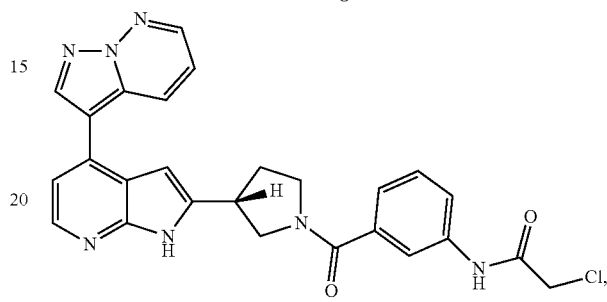
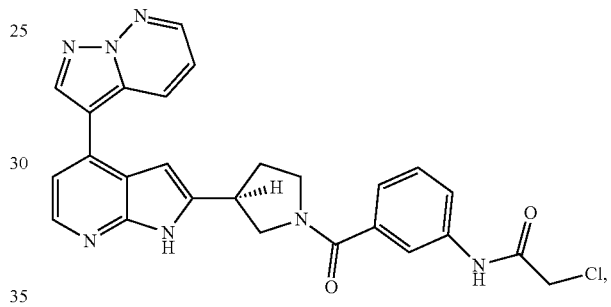
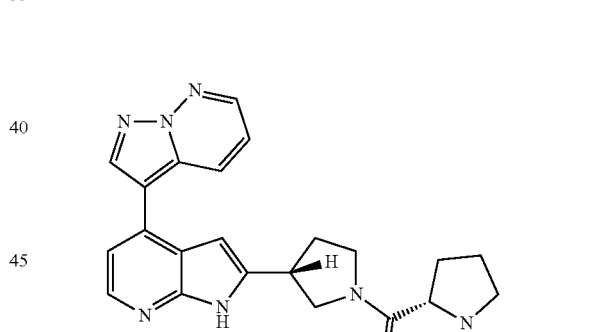
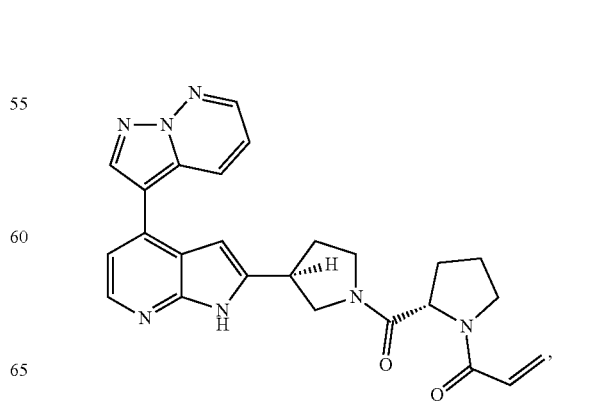

253
-continued
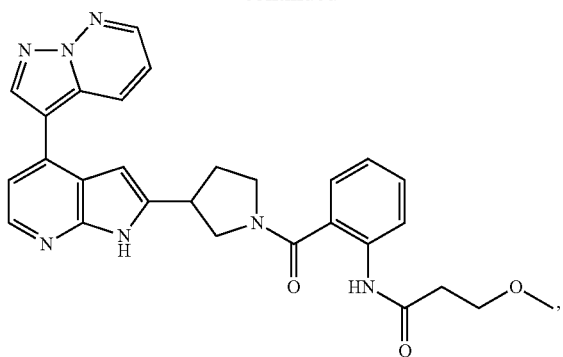
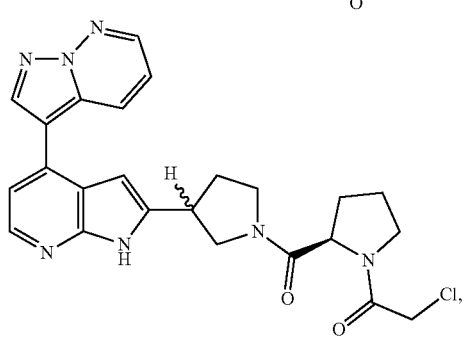
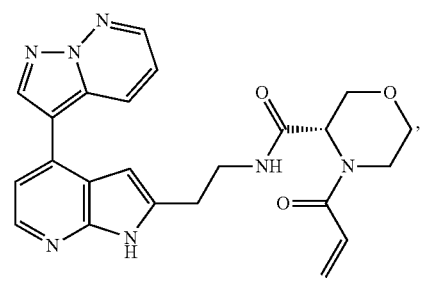
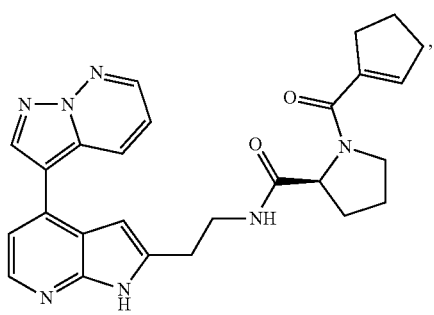
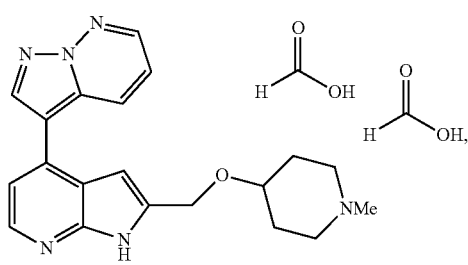
254
-continued
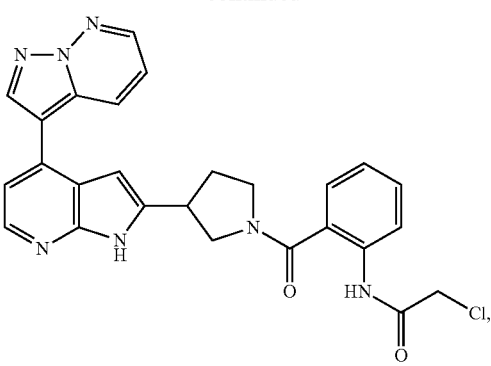
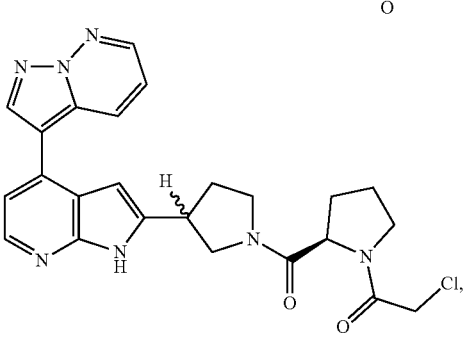
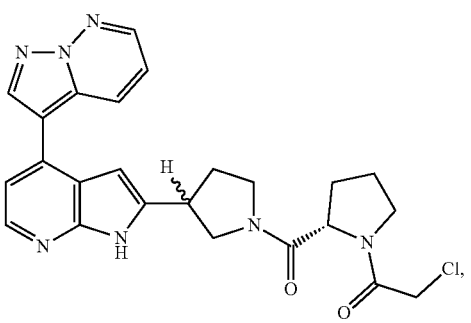
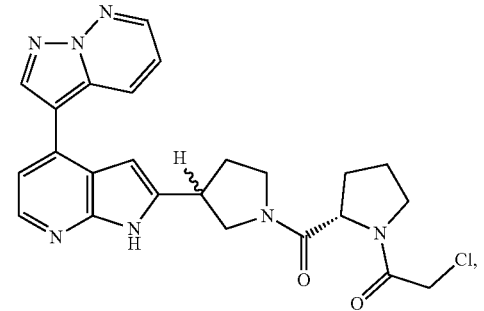
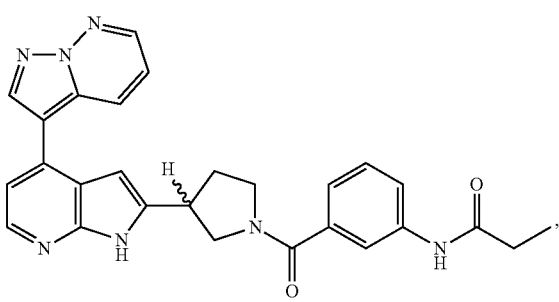

255
-continued
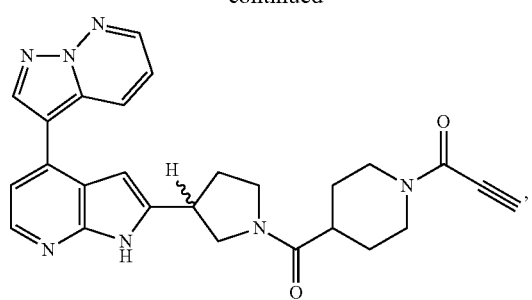
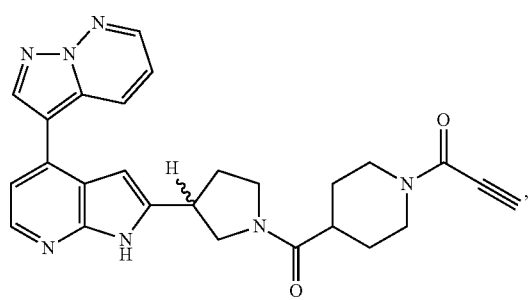
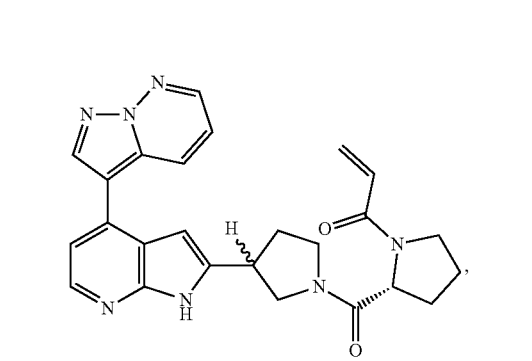
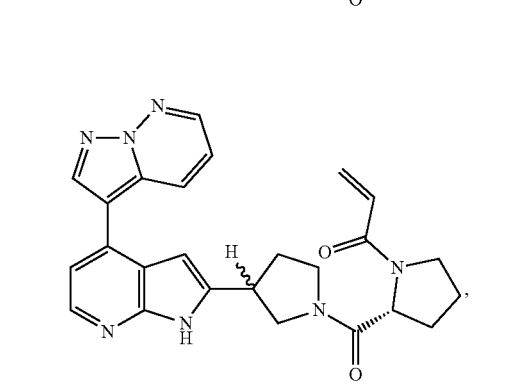
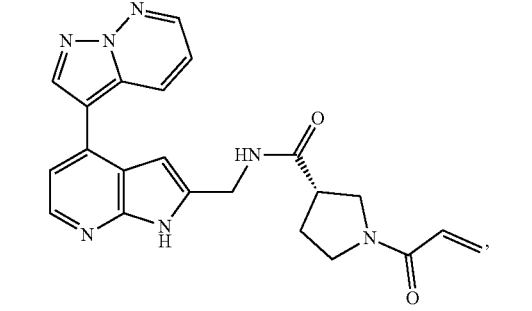
256
-continued
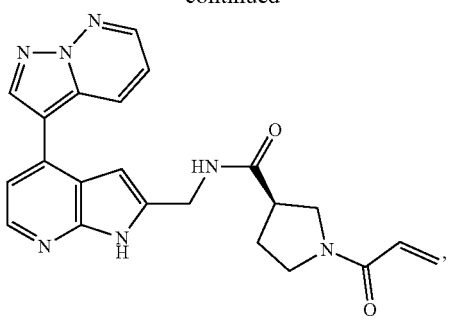
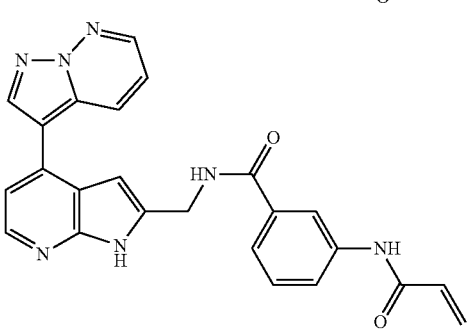
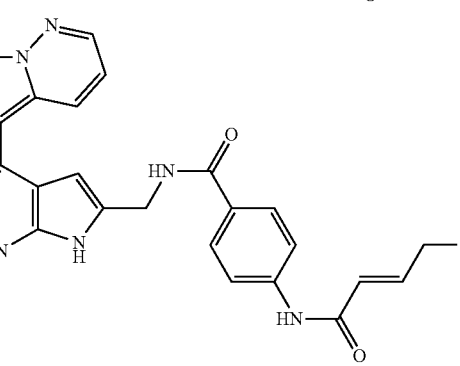
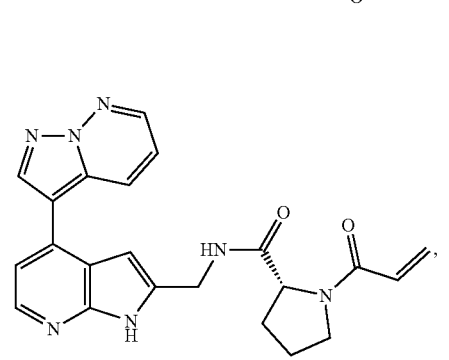
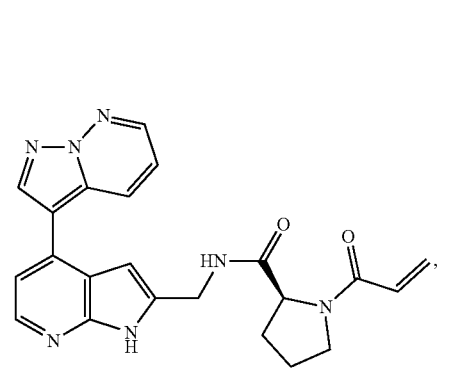

257
-continued
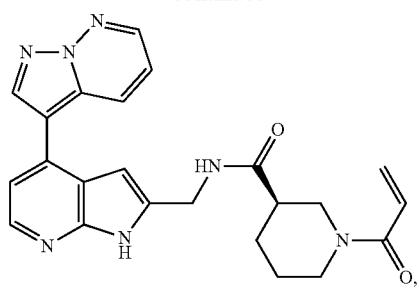
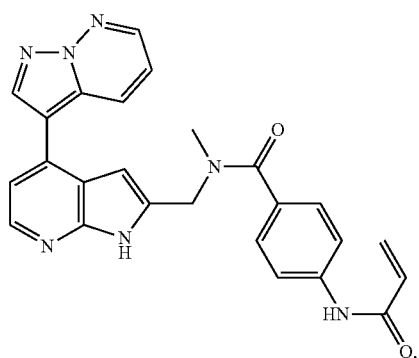
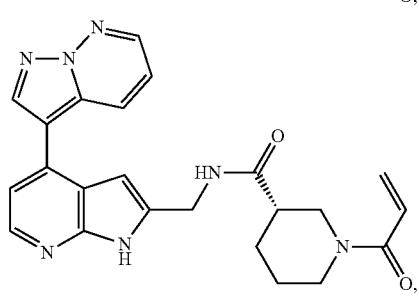
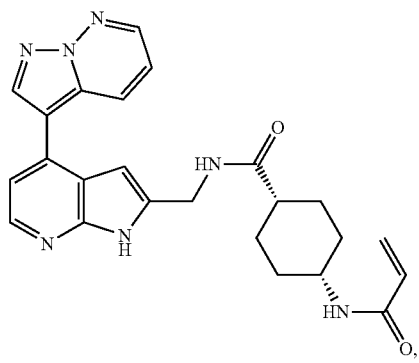
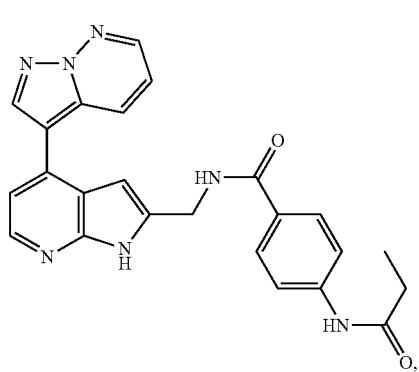
258
-continued
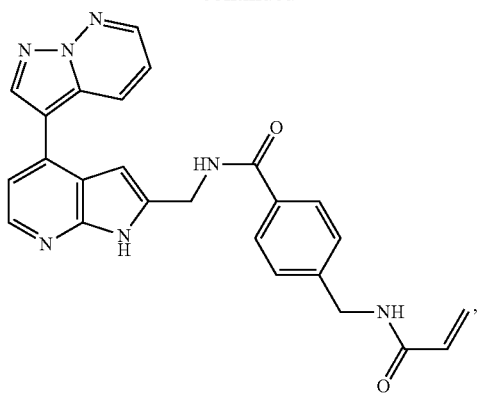
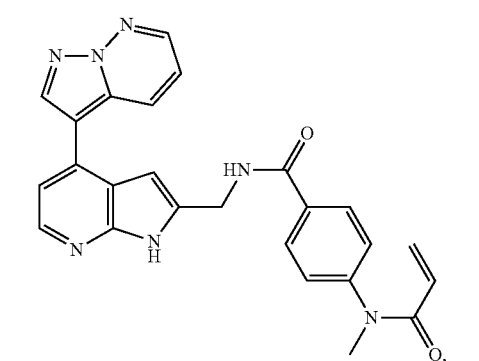
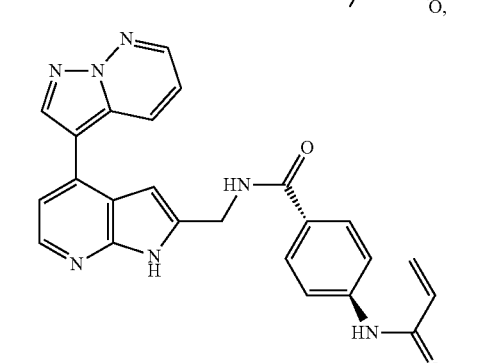
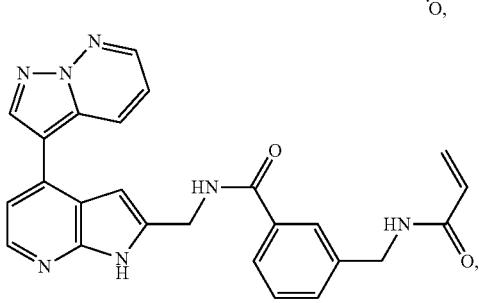
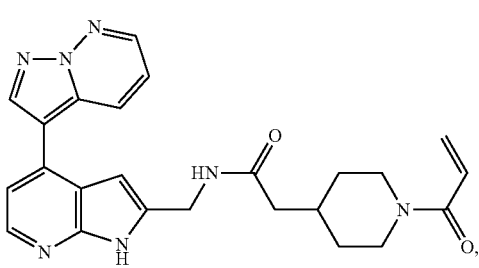

259
-continued
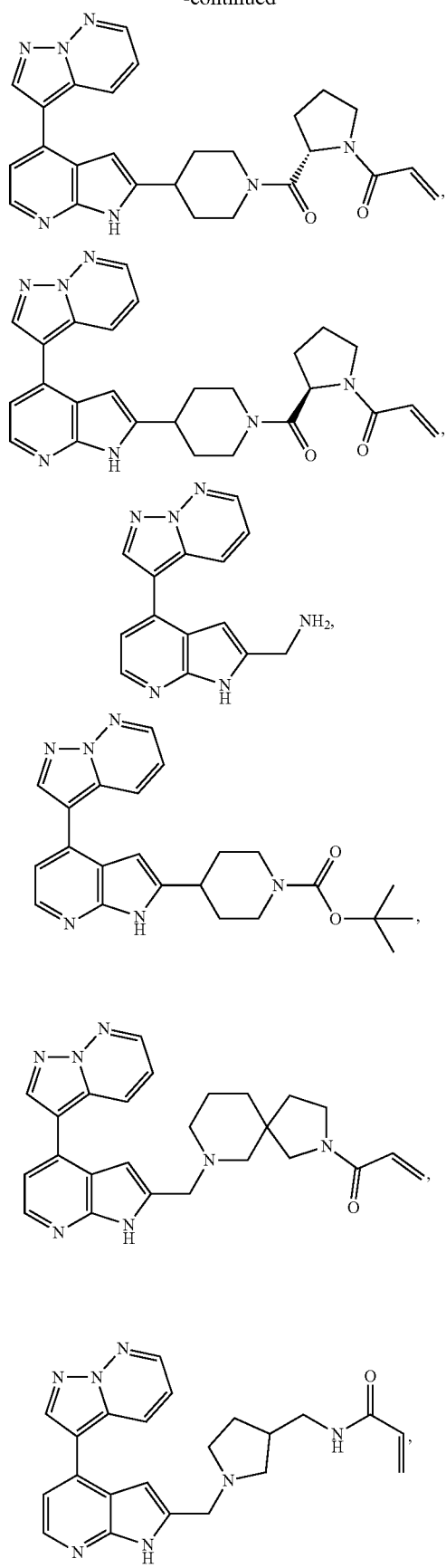
260
-continued
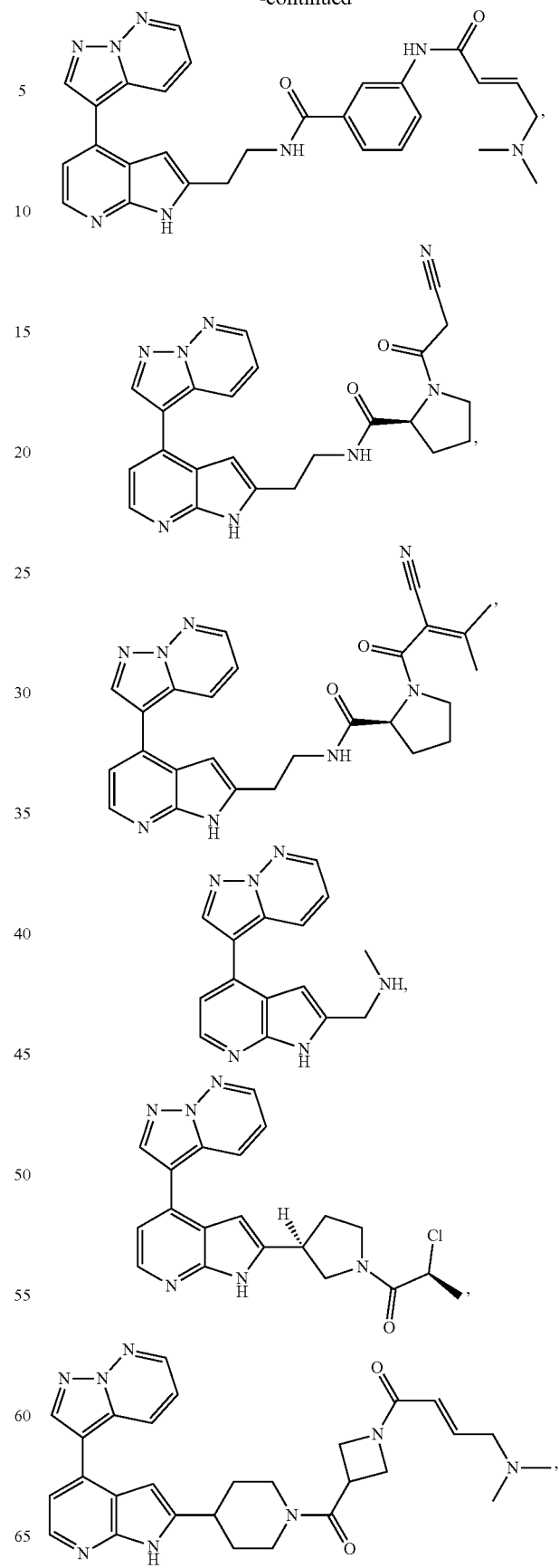

261
-continued
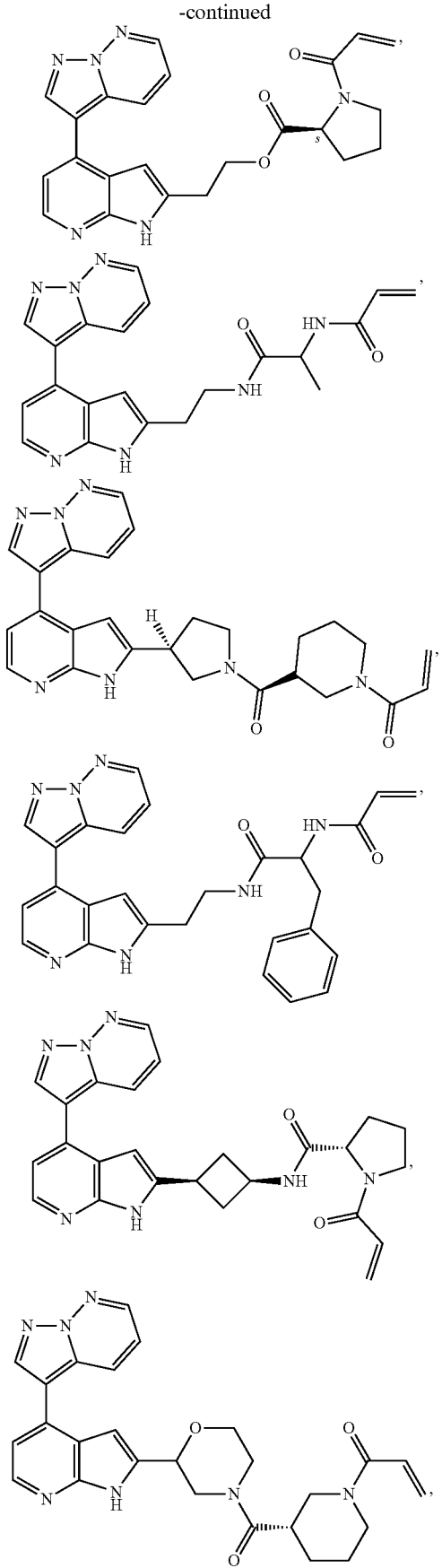
262
-continued
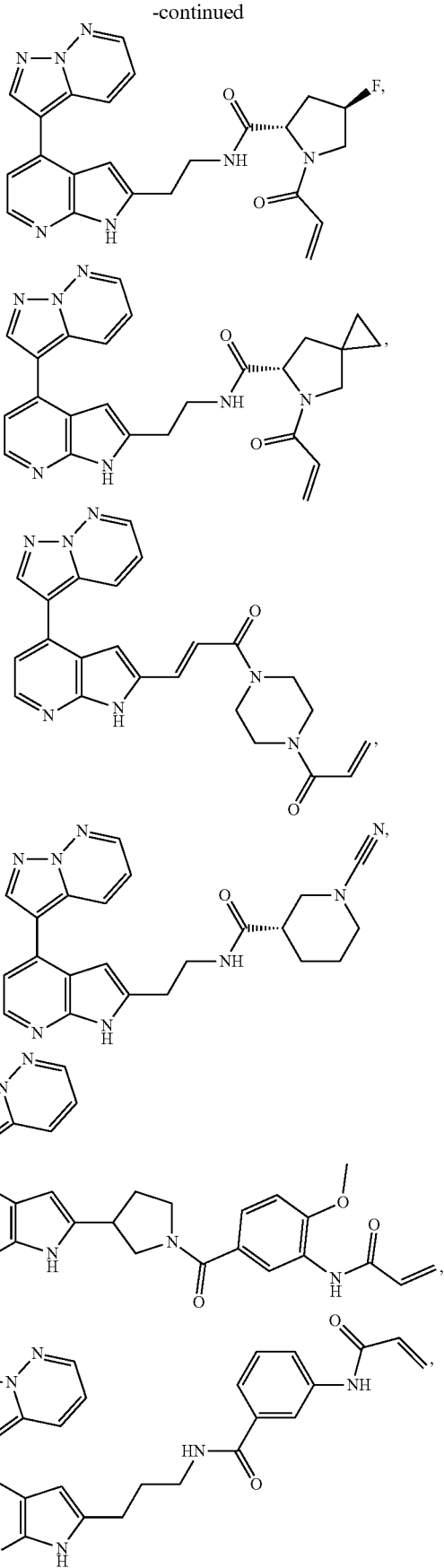

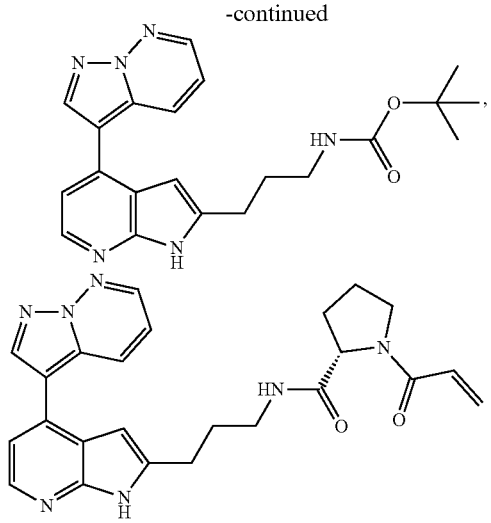
and
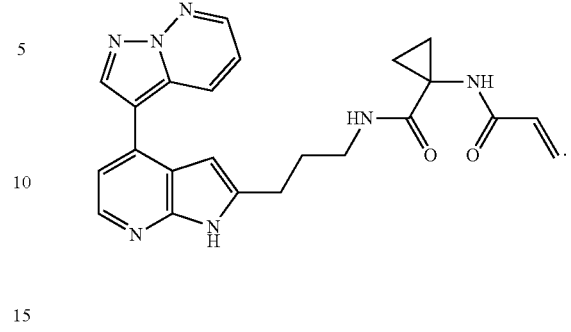
14. A pharmaceutical formulation comprising a compound of claim 1, or a pharmaceutically acceptable salt or N-oxide thereof, and a pharmaceutically acceptable excipient.
* * * * *